(12) United States Patent
Urnov et al.

(10) Patent No.: US 12,275,935 B2
(45) Date of Patent: Apr. 15, 2025

(54) GAPPED AND TUNABLE REPEAT UNITS FOR USE IN GENOME EDITING AND GENE REGULATION COMPOSITIONS

(71) Applicant: Altius Institute for Biomedical Sciences, Seattle, WA (US)

(72) Inventors: Fyodor Urnov, Seattle, WA (US); John A. Stamatoyannopoulos, Seattle, WA (US)

(73) Assignee: Altius Institute for Biomedical Sciences, Seattle, WA (US)

( * ) Notice: Subject to any disclaimer, the term of this patent is extended or adjusted under 35 U.S.C. 154(b) by 1150 days.

(21) Appl. No.: 17/254,454

(22) PCT Filed: Jun. 26, 2019

(86) PCT No.: PCT/US2019/039326
§ 371 (c)(1),
(2) Date: Dec. 21, 2020

(87) PCT Pub. No.: WO2020/006132
PCT Pub. Date: Jan. 2, 2020

(65) Prior Publication Data
US 2021/0371847 A1 Dec. 2, 2021

Related U.S. Application Data

(60) Provisional application No. 62/852,158, filed on May 23, 2019, provisional application No. 62/716,217, filed on Aug. 8, 2018, provisional application No. 62/690,890, filed on Jun. 27, 2018.

(51) Int. Cl.
*C12N 9/60* (2006.01)
*C07K 14/195* (2006.01)
*C12N 15/10* (2006.01)
*C12N 15/63* (2006.01)

(52) U.S. Cl.
CPC .......... *C12N 15/102* (2013.01); *C07K 14/195* (2013.01); *C12N 15/63* (2013.01); *C07K 2319/50* (2013.01)

(58) Field of Classification Search
CPC ........ C12N 9/22; C12N 15/63; C12N 9/1007; C12N 15/102; C12N 15/09; C07K 14/195; C07K 2319/00; C12Y 301/21004; C12P 19/34
See application file for complete search history.

(56) References Cited

U.S. PATENT DOCUMENTS

| | | |
|---|---|---|
| 2012/0270273 A1 | 10/2012 | Zhang et al. |
| 2013/0210151 A1 | 8/2013 | Edgell et al. |
| 2014/0134741 A1 | 5/2014 | Gregory et al. |
| 2014/0193915 A1 | 7/2014 | Lamb et al. |
| 2014/0304847 A1 | 10/2014 | Kuhn et al. |
| 2016/0264999 A1 | 9/2016 | Rao et al. |
| 2018/0010152 A1 | 1/2018 | Gregory |
| 2018/0087072 A1 | 3/2018 | Miller et al. |

FOREIGN PATENT DOCUMENTS

| | | |
|---|---|---|
| WO | WO2010079430 | 7/2010 |
| WO | WO2011146121 | 11/2011 |
| WO | WO 2012/168304 | 12/2012 |
| WO | WO 2013/015220 | 10/2013 |
| WO | WO 2014/018601 | 1/2014 |
| WO | WO 2014/078819 | 5/2014 |
| WO | WO 2018/017774 | 1/2018 |
| WO | WO 2018/035387 | 2/2018 |
| WO | 2018140654 | 8/2018 |

OTHER PUBLICATIONS

Kisselev L., (Structure, 2002, vol. 10: 8-9.*
Kwiatkowski et al., (Biochemistry 38:11643-11650, 1999.*
Wristlock et al., (Quarterly Reviews of Biophysics 2003, vol. 36 (3): 307-340.*
Davos et al., (Proteins: Structure, Function and Genetics, 2000, vol. 41: 98-107.*
"Hypothetical protein", (2018), GenBank Accession WP_108671537.1.
Richter et al., (2014) "A Tal Effector Repeat Architecture for Frameshift Binding", Nature Communications, 5:1-9.
Chimeric nuclease and Apoptosis from Wikipedia. Printed on Jun. 10, 2022. 2 pages.
Fu et al., (2014) "Promises and Pitfalls of Intracellular Delivery of Proteins." Bioconjugate Chemistry, vol. 25, pp. 1602-1608.
Kotterman et al., (2014) "Engineering adeno-associated viruses for clinical gene therapy." Nature Reviews, vol. 15, pp. 445-451.
Lenzi et al., (2014) NCBI Bookshelf, A service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.
Miller et al., (2011) "A Tale nuclease architecture for efficient genome editing", Nature Biotechnology, 29:143-148.
Namdev et al., (2016) "Challenges and approaches for Oral protein and peptide drug delivery." Research J. Pharm and Tech., vol. 9, No. 3, pp. 305-312.
Rehman et al., (2016) "Delivery of Therapeutic Proteins: Challenges and Strategies." Current Drug Targets, vol. 17, pp. 1172-1188.

(Continued)

*Primary Examiner* — Robert B Mondesi
*Assistant Examiner* — Mohammad Y Meah
(74) *Attorney, Agent, or Firm* — Shweta Chandra; Bozicevic, Field & Francis LLP

(57) ABSTRACT

Provided herein are DNA binding domains comprising a plurality of repeat units, wherein each repeat unit is expanded or contracted in length. Also provided herein are DNA binding domains comprising a plurality of repeat units, wherein each repeat unit is separated from a neighboring repeat unit by a linker. In certain aspects, the linker includes a recognition site. Also disclosed are DNA binding proteins that include a fragment of N-cap sequence of a TALE protein. The TALE protein may be a *Xanthomonas* TALE protein.

16 Claims, 2 Drawing Sheets
Specification includes a Sequence Listing.

(56) References Cited

OTHER PUBLICATIONS

Shim et al., (2018) "Nonviral Delivery Systems for Cancer Gene Therapy: Strategies and Challenges." Current Gene Therapy, vol. 18, pp. 3-20.

Burstein et al. (2016) "Genomic analysis of 38 Legionella species identifies large and diverse effector repertoires" Nature Genetics 48:2 167-175.

Database UniProt [Online] (Sep. 7, 2016), "SubName: Full=Avrbs3 family type III effector protein {ECO 0000313 EMBL: OAI59848. 1;". XP55890219, retrieved from EBI accession No. UNIPROT:A0A177RHNS8.

Database UniProt [Online] Mar. 15, 2017 (Mar. 15, 2017), "SubName: Full=Type-2 restriction enzyme D3 domain-containing protein {EC0:0|EMBOL: 0SH0M4436511.13};", XP55890125, retrieved from EBI accession No. UNIPROT :AQOA1M7IV76.

Jankele et al. (2014) "TAL effectors: tools for DNA targeting", Briefings in Functional Genomics, 13(5):409-419.

\* cited by examiner

GAPPED AND TUNABLE REPEAT UNITS FOR USE IN GENOME EDITING AND GENE REGULATION COMPOSITIONS

CROSS-REFERENCE TO RELATED APPLICATIONS

This application claims priority pursuant to 35 U.S.C. § 119(e) to U.S. Provisional Application No. 62/690,890, filed Jun. 27, 2018, U.S. Provisional Application No. 62/716,217, filed Aug. 8, 2018, and U.S. Provisional Application No. 62/852,158, filed May 23, 2019, the disclosures of which are incorporated herein by reference in their entirety.

INCORPORATION BY REFERENCE OF SEQUENCE LISTING PROVIDED AS A TEXT FILE

A Sequence Listing is provided herewith as a text file, "ALTI-724 Seq List_ST25.txt," created on Aug. 9, 2021 and having a size of 486 KB. The contents of the text file are incorporated by reference herein in their entirety.

INTRODUCTION

Genome editing and gene regulation techniques require the development of nucleic acid binding domains having strong and specific binding to target genes. Provided herein are DNA binding domains with tunable binding activity. Additionally, genome editing and gene regulation compositions having functional linker regions are provided, yielding compositions that exhibit dual activities. Also provided herein are compositions and methods for genome editing and gene regulation, where the nucleic acid binding domain is derived from DNA binding proteins from bacteria from the genus *Xanthomonas*.

SUMMARY

In various aspects, the present disclosure provides a composition comprising a modular nucleic acid binding domain comprising a plurality of repeat units, wherein a repeat unit of the plurality of repeat units recognizes a target nucleic acid base and wherein the plurality of repeat units has one or more of the following characteristics: (a) at least one repeat unit comprising greater than 39 amino acid residues; (b) at least one repeat unit comprising greater than 35 amino acid residues derived from the genus of *Ralstonia*; (c) at least one repeat unit comprising less than 32 amino acid residues; and (d) each repeat unit of the plurality of repeat units is separated from a neighboring repeat unit by a linker comprising a recognition site.

In some aspects, the at least one repeat unit comprises an amino acid selected from glycine, alanine, threonine or histidine at a position after an amino acid residue at position 35. In some aspects, the at least one repeat unit comprises an amino acid selected from glycine, alanine, threonine or histidine at a position after an amino acid residue at position 39. In some aspects, the recognition site is for a small molecule, a protease, or a kinase. In some aspects, the recognition site serves as a localization signal.

In further aspects, the composition further comprises a cleavage domain linked to the modular nucleic acid binding domain to form a non-naturally occurring fusion protein. In some aspects, the modular nucleic acid binding domain comprises a potency for a target site greater than 65% and a specificity ratio for the target site of 50:1; and a functional domain; wherein the modular nucleic acid binding domain comprises a plurality of repeat units, wherein at least one repeat unit of the plurality comprises a binding region configured to bind to a target nucleic acid base in the target site, wherein the potency comprises indel percentage at the target site, and wherein the specificity ratio comprises indel percentage at the target site over indel percentage at a top-ranked off-target site of the non-naturally occurring fusion protein.

In some aspects, the repeat unit comprises a sequence of $A_{1-11}X_1X_2B_{14-35}$, wherein each amino acid residue of $A_{1-11}$ comprises any amino acid residue; wherein $X_1X_2$ comprises the binding region; wherein each amino acid residue of $B_{14-35}$ comprises any amino acid; and wherein a first repeat unit of the plurality of repeat units comprises at least one residue in $A_{1-11}$, $B_{14-35}$, or a combination thereof that differs from a corresponding residue in a second repeat unit of the plurality of repeat units.

In some aspects, the binding region comprises an amino acid residue at position 13 or an amino acid residue at position 12 and the amino acid residue at position 13. In further aspects, the amino acid residue at position 13 binds to the target nucleic acid base. In still further aspects, the amino acid residue at position 12 stabilizes the configuration of the binding region. In some aspects, the indel percentage is measured by deep sequencing. In some aspects, the modular nucleic acid binding domain further comprises one or more properties selected from the following: (a) binds the target site, wherein the target site comprises a 5' guanine; (b) comprises from 7 repeat units to 25 repeat units; and (c) upon binding to the target site, the modular nucleic acid binding domain is separated from a second modular nucleic acid binding domain bound to a second target site by from 2 to 50 base pairs.

In some aspects, the plurality of repeat units comprises a *Ralstonia* repeat unit, a *Xanthomonas* repeat unit, a *Legionella* repeat unit, or any combination thereof. In further aspects, the *Ralstonia* repeat unit is a *Ralstonia solanacearum* repeat unit, the *Xanthomonas* repeat unit is a *Xanthomonas* spp. repeat unit, and the *Legionella* repeat unit is a *Legionella quateirensis* repeat unit. In still further aspects, the $B_{14-35}$ of at least one repeat unit of the plurality of repeat units has at least 92% sequence identity to GGKQALEAVRAQLLDLRAAPYG (SEQ ID NO: 280).

In some aspects, the binding region comprises HD binding to cytosine, NG binding to thymidine, NK binding to guanine, SI binding to adenosine, RS binding to adenosine, HN binding to guanine, or NT binds to adenosine. In some aspects, the at least one repeat unit comprises any one of SEQ ID NO: 267-SEQ ID NO: 279. In some aspects, the at least one repeat unit comprises at least 80%, at least 85%, at least 90%, at least 95%, at least 96%, at least 97%, at least 98%, at least 99%, or a 100% sequence identity with any one of SEQ ID NO: 168-SEQ ID NO: 263. In some aspects, the at least one repeat unit comprises at least 80%, at least 85%, at least 90%, at least 95%, at least 96%, at least 97%, at least 98%, at least 99%, or a 100% sequence identity with SEQ ID NO: 209, SEQ ID NO: 197, SEQ ID NO: 233, SEQ ID NO: 253, SEQ ID NO: 203, or SEQ ID NO: 218. In some aspects, the at least one repeat unit comprises any one of SEQ ID NO: 168-SEQ ID NO: 263. In some aspects, the at least one repeat unit comprises SEQ ID NO: 209, SEQ ID NO: 197, SEQ ID NO: 233, SEQ ID NO: 253, SEQ ID NO: 203, or SEQ ID NO: 218.

In some aspects, the target nucleic acid base is cytosine, guanine, thymidine, adenosine, uracil, or a combination thereof. In some aspects, the modular nucleic acid binding domain comprises an N-terminus amino acid sequence, a C-terminus amino acid sequence, or a combination thereof. In further aspects, the N-terminus amino acid sequence is from *Xanthomonas* spp., *Legionella quateirensis*, or *Ralstonia solanacearum*. In still further aspects, the N-terminus amino acid sequence comprises at least 80%, at least 85%, at least 90%, at least 95%, at least 96%, at least 97%, at least 98%, at least 99%, or a 100% sequence identity to SEQ ID NO: 264, SEQ ID NO: 300, SEQ ID NO: 335, SEQ ID NO: 303, SEQ ID NO: 301, SEQ ID NO: 304, or SEQ ID NO: 320, SEQ ID NO: 321, or SEQ ID NO: 322. In still further aspects, the N-terminus amino acid sequence comprises SEQ ID NO: 264, SEQ ID NO: 300, SEQ ID NO: 335, SEQ ID NO: 303, SEQ ID NO: 301, SEQ ID NO: 304, or SEQ ID NO: 320, SEQ ID NO: 321, or SEQ ID NO: 322.

In some aspects, the C-terminus amino acid sequence is from *Xanthomonas* spp., *Legionella quateirensis*, or *Ralstonia solanacearum*. In further aspects, the C-terminus amino acid sequence comprises at least 80%, at least 85%, at least 90%, at least 95%, at least 96%, at least 97%, at least 98%, at least 99%, or a 100% sequence identity to SEQ ID NO: 266, SEQ ID NO: 298, or SEQ ID NO: 306. In still further aspects, the C-terminus amino acid sequence comprises SEQ ID NO: 266, SEQ ID NO: 298, or SEQ ID NO: 306. In some aspects, the C-terminus amino acid sequence serves as a linker between the modular nucleic acid binding domain and a functional domain.

In some aspects, the modular nucleic acid binding domain comprises a half repeat. In some aspects, the half repeat comprises at least 80%, at least 85%, at least 90%, at least 95%, at least 96%, at least 97%, at least 98%, at least 99%, or a 100% sequence identity to SEQ ID NO: 265, SEQ ID NO: 327-SEQ ID NO: 334, or SEQ ID NO: 290. In some aspects, the functional domain is a cleavage domain or a repression domain. In some aspects, the cleavage domain comprises at least 33.3% divergence from SEQ ID NO: 163 and is immunologically orthogonal to SEQ ID NO: 163. In some aspects, the composition comprises one or more of the following characteristics: (a) induces greater than 1% indels at the target site; (b) the cleavage domain comprises a molecular weight of less than 23 kDa; (c) the cleavage domain comprises less than 196 amino acids; and (d) capable of cleaving across a spacer region greater than 24 base pairs.

In some aspects, the composition induces greater than 5%, greater than 10%, greater than 20%, greater than 30%, greater than 40%, greater than 50%, greater than 60%, greater than 70%, greater than 80%, or greater than 90% indels at the target site. In some aspects, the cleavage domain comprises at least 35%, at least 40%, at least 45%, at least 50%, at least 55%, at least 60%, at least 65%, at least 70%, or at least 75% divergence from SEQ ID NO: 163. In some aspects, the cleavage domain comprises a sequence selected from SEQ ID NO: 316-SEQ ID NO: 319.

In some aspects, the cleavage domain comprises a nucleic acid sequence encoding for a sequence having at least 80% sequence identity with SEQ ID NO: 1-SEQ ID NO: 81. In some aspects, the cleavage domain comprises a nucleic acid sequence encoding for a sequence selected from SEQ ID NO: 1-SEQ ID NO: 81. In some aspects, the nucleic acid sequence comprises at least 80% sequence identity with SEQ ID NO: 82-SEQ ID NO: 162. In some aspects, the nucleotide sequence encoding for the sequence comprises any one of SEQ ID NO: 82-SEQ ID NO: 162.

In some aspects, the repression domain comprises KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2. In some aspects, the plurality of repeat units comprises 3 to 60 repeat units.

In some aspects, the target site is a nucleic acid sequence within a PDCD1 gene, a CTLA4 gene, a LAGS gene, a TET2 gene, a BTLA gene, a HAVCR2 gene, a CCR5 gene, a CXCR4 gene, a TRA gene, a TRB gene, a B2M gene, an albumin gene, a HBB gene, a HBA1 gene, a TTR gene, a NR3C1 gene, a CD52 gene, an erythroid specific enhancer of the BCL11A gene, a CBLB gene, a TGFBR1 gene, a SERPINA1 gene, a HBV genomic DNA in infected cells, a CEP290 gene, a DMD gene, a CFTR gene, or an IL2RG gene.

In other aspects, a nucleic acid sequence encoding a chimeric antigen receptor (CAR), alpha-L iduronidase (IDUA), iduronate-2-sulfatase (IDS), or Factor 9 (F9), is inserted at the target site.

In various aspects, the present disclosure provides a method of genome editing, the method comprising: administering any of the above compositions and inducing a double stranded break.

Also provided herein is a non-naturally occurring DNA binding polypeptide that includes from N- to C-terminus: a N-terminus region comprising at least residues N+110 to N+1 of a TALE protein, where the N-terminus region does not include residues N+288 to N+116 of the TALE protein; a plurality of TALE repeat units derived from a TALE protein; and C-terminus region of a TALE protein. The N-terminus region may not include at least amino acids N+288 to N+116 of the TALE protein. The N-terminus region may not include amino acids N+288 to up to N+116 of the TALE protein. The N-terminus region may not include at least amino acids N+288 to up to N+111 of the TALE protein. The N-terminus region may include residues N+1 to up to N+115 of the TALE protein. The N-terminus region may include residues N+1 to up to N+110 of the TALE protein. The C-terminus region may include full length C-terminus region of a TALE protein or a fragment thereof, e.g., residues C+1 to C+63 of the TALE protein. The DNA binding polypeptide may be fused to a heterologous functional domain, such as, enzyme, a transcriptional activator, a transcriptional repressor, or a DNA nucleotide modifier. The N-terminus region, the TALE repeat units, and the C-terminus region may be derived from the same TALE protein or from different TALE proteins. The TALE proteins from which the N-terminus region, the TALE repeat units, and the C-terminus region may be derived include *Xanthomonas* TALE proteins, such as, AvrBs3, AVRHAH1, AvrXa7, AVRB6, or AvrXa10.

In various aspects, the present disclosure provides a method of genome editing, the method comprising: administering any of the above polypeptides or compositions thereof and inducing a double stranded break.

In various aspects, the present disclosure provides method of gene repression, the method comprising administering any of the above polypeptides or compositions thereof and repressing gene expression.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1A:
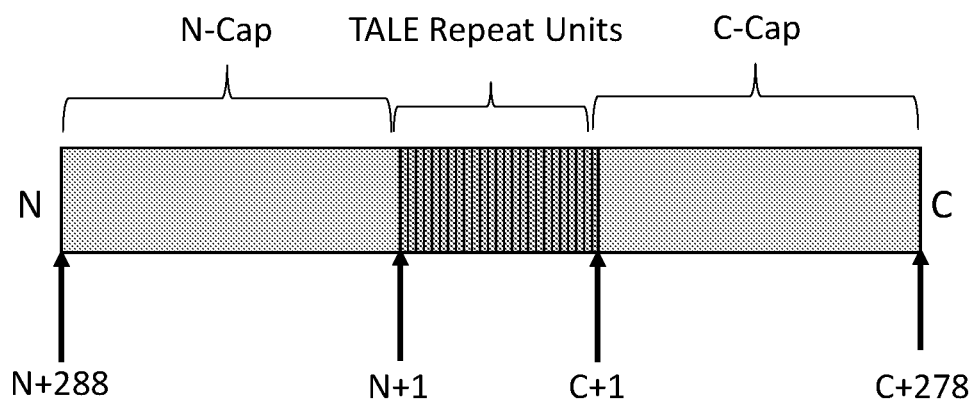
FIGS. 1A-1C show schematics of the domain structure of DNA binding proteins (not drawn to scale).

The present disclosure provides compositions and methods for genome editing and gene regulation (including activation and repression) with DNA binding domains fused to functional domains via linkers that serve as recognition sites for further activity (e.g., a non-nuclease enzyme activity). The present disclosure also provides compositions and methods for genome editing and gene regulation with DNA binding domains that can have enhanced binding to a target nucleic acid sequence. Enhanced binding to a target nucleic acid sequence can be achieved with the DNA binding domains of the present disclosure in which repeat units can be varied in length to tune for binding activity.

Linkers Comprising Recognition Sites

In some embodiments, the present disclosure provides DNA binding domains with gapped repeat units for use as gene editing complexes. A DNA binding domain with gapped repeat units can comprise of a plurality of repeat units in which each repeat unit of the plurality of repeat units is separated from a neighboring repeat unit by a linker. This linker can comprise a recognition site for additional functionality and activity. For example, the linker can comprise a recognition site for a small molecule. As another example, the linker can serve as a recognition site for a protease. In yet another example, the linker can serve as a recognition site for a kinase. In other embodiments, the recognition site can serve as a localization signal.

Each repeat unit of a DNA binding domain (e.g., RNBDs, MAP-NBDs, TALEs) comprises a secondary structure in which the RVD interfaces with and binds to a target nucleic acid base on double stranded DNA, while the remainder of the repeat unit protrudes from the surface of the DNA. Thus, the linkers comprising a recognition site between each repeat unit are removed from the surface of the DNA and are solvent accessible. In some embodiments, these solvent accessible linkers comprising recognition sites can have extra activity while mediating gene editing.

Examples of a left and a right DNA binding domain comprising repeat units derived from *Xanthomonas* spp. are shown below in TABLE 1 for AAVS1 and GA7. "X," shown in bold and underlining, represents a linker comprising a recognition site and can comprise 1-40 amino acid residues. An amino acid residue of the linker can comprise a glycine, an alanine, a threonine, or a histidine.

In some embodiments, "derived" indicates that a protein is from a particular source (e.g., *Ralstonia*), is a variant of a protein from a particular source (e.g., *Ralstonia*), is a mutated or modified form of the protein from a particular source (e.g., *Ralstonia*), and shares at least 30% sequence identity with, at least 40% sequence identity with, at least 50% sequence identity with, at least 60% sequence identity with, at least 70% sequence identity with, at least 80% sequence identity with, or at least 90% sequence identity with a protein from a particular source (e.g., *Ralstonia*, *Xanthomonas*, or *Legionella*).

TABLE 1

Exemplary Left or Right Gapped DNA Binding Domains

| SEQ ID NO | Construct | Sequence |
| --- | --- | --- |
| SEQ ID NO: 307 | AAVS1_Left | LTPDQVVAIASHDGGKQALETVQRLLPVLCQDHGXLTPDQVV AIASHDGGKQALETVQRLLPVLCQDHGXLTPDQVVAIASHDG GKQALETVQRLLPVLCQDHGXLTPDQVVAIASHDGGKQALET VQRLLPVLCQDHGXLTPDQVVAIASNGGGKQALETVQRLLPV LCQDHGXLTPDQVVAIASHDGGKQALETVQRLLPVLCQDHGX LTPDQVVAIASHDGGKQALETVQRLLPVLCQDHGXLTPDQVV AIASNIGGKQALETVQRLLPVLCQDHGXLTPDQVVAIASHDGG KQALETVQRLLPVLCQDHGXLTPDQVVAIASHDGGKQALETV QRLLPVLCQDHGXLTPDQVVAIASHDGGKQALETVQRLLPVL CQDHGXLTPDQVVAIASHDGGKQALETVQRLLPVLCQDHGXL TPDQVVAIASNIGGKQALETVQRLLPVLCQDHGXLTPDQVVAI ASHDGGKQALETVQRLLPVLCQDHGXLTPDQVVAIASNIGGK QALETVQRLLPVLCQDHGXLTPDQVVAIASNHGGKQALETVQ RLLPVLCQDHGXLTPDQVVAIASNGGG |
| SEQ ID NO: 308 | AAVS1_Right | LTPDQVVAIASNGGGKQALETVQRLLPVLCQDHGXLTPDQVV AIASNGGGKQALETVQRLLPVLCQDHGXLTPDQVVAIASNGG GKQALETVQRLLPVLCQDHGXLTPDQVVAIASHDGGKQALET VQRLLPVLCQDHGXLTPDQVVAIASNGGGKQALETVQRLLPV LCQDHGXLTPDQVVAIASNHGGKQALETVQRLLPVLCQDHGX LTPDQVVAIASNGGGKQALETVQRLLPVLCQDHGXLTPDQVV AIASHDGGKQALETVQRLLPVLCQDHGXLTPDQVVAIASNIGG KQALETVQRLLPVLCQDHGXLTPDQVVAIASHDGGKQALETV QRLLPVLCQDHGXLTPDQVVAIASHDGGKQALETVQRLLPVL CQDHGXLTPDQVVAIASNIGGKQALETVQRLLPVLCQDHGXL TPDQVVAIASNIGGKQALETVQRLLPVLCQDHGXLTPDQVVAI ASNGGGKQALETVQRLLPVLCQDHGXLTPDQVVAIASHDGGK QALETVQRLLPVLCQDHGXLTPDQVVAIASHDGGKQALETVQ RLLPVLCQDHGXLTPDQVVAIASNGGGKQALESIVAQLSRPDP ALA |
| SEQ ID NO: 309 | GA7.2 Left | LTPDQVVAIASNHGGKQALETVQRLLPVLCQDHGXLTPDQVV AIASHDGGKQALETVQRLLPVLCQDHGXLTPDQVVAIASNGG GKQALETVQRLLPVLCQDHGXLTPDQVVAIASHDGGKQALET VQRLLPVLCQDHGXLTPDQVVAIASNIGGKQALETVQRLLPVL CQDHGXLTPDQVVAIASNHGGKQALETVQRLLPVLCQDHGXL |

TABLE 1-continued

Exemplary Left or Right Gapped DNA Binding Domains

| SEQ ID NO | Construct | Sequence |
|---|---|---|
| | | TPDQVVAIASHDGGKQALETVQRLLPVLCQDHGXLTPDQVVA<br>IASHDGGKQALETVQRLLPVLCQDHGXLTPDQV̄V̄AIASHDGG<br>KQALETVQRLLPVLCQDHGXLTPDQV̄V̄AIASNIGGKQALETV<br>QRLLPVLCQDHGXLTPDQV̄V̄AIASNHGGKQALETVQRLLPVL<br>CQDHGXLTPDQV̄V̄AIASHDGGKQALETVQRLLPVLCQDHGXL<br>TPDQV̄V̄AIASNGGGKQALETVQRLLPVLCQDHGXLTPDQV̄V̄A<br>IASHDGGKQALETVQRLLPVLCQDHGXLTPDQV̄V̄AIASNIGGK<br>QALETVQRLLPVLCQDHGXLTPDQV̄V̄AIASNHGGKQALETVQ<br>RLLPVLCQDHGXLTPDQV̄V̄AIASHDGGKQALETVQRLLPVLC<br>QDHGXLTPDQV̄V̄AIASHDGGKQALETVQRLLPVLCQDHGXLT<br>PDQV̄V̄AIASNGGGK |
| SEQ ID NO: 310 | GA7.2 Right | LTPDQVVAIASHDGGKQALETVQRLLPVLCQDHGXLTPDQVV<br>AIASHDGGKQALETVQRLLPVLCQDHGXLTPDQV̄V̄AIASHDG<br>GKQALETVQRLLPVLCQDHGXLTPDQV̄V̄AIASHDGGKQALET<br>VQRLLPVLCQDHGXLTPDQV̄V̄AIASHDGGKQALETVQRLLPV<br>LCQDHGXLTPDQV̄V̄AIASNGGGKQALETVQRLLPVLCQDHGX<br>LTPDQV̄V̄AIASHDGGKQALETVQRLLPVLCQDHGXLTPDQV̄V̄<br>AIASNGGGKQALETVQRLLPVLCQDHGXLTPDQV̄V̄AIASHDG<br>GKQALETVQRLLPVLCQDHGXLTPDQV̄V̄AIASNIGGKQALET<br>VQRLLPVLCQDHGXLTPDQV̄V̄AIASNGGGKQALETVQRLLPV<br>LCQDHGXLTPDQV̄V̄AIASNGGGKQALETVQRLLPVLCQDHGX<br>LTPDQV̄V̄AIASHDGGKQALETVQRLLPVLCQDHGXLTPDQV̄V̄<br>AIASNGGGKQALETVQRLLPVLCQDHGXLTPDQV̄V̄AIASHDG<br>GKQALETVQRLLPVLCQDHGXLTPDQV̄V̄AIASNGGGKQALET<br>VQRLLPVLCQDHGXLTPDQV̄V̄AIASNIGGKQALETVQRLLPVL<br>CQDHGXLTPDQV̄V̄AIASHDGGKQALETVQRLLPVLCQDHGXL<br>TPDQV̄V̄AIASHDGGKQALETVQRLLPVLCQDHGXLTPDQV̄V̄A<br>IASNIGGKQALETVQRLLPVLCQDHGXLTPDQV̄V̄ASASNGGG<br>KQALESIVAQLSRPDPALA |

Tunable Repeat Units

In some embodiments, the present disclosure provides DNA binding domains (e.g., RNBDs, MAP-NBDs, TALEs) with expanded repeat units. For example, a DNA binding domain (e.g., RNBDs, MAP-NBDs, TALEs) comprises a plurality of repeat units in which each repeat unit is usually 33-35 amino acid residues in length. The present disclosure provides repeat units, which are greater than 35 amino acid residues in length. In some embodiments, the present disclosure provides repeat units, which are greater than 39 amino acid residues in length. In some embodiments, the present disclosure provides repeat units which are 35 to 40 amino acid residues long, 39 to 40 amino acid residues long, 35 to 45 amino acid residues long, 39 to 45 amino acid residues long, 35 to 50 amino acid residues long, 39 to 50 amino acid residues long, 35 to 50 amino acid residues long, 35 to 60 amino acid residues long, 39 to 60 amino acid residues long, 35 to 70 amino acid residues long, 39 to 70 amino acid residues long, 35 to 79 amino acid residues long, or 39 to 79 amino acid residues long.

In other embodiments, the present disclosure provides DNA binding domains (e.g., RNBDs, MAP-NBDs, TALEs) with contracted repeat units. For example, the present disclosure provides repeat units, which are less than 32 amino acid residues in length. In some embodiments, the present disclosure provides repeat units, which are 15 to 32 amino acid residues in length, 16 to 32 amino acid residues in length, 17 to 32 amino acid residues in length, 18 to 32 amino acid residues in length, 19 to 32 amino acid residues in length, 20 to 32 amino acid residues in length, 21 to 32 amino acid residues in length, 22 to 32 amino acid residues in length, 23 to 32 amino acid residues in length, 24 to 32 amino acid residues in length, 25 to 32 amino acid residues in length, 26 to 32 amino acid residues in length, 27 to 32 amino acid residues in length, 28 to 32 amino acid residues in length, 29 to 32 amino acid residues in length, 30 to 32 amino acid residues in length, or 31 to 32 amino acid residues in length.

In some embodiments, said expanded repeat units can be tuned to modulate binding of each repeat unit to its target nucleic acid, resulting in the ability to overall modulate binding of the DNA binding domain to a target gene of interest. For example, expanding repeat units can improve binding affinity of the repeat unit to its target nucleic acid base and thereby increase binding affinity of the DNA binding domain to a target gene. In some embodiments, expanding repeat units can improve specificity of the DNA binding domain for a target gene. In other embodiments, contracting repeat units can improve binding affinity of the repeat unit to its target nucleic acid base and thereby increase binding affinity of the DNA binding domain for a target gene.

Described in further detail below are DNA binding domains from the genus of *Ralstonia*, the genus of animal pathogens (e.g., *Legionella, Burkholderia, Paraburkholderia*, or *Francisella*), and the genus of *Xanthomonas*, which can comprise linkers comprising recognition sites, expanded repeat units, or contracted repeat units, as described in detail above.

In some embodiments, the present disclosure provides a composition comprising a modular nucleic acid binding domain comprising a plurality of repeat units, wherein a repeat unit of the plurality of repeat units recognizes a target nucleic acid base and wherein the plurality of repeat units has one or more of the following characteristics: (a) at least one repeat unit comprising greater than 39 amino acid residues; (b) at least one repeat unit comprising greater than 35 amino acid residues derived from the genus of *Ralstonia*; (c) at least one repeat unit comprising less than 32 amino acid residues; and (d) each repeat unit of the plurality of repeat units is separated from a neighboring repeat unit by a linker comprising a recognition site.

In some embodiments, the at least one repeat unit comprises an amino acid selected from glycine, alanine, threonine or histidine at a position after an amino acid residue at position 35. In some embodiments, the at least one repeat unit comprises an amino acid selected from glycine, alanine, threonine or histidine at a position after an amino acid residue at position 39. In some aspects, the recognition site is for a small molecule, a protease, or a kinase. In some aspects, the recognition site serves as a localization signal.

Ralstonia-Derived DNA Binding Domains

The present disclosure provides modular nucleic acid binding domains (NBDs) derived from the genus of bacteria. For example, in some embodiments, the present disclosure provides NBDs derived from bacteria that serve as plant pathogens, such as from the genus of Xanthomonas spp. and Ralstonia. In particular embodiments, the present disclosure provides NBDs from the genus of Ralstonia. Also provided herein are NBDs from the animal pathogen, Legionella. Provided herein are sequences of repeat units derived from the genus of Ralstonia, which can be linked together to form non-naturally occurring modular nucleic acid binding domains (NBDs), capable of targeting and binding any target nucleic acid sequence (e.g., DNA sequence).

In some embodiments, "modular" indicates that a particular composition such as a nucleic acid binding domain, comprises a plurality of repeat units that can be switched and replaced with other repeat units. For example, any repeat unit in a modular nucleic acid binding domain can be switched with a different repeat unit. In some embodiments, modularity of the nucleic acid binding domains disclosed herein allows for switching the target nucleic acid base for a particular repeat unit by simply switching it out for another repeat unit. In some embodiments, modularity of the nucleic acid binding domains disclosed herein allows for swapping out a particular repeat unit for another repeat unit to increase the affinity of the repeat unit for a particular target nucleic acid. Overall, the modular nature of the nucleic acid binding domains disclosed herein enables the development of genome editing complexes that can precisely target any nucleic acid sequence of interest.

In particular embodiments, modular nucleic acid binding domains (NBDs), also referred to herein as "DNA binding polypeptides," are provided herein from the genus of Ralstonia solanacearum. In some embodiments, modular nucleic acid binding domains derived from Ralstonia (RNBDs) can be engineered to bind to a target gene of interest for purposes of gene editing or gene regulation. An RNBD can be engineered to target and bind a specific nucleic acid sequence. The nucleic acid sequence can be DNA or RNA.

In some embodiments, the RNBD can comprise a plurality of repeat units, wherein each repeat unit recognizes and binds to a single nucleotide (in DNA or RNA) or base pair. Each repeat unit in the plurality of repeat units can be specifically selected to target and bind to a specific nucleic acid sequence, thus contributing to the modular nature of the DNA binding polypeptide. A non-naturally occurring *Ralstonia*-derived modular nucleic acid binding domain can comprise a plurality of repeat units, wherein each repeat unit of the plurality of repeat units recognizes a single target nucleotide, base pair, or both.

In some embodiments, the repeat unit of a modular nucleic acid binding domain can be derived from a bacterial protein. For example, the bacterial protein can be a transcription activator like effector-like protein (TALE-like protein). The bacterial protein can be derived from *Ralstonia solanacearum*. Repeat units derived from *Ralstonia solanacearum* can be 33-35 amino acid residues in length. In some embodiments, the repeat can be derived from the naturally occurring *Ralstonia solanacearum* TALE-like protein.

TABLE 2 below shows exemplary repeat units derived from the genus of *Ralstonia*, which are capable of binding a target nucleic acid.

TABLE 2

Exemplary *Ralstonia*-derived Repeat Units

| SEQ ID NO | Sequence |
|---|---|
| SEQ ID NO: 168 | LDTEQVVAIASHNGGKQALEAVKADLLDLLGAPYV |
| SEQ ID NO: 169 | LDTEQVVAIASHNGGKQALEAVKADLLDLRGAPYA |
| SEQ ID NO: 170 | LDTEQVVAIASHNGGKQALEAVKADLLELRGAPYA |
| SEQ ID NO: 171 | LDTEQVVAIASHNGGKQALEAVKAHLLDLRGAPYA |
| SEQ ID NO: 172 | LNTEQVVAIASHNGGKQALEAVKADLLDLRGAPYA |
| SEQ ID NO: 173 | LNTEQVVAIASNNGGKQALEAVKTHLLDLRGARYA |
| SEQ ID NO: 174 | LNTEQVVAIASNPGGKQALEAVRALFPDLRAAPYA |
| SEQ ID NO: 175 | LNTEQVVAIASSHGGKQALEAVRALFPDLRAAPYA |
| SEQ ID NO: 176 | LNTEQVVAVASNKGGKQALEAVGAQLLALRAVPYA |
| SEQ ID NO: 177 | LNTEQVVAVASNKGGKQALEAVGAQLLALRAVPYE |
| SEQ ID NO: 178 | LSAAQVVAIASHDGGKQALEAVGTQLVALRAAPYA |
| SEQ ID NO: 179 | LSIAQVVAVASRSGGKQALEAVRAQLLALRAAPYG |
| SEQ ID NO: 180 | LSPEQVVAIASNHGGKQALEAVRALFRGLRAAPYG |
| SEQ ID NO: 181 | LSPEQVVAIASNNGGKQALEAVKAQLLELRAAPYE |
| SEQ ID NO: 182 | LSTAQLVAIASNPGGKQALEAIRALFRELRAAPYA |
| SEQ ID NO: 183 | LSTAQLVAIASNPGGKQALEAVRALFRELRAAPYA |
| SEQ ID NO: 184 | LSTAQLVAIASNPGGKQALEAVRAPFREVRAAPYA |
| SEQ ID NO: 185 | LSTAQLVSIASNPGGKQALEAVRALFRELRAAPYA |
| SEQ ID NO: 186 | LSTAQVAAIASHDGGKQALEAVGTQLVVLRAAPYA |
| SEQ ID NO: 187 | LSTAQVATIASSIGGRQALEALKVQLPVLRAAPYG |
| SEQ ID NO: 188 | LSTAQVATIASSIGGRQALEAVKVQLPVLRAAPYG |
| SEQ ID NO: 189 | LSTAQVVAIAANNGGKQALEAVRALLPVLRVAPYE |
| SEQ ID NO: 190 | LSTAQVVAIAGNGGGKQALEGIGEQLLKLRTAPYG |
| SEQ ID NO: 191 | LSTAQVVAIASHDGGKQALEAAGTQLVALRAAPYA |
| SEQ ID NO: 192 | LSTAQVVAIASHDGGKQALEAVGAQLVELRAAPYA |
| SEQ ID NO: 193 | LSTAQVVAIASHDGGKQALEAVGTQLVALRAAPYA |
| SEQ ID NO: 194 | LSTAQVVAIASHDGGNQALEAVGTQLVALRAAPYA |
| SEQ ID NO: 195 | LSTAQVVAIASHNGGKQALEAVKAQLLDLRGAPYA |
| SEQ ID NO: 196 | LSTAQVVAIASNDGGKQALEEVEAQLLALRAAPYE |
| SEQ ID NO: 197 | LSTAQVVAIASNGGGKQALEGIGEQLLKLRTAPYG |
| SEQ ID NO: 198 | LSTAQVVAIASNGGGKQALEGIGEQLRKLRTAPYG |
| SEQ ID NO: 199 | LSTAQVVAIASNPGGKQALEAVRALFRELRAAPYA |

TABLE 2-continued Exemplary *Ralstonia*-derived Repeat Units

| SEQ ID NO | Sequence |
|---|---|
| SEQ ID NO: 200 | LSTAQVVAIASQNGGKQALEAVKAQLLDLRGAPYA |
| SEQ ID NO: 201 | LSTAQVVAIASSHGGKQALEAVRALFRELRAAPYG |
| SEQ ID NO: 202 | LSTAQVVAIASSNGGKQALEAVWALLPVLRATPYD |
| SEQ ID NO: 203 | LSTAQVVAIATRSGGKQALEAVRAQLLDLRAAPYG |
| SEQ ID NO: 204 | LSTAQVVAVAGRNGGKQALEAVRAQLPALRAAPYG |
| SEQ ID NO: 205 | LSTAQVVAVASSNGGKQALEAVWALLPVLRATPYD |
| SEQ ID NO: 206 | LSTAQVVTIASSNGGKQALEAVWALLPVLRATPYD |
| SEQ ID NO: 207 | LSTEQVVAIAGHDGGKQALEAVGAQLVALRAAPYA |
| SEQ ID NO: 208 | LSTEQVVAIASHDGGKQALEAVGAQLVALLAAPYA |
| SEQ ID NO: 209 | LSTEQVVAIASHDGGKQALEAVGAQLVALRAAPYA |
| SEQ ID NO: 210 | LSTEQVVAIASHDGGKQALEAVGGQLVALRAAPYA |
| SEQ ID NO: 211 | LSTEQVVAIASHDGGKQALEAVGTQLVALRAAPYA |
| SEQ ID NO: 212 | LSTEQVVAIASHDGGKQALEAVGVQLVALRAAPYA |
| SEQ ID NO: 213 | LSTEQVVAIASHDGGKQALEAVVAQLVALRAAPYA |
| SEQ ID NO: 214 | LSTEQVVAIASHDGGKQPLEAVGAQLVALRAAPYA |
| SEQ ID NO: 215 | LSTEQVVAIASHGGGKQVLEGIGEQLLKLRAAPYG |
| SEQ ID NO: 216 | LSTEQVVAIASHKGGKQALEGIGEQLLKLRAAPYG |
| SEQ ID NO: 217 | LSTEQVVAIASHNGGKQALEAVKADLLDLRGAPYA |
| SEQ ID NO: 218 | LSTEQVVAIASHNGGKQALEAVKADLLELRGAPYA |
| SEQ ID NO: 219 | LSTEQVVAIASHNGGKQALEAVKAHLLDLRGAPYA |
| SEQ ID NO: 220 | LSTEQVVAIASHNGGKQALEAVKAHLLDLRGVPYA |
| SEQ ID NO: 221 | LSTEQVVAIASHNGGKQALEAVKAHLLELRGAPYA |
| SEQ ID NO: 222 | LSTEQVVAIASHNGGKQALEAVKAQLLDLRGAPYA |
| SEQ ID NO: 223 | LSTEQVVAIASHNGGKQALEAVKAQLLELRGAPYA |
| SEQ ID NO: 224 | LSTEQVVAIASHNGGKQALEAVKAQLPVLRRAPYG |
| SEQ ID NO: 225 | LSTEQVVAIASHNGGKQALEAVKTQLLELRGAPYA |
| SEQ ID NO: 226 | LSTEQVVAIASHNGGKQALEAVRAQLPALRAAPYG |
| SEQ ID NO: 227 | LSTEQVVAIASHNGSKQALEAVKAQLLDLRGAPYA |
| SEQ ID NO: 228 | LSTEQVVAIASNGGKQALEGIGKQLQELRAAPHG |
| SEQ ID NO: 229 | LSTEQVVAIASNGGGKQALEGIGKQLQELRAAPYG |
| SEQ ID NO: 230 | LSTEQVVAIASNHGGKQALEAVRALFRELRAAPYA |
| SEQ ID NO: 231 | LSTEQVVAIASNHGGKQALEAVRALFRGLRAAPYG |
| SEQ ID NO: 232 | LSTEQVVAIASNKGGKQALEAVKADLLDLRGAPYV |
| SEQ ID NO: 233 | LSTEQVVAIASNKGGKQALEAVKAHLLDLLGAPYV |
| SEQ ID NO: 234 | LSTEQVVAIASNKGGKQALEAVKAQLLALRAAPYA |
| SEQ ID NO: 235 | LSTEQVVAIASNKGGKQALEAVKAQLLELRGAPYA |
| SEQ ID NO: 236 | LSTEQVVAIASNNGGKQALEAVKALLLELRAAPYE |
| SEQ ID NO: 237 | LSTEQVVAIASNNGGKQALEAVKAQLLALRAAPYE |
| SEQ ID NO: 238 | LSTEQVVAIASNNGGKQALEAVKAQLLDLRGAPYA |
| SEQ ID NO: 239 | LSTEQVVAIASNNGGKQALEAVKAQLLVLRAAPYG |
| SEQ ID NO: 240 | LSTEQVVAIASNNGGKQALEAVKAQLPALRAAPYE |
| SEQ ID NO: 241 | LSTEQVVAIASNNGGKQALEAVKAQLPVLRRAPCG |
| SEQ ID NO: 242 | LSTEQVVAIASNNGGKQALEAVKAQLPVLRRAPYG |
| SEQ ID NO: 243 | LSTEQVVAIASNNGGKQALEAVKARLLDLRGAPYA |
| SEQ ID NO: 244 | LSTEQVVAIASNNGGKQALEAVKTQLLALRTAPYE |
| SEQ ID NO: 245 | LSTEQVVAIASNPGGKQALEAVRALFPDLRAAPYA |
| SEQ ID NO: 246 | LSTEQVVAIASSHGGKQALEAVRALFPDLRAAPYA |
| SEQ ID NO: 247 | LSTEQVVAIASSHGGKQALEAVRALLPVLRATPYD |
| SEQ ID NO: 248 | LSTEQVVAVASHNGGKQALEAVRAQLLDLRAAPYE |
| SEQ ID NO: 249 | LSTEQVVAVASNKGGKQALAAVEAQLLRLRAAPYE |
| SEQ ID NO: 250 | LSTEQVVAVASNKGGKQALEEVEAQLLRLRAAPYE |
| SEQ ID NO: 251 | LSTEQVVAVASNKGGKQVLEAVGAQLLALRAVPYE |
| SEQ ID NO: 252 | LSTEQVVAVASNNGGKQALKAVKAQLLALRAAPYE |
| SEQ ID NO: 253 | LSTEQVVIANSIGGKQALEAVKVQLPVLRAAPYE |
| SEQ ID NO: 254 | LSTGQVVAIASNGGGKRQALEAVREQLLALRAVPYE |
| SEQ ID NO: 255 | LSVAQVVTIASHNGGKQALEAVRAQLLALRAAPYG |
| SEQ ID NO: 256 | LTIAQVVAVASHNGGKQALEAIGAQLLALRAAPYA |
| SEQ ID NO: 257 | LTIAQVVAVASHNGGKQALEVIGAQLLALRAAPYA |
| SEQ ID NO: 258 | LTPQQVVAIAANTGGKQALGAITTQLPILRAAPYE |
| SEQ ID NO: 259 | LTPQQVVAIASNTGGKQALEAVTVQLRVLRGARYG |
| SEQ ID NO: 260 | LTPQQVVAIASNTGGKRALEAVCVQLPVLRAAPYR |
| SEQ ID NO: 261 | LTPQQVVAIASNTGGKRALEAVRVQLPVLRAAPYE |
| SEQ ID NO: 262 | LTTAQVVAIASNDGKQALEAVGAQLLVLRAVPYE |
| SEQ ID NO: 263 | LTTAQVVAIASNDGGKQTLEVAGAQLLALRAVPYE |
| SEQ ID NO: 336 | LSTAQVVAVASGSGGKPALEAVRAQLLALRAAPYG |
| SEQ ID NO: 337 | LSTAQVVAVASGSGGKPALEAVRAQLLALRAAPYG |
| SEQ ID NO: 338 | LNTAQIVAIASHDGGKPALEAVWAKLPVLRGAPYA |
| SEQ ID NO: 339 | LNTAQVVAIASHDGGKPALEAVRAKLPVLRGVPYA |
| SEQ ID NO: 340 | LNTAQVVAIASHDGGKPALEAVWAKLPVLRGVPYA |
| SEQ ID NO: 341 | LNTAQVVAIASHDGGKPALEAVWAKLPVLRGVPYE |
| SEQ ID NO: 342 | LSTAQVVAIASHDGGKPALEAVWAKLPVLRGAPYA |
| SEQ ID NO: 343 | LSTAQVVAVASHDGGKPALEAVRKQLPVLRGVPHQ |
| SEQ ID NO: 344 | LSTAQVVAVASHDGGKPALEAVRKQLPVLRGVPHQ |
| SEQ ID NO: 345 | LNTAQVVAIASHDGGKPALEAVWAKLPVLRGVPYA |
| SEQ ID NO: 346 | LSTEQVVAIASHNGGKLALEAVKAHLLDLRGAPYA |
| SEQ ID NO: 347 | LSTEQVVAIASHNGGKPALEAVKAHLLALRAAPYA |

TABLE 2-continued

Exemplary *Ralstonia*-derived Repeat Units

| SEQ ID NO | Sequence |
|---|---|
| SEQ ID NO: 348 | LNTAQVVAIASHYGGKPALEAVWAKLPVLRGVPYA |
| SEQ ID NO: 349 | LNTEQVVAIASNNGGKPALEAVKAQLLELRAAPYE |
| SEQ ID NO: 350 | LSPEQVVAIASNNGGKPALEAVKALLLALRAAPYE |
| SEQ ID NO: 351 | LSPEQVVAIASNNGGKPALEAVKAQLLELRAAPYE |
| SEQ ID NO: 352 | LSTEQVVAIASNNGGKPALEAVKALLLALRAAPYE |
| SEQ ID NO: 353 | LSTEQVVAIASNNGGKPALEAVKALLLELRAAPYE |
| SEQ ID NO: 354 | LSPEQVVAIASNNGGKPALEAVKALLLALRAAPYE |
| SEQ ID NO: 355 | LSPEQVVAIASNNGGKPALEAVKAQLLELRAAPYE |
| SEQ ID NO: 356 | LSTEQVVAIASNNGGKPALEAVKALLLELRAAPYE |

In some embodiments, an RNBD of the present disclosure can comprise between 1 to 50 *Ralstonia solanacearum*-derived repeat units. In some embodiments, an RNBD of the present disclosure can comprise between 9 and 36 *Ralstonia solanacearum*-derived repeat units. Preferably, in some embodiments, an RNBD of the present disclosure can comprise between 12 and 30 *Ralstonia solanacearum*-derived repeat units. An RNBD described herein can comprise between 5 to 10 *Ralstonia solanacearum*-derived repeat units, between 10 to 15 *Ralstonia solanacearum*-derived repeat units, between 15 to 20 *Ralstonia solanacearum*-derived repeat units, between 20 to 25 *Ralstonia solanacearum*-derived repeat units, between 25 to 30 *Ralstonia solanacearum*-derived repeat units, or between 30 to 35 *Ralstonia solanacearum*-derived repeat units, between 35 to 40 *Ralstonia solanacearum*-derived repeat units. An RNBD described herein can comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 *Ralstonia solanacearum*-derived repeat units.

A *Ralstonia solanacearum*-derived repeat unit can be derived from a wild-type repeat unit, such as any one of SEQ ID NO: 168-SEQ ID NO: 263 or SEQ ID NO: 336-SEQ ID NO: 356. A *Ralstonia solanacearum*-repeat unit can have at least 80% sequence identity with any one of SEQ ID NO: 168-SEQ ID NO: 263 or SEQ ID NO: 336-SEQ ID NO: 356. A *Ralstonia solanacearum*-derived repeat unit can also comprise a modified *Ralstonia solanacearum*-derived repeat unit enhanced for specific recognition of a nucleotide or base pair. An RNBD described herein can comprise one or more wild-type *Ralstonia solanacearum*-derived repeat units, one or more modified *Ralstonia solanacearum*-derived repeat units, or a combination thereof. In some embodiments, a modified *Ralstonia solanacearum*-derived repeat unit can comprise 1, 2, 3, 4, 5, 6, 7, 8, 9, 10, 11, 12, 13, 14, 15, 16, 17, 18, 19, 20, 21, 22, 23, 24, 25, 26, 27, 28, or 29 mutations that can enhance recognition of a specific nucleotide or base pair. In some embodiments, a modified *Ralstonia solanacearum*-derived repeat unit can comprise more than 1 modification, for example 1 to 5 modifications, 5 to 10 modifications, 10 to 15 modifications, 15 to 20 modifications, 20 to 25 modification, or 25-29 modifications. In some embodiments, An RNBD can comprise more than one modified *Ralstonia solanacearum*-derived repeat units, wherein each of the modified *Ralstonia solanacearum*-derived repeat units can have a different number of modifications.

The *Ralstonia solanacearum*-derived repeat units comprise amino acid residues at positions 12 and 13, what is referred to herein as, a repeat variable diresidue (RVD). The RVD can modulate binding affinity of the repeat unit for a particular nucleic acid base (e.g., adenosine, guanine, cytosine, thymidine, or uracil (in RNA sequences)). In some embodiments, a single amino acid residue can modulate binding to the target nucleic acid base. In some embodiments, two amino acid residues (RVD) can modulate binding to the target nucleic acid base. In some embodiments, any repeat unit disclosed herein can have an RVD selected from HD, HG, HK, HN, ND, NG, NH, NK, NN, NP, NT, QN, RN, RS, SH, SI, or SN. In some embodiments, an RVD of HD can bind to cytosine. In some embodiments, an RVD of NG can bind to thymidine. In some embodiments, an RVD of NK can bind to guanine. In some embodiments, an RVD of SI can bind to adenosine. In some embodiments, an RVD of RS can bind to adenosine. In some embodiments, an RVD of HN can bind to guanine. In some embodiments, an RVD of NT can bind to adenosine.

In some embodiments, a repeat unit having at least 80% sequence identity with SEQ ID NO: 209 can be included in a DNA binding domain of the present disclosure to bind to cytosine. In some embodiments, a repeat unit having at least 80% sequence identity with SEQ ID NO: 197 can be included in a DNA binding domain of the present disclosure to bind to thymidine. In some embodiments, a repeat unit having at least 80% sequence identity with SEQ ID NO: 233 can be included in a DNA binding domain of the present disclosure to bind to guanine. In some embodiments, a repeat unit having at least 80% sequence identity with SEQ ID NO: 253 can be included in a DNA binding domain of the present disclosure to bind to adenosine. In some embodiments, a repeat unit having at least 80% sequence identity with SEQ ID NO: 203 can be included in a DNA binding domain of the present disclosure to bind to adenosine. In some embodiments, a repeat unit having at least 80% sequence identity with SEQ ID NO: 218 can be included in a DNA binding domain of the present disclosure to bind to guanine. In some embodiments, the repeat unit of SEQ ID NO: 209 can be included in a DNA binding domain of the present disclosure to bind to cytosine. In some embodiments, the repeat unit of SEQ ID NO: 197 can be included in a DNA binding domain of the present disclosure to bind to thymidine. In some embodiments, the repeat unit of SEQ ID NO: 233 can be included in a DNA binding domain of the present disclosure to bind to guanine. In some embodiments, the repeat unit of SEQ ID NO: 253 can be included in a DNA binding domain of the present disclosure to bind to adenosine. In some embodiments, the repeat unit of SEQ ID NO: 203 can be included in a DNA binding domain of the present disclosure to bind to adenosine. In some embodiments, the repeat unit of SEQ ID NO: 218 can be included in a DNA binding domain of the present disclosure to bind to guanine.

In some embodiments, the present disclosure provides repeat units as set forth in SEQ ID NO: 267-SEQ ID NO: SEQ ID NO: 279. Unspecified amino acid residues in SEQ ID NO: 267-SEQ ID NO: SEQ ID NO: 279 can be any amino acid residues. In particular embodiments, unspecified amino acid residues in SEQ ID NO: 267-SEQ ID NO: SEQ ID NO: 279 can be those set forth in the Variable Definition column of TABLE 3.

TABLE 3 shows consensus sequences of *Ralstonia*-derived repeat units.

TABLE 3

Consensus Sequences of *Ralstonia*-derived Repeat Units

| RVD | Consensus Sequence | Variable Definition |
|---|---|---|
| HN | $LX_1X_2X_3QVVX_4X_5ASHNGX_6KQALEX_7X_8X_9X_{10}X_{11}LX_{12}X_{13}LX_{14}X_{15}X_{16}PYX_{17}$ (SEQ ID NO: 267) | $X_1$: D\|N\|S\|T, $X_2$: I\|T\|V, $X_3$: A\|E, $X_4$: A\|T, $X_5$: I\|V, $X_6$: G\|S, $X_7$: A\|V, $X_8$: I\|V, $X_9$: G\|K\|R, $X_{10}$: A\|T, $X_{11}$: D\|H\|Q, $X_{12}$: L\|P, $X_{13}$: A\|D\|E\|V, $X_{14}$: L\|R, $X_{15}$: A\|G\|R, $X_{16}$: A\|V, $X_{17}$: A\|E\|G\|V |
| NN | $LX_1X_2X_3QVVAX_4AX_5NNGGKQALX_6AVX_7X_8X_9LX_{10}X_{11}LRX_{12}AX_{13}X_{14}X_{15}$ (SEQ ID NO: 268) | $X_1$: N\|S, $X_2$: P\|T, $X_3$: A\|E, $X_4$: I\|V, $X_5$: A\|S, $X_6$: E\|K, $X_7$: K\|R, $X_8$: A\|T, $X_9$: H\|L\|Q\|R, $X_{10}$: L\|P, $X_{11}$: A\|D\|E\|V, $X_{12}$: A\|G\|R\|T\|V, $X_{13}$: P\|R, $X_{14}$: C\|Y, $X_{15}$: A\|E\|G |
| NP | $LX_1TX_2QX_3VX_4IASNPGGKQALEAX_5RAX_6FX_7X_8X_9RAAPYA$ (SEQ ID NO: 269) | $X_1$: N\|S, $X_2$: A\|E, $X_3$: L\|V, $X_4$: A\|S, $X_5$: I\|V, $X_6$: L\|P, $X_7$: P\|R, $X_8$: D\|E, $X_9$: L\|V |
| SH | $LX_1TX_2QVVAIASSHGGKQALEAVRALX_3X_4X_5LRAX_6PYX_7$ (SEQ ID NO: 270) | $X_1$: N\|S, $X_2$: A\|E, $X_3$: F\|L, $X_4$: P\|R, $X_5$: D\|E\|V, $X_6$: A\|T, $X_7$: A\|D\|G |
| NK | $LX_1TEQVVAX_2ASNKGGKQX_3LX_4X_5VX_6AX_7LLX_8LX_9X_{10}X_{11}PYX_{12}$ (SEQ ID NO: 271) | $X_1$: N\|S, $X_{10}$: A\|G, $X_{11}$: A\|V, $X_{12}$: A\|E\|V, $X_2$: I\|V, $X_3$: A\|V, $X_4$: A\|E, $X_5$: A\|E, $X_6$: E\|G\|K, $X_7$: D\|H\|Q, $X_8$: A\|D\|E\|R, $X_9$: L\|R |
| HD | $LSX_1X_2QVX_3AIAX_4HDGGX_5QX_6LEAX_7X_8X_9QLVX_{10}LX_{11}AAPYA$ (SEQ ID NO: 272) | $X_1$: A\|T, $X_2$: A\|E, $X_3$: A\|V, $X_4$: G\|S, $X_5$: K\|N, $X_6$: A\|P, $X_7$: A\|V, $X_8$: G\|V, $X_9$: A\|G\|T\|V, $X_{10}$: A\|E\|V, $X_{11}$: L\|R |
| RS | $LSX_1AQVVAX_2AX_3RSGGKQALEAVRAQLLX_4LRAAPYG$ (SEQ ID NO: 273) | $X_1$: I\|T, $X_2$: I\|V, $X_3$: S\|T, $X_4$: A\|D |
| NH | $LSX_1EQVVAIASNHGGKQALEAVRALFRX_2LRAAPYX_3$ (SEQ ID NO: 274) | $X_1$: P\|T, $X_2$: E\|G, $X_3$: A\|G |
| SI | $LSTX_1QVX_2X_3IAX_4SIGGX_5QALEAX_6KVQLPVLRAAPYX_7$ (SEQ ID NO: 275) | $X_1$: A\|E, $X_2$: A\|V, $X_3$: T\|V, $X_4$: N\|S, $X_5$: K\|R, $X_6$: L\|V, $X_7$: E\|G |
| ND | $LX_1TAQVVAIASNDGGKQX_2LEX_3X_4X_5AQLLX_6LRAX_7PYE$ (SEQ ID NO: 276) | $X_1$: S\|T, $X_2$: A\|T, $X_3$: A\|E\|V, $X_4$: A\|V, $X_5$: E\|G, $X_6$: A\|V, $X_7$: A\|V |
| SN | $LSTAQVVX_1X_2ASSNGGKQALEAVWALLPVLRATPYD$ (SEQ ID NO: 277) | $X_1$: A\|T, $X_2$: I\|V |
| NG | $LSTX_1QVVAIAX_2NGGGX_3QALEX_4X_5X_6X_7QLX_8X_9LRX_{10}X_{11}PX_{12}X_{13}$ (SEQ ID NO: 278) | $X_1$: A\|E\|G, $X_2$: G\|S, $X_3$: K\|R, $X_4$: A\|G, $X_5$: I\|V, $X_6$: G\|R, $X_7$: E\|K, $X_8$: L\|Q\|R, $X_9$: A\|E\|K, $X_{10}$: A\|T, $X_{11}$: A\|V, $X_{12}$: H\|Y, $X_{13}$: E\|G |
| NT | $LTPQQVVAIAX_1NTGGKX_2ALX_3AX_4X_5X_6QLX_7X_8LRX_9AX_{10}YX_{11}$ (SEQ ID NO: 279) | $X_1$: A\|S, $X_{10}$: P\|R, $X_{11}$: E\|G\|R, $X_2$: Q\|R, $X_3$: E\|G, $X_4$: I\|V, $X_5$: C\|R\|T, $X_6$: T\|V, $X_7$: P\|R, $X_8$: I\|V, $X_9$: A\|G |

In some aspects, the at least one repeat unit comprises any one of SEQ ID NO: 267-SEQ ID NO: 279. In some embodiments, the present disclosure provides a modular nucleic acid binding domain (e.g., RNBD or MAP-NBD), wherein the modular nucleic acid binding domain comprises a repeat unit with a sequence of $A_{1-11}X_1X_2B_{14-35}$ (SEQ ID NO: 448), wherein $A_{1-11}$ comprises 11 amino acid residues and wherein each amino acid residue of $A_{1-11}$ can be any amino acid. In some embodiments, $A_{1-11}$ can be any amino acids in position 1 through position 11 of any one of SEQ ID NO: 168-SEQ ID NO: 263 or SEQ ID NO: 336-SEQ ID NO: 356. $X_1X_2$ comprises any repeat variable diresidue (RVD) disclosed herein and comprises at least one amino acid at position 12 or position 13. As described herein, this RVD contacts and binds to a target nucleic acid base of a target site. Said RVD can be the RVD of any repeat unit disclosed herein, such as position 12 and position 13 of any one of SEQ ID NO: 168-SEQ ID NO: 263 or SEQ ID NO: 336-SEQ ID NO: 356. $B_{14-35}$ can comprise 22 amino acid residues and each amino acid residue of $B_{14-35}$ can be any amino acid. In some embodiments, $B_{14-35}$ can be any amino acid in position 14 through position 35 of any one of SEQ ID NO: 168-SEQ ID NO: 263 or SEQ ID NO: 336-SEQ ID NO: 356. In particular embodiments, a modular nucleic acid binding domain (e.g., RNBD or MAP-NBD) having the above sequence of $A_{1-11}X_1X_2B_{14-35}$ (SEQ ID NO: 448) can have a first repeat unit with at least one residue in $A_{1-11}$, $B_{14-35}$, or a combination thereof that differs from a corresponding residue in a second repeat unit in the modular nucleic acid binding domain (e.g., RNBD or MAP-NBD). In other words, at least two repeat units in a modular nucleic acid binding domain (e.g., RNBD or MAP-NBD) described herein can have different amino acid residues with respect to each other, at the same position outside the RVD region. Thus, in some embodiments, a modular nucleic acid binding domain (e.g., RNBD or MAP-NBD) described herein can have variant backbones with respect to each repeat unit in the plurality of repeat units that make up the modular nucleic acid binding domain. In some embodiments, an RNBD of the present disclosure can have a sequence of GGKQALEAVRAQLLDLRAAPYG (SEQ ID NO: 280) at $B_{14-35}$.

In some embodiments, a modular nucleic acid binding sequence (e.g., RNBD) can comprise one or more of the following characteristics: the modular nucleic acid binding sequence (e.g., RNBD) can bind a nucleic acid sequence, wherein the target site comprises a 5' guanine, the modular nucleic acid binding domain (e.g., RNBD) can comprise 7 repeat units to 25 repeat units, a first modular nucleic acid binding sequence (e.g., RNBD) can bind a target nucleic acid sequence and be separated from a second modular nucleic acid binding domain (e.g., RNBD) from 2 to 50 base pairs, or any combination thereof.

In some embodiments, an RNBD of the present disclosure can have the full length naturally occurring N-terminus of a naturally occurring *Ralstonia solanacearum*-derived protein. In some embodiments, any truncation of the full length naturally occurring N-terminus of a naturally occurring *Ralstonia solanacearum*-derived protein can be used at the N-terminus of an RNBD of the present disclosure. For example, in some embodiments, amino acid residues at positions 1 (H) to position 137 (F) of the naturally occurring *Ralstonia solanacearum*-derived protein N-terminus can be used. In particular embodiments, said truncated N-terminus from position 1 (H) to position 137 (F) can have a sequence as follows: FGKLVALGYSREQIRKLKQESLSEIAKYHT-TLTGQGFTHADICRISRRRQSLRVVARNYPE-LAAALPE LTRAHIVDIARQRSGDLALQALLPVATAL-TAAPLRLSASQIATVAQYGERPAIQALYRLRRKLTRAPL H (SEQ ID NO: 264). In some embodiments, the naturally occurring N-terminus of Ralstonia solanacearum can be truncated to any length and used at the N-terminus of the engineered DNA binding domain. For example, the naturally occurring N-terminus of Ralstonia solanacearum can be truncated to amino acid residues at position 1 (H) to position 120 (K) as follows: KQESLSEIAKYHTTLTGQGFTHAD-ICRISRRRQSLRVVARNYPELAAALPELTRAHIVDI-ARQ RSGDLALQALLPVATALTAAPLRLSASQI-ATVAQYGERPAIQALYRLRRKLTRAPLH (SEQ ID NO: 303) and used at the N-terminus of the RNBD. The naturally occurring N-terminus of Ralstonia solanacearum can be truncated amino acid residues at positions 1 to 115 and used at the N-terminus of the engineered DNA binding domain as set forth in SEQ ID NO: 320. The naturally occurring N-terminus of Ralstonia solanacearum can be truncated to amino acid residues at positions 1 to 50, 1 to 70, 1 to 100, 1 to 120, 1 to 130, 10 to 40, 60 to 100, or 100 to 120 and used at the N-terminus of the engineered DNA binding domain. Truncation of the N-termini can be particularly advantageous for obtaining DNA binding domains, which are smaller in size including number of amino acids and overall molecular weight. A reduced number of amino acids can allow for more efficient packaging into a viral vector and a smaller molecular weight can result in more efficient loading of the DNA binding domains in non-viral vectors for delivery.

In some embodiments, the N-terminus, referred to as the amino terminus or the "NH2" domain, can recognize a length repeat unit of 33-35 amino acid residues is followed by a half-repeat also derived from Ralstonia solanacearum. The half repeat can have 15 to 23 amino acid residues, for example, the half repeat can have 19 amino acid residues. In particular embodiments, the half-repeat can have a sequence as follows: LSTAQVVAIACISGQQALE (SEQ ID NO: 265).

In some embodiments, an RNBD of the present disclosure can have the full length naturally occurring C-terminus of a naturally occurring Ralstonia solanacearum-derived protein. In some embodiments, any truncation of the full length naturally occurring C-terminus of a naturally occurring Ralstonia solanacearum-derived protein can be used at the C-terminus of an RNBD of the present disclosure. For example, in some embodiments, the RNBD can comprise amino acid residues at position 1 (A) to position 63 (S) as follows: AIEAHMPTLRQASHSLSPERVAAIACIGGR-SAVEAVRQGLPVKAIRRIRREKAPVAGPPPAS (SEQ ID NO: 266) of the naturally occurring Ralstonia solanacearum-derived protein C-terminus. In some embodiments, the naturally occurring C-terminus of Ralstonia solanacearum can be truncated to any length and used at the C-terminus of the RNBD. For example, the naturally occurring C-terminus of Ralstonia solanacearum can be truncated to amino acid residues at positions 1 to 63 and used at the C-terminus of the RNBD. The naturally occurring C-terminus of Ralstonia solanacearum can be truncated amino acid residues at positions 1 to 50 and used at the C-terminus of the RNBD. The naturally occurring C-terminus of Ralstonia solanacearum can be truncated to amino acid residues at positions 1 to 63, 1 to 50, 1 to 70, 1 to 100, 1 to 120, 1 to 130, 10 to 40, 60 to 100, or 100 to 120 and used at the C-terminus of the RNBD.

TABLE 4 shows N-termini, C-termini, and half-repeats derived from Ralstonia.

TABLE 4

Ralstonia-Derived N-terminus, C-terminus, and Half-Repeat

| SEQ ID NO | Description | Sequence |
| --- | --- | --- |
| SEQ ID NO: 320 | Truncated N-terminus; positions 1 (H) to 115(S) of the naturally occurring Ralstonia solanacearum-derived protein N-terminus | SEIAKYHTTLTGQGFTHADICRISRRRQSLRV VARNYPELAAALPELTRAHIVDIARQRSGDL ALQALLPVATALTAAPLRLSASQIATVAQYG ERPAIQALYRLRRKLTRAPLH |
| SEQ ID NO: 264 | Truncated N-terminus; positions 1 (H) to 137 (F) of the naturally occurring Ralstonia solanacearum-derived protein N-terminus | FGKLVALGYSREQIRKLKQESLSEIAKYHTT LTGQGFTHADICRISRRRQSLRVVARNYPEL AAALPELTRAHIVDIARQRSGDLALQALLPV ATALTAAPLRLSASQIATVAQYGERPAIQAL YRLRRKLTRAPLH |
| SEQ ID NO: 303 | Truncated N-terminus; positions 1 (H) to 120 (K) of the naturally occurring Ralstonia solanacearum-derived protein N-terminus | KQESLSEIAKYHTTLTGQGFTHADICRISRRR QSLRVVARNYPELAAALPELTRAHIVDIARQ RSGDLALQALLPVATALTAAPLRLSASQIAT VAQYGERPAIQALYRLRRKLTRAPLH |
| SEQ ID NO: 265 | Half-repeat | LSTAQVVAIACISGQQALE |
| SEQ ID NO: 266 | Truncated C-terminus; positions 1 (A) to 63 (S) of the naturally occurring Ralstonia solanacearum-derived protein C-terminus | AIEAHMPTLRQASHSLSPERVAAIACIGGRS AVEAVRQGLPVKAIRRIRREKAPVAGPPPAS | guanine. In some embodiments, the N-terminus can be engineered to bind a cytosine, adenosine, thymidine, guanine, or uracil.

In some embodiments, an RNBD of the present disclosure can have a DNA binding domain, in which the final full In some embodiments, an RNBD can be engineered to target and bind to a site in the PDCD1 gene. For example, an RNBD with the sequence FGKLVALGYS-REQIRKLKQESLSEIAKYHTTLTGQGFTHADICRIS-RRRQSLRVVARNYPELA AALPELTRAHIVDIAR- QRSGDLALQALLPVATALTAAPLRLSASQIATVAQYGERPAIQALY RLRRKLTRAPLHLTPQQVVAIASNTGGKRALEAVCVQLPVLRAAPYRLSTEQVVAIASHDG GKQALEAVGAQLVALRAAPYALSTEQVVAIASHDGGKQALEAVGAQLVALRAAPYALST AQVVAIASNGGGKQALEGIGEQLLKLRTAPYGLSTEQVVAIASNKGGKQALEAVKAHLLDL LGAPYVLSTEQVVAIASNKGGKQALEAVKAHLLDLLGAPYVLSTEQVVAIASNKGGKQAL EAVKAHLLDLLGAPYVLSTEQVVVIANSIGGKQALEAVKVQLPVLRAAPYELSTEQVVAIA SHDGGKQALEAVGAQLVALRAAPYALSTEQVVVIANSIGGKQALEAVKVQLPVLRAAPYE LSTEQVVAIASNKGGKQALEAVKAHLLDLLGAPYVLSTAQVVAIASNGGGKQALEGIGEQL LKLRTAPYGLSTAQVVAIASNGGGKQALEGIGEQLLKLRTAPYGLSTAQVVAIASNGGGKQ ALEGIGEQLLKLRTAPYGLSTEQVVAIASHDGGKQALEAVGAQLVALRAAPYALSTEQVVA IASHDGGKQALEAVGAQLVALRAAPYALSTEQVVA IASHDGGKQALEAVGAQLVALRAAP YALSTAQVVAIASNGGGKQALEGIGEQLLKLRTAPYGLSTAQVVAIASNGGGKQALEGIGE QLLKLRTAPYGLSTAQVVAIACISGQQALEAIEAHMPTLRQASHSLSPERVAAIACIGGRSAV EAVRQGLPVKAIRRIRREKAPVAGPPPAS (SEQ ID NO: 311) can bind to the GACCTGGGACAGTTTCCCTT (SEQ ID NO: 312) nucleic acid sequence in the PDCD1 gene. As another example, an RNBD with the sequence FGKLVALGYSREQIRKLKQESLSEIAKYHTTLTGQGFTHADICRISRRRQSLRVVARNYPELA AALPELTRAHIVDIARQRSGDLALQALLPVATALTAAPLRLSASQIATVAQYGERPAIQALY RLRRKLTRAPLHLTPQQVVAIASNTGGKRALEAVCVQLPVLRAAPYRLSTAQVVAIASNGG GKQALEGIGEQLLKLRTAPYGLSTEQVVAIASHDGGKQALEAVGAQLVALRAAPYALSTA QVVAIASNGGGKQALEGIGEQLLKLRTAPYGLSTEQVVAIASHNGGKQALEAVKADLLELR GAPYALSTEQVVAIASHDGGKQALEAVGAQLVALRAAPYALSTEQVVVIANSIGGKQALEA VKVQLPVLRAAPYELSTAQVVAIASNGGGKQALEGIGEQLLKLRTAPYGLSTEQVVAIASH NGGKQALEAVKADLLELRGAPYALSTEQVVAIASHDGGKQALEAVGAQLVALRAAPYALS TEQVVAIASHDGGKQALEAVGAQLVALRAAPYALSTAQVVAIASNGGGKQALEGIGEQLL KLRTAPYGLSTEQVVAIASHNGGKQALEAVKADLLELRGAPYALSTEQVVAIASHNGGKQ ALEAVKADLLELRGAPYALSTEQVVVIANSIGGKQALEAVKVQLPVLRAAPYELSTEQVVA IASHNGGKQALEAVKADLLELRGAPYALSTEQVVAIASHDGGKQALEAVGAQLVALRAAP YALSTAQVVAIACISGQQALEAIEAHMPTLRQASHSLSPERVAAIACIGGRSAVEAVRQGLP VKAIRRIRREKAPVAGPPPAS (SEQ ID NO: 313) can bind to the GATCTGCATGCCTGGAGC (SEQ ID NO: 314) nucleic acid sequence in the PDCD1 gene. As yet another example, an RNBD with the sequence FGKLVALGYSREQIRKLKQESLSEIAKYHTTLTGQGFTHADICRISRRRQSLRVVARNYPELA AALPELTRAHIVDIARQRSGDLALQALLPVATALTAAPLRLSASQIATVAQYGERPAIQALY RLRRKLTRAPLHLTPQQVVAIASNTGGKRALEAVCVQLPVLRAAPYRLSTAQVVAIASNGG GKQALEGIGEQLLKLRTAPYGLSTEQVVAIASHDGGKQALEAVGAQLVALRAAPYALSTA QVVAIASNGGGKQALEGIGEQLLKLRTAPYGLSTEQVVAIASHNGGKQALEAVKADLLELR GAPYALSTEQVVAIASHDGGKQALEAVGAQLVALRAAPYALSTAQVVAIATRSGGKQALE AVRAQLLDLRAAPYGLSTAQVVAIASNGGGKQALEGIGEQLLKLRTAPYGLSTEQVVAIAS HNGGKQALEAVKADLLELRGAPYALSTEQVVAIASHDGGKQALEAVGAQLVALRAAPYA LSTEQVVAIASHDGGKQALEAVGAQLVALRAAPYALSTAQVVAIASNGGGKQALEGIGEQ LLKLRTAPYGLSTEQVVAIASHNGGKQALEAVKADLLELRGAPYALSTEQVVAIASHNGGK QALEAVKADLLELRGAPYALSTAQVVAIATRSGGKQALEAVRAQLLDLRAAPYGLSTEQV VAIASHNGGKQALEAVKADLLELRGAPYALSTEQVVAIASHDGGKQALEAVGAQLVALRA APYALSTAQVVAIACISGQQALEAIEAHMPTLRQASHSLSPERVAAIACIGGRSAVEAVRQG LPVKAIRRIRREKAPVAGPPPAS (SEQ ID NO: 315) can bind to the GATCTGCATGCCTGGAGC (SEQ ID NO: 314) nucleic acid sequence in the PDCD1 gene. Any one of SEQ ID NO: 311, SEQ ID NO; 313, or SEQ ID NO: 315 can be fused to any repression domain described herein (e.g., KRAB) to yield a gene repressor capable of repressing expression of the target gene.

*Xanthomonas* Derived Transcription Activator Like Effector (TALE)

The present disclosure provides a modular nucleic acid binding domain derived from *Xanthomonas* spp., also referred to herein as a transcription activator-like effector (TALE) protein, can comprise a plurality of repeat units. A repeat unit of the plurality of repeat units recognizes a single target nucleotide, base pair, or both. A repeat unit from *Xanthomonas* spp. can comprise 33-35 amino acid residues. In some embodiments, a repeat unit can be from *Xanthomonas* spp. and have a sequence of (SEQ ID NO: 299)
MDPIRSRTPSPARELLPGPQPDGVQPTADRGVSPPAGGPLDGLPARRTMS

RTRLPSPPAPSPAFSAGSFSDLLRQFDPSLFNTSLFDSLPPFGAHHTEAA

TGEWDEVQSGLRAADAPPPTMRVAVTAARPPRAKPAPRRRAAQPSDASPA

AQVDLRTLGYSQQQQEKIKPKVRSTVAQHHEALVGHGFTHAHIVALSQHP

AALGTVAVKYQDMIAALPEATHEAIVGVGKQWSGARALEALLTVAGELRG

PPLQLDTGQLLKIAKRGGVTAVEAVHAWRNALTGAPLNLTPEQVVAIASH

DGGKQALETVQRLLPVLCQAHGLTPQQVVAIASNGGGKQALETVQRLLPV

LCQAHGLTPQQVVAIASNSGGKQALETVQRLLPVLCQAHGLTPEQVVAIA

SNGGGKQALETVQRLLPVLCQAHGLTPEQVVAIASNIGGKQALETVQALL

PVLCQAHGLTPEQVVAIASNIGGKQALETVQALLPVLCQAHGLTPEQVVA

IASNIGGKQALETVQALLPVLCQAHGLTPEQVVAIASHDGGKQALETVQR

LLPVLCQAHGLTPEQVVAIASHDGGKQALETVQRLLPVLCQAHGLTPQQV

VAIASNGGGKQALETVQRLLPVLCQAHGLTPEQVVAIASNSGGKQALETV

QALLPVLCQAHGLTPEQVVAIASNSGGKQALETVQRLLPVLCQAHGLTPE

QVVAIASHDGGKQALETVQRLLPVLCQAHGLTPEQVVAIASHDGGKQALE

TVQRLLPVLCQAHGLTPEQVVAIASHDGGKQALETVQRLLPVLCQAHGLT

```
PQQVVAIASNGGGGRPALETVQRLLPVLCQAHGLTPEQVVAIASHDGGKQA

LETVQRLLPVLCQAHGLTPQQVVAIASNGGGRPALESIVAQLSRPDPALA

ALTNDHLVALACLGGRPALDAVKKGLPHAPALIKRTNRRIPERTSHRVAD

HAQVRVLGFFQCHSHPAQAFDDAMTQFGMSRHGLLQLFRRVGVTELEAR

SGTLPPASQRWDRILQASGMKRAKPSPTSTQTPDQASLHAFADSLERDLD

APSPMHEGDQTRASSRKRSRSDRAVTGPSAQQSFEVRVPEQRDALHLPLS

WRVKRPRTSIGGGLPDPGTPTAADLAASSTVMREQDEDPFAGAADDFPAF

NEEELAWLMELLPQ.
```

In some embodiments, a TALE of the present disclosure can comprise between 1 to 50 *Xanthomonas* spp.-derived repeat units. In some embodiments, a TALE of the present disclosure can comprise between 9 and 36 *Xanthomonas* spp.-derived repeat units. Preferably, in some embodiments, a TALE of the present disclosure can comprise between 12 and 30 *Xanthomonas* spp.-derived repeat units. A TALE described herein can comprise between 5 to 10 *Xanthomonas* spp.-derived repeat units, between 10 to 15 *Xanthomonas* spp.-derived repeat units, between 15 to 20 *Xanthomonas* spp.-derived repeat units, between 20 to 25 *Xanthomonas* spp.-derived repeat units, between 25 to 30 *Xanthomonas* spp.-derived repeat units, or between 30 to 35 *Xanthomonas* spp.-derived repeat units, between 35 to 40 *Xanthomonas* spp.-derived repeat units. A TALE described herein can comprise at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or more *Xanthomonas* spp.-derived repeat units, such as, repeat units derived from *Xanthomonas* spp. protein having the amino acid sequence set forth in SEQ ID NO:299.

A *Xanthomonas* spp.-derived repeat units can be derived from a wild-type repeat unit, such as any one of SEQ ID NO: 323-SEQ ID NO: 326. For example, a *Xanthomonas* spp.-derived repeat units can have a sequence of LTPDQVVA-IASNHGGKQALETVQRLLPVLCQDHG (SEQ ID NO: 323) comprising an RVD of NH, which recognizes guanine. A *Xanthomonas* spp.-derived repeat units can have a sequence of LTPDQVVA-IASNGGGKQALETVQRLLPVLCQDHG (SEQ ID NO: 324) comprising an RVD of NG, which recognizes thymidine. A *Xanthomonas* spp.-derived repeat units can have a sequence of LTPDQVVA-IASNIGGKQALETVQRLLPVLCQDHG (SEQ ID NO: 325) comprising an RVD of NI, which recognizes adenosine. A *Xanthomonas* spp.-derived repeat units can have a sequence of LTPDQVVA-IASHDGGKQALETVQRLLPVLCQDHG (SEQ ID NO: 326) comprising an RVD of HD, which recognizes cytosine.

A *Xanthomonas* spp.-derived repeat unit can also comprise a modified *Xanthomonas* spp.-derived repeat units enhanced for specific recognition of a nucleotide or base pair. A TALE described herein can comprise one or more wild-type *Xanthomonas* spp.-derived repeat units, one or more modified *Xanthomonas* spp.-derived repeat units, or a combination thereof. In some embodiments, a modified *Xanthomonas* spp.-derived repeat units can comprise 1, 2, 3, 4, 5, 6, 7, 8, 9, 10, 11, 12, 13, 14, 15, 16, 17, 18, 19, 20, 21, 22, 23, 24, 25, 26, 27, 28, or 29 mutations that can enhance recognition of a specific nucleotide or base pair. In some embodiments, a modified *Xanthomonas* spp.-derived repeat unit can comprise more than 1 modification, for example 1 to 5 modifications, 5 to 10 modifications, 10 to 15 modifications, 15 to 20 modifications, 20 to 25 modification, or 25-29 modifications. In some embodiments, A TALE can comprise more than one modified *Xanthomonas* spp.-derived repeat units, wherein each of the modified *Xanthomonas* spp.-derived repeat units can have a different number of modifications.

In some embodiments, a TALE of the present disclosure can have the full length naturally occurring N-terminus of a naturally occurring *Xanthomonas* spp.-derived protein, such as the N-terminus of SEQID NO: 299. The N-terminus sequence in SEQ ID NO:299 is indicated by underlining.

In some embodiments, a TALE of the present disclosure can comprise the amino acid residues at position 1 (N) through position 137 (M) of the naturally occurring *Xanthomonas* spp.-derived protein as follows:

```
                                          (SEQ ID NO: 300)
MVDLRTLGYSQQQQEKIKPKVRSTVAQHHEALVGHGFTHAHIVALSQHPA

ALGTVAVKYQDMIAALPEATHEAIVGVGKQWSGARALEALLTVAGELRGP

PLQLDTGQLLKIAKRGGVTAVEAVHAWRNALTGAPLN.
```

The amino acid sequence set forth in SEQ ID NO:300 includes a M added to the N-terminus which is not present in the wild type N-terminus region of a TALE protein. The N-terminus fragment sequence set out in SEQ ID NO:300 is generated by deleting amino acids N+288 through N+137 of the N-terminus region of a TALE protein, adding a M, such that amino acids N+136 through N+1 of the N-terminus region of the TALE protein are present.

In some embodiments, the N-terminus can be truncated such that the fragment of the N-terminus includes amino acids from position 1 (N) through position 120 (K) of the naturally occurring *Xanthomonas* spp.-derived protein as follows:

```
                                          (SEQ ID NO: 301)
KPKVRSTVAQHHEALVGHGFTHAHIVALSQHPAALGTVAVKYQDMIAALP

EATHEAIVGVGKQWSGARALEALLTVAGELRGPPLQLDTGQLLKIAKRGG

VTAVEAVHAWRNALTGAPLN.
```

In some embodiments, the N-terminus can be truncated such that the fragment of the N-terminus includes amino acids from position 1 (N) through position 115 (S) of the naturally occurring *Xanthomonas* spp.-derived protein as follows:

```
                                          (SEQ ID NO: 321)
STVAQHHEALVGHGFTHAHIVALSQHPAALGTVAVKYQDMIAALPEATHE

AIVGVGKQWSGARALEALLTVAGELRGPPLQLDTGQLLKIAKRGGVTAVE

AVHAWRNALTGAPLN.
```

In some embodiments, the N-terminus can be truncated such that the fragment of the N-terminus includes amino acids from position 1 (N) through position 110 (H) of the naturally occurring *Xanthomonas* spp.-derived protein as follows:

```
                                          (SEQ ID NO: 447)
HHEALVGHGFTHAHIVALSQHPAALGTVAVKYQDMIAALPEATHEAIVGV

GKQWSGARALEALLTVAGELRGPPLQLDTGQLLKIAKRGGVTAVEAVHAW

RNALTGAPLN.
```

In some embodiments, any truncation of the naturally occurring *Xanthomonas* spp.-derived protein can be used at the N-terminus of a TALE disclosed herein. The naturally occurring N-terminus of *Xanthomonas* spp. can be truncated to amino acid residues at positions 1 to 50, 1 to 70, 1 to 100, 1 to 120, 1 to 130, 10 to 40, 60 to 100, or 100 to 120 and used at the N-terminus of the TALE.

Figure 1B:
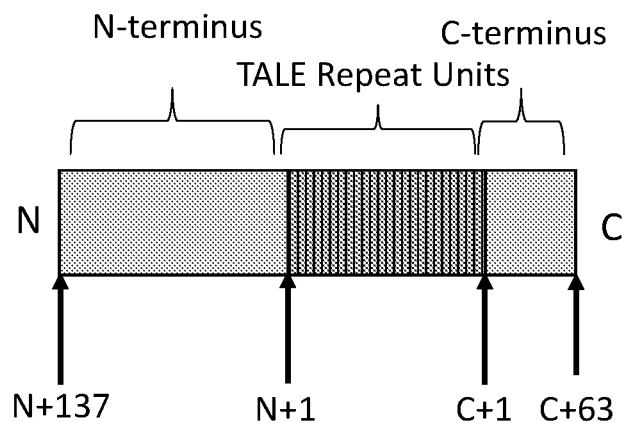
Figure 1C:
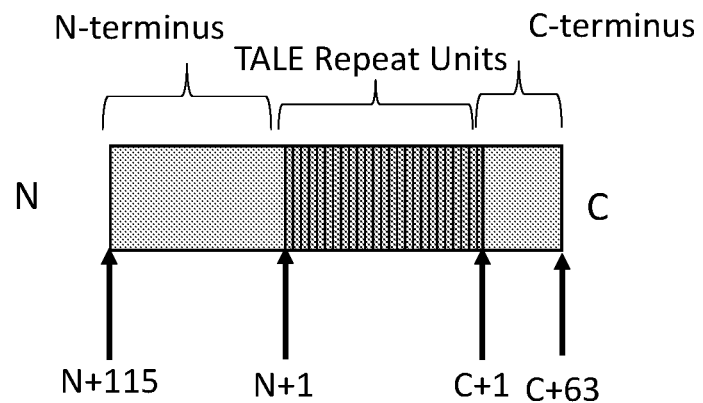

FIGS. 1A-1C show schematics of the domain structure of a TALE protein (not drawn to scale). 'N' and 'C' indicate the amino and carboxy termini, respectively. The TALE repeat domain comprising TALE repeat units, N-Cap and C-Cap regions are labeled and the residue numbering scheme for the N-Cap and C-Cap regions and the N-terminus and C-terminus fragments are indicated. FIG. 1A includes the full-length N-cap region that extends from amino acid position N+1 to N+288 and full-length C-cap region that extends from amino acid position C+1 through C+278. FIG. 1B provides a schematic of a DNA binding protein comprising TALE repeat units and a truncated N-terminus that extends from amino acid position N+1 to N+136 (the notation N+137 indicates that a methionine added to the N-terminus increases the length to 137) and a truncated C-terminus that extends from amino acid position C+1 through C+63. FIG. 1C provides a schematic of a DNA binding protein comprising TALE repeat units and a truncated N-terminus that extends from amino acid position N+1 to N+115 and a truncated C-terminus that extends from amino acid position C+1 through C+63. In certain cases, the last repeat domain may be a half-repeat or a partial repeat as disclosed herein.

In some embodiments, a TALE of the present disclosure can have a DNA binding domain, in which the final full length repeat unit of 33-35 amino acid residues is followed by a half-repeat also derived from *Xanthomonas* spp. The half repeat can have 15 to 23 amino acid residues, for example, the half repeat can have 19 amino acid residues. In particular embodiments, the half-repeat can have a sequence as set forth in LTPQQVVAIASNGGGRPALE (SEQ ID NO: 297). In some embodiments, the half-repeat can have a sequence as set forth in SEQ ID NO: 327, 328, 329, 330, 331, 332, 333, or 334.

TABLE 5

Xanthomonas Repeat Sequences

| SEQ ID NO | Amino Acid Sequence | Description |
|---|---|---|
| 323 | LTPDQVVAIASNHGGKQALE TVQRLLPVLCQDHG | RVD of NH recognizing guanine |
| 324 | LTPDQVVAIASNGGGKQALE TVQRLLPVLCQDHG | RVD of NG recognizing thymidine |
| 325 | LTPDQVVAIASNIGGKQALE TVQRLLPVLCQDHG | RVD of NI recognizing adenosine |
| SEQ ID NO: 326 | LTPDQVVAIASHDGGKQALE TVQRLLPVLCQDHG | RVD of HD recognizing cytosine |
| SEQ ID NO: 297 | LTPQQVVAIASNGGGRPALE | Half repeat |
| SEQ ID NO: 327 | LTPEQVVAIASNGGGRPALE | Half repeat |

TABLE 5-continued

Xanthomonas Repeat Sequences

| SEQ ID NO | Amino Acid Sequence | Description |
|---|---|---|
| SEQ ID NO: 328 | LTPDQVVAIASNGGGRPALE | Half repeat |
| SEQ ID NO: 329 | LTPEQVVAIASNIGGRPALE | Half repeat |
| SEQ ID NO: 330 | LTPDQVVAIASNIGGRPALE | Half repeat |
| SEQ ID NO: 331 | LTPEQVVAIASHDGGRPALE | Half repeat |
| SEQ ID NO: 332 | LTPDQVVAIASHDGGRPALE | Half repeat |
| SEQ ID NO: 333 | LTPEQVVAIASNHGGRPALE | Half repeat |
| SEQ ID NO: 334 | LTPDQVVAIASNHGGRPALE | Half repeat |

In some embodiments, a TALE of the present disclosure can have the full length naturally occurring C-terminus of a naturally occurring *Xanthomonas* spp.-derived protein, such as the C-terminus of SEQ ID NO: 299. The C-terminus of the TALE protein sequence set forth in SEQ ID NO:299 is italicized. In some embodiments, the C-terminus can be a fragment of the full length naturally occurring C-terminus of a naturally occurring *Xanthomonas* spp.-derived protein. In some embodiments, the C-terminus can be less than 250 amino acids long. In some embodiments, the C-terminus can be positions 1 (S) through position 278 (Q) of the naturally occurring *Xanthomonas* spp.-derived protein as follows: SIVAQLSRPDPALAALTNDHLVALACLGGRPAL-DAVKKGLPHAPALIKRTNRRIPERTSHRV ADHAQVVRVLGFFQCHSHPAQAFD-DAMTQFGMSRHGLLQLFRRVGVTELEARSGTLPPAS QRWDRILQASGMKRAKPSPTSTQTPDQASLHAFAD-SLERDLDAPSPTHEGDQRRASSRKRS RSDRAVTGP-SAQQSFEVRAPEQRDALHLPLSWRVKRPRTSIGG-GLPDPGTPTAADLAASSTV MREQDEDPFAGAADDFPAFNEEELAWLMELLPQ (SEQ ID NO: 302). In some embodiments, any truncation of the full length naturally occurring C-terminus of a naturally occurring *Xanthomonas* spp.-derived protein can be used at the C-terminus of a TALE of the present disclosure. For example, in some embodiments, the naturally occurring N-terminus of *Xanthomonas* spp. can be truncated to amino acid residues at position 1 (S) to position 63 (X) as follows: SIVAQLSRPDPALAALTNDHLVALACLGGRPAL-DAVKKGLPHAPALIKRTNRRIPERTSHRV A (SEQ ID NO: 298). The naturally occurring C-terminus of *Xanthomonas* spp. can be truncated amino acid residues at positions 1 to 50 and used at the C-terminus of the engineered DNA binding domain. The naturally occurring C-terminus of *Xanthomonas* spp. can be truncated to amino acid residues at positions 1 to 63, 1 to 50, 1 to 70, 1 to 100, 1 to 120, 1 to 130, 10 to 40, 60 to 100, or 100 to 120 and used at the C-terminus of the engineered DNA binding domain.

The terms "N-cap" polypeptide and "N-terminal sequence" are used to refer to an amino acid sequence (polypeptide) that flanks the N-terminal portion of the first TALE repeat unit. The N-cap sequence can be of any length (including no amino acids), so long as the TALE-repeat unit(s) function to bind DNA. An N-terminal fragment and grammatical equivalents thereof refers to a shortened sequence of an N-terminal sequence which fragment is sufficient for the TALE repeat units to bind to DNA.

The term "C-cap" or "C-terminal region" refers to optionally present amino acid sequences that may be flanking the C-terminal portion of the last TALE repeat unit. The C-cap can also comprise any part of a terminal C-terminal TALE repeat, including 0 residues, truncations of a TALE repeat or a full TALE repeat. A C-terminal fragment and grammatical equivalents thereof refers to a shortened sequence of a C-terminal sequence which fragment is sufficient for the TALE repeat units to bind to DNA.

Animal Pathogen Derived Modular Nucleic Acid Binding Domains

The present disclosure provides a modular nucleic acid binding domain derived from an animal pathogen protein (MAP-NBD) can comprise a plurality of repeat units, wherein a repeat unit of the plurality of repeat units recognizes a single target nucleotide, base pair, or both.

In some embodiments, the repeat unit can be derived from an animal pathogen, and can be referred to as a non-naturally occurring modular nucleic acid binding domain derived from an animal pathogen protein (MAP-NBD), or "modular animal pathogen-nucleic acid binding domain" (MAP-NBD). For example, in some cases, the animal pathogen can be from the Gram-negative bacterium genus, *Legionella*. In other cases, the animal pathogen can be from *Burkholderia*. In some cases, the animal pathogen can be from *Paraburkholderia*. In other cases, the animal pathogen can be from *Francisella*.

In particular embodiments, the repeat unit can be derived from a species of the genus of *Legionella*, such as *Legionella quateirensis*, the genus of *Burkholderia*, the genus of *Paraburkholderia*, or the genus of *Francisella*. In some embodiments, the repeat unit can comprise from 19 amino acid residues to 35 amino acid residues. In particular embodiments, the repeat unit can comprise 33 amino acid residues. In other embodiments, the repeat unit can comprise 35 amino acid residues. In some embodiments, the MAP-NBD is non-naturally occurring, and comprises a plurality of repeat units and wherein a repeat unit of the plurality of repeat units recognizes a single target nucleic acid.

In some embodiments, a repeat unit can be derived from a *Legionella quateirensis* protein with the following sequence:

```
                                            (SEQ ID NO: 281)
MPDLELNFAIPLHLFDDETVFTHDATNDNSQASSSYSSKSSPASANARKR

TSRKEMSGPPSKEPANTKSRRANSQNNKLSLADRLTKYNIDEEFYQTRSD

SLLSLNYTKKQIERLILYKGRTSAVQQLLCKHEELLNLISPDGLGHKELI

KIAARNGGGNNLIAVLSCYAKLKEMGFSSQQIIRMVSHAGGANNLKAVTA
```

-continued

```
NHDDLQNMGFNVEQIVRMVSHNGGSKNLKAVTDNHDDLKNMGFNAEQIVR

MVSHGGGSKNLKAVTDNHDDLKNMGFNAEQIVSMVSNNGGSKNLKAVTDN

HDDLKNMGFNAEQIVSMVSNGGGSLNLKAVKKYHDALKDRGFNTEQIVRM

VSHDGGSLNLKAVKKYHDALRERKFNVEQIVSIVSHGGGSLNLKAVKKYH

DVLKDREFNAEQIVRMVSHDGGSLNLKAVTDNHDDLKNMGFNAEQIVRMV

SHKGGSKNLALVKEYFPVFSSFHFTADQIVALICQSKQCFRNLKKNHQQW

KNKGLSAEQIVDLILQETPPKPNFNNTSSSTPSPSAPSFFQGPSTPIPTP

VLDNSPAPIFSNPVCFFSSRSENNTEQYLQDSTLDLDSQLGDPTKNFNVN

NFWSLFPFDDVGYHPHSNDVGYHLHSDEESPFFDF.
```

In some embodiments, a repeat from a *Legionella quateirensis* protein can comprise a repeat with a canonical RVD or a non-canonical RVD. In some embodiments, a canonical RVD can comprise NN, NG, HD, or HD. In some embodiments, a non-canonical RVD can comprise RN, HA, HN, HG, HG, or HK.

In some embodiments, a repeat of SEQ ID NO: 282 comprises an RVD of HA and primarily recognizes a base of adenine (A). In some embodiments, a repeat of SEQ ID NO: 283 comprises an RVD of HN and recognizes a base comprising guanine (G). In some embodiments, a repeat of S SEQ ID NO: 284 comprises an RVD of HG and recognizes a base comprising thymine (T). In some embodiments, a repeat of SEQ ID NO: 285 comprises an RVD of NN and recognizes a base comprising guanine (G). In some embodiments, a repeat of SEQ ID NO: 286 comprises an RVD of NG and recognizes a base comprising thymine (T). In some embodiments, a repeat of SEQ ID NO: 287 comprises an RVD of HD and recognizes a base comprising cytosine (C). In some embodiments, a repeat of SEQ ID NO: 288 comprises an RVD of HG and recognizes a base comprising thymine (T). In some embodiments, a repeat of SEQ ID NO: 289 comprises an RVD of HD and recognizes a base comprising cytosine (C). In some embodiments, a half-repeat of SEQ ID NO: 290 comprises an RVD of HK and recognizes a base comprising guanine (G). In some embodiments, a repeat of SEQ ID NO: 357 comprises an RVD of RN and recognizes a base comprising guanine (G).

TABLE 6 illustrates exemplary repeats from *Legionella quateirensis, Burkholderia, Paraburkholderia*, or *Francisella* that can make up a MAP-NBD of the present disclosure and the RVD at position 12 and 13 of the particular repeat. A MAP-NBD of the present disclosure can comprise at least one of the repeats disclosed in TABLE 5 including any one of SEQ ID NO: 357, SEQ ID NO: 282-SEQ ID NO: 290, or SEQ ID NO: 358-SEQ ID NO: 446. A MAP-NBD of the present disclosure can comprise any combination of repeats disclosed in TABLE 5 including any one of SEQ ID NO: 357, SEQ ID NO: 282-SEQ ID NO: 290, or SEQ ID NO: 358-SEQ ID NO: 446.

TABLE 6

Animal Pathogen Derived Repeat Units

| SEQ ID NO | Organism | Repeat Unit Sequence | RVD |
|---|---|---|---|
| SEQ ID NO: 357 | L. quateirensis | LGHKELIKIAARNGGGNNLIAVLSCYAKLKEMG | RN |
| SEQ ID NO: 282 | L. quateirensis | FSSQQIIRMVSHAGGANNLKAVTANHDDLQNMG | HA |
| SEQ ID NO: 283 | L. quateirensis | FNVEQIVRMVSHNGGSKNLKAVTDNHDDLKNMG | HN |

TABLE 6-continued

Animal Pathogen Derived Repeat Units

| SEQ ID NO | Organism | Repeat Unit Sequence | RVD |
|---|---|---|---|
| SEQ ID NO: 284 | L. quateirensis | FNAEQIVRMVSHGGGSKNLKAVTDNHDDLKNMG | HG |
| SEQ ID NO: 285 | L. quateirensis | FNAEQIVSMVSNNGGSKNLKAVTDNHDDLKNMG | NN |
| SEQ ID NO: 286 | L. quateirensis | FNAEQIVSMVSNGGGSLNLKAVKKYHDALKDRG | NG |
| SEQ ID NO: 287 | L. quateirensis | FNTEQIVRMVSHDGGSLNLKAVKKYHDALRERK | HD |
| SEQ ID NO: 288 | L. quateirensis | FNVEQIVSIVSHGGGSLNLKAVKKYHDVLKDRE | HG |
| SEQ ID NO: 289 | L. quateirensis | FNAEQIVRMVSHDGGSLNLKAVTDNHDDLKNMG | HD |
| SEQ ID NO: 290 (half-repeat) | L. quateirensis | FNAEQIVRMVSHKGGSKNL | HK |
| SEQ ID NO: 358 | L. quateirensis | FSAEQIVRIAAHDGGSRNIEAVQQAQHVLKELG | HD |
| SEQ ID NO: 359 | L. quateirensis | FSAEQIVSIVAHDGGSRNIEAVQQAQHILKELG | HD |
| SEQ ID NO: 360 | L. quateirensis | FSRQQILRIASHDGGSKNIAAVQKFLPKLMNFGFN | HD |
| SEQ ID NO: 361 | L. quateirensis | FSAEQIVRIAAHDGGSLNIDAVQQAQQALKELG | HD |
| SEQ ID NO: 362 | L. quateirensis | FSTEQIVCIAGHGGGSLNIKAVLLAQQALKDLG | HG |
| SEQ ID NO: 363 | L. quateirensis | FSSEQIVRVAAHGGGSLNIKAVLQAHQALKELD | HG |
| SEQ ID NO: 364 | L. quateirensis | FSAEQIVHIAAHGGGSLNIKAILQAHQTLKELN | HG |
| SEQ ID NO: 365 | L. quateirensis | FSAEQIVRIAAHIGGSRNIEAIQQAHHALKELG | HI |
| SEQ ID NO: 366 | L. quateirensis | FSAEQIVRIAAHIGGSHNLKAVLQAQQALKELD | HI |
| SEQ ID NO: 367 | L. quateirensis | FSAKHIVRIAAHIGGSLNIKAVQQAQQALKELG | HI |
| SEQ ID NO: 368 | L. quateirensis | FNAEQIVRMVSHKGGSKNLALVKEYFPVFSSFH | HK |
| SEQ ID NO: 369 | L. quateirensis | FNAEQIVRMVSHKGGSKNLALVKEYFPVFSSFHFT | HK |
| SEQ ID NO: 370 | L. quateirensis | FSADQIVRIAAHKGGSHNIVAVQQAQQALKELD | HK |
| SEQ ID NO: 371 | L. quateirensis | FNVEQIVRMVSHNGGSKNLKAVTDNHDDLKNMGFN | HN |
| SEQ ID NO: 372 | L. quateirensis | FSADQVVKIAGHSGGSNNIAVMLAVFPRLRDFGFK | HS |
| SEQ ID NO: 373 | L. quateirensis | FSAEQIVSIAAHVGGSHNIEAVQKAHQALKELD | HV |
| SEQ ID NO: 374 | L. quateirensis | FNAEQIVSMVSNNGGSKNLKAVTDNHDDLKNMGFN | NN |
| SEQ ID NO: 375 | L. quateirensis | FSHKELIKIAARNGGGNNLIAVLSCYAKLKEMG | RN |
| SEQ ID NO: 376 | L. quateirensis | FSHKELIKIAARNGGGNNLIAVLSCYAKLKEMGFS | RN |
| SEQ ID NO: 377 | Burkholderia | FSSGETVGATVGAGGTETVAQGGTASNTTVSSGGY | GA |
| SEQ ID NO: 378 | Burkholderia | FSGGMATSTTVGSGGTQDVLAGGAAVGGTVGTGGV | GS |
| SEQ ID NO: 379 | Burkholderia | FSAADIVKIAGKIGGAQALQAFITHRAALIQAGFS | KI |
| SEQ ID NO: 380 | Burkholderia | FNPTDIVKIAGNDGGAQALQAVLELEPALRERGFS | ND |
| SEQ ID NO: 381 | Burkholderia | FNPTDIVRMAGNDGGAQALQAVFELEPAFRERSFS | ND |
| SEQ ID NO: 382 | Burkholderia | FNPTDIVRMAGNDGGAQALQAVLELEPAFRERGFS | ND |
| SEQ ID NO: 383 | Burkholderia | FSQVDIVKIASNDGGAQALYSVLDVEPTFRERGFS | ND |
| SEQ ID NO: 384 | Burkholderia | FSRADIVKIAGNDGGAQALYSVLDVEPPLRERGFS | ND |
| SEQ ID NO: 385 | Burkholderia | FSRGDIVKIAGNDGGAQALYSVLDVEPPLRERGFS | ND |
| SEQ ID NO: 386 | Burkholderia | FNRADIVRIAGNGGAQALYSVRDAGPTLGKRGFS | NG |
| SEQ ID NO: 387 | Burkholderia | FRQADIVKIASNGGSAQALNAVIKLGPTLRQRGFS | NG |

TABLE 6-continued

Animal Pathogen Derived Repeat Units

| SEQ ID NO | Organism | Repeat Unit Sequence | RVD |
|---|---|---|---|
| SEQ ID NO: 388 | Burkholderia | FRQADIVKMASNGGSAQALNAVIKLGPTLRQRGFS | NG |
| SEQ ID NO: 389 | Burkholderia | FSRADIVKIAGNGGGAQALQAVLELEPTFRERGFS | NG |
| SEQ ID NO: 390 | Burkholderia | FSRADIVRIAGNGGAQALYSVLDVGPTLGKRGFS | NG |
| SEQ ID NO: 391 | Burkholderia | FSRGDIVRIAGNGGAQALQAVLELEPTLGERGFS | NG |
| SEQ ID NO: 392 | Burkholderia | FSRADIVKIAGNGGAQALQAVITHRAALTQAGFS | NG |
| SEQ ID NO: 393 | Burkholderia | FSRGDTVKIAGNIGGAQALQAVLELEPTLRERGFS | NI |
| SEQ ID NO: 394 | Burkholderia | FNPTDIVKIAGNIGGAQALQAVLELEPAFRERGFS | NI |
| SEQ ID NO: 395 | Burkholderia | FSAADIVKIAGNIGGAQALQAIFTHRAALIQAGFS | NI |
| SEQ ID NO: 396 | Burkholderia | FSAADIVKIAGNIGGAQALQAVITHRATLTQAGFS | NI |
| SEQ ID NO: 397 | Burkholderia | FSATDIVKIASNIGGAQALQAVISRRAALIQAGFS | NI |
| SEQ ID NO: 398 | Burkholderia | FSQPDIVKIAGNIGGAQALQAVLELEPAFRERGFS | NI |
| SEQ ID NO: 399 | Burkholderia | FSRADIVKIAGNIGGAQALQAVLELESTFRERSFN | NI |
| SEQ ID NO: 400 | Burkholderia | FSRADIVKIAGNIGGAQALQAVLELESTLRERSFN | NI |
| SEQ ID NO: 401 | Burkholderia | FSRGDIVKMAGNIGGAQALQAGLELEPAFRERGFS | NI |
| SEQ ID NO: 402 | Burkholderia | FSRGDIVKMAGNIGGAQALQAVLELEPAFHERSFC | NI |
| SEQ ID NO: 403 | Burkholderia | FTLTDIVKMAGNIGGAQALKAVLEHGPTLRQRDLS | NI |
| SEQ ID NO: 404 | Burkholderia | FTLTDIVKMAGNIGGAQALKVVLEHGPTLRQRDLS | NI |
| SEQ ID NO: 405 | Burkholderia | FNPTDIVKIAGNNGGAQALQAVLELEPALRERGFS | NN |
| SEQ ID NO: 406 | Burkholderia | FNPTDIVKIAGNNGGAQALQAVLELEPALRERSFS | NN |
| SEQ ID NO: 407 | Burkholderia | FNPTDMVKIAGNNGGAQALQAVLELEPALRERGFS | NN |
| SEQ ID NO: 408 | Burkholderia | FSAADIVKIASNNGGAQALQALIDHWSTLSGKTKA | NN |
| SEQ ID NO: 409 | Burkholderia | FSAADIVKIASNNGGAQALQAVISRRAALIQAGFS | NN |
| SEQ ID NO: 410 | Burkholderia | FSAADIVKIASNNGGAQALQAVITHRAALAQAGFS | NN |
| SEQ ID NO: 411 | Burkholderia | FSAADIVKIASNNGGARALQALIDHWSTLSGKTKA | NN |
| SEQ ID NO: 412 | Burkholderia | FTLTDIVEMAGNNGGAQALKAVLEHGSTLDERGFT | NN |
| SEQ ID NO: 413 | Burkholderia | FTLTDIVKMAGNNGGAQALKAVLEHGPTLDERGFT | NN |
| SEQ ID NO: 414 | Burkholderia | FTLTDIVKMAGNNGGAQALKVVLEHGPTLRQRGFS | NN |
| SEQ ID NO: 415 | Burkholderia | FTLTDIVKMASNNGGAQALKAVLEHGPTLDERGFT | NN |
| SEQ ID NO: 416 | Burkholderia | FSAADIVKIAGNSGGAQALQAVISHRAALTQAGFS | NS |
| SEQ ID NO: 417 | Burkholderia | FSGGDAVSTVVRSGGAQSVASGGTASGTTVSAGAT | RS |
| SEQ ID NO: 418 | Burkholderia | FRQTDIVKMAGSGGSAQALNAVIKHGPTLRQRGFS | SG |
| SEQ ID NO: 419 | Burkholderia | FSLIDIVEIASNGGAQALKAVLKYGPVLTQAGRS | SN |
| SEQ ID NO: 420 | Burkholderia | FSGGDAAGTVVSSGGAQNVTGGLASGTTVAGGAA | SS |
| SEQ ID NO: 421 | Paraburkholderia | FNLTDIVEMAANSGGAQALKAVLEHGPTLRQRGLS | NS |
| SEQ ID NO: 422 | Paraburkholderia | FNRASIVKIAGNSGGAQALQAVLKHGPTLDERGFN | NS |
| SEQ ID NO: 423 | Paraburkholderia | FSQANIVKMAGNSGGAQALQAVLDLELVFRERGFS | NS |
| SEQ ID NO: 424 | Paraburkholderia | FSQPDIVKMAGNSGGAQALQAVLDLELAFRERGFS | NS |
| SEQ ID NO: 425 | Paraburkholderia | FSLIDIVEIASNGGAQALKAVLKYGPVLMQAGRS | SN |

TABLE 6-continued

Animal Pathogen Derived Repeat Units

| SEQ ID NO | Organism | Repeat Unit Sequence | RVD |
|---|---|---|---|
| SEQ ID NO: 426 | Francisella | YKSEDIIRLASHDGGSVNLEAVLRLHSQLTRLG | HD |
| SEQ ID NO: 427 | Francisella | YKPEDIIRLASHGGGSVNLEAVLRLNPQLIGLG | HG |
| SEQ ID NO: 428 | Francisella | YKSEDIIRLASHGGGSVNLEAVLRLHSQLTRLG | HG |
| SEQ ID NO: 429 | Francisella | YKSEDIIRLASHGGGSVNLEAVLRLNPQLIGLG | HG |
| SEQ ID NO: 430 | Paraburkholderia | FNLTDIVEMAGKGGGAQALKAVLEHGPTLRQRGFN | KG |
| SEQ ID NO: 431 | Paraburkholderia | FRQADIIKIAGNDGGAQALQAVIEHGPTLRQHGFN | ND |
| SEQ ID NO: 432 | Paraburkholderia | FSQADIVKIAGNDGGTQALHAVLDLERMLGERGFS | ND |
| SEQ ID NO: 433 | Paraburkholderia | FSRADIVKIAGNGGGAQALKAVLEHEATLDERGFS | NG |
| SEQ ID NO: 434 | Paraburkholderia | FSRADIVRIAGNGGGAQALYSVLDVEPTLGKRGFS | NG |
| SEQ ID NO: 435 | Paraburkholderia | FSQPDIVKMASNIGGAQALQAVLELEPALRERGFS | NI |
| SEQ ID NO: 436 | Paraburkholderia | FSQPDIVKMAGNIGGAQALQAVLSLGPALRERGFS | NI |
| SEQ ID NO: 437 | Paraburkholderia | FSQPEIVKIAGNIGGAQALHTVLELEPTLHKRGFN | NI |
| SEQ ID NO: 438 | Paraburkholderia | FSQSDIVKIAGNIGGAQALQAVLDLESMLGKRGFS | NI |
| SEQ ID NO: 439 | Paraburkholderia | FSQSDIVKIAGNIGGAQALQAVLELEPTLRESDFR | NI |
| SEQ ID NO: 440 | Paraburkholderia | FNPTDIVKIAGNKGGAQALQAVLELEPALRERGFN | NK |
| SEQ ID NO: 441 | Paraburkholderia | FSPTDIIKIAGNNGGAQALQAVLDLELMLRERGFS | NN |
| SEQ ID NO: 442 | Paraburkholderia | FSQADIVKIAGNNGGAQALYSVLDVEPTLGKRGFS | NN |
| SEQ ID NO: 443 | Paraburkholderia | FSRGDIVTIAGNNGGAQALQAVLELEPTLRERGFN | NN |
| SEQ ID NO: 444 | Paraburkholderia | FSRIDIVKIAANNGGAQALHAVLDLGPTLRECGFS | NN |
| SEQ ID NO: 445 | Paraburkholderia | FSQADIVKIVGNNGGAQALQAVFELEPTLRERGFN | NN |
| SEQ ID NO: 446 | Paraburkholderia | FSQPDIVRITGNRGGAQALQAVLALELTLRERGFS | NR |

In any one of the animal pathogen-derived repeat domains of SEQ ID NO: 357, SEQ ID NO: 282-SEQ ID NO: 290, or SEQ ID NO: 358-SEQ ID NO: 446, there can be considerable sequence divergence between repeats of a MAP-NBD outside of the RVD.

In some embodiments, a MAP-NBD of the present disclosure can comprise between 1 to 50 animal pathogen-derived repeat units. In some embodiments, a MAP-NBD of the present disclosure can comprise between 9 and 36 animal pathogen-derived repeat units. Preferably, in some embodiments, a MAP-NBD of the present disclosure can comprise between 12 and 30 animal pathogen-derived repeat units. A MAP-NBD described herein can comprise between 5 to 10, 10 to 15, 15-20, 20 to 25, 25 to 30, 30 to 35, or 35 to 40, e.g., 15-25 animal pathogen-derived repeat units. A MAP-NBD described herein can comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 animal pathogen-derived repeat units, e.g.

A MAP-NBD described herein can comprise 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 animal pathogen-derived repeat units.

An animal pathogen-derived repeat units can be derived from a wild-type repeat unit, such as any one of SEQ ID NO: 357, SEQ ID NO: 282-SEQ ID NO: 290, or SEQ ID NO: 358-SEQ ID NO: 446. An animal pathogen-derived repeat unit can also comprise a modified animal pathogen-derived repeat units enhanced for specific recognition of a nucleotide or base pair. A MAP-NBD described herein can comprise one or more wild-type animal pathogen-derived repeat units, one or more modified animal pathogen-derived repeat units, or a combination thereof. In some embodiments, a modified animal pathogen-derived repeat units can comprise 1, 2, 3, 4, 5, 6, 7, 8, 9, 10, 11, 12, 13, 14, 15, 16, 17, 18, 19, 20, 21, 22, 23, 24, 25, 26, 27, 28, or 29 mutations that can enhance recognition of a specific nucleotide or base pair. In some embodiments, a modified animal pathogen-derived repeat unit can comprise more than 1 modification, for example 1 to 5 modifications, 5 to 10 modifications, 10 to 15 modifications, 15 to 20 modifications, 20 to 25 modification, or 25-29 modifications. In some embodiments, A MAP-NBD can comprise more than one modified animal pathogen-derived repeat units, wherein each of the modified animal pathogen-derived repeat units can have a different number of modifications.

In some embodiments, a MAP-NBD of the present disclosure can have the full length naturally occurring N-terminus of a naturally occurring Legionella quateirensis-derived protein, such as the N-terminus of SEQ ID NO: 281. A N-terminus can be the full length N-terminus sequence and can have a sequence of MPDLELNFAIPLHLFDDE- TVFTHDATNDNSQASSSYS-
SKSSPASANARKRTSRKEMSGPPSK EPANTKSR-
RANSQNNKLSLADRLTKYNIDEEFYQTRSDSLLSLNY
TKKQIERLILYKGRTSA VQQLLCKHEELLNLISPDG
(SEQ ID NO: 291). In some embodiments, any truncation of SEQ ID NO: 291 can be used as the N-terminus in a MAP-NBD of the present disclosure. For example, in some embodiments, a MAP-NBD comprises a truncated N-terminus including amino acid residues at position 1 (G) to position 137 (S) of the naturally occurring *Legionella quateirensis* N-terminus as follows: NFAIPLHLFDDE-TVFTHDATNDNSQASSSYS-
SKSSPASANARKRTSRKEMSGPPSKEPANTK SRRANSQNNKLSLADRLTKYNIDEEFYQTRSD-SLLSLNYTKKQIERLILYKGRTSAVQQLLC KHEELLN-LISPDG (SEQ ID NO: 335). For example, in some embodiments, a MAP-NBD comprises a truncated N-terminus including amino acid residues at position 1 (G) to position 120 (S) of the naturally occurring *Legionella quateirensis* N-terminus as follows: DATNDNSQASSSYS-SKSSPASANARKRTSRKEMSGPPSKEPANTKSR-RANSQNNKLSLADR LTKYNIDEEFYQTRSD-SLLSLNYTKKQIERLILYKGRTSAVQQLLCKHEELLN LISPDG (SEQ ID NO: 304). In some embodiments, a MAP-NBD comprises a truncated N-terminus including amino acid residues at position 1 (G) to position 115 (K) of the naturally occurring *Legionella quateirensis* N-terminus as follows: NSQASSSYS-SKSSPASANARKRTSRKEMSGPPSKEPANTKSR-RANSQNNKLSLADRLTKYNI DEEFYQTRSD-SLLSLNYTKKQIERLILYKGRTSAVQQLLCKHEELLN LISPDG (SEQ ID NO: 322). In some embodiments, any truncation of the naturally occurring *Legionella quateirensis*-derived protein can be used at the N-terminus of a DNA binding domain disclosed herein. The naturally occurring N-terminus of *Legionella quateirensis* can be truncated to amino acid residues at positions 1 to 50, 1 to 70, 1 to 100, 1 to 120, 1 to 130, 10 to 40, 60 to 100, or 100 to 120 and used at the N-terminus of the MAP-NBD.

In some embodiments, a MAP-NBD of the present disclosure can have the full length naturally occurring C-terminus of a naturally occurring *Legionella quateirensis*-derived protein. In some embodiments, A MAP-NBD of the present disclosure can have at its C-terminus amino acid residues at position 1 (A) to position 176 (F) of the naturally occurring *Legionella quateirensis*-derived protein as follows:

```
                                        (SEQ ID NO: 305)
ALVKEYFPVFSSFHFTADQIVALICQSKQCFRNLKKNHQQWKNKGLSAEQ

IVDLILQETPPKPNFNNTSSSTPSPSAPSFFQGPSTPIPTPVLDNSPAPI

FSNPVCFFSSRSENNTEQYLQDSTLDLDSQLGDPTKNFNVNNFWSLFPFD

DVGYHPHSNDVGYHLHSDEESPFFDF.
```

In some embodiments, a MAP-NBD of the present disclosure can have at its C-terminus amino acid residues at position 1 (A) to position 63 (P) of the naturally occurring *Legionella quateirensis*-derived protein as follows:

```
                                        (SEQ ID NO: 306)
ALVKEYFPVFSSFHFTADQIVALICQSKQCFRNLKKNHQQWKNKGLSAEQ

IVDLILQETPPKP.
```

In some embodiments, the present disclosure provides methods for identifying an animal pathogen-derived repeat unit. For example, a consensus sequence can be defined comprising a first repeat motif, a spacer, and a second repeat motif. The consensus sequence can be 1xxx211x1xxx33x2x1xxxxxxxxx1xxxx1xxx211x1xxx33x 2x1xxxxxxxxx1 (SEQ ID NO: 292), 1xxx211x1xxx33x2x1xxxxxxxxx1xxxxx1xxx211x1xxx33 x2x1xxxxxxxxx1 (SEQ ID NO: 293), 1xxx211x1xxx33x2x1xxxxxxxxx1xxxxxx1xxx211x1xxx33 x2x1xxxxxxxxx1 (SEQ ID NO: 294), 1xxx211x1xxx33x2x1xxxxxxxxx1xxxxxxx1xxx211x1xxx3 3x2x1xxxxxxxxx1 (SEQ ID NO: 295), 1xxx211x1xxx33x2x1xxxxxxxxx1xxxxxxxx1xxx211x1xxx 33x2x1xxxxxxxxx1 (SEQ ID NO: 296). For any one of SEQ ID NO: 292-SEQ ID NO: 296, x can be any amino acid residue, 1, 2, and 3 are flexible residues that are defined as follows: 1 can be selected from any one of A, F, I, L, M, T, or V, 2 can be selected from any one of D, E, K, N, M, S, R, or Q, and 3 can be selected from any one of A, G, N, or S. Thus, in some embodiments, a MAP-NBD can be derived from an animal pathogen comprising the consensus sequence of SEQ ID NO: 292, SEQ ID NO: 293, SEQ ID NO: 294, SEQ ID NO: 295, or SEQ ID NO: 296. Any one of consensus sequences of SEQ ID NO: 292-SEQ ID NO: 296 can be compared against all sequences downloaded from NCBI, MGRast, JGI, and EBI databases to identify matches corresponding to animal pathogen proteins containing repeat units of a DNA-binding repeat unit.

In some embodiments, a MAP-NBD repeat unit can itself have a consensus sequence of 1xxx211x1xxx33x2x1xxxxxxxxx1 (SEQ ID NO: 452), wherein x can be any amino acid residue, 1, 2, and 3 are flexible residues that are defined as follows: 1 can be selected from any one of A, F, I, L, M, T, or V, 2 can be selected from any one of D, E, K, N, M, S, R, or Q, and 3 can be selected from any one of A, G, N, or S.

Mixed DNA Binding Domains

In some embodiments, the present disclosure provides DNA binding domains in which the repeat units, the N-terminus, and the C-terminus can be derived from any one of *Ralstonia solanacearum, Xanthomonas* spp., *Legionella quateirensis, Burkholderia, Paraburkholderia*, or *Francisella*. For example, the present disclosure provides a DNA binding domain wherein the plurality of repeat units are selected from any one of SEQ ID NO: 168-SEQ ID NO: 263 or SEQ ID NO: 336-SEQ ID NO 356 and can further comprise an N-terminus and/or C-terminus from *Xanthomonas* spp., (N-termini: SEQ ID NO: 298, SEQ ID NO: 300, SEQ ID NO: 301, and SEQ ID NO: 321; C-termini: SEQ ID NO: 302 and SEQ ID NO: 298) or *Legionella quateirensis* (N-termini: SEQ ID NO: 304 or SEQ ID NO: 322; C-termini: SEQ ID NO: 305 and SEQ ID NO: 306). In some embodiments, the present disclosure provides modular DNA binding domains in which the repeat units can be from *Ralstonia solanacearum* (e.g., any one of SEQ ID NO: 168-SEQ ID NO: 263 or SEQ ID NO: 336-SEQ ID NO 356), *Xanthomonas* spp. (e.g., any one of SEQ ID NO: 323-SEQ ID NO: 334), an animal pathogen such as *Legionella quateirensis, Burkholderia, Paraburkholderia*, or *Francisella* (e.g., any one of SEQ ID NO: 357, SEQ ID NO: 282-SEQ ID NO: 290, or SEQ ID NO: 358-SEQ ID NO: 446), or any combination thereof.

Nucleases for Genome Editing

Genome editing can include the process of modifying a DNA of a cell in order to introduce or knock out a target gene or a target gene region. In some instances, a subject may have a disease in which a protein is aberrantly expressed or completely lacking. One therapeutic strategy for treating this disease can be introduction of a target gene or a target gene region to correct the aberrant or missing protein. For example, genome editing can be used to modify the DNA of a cell in the subject in order to introduce a functional gene, which gives rise to a functional protein. Introduction of this functional gene and expression of the functional protein can relieve the disease state of the subject.

In other instances, a subject may have a disease in which protein is overexpressed or is targeted by a virus for infection of a cell. Alternatively, a therapy such as a cell therapy for cancer can be ineffective due to repression of certain processes by tumor cells (e.g., checkpoint inhibition). Still alternatively, it may be desirable to eliminate a particular protein expressed at the surface of a cell in order to generate a universal, off-the-shelf cell therapy for a subject in need thereof (e.g., TCR). In such cases, it can be desirable to partially or completely knock out the gene encoding for such a protein. Genome editing can be used to modify the DNA of a cell in the subject in order to partially or completely knock out the target gene, thus reducing or eliminating expression of the protein of interest.

Genome editing can include the use of any nuclease as described herein in combination with any DNA binding domain disclosed herein in order to bind to a target gene or target gene region and induce a double strand break, mediated by the nuclease. Genes can be introduced during this process, or DNA binding domains can be designed to cut at regions of the DNA such that after non-homologous end joining, the target gene or target gene region is removed. Genome editing systems that are further disclosed and described in detail herein can include DNA binding domains from *Xanthomonas, Ralstonia,* or *Legionella* fused to nucleases.

The specificity and efficiency of genome editing can be dependent on the nuclease responsible for cleavage. More than 3,000 type II restriction endonucleases have been identified. They recognize short, usually palindromic, sequences of 4-8 bp and, in the presence of Mg2+, cleave the DNA within or in close proximity to the recognition sequence. Naturally, type IIs restriction enzymes themselves have a DNA recognition domain that can be separated from the catalytic, or cleavage, domain. As such, since cleavage occurs at a site adjacent to the DNA sequence bound by the recognition domain, these enzymes can be referred to as exhibiting "shifted" cleavage. These type IIs restriction enzymes having both the recognition domain and the cleavage domain can be 400-600 amino acids. The main criterion for classifying a restriction endonuclease as a type II enzyme is that it cleaves specifically within or close to its recognition site and that it does not require ATP hydrolysis for its nucleolytic activity. An example of a type II restriction endonucleases is FokI, which consists of a DNA recognition domain and a non-specific DNA cleavage domain. FokI cleaves DNA nine and thirteen bases downstream of an asymmetric sequence (recognizing a DNA sequence of GGATG).

In some embodiments, the DNA cleavage domain at the C-terminus of FokI itself can be combined with a variety of DNA-binding domains (e.g., RNBDs, TALEs, MAP-NBDs) of other molecules for genome editing purposes. This cleavage domain can be 180 amino acids in length and can be directly linked to a DNA binding domain (e.g., RNBDs, TALEs, MAP-NBDs). In some embodiments, the FokI cleavage domain only comprises a single catalytic site. Thus, in order to cleave phosphodiester bonds, these enzymes form transient homodimers, providing two catalytic sites capable of cleaving double stranded DNA. In some embodiments, a single DNA-binding domains (e.g., RNBDs, TALEs, MAP-NBDs) linked to a Type IIS cleaving domain may not nick the double stranded DNA at the targeted site. In some embodiments, cleaving of target DNA only occurs when a pair of DNA-binding domains (e.g., RNBDs, TALEs, MAP-NBDs), each linked to a Type IIS cleaving domain (e.g., any one of SEQ ID NO: 1-SEQ ID NO: 81 (nucleotide sequences of SEQ ID NO: 82-SEQ ID NO: 162)) bind to opposing strands of DNA and allow for formation of a transient homodimer in the spacer region (the base pairs between the C-terminus of the DNA binding domain on a top strand of DNA and the C-terminus of the DNA binding domain on a bottom strand of DNA). Said spacer region can be greater than 2 base pairs, greater than 5 base pairs, greater than 10 base pairs, greater than 15 base pairs, greater than 24 base pairs, greater than 25 base pairs, greater than 30 base pairs, greater than 35 base pairs, greater than 40 base pairs, greater than 45 base pairs, or greater than 50 base pairs. In some embodiments, the spacer region can be anywhere from 2 to 50 base pairs, 5 to 40 base pairs, 10 to 30 base pairs, 14 to 40 base pairs, 24 to 30 base pairs, 24 to 40 base pairs, or 24 to 50 base pairs. In some embodiments, the nuclease disclosed herein (e.g., any one of SEQ ID NO: 1-SEQ ID NO: 81 (nucleotide sequences of SEQ ID NO: 82-SEQ ID NO: 162) can be capable of cleaving over a spacer region of greater than 24 base pairs upon formation of a transient homodimer.

In some instances, such enzymes can comprise one or more mutations relative to SEQ ID NO: 1-SEQ ID NO: 81 (nucleotide sequences of SEQ ID NO: 82-SEQ ID NO: 162). In some cases, the non-naturally occurring enzymes described herein can comprise about 1, 2, 3, 4, 5, 6, 7, 8, 9, 10, or more mutations. A mutation can be engineered to enhance cleavage efficiency. A mutation can abolish cleavage activity. In some cases, a mutation can enhance homodimerization. For example, FokI can have a mutation at one or more amino acid residue positions 446, 447, 479, 483, 484, 486, 487, 490, 491, 496, 498, 499, 500, 531, 534, 537, and 538 to modulate homodimerization, and similar mutations can be designed based on the phylogenetic analysis of SEQ ID NO: 1-SEQ ID NO: 81 (nucleotide sequences of SEQ ID NO: 82-SEQ ID NO: 162).

TABLE 7 shows exemplary amino acid sequences (SEQ ID NO: 1-SEQ ID NO: 81) of endonucleases for genome editing and the corresponding back-translated nucleic acid sequences (SEQ ID NO: 82-SEQ ID NO: 162) of the endonucleases, which were obtained using Geneious software and selecting for human codon optimization.

TABLE 7

Amino Acid and Nucleic Acid Sequences of Endonucleases

| SEQ ID NO | Amino Acid Sequence | SEQ ID NO | Back Translated Nucleic Acid Sequences |
|---|---|---|---|
| 1 | FLVKGAMEIKKSEL RHKLRHVPHEYIELI EIAQDSKQNRLLEF KVVEFFKKIYGYRG | 82 | TTCCTGGTGAAGGGCGCCATGGAGATCAAGAAGAGCGAGCTGA GGCACAAGCTGAGGCACGTGCCCCACGAGTACATCGAGCTGAT CGAGATCGCCCAGGACAGCAAGCAGAACAGGCTGCTGGAGTTC AAGGTGGTGGAGTTCTTCAAGAAGATCTACGGCTACAGGGGCA |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
| | KHLGGSRKPDGALF TDGLVLNHGIILDT KAYKDGYRLPISQA DEMQRYVDENNKR SQVINPNEWWEIYP TSITDFKFLFVSGFF QGDYRKQLERVSH LTKCQGAVMSVEQ LLLGGEKIKEGSLTL EEVGKKFKNDEIVF | | AGCACCTGGGCGGCAGCAGGAAGCCCGACGGCGCCCTGTTCAC CGACGGCCTGGTGCTGAACCACGGCATCATCCTGGACACCAAGG CCTACAAGGACGGCTACAGGCTGCCCATCAGCCAGGCCGACGA GATGCAGAGGTACGTGGACGAGAACAACAAGAGGAGCCAGGTG ATCAACCCCAACGAGTGGTGGGAGATCTACCCCACCAGCATCAC CGACTTCAAGTTCCTGTTCGTGAGCGGCTTCTTCCAGGGCGACT ACAGGAAGCAGCTGGAGAGGGTGAGCCACCTGACCAAGTGCCA GGGCGCCGTGATGAGCGTGGAGCAGCTGCTGCTGGGCGGCGAG AAGATCAAGGAGGGCAGCCTGACCCTGGAGGAGGTGGGCAAGA AGTTCAAGAACGACGAGATCGTGTTC |
| 2 | QIVKSSIEMSKANM RDNLQMLPHDYIEL IEISQDPYQNRIFEM KVMDLFINEYGFSG SHLGGSRKPDGAM YAHGFGVIVDTKA YKDGYNLPISQADE MERYVRENIDRNEH VNSNRWWNIFPEDT NEYKFLFVSGFPKG NFEKQLERISIDTGV QGGALSVEHLLLGA EYIKRGILTLYDFKN SFLNKEIQF | 83 | CAGATCGTGAAGAGCAGCATCGAGATGAGCAAGGCCAACATGA GGGACAACCTGCAGATGCTGCCCCACGACTACATCGAGCTGATC GAGATCAGCCAGGACCCCTACCAGAACAGGATCTTCGAGATGA AGGTGATGGACCTGTTCATCAACGAGTACGGCTTCAGCGGCAGC CACCTGGGCGGCAGCAGGAAGCCCGACGGCGCCATGTACGCCC ACGGCTTCGGCGTGATCGTGGACACCAAGGCCTACAAGGACGG CTACAACCTGCCCATCAGCCAGGCCGACGAGATGGAGAGGTAC GTGAGGGAGAACATCGACAGGAACGAGCACGTGAACAGCAACA GGTGGTGGAACATCTTCCCCGAGGACACCAACGAGTACAAGTTC CTGTTCGTGAGCGGCTTCTTCAAGGGCAACTTCGAGAAGCAGCT GGAGAGGATCAGCATCGACACCGGCGTGCAGGGCGGCGCCCTG AGCGTGGAGCACCTGCTGCTGGGCGCCGAGTACATCAAGAGGG GCATCCTGACCCTGTACGACTTCAAGAACAGCTTCCTGAACAAG GAGATCCAGTTC |
| 3 | QTIKSSIEELKSELR TQLNVISHDYLQLV DISQDSQQNRLFEM KVMDLFINEFGYNG SHLGGSRKPDGILY TEGLSKDYGIIVDT KAYKDGYNLPIAQ ADEMERYIRENIDR NEVVNPNRWWEVF PSKINDYKFLFVSA YFKGNFKEQLERISI NTGILGGAISVEHLL LGAEYFKRGILSLE DVRDKFCNTEIEF | 84 | CAGACCATCAAGAGCAGCATCGAGGAGCTGAAGAGCGAGCTGA GGACCCAGCTGAACGTGATCAGCCACGACTACCTGCAGCTGGTG GACATCAGCCAGGACAGCCAGCAGAACAGGCTGTTCGAGATGA AGGTGATGGACCTGTTCATCAACGAGTTCGGCTACAACGGCAGC CACCTGGGCGGCAGCAGGAAGCCCGACGGCATCCTGTACACCG AGGGCCTGAGCAAGGACTACGGCATCATCGTGGACACCAAGGC CTACAAGGACGGCTACAACCTGCCCATCGCCCAGGCCGACGAG ATGGAGAGGTACATCAGGGAGAACATCGACAGGAACGAGGTGG TGAACCCCAACAGGTGGTGGGAGGTGTTCCCCAGCAAGATCAA CGACTACAAGTTCCTGTTCGTGAGCGCCTACTTCAAGGGCAACT TCAAGGAGCAGCTGGAGAGGATCAGCATCAACACCGGCATCCT GGGCGGCGCCATCAGCGTGGAGCACCTGCTGCTGGGCGCCGAG TACTTCAAGAGGGGCATCCTGAGCCTGGAGGACGTGAGGGACA AGTTCTGCAACACCGAGATCGAGTTC |
| 4 | GKSEVETIKEQMRG ELTHLSHEYLGLLD LAYDSKQNRLFELK TMQLLTEECGFEGL HLGGSRKPDGIVYT KDENEQVGKENYGI IIDTKAYSGGYSLPI SQADEMERYIGENQ TRDIRINPNEWWKN FGDGVTEYYYLFV AGHFKGKYQEQIDR INCNKNIKGAAVSI QQLLRIVNDYKAG KLTHEDMKLKIFHY | 85 | GGCAAGAGCGAGGTGGAGACCATCAAGGAGCAGATGAGGGGC GAGCTGACCCACCTGAGCCACGAGTACCTGGGCCTGCTGGACCT GGCCTACGACAGCAAGCAGAACAGGCTGTTCGAGCTGAAGACC ATGCAGCTGCTGACCGAGGAGTGCGGCTTCGAGGGCCTGCACCT GGGCGGCAGCAGGAAGCCCGACGGCATCGTGTACACCAAGGAC GAGAACGAGCAGGTGGGCAAGGAGAACTACGGCATCATCATCG ACACCAAGGCCTACAGCGGCGGCTACAGCCTGCCCATCAGCCA GGCCGACGAGATGGAGAGGTACATCGGCGAGAACCAGACCAGG GACATCAGGATCAACCCCAACGAGTGGTGGAAGAACTTCGGCG ACGGCGTGACCGAGTACTACTACCTGTTCGTGGCCGGCCACTTC AAGGGCAAGTACCAGGAGCAGATCGACAGGATCAACTGCAACA AGAACATCAAGGGCGCCGCCGTGAGCATCCAGCAGCTGCTGAG GATCGTGAACGACTACAAGGCCGGCAAGCTGACCCACGAGGAC ATGAAGCTGAAGATCTTCCACTAC |
| 5 | MKILELLINECGYK GLHLGGARKPDGII YTEKEKYNYGVIID TKAYSKGYNLPIGQ IDEMIRYIIENNERNI KRNTNCWWNNFEK NVNEFYFSFISGEFT GNIEEKLNRIFISTNI KGNAMSVKTLLYL ANEIKANRISYIELL NYFDNKV | 86 | ATGAAGATCCTGGAGCTGCTGATCAACGAGTGCGGCTACAAGG GCCTGCACCTGGGCGGCGCCAGGAAGCCCGACGGCATCATCTAC ACCGAGAAGGAGAAGTACAACTACGGCGTGATCATCGACACCA AGGCCTACAGCAAGGGCTACAACCTGCCCATCGGCCAGATCGA CGAGATGATCAGGTACATCATCGAGAACAACGAGAGGAACATC AAGAGGAACACCAACTGCTGGTGGAACAACTTCGAGAAGAACG TGAACGAGTTCTACTTCAGCTTCATCAGCGGCGAGTTCACCGGC AACATCGAGGAGAAGCTGAACAGGATCTTCATCAGCACCAACA TCAAGGGCAACGCCATGAGCGTGAAGACCCTGCTGTACCTGGCC AACGAGATCAAGGCCAACAGGATCAGCTACATCGAGCTGCTGA ACTACTTCGACAACAAGGTG |
| 6 | AKSSQSETKEKLRE KLRNLPHEYLSLVD LAYDSKQNRLFEM KVIELLTEECGFQG LHLGGSRRPDGVLY TAGLTDNYGIILDT | 87 | GCCAAGAGCAGCCAGAGCGAGACCAAGGAGAAGCTGAGGGAG AAGCTGAGGAACCTGCCCCACGAGTACCTGAGCCTGGTGGACCT GGCCTACGACAGCAAGCAGAACAGGCTGTTCGAGATGAAGGTG ATCGAGCTGCTGACCGAGGAGTGCGGCTTCCAGGGCCTGCACCT GGGCGGCAGCAGGAGGCCCGACGGCGTGCTGTACACCGCCGGC CTGACCGACAACTACGGCATCATCCTGGACACCAAGGCCTACAG |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
|  | KAYSSGYSLPIAQA DEMERYVRENQTR DELVNPNQWWENF ENGLGTFYFLFVAG HFNGNVQAQLERIS RNTGVLGAAASISQ LLLLADAIRGGRMD RERLRHLMFQNEEF L | | CAGCGGCTACAGCCTGCCCATCGCCCAGGCCGACGAGATGGAG AGGTACGTGAGGGAGAACCAGACCAGGGACGAGCTGGTGAACC CCAACCAGTGGTGGGAGAACTTCGAGAACGGCCTGGGCACCTTC TACTTCCTGTTCGTGGCCGGCCACTTCAACGGCAACGTGCAGGC CCAGCTGGAGAGGATCAGCAGGAACACCGGCGTGCTGGGCGCC GCCGCCAGCATCAGCCAGCTGCTGCTGCTGGCCGACGCCATCAG GGGCGGCAGGATGGACAGGGAGAGGCTGAGGCACCTGATGTTC CAGAACGAGGAGTTCCTG |
| 7 | NSEKSEFTQEKDNL REKLDTLSHEYLSL VDLAFDSQQNRLFE MKTVELLTKECNY KGVHLGGSRKPDGI IYTENSTDNYGVIID TKAYSNGYNLPISQ VDEMVRYVEENNK REKERNSNEWWKE FGDNINKFYFSFISG KFIGNIEEKLQRITIF TNVYGNAMTIITLL YLANEIKANRLKTM EVVKYFDNKV | 88 | AACAGCGAGAAGAGCGAGTTCACCCAGGAGAAGGACAACCTGA GGGAGAAGCTGGACACCCTGAGCCACGAGTACCTGAGCCTGGT GGACCTGGCCTTCGACAGCCAGCAGAACAGGCTGTTCGAGATG AAGACCGTGGAGCTGCTGACCAAGGAGTGCAACTACAAGGGCG TGCACCTGGGCGGCAGCAGGAAGCCCGACGGCATCATCTACAC CGAGAACAGCACCGACAACTACGGCGTGATCATCGACACCAAG GCCTACAGCAACGGCTACAACCTGCCCATCAGCCAGGTGGACG AGATGGTGAGGTACGTGGAGGAGAACAACAAGAGGGAGAAGG AGAGGAACAGCAACGAGTGGTGGAAGGAGTTCGGCGACAACAT CAACAAGTTCTACTTCAGCTTCATCAGCGGCAAGTTCATCGGCA ACATCGAGGAGAAGCTGCAGAGGATCACCATCTTCACCAACGT GTACGGCAACGCCATGACCATCATCACCCTGCTGTACCTGGCCA ACGAGATCAAGGCCAACAGGCTGAAGACCATGGAGGTGGTGAA GTACTTCGACAACAAGGTG |
| 8 | NLTCSDLTEIKEEVR NALTHLSHEYLALI DLAYDSTQNRLFE MKTLQLLVEECGY QGTHLGGSRKPDGI CYSEEAKSEGLEAN YGIIIDTKSYSGGYG LPISQADEMERYIRE NQTRDAEVNRNKW WEAFPETIDIFYFMF VAGHFKGNYFNQL ERLQRSTGIKGAAV DIKTLLLTANRCKT GELDHAGIESCFFN NCRL | 89 | AACCTGACCTGCAGCGACCTGACCGAGATCAAGGAGGAGGTGA GGAACGCCCTGACCCACCTGAGCCACGAGTACCTGGCCCTGATC GACCTGGCCTACGACAGCACCCAGAACAGGCTGTTCGAGATGA AGACCCTGCAGCTGCTGGTGGAGGAGTGCGGCTACCAGGGCAC CCACCTGGGCGGCAGCAGGAAGCCCGACGGCATCTGCTACAGC GAGGAGGCCAAGAGCGAGGGCCTGGAGGCCAACTACGGCATCA TCATCGACACCAAGAGCTACAGCGGCGGCTACGGCCTGCCCATC AGCCAGGCCGACGAGATGGAGAGGTACATCAGGGAGAACCAGA CCAGGGACGCCGAGGTGAACAGGAACAAGTGGTGGGAGGCCTT CCCCGAGACCATCGACATCTTCTACTTCATGTTCGTGGCCGGCC ACTTCAAGGGCAACTACTTCAACCAGCTGGAGAGGCTGCAGAG GAGCACCGGCATCAAGGGCGCCGCCGTGGACATCAAGACCCTG CTGCTGACCGCCAACAGGTGCAAGACCGGCGAGCTGGACCACG CCGGCATCGAGAGCTGCTTCTTCAACAACTGCAGGCTG |
| 9 | DNVKSNFNQEKDE LREKLDTLSHEYLY LLDLAYDSKQNKLF EMKILELLINECGY RGLHLGGVRKPDGI IYTEKEKYNYGVIID TKAYSKGYNLPIGQ IDEMIRYIIENNERNI KRNTNCWWNNFEK NVNEFYFSFISGEFT GNIEEKLNRIFISTNI KGNAMSVKTLLYL ANEIKANRISFLEME KYFDNKV | 90 | GACAACGTGAAGAGCAACTTCAACCAGGAGAAGGACGAGCTGA GGGAGAAGCTGGACACCCTGAGCCACGAGTACCTGTACCTGCTG GACCTGGCCTACGACAGCAAGCAGAACAAGCTGTTCGAGATGA AGATCCTGGAGCTGCTGATCAACGAGTGCGGCTACAGGGGCCTG CACCTGGGCGGCGTGAGGAAGCCCGACGGCATCATCTACACCG AGAAGGAGAAGTACAACTACGGCGTGATCATCGACACCAAGGC CTACAGCAAGGGCTACAACCTGCCCATCGGCCAGATCGACGAG ATGATCAGGTACATCATCGAGAACAACGAGAGGAACATCAAGA GGAACACCAACTGCTGGTGGAACAACTTCGAGAAGAACGTGAA CGAGTTCTACTTCAGCTTCATCAGCGGCGAGTTCACCGGCAACA TCGAGGAGAAGCTGAACAGGATCTTCATCAGCACCAACATCAA GGGCAACGCCATGAGCGTGAAGACCCTGCTGTACCTGGCCAAC GAGATCAAGGCCAACAGGATCAGCTTCCTGGAGATGGAGAAGT ACTTCGACAACAAGGTG |
| 10 | EGIKSNISLLKDELR GQISHISHEYLSLID LAFDSKQNRLFEMK VLELLVNEYGFKGR HLGGSRKPDGIVYS TTLEDNFGIIVDTKA YSEGYSLPISQADE MERYVRENSNRDE EVNPNKWWENFSE EVKKYYFVFISGSF KGKFEEQLRRLSMT TGVNGSAVNVVNL LLGAEKIRSGEMTIE ELERAMFNNSEFI | 91 | GAGGGCATCAAGAGCAACATCAGCCTGCTGAAGGACGAGCTGA GGGGCCAGATCAGCCACATCAGCCACGAGTACCTGAGCCTGATC GACCTGGCCTTCGACAGCAAGCAGAACAGGCTGTTCGAGATGA AGGTGCTGGAGCTGCTGGTGAACGAGTACGGCTTCAAGGGCAG GCACCTGGGCGGCAGCAGGAAGCCCGACGGCATCGTGTACAGC ACCACCCTGGAGGACAACTTCGGCATCATCGTGGACACCAAGGC CTACAGCGAGGGCTACAGCCTGCCCATCAGCCAGGCCGACGAG ATGGAGAGGTACGTGAGGGAGAACAGCAACAGGGACGAGGAG GTGAACCCCAACAAGTGGTGGGAGAACTTCAGCGAGGAGGTGA AGAAGTACTACTTCGTGTTCATCAGCGGCAGCTTCAAGGGCAAG TTCGAGGAGCAGCTGAGGAGGCTGAGCATGACCACCGGCGTGA ACGGCAGCGCCGTGAACGTGGTGAACCTGCTGCTGGGCGCCGA GAAGATCAGGAGCGGCGAGATGACCATCGAGGAGCTGGAGAGG GCCATGTTCAACAACAGCGAGTTCATC |
| 11 | ISKTNVLELKDKVR DKLKYVDNRYLALI DLAYDGTANRDFEI | 92 | ATCAGCAAGACCAACGTGCTGGAGCTGAAGGACAAGGTGAGGG ACAAGCTGAAGTACGTGGACAACAGGTACCTGGCCCTGATCGA CCTGGCCTACGACGGCACCGCCAACAGGGACTTCGAGATCCAG |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
|  | QTIDLLINELKFKGV RLGESRKPDGIISYD INGVIIDNKAYSSGY NLPINQADEMIRYIE ENQTRDKKINPNK WWESFDDKVKDFN YLFVSSFFKGNFKN NLKHIANRTGVNG GVINVENLLYFAEE LKSGRLSYVDLFKM YDNDEINI |  | ACCATCGACCTGCTGATCAACGAGCTGAAGTTCAAGGGCGTGAG GCTGGGCGAGAGCAGGAAGCCCGACGGCATCATCAGCTACGAC ATCAACGGCGTGATCATCGACAACAAGGCCTACAGCAGCGGCT ACAACCTGCCCATCAACCAGGCCGACGAGATGATCAGGTACATC GAGGAGAACCAGACCAGGGACAAGAAGATCAACCCCAACAAGT GGTGGGAGAGCTTCGACGACAAGGTGAAGGACTTCAACTACCT GTTCGTGAGCAGCTTCTTCAAGGGCAACTTCAAGAACAACCTGA AGCACATCGCCAACAGGACCGGCGTGAACGGCGGCGTGATCAA CGTGGAGAACCTGCTGTACTTCGCCGAGGAGCTGAAGAGCGGC AGGCTGAGCTACGTGGACCTGTTCAAGATGTACGACAACGACG AGATCAACATC |
| 12 | ISKTNVLELKDKVR DKLKYVDHRYLALI DLAYDGTANRDFEI QTIDLLINELKFKGV RLGESRKPDGIISYD INGVIIDNKAYSTGY NLPINQADEMIRYIE ENQTRDKKINSNK WWESFDDKVKNFN YLFVSSFFKGNFKN NLKHIANRTGVNG GAINVENLLYFAEE LKAGRLSYVDSFTM YDNDEIYV | 93 | ATCAGCAAGACCAACGTGCTGGAGCTGAAGGACAAGGTGAGGG ACAAGCTGAAGTACGTGGACCACAGGTACCTGGCCCTGATCGAC CTGGCCTACGACGGCACCGCCAACAGGGACTTCGAGATCCAGA CCATCGACCTGCTGATCAACGAGCTGAAGTTCAAGGGCGTGAGG CTGGGCGAGAGCAGGAAGCCCGACGGCATCATCAGCTACGACA TCAACGGCGTGATCATCGACAACAAGGCCTACAGCACCGGCTAC AACCTGCCCATCAACCAGGCCGACGAGATGATCAGGTACATCG AGGAGAACCAGACCAGGGACAAGAAGATCAACAGCAACAAGT GGTGGGAGAGCTTCGACGACAAGGTGAAGAACTTCAACTACCT GTTCGTGAGCAGCTTCTTCAAGGGCAACTTCAAGAACAACCTGA AGCACATCGCCAACAGGACCGGCGTGAACGGCGGCGCCATCAA CGTGGAGAACCTGCTGTACTTCGCCGAGGAGCTGAAGGCCGGC AGGCTGAGCTACGTGGACAGCTTCACCATGTACGACAACGACG AGATCTACGTG |
| 13 | KAEKSEFLIEKDKL REKLDTLPHDYLSM VDLAYDSKQNRLFE MKTIELLINECNYK GLHLGGTRKPDGIV YTNNEVENYGIIIDT KAYSKGYNLPISQV DEMTRYVEENNKR EKKRNPNEWWNNF DSNVKKFYFSFISG KFVGNIEEKLQRITL FTEIYGNAITVTTLL YIANEIKANRMKKS DIMEYFNDKV | 94 | AAGGCCGAGAAGAGCGAGTTCCTGATCGAGAAGGACAAGCTGA GGGAGAAGCTGGACACCCTGCCCCACGACTACCTGAGCATGGT GGACCTGGCCTACGACAGCAAGCAGAACAGGCTGTTCGAGATG AAGACCATCGAGCTGCTGATCAACGAGTGCAACTACAAGGGCC TGCACCTGGGCGGCACCAGGAAGCCCGACGGCATCGTGTACAC CAACAACGAGGTGGAGAACTACGGCATCATCATCGACACCAAG GCCTACAGCAAGGGCTACAACCTGCCCATCAGCCAGGTGGACG AGATGACCAGGTACGTGGAGGAGAACAACAAGAGGGAGAAGA AGAAGAACCCCAACGAGTGGTGGAACAACTTCGACAGCAACGT GAAGAAGTTCTACTTCAGCTTCATCAGCGGCAAGTTCGTGGGCA ACATCGAGGAGAAGCTGCAGAGGATCACCCTGTTCACCGAGAT CTACGGCAACGCCATCACCGTGACCACCCTGCTGTACATCGCCA ACGAGATCAAGGCCAACAGGATGAAGAAGAGCGACATCATGGA GTACTTCAACGACAAGGTG |
| 14 | ISKTNVLELKDKVR DKLKYVDHRYLALI DLAYDGTANRDFEI QTIDLLINELKFKGV RLGESRKPDGIISYN INGVIIDNKAYSTGY NLPINQADEMIRYIE ENQTRDEKINSNKW WESFDDEVKDFNY LFVSSFFKGNFKNN LKHIANRTGVNGG AINVENLLYFAEEL KAGRLSYVDSFTM YDNDEIYV | 95 | ATCAGCAAGACCAACGTGCTGGAGCTGAAGGACAAGGTGAGGG ACAAGCTGAAGTACGTGGACCACAGGTACCTGGCCCTGATCGAC CTGGCCTACGACGGCACCGCCAACAGGGACTTCGAGATCCAGA CCATCGACCTGCTGATCAACGAGCTGAAGTTCAAGGGCGTGAGG CTGGGCGAGAGCAGGAAGCCCGACGGCATCATCAGCTACAACA TCAACGGCGTGATCATCGACAACAAGGCCTACAGCACCGGCTAC AACCTGCCCATCAACCAGGCCGACGAGATGATCAGGTACATCG AGGAGAACCAGACCAGGGACGAGAAGATCAACAGCAACAAGT GGTGGGAGAGCTTCGACGACGAGGTGAAGGACTTCAACTACCT GTTCGTGAGCAGCTTCTTCAAGGGCAACTTCAAGAACAACCTGA AGCACATCGCCAACAGGACCGGCGTGAACGGCGGCGCCATCAA CGTGGAGAACCTGCTGTACTTCGCCGAGGAGCTGAAGGCCGGC AGGCTGAGCTACGTGGACAGCTTCACCATGTACGACAACGACG AGATCTACGTG |
| 15 | ISKTNILELKDVRD KLKYVDHRYLALID LAYDGTANRDFEIQ TIDLLINELKFKGVR LGESRKPDGIISYNI NGVIIDNKAYSTGY NLPINQADEMIRYIE ENQTRDEKINSNKW WESFDEKVKDFNY LFVSSFFKGNFKNN LKHIANRTGVNGG AINVENLLYFAEEL KAGRISYLDSFKMY NNDEIYL | 96 | ATCAGCAAGACCAACATCCTGGAGCTGAAGGACAAGGTGAGGG ACAAGCTGAAGTACGTGGACCACAGGTACCTGGCCCTGATCGAC CTGGCCTACGACGGCACCGCCAACAGGGACTTCGAGATCCAGA CCATCGACCTGCTGATCAACGAGCTGAAGTTCAAGGGCGTGAGG CTGGGCGAGAGCAGGAAGCCCGACGGCATCATCAGCTACAACA TCAACGGCGTGATCATCGACAACAAGGCCTACAGCACCGGCTAC AACCTGCCCATCAACCAGGCCGACGAGATGATCAGGTACATCG AGGAGAACCAGACCAGGGACGAGAAGATCAACAGCAACAAGT GGTGGGAGAGCTTCGACGAGAAGGTGAAGGACTTCAACTACCT GTTCGTGAGCAGCTTCTTCAAGGGCAACTTCAAGAACAACCTGA AGCACATCGCCAACAGGACCGGCGTGAACGGCGGCGCCATCAA CGTGGAGAACCTGCTGTACTTCGCCGAGGAGCTGAAGGCCGGC AGGATCAGCTACCTGGACAGCTTCAAGATGTACAACAACGACG AGATCTACCTG |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
| 16 | ISKTNVLELKDKVR DKLKYVDHRYLALI DLAYDGTANRDFEI QTIDLLINELKFKGV RLGESRKPDGIISYN INGVIIDNKAYSTGY NLPINQADEMIRYIE ENQTRDEKINSNKW WESFDDKVKDFNY LFVSSFFKGNFKNN LKHIANRTGVSGGA INVENLLYFAEELK AGRLSYVDSFKMY DNDEIYV | 97 | ATCAGCAAGACCAACGTGCTGGAGCTGAAGGACAAGGTGAGGG ACAAGCTGAAGTACGTGGACCACAGGTACCTGGCCCTGATCGAC CTGGCCTACGACGGCACCGCCAACAGGGACTTCGAGATCCAGA CCATCGACCTGCTGATCAACGAGCTGAAGTTCAAGGGCGTGAGG CTGGGCGAGAGCAGGAAGCCCGACGGCATCATCAGCTACAACA TCAACGGCGTGATCATCGACAACAAGGCCTACAGCACCGGCTAC AACCTGCCCATCAACCAGGCCGACGAGATGATCAGGTACATCG AGGAGAACCAGACCAGGGACGAGAAGATCAACAGCAACAAGT GGTGGGAGAGCTTCGACGACAAGGTGAAGGACTTCAACTACCT GTTCGTGAGCAGCTTCTTCAAGGGCAACTTCAAGAACAACCTGA AGCACATCGCCAACAGGACCGGCGTGAGCGGCGGCGCCATCAA CGTGGAGAACCTGCTGTACTTCGCCGAGGAGCTGAAGGCCGGC AGGCTGAGCTACGTGGACAGCTTCAAGATGTACGACAACGACG AGATCTACGTG |
| 17 | ISKTNVLELKDKVR NKLKYVDHRYLALI DLAYDGTANRDFEI QTIDLLINELKFKGV RLGESRKPDGIISYD INGVIIDNKSYSTGY NLPINQADEMIRYIE ENQTRDEKINSNKW WESFDEKVKDFNY LFVSSFFKGNFKNN LKHIANRTGVNGG AINVENLLYFAEEL KSGRLSYVDSFTMY DNDEIYV | 98 | ATCAGCAAGACCAACGTGCTGGAGCTGAAGGACAAGGTGAGGA ACAAGCTGAAGTACGTGGACCACAGGTACCTGGCCCTGATCGAC CTGGCCTACGACGGCACCGCCAACAGGGACTTCGAGATCCAGA CCATCGACCTGCTGATCAACGAGCTGAAGTTCAAGGGCGTGAGG CTGGGCGAGAGCAGGAAGCCCGACGGCATCATCAGCTACGACA TCAACGGCGTGATCATCGACAACAAGAGCTACAGCACCGGCTA CAACCTGCCCATCAACCAGGCCGACGAGATGATCAGGTACATCG AGGAGAACCAGACCAGGGACGAGAAGATCAACAGCAACAAG TGGTGGGAGAGCTTCGACGAGAAGGTGAAGGACTTCAACTACCT GTTCGTGAGCAGCTTCTTCAAGGGCAACTTCAAGAACAACCTGA AGCACATCGCCAACAGGACCGGCGTGAACGGCGGCGCCATCAA CGTGGAGAACCTGCTGTACTTCGCCGAGGAGCTGAAGAGCGGC AGGCTGAGCTACGTGGACAGCTTCACCATGTACGACAACGACG AGATCTACGTG |
| 18 | ISKTNVLELKDKVR DKLKYVDHRYLSLI DLAYDGNANRDFEI QTIDLLINELNFKGV RLGESRKPDGIISYN INGVIIDNKAYSTGY NLPINQADEMIRYIE ENQTRDEKINSNKW WESFDDKVKDFNY LFVSSFFKGNFKNN LKHIANRTGVSGGA INVENLLYFAEELK AGRLSYADSFTMY DNDEIYV | 99 | ATCAGCAAGACCAACGTGCTGGAAGCTGAAGGACAAGGTGAGGG ACAAGCTGAAGTACGTGGACCACAGGTACCTGAGCCTGATCGA CCTGGCCTACGACGGCAACGCCAACAGGGACTTCGAGATCCAG ACCATCGACCTGCTGATCAACGAGCTGAACTTCAAGGGCGTGAG GCTGGGCGAGAGCAGGAAGCCCGACGGCATCATCAGCTACAAC ATCAACGGCGTGATCATCGACAACAAGGCCTACAGCACCGGCT ACAACCTGCCCATCAACCAGGCCGACGAGATGATCAGGTACATC GAGGAGAACCAGACCAGGGACGAGAAGATCAACAGCAACAAG TGGTGGGAGAGCTTCGACGACAAGGTGAAGGACTTCAACTACCT GTTCGTGAGCAGCTTCTTCAAGGGCAACTTCAAGAACAACCTGA AGCACATCGCCAACAGGACCGGCGTGAGCGGCGGCGCCATCAA CGTGGAGAACCTGCTGTACTTCGCCGAGGAGCTGAAGGCCGGC AGGCTGAGCTACGCCGACAGCTTCACCATGTACGACAACGACG AGATCTACGTG |
| 19 | IAKTNVLGLKDKVR DRLKYVDHRYLALI DLAYDGTANRDFEI QTIDLLINELKFKGV RLGESRKPDGIISYN VNGVIIDNKAYSKG YNLPINQADEMIRYI EENQTRDEKINANK WWESFDDKVEEFS YLFVSSFFKGNFKN NLKHIANRTGVNG GAINVENLLYFAEE LKSGRLSYMDSFSL YDNDEICV | 100 | ATCGCCAAGACCAACGTGCTGGGCCTGAAGGACAAGGTGAGGG ACAGGCTGAAGTACGTGGACCACAGGTACCTGGCCCTGATCGAC CTGGCCTACGACGGCACCGCCAACAGGGACTTCGAGATCCAGA CCATCGACCTGCTGATCAACGAGCTGAAGTTCAAGGGCGTGAGG CTGGGCGAGAGCAGGAAGCCCGACGGCATCATCAGCTACAACG TGAACGGCGTGATCATCGACAACAAGGCCTACAGCAAGGGCTA CAACCTGCCCATCAACCAGGCCGACGAGATGATCAGGTACATCG AGGAGAACCAGACCAGGGACGAGAAGATCAACGCCAACAAGTG GTGGGAGAGCTTCGACGACAAGGTGGAGGAGTTCAGCTACCTG TTCGTGAGCAGCTTCTTCAAGGGCAACTTCAAGAACAACCTGAA GCACATCGCCAACAGGACCGGCGTGAACGGCGGCGCCATCAAC GTGGAGAACCTGCTGTACTTCGCCGAGGAGCTGAAGAGCGGCA GGCTGAGCTACATGGACAGCTTCAGCCTGTACGACAACGACGA GATCTGCGTG |
| 20 | ELKDEQSEKRKAKF LKETKLPMKYIELL DIAYDGKRNRDFEI VTMELFREVYRLNS KLLGGGRKPDGLIY TDDFGVIVDTKAYG EGYSKSINQADEMI RYIEDNKRRDEKRN PIKWWESFPSSISQN NFYFLWVSSKFVGK | 101 | GAGCTGAAGGACGAGCAGAGCGAGAAGAGGAAGGCCAAGTTCC TGAAGGAGACCAAGCTGCCCATGAAGTACATCGAGCTGCTGGA CATCGCCTACGACGGCAAGAGGAACAGGGACTTCGAGATCGTG ACCATGGAGCTGTTCAGGGAGGTGTACAGGCTGAACAGCAAGC TGCTGGGCGGCGGCAGGAAGCCCGACGGCCTGATCTACACCGA CGACTTCGGCGTGATCGTGGACACCAAGGCCTACGGCGAGGGCT ACAGCAAGAGCATCAACCAGGCCGACGAGATGATCAGGTACAT CGAGGACAACAAGAGGAGGGACGAGAAGAGGAACCCCATCAA GTGGTGGGAGAGCTTCCCCAGCAGCATCAGCCAGAACAACTTCT ACTTCCTGTGGGTGAGCAGCAAGTTCGTGGGCAAGTTCCAGGAG |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
| | FQEQLAYTANETQT KGGAINVEQILIGA DLIMQKMLDINTIPS PPENQEIIF | | CAGCTGGCCTACACCGCCAACGAGACCCAGACCAAGGGCGGCG CCATCAACGTGGAGCAGATCCTGATCGGCGCCGACCTGATCATG CAGAAGATGCTGGACATCAACACCATCCCCAGCTTCTTCGAGAA CCAGGAGATCATCTTC |
| 21 | IFKTNVLELKDSIRE KLDYIDHRYLSLVD LAYDSKANRDFEIQ TIDLLINELDFKGLR LGESRKPDGIISYDI NGVIIDNKAYSKGY NLPINQADEMIRYIQ ENQSRNEKINPNKW WENFEDKVIKFNYL FISSLFVGGFKKNLQ HIANRTGVNGGAID VENLLYFAEEIKSG RLTYKDSFSRYIND EIKM | 102 | ATCTTCAAGACCAACGTGCTGGAGCTGAAGGACAGCATCAGGG AGAAGCTGGACTACATCGACCACAGGTACCTGAGCCTGGTGGA CCTGGCCTACGACAGCAAGGCCAACAGGGACTTCGAGATCCAG ACCATCGACCTGCTGATCAACGAGCTGGACTTCAAGGGCCTGAG GCTGGGCGAGAGCAGGAAGCCCGACGGCATCATCAGCTACGAC ATCAACGGCGTGATCATCGACAACAAGGCCTACAGCAAGGGCT ACAACCTGCCCATCAACCAGGCCGACGAGATGATCAGGTACATC CAGGAGAACCAGAGCAGGAACGAGAAGATCAACCCCAACAAGT GGTGGGAGAACTTCGAGGACAAGGTGATCAAGTTCAACTACCT GTTCATCAGCAGCCTGTTCGTGGGCGGCTTCAAGAAGAACCTGC AGCACATCGCCAACAGGACCGGCGTGAACGGCGGCGCCATCGA CGTGGAGAACCTGCTGTACTTCGCCGAGGAGATCAAGAGCGGC AGGCTGACCTACAAGGACAGCTTCAGCAGGTACATCAACGACG AGATCAAGATG |
| 22 | LPVKSEVSVFKDYL RTHLTHVDHRYLIL VDLGFDGSSDRDYE MKTAELFTAELGF MGARLGDTRKPDV CVYHGANGLIIDNK AYGKGYSLPIKQAD EIYRYIEENKERDA RLNPNQWWKVFDE SVTHFRFAFISGSFT GGFKDRIELISMRSG ICGAAVNSVNLLLM AEELKSGRLDYEE WFQYFDCNDEISF | 103 | CTGCCCGTGAAGAGCGAGGTGAGCGTGTTCAAGGACTACCTGA GGACCCACCTGACCCACGTGGACCACAGGTACCTGATCCTGGTG GACCTGGGCTTCGACGGCAGCAGCGACAGGGACTACGAGATGA AGACCGCCGAGCTGTTCACCGCCGAGCTGGGCTTCATGGGCGCC AGGCTGGGCGACACCAGGAAGCCCGACGTGTGCGTGTACCACG GCGCCAACGGCCTGATCATCGACAACAAGGCCTACGGCAAGGG CTACAGCCTGCCCATCAAGCAGGCCGACGAGATCTACAGGTACA TCGAGGAGAACAAGGAGAGGGACGCCAGGCTGAACCCCAACCA GTGGTGGAAGGTGTTCGACGAGAGCGTGACCCACTTCAGGTTCG CCTTCATCAGCGGCAGCTTCACCGGCGGCTTCAAGGACAGGATC GAGCTGATCAGCATGAGGAGCGGCATCTGCGGCGCCGCCGTGA ACAGCGTGAACCTGCTGCTGATGGCCGAGGAGCTGAAGAGCGG CAGGCTGGACTACGAGGAGTGGTTCCAGTACTTCGACTGCAACG ACGAGATCAGCTTC |
| 23 | ISVKSDMAVVKDSV RERLAHVSHEYLILI DLGFDGTSDRDYEI QTAELFTRELDFLG GRLGDTRKPDVCIY YGKDGMIIDNKAY GKGYSLPIKQADEM YRYLEENKERNEKI NPNRWWKVFDEGV TDYRFAFVSGSFTG GFKDRLENIHMRSG LCGGAIDSVTLLLL AEELKAGRMEYSEF FRLFDCNDEVTF | 104 | ATCAGCGTGAAGAGCGACATGGCCGTGGTGAAGGACAGCGTGA GGGAGAGGCTGGCCCACGTGAGCCACGAGTACCTGATCCTGATC GACCTGGGCTTCGACGGCACCAGCGACAGGGACTACGAGATCC AGACCGCCGAGCTGTTCACCAGGGAGCTGGACTTCCTGGGCGGC AGGCTGGGCGACACCAGGAAGCCCGACGTGTGCATCTACTACG GCAAGGACGGCATGATCATCGACAACAAGGCCTACGGCAAGGG CTACAGCCTGCCCATCAAGCAGGCCGACGAGATGTACAGGTACC TGGAGGAGAACAAGGAGAGGAACGAGAAGATCAACCCCAACA GGTGGTGGAAGGTGTTCGACGAGGGCGTGACCGACTACAGGTT CGCCTTCGTGAGCGGCAGCTTCACCGGCGGCTTCAAGGACAGGC TGGAGAACATCCACATGAGGAGCGGCCTGTGCGGCGGCGCCAT CGACAGCGTGACCCTGCTGCTGCTGGCCGAGGAGCTGAAGGCC GGCAGGATGGAGTACAGCGAGTTCTTCAGGCTGTTCGACTGCAA CGACGAGGTGACCTTC |
| 24 | ELKDKAADAVKAK FLKLTGLSMKYIEL LDIAYDSSRNRDFEI LTADLFKNVYGLD AMHLGGGRKPDAI AQTSHFGIIIDTKAY GNGYSKSISQEDEM VRYIEDNQQRSITR NSVEWWKNFNSSIP STAFYFLWVSSKFV GKFDDQLLATYNR TNTCGGALNVEQLL IGAYKVKAGLLGIG QIPSYFKNKEIAW | 105 | GAGCTGAAGGACAAGGCCGCCGACGCCGTGAAGGCCAAGTTCC TGAAGCTGACCGGCCTGAGCATGAAGTACATCGAGCTGCTGGAC ATCGCCTACGACAGCAGCAGGAACAGGGACTTCGAGATCCTGA CCGCCGACCTGTTCAAGAACGTGTACGGCCTGGACGCCATGCAC CTGGGCGGCGGCAGGAAGCCCGACGCCATCGCCCAGACCAGCC ACTTCGGCATCATCATCGACACCAAGGCCTACGGCAACGGCTAC AGCAAGAGCATCAGCCAGGAGGACGAGATGGTGAGGTACATCG AGGACAACCAGCAGAGGAGCATCACCAGGAACAGCGTGGAGTG GTGGAAGAACTTCAACAGCAGCATCCCCAGCACCGCCTTCTACT TCCTGTGGGTGAGCAGCAAGTTCGTGGGCAAGTTCGACGACCAG CTGCTGGCCACCTACAACAGGACCAACACCTGCGGCGGCGCCCT GAACGTGGAGCAGCTGCTGATCGGCGCCTACAAGGTGAAGGCC GGCCTGCTGGGCATCGGCCAGATCCCCAGCTACTTCAAGAACAA GGAGATCGCCTGG |
| 25 | ISVKSDMAVVKDSV RERLAHVSHEYLLL IDLGFDGTSDRDYEI QTAELLTRELDFLG GRLGDTRKPDVCIY YGKDGMIIDNKAY GKGYSLPIKQADEM YRYLEENKERNEKI NPNRWWKVFDEGV | 106 | ATCAGCGTGAAGAGCGACATGGCCGTGGTGAAGGACAGCGTGA GGGAGAGGCTGGCCCACGTGAGCCACGAGTACCTGCTGCTGATC GACCTGGGCTTCGACGGCACCAGCGACAGGGACTACGAGATCC AGACCGCCGAGCTGCTGACCAGGGAGCTGGACTTCCTGGGCCGG CAGGCTGGGCGACACCAGGAAGCCCGACGTGTGCATCTACTAC GGCAAGGACGGCATGATCATCGACAACAAGGCCTACGGCAAGG GCTACAGCCTGCCCATCAAGCAGGCCGACGAGATGTACAGGTA CCTGGAGGAGAACAAGGAGAGGAACGAGAAGATCAACCCCAAC AGGTGGTGGAAGGTGTTCGACGAGGGCGTGACCGACTACAGGT |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
|  | TDYRFAFVSGSFTG GFKDRLENIHMRSG LCGGAIDSVTLLLL AEELKAGRMEYSEF FRLFDCNDEVTF | | TCGCCTTCGTGAGCGGCAGCTTCACCGGCGGCTTCAAGGACAGG CTGGAGAACATCCACATGAGGAGCGGCCTGTGCGGCGGCGCCA TCGACAGCGTGACCCTGCTGCTGCTGGCCGAGGAGCTGAAGGCC GGCAGGATGGAGTACAGCGAGTTCTTCAGGCTGTTCGACTGCAA CGACGAGGTGACCTTC |
| 26 | ELKDEQAEKRKAK FLKETNLPMKYIEL LDIAYDGKRNRDFE IVTMELFRNVYRLH SKLLGGGRKPDGLL YQDRFGVIVDTKAY GKGYSKSINQADE MIRYIEDNKRRDEN RNPIKWWEAFPDTI PQEEFYFMWVSSKF IGKFQEQLDYTSNE TQIKGAALNVEQLL LGADLVLKGQLHIS DLPSYFQNKEIEF | 107 | GAGCTGAAGGACGAGCAGGCCGAGAAGAGGAAGGCCAAGTTCC TGAAGGAGACCAACCTGCCCATGAAGTACATCGAGCTGCTGGA CATCGCCTACGACGGCAAGAGGAACAGGGACTTCGAGATCGTG ACCATGGAGCTGTTCAGGAACGTGTACAGGCTGCACAGCAAGCT GCTGGGCGGCGGCAGGAAGCCCGACGGCCTGCTGTACCAGGAC AGGTTCGGCGTGATCGTGGACACCAAGGCCTACGGCAAGGGCT ACAGCAAGAGCATCAACCAGGCCGACGAGATGATCAGGTACAT CGAGGACAACAAGAGGAGGGACGAGAACAGGAACCCCATCAA GTGGTGGGAGGCCTTCCCCGACACCATCCCCCAGGAGGAGTTCT ACTTCATGTGGGTGAGCAGCAAGTTCATCGGCAAGTTCCAGGAG CAGCTGGACTACACCAGCAACGAGACCCAGATCAAGGGCGCCG CCCTGAACGTGGAGCAGCTGCTGCTGGGCGCCGACCTGGTGCTG AAGGGCCAGCTGCACATCAGCGACCTGCCCAGCTACTTCCAGAA CAAGGAGATCGAGTTC |
| 27 | RNLDNVERDNRKA EFLAKTSLPPRFIEL LSIAYESKSNRDFE MITAELFKDVYGLG AVHLGNAKKPDAL AFNDDFGIIIDTKAY SNGYSKNINQEDEM VRYIEDNQIRSPDR NNNEWWLSFPPSIP ENDFHFLWVSSYFT GRFEEQLQETSART GGTTGGALDVEQL LIGGSLIQEGSLAPH EVPAYMQNRVIHF | 108 | AGGAACCTGGACAACGTGGAGAGGGACAACAGGAAGGCCGAGT TCCTGGCCAAGACCAGCCTGCCCCCCAGGTTCATCGAGCTGCTG AGCATCGCCTACGAGAGCAAGAGCAACAGGGACTTCGAGATGA TCACCGCCGAGCTGTTCAAGGACGTGTACGGCCTGGGCGCCGTG CACCTGGGCAACGCCAAGAAGCCCGACGCCCTGGCCTTCAACG ACGACTTCGGCATCATCATCGACACCAAGGCCTACAGCAACGGC TACAGCAAGAACATCAACCAGGAGGACGAGATGGTGAGGTACA TCGAGGACAACCAGATCAGGAGCCCCGACAGGAACAACAACGA GTGGTGGCTGAGCTTCCCCCCCAGCATCCCCGAGAACGACTTCC ACTTCCTGTGGGTGAGCAGCTACTTCACCGGCAGGTTCGAGGAG CAGCTGCAGGAGACCAGCGCCAGGACCGGCGGCACCACCGGCG GCGCCCTGGACGTGGAGCAGCTGCTGATCGGCGGCAGCCTGATC CAGGAGGGCAGCCTGGCCCCCACGAGGTGCCCGCCTACATGC AGAACAGGGTGATCCACTTC |
| 28 | SPVKSEVSVFKDYL RTHLTHVDHRYLIL VDLGFDGSSDRDYE MKTAELFTAELGF MGARLGDTRKPDV CVYHGAHGLIIDNK AYGKGYSLPIKQAD EIYRYIEENKERAV RLNPNQWWKVFDE SVAHFRFAFISGSFT GGFKDRIELISMRSG ICGAAVNSVNLLLM AEELKSGRLNYEE WFQYFDCNDEISL | 109 | AGCCCCGTGAAGAGCGAGGTGAGCGTGTTCAAGGACTACCTGA GGACCCACCTGACCCACGTGGACCACAGGTACCTGATCCTGGTG GACCTGGGCTTCGACGGCAGCAGCGACAGGGACTACGAGATGA AGACCGCCGAGCTGTTCACCGCCGAGCTGGGCTTCATGGGCGCC AGGCTGGGCGACACCAGGAAGCCCGACGTGTGCGTGTACCACG GCGCCCACGGCCTGATCATCGACAACAAGGCCTACGGCAAGGG CTACAGCCTGCCCATCAAGCAGGCCGACGAGATCTACAGGTACA TCGAGGAGAACAAGGAGAGGGCCGTGAGGCTGAACCCCAACCA GTGGTGGAAGGTGTTCGACGAGAGCGTGGCCCACTTCAGGTTCG CCTTCATCAGCGGCAGCTTCACCGGCGGCTTCAAGGACAGGATC GAGCTGATCAGCATGAGGAGCGGCATCTGCGGCGCCGCCGTGA ACAGCGTGAACCTGCTGCTGATGGCCGAGGAGCTGAAGAGCGG CAGGCTGAACTACGAGGAGTGGTTCCAGTACTTCGACTGCAACG ACGAGATCAGCCTG |
| 29 | TLVDIEKERKKAYF LKETSLSPRYIELLEI AFDPKRNRDFEVIT AELLKAGYGLKAK VLGGGRRPDGIAYT KDYGLIVDTKAYSN GYGKNIGQADEMIR YIEDNQKRDNKRNP IEWWREFEVQIPAN SYYYLWVSGRFTG RFDEQLVYTSSQTN TRGGALEVEQLLW GADAVMKGKLNVS DLPKYMNNSIIKL | 110 | ACCCTGGTGGACATCGAGAAGGAGAGGAAGAAGGCCTACTTCC TGAAGGAGACCAGCCTGAGCCCCAGGTACATCGAGCTGCTGGA GATCGCCTTCGACCCCAAGAGGAACAGGGACTTCGAGGTGATC ACCGCCGAGCTGCTGAAGGCCGGCTACGGCCTGAAGGCCAAGG TGCTGGGCGGCGGCAGGAGGCCCGACGGCATCGCCTACACCAA GGACTACGGCCTGATCGTGGACACCAAGGCCTACAGCAACGGC TACGGCAAGAACATCGGCCAGGCCGACGAGATGATCAGGTACA TCGAGGACAACCAGAAGAGGGACAACAAGAGGAACCCCATCGA GTGGTGGAGGGAGTTCGAGGTGCAGATCCCCGCCAACAGCTACT ACTACCTGTGGGTGAGCGGCAGGTTCACCGGCAGGTTCGACGAG CAGCTGGTGTACACCAGCAGCCAGACCAACACCAGGGGCGGCG CCCTGGAGGTGGAGCAGCTGCTGTGGGGCGCCGACGCCGTGAT GAAGGGCAAGCTGAACGTGAGCGACCTGCCCAAGTACATGAAC AACAGCATCATCAAGCTG |
| 30 | ELRDKVIEEQKAIFL QKTKLPLSYIELLEI ARDKRSRDFELITI ELFKNIYKINARILG GARKPDGVLYMPE FGVIVDTKAYADG YSKSIAQADEMIRYI EDNKRRDPSRNSTK | 111 | GAGCTGAGGGACAAGGTGATCGAGGAGCAGAAGGCCATCTTCC TGCAGAAGACCAAGCTGCCCCTGAGCTACATCGAGCTGCTGGAG ATCGCCAGGGACAAGAGGAGCAGGGACTTCGAGCTGATCA CCATCGAGCTGTTCAAGAACATCTACAAGATCAACGCCAGGATC CTGGGCGGCGCCAGGAAGCCCGACGGCGTGCTGTACATGCCCG AGTTCGGCGTGATCGTGGACACCAAGGCCTACGCCGACGGCTAC AGCAAGAGCATCGCCCAGGCCGACGAGATGATCAGGTACATCG AGGACAACAAGAGGAGGGACCCCAGCAGGAACAGCACCAAGT |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
|  | WWEHFPTSIPANNF YFLWVSSVFVNKFH EQLSYTAQETQTVG AALSVEQLLLGADS VLKGNLTTEKFIDSF KNQEIVF | | GGTGGGAGCACTTCCCCACCAGCATCCCCGCCAACAACTTCTAC TTCCTGTGGGTGAGCAGCGTGTTCGTGAACAAGTTCCACGAGCA GCTGAGCTACACCGCCCAGGAGACCCAGACCGTGGGCGCCGCC CTGAGCGTGGAGCAGCTGCTGCTGGGCGCCGACAGCGTGCTGA AGGGCAACCTGACCACCGAGAAGTTCATCGACAGCTTCAAGAA CCAGGAGATCGTGTTC |
| 31 | GATKSDLSLLKDDI RKKLNHINHKYLVL IDLGFDGTADRDYE LQTADLLTSELAFK GARLGDSRKPDVC VYHDKNGLIIDNKA YGSGYSLPIKQADE MLRYIEENQKRDK ALNPNEWWTIFDD AVSKFNPAFVSGEF TGGFKDRLENISRR SYTNGAAINSVNLL LLAEEIKSGRISYGD AFTKFECNDEIII | 112 | GGCGCCACCAAGAGCGACCTGAGCCTGCTGAAGGACGACATCA GGAAGAAGCTGAACCACATCAACCACAAGTACCTGGTGCTGAT CGACCTGGGCTTCGACGGCACCGCCGACAGGGACTACGAGCTG CAGACCGCCGACCTGCTGACCAGCGAGCTGGCCTTCAAGGGCGC CAGGCTGGGCGACAGCAGGAAGCCCGACGTGTGCGTGTACCAC GACAAGAACGGCCTGATCATCGACAACAAGGCCTACGGCAGCG GCTACAGCCTGCCCATCAAGCAGGCCGACGAGATGCTGAGGTA CATCGAGGAGAACCAGAAGAGGGACAAGGCCCTGAACCCCAAC GAGTGGTGGACCATCTTCGACGACGCCGTGAGCAAGTTCAACTT CGCCTTCGTGAGCGGCGAGTTCACCGGCGGCTTCAAGGACAGGC TGGAGAACATCAGCAGGAGGAGCTACACCAACGGCGCCGCCAT CAACAGCGTGAACCTGCTGCTGCTGGCCGAGGAGATCAAGAGC GGCAGGATCAGCTACGGCGACGCCTTCACCAAGTTCGAGTGCAA CGACGAGATCATCATC |
| 32 | ELRNAALDKQKVN FINKTGLPMKYIELL EIAFDGSRNRDFEM VTADLFKNVYGFNS ILLGGGRKPDGLIFT DRFGVIIDTKAYGN GYSKSIGQEDEMVR YIEDNQLRDSNRNS VEWWKNFDEKIESE NFYFMWISSKFIGQ FSDQLQSTSDRTNT KGAALNVEQLLLG AAAARDGKLDINSL PIYMNNKEILW | 113 | GAGCTGAGGAACGCCGCCCTGGACAAGCAGAAGGTGAACTTCA TCAACAAGACCGGCCTGCCCATGAAGTACATCGAGCTGCTGGAG ATCGCCTTCGACGGCAGCAGGAACAGGGACTTCGAGATGGTGA CCGCCGACCTGTTCAAGAACGTGTACGGCTTCAACAGCATCCTG CTGGGCGGCGGCAGGAAGCCCGACGGCCTGATCTTCACCGACA GGTTCGGCGTGATCATCGACACCAAGGCCTACGGCAACGGCTAC AGCAAGAGCATCGGCCAGGAGGACGAGATGGTGAGGTACATCG AGGACAACCAGCTGAGGGACAGCAACAGGAACAGCGTGGAGTG GGTGGAAGAACTTCGACGAGAAGATCGAGAGCGAGAACTTCTAC TTCATGTGGATCAGCAGCAAGTTCATCGGCCAGTTCAGCGACCA GCTGCAGAGCACCAGCGACAGGACCAACACCAAGGGCGCCGCC CTGAACGTGGAGCAGCTGCTGCTGGGCGCCGCCGCCGCCAGGG ACGGCAAGCTGGACATCAACAGCCTGCCCATCTACATGAACAAC AAGGAGATCCTGTGG |
| 33 | ELKDEQSEKRKAYF LKETNLPLKYIELLD IAYDGKRNRDFEIV TMELFRNVYRLQSK LLGGVRKPDGLLY KHRFGIIVDTKAYG EGYSKSISQADEMI RYIEDNKRRDENRN STKWWEHFPDCIPK QSFYFMWVSSKFV GKFQEQLDYTANET KTNGAALNVEQLL WGADLVAKGKLDI SQLPSYFQNKEIEF | 114 | GAGCTGAAGGACGAGCAGAGCGAGAAGAGGAAGGCCTACTTCC TGAAGGAGACCAACCTGCCCCTGAAGTACATCGAGCTGCTGGAC ATCGCCTACGACGGCAAGAGGAACAGGGACTTCGAGATCGTGA CCATGGAGCTGTTCAGGAACGTGTACAGGCTGCAGAGCAAGCT GCTGGGCGGCGTGAGGAAGCCCGACGGCCTGCTGTACAAGCAC AGGTTCGGCATCATCGTGGACACCAAGGCCTACGGCGAGGGCT ACAGCAAGAGCATCAGCCAGGCCGACGAGATGATCAGGTACAT CGAGGACAACAAGAGGAGGGACGAGAACAGGAACAGCACCAA GTGGTGGGAGCACTTCCCCGACTGCATCCCCAAGCAGAGCTTCT ACTTCATGTGGGTGAGCAGCAAGTTCGTGGGCAAGTTCCAGGAG CAGCTGGACTACACCGCCAACGAGACCAAGACCAACGGCGCCG CCCTGAACGTGGAGCAGCTGCTGTGGGGCGCCGACCTGGTGGCC AAGGGCAAGCTGGACATCAGCCAGCTGCCCAGCTACTTCCAGA ACAAGGAGATCGAGTTC |
| 34 | HNNKFKNYLRENSE LSFKFIELIDIAYDG NRNRDMEIITAELL KEIYGLNVKLLGGG RKPDILAYTDDIGIII DTKAYKDGYGKQI NQADEMIRYIEDNQ RRDLIRNPNEWWR YFPKSISKEKIYFM WISSYFKNNFYEQV QYTAQETKSIGAAL NVRQLLLCADAIQK EVLSLDTFLGSFRN EEINL | 115 | CACAACAACAAGTTCAAGAACTACCTGAGGGAGAACAGCGAGC TGAGCTTCAAGTTCATCGAGCTGATCGACATCGCCTACGACGGC AACAGGAACAGGGACATGGAGATCATCACCGCCGAGCTGCTGA AGGAGATCTACGGCCTGAACGTGAAGCTGCTGGGCGGCGGCAG GAAGCCCGACATCCTGGCCTACACCGACGACATCGGCATCATCA TCGACACCAAGGCCTACAAGGACGGCTACGGCAAGCAGATCAA CCAGGCCGACGAGATGATCAGGTACATCGAGGACAACCAGAGG AGGGACCTGATCAGGAACCCCAACGAGTGGTGGAGGTACTTCC CCAAGAGCATCAGCAAGGAGAAGATCTACTTCATGTGGATCAG CAGCTACTTCAAGAACAACTTCTACGAGCAGGTGCAGTACACCG CCCAGGAGACCAAGAGCATCGGCGCCGCCCTGAACGTGAGGCA GCTGCTGCTGTGCGCCGACGCCATCCAGAAGGAGGTGCTGAGCC TGGACACCTTCCTGGGCAGCTTCAGGAACGAGGAGATCAACCTG |
| 35 | LPVKSEVSILKDYL RSHLTHIDHKYLILV DLGYDGTSDRDYEI QTAQLLTAELSFLG GRLGDTRKPDVCIY YEDNGLIIDNKAYG KGYSLPMKQADEM YRYIEENKERSELL | 116 | CTGCCCGTGAAGAGCGAGGTGAGCATCCTGAAGGACTACCTGA GGAGCCACCTGACCCACATCGACCACAAGTACCTGATCCTGGTG GACCTGGGCTACGACGGCACCAGCGACAGGGACTACGAGATCC AGACCGCCCAGCTGCTGACCGCCGAGCTGAGCTTCCTGGGCGGC AGGCTGGGCGACACCAGGAAGCCCGACGTGTGCATCTACTACG AGGACAACGGCCTGATCATCGACAACAAGGCCTACGGCAAGGG CTACAGCCTGCCCATGAAGCAGGCCGACGAGATGTACAGGTAC ATCGAGGAGAACAAGGAGAGGAGCGAGCTGCTGAACCCCAACT |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
| | NPNCWWNIFDKDV KTFHFAFLSGEFTG GFRDRLNHISMRSG MRGAAVNSANLLI MAEKLKAGTMEYE EFFRLFDTNDEILF | | GCTGGTGGAACATCTTCGACAAGGACGTGAAGACCTTCCACTTC GCCTTCCTGAGCGGCGAGTTCACCGGCGGCTTCAGGGACAGGCT GAACCACATCAGCATGAGGAGCGGCATGAGGGGCGCCGCCGTG AACAGCGCCAACCTGCTGATCATGGCCGAGAAGCTGAAGGCCG GCACCATGGAGTACGAGGAGTTCTTCAGGCTGTTCGACACCAAC GACGAGATCCTGTTC |
| 36 | LPVKSQVSILKDYL RSYLSHVDHKYLIL LDLGFDGTSDRDYE IWTAQLLTAELSFL GGRLGDTRKPDVCI YYEDNGLIIDNKAY GKGYSLPIKQADEM YRYIEENKERSDLL NPNCWWNIFGEGV KTFRFAFLSGEFTG GFKDRLNHISMRSG IKGAAVNSANLLIM AEQLKSGTMSYEEF FQLFDYNDEIIF | 117 | CTGCCCGTGAAGAGCCAGGTGAGCATCCTGAAGGACTACCTGA GGAGCTACCTGAGCCACGTGGACCACAAGTACCTGATCCTGCTG GACCTGGGCTTCGACGGCACCAGCGACAGGGACTACGAGATCT GGACCGCCCAGCTGCTGACCGCCGAGCTGAGCTTCCTGGGCGGC AGGCTGGGCGACACCAGGAAGCCCGACGTGTGCATCTACTACG AGGACAACGGCCTGATCATCGACAACAAGGCCTACGGCAAGGG CTACAGCCTGCCCATCAAGCAGGCCGACGAGATGTACAGGTAC ATCGAGGAGAACAAGGAGAGGAGCGACCTGCTGAACCCCAACT GCTGGTGGAACATCTTCGGCGAGGGCGTGAAGACCTTCAGGTTC GCCTTCCTGAGCGGCGAGTTCACCGGCGGCTTCAAGGACAGGCT GAACCACATCAGCATGAGGAGCGGCATCAAGGGCGCCGCCGTG AACAGCGCCAACCTGCTGATCATGGCCGAGCAGCTGAAGAGCG GCACCATGAGCTACGAGGAGTTCTTCCAGCTGTTCGACTACAAC GACGAGATCATCTTC |
| 37 | VSKTNILELKDNTR EKLVYLDHRYLSLF DLAYDDKASRDFEI QTIDLLINELQFKGL RLGERRKPDGIISYG VNGVIIDNKAYSKG YNLPIRQADEMIRYI QENQSRDEKLNPNK WWENFEEETSKFN YLFISSKFISGFKKN LQYIADRTGVNGG AINVENLLCFAEML KSGKLEYNDFFNQY NNDEIIM | 118 | GTGAGCAAGACCAACATCCTGGAGCTGAAGGACAACACCAGGG AGAAGCTGGTGTACCTGGACCACAGGTACCTGAGCCTGTTCGAC CTGGCCTACGACGACAAGGCCAGCAGGGACTTCGAGATCCAGA CCATCGACCTGCTGATCAACGAGCTGCAGTTCAAGGGCCTGAGG CTGGGCGAGAGGAGGAAGCCCGACGGCATCATCAGCTACGGCG TGAACGGCGTGATCATCGACAACAAGGCCTACAGCAAGGGCTA CAACCTGCCCATCAGGCAGGCCGACGAGATGATCAGGTACATCC AGGAGAACCAGAGCAGGGACGAGAAGCTGAACCCCAACAAGTG GTGGGAGAACTTCGAGGAGGAGACCAGCAAGTTCAACTACCTG TTCATCAGCAGCAAGTTCATCAGCGGCTTCAAGAAGAACCTGCA GTACATCGCCGACAGGACCGGCGTGAACGGCGGCGCCATCAAC GTGGAGAACCTGCTGTGCTTCGCCGAGATGCTGAAGAGCGGCA AGCTGGAGTACAACGACTTCTTCAACCAGTACAACAACGACGA GATCATCATG |
| 38 | LPVKSQVSILKDYL RSCLSHVDHKYLIL LDLGFDGTSDRDYE IQTAQLLTAELSFLG GRLGDTRKPDVCIY YEDNGLIIDNKAYG KGYSLPIKQADEMY RYIEENKERSELLNP NCWWNIFDEGVKT FRFAFLSGEFTGGF KDRLNHISMRSGIK GAAVNSANLLIIAE QLKSGTMSYEEFFQ LFDQNDEITV | 119 | CTGCCCGTGAAGAGCCAGGTGAGCATCCTGAAGGACTACCTGA GGAGCTGCCTGAGCCACGTGGACCACAAGTACCTGATCCTGCTG GACCTGGGCTTCGACGGCACCAGCGACAGGGACTACGAGATCC AGACCGCCCAGCTGCTGACCGCCGAGCTGAGCTTCCTGGGCGGC AGGCTGGGCGACACCAGGAAGCCCGACGTGTGCATCTACTACG AGGACAACGGCCTGATCATCGACAACAAGGCCTACGGCAAGGG CTACAGCCTGCCCATCAAGCAGGCCGACGAGATGTACAGGTAC ATCGAGGAGAACAAGGAGAGGAGCGAGCTGCTGAACCCCAACT GCTGGTGGAACATCTTCGACGAGGGCGTGAAGACCTTCAGGTTC GCCTTCCTGAGCGGCGAGTTCACCGGCGGCTTCAAGGACAGGCT GAACCACATCAGCATGAGGAGCGGCATCAAGGGCGCCGCCGTG AACAGCGCCAACCTGCTGATCATCGCCGAGCAGCTGAAGAGCG GCACCATGAGCTACGAGGAGTTCTTCCAGCTGTTCGACCAGAAC GACGAGATCACCGTG |
| 39 | MSSKSEISVIKDNIR KRLNHINHKYLVLI DLGFDGTADRDYE LQTADLLTSELSFK GARLGDTRKPDVC VYHGTNGLIIDNKA YGKGYSLPIKQADE MLRYIEENQKRDKS LNPNEWWTIFDDA VSKFNFAFVSGEFT GGFKDRLENISRRSS VNGAAINSVNLLLL AEEIKSGRMSYSDA FKNFDCNKEITI | 120 | ATGAGCAGCAAGAGCGAGATCAGCGTGATCAAGGACAACATCA GGAAGAGGCTGAACCACATCAACCACAAGTACCTGGTGCTGAT CGACCTGGGCTTCGACGGCACCGCCGACAGGGACTACGAGCTG CAGACCGCCGACCTGCTGACCAGCGAGCTGAGCTTCAAGGGCG CCAGGCTGGGCGACACCAGGAAGCCCGACGTGTGCGTGTACCA CGGCACCAACGGCCTGATCATCGACAACAAGGCCTACGGCAAG GGCTACAGCCTGCCCATCAAGCAGGCCGACGAGATGCTGAGGT ACATCGAGGAGAACCAGAAGAGGGACAAGAGCCTGAACCCCAA CGAGTGGTGGACCATCTTCGACGACGCCGTGAGCAAGTTCAACT TCGCCTTCGTGAGCGGCGAGTTCACCGGCGGCTTCAAGGACAGG CTGGAGAACATCAGCAGGAGGAGCAGCGTGAACGGCGCCGCCA TCAACAGCGTGAACCTGCTGCTGCTGGCCGAGGAGATCAAGAG CGGCAGGATGAGCTACAGCGACGCCTTCAAGAACTTCGACTGCA ACAAGGAGATCACCATC |
| 40 | RNLDKVERDSRKA EFLAKTSLPPRFIEL LSIAYESKSNRDFE MITAEFFKDVYGLG AVHLGNARKPDAL AFTDNFGIVIDTKA YSNGYSKNINQEDE | 121 | AGGAACCTGGACAAGGTGGAGAGGGACAGCAGGAAGGCCGAG TTCCTGGCCAAGACCAGCCTGCCCCCCAGGTTCATCGAGCTGCT GAGCATCGCCTACGAGAGCAAGAGCAACAGGGACTTCGAGATG ATCACCGCCGAGTTCTTCAAGGACGTGTACGGCCTGGGCGCCGT GCACCTGGGCAACGCCAGGAAGCCCGACGCCCTGGCCTTCACCG ACAACTTCGGCATCGTGATCGACACCAAGGCCTACAGCAACGGC TACAGCAAGAACATCAACCAGGAGGACGAGATGGTGAGGTACA |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
| | MVRYIEDNQIRSPE RNKNEWWLSFPPSI PENNFHFLWVSSYF TGYFEEQLQETSDR AGGMTGGALDIEQ LLIGGSLVQEGKLA PHDIPEYMQNRVIH F | | TCGAGGACAACCAGATCAGGAGCCCCGAGAGGAACAAGAACGA GTGGTGGCTGAGCTTCCCCCCAGCATCCCCGAGAACAACTTCC ACTTCCTGTGGGTGAGCAGCTACTTCACCGGCTACTTCGAGGAG CAGCTGCAGGAGACCAGCGACAGGGCCGGCGGCATGACCGGCG GCGCCCTGGACATCGAGCAGCTGCTGATCGGCGGCAGCCTGGTG CAGGAGGGCAAGCTGGCCCCCCACGACATCCCCGAGTACATGC AGAACAGGGTGATCCACTTC |
| 41 | APVKSEVSLCKDIL RSHLTHVDHKYLIL LDLGFDGTSDRDYE IQTAQLLTAELDFK GARLGDTRKPDVC VYYGEDGLILDNKA YGKGYSLPIKQADE MYRYIEENKERNER LNPNKWWEIFDKD VVRYHFAFVSGTFT GGFKERLDNIRMRS GICGAAVNSMNLLL MAEELKSGRLGYK ECFALFDCNDEIAF | 122 | GCCCCCGTGAAGAGCGAGGTGAGCCTGTGCAAGGACATCCTGA GGAGCCACCTGACCCACGTGGACCACAAGTACCTGATCCTGCTG GACCTGGGCTTCGACGGCACCAGCGACAGGGACTACGAGATCC AGACCGCCCAGCTGCTGACCGCCGAGCTGGACTTCAAGGGCGCC AGGCTGGGCGACACCAGGAAGCCCGACGTGTGCGTGTACTACG GCGAGGACGGCCTGATCCTGGACAACAAGGCCTACGGCAAGGG CTACAGCCTGCCCATCAAGCAGGCCGACGAGATGTACAGGTAC ATCGAGGAGAACAAGGAGAGGAACGAGAGGCTGAACCCCAAC AAGTGGTGGGAGATCTTCGACAAGGACGTGGTGAGGTACCACTT CGCCTTCGTGAGCGGCACCTTCACCGGCGGCTTCAAGGAGAGGC TGGACAACATCAGGATGAGGAGCGGCATCTGCGGCGCCGCCGT GAACAGCATGAACCTGCTGCTGATGGCCGAGGAGCTGAAGAGC GGCAGGCTGGGCTACAAGGAGTGCTTCGCCCTGTTCGACTGCAA CGACGAGATCGCCTTC |
| 42 | SCVKDEVNDIVDRV RVKLKNIDHKYLILI SLAYSDETERTKKN SDARDFEIQTAELFT KELGFNGIRLGESN KPDVLISFGANGTII DNKSYKDGFNIPRV TSDQMIRYINENNQ RTTQLNPNEWWKN FDSSVSNYTFLFVTS FLKGSFKNQIEYISN ATNGTRGAAINVES LLYISEDIKSGKIKQ SDFYSEFKNDEIVY | 123 | AGCTGCGTGAAGGACGAGGTGAACGACATCGTGGACAGGGTGA GGGTGAAGCTGAAGAACATCGACCACAAGTACCTGATCCTGATC AGCCTGGCCTACAGCGACGAGACCGAGAGGACCAAGAAGAACA GCGACGCCAGGGACTTCGAGATCCAGACCGCCGAGCTGTTCACC AAGGAGCTGGGCTTCAACGGCATCAGGCTGGGCGAGAGCAACA AGCCCGACGTGCTGATCAGCTTCGGCGCCAACGGCACCATCATC GACAACAAGAGCTACAAGGACGGCTTCAACATCCCCAGGGTGA CCAGCGACCAGATGATCAGGTACATCAACGAGAACAACCAGAG GACCACCCAGCTGAACCCCAACGAGTGGTGGAAGAACTTCGAC AGCAGCGTGAGCAACTACACCTTCCTGTTCGTGACCAGCTTCCT GAAGGGCAGCTTCAAGAACCAGATCGAGTACATCAGCAACGCC ACCAACGGCACCAGGGGCGCCGCCATCAACGTGGAGAGCCTGC TGTACATCAGCGAGGACATCAAGAGCGGCAAGATCAAGCAGAG CGACTTCTACAGCGAGTTCAAGAACGACGAGATCGTGTAC |
| 43 | SQGDKAREQLKAK FLAKTNLLPRYVEL LDIAYDSKRNRDFE MVTAELFNFAYLLP AVHLGGVRKPDAL VATKKFGIIVDTKA YANGYSRNANQAD EMARYITENQKRDP KTNPNRWWDNFDA RIPPNAYYFLWVSS FFTGQFDDQLSYTA HRTNTHGGALNVE QLLIGANMIQTGQL DRNKLPEYMQDKEI TF | 124 | AGCCAGGGCGACAAGGCCAGGGAGCAGCTGAAGGCCAAGTTCC TGGCCAAGACCAACCTGCTGCCCAGGTACGTGGAGCTGCTGGAC ATCGCCTACGACAGCAAGAGGAACAGGGACTTCGAGATGGTGA CCGCCGAGCTGTTCAACTTCGCCTACCTGCTGCCCGCCGTGCAC CTGGGCGGCGTGAGGAAGCCCGACGCCCTGGTGGCCACCAAGA AGTTCGGCATCATCGTGGACACCAAGGCCTACGCCAACGGCTAC AGCAGGAACGCCAACCAGGCCGACGAGATGGCCAGGTACATCA CCGAGAACCAGAAGAGGGACCCCAAGACCAACCCCAACAGGTG GTGGGACAACTTCGACGCCAGGATCCCCCCCAACGCCTACTACT TCCTGTGGGTGAGCAGCTTCTTCACCGGCCAGTTCGACGACCAG CTGAGCTACACCGCCCACAGGACCAACACCCACGGCGGCGCCCT GAACGTGGAGCAGCTGCTGATCGGCGCCAACATGATCCAGACC GGCCAGCTGGACAGGAACAAGCTGCCCGAGTACATGCAGGACA AGGAGATCACCTTC |
| 44 | KVQKSNILDVIEKC REKINNIPHEYLALI PMSFDENESTMFEI KTIELLTEHCKFDG LHCGGASKPDGLIY SEDYGVIIDTKSYK DGFNIQTPERDKMK RYIEENQNRNPQHN KTRWWDEFPHNISN FLFLFVSGKFGGNF KEQLRILSEQTNNT LGGALSSYVLLNIA EQIAINKIDHCDFKT RISCLDEVA | 125 | AAGGTGCAGAAGAGCAACATCCTGGACGTGATCGAGAAGTGCA GGGAGAAGATCAACAACATCCCCCACGAGTACCTGGCCCTGATC CCCATGAGCTTCGACGAGAACGAGAGCACCATGTTCGAGATCA AGACCATCGAGCTGCTGACCGAGCACTGCAAGTTCGACGGCCTG CACTGCGGCGGCGCCAGCAAGCCCGACGGCCTGATCTACAGCG AGGACTACGGCGTGATCATCGACACCAAGAGCTACAAGGACGG CTTCAACATCCAGACCCCCGAGAGGGACAAGATGAAGAGGTAC ATCGAGGAGAACCAGAACAGGAACCCCCAGCACAACAAGACCA GGTGGTGGGACGAGTTCCCCCACAACATCAGCAACTTCCTGTTC CTGTTCGTGAGCGGCAAGTTCGGCGGCAACTTCAAGGAGCAGCT GAGGATCCTGAGCGAGCAGACCAACAACACCCTGGGCGGCGCC CTGAGCAGCTACGTGCTGCTGAACATCGCCGAGCAGATCGCCAT CAACAAGATCGACCACTGCGACTTCAAGACCAGGATCAGCTGCC TGGACGAGGTGGCC |
| 45 | VPVKSEVSLCKDYL RSYLTHVDHKYLIL LDLGFDGTSDRDYE IQTAQLLTAELDFK | 126 | GTGCCCGTGAAGAGCGAGGTGAGCCTGTGCAAGGACTACCTGA GGAGCTACCTGACCCACGTGGACCACAAGTACCTGATCCTGCTG GACCTGGGCTTCGACGGCACCAGCGACAGGGACTACGAGATCC AGACCGCCCAGCTGCTGACCGCCGAGCTGGACTTCAAGGGCGCC |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
|  | GARLGDTRKPDVC VYYGEDGLIIDNKA YGKGYSLPIKQADE IYRYIEENKKRDEK LNPNKWWEIFDKG VVRYHFAFVSGAFT GGFKERLDNIRMRS GICGAAINSMNLLL MAEELKSGRLGYEE CFALFDCNDEITF |  | AGGCTGGGCGACACCAGGAAGCCCGACGTGTGCGTGTACTACG GCGAGGACGGCCTGATCATCGACAACAAGGCCTACGGCAAGGG CTACAGCCTGCCCATCAAGCAGGCCGACGAGATCTACAGGTACA TCGAGGAGAACAAGAAGAGGGACGAGAAGCTGAACCCCAACA AGTGGTGGGAGATCTTCGACAAGGGCGTGGTGAGGTACCACTTC GCCTTCGTGAGCGGCGCCTTCACCGGCGGCTTCAAGGAGAGGCT GGACAACATCAGGATGAGGAGCGGCATCTGCGGCGCCGCCATC AACAGCATGAACCTGCTGCTGATGGCCGAGGAGCTGAAGAGCG GCAGGCTGGGCTACGAGGAGTGCTTCGCCCTGTTCGACTGCAAC GACGAGATCACCTTC |
| 46 | VPVKSEVSLCKDYL RSHLNHVDHRYLIL LDLGFDGTSDRDYE IQTAQLLTGELNFK GARLGDTRKPDVC VYYGEDGLIIDNKA YGKGYSLPIKQADE MYRYIEENKERNEK LNPNKWWEIFDKD VIHYHFAFVSGAFT GGFKERLENIRMRS GIYGAAVNSMNLLL MAEELKSGRLDYK ECFKLFDCNDEIVL | 127 | GTGCCCGTGAAGAGCGAGGTGAGCCTGTGCAAGGACTACCTGA GGAGCCACCTGAACCACGTGGACCACAGGTACCTGATCCTGCTG GACCTGGGCTTCGACGGCACCAGCGACAGGGACTACGAGATCC AGACCGCCCAGCTGCTGACCGGCGAGCTGAACTTCAAGGGCGC CAGGCTGGGCGACACCAGGAAGCCCGACGTGTGCGTGTACTAC GGCGAGGACGGCCTGATCATCGACAACAAGGCCTACGGCAAGG GCTACAGCCTGCCCATCAAGCAGGCCGACGAGATGTACAGGTA CATCGAGGAGAACAAGGAGAGGAACGAGAAGCTGAACCCCAAC AAGTGGTGGGAGATCTTCGACAAGGACGTGATCCACTACCACTT CGCCTTCGTGAGCGGCGCCTTCACCGGCGGCTTCAAGGAGAGGC TGGAGAACATCAGGATGAGGAGCGGCATCTACGGCGCCGCCGT GAACAGCATGAACCTGCTGCTGATGGCCGAGGAGCTGAAGAGC GGCAGGCTGGACTACAAGGAGTGCTTCAAGCTGTTCGACTGCAA CGACGAGATCGTGCTG |
| 47 | VPVKSEVSLLKDYL RSHLVHVDHKYLV LLDLGFDGTSDRDY EIQTAQLLTGELNF KGARLGDTRKPDV CVYYGEDGLIIDNK AYGKGYSLPIKQAD EMYRYIEENKERNE KLNPNKWWEIFGN DVIHYHFAFVSGAF TGGFKERLDNIRMR SGIYGAAVNSMNLL LAEELKSGRLGYK ECFKLFDCNDEIVL | 128 | GTGCCCGTGAAGAGCGAGGTGAGCCTGCTGAAGGACTACCTGA GGAGCCACCTGGTGCACGTGGACCACAAGTACCTGGTGCTGCTG GACCTGGGCTTCGACGGCACCAGCGACAGGGACTACGAGATCC AGACCGCCCAGCTGCTGACCGGCGAGCTGAACTTCAAGGGCGC CAGGCTGGGCGACACCAGGAAGCCCGACGTGTGCGTGTACTAC GGCGAGGACGGCCTGATCATCGACAACAAGGCCTACGGCAAGG GCTACAGCCTGCCCATCAAGCAGGCCGACGAGATGTACAGGTA CATCGAGGAGAACAAGGAGAGGAACGAGAAGCTGAACCCCAAC AAGTGGTGGGAGATCTTCGGCAACGACGTGATCCACTACCACTT CGCCTTCGTGAGCGGCGCCTTCACCGGCGGCTTCAAGGAGAGGC TGGACAACATCAGGATGAGGAGCGGCATCTACGGCGCCGCCGT GAACAGCATGAACCTGCTGCTGGCCGAGGAGCTGAAGAGC GGCAGGCTGGGCTACAAGGAGTGCTTCAAGCTGTTCGACTGCAA CGACGAGATCGTGCTG |
| 48 | ECVKDNVVDIKDR VRNKLIHLDHKYLA LIDLAYSDAASRAK KNADAREFEIQTAD LFTKELSFNGQRLG DSRKPDVIISYGLDG TIVDNKSYKDGFNI SRTCADEMSRYINE NNLRQKSLNPNEW WKNFDSTITAYTFL FITSYLKGQFEDQLE YVSNANGGIKGAAI GVESLLYLSEGIKA GRISHADFYSNFNN KEMIY | 129 | GAGTGCGTGAAGGACAACGTGGTGGACATCAAGGACAGGGTGA GGAACAAGCTGATCCACCTGGACCACAAGTACCTGGCCCTGATC GACCTGGCCTACAGCGACGCCGCCAGCAGGGCCAAGAAGAACG CCGACGCCAGGGAGTTCGAGATCCAGACCGCCGACCTGTTCACC AAGGAGCTGAGCTTCAACGGCCAGAGGCTGGGCGACAGCAGGA AGCCCGACGTGATCATCAGCTACGGCCTGGACGGCACCATCGTG GACAACAAGAGCTACAAGGACGGCTTCAACATCAGCAGGACCT GCGCCGACGAGATGAGCAGGTACATCAACGAGAACAACCTGAG GCAGAAGAGCCTGAACCCCAACGAGTGGTGGAAGAACTTCGAC AGCACCATCACCGCCTACACCTTCCTGTTCATCACCAGCTACCTG AAGGGCCAGTTCGAGGACCAGCTGGAGTACGTGAGCAACGCCA ACGGCGGCATCAAGGGCGCCGCCATCGGCGTGGAGAGCCTGCT GTACCTGAGCGAGGGCATCAAGGCCGGCAGGATCAGCCACGCC GACTTCTACAGCAACTTCAACAACAAGGAGATGATCTAC |
| 49 | IAKSDFSIIKDNIRRK LQYVNHKYLLLIDL GFDSDSNRDYEIQT AELLTTELAFKGAR LGDTRKPDVCVYY GENGLIIDNKAYSK GYSLPMSQADEMV RYIEENKARQSSINP NQWWKIFEDTVCN FNYAFVSGEFTGGF KDRLNNICERTRVS GGAINTINLLLLAEE LKSGRMSYPKCFSY FDTNDEVHI | 130 | ATCGCCAAGAGCGACTTCAGCATCATCAAGGACAACATCAGGA GGAAGCTGCAGTACGTGAACCACAAGTACCTGCTGCTGATCGAC CTGGGCTTCGACAGCGACAGCAACAGGGACTACGAGATCCAGA CCGCCGAGCTGCTGACCACCGAGCTGGCCTTCAAGGGCGCCAGG CTGGGCGACACCAGGAAGCCCGACGTGTGCGTGTACTACGGCG AGAACGGCCTGATCATCGACAACAAGGCCTACAGCAAGGGCTA CAGCCTGCCCATGAGCCAGGCCGACGAGATGGTGAGGTACATC GAGGAGAACAAGGCCAGGCAGGCCAGCAGCATCAACCCCAACCAGT GGTGGAAGATCTTCGAGGACACCGTGTGCAACTTCAACTACGCC TTCGTGAGCGGCGAGTTCACCGGCGGCTTCAAGGACAGGCTGAA CAACATCTGCGAGAGGACCAGGGTGAGCGGCGGCGCCATCAAC ACCATCAACCTGCTGCTGCTGGCCGAGGAGCTGAAGAGCGGCA GGATGAGCTACCCCAAGTGCTTCAGCTACTTCGACACCAACGAC GAGGTGCACATC |
| 50 | LKYLGIKKQNRAFE IITAELFNTSYKLSA |  131 | CTGAAGTACCTGGGCATCAAGAAGCAGAACAGGGCCTTCGAGA TCATCACCGCCGAGCTGTTCAACACCAGCTACAAGCTGAGCGCC |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
| | THLGGGRRPDVLV YNDNFGIIVDTKAY KDGYGRNVNQEDE MVRYITENNIRKQD INKNDWWKYFSKSI PSTSYYHLWISSQF VGMFSDQLRETSSR TGENGGAMNVEQL LIGANQVLNNVLDP NCLPKYMENKEIIF | | ACCCACCTGGGCGGCGGCAGGAGGCCCGACGTGCTGGTGTACA ACGACAACTTCGGCATCATCGTGGACACCAAGGCCTACAAGGA CGGCTACGGCAGGAACGTGAACCAGGAGGACGAGATGGTGAGG TACATCACCGAGAACAACATCAGGAAGCAGGACATCAACAAGA ACGACTGGTGGAAGTACTTCAGCAAGAGCATCCCCAGCACCAG CTACTACCACCTGTGGATCAGCAGCCAGTTCGTGGGCATGTTCA GCGACCAGCTGAGGGAGACCAGCAGCAGGACCGGCGAGAACGG CGGCGCCATGAACGTGGAGCAGCTGCTGATCGGCGCCAACCAG GTGCTGAACAACGTGCTGGACCCCAACTGCCTGCCCAAGTACAT GGAGAACAAGGAGATCATCTTC |
| 51 | VPVKSEVSLCKDYL RSHLNHVDHKYLIL LDLGFDGTSDRDYE IQTAQLLTGELNFK GARLGDTRKPDVC VYYGEDGLIIDNKA YGKGYSLPIKQADE MYRYIEENKERNEK LNPNKWWEIFDKD VIHYHFAFVSGAFT GGFRERLENIRMRS GIYGAAVNSMNLLL MAEELKSGRLGYK ECFKLFDCNDEIVL | 132 | GTGCCCGTGAAGAGCGAGGTGAGCCTGTGCAAGGACTACCTGA GGAGCCACCTGAACCACGTGGACCACAAGTACCTGATCCTGCTG GACCTGGGCTTCGACGGCACCAGCGACAGGGACTACGAGATCC AGACCGCCCAGCTGCTGACCGGCGAGCTGAACTTCAAGGGCGC CAGGCTGGGCGACACCAGGAAGCCCGACGTGTGCGTGTACTAC GGCGAGGACGGCCTGATCATCGACAACAAGGCCTACGGCAAGG GCTACAGCCTGCCCATCAAGCAGGCCGACGAGATGTACAGGTA CATCGAGGAGAACAAGGAGAGGAACGAGAAGCTGAACCCCAAC AAGTGGTGGGAGATCTTCGACAAGGACGTGATCCACTACCACTT CGCCTTCGTGAGCGGCGCCTTCACCGGCGGCTTCAGGGAGAGGC TGGAGAACATCAGGATGAGGAGCGGCATCTACGGCGCCGCCGT GAACAGCATGAACCTGCTGCTGATGGCCGAGGAGCTGAAGAGC GGCAGGCTGGGCTACAAGGAGTGCTTCAAGCTGTTCGACTGCAA CGACGAGATCGTGCTG |
| 52 | VPVKSEVSLLKDYL RTHLLHVDHRYLIL LDLGFDGTSDRDYE IQTAQLLTGELNFK GARLGDTRKPDVC VYYGEDGLIIDNKA YGKGYSLPIKQADE MYRYIEENKERNEK LNPNKWWEIFDND VIHYHFAFISGAFTG GFKERLDNIRMRSG IYGAAVNSMNLLL MAEELKSGRLGYK ECFKLFDCNDEIVL | 133 | GTGCCCGTGAAGAGCGAGGTGAGCCTGCTGAAGGACTACCTGA GGACCCACCTGCTGCACGTGGACCACAGGTACCTGATCCTGCTG GACCTGGGCTTCGACGGCACCAGCGACAGGGACTACGAGATCC AGACCGCCCAGCTGCTGACCGGCGAGCTGAACTTCAAGGGCGC CAGGCTGGGCGACACCAGGAAGCCCGACGTGTGCGTGTACTAC GGCGAGGACGGCCTGATCATCGACAACAAGGCCTACGGCAAGG GCTACAGCCTGCCCATCAAGCAGGCCGACGAGATGTACAGGTA CATCGAGGAGAACAAGGAGAGGAACGAGAAGCTGAACCCCAAC AAGTGGTGGGAGATCTTCGACAACGACGTGATCCACTACCACTT CGCCTTCATCAGCGGCGCCTTCACCGGCGGCTTCAAGGAGAGGC TGGACAACATCAGGATGAGGAGCGGCATCTACGCGCCGCCGT GAACAGCATGAACCTGCTGCTGATGGCCGAGGAGCTGAAGAGC GGCAGGCTGGGCTACAAGGAGTGCTTCAAGCTGTTCGACTGCAA CGACGAGATCGTGCTG |
| 53 | VPVKSEVSLCKDYL RSHLNHVDHKYLIL LDLGFDGTSDRDYE IQTAQLLTGELNFK GARLGDTRKPDVC VYYGEDGLIIDNKA YGKGYSLPIKQADE MYRYIEENKERNEK LNPNKWWEIFDND VIHYHFAFVSGAFT GGFRERLENIRMRS GIYGAAVNSMNLLL MAEELKSGRLGYK ECFKLFDCNDEIVL | 134 | GTGCCCGTGAAGAGCGAGGTGAGCCTGTGCAAGGACTACCTGA GGAGCCACCTGAACCACGTGGACCACAAGTACCTGATCCTGCTG GACCTGGGCTTCGACGGCACCAGCGACAGGGACTACGAGATCC AGACCGCCCAGCTGCTGACCGGCGAGCTGAACTTCAAGGGCGC CAGGCTGGGCGACACCAGGAAGCCCGACGTGTGCGTGTACTAC GGCGAGGACGGCCTGATCATCGACAACAAGGCCTACGGCAAGG GCTACAGCCTGCCCATCAAGCAGGCCGACGAGATGTACAGGTA CATCGAGGAGAACAAGGAGAGGAACGAGAAGCTGAACCCCAAC AAGTGGTGGGAGATCTTCGACAACGACGTGATCCACTACCACTT CGCCTTCGTGAGCGGCGCCTTCACCGGCGGCTTCAGGGAGAGGC TGGAGAACATCAGGATGAGGAGCGGCATCTACGGCGCCGCCGT GAACAGCATGAACCTGCTGCTGATGGCCGAGGAGCTGAAGAGC GGCAGGCTGGGCTACAAGGAGTGCTTCAAGCTGTTCGACTGCAA CGACGAGATCGTGCTG |
| 54 | VPVKSEMSLLKDYL RTHLLHVDHRYLIL LDLGFDGASDRDYE IQTAQLLTGELNFK GARLGDTRKPDVC VYYGEDGLIIDNKA YGKGYSLPIKQADE MYRYIEENKERNEK LNPNKWWEIFDND VIHYHFAFVSGAFT GGFKERLDNIRMRS GIYGAAVNSMNLLL MAEELKSGRLGYK ECFKLFDCNDEIVL | 135 | GTGCCCGTGAAGAGCGAGATGAGCCTGCTGAAGGACTACCTGA GGACCCACCTGCTGCACGTGGACCACAGGTACCTGATCCTGCTG GACCTGGGCTTCGACGGCGCCAGCGACAGGGACTACGAGATCC AGACCGCCCAGCTGCTGACCGGCGAGCTGAACTTCAAGGGCGC CAGGCTGGGCGACACCAGGAAGCCCGACGTGTGCGTGTACTAC GGCGAGGACGGCCTGATCATCGACAACAAGGCCTACGGCAAGG GCTACAGCCTGCCCATCAAGCAGGCCGACGAGATGTACAGGTA CATCGAGGAGAACAAGGAGAGGAACGAGAAGCTGAACCCCAAC AAGTGGTGGGAGATCTTCGACAACGACGTGATCCACTACCACTT CGCCTTCGTGAGCGGCGCCTTCACCGGCGGCTTCAAGGAGAGGC TGGACAACATCAGGATGAGGAGCGGCATCTACGGCGCCGCCGT GAACAGCATGAACCTGCTGCTGATGGCCGAGGAGCTGAAGAGC GGCAGGCTGGGCTACAAGGAGTGCTTCAAGCTGTTCGACTGCAA CGACGAGATCGTGCTG |
| 55 | ILVDKEREMRKAKF LKETVLDSKFISLLD LAADATKSRDFEIV | 136 | ATCCTGGTGGACAAGGAGAGGGAGATGAGGAAGGCCAAGTTCC TGAAGGAGACCGTGCTGGACAGCAAGTTCATCAGCCTGCTGGAC CTGGCCGCCGACGCCACCAAGAGCAGGGACTTCGAGATCGTGA |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
| | TAELFKEAYNLNS V LLGGSNKPDGLVFT DDFGILLDTKAYKN GFSIYAKDRDQMIR YVDDNNKRDKIRN PNEWWKSFSPLIPN DKFYYLWVSNFFK GQFKNQIEYVNRET NTYGAVLNVEQLL YGADAVIKGIINPN KLHEYFSNDEIKF | | CCGCCGAGCTGTTCAAGGAGGCCTACAACCTGAACAGCGTGCTG CTGGGCGGCAGCAACAAGCCCGACGGCCTGGTGTTCACCGACG ACTTCGGCATCCTGCTGGACACCAAGGCCTACAAGAACGGCTTC AGCATCTACGCCAAGGACAGGGACCAGATGATCAGGTACGTGG ACGACAACAACAAGAGGGACAAGATCAGGAACCCCAACGAGTG GTGGAAGAGCTTCAGCCCCCTGATCCCCAACGACAAGTTCTACT ACCTGTGGGTGAGCAACTTCTTCAAGGGCCAGTTCAAGAACCAG ATCGAGTACGTGAACAGGGAGACCAACACCTACGGCGCCGTGC TGAACGTGGAGCAGCTGCTGTACGGCGCCGACGCCGTGATCAA GGGCATCATCAACCCCAACAAGCTGCACGAGTACTTCAGCAACG ACGAGATCAAGTTC |
| 56 | TVDEKERLELKEYF ISNTRIPSKYITLLDL AYDGNANRDFEIVT AELFKDIFKLQSKH MGGTRKPDILIWTD KFGVIADTKAYSKG YKKNISEADKMVR YVNENTNRNKVDN TNEWWNSFDSRIPK DAYYFLWISSEFVG KFDEQLTETSSRTG RNGASINVYQLLRG ADLVQKSKFNIHDL PNLMQNNEIKF | 137 | ACCGTGGACGAGAAGGAGAGGCTGGAGCTGAAGGAGTACTTCA TCAGCAACACCAGGATCCCCAGCAAGTACATCACCCTGCTGGAC CTGGCCTACGACGGCAACGCCAACAGGGACTTCGAGATCGTGA CCGCCGAGCTGTTCAAGGACATCTTCAAGCTGCAGAGCAAGCAC ATGGGCGGCACCAGGAAGCCCGACATCCTGATCTGGACCGACA AGTTCGGCGTGATCGCCGACACCAAGGCCTACAGCAAGGGCTA CAAGAAGAACATCAGCGAGGCCGACAAGATGGTGAGGTACGTG AACGAGAACACCAACAGGAACAAGGTGGACAACACCAACGAGT GGTGGAACAGCTTCGACAGCAGGATCCCCAAGGACGCCTACTA CTTCCTGTGGATCAGCAGCGAGTTCGTGGGCAAGTTCGACGAGC AGCTGACCGAGACCAGCAGCAGGACGGGCAGGAACGGCGCCAG CATCAACGTGTACCAGCTGCTGAGGGGCGCCGACCTGGTGCAGA GAGCAAGTTCAACATCCACGACCTGCCCAACCTGATGCAGAAC AACGAGATCAAGTTC |
| 57 | TLQKSDIEKFKNQL RTELTNIDHSYLKGI DIASKKTTTNVENT EFEAISTKVFTDELG FFGEHLGGSNKPDG LIWDNDCAIILDSK AYSEGFPLTASHTD AMGRYLRQFKERK EEIKPTWWDIAPDN LANTYFAYVSGSFS GNYKAQLQKFRQD TNHMGGALEFVKL LLLANNYKAHKMSI NEVKESILDYNISY | 138 | ACCCTGCAGAAGAGCGACATCGAGAAGTTCAAGAACCAGCTGA GGACCGAGCTGACCAACATCGACCACAGCTACCTGAAGGGCAT CGACATCGCCAGCAAGAAGACCACCACCAACGTGGAGAACACC GAGTTCGAGGCCATCAGCACCAAGGTGTTCACCGACGAGCTGG GCTTCTTCGGCGAGCACCTGGGCGGCAGCAACAAGCCCGACGG CCTGATCTGGGACAACGACTGCGCCATCATCCTGGACAGCAAGG CCTACAGCGAGGGCTTCCCCCTGACCGCCAGCCACACCGACGCC ATGGGCAGGTACCTGAGGCAGTTCAAGGAGAGGAAGGAGGAGA TCAAGCCCACCTGGTGGGACATCGCCCCCGACAACCTGGCCAAC ACCTACTTCGCCTACGTGAGCGGCAGCTTCAGCGGCAACTACAA GGGCCAGCTGCAGAAGTTCAGGCAGGACACCAACCACATGGGC GGCGCCCTGGAGTTCGTGAAGCTGCTGCTGCTGGCCAACAACTA CAAGGCCCACAAGATGAGCATCAACGAGGTGAAGGAGAGCATC CTGGACTACAACATCAGCTAC |
| 58 | VKEKTDAALVKER VRLQLHNINHKYLA LIDYAFSGKNNS RD FEVYTIDLLVNELTF GGLHLGGTRKPDGI FYHGSNGIIIDNKAY AKGFVITRNMADE MIRYVQENNDRNPE RNPNCWWKGFPHD VTRYNYVFISSMFK GEVEHMLDNIRQST GIDGCVLTIENLLY YADAIKGGTLSKAT FINGFNANKEMVF | 139 | GTGAAGGAGAAGACCGACGCCGCCCTGGTGAAGGAGAGGGTGA GGCTGCAGCTGCACAACATCAACCACAAGTACCTGGCCCTGATC GACTACGCCTTCAGCGGCAAGAACAACAGCAGGGACTTCGAGG TGTACACCATCGACCTGCTGGTGAACGAGCTGACCTTCGGCGGC CTGCACCTGGGCGGCACCAGGAAGCCCGACGGCATCTTCTACCA CGGCAGCAACGGCATCATCATCGACAACAAGGCCTACGCCAAG GGCTTCGTGATCACCAGGAACATGGCCGACGAGATGATCAGGT ACGTGCAGGAGAACAACGACAGGAACCCCGAGAGGAACCCCAA CTGCTGGTGGAAGGGCTTCCCCCACGACGTGACCAGGTACAACT ACGTGTTCATCAGCAGCATGTTCAAGGGCGAGGTGGAGCACATG CTGGACAACATCAGGCAGAGCACCGGCATCGACGGCTGCGTGC TGACCATCGAGAACCTGCTGTACTACGCCGACGCCATCAAGGGC GGCACCCTGAGCAAGGCCACCTTCATCAACGGCTTCAACGCCAA CAAGGAGATGGTGTTC |
| 59 | VKETTDSVIIKDRV RLKLHHVNHKYLT LIDYAFSGKNNCMD FEVYTIDLLVNELA FNGVHLGGTRKPD GIFYHNRNGIIIDNK AYSHGFTLSRAMA DEMIRYIQENNDRN PERNPNKWWENFD KGVNQFNFVFISSLF KGEIEHMLTNIKQS TDGVEGCVLSAENL LYFAEAMKSGVMP KTEFISYFGAGKEIQ F | 140 | GTGAAGGAGACCACCGACAGCGTGATCATCAAGGACAGGGTGA GGCTGAAGCTGCACCACGTGAACCACAAGTACCTGACCCTGATC GACTACGCCTTCAGCGGCAAGAACAACTGCATGGACTTCGAGGT GTACACCATCGACCTGCTGGTGAACGAGCTGGCCTTCAACGGCG TGCACCTGGGCGGCACCAGGAAGCCCGACGGCATCTTCTACCAC AACAGGAACGGCATCATCATCGACAACAAGGCCTACAGCCACG GCTTCACCCTGAGCAGGGCCATGGCCGACGAGATGATCAGGTAC ATCCAGGAGAACAACGACAGGAACCCCGAGAGGAACCCCAACA AGTGGTGGGAGAACTTCGACAAGGGCGTGAACCAGTTCAACTTC GTGTTCATCAGCAGCCTGTTCAAGGGCGAGATCGAGCACATGCT GACCAACATCAAGCAGAGCACCGACGGCGTGGAGGGCTGCGTG CTGAGCGCCGAGAACCTGCTGTACTTCGCCGAGGCCATGAAGAG CGGCGTGATGCCCAAGACCGAGTTCATCAGCTACTTCGGCGCCG GCAAGGAGATCCAGTTC |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
| 60 | SACKADITELKDKI RKSLKVLDHKYLV LVDLAYSDASTKSK KNSDAREFEIQTAD LFTKELKFDGMRLG DSNRPDVIISHDNFG TIIDNKSYKDGFNID KKCADEMSRYINEN QRRIPELPKNEWWK NFDVNVDIFTFLFIT SYLKGNFKDQLEYI SKSQSDIKGAAISVE HLLYISEKVKNGSM DKADFFKLFNNDEI RV | 141 | AGCGCCTGCAAGGCCGACATCACCGAGCTGAAGGACAAGATCA GGAAGAGCCTGAAGGTGCTGGACCACAAGTACCTGGTGCTGGT GGACCTGGCCTACAGCGACGCCAGCACCAAGAGCAAGAAGAAC AGCGACGCCAGGGAGTTCGAGATCCAGACCGCCGACCTGTTCAC CAAGGAGCTGAAGTTCGACGGCATGAGGCTGGGCGACAGCAAC AGGCCCGACGTGATCATCAGCCACGACAACTTCGGCACCATCAT CGACAACAAGAGCTACAAGGACGGCTTCAACATCGACAAGAAG TGCGCCGACGAGATGAGCAGGTACATCAACGAGAACCAGAGGA GGATCCCCGAGCTGCCCAAGAACGAGTGGTGGAAGAACTTCGA CGTGAACGTGGACATCTTCACCTTCCTGTTCATCACCAGCTACCT GAAGGGCAACTTCAAGGACCAGCTGGAGTACATCAGCAAGAGC CAGAGCGACATCAAGGGCGCCGCCATCAGCGTGGAGCACCTGC TGTACATCAGCGAGAAGGTGAAGAACGGCAGCATGGACAAGGC CGACTTCTTCAAGCTGTTCAACAACGACGAGATCAGGGTG |
| 61 | VLKDKHLEKIKEKF LENTSLDPRFISLIEI SRDKKQNRAFEIITA ELFNTSYNLSAIHLG GGRRPDVLAYNDN FGIIVDTKAYKNGY GRNVNQEDEMVRY ITENKIRKQDISKNN WWKYFSKSIPSTSY YHLWISSEFVGMFS DQLRETSSRTGENG GAMNVEQLLIGAN QVLNNVLDPNRLPE YMENKEIIF | 142 | GTGCTGAAGGACAAGCACCTGGAGAAGATCAAGGAGAAGTTCC TGGAGAACACCAGCCTGGACCCCAGGTTCATCAGCCTGATCGAG ATCAGCAGGGACAAGAAGCAGAACAGGGCCTTCGAGATCATCA CCGCCGAGCTGTTCAACACCAGCTACAACCTGAGCGCCATCCAC CTGGGCGGCGGCAGGAGGCCCGACGTGCTGGCCTACAACGACA ACTTCGGCATCATCGTGGACACCAAGGCCTACAAGAACGGCTAC GGCAGGAACGTGAACCAGGAGGACGAGATGGTGAGGTACATCA CCGAGAACAAGATCAGGAAGCAGGACATCAGCAAGAACAACTG GTGGAAGTACTTCAGCAAGAGCATCCCCAGCACCAGCTACTACC ACCTGTGGATCAGCAGCGAGTTCGTGGGCATGTTCAGCGACCAG CTGAGGGAGACCAGCAGCAGGACCGGCGAGAACGGCGGCGCCA TGAACGTGGAGCAGCTGCTGATCGGCGCCAACCAGGTGCTGAA CAACGTGCTGGACCCCAACAGGCTGCCCGAGTACATGGAGAAC AAGGAGATCATCTTC |
| 62 | ALKDKHLEKIKEKF LENTSLDPRFISLIEI SRDKKQNRAFEIITA ELFNTSYKLSATHL GGGRRPDVLVYND NFGIIVDTKAYKDG YGRNVNQEDEMVR YITENNIRKQDINKN DWWKYFSKSIPSTS YYHLWISSQFVGMF SDQLRETSSRTGEN GGAMNVEQLLIGA NQVLNNVLDPNCLP KYMENKEIIF | 143 | GCCCTGAAGGACAAGCACCTGGAGAAGATCAAGGAGAAGTTCC TGGAGAACACCAGCCTGGACCCCAGGTTCATCAGCCTGATCGAG ATCAGCAGGGACAAGAAGCAGAACAGGGCCTTCGAGATCATCA CCGCCGAGCTGTTCAACACCAGCTACAAGCTGAGCGCCACCCAC CTGGGCGGCGGCAGGAGGCCCGACGTGCTGGTGTACAACGACA ACTTCGGCATCATCGTGGACACCAAGGCCTACAAGGACGGCTAC GGCAGGAACGTGAACCAGGAGGACGAGATGGTGAGGTACATCA CCGAGAACAACATCAGGAAGCAGGACATCAACAAGAACAACTG GTGGAAGTACTTCAGCAAGAGCATCCCCAGCACCAGCTACTACC ACCTGTGGATCAGCAGCCAGTTCGTGGGCATGTTCAGCGACCAG CTGAGGGAGACCAGCAGCAGGACCGGCGAGAACGGCGGCGCCA TGAACGTGGAGCAGCTGCTGATCGGCGCCAACCAGGTGCTGAA CAACGTGCTGGACCCCAACTGCCTGCCCAAGTACATGGAGAACA AGGAGATCATCTTC |
| 63 | VLEKSDIEKFKNQL RTELTNIDHSYLKGI DIASKKKTSNVENT EFEAISTKIFTDELG FSGKHLGGSNKPDG LLWDDDCAIILDSK AYSEGFPLTASHTD AMGRYLRQFTERK EEIKPTWWDIAPEH LDNTYFAYVSGFS GNYKEQLQKFRQD TNHLGGALEFVKLL LLANNYKTQKMSK KEVKKSILDYNISY | 144 | GTGCTGGAGAAGAGCGACATCGAGAAGTTCAAGAACCAGCTGA GGACCGAGCTGACCAACATCGACCACAGCTACCTGAAGGGCAT CGACATCGCCAGCAAGAAGAAGACCAGCAACGTGGAGAACACC GAGTTCGAGGCCATCAGCACCAAGATCTTCACCGACGAGCTGGG CTTCAGCGGCAAGCACCTGGGCGGCAGCAACAAGCCCGACGGC CTGCTGTGGGACGACGACTGCGCCATCATCCTGGACAGCAAGGC CTACAGCGAGGGCTTCCCCCTGACCGCCAGCCACACCGACGCCA TGGGCAGGTACCTGAGGCAGTTCACCGAGAGGAAGGAGGAGAT CAAGCCCACCTGGTGGGACATCGCCCCCGAGCACCTGGACAAC CTACTTCGCCTACGTGAGCGGCAGCTTCAGCGGCAACTACAA GGAGCAGCTGCAGAAGTTCAGGCAGGACACCAACCACCTGGGC GGCGCCCTGGAGTTCGTGAAGCTGCTGCTGCTGGCCAACAACTA CAAGACCCAGAAGATGAGCAAGAAGGAGGTGAAGAAGAGCAT CCTGGACTACAACATCAGCTAC |
| 64 | AEADVTSEKIKNHF RRVTELPERYLELL DIAFDHKRNRDFEM VTAGLFKDVYGLES VHLGGANKPDGVV YNDNFGIILDTKAY ENGYGKHISQIDEM VRYIDDNRLRDTTR NPNKWWENFDADI PSDQFYYLWVSGKF LPNFAEQLKQTNYR SHANGGGLEVQQL | 145 | GCCGAGGCCGACGTGACCAGCGAGAAGATCAAGAACCACTTCA GGAGGGTGACCGAGCTGCCCGAGAGGTACCTGGAGCTGCTGGA CATCGCCTTCGACCACAAGAGGAACAGGGACTTCGAGATGGTG ACCGCCGGCCTGTTCAAGGACGTGTACGGCCTGGAGAGCGTGCA CCTGGGCGGCGCCAACAAGCCCGACGGCGTGGTGTACAACGAC AACTTCGGCATCATCCTGGACACCAAGGCCTACGAGAACGGCTA CGGCAAGCACATCAGCCAGATCGACGAGATGGTGAGGTACATC GACGACAACAGGCTGAGGGACACCACCAGGAACCCCAACAAGT GGTGGGAGAACTTCGACGCCGACATCCCCAGCGACCAGTTCTAC TACCTGTGGGTGAGCGGCAAGTTCCTGCCCAACTTCGCCGAGCA GCTGAAGCAGACCAACTACAGGAGCCACGCCAACGGCGGCGGC CTGGAGGTGCAGCAGCTGCTGCTGGGCGCCGACGCCGTGAAGA |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
| | LLGADAVKRRKLD VNTIPNYMKNEVIT L | | GGAGGAAGCTGGACGTGAACACCATCCCCAACTACATGAAGAA CGAGGTGATCACCCTG |
| 65 | AEADLNSEKIKNHY RKITNLPEKYIELLD IAFDHRRHQDFEIVT AGLFKDCYGLSSIH LGGQNKPDGVVFN NKFGIILDTKAYEK GYGMHIGQIDEMC RYIDDNKKRDIVRQ PNEWWKNFGDNIP KDQFYYLWISGKFL PRFNEQLKQTHYRT SINGGGLEVSQLLL GANAAMKGKLDV NTLPKHMNNQVIKL | 146 | GCCGAGGCCGACCTGAACAGCGAGAAGATCAAGAACCACTACA GGAAGATCACCAACCTGCCCGAGAAGTACATCGAGCTGCTGGA CATCGCCTTCGACCACAGGAGGCACCAGGACTTCGAGATCGTGA CCGCCGGCCTGTTCAAGGACTGCTACGGCCTGAGCAGCATCCAC CTGGGCGGCCAGAACAAGCCCGACGGCGTGGTGTTCAACAACA AGTTCGGCATCATCCTGGACACCAAGGCCTACGAGAAGGGCTAC GGCATGCACATCGGCCAGATCGACGAGATGTGCAGGTACATCG ACGACAACAAGAAGAGGGACATCGTGAGGCAGCCCAACGAGTG GTGGAAGAACTTCGGCGACAACATCCCCAAGGACCAGTTCTACT ACCTGTGGATCAGCGGCAAGTTCCTGCCCAGGTTCAACGAGCAG CTGAAGCAGACCCACTACAGGACCAGCATCAACGGCGGCGGCC TGGAGGTGAGCCAGCTGCTGCTGGGCGCCAACGCCGCCATGAA GGGCAAGCTGGACGTGAACACCCTGCCCAAGCACATGAACAAC CAGGTGATCAAGCTG |
| 66 | VLKDAALQKTKNT LLNELTEIDPADIEV IEMSWKKATTRSQN TLEATLFEVKVVEIF KKYFELNGEHLGG QNRPDGAVYYNST YGIILDTKAYSNGY NIPVDQQREMVDYI TDVIDKNQNVTPNR WWEAFPATLLKNNI YYLWVAGGFTGKY LDQLTRTHNQTNM DGGAMTTEVLLRL ANKVSSGNLKTTDI PKLMTNKLILS | 147 | GTGCTGAAGGACGCCGCCCTGCAGAAGACCAAGAACACCCTGC TGAACGAGCTGACCGAGATCGACCCCGCCGACATCGAGGTGAT CGAGATGAGCTGGAAGAAGGCCACCACCAGGAGCCAGAACACC CTGGAGGCCACCCTGTTCGAGGTGAAGGTGGTGGAGATCTTCAA GAAGTACTTCGAGCTGAACGGCGAGCACCTGGGCGGCCAGAAC AGGCCCGACGGCGCCGTGTACTACAACAGCACCTACGGCATCAT CCTGGACACCAAGGCCTACAGCAACGGCTACAACATCCCCGTGG ACCAGCAGAGGGAGATGGTGGACTACATCACCGACGTGATCGA CAAGAACCAGAACGTGACCCCCAACAGGTGGTGGGAGGCCTTC CCCGCCACCCTGCTGAAGAACAACATCTACTACCTGTGGGTGGC CGGCGGCTTCACCGGCAAGTACCTGGACCAGCTGACCAGGACCC ACAACCAGACCAACATGGACGGCGGCGCCATGACCACCGAGGT GCTGCTGAGGCTGGCCAACAAGGTGAGCAGCGGCAACCTGAAG ACCACCGACATCCCCAAGCTGATGACCAACAAGCTGATCCTGAG C |
| 67 | AEADLDSERIKNHY RKITNLPEKYIELLD IAFDHHRHQDFEIIT AGLFKDCYGLSSIH LGGQNKPDGVVFN GKFGIILDTKAYEK GYGMHINQIDEMC RYIEDNKQRDKIRQ PNEWWNNFGDNIP ENKFYYLWVSGKF LPKFNEQLKQTHYR TGINGGGLEVSQLL LGADAVMKGALNV NILPTYMHNNVIQ | 148 | GCCGAGGCCGACCTGGACAGCGAGAGGATCAAGAACCACTACA GGAAGATCACCAACCTGCCCGAGAAGTACATCGAGCTGCTGGA CATCGCCTTCGACCACCACAGGCACCAGGACTTCGAGATCATCA CCGCCGGCCTGTTCAAGGACTGCTACGGCCTGAGCAGCATCCAC CTGGGCGGCCAGAACAAGCCCGACGGCGTGGTGTTCAACGGCA AGTTCGGCATCATCCTGGACACCAAGGCCTACGAGAAGGGCTAC GGCATGCACATCAACCAGATCGACGAGATGTGCAGGTACATCG AGGACAACAAGCAGAGGGACAAGATCAGGCAGCCCAACGAGTG GTGGAACAACTTCGGCGACAACATCCCCGAGAACAAGTTCTACT ACCTGTGGGTGAGCGGCAAGTTCCTGCCCAAGTTCAACGAGCAG CTGAAGCAGACCCACTACAGGACCGGCATCAACGGCGGCGGCC TGGAGGTGAGCCAGCTGCTGCTGGGCGCCGACGCCGTGATGAA GGGCGCCCTGAACGTGAACATCCTGCCCACCTACATGCACAACA ACGTGATCCAG |
| 68 | EISDIALQKEKAYFY KNTALSKRHISILEI AFDGSKNRDLEILS AEVFKDYYQLESIH LGGGLKPDGIAFNQ NFGIIVDTKAYKGV YSRSRAEADKMFR YIEDNKKRDPKRNQ SLWWRSFNEHIPAN NFYFLWISGKFQRN FDTQINQLNYETGY RGGALSARQFLIGA DAIQKGKIDINDLPS YFNNSVISF | 149 | GAGATCAGCGACATCGCCCTGCAGAAGGAGAAGGCCTACTTCT ACAAGAACACCGCCCTGAGCAAGAGGCACATCAGCATCCTGGA GATCGCCTTCGACGGCAGCAAGAACAGGGACCTGGAGATCCTG AGCGCCGAGGTGTTCAAGGACTACTACCAGCTGGAGAGCATCC ACCTGGGCGGCGGCCTGAAGCCCGACGGCATCGCCTTCAACCAG AACTTCGGCATCATCGTGGACACCAAGGCCTACAAGGGCGTGTA CAGCAGGAGCAGGGCCGAGGCCGACAAGATGTTCAGGTACATC GAGGACAACAAGAAGAGGGACCCCAAGAGGAACCAGAGCCTGT GGTGGAGGAGCTTCAACGAGCACATCCCCGCCAACAACTTCTAC TTCCTGTGGATCAGCGGCAAGTTCCAGAGGAACTTCGACACCCA GATCAACCAGCTGAACTACGAGACCGGCTACAGGGGCGGCGCC CTGAGCGCCAGGCAGTTCCTGATCGGCGCCGACGCCATCCAGAA GGGCAAGATCGACATCAACGACCTGCCCAGCTACTTCAACAACA GCGTGATCAGCTTC |
| 69 | TSREKSRLNLKEYF VSNTNLPNKFITLLD LAYDGKANRDFELI TSELFREIYKLNTRH LGGTRKPDILIWNE NFGIIADTKAYSKG YKKNISEEDKMVR YIDENIKRSKDYNP NEWWKVFDNEISS | 150 | ACCAGCAGGGAGAAGAGCAGGCTGAACCTGAAGGAGTACTTCG TGAGCAACACCAACCTGCCCAACAAGTTCATCACCCTGCTGGAC CTGGCCTACGACGGCAAGGCCAACAGGGACTTCGAGCTGATCA CCAGCGAGCTGTTCAGGGAGATCTACAAGCTGAACACCAGGCA CCTGGGCGGCACCAGGAAGCCCGACATCCTGATCTGGAACGAG AACTTCGGCATCATCGCCGACACCAAGGCCTACAGCAAGGGCTA CAAGAAGAACATCAGCGAGGAGGACAAGATGGTGAGGTACATC GACGAGAACATCAAGAGGAGCAAGGACTACAACCCCAACGAGT GGTGGAAGGTGTTCGACAACGAGATCAGCAGCAACAACTACTT |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
| | NNYFYLWISSEFIGK FEEQLQETAQRTNV KGASINVYQLLMG AHKVQTKELNVNSI PKYMNNTEIKF | | CTACCTGTGGATCAGCAGCGAGTTCATCGGCAAGTTCGAGGAGC AGCTGCAGGAGACCGCCCAGAGGACCAACGTGAAGGGCGCCAG CATCAACGTGTACCAGCTGCTGATGGGCGCCCACAAGGTGCAGA CCAAGGAGCTGAACGTGAACAGCATCCCCAAGTACATGAACAA CACCGAGATCAAGTTC |
| 70 | NCIKDSIIDIKDRVR TKLVHLDHKYLALI DLAFSDADTRTKKN SDAREFEIQTADLFT KELSFNGQRLGDSR KPDIIISFDKIGTIIDN KSYKDGFNISRPCA DEMIRYINENNLRK KSLNANEWWNKFD PTITAYSFLFITSYLK GQFQEQLEYISNAN GGIKGAAIGIENLLY LSEALKSGKISHKD FYQNFNNKEITY | 151 | AACTGCATCAAGGACAGCATCATCGACATCAAGGACAGGGTGA GGACCAAGCTGGTGCACCTGGACCACAAGTACCTGGCCCTGATC GACCTGGCCTTCAGCGACGCCGACACCAGGACCAAGAAGAACA GCGACGCCAGGGAGTTCGAGATCCAGACCGCCGACCTGTTCACC AAGGAGCTGAGCTTCAACGGCCAGAGGCTGGGCGACAGCAGGA AGCCCGACATCATCATCAGCTTCGACAAGATCGGCACCATCATC GACAACAAGAGCTACAAGGACGGCTTCAACATCAGCAGGCCCT GCGCCGACGAGATGATCAGGTACATCAACGAGAACAACCTGAG GAAGAAGAGCCTGAACGCCAACAAGTGGTGGAACAAGTTCGAC CCCACCATCACCGCCTACAGCTTCCTGTTCATCACCAGCTACCTG AAGGGCCAGTTCCAGGAGCAGCTGGAGTACATCAGCAACGCCA ACGGCGGCATCAAGGGCGCCGCCATCGGCATCGAGAACCTGCT GTACCTGAGCGAGGCCCTGAAGAGCGGCAAGATCAGCCACAAG GACTTCTACCAGAACTTCAACAACAAGGAGATCACCTAC |
| 71 | LPQKDQVQQQDE LRPMLKNVDHRYL QLVELALDSDQNSE YSQFEQLTMELVLK HLDFDGKPLGGSNK PDGIAWDNDGNFIIF DTKAYNKGYSLAG NTDKVKRYIDDVR DRDTSRTSTWWQL VPKSIDVHNLLRFV YVSGNFTGNYMKL LDSLRSWSNAQGG LASVEKLLLTSELY LRNMYSHQELIDSW TDNNVKH | 152 | CTGCCCCAGAAGGACCAGGTGCAGCAGCAGCAGGACGAGCTGA GGCCCATGCTGAAGAACGTGGACCACAGGTACCTGCAGCTGGT GGAGCTGGCCCTGGACAGCGACCAGAACAGCGAGTACAGCCAG TTCGAGCAGCTGACCATGGAGCTGGTGCTGAAGCACCTGGACTT CGACGGCAAGCCCCTGGGCGGCAGCAACAAGCCCGACGGCATC GCCTGGGACAACGACGGCAACTTCATCATCTTCGACACCAAGGC CTACAACAAGGGCTACAGCCTGGCCGGCAACACCGACAAGGTG AAGAGGTACATCGACGACGTGAGGGACAGGGACACCAGCAGGA CCAGCACCTGGTGGCAGCTGGTGCCCAAGAGCATCGACGTGCAC AACCTGCTGAGGTTCGTGTACGTGAGCGGCAACTTCACCGGCAA CTACATGAAGCTGCTGGACAGCCTGAGGAGCTGGAGCAACGCC CAGGGCGGCCTGGCCAGCGTGGAGAAGCTGCTGCTGACCAGCG AGCTGTACCTGAGGAACATGTACAGCCACCAGGAGCTGATCGA CAGCTGGACCGACAACAACGTGAAGCAC |
| 72 | TTDAVVVKDRARV RLHNINHKYLTLID YAFSGKNNCTEFEI YTIDLLVNELAFNGI HLGGTRKPDGIFDY NQQGIIIDNKAYSK GFTITRSMADEMVR YVQENNDRNPERN KTQWWLNFGDNV NHFNFVFISSMFKG EVRHMLNNIKQSTG VDGCVLTAENLLYF ADAIKGGTVKRTDF INLFGKNDEL | 153 | ACCACCGACGCCGTGGTGGTGAAGGACAGGGCCAGGGTGAGGC TGCACAACATCAACCACAAGTACCTGACCCTGATCGACTACGCC TTCAGCGGCAAGAACAACTGCACCGAGTTCGAGATCTACACCAT CGACCTGCTGGTGAACGAGCTGGCCTTCAACGGCATCCACCTGG GCGGCACCAGGAAGCCCGACGGCATCTTCGACTACAACCAGCA GGGCATCATCATCGACAACAAGGCCTACAGCAAGGGCTTCACC ATCACCAGGAGCATGGCCGACGAGATGGTGAGGTACGTGCAGG AGAACAACGACAGGAACCCCGAGAGGAACAAGACCCAGTGGTG GCTGAACTTCGGCGACAACGTGAACCACTTCAACTTCGTGTTCA TCAGCAGCATGTTCAAGGGCGAGGTGAGGCACATGCTGAACAA CATCAAGCAGAGCACCGGCGTGACGGCTGCGTGCTGACCGCC GAGAACCTGCTGTACTTCGCCGACGCCATCAAGGGCGGCACCGT GAAGAGGACCGACTTCATCAACCTGTTCGGCAAGAACGACGAG CTG |
| 73 | LPKKDNVQRQQDE LRPLLKHVDHRYLQ LVELALDSSQNSEY SMLESMTMELLLTH LDFDGASLGGASKP DGIAWDKDGNFLIV DTKAYDNGYS LAG NTDKVARYIDDVR AKDPNRASTWWTQ VPESLNVDDNLSFM YVSGSFTGNYQRLL KDLRARTNARGGL TTVEKLLLTSEAYL AKSGYGHTQLLND WTDDNIDH | 154 | CTGCCCAAGAAGGACAACGTGCAGAGGCAGCAGGACGAGCTGA GGCCCCTGCTGAAGCACGTGGACCACAGGTACCTGCAGCTGGTG GAGCTGGCCCTGGACAGCAGCCAGAACAGCGAGTACAGCATGC TGGAGAGCATGACCATGGAGCTGCTGCTGACCCACCTGGACTTC GACGGCGCCAGCCTGGGCGGCGCCAGCAAGCCCGACGGCATCG CCTGGGACAAGGACGGCAACTTCCTGATCGTGGACACCAAGGC CTACGACAACGGCTACAGCCTGGCCGGCAACACCGACAAGGTG GCCAGGTACATCGACGACGTGAGGGCCAAGGACCCCAACAGGG CCAGCACCTGGTGGACCCAGGTGCCCGAGAGCCTGAACGTGGA CGACAACCTGAGCTTCATGTACGTGAGCGGCAGCTTCACCGGCA ACTACCAGAGGCTGCTGAAGGACCTGAGGGCCAGGACCAACGC CAGGGGCGGCCTGACCACCGTGGAGAAGCTGCTGCTGACCAGC GAGGCCTACCTGGCCAAGAGCGGCTACGGCCACACCCAGCTGCT GAACGACTGGACCGACGACAACATCGACCAC |
| 74 | QIKDKYLEDLKLEL YKKTNLPNKYYEM VDIAYDGKRNREFE IYTSDLMQEIYGFK TTLLGGTRKPDVVS YSDAHGYIIDTKAY | 155 | CAGATCAAGGACAAGTACCTGGAGGACCTGAAGCTGGAGCTGT ACAAGAAGACCAACCTGCCCAACAAGTACTACGAGATGGTGGA CATCGCCTACGACGGCAAGAGGAACAGGGAGTTCGAGATCTAC ACCAGCGACCTGATGCAGGAGATCTACGGCTTCAAGACCACCCT GCTGGGCGGCACCAGGAAGCCCGACGTGGTGAGCTACAGCGAC GCCCACGGCTACATCATCGACACCAAGGCCTACGCCAACGGCTA |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
| | ANGYRKEIKQEDE MVRYIEDNQLKDV LRNPNKWWECFDD AEHKKEYYFLWISS KFVGEFSSQLQDTS RRTGIKGGAVNIVQ LLLGAHLVYSGEIS KDQFAAYMNNTEI NF | | CAGGAAGGAGATCAAGCAGGAGGACGAGATGGTGAGGTACATC GAGGACAACCAGCTGAAGGACGTGCTGAGGAACCCCAACAAGT GGTGGGAGTGCTTCGACGACGCCGAGCACAAGAAGGAGTACTA CTTCCTGTGGATCAGCAGCAAGTTCGTGGGCGAGTTCAGCAGCC AGCTGCAGGACACCAGCAGGAGGACCGGCATCAAGGGCGGCGC CGTGAACATCGTGCAGCTGCTGCTGGGCGCCCACCTGGTGTACA GCGGCGAGATCAGCAAGGACCAGTTCGCCGCCTACATGAACAA CACCGAGATCAACTTC |
| 75 | MNPRNEIVIAKHLS GGNRPEIVCYHPED KPDHGLILDSKAYK SGFTIPSGERDKMV RYIEEYITKNQLQNP NEWWKNLKGAEYP GIVGFGFISNSFLGH YRKQLDYIMRRTKI KGSSITTEHLLKTVE DVLSEKGNVIDFFK YFLE | 156 | ATGAACCCCAGGAACGAGATCGTGATCGCCAAGCACCTGAGCG GCGGCAACAGGCCCGAGATCGTGTGCTACCACCCCGAGGACAA GCCCGACCACGGCCTGATCCTGGACAGCAAGGCCTACAAGAGC GGCTTCACCATCCCCAGCGGCGAGAGGGACAAGATGGTGAGGT ACATCGAGGAGTACATCACCAAGAACCAGCTGCAGAACCCCAA CGAGTGGTGGAAGAACCTGAAGGGCGCCGAGTACCCCGGCATC GTGGGCTTCGGCTTCATCAGCAACAGCTTCCTGGGCCACTACAG GAAGCAGCTGGACTACATCATGAGGAGGACCAAGATCAAGGGC AGCAGCATCACCACCGAGCACCTGCTGAAGACCGTGGAGGACG TGCTGAGCGAGAAGGGCAACGTGATCGACTTCTTCAAGTACTTC CTGGAG |
| 76 | EIKNQEIEELKQIAL NKYTALPSEWVELI EISRDKDQSTIFEMK VAELFKTCYRIKSL HLGGASKPDCLLW DDSFSVIVDAKAYK DGFPFQASEKDKM VRYLRECERKDKA ENATEWWNNFPPE LNSNQLFFMFASSF FSSTAEKHLESVSIA SKFSGCAWDVDNL LSGANFFLQNPQAT LQYHLIRVFSNKVV D | 157 | GAGATCAAGAACCAGGAGATCGAGGAGCTGAAGCAGATCGCCC TGAACAAGTACACCGCCCTGCCCAGCGAGTGGGTGGAGCTGATC GAGATCAGCAGGGACAAGGACCAGAGCACCATCTTCGAGATGA AGGTGGCCGAGCTGTTCAAGACCTGCTACAGGATCAAGAGCCTG CACCTGGGCGGCGCCAGCAAGCCCGACTGCCTGCTGTGGGACG ACAGCTTCAGCGTGATCGTGGACGCCAAGGCCTACAAGGACGG CTTCCCCTTCCAGGCCAGCGAGAAGGACAAGATGGTGAGGTACC TGAGGGAGTGCGAGAGGAAGGACAAGGCCGAGAACGCCACCG AGTGGTGGAACAACTTCCCCCCCGAGCTGAACAGCAACCAGCTG TTCTTCATGTTCGCCAGCAGCTTCTTCAGCAGCACCGCCGAGAA GCACCTGGAGAGCGTGAGCATCGCCAGCAAGTTCAGCGGCTGC GCCTGGGACGTGGACAACCTGCTGAGCGGCGCCAACTTCTTCCT GCAGAACCCCCAGGCCACCCTGCAGTACCACCTGATCAGGGTGT TCAGCAACAAGGTGGTGGAC |
| 77 | LPHKDNVIKQQDEL RPMLKHVNHKYLQ LVELAFESSRNSEYS QFETLTMELVLKYL DFSGKSLGGANKPD GIAWDPLGNFLIFD TKAYKHGYTLSNN TDRVARYINDVRD KDIQRISRWWQSIPT YIDVKNKLQFVYIS GSFTGHYLRLLNDL RSRTRAKGGLVTVE KLLLTTERYLAEAD YTHKELFDDWMDD NIEH | 158 | CTGCCCCACAAGGACAACGTGATCAAGCAGCAGGACGAGCTGA GGCCCATGCTGAAGCACGTGAACCACAAGTACCTGCAGCTGGTG GAGCTGGCCTTCGAGAGCAGCAGGAACAGCGAGTACAGCCAGT TCGAGACCCTGACCATGGAGCTGGTGCTGAAGTACCTGGACTTC AGCGGCAAGAGCCTGGGCGGCGCCAACAAGCCCGACGGCATCG CCTGGGACCCCCTGGGCAACTTCCTGATCTTCGACAAGGCC TACAAGCACGGCTACACCCTGAGCAACAACACCGACAGGGTGG CCAGGTACATCAACGACGTGAGGGACAAGGACATCCAGAGGAT CAGCAGGTGGTGGCAGAGCATCCCCACCTACATCGACGTGAAG AACAAGCTGCAGTTCGTGTACATCAGCGGCAGCTTCACCGGCCA CTACCTGAGGCTGCTGAACGACCTGAGGAGCAGGACCAGGGCC AAGGGCGGCCTGGTGACCGTGGAGAAGCTGCTGCTGACCACCG AGAGGTACCTGGCCGAGGCCGACTACACCCACAAGGAGCTGTT CGACGACTGGATGGACGACAACATCGAGCAC |
| 78 | RISPSNLEQTKQQLR EELINLDHQYLDILD FSIAGNVGARQFEV RIVELLNEIIIAKHLS GGNRPEIIGFNPKEN PEDCIIMDSKAYKE GFNIPANERDKMIR YVEEYNAKDNTLN NNKWWKNFESPNY PTNQVKFSFVSSSFI GQFTNQLTYINNRT NVNGSAITAETLLR KVENVMNVNTEYN LNNFFEELGSNTLV A | 159 | AGGATCAGCCCCAGCAACCTGGAGCAGACCAAGCAGCAGCTGA GGGAGGAGCTGATCAACCTGGACCACCAGTACCTGGACATCCTG GACTTCAGCATCGCCGGCAACGTGGGCGCCAGGCAGTTCGAGGT GAGGATCGTGGAGCTGCTGAACGAGATCATCATCGCCAAGCAC CTGAGCGGCGGCAACAGGCCCGAGATCATCGGCTTCAACCCCA AGGAGAACCCCGAGGACTGCATCATCATGGACAGCAAGGCCTA CAAGGAGGGCTTCAACATCCCCGCCAACGAGAGGGACAAGATG ATCAGGTACGTGGAGGAGTACAACGCCAAGGACAACACCCTGA ACAACAAGTGGTGGAAGAACTTCGAGAGCCCCAACTACCC CACCAACCAGGTGAAGTTCAGCTTCGTGAGCAGCAGCTTCATCG GCCAGTTCACCAACCAGCTGACCTACATCAACAACAGGACCAAC GTGAACGGCAGCGCCATCACCGCCGAGACCCTGCTGAGGAAGG TGGAGAACGTGATGAACGTGAACACCGAGTACAACCTGAACAA CTTCTTCGAGGAGCTGGGCAGCAACACCCTGGTGGCC |
| 79 | TFDSTVADNLKNLI LPKLKELDHKYLQA IDIAYKRSNTTNHE NTLLEVLSADLFTK | 160 | ACCTTCGACAGCACCGTGGCCGACAACCTGAAGAACCTGATCCT GCCCAAGCTGAAGGAGCTGGACCACAAGTACCTGCAGGCCATC GACATCGCCTACAAGAGGAGCAACACCACCAACCACGAGAACA CCCTGCTGGAGGTGCTGAGCGCCGACCTGTTCACCAAGGAGATG |

TABLE 7-continued

Amino Acid and Nucleic Acid Sequences of Endonucleases

| SEQ ID NO | Amino Acid Sequence | SEQ ID NO | Back Translated Nucleic Acid Sequences |
|---|---|---|---|
|  | EMDYHGKHLGGAN KPDGFVYDEETGWI LDSKAYRDGFAVT AHTTDAMGRYIDQ YRDRDDKSTWWED FPKDLPQTYFAYVS GFYIGKYQEQLQDF ENRKHMKGGLIEV AKLILLAEKYKENK ITHDQITLQILNDHIS Q |  | GACTACCACGGCAAGCACCTGGGCGGCGCCAACAAGCCCGACG GCTTCGTGTACGACGAGGAGACCGGCTGGATCCTGGACAGCAA GGCCTACAGGGACGGCTTCGCCGTGACCGCCCACACCACCGACG CCATGGGCAGGTACATCGACCAGTACAGGGACAGGGACGACAA GAGCACCTGGTGGGAGGACTTCCCCAAGGACCTGCCCCAGACCT ACTTCGCCTACGTGAGCGGCTTCTACATCGGCAAGTACCAGGAG CAGCTGCAGGACTTCGAGAACAGGAAGCACATGAAGGGCGGCC TGATCGAGGTGGCCAAGCTGATCCTGCTGGCCGAGAAGTACAA GGAGAACAAGATCACCCACGACCAGATCACCCTGCAGATCCTG AACGACCACATCAGCCAG |
| 80 | PLDVVEQMKAELR PLLNHVNHRLLAIID FSYNMSRGDDKRL EDYTAQIYKLISHD THLLAGPSRPDVVS VINDLGIIIDSKAYK QGFNIPQAEEDKMV RYLDESIRRDPAINP TKWWEYLGASTEY VFQFVSSSFSSGASA KLRQIHRRSSIEGSII TAKNLLLLAENFLC TNTINIDLFRQNNEI | 161 | CCCCTGGACGTGGTGGAGCAGATGAAGGCCGAGCTGAGGCCCC TGCTGAACCACGTGAACCACAGGCTGCTGGCCATCATCGACTTC AGCTACAACATGAGCAGGGGCGACGACAAGAGGCTGGAGGACT ACACCGCCCAGATCTACAAGCTGATCAGCCACGACACCCACCTG CTGGCCGGCCCCAGCAGGCCCGACGTGGTGAGCGTGATCAACG ACCTGGGCATCATCATCGACAGCAAGGCCTACAAGCAGGGCTTC AACATCCCCCAGGCCGAGGAGGACAAGATGGTGAGGTACCTGG ACGAGAGCATCAGGAGGGACCCCGCCATCAACCCCACCAAGTG GTGGGAGTACCTGGGCGCCAGCACCGAGTACGTGTTCCAGTTCG TGAGCAGCAGCTTCAGCAGCGGCGCCAGCGCCAAGCTGAGGCA GATCCACAGGAGGAGCAGCATCGAGGGCAGCATCATCACCGCC AAGAACCTGCTGCTGCTGGCCGAGAACTTCCTGTGCACCAACAC CATCAACATCGACCTGTTCAGGCAGAACAACGAGATC |
| 81 | QLVPSYITQTKLRLS GLINYIDHSYFDLID LGFDGRQNRLYELR IVELLNLINSLKALH LSGGNRPEIIAYSPD VNPINGVIMDSKSY RGGFNIPNSERDKM IRYINEYNQKNPTL NSNRWWENFRAPD YPQSPLKYSFVSGN FIGQFLNQIQYILTQ TGINGGAITSEKLIE KVNAVLNPNISYTI NNFFNDLGCNRLV Q | 162 | CAGCTGGTGCCCAGCTACATCACCCAGACCAAGCTGAGGCTGAG CGGCCTGATCAACTACATCGACCACAGCTACTTCGACCTGATCG ACCTGGGCTTCGACGGCAGGCAGAACAGGCTGTACGAGCTGAG GATCGTGGAGCTGCTGAACCTGATCAACAGCCTGAAGGCCCTGC ACCTGAGCGGCGGCAACAGGCCCGAGATCATCGCCTACAGCCC CGACGTGAACCCCATCAACGGCGTGATCATGGACAGCAAGAGC TACAGGGGCGGCTTCAACATCCCCAACAGCGAGAGGGACAAGA TGATCAGGTACATCAACGAGTACAACCAGAAGAACCCCACCCT GAACAGCAACAGGTGGTGGGAGAACTTCAGGGCCCCCGACTAC CCCCAGAGCCCCCTGAAGTACAGCTTCGTGAGCGGCAACTTCAT CGGCCAGTTCCTGAACCAGATCCAGTACATCCTGACCCAGACCG GCATCAACGGCGGCGCCATCACCAGCGAGAAGCTGATCGAGAA GGTGAACGCCGTGCTGAACCCCAACATCAGCTACACCATCAACA ACTTCTTCAACGACCTGGGCTGCAACAGGCTGGTGCAG |

In some embodiments, an endonuclease of the present disclosure can have a sequence of $X_1X_2X_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}X_{25}X_{26}X_{27}X_{28}X_{29}X_{30}X_{31}X_{32}X_{33}X_{34}X_{35}X_{36}X_{37}X_{38}X_{39}X_{40}X_{41}X_{42}X_{43}X_{44}X_{45}X_{46}X_{47}X_{48}X_{49}X_{50}X_{51}X_{52}X_{53}X_{54}X_{55}GX_{56}HLGGX_{57}RX_{58}PDGX_{59}X_{60}X_{61}X_{62}X_{63}X_{64}X_{65}X_{66}X_{67}X_{68}X_{69}X_{70}X_{71}X_{72}X_{73}X_{74}GX_{75}IX_{76}DTKX_{77}YX_{78}X_{79}GYX_{80}L$ $PIX_{81}QX_{82}DEMX_{83}RYX_{84}X_{85}ENX_{86}X_{87}RX_{88}X_{89}X_{90}X_{91}NX_{92}NX_{93}WWX_{94}X_{95}X_{96}X_{97}X_{98}X_{99}X_{100}X_{101}$ $X_{102}X_{103}X_{104}X_{105}X_{106}FX_{107}X_{108}X_{109}X_{110}FX_{111}GX_{112}$ $X_{113}X_{114}X_{115}X_{116}X_{117}X_{118}RX_{119}X_{120}X_{121}X_{122}X_{123}$ $X_{124}X_{125}X_{126}GX_{127}X_{128}X_{129}X_{130}X_{131}X_{132}X_{133}LLX_{134}$ $X_{135}X_{136}X_{137}X_{138}X_{139}X_{140}X_{141}X_{142}X_{143}X_{144}X_{145}$ $X_{146}X_{147}X_{148}X_{149}X_{150}X_{151}X_{152}X_{153}FX_{154}X_{155}X_{156}X_{157}$ $X_{158}X_{159}X_{160}$ (SEQ ID NO: 316), wherein $X_1$ is F, Q, N, D, or absent, $X_2$ is L, I, T, S, N, or absent, $X_3$ is V, I, G, A, E, T, or absent, $X_4$ is K, C, or absent, $X_5$ is G, S, or absent, $X_6$ is A, S, E, D, N, or absent, $X_7$ is M, I, V, Q, F, L, or absent, $X_8$ is E, S, T, N, or absent, $X_9$ is I, M, E, T, Q, or absent, $X_{10}$ is K, S, L, I, T, E, or absent, $X_{11}$ is K or absent, $X_{12}$ is S, A, E, D, or absent, $X_{13}$ is E, N, Q, K, or absent, $X_{14}$ is L, M, V, or absent, $X_{15}$ is R or absent, $X_{16}$ is H, D, T, G, E, N, or absent, $X_{17}$ is K, N, Q, E, A, or absent, $X_{18}$ is L or absent, $X_{19}$ is R, Q, N, T, D, or absent, $X_{20}$ is H, M, V, N, T, or absent, $X_{21}$ is V, L, I, or absent, $X_{22}$ is P, S, or absent, $X_{23}$ is H or absent, $X_{24}$ is E, D, or absent, $X_{25}$ is Y or absent, $X_{26}$ is I, L, or absent, $X_{27}$ is E, Q, G, S, A, Y, or absent, $X_{28}$ is L or absent, $X_{29}$ is I, V, L, or absent, $X_{30}$ is E, D, or absent, $X_{31}$ is I, L, or absent, $X_{32}$ is A, S, or absent, $X_{33}$ is Q, Y, F, or absent, $X_{34}$ is D or absent, $X_{35}$ is S, P, or absent, $X_{36}$ is K, Y, Q, T, or absent, $X_{37}$ is Q or absent, $X_{38}$ is N or absent, $X_{39}$ is R, K, or absent, $X_{40}$ is L, I, or absent, $X_{41}$ is L, F, or absent, $X_{42}$ is E or absent, $X_{43}$ is F, M, L, or absent, $X_{44}$ is V, T, or I, $X_{45}$ is V, M, L, or I, $X_{46}$ is E, D, or Q, $X_{47}$ is F or L, $X_{48}$ is F or L, $X_{49}$ is K, I, T, or V, $X_{50}$ is K, N, or E, $X_{51}$ is I or E, $X_{52}$ is Y, F, or C, $X_{53}$ is G, or N, $X_{54}$ is Y, or F, $X_{55}$ is R, S, N, E, K, or Q, $X_{56}$ is K, S, L, V, or T, $X_{57}$ is S, A, or V, $X_{58}$ is K or R, $X_{59}$ is A, I, or V, $X_{60}$ is L, M, V, I, or C, $X_{61}$ is F or Y, $X_{62}$ is T, A, or S, $X_{63}$ is K, E, or absent, $X_{64}$ is D, E, or absent, $X_{65}$ is E, A, or absent, $X_{66}$ is N, K, or absent, $X_{67}$ is E, S, or absent, $X_{68}$ is D, E, Q, A, or absent, $X_{69}$ is G, V, K, N, or absent, $X_{70}$ is L, G, E, S, or absent, $X_{71}$ is V, S, K, T, E, or absent, $X_{72}$ is L, H, K, E, Y, D, or A, $X_{73}$ is N, G, or D, $X_{74}$ is H, F, or Y, $X_{75}$ is I, or V, $X_{76}$ is L, V, or I, $X_{77}$ is A or S, $X_{78}$ is K or S, $X_{79}$ is D, G, K, S, or N, $X_{80}$ is R, N, S, or G, $X_{81}$ is S, A, or G, $X_{82}$ is A, I, or V, $X_{83}$ is Q, E, I, or V, $X_{84}$ is V or I, $X_{85}$ is D, R, G, I, or E, $X_{86}$ is N, I, or Q, $X_{87}$ is K, D, T, E, or K, $X_{88}$ is S, N, D, or E, $X_{89}$ is Q, E, I, K, or A, $X_{90}$ is V, H, R, K, L, or E, $X_{91}$ is I, V, or R, $X_{92}$ is P, S, T, or R, $X_{93}$ is E, R, C, Q, or K, $X_{94}$ is E, N, or K, $X_{95}$ is I, V, N, E, or A, $X_{96}$ is Y or F, $X_{97}$ is P, G, or E, $X_{98}$ is T, E, S, D, K, or N, $X_{99}$ is S, D, K, G, N, or T, $X_{100}$ is I, T, V, or L, $X_{101}$ is T, N, G, or D, $X_{102}$ is D, E, T, K, or I, $X_{103}$ is F or Y, $X_{104}$ is K or Y, $X_{105}$ is F or Y, $X_{106}$ is L, S, or M, $X_{107}$ is V or I, $X_{108}$ is S or A, $X_{109}$ is G or A, $X_{110}$ is F, Y, H, E, or K, Xiii is Q, K, T, N, or I, $X_{112}$ is D, N, or K, $X_{113}$ is Y, F, I, or V, $X_{114}$ is R, E, K, Q, or F, $X_{115}$ is K, E, A, or N, $X_{116}$ is Q or K, $X_{117}$ is L or I, $X_{118}$ is E, D, N, or Q, $X_{119}$ is V, I, or L, $X_{120}$ is S, N, F, T, or Q, $X_{121}$ is H, I, C, or R, $X_{122}$ is L, D, N, S, or F, $X_{123}$ is T or K, $X_{124}$ is K, G, or N, $X_{125}$ is C, V, or I, $X_{126}$ is Q, L, K, or Y, $X_{127}$ is A, G, or N, $X_{128}$ is V or A, $X_{129}$ is M, L, I, V, or A, $X_{130}$ is S, T, or D, $X_{131}$ is V or I, $X_{132}$ is E, Q, K, S, or I, $X_{133}$ is Q, H, or T, $X_{134}$ is L, R, or Y, $X_{135}$ is G, I, L, or T, $X_{136}$ is G, A, or V, $X_{137}$ is E, N, or D, $X_{138}$ is K, Y, D, E, A, or R, $X_{139}$ is I, F, Y, or C, $X_{140}$ is K or R, $X_{141}$ is E, R, A, G, or T, $X_{142}$ is G or N, $X_{143}$ is S, I, K, R, or E, $X_{144}$ is L, I, or M, $X_{145}$ is T, S, D, or K, $X_{146}$ is L, H, Y, R, T, or F, $X_{147}$ is E, Y, I, M, A, or L, $X_{148}$ is E, D, R, or G, $X_{149}$ is V, F, M, L, or I, $X_{150}$ is G, K, R, L, V, or E, $X_{151}$ is K, N, D, L, H, or S, $X_{152}$ is K, L, C, or absent, $X_{153}$ is K, S, I, Y, M, or F, $X_{154}$ is K, L, C, H, D, Q, or N, $X_{155}$ is N or Y, $X_{156}$ is D, K, T, E, C, or absent, $X_{157}$ is E, V, R, or absent, $X_{158}$ is I, F, L, or absent, $X_{159}$ is V, Q, E, L, or absent, and $X_{160}$ is F or absent.

In some embodiments, an endonuclease of the present disclosure can have a sequence of $X_1X_2X_3X_4X_5X_6X_7X_8X_9X_{10}X_{11}X_{12}X_{13}X_{14}X_{15}X_{16}X_{17}X_{18}$ $X_{19}X_{20}X_{21}X_{22}X_{23}X_{24}X_{25}X_{26}X_{27}X_{28}X_{29}X_{30}X_{31}$ $X_{32}X_{33}X_{34}X_{35}X_{36}X_{37}X_{38}X_{39}X_{40}X_{41}X_{42}X_{43}X_{44}X_{45}X_{46}X_{47}$ $X_{48}X_{49}X_{50}X_{51}X_{52}X_{53}X_{54}X_{55}GX_{56}HLGGX_{57}$ $RX_{58}PDGX_{59}X_{60}X_{61}X_{62}X_{63}X_{64}X_{65}X_{66}X_{67}X_{68}X_{69}X_{70}X_{71}$ $X_{72}X_{73}X_{74}GX_{75}X_{76}DTKX_{77}YX_{78}X_{79}GYX_{80}L$ $PIX_{81}QX_{82}DEMX_{83}RYX_{84}X_{85}ENX_{86}X_{87}RX_{88}X_{89}X_{90}X_{91}$ $NX_{92}NX_{93}WWX_{94}X_{95}X_{96}X_{97}X_{98}X_{99}X_{100}X_{101}$ $X_{102}X_{103}X_{104}X_{105}X_{106}FX_{107}X_{108}X_{109}X_{110}FX_{111}GX_{112}$ $X_{113}X_{114}X_{115}X_{116}X_{117}X_{118}RX_{119}X_{120}X_{121}X_{122}X_{123}$ $X_{124}X_{125}X_{126}GX_{127}X_{128}X_{129}X_{130}X_{131}X_{132}X_{133}LLX_{134}$ $X_{135}X_{136}X_{137}X_{138}X_{139}X_{140}X_{141}X_{142}X_{143}X_{144}X_{145}$ $X_{146}X_{147}X_{148}X_{149}X_{150}X_{151}X_{152}X_{153}FX_{154}X_{155}X_{156}X_{157}$ $X_{158}X_{159}X_{160}$ (SEQ ID NO: 317), wherein $X_1$ is F, Q, N, or absent, $X_2$ is L, I, T, S, or absent, $X_3$ is V, I, G, A, E, T, or absent, $X_4$ is K, C, or absent, $X_5$ is G, S, or absent, $X_6$ is A, S, E, D, or absent, $X_7$ is M, I, V, Q, F, L, or absent, $X_8$ is E, S, T, or absent, $X_9$ is I, M, E, T, Q, or absent, $X_{10}$ is K, S, L, I, T, E, or absent, $X_{11}$ is K or absent, $X_{12}$ is S, A, E, D, or absent, $X_{13}$ is E, N, Q, K, or absent, $X_{14}$ is L, M, V, or absent, $X_{15}$ is R or absent, $X_{16}$ is H, D, T, G, E, N, or absent, $X_{17}$ is K, N, Q, E, A, or absent, $X_{18}$ is L or absent, $X_{19}$ is R, Q, N, T, D, or absent, $X_{20}$ is H, M, V, N, T, or absent, $X_{21}$ is V, L, I, or absent, $X_{22}$ is P, S, or absent, $X_{23}$ is H or absent, $X_{24}$ is E, D, or absent, $X_{25}$ is Y or absent, $X_{26}$ is I, L, or absent, $X_{27}$ is E, Q, G, S, A, or absent, $X_{28}$ is L or absent, $X_{29}$ is I, V, L, or absent, $X_{30}$ is E, D, or absent, $X_{31}$ is I, L, or absent, $X_{32}$ is A, S, or absent, $X_{33}$ is Q, Y, F, or absent, $X_{34}$ is D or absent, $X_{35}$ is S, P, or absent, $X_{36}$ is K, Y, Q, T, or absent, $X_{37}$ is Q or absent, $X_{38}$ is N or absent, $X_{39}$ is R or absent, $X_{40}$ is L, I, or absent, $X_{41}$ is L, F, or absent, $X_{42}$ is E or absent, $X_{43}$ is F, M, L, or absent, $X_{44}$ is V, T, or I, $X_{45}$ is V, M, L, or I, $X_{46}$ is E, D, or Q, $X_{47}$ is F or L, $X_{48}$ is F or L, $X_{49}$ is K, I, T, or V, $X_{50}$ is K, N, or E, $X_{51}$ is I or E, $X_{52}$ is Y, F, or C, $X_{53}$ is G, or N, $X_{54}$ is Y, or F, $X_{55}$ is R, S, N, E, K, or Q, $X_{56}$ is K, S, L, V, or T, $X_{57}$ is S or A, $X_{58}$ is K or R, $X_{59}$ is A, I, or V, $X_{60}$ is L, M, V, I, or C, $X_{61}$ is F or Y, $X_{62}$ is T, A, or S, $X_{63}$ is K, E, or absent, $X_{64}$ is D, E, or absent, $X_{65}$ is E, A, or absent, $X_{66}$ is N, K, or absent, $X_{67}$ is E, S, or absent, $X_{68}$ is D, E, Q, A, or absent, $X_{69}$ is G, V, K, N, or absent, $X_7O$ is L, G, E, S, or absent, $X_{71}$ is V, S, K, T, E, or absent, $X_{72}$ is L, H, K, E, Y, D, or A, $X_{73}$ is N, G, or D, $X_{74}$ is H, F, or Y, $X_{75}$ is I, or V, $X_{76}$ is L, V, or I, $X_{77}$ is A or S, $X_{78}$ is K or S, $X_{79}$ is D, G, K, S, or N, $X_{80}$ is R, N, S, or G, $X_{81}$ is S, A, or G, $X_{82}$ is A, I, or V, $X_{83}$ is Q, E, I, or V, $X_{84}$ is V or I, $X_{85}$ is D, R, G, I, or E, $X_{86}$ is N, I, or Q, $X_{87}$ is K, D, T, E, or K, $X_{88}$ is S, N, D, or E, $X_{89}$ is Q, E, I, K, or A, $X_{90}$ is V, H, R, K, L, or E, $X_{91}$ is I, V, or R, $X_{92}$ is P, S, T, or R, $X_{93}$ is E, R, C, Q, or K, $X_{94}$ is E, N, or K, $X_{95}$ is I, V, N, E, or A, $X_{96}$ is Y or F, $X_{97}$ is P, G, or E, $X_{98}$ is T, E, S, D, K, or N, $X_{99}$ is S, D, K, G, N, or T, $X_{100}$ is I, T, V, or L, $X_{101}$ is T, N, G, or D, $X_{102}$ is D, E, T, K, or I, $X_{103}$ is F or Y, $X_{104}$ is K or Y, $X_{105}$ is F or Y, $X_{106}$ is L, S, or M, $X_{107}$ is V or I, $X_{108}$ is S or A, $X_{109}$ is G or A, $X_{110}$ is F, Y, H, E, or K, $X_{110}$ is Q, K, T, N, or I, $X_{112}$ is D, N, or K, $X_{113}$ is Y, F, I, or V, $X_{114}$ is R, E, K, Q, or F, $X_{115}$ is K, E, A, or N, $X_{116}$ is Q or K, $X_{117}$ is L or I, $X_{118}$ is E, D, N, or Q, $X_{119}$ is V, I, or L, $X_{120}$ is S, N, F, T, or Q, $X_{121}$ is H, I, C, or R, $X_{122}$ is L, D, N, S, or F, $X_{123}$ is T or K, $X_{124}$ is K, G, or N, $X_{125}$ is C, V, or I, $X_{126}$ is Q, L, K, or Y, $X_{127}$ is A, G, or N, $X_{128}$ is V or A, $X_{129}$ is M, L, I, V, or A, $X_{130}$ is S, T, or D, $X_{131}$ is V or I, $X_{132}$ is E, Q, K, S, or I, $X_{133}$ is Q, H, or T, $X_{134}$ is L, R, or Y, $X_{135}$ is G, I, L, or T, $X_{136}$ is G, A, or V, $X_{137}$ is E, N, or D, $X_{138}$ is K, Y, D, E, A, or R, $X_{139}$ is I, F, Y, or C, $X_{140}$ is K or R, $X_{141}$ is E, R, A, G, or T, $X_{142}$ is G or N, $X_{143}$ is S, I, K, R, or E, $X_{144}$ is L, I, or M, $X_{145}$ is T, S, D, or K, $X_{146}$ is L, H, Y, R, or T, $X_{147}$ is E, Y, I, M, or A, $X_{148}$ is E, D, R, or G, $X_{149}$ is V, F, M, L, or I, $X_{150}$ is G, K, R, L, V, or E, $X_{151}$ is K, N, D, L, H, or S, $X_{152}$ is K, L, C, or absent, $X_{153}$ is K, S, I, Y, M, or F, $X_{154}$ is K, L, C, H, D, Q, or N, $X_{155}$ is N or Y, $X_{156}$ is D, K, T, E, C, or absent, $X_{157}$ is E, V, R, or absent, $X_{158}$ is I, F, L, or absent, $X_{159}$ is V, Q, E, L, or absent, and $X_{160}$ is F or absent.

In some embodiments, an endonuclease of the present disclosure can have a sequence of $X_1$LVKSSX$_2$EEX$_3$KEELREKLX$_4$HLSHEYLX$_5$LX$_6$DLAY DSKQNRLFEMKVX$_7$ELLINECGYX$_8$G LHLGGSRKPDGIX$_9$YTEGLKX$_{10}$NYGIIIDTKAYSDGY NLPISQADEMERYIRENNTRNX$_{11}$X$_{12}$V NPNEWWENFPX$_{13}$NINEFYFLFVSGHFKGNX$_{14}$EEQLE RISIX$_{15}$TX$_{16}$IKGAAMSVX$_{17}$TLLLLAN EIKAGRLX$_{18}$LEEVX$_{19}$KYFDNKEIX$_{20}$F (SEQ ID NO: 318), wherein $X_1$ is F, Q, N, D, or absent, $X_2$ is M, I, V, Q, F, L, or absent, $X_3$ is K, S, L, I, T, E, or absent, $X_4$ is R, Q, N, T, D, or absent, $X_5$ is E, Q, G, S, A, Y, or absent, $X_6$ is I, V, L, or absent, $X_7$ is V, M, L, or I, $X_8$ is R, S, N, E, K, or Q, $X_9$ is L, M, V, I, or C, $X_{10}$ is L, H, K, E, Y, D, or A, $X_{11}$ is Q, E, I, K, or A, $X_{12}$ is V, H, R, K, L, or E, $X_{13}$ is T, E, S, D, K, or N, $X_{14}$ is Y, F, I, or V, $X_{15}$ is L, D, N, S, or F, $X_{16}$ is K, G, or N, $X_{17}$ is E, Q, K, S, or I, $X_{18}$ is T, S, D, or K, $X_{19}$ is G, K, R, L, V, or E, and $X_{20}$ is V, Q, E, L, or absent.

In some embodiments, an endonuclease of the present disclosure can have a sequence of $X_1$LVKSSX$_2$EEX$_3$KEELREKLX$_4$HLSHEYLX$_5$LX$_6$DLAY DSKQNRLFEMKVX$_7$ELLINECGYX$_8$G LHLGGSRKPDGIX$_9$YTEGLKX$_{10}$NYGIIIDTKAYSDGY NLPISQADEMERYIRENNTRNX$_{11}$X$_{12}$V NPNEWWENFPX$_{13}$NINEFYFLFVSGHFKGNX$_{14}$EEQLE RISIX$_{15}$TX$_{16}$IKGAAMSVX$_{17}$TLLLLAN EIKAGRLX$_{18}$LEEVX$_{19}$KYFDNKEIX$_{20}$F (SEQ ID NO: 319), wherein $X_1$ is F, Q, N, or absent, $X_2$ is M, I, V, Q, F, L, or absent, $X_3$ is K, S, L, I, T, E, or absent, $X_4$ is R, Q, N, T, D, or absent, $X_5$ is E, Q, G, S, A, or absent, $X_6$ is I, V, L, or absent, $X_7$ is V, M, L, or I, $X_8$ is R, S, N, E, K, or Q, $X_9$ is L, M, V, I, or C, $X_{10}$ is L, H, K, E, Y, D, or A, $X_{11}$ is Q, E, I, K, or A, $X_{12}$ is V, H, R, K, L, or E, $X_{13}$ is T, E, S, D, K, or N, $X_{14}$ is Y, F, I, or V, $X_{15}$ is L, D, N, S, or F, $X_{16}$ is K, G, or N, $X_{17}$ is E, Q, K, S, or I, $X_{18}$ is T, S, D, or K, $X_{19}$ is G, K, R, L, V, or E, and $X_{20}$ is V, Q, E, L, or absent. In some aspects, the cleavage domain comprises a sequence selected from SEQ ID NO: 316-SEQ ID NO: 319.

In some embodiments, an endonuclease of the present disclosure can have conserved amino acid residues at position 76 (D or E), position 98 (D), and position 100 (K), which together preserve catalytic function. In some embodiments, an endonuclease of the present disclosure can have conserved amino acid residues at position 114 (D) and position 118 (R), which together preserve dimerization of two cleavage domains.

In some embodiments, endonucleases disclosed herein (e.g., SEQ ID NO: 1-SEQ ID NO: 81 (nucleic acid sequences of SEQ ID NO: 82-SEQ ID NO: 162)) can have at least 33.3% divergence from SEQ ID NO: 163 (FokI) and, is immunologically orthogonal to SEQ ID NO: 163 (FokI). In some embodiments, an immunologically orthogonal endonuclease (e.g., SEQ ID NO: 1-SEQ ID NO: 81 (nucleic acid sequences of SEQ ID NO: 82-SEQ ID NO: 162)) can be administered to a patient that has already received, and is thus can have an adverse immune reaction to, FokI. In some embodiments, endonucleases disclosed herein (e.g., SEQ ID NO: 1-SEQ ID NO: 81 (nucleic acid sequences of SEQ ID NO: 82-SEQ ID NO: 162)) can have at least 35%, at least 40%, at least 45%, at least 50%, at least 55%, at least 60%, at least 65%, at least 70%, or at least 75% divergence from SEQ ID NO: 163 (FokI).

In some embodiments, an endonuclease disclosed herein (e.g., SEQ ID NO: 1-SEQ ID NO: 81 (nucleic acid sequences of SEQ ID NO: 82-SEQ ID NO: 162)) can be fused to any nucleic acid binding domain disclosed herein to form a non-naturally occurring fusion protein. This fusion protein can have one or more of the following characteristics: (a) induces greater than 1% indels (insertions/deletions) at a target site; (b) the cleavage domain comprises a molecular weight of less than 23 kDa; (c) the cleavage domain comprises less than 196 amino acids; and (d) capable of cleaving across a spacer region greater than 24 base pairs. In some embodiments, the non-naturally occurring fusion protein can induce greater than 5%, greater than 10%, greater than 20%, greater than 30%, greater than 40%, greater than 50%, greater than 60%, greater than 70%, greater than 80%, or greater than 90% indels at the target site. In some embodiments, indels are generated via the non-homologous end joining (NHEJ) pathway upon administration of a genome editing complex disclosed herein to a subject. Indels can be measured using deep sequencing, DNA Binding Domains Fused to SEQ ID NO: 1-SEQ ID NO: 81 (Nucleic Acid Sequences of SEQ ID NO: 82-SEQ ID NO: 162)

The present disclosure provides for novel compositions of endonucleases with modular nucleic acid binding domains (e.g., TALEs, RNBDs, or MAP-NBDs) described herein. In some instances the novel endonucleases can be fused to a DNA binding domain from *Xanthomonas* spp. (TALE), *Ralstonia* (RNBD), or an animal pathogen (MAP-NBD) resulting in genome editing complexes. A TALEN, RNBD-nuclease, or MAP-NBD-nuclease can include multiple components including the DNA binding domain, an optional linker, and a repressor domain. The genome editing complexes described herein can be used to selectively bind and cleave to a target gene sequence for genome editing purposes. For example, a DNA binding domain from *Xanthomonas, Ralstonia*, or an animal pathogen of the present disclosure can be used to direct the binding of a genome editing complex to a desired genomic sequence.

The genome editing complexes described herein, comprising a DNA binding domain fused to an endonuclease, can be used to edit genomic loci of interest by binding to a target nucleic acid sequence via the DNA binding domain and cleaving phosphodiester bonds of target double stranded DNA via the endonuclease.

In some aspects, DNA binding domains fused to nucleases can create a site-specific double-stranded DNA break when fused to a nuclease. Such breaks can then be subsequently repaired by cellular machinery, through either homology-dependent repair or non-homologous end joining (NHEJ). Genome editing, using DNA binding domains fused to nucleases described herein, can thus be used to delete a sequence of interest (e.g., an aberrantly expressed or mutated gene) or to introduce a nucleic acid sequence of interest (e.g., a functional gene). DNA binding domains of the present disclosure can be programmed to delivery virtually any nuclease, including those disclosed herein, to any target site for therapeutic purposes, including ex vivo engineered cell therapies obtained using the compositions disclosed herein or gene therapy by direct in vivo administration of the compositions disclosed herein. In addition, the DNA binding domain can bind to specific DNA sequences and in some cases they can activate the expression of host genes. In some instances, the disclosure provides for enzymes, e.g., SEQ ID NO: 1-SEQ ID NO: 81 (or any one of nucleic acid sequences of SEQ ID NO: 82-SEQ ID NO: 162) that can be fused to the DNA binding domains of TALEs, RNBDs, and MAP-NBDs. In some instances, enzymes of the disclosure, including SEQ ID NO: 1 (nucleic acid sequence of SEQ ID NO: 82), SEQ ID NO: 4 (nucleic acid sequence of SEQ ID NO: 85), and SEQ ID NO: 8 (nucleic acid sequence of SEQ ID NO: 89), can achieve greater than 30% indels via the NHEJ pathway on a target gene when fused to a DNA binding domain of a TALE, RNBD, and MAP-NBD.

A non-naturally occurring fusion protein of the disclosure, e.g., any one of SEQ ID NO: 1-SEQ ID NO: 81 (or any one of nucleic acid sequences of SEQ ID NO: 82-SEQ ID NO: 162) fused to a DNA binding domain, can comprise a repeat unit. A repeat unit can be from a wild-type DNA-binding domain (*Ralstonia solanacearum, Xanthomonas* spp., or an animal pathogen) or a modified repeat unit enhanced for specific recognition of a particular nucleic acid base. A modified repeat unit can comprise 1, 2, 3, 4, 5, 6, 7, 8, 9, 10, 15, 20, 25 or more mutations that can enhance the repeat module for specific recognition of a particular nucleic acid base. In some embodiments, a modified repeat unit is modified at amino acid position 2, 3, 4, 11, 12, 13, 21, 23, 24, 25, 26, 27, 28, 30, 31, 32, 33, 34, or 35. In some embodiments, a modified repeat unit is modified at amino acid positions 12 or 13.

As described in further detail below, a non-naturally occurring fusion protein of the disclosure, e.g., anyone of SEQ ID NO: 1-SEQ ID NO: 81 (or any one of nucleic acid sequences of SEQ ID NO: 82-SEQ ID NO: 162) fused to a plurality of repeat units (e.g., derived from *Ralstonia solanacearum, Xanthomonas* spp., or an animal pathogen), can further comprise a C-terminal truncation, which can served as a linker between the DNA binding domain and the nuclease.

A non-naturally occurring fusion protein of the disclosure, e.g., anyone of SEQ ID NO: 1-SEQ ID NO: 81 (or any one of nucleic acid sequences of SEQ ID NO: 82-SEQ ID NO: 162) fused to a DNA binding domain, can further comprise an N-terminal cap as described in further detail below. An N-terminal cap can be a polypeptide portion flanking the DNA-binding repeat unit. An N-terminal cap can be any length and can comprise from 0 to 136 amino acid residues in length. An N-terminal cap can be 5, 10, 15, 20, 25, 30, 35, 40, 45, 50, 60, 70, 80, 90, 100, 110, 120, or 130 amino acid residues in length. In some embodiments, an N-terminal cap can modulate structural stability of the DNA-binding repeat units. In some embodiments, an N-terminal cap can modulate nonspecific interactions. In some cases, an N-terminal cap can decrease nonspecific interaction. In some cases, an N-terminal cap can reduce off-target effect. As used here, off-target effect refers to the interaction of a genome editing complex with a sequence that is not the target binding site of interest. An N-terminal cap can further comprise a wild-type N-terminal cap sequence of a protein from *Ralstonia solanacearum, Xanthomonas* spp., or an animal pathogen or can comprise a modified N-terminal cap sequence.

In some embodiments, a DNA binding domain comprises at least one repeat unit having a repeat variable diresidue (RVD), which contacts a target nucleic acid base. In some embodiments, a DNA binding domain comprises more than one repeat unit, each having an RVD, which contacts a target nucleic acid base. In some embodiments, the DNA binding domain comprises 1 to 50 RVDs. In some embodiments, the DNA binding domain components of the fusion proteins can be at least 14 RVDs, at least 15 RVDs, at least 16 RVDs, at least 17 RVDs, at least 18 RVDs, at least 19 RVDs, at least 20 RVDs in length, or at least 21 RVDs in length. In some embodiments, the DNA binding domains can be 16 to 21 RVDs in length.

In some embodiments, any one of the DNA binding domains described herein can bind to a region of interest of any gene. For example, the DNA binding domains described herein can bind upstream of the promoter region, upstream of the gene transcription start site, or downstream of the transcription start site. In certain embodiments, the DNA binding domain binding region is no farther than 50 base pairs downstream of the transcription start site. In some embodiments, the DNA binding domain is designed to bind in proximity to the transcription start site (TSS). In other embodiments, the TALE can be designed to bind in the 5' UTR region.

A DNA binding domain described herein can comprise between 1 to 50 repeat units. A DNA binding domain described herein can comprise between 5 and 45, between 8 to 45, between 10 to 40, between 12 to 35, between 15 to 30, between 20 to 30, between 8 to 40, between 8 to 35, between 8 to 30, between 10 to 35, between 10 to 30, between 10 to 25, between 10 to 20, or between 15 to 25 repeat units.

A DNA binding domain described herein can comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, or more repeat units. A DNA binding domain described herein can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, or 50 repeat units. A DNA binding domain described herein can comprise 5 repeat units. A DNA binding domain described herein can comprise 10 repeat units. A DNA binding domain described herein can comprise 11 repeat units. A DNA binding domain described herein can comprise 12 repeat units, or another suitable number.

A repeat unit of a DNA binding domain can be 18, 19, 20, 21, 22, 23, 24, 25, 26, 27, 28, 29, 30, 31, 32, 33, 34, 35, 36, 37, 38, 39 or 40 residues in length.

In some embodiments, the effector can be a protein secreted from *Xanthomonas* or *Ralstonia* bacteria upon plant infection. In some embodiments, the effector can be a protein that is a mutated form of, or otherwise derived from, a protein secreted from *Xanthomonas* or *Ralstonia* bacteria. The effector can further comprise a DNA-binding module which includes a variable number of about 33-35 amino acid residue repeat units. Each amino acid repeat unit recognizes one base pair through two adjacent amino acids (e.g., at amino acid positions 12 and 13 of the repeat unit). As such, amino acid positions 12 and 13 of the repeat unit can also be referred to as repeat variable diresidue (RVD).

Linkers

A nuclease, e.g., anyone of SEQ ID NO: 1-SEQ ID NO: 81 (or any one of nucleic acid sequences of SEQ ID NO: 82-SEQ ID NO: 162) fused to a DNA binding domain (e.g., an RNBD, a MAP-NBD, a TALE), can further include a linker connecting SEQ ID NO: 1-SEQ ID NO: 81 (or any one of nucleic acid sequences of SEQ ID NO: 82-SEQ ID NO: 162) to the DNA binding domain. A linker used herein can be a short flexible linker comprising 0 base pairs, 3 to 6 base pairs, 6 to 12 base pairs, 12 to 15 base pairs, 15 to 21 base pairs, 21 to 24 base pairs, 24 to 30 base pairs, 30 to 36 base pairs, 36 to 42 base pairs, 42 to 48 base pairs, or 1-48 base pairs. The nucleic acid sequence of the linker can encode for an amino acid sequence comprising 0 residues, 1-3 residues, 4-7 residues, 8-10 residues, 10-12 residues, 12-15 residues, or 1-15 residues. Linkers can include, but are not limited to, residues such as glycine, methionine, aspartic acid, alanine, lysine, serine, leucine, threonine, tryptophan, or any combination thereof.

When linking a repressor domain to an RNBD, MAP-NBD, or TALE, the linker can have a nucleic acid sequence of GGCGGTGGCGGAGGGATGGATGCTAAGT-CACTAACTGCCTGGTCC (SEQ ID NO: 165) and an amino acid sequence of GGGGGMDAKSLTAWS (SEQ ID NO: 166).

A nuclease, e.g., anyone of SEQ ID NO: 1-SEQ ID NO: 81 (or any one of nucleic acid sequences of SEQ ID NO: 82-SEQ ID NO: 162) can be connected to a DNA binding domain via a linker, a linker can be between 1 to 70 amino acid residues in length. A linker can be from 5 to 45, from 5 to 40, from 5 to 35, from 5 to 30, from 5 to 25, from 5 to 20, from 5 to 15, from 10 to 40, from 10 to 35, from 10 to 30, from 10 to 25, from 10 to 20, from 12 to 40, from 12 to 35, from 12 to 30, from 12 to 25, from 12 to 20, from 14 to 40, from 14 to 35, from 14 to 30, from 14 to 25, from 14 to 20, from 14 to 16, from 15 to 40, from 15 to 35, from 15 to 30, from 15 to 25, from 15 to 20, from 15 to 18, from 18 to 40, from 18 to 35, from 18 to 30, from 18 to 25, from 18 to 24, from 20 to 40, from 20 to 35, from 20 to 30, from 25 to 30, from 25 to 70, from 30 to 70, from 5 to 70, from 35 to 70, from 40 to 70, from 45 to 70, from 50 to 70, from 55 to 70, from 60 to 70, or from 65 to 70 amino acid residues in length.

A linker for linking a nuclease, e.g., anyone of SEQ ID NO: 1-SEQ ID NO: 81 (or any one of nucleic acid sequences of SEQ ID NO: 82-SEQ ID NO: 162) to a DNA binding domain can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, or 70 amino acid residues in length.

In some embodiments, the linker can be the N-terminus of a naturally occurring *Ralstonia solanacearum*-derived protein, *Xanthomonas* spp.-derived protein, or *Legionella quateirensis*-derived protein, wherein any functional domain disclosed herein is fused to the N-terminus of the engineered DNA binding domain. In some embodiments, the linker comprising the N-terminus can comprise the full length naturally occurring N-terminus of a naturally occurring *Ralstonia solanacearum*-derived protein, *Xanthomonas* spp.-derived protein, or *Legionella quateirensis*-derived protein, or a truncation of the naturally occurring N-terminus, such as amino acid residues at positions 1 to 137 of the naturally occurring *Ralstonia solanacearum*-derived protein N-terminus (e.g., SEQ ID NO: 264), positions 1 (H) to 115 (S) of the naturally occurring *Ralstonia solanacearum*-derived protein N-terminus (SEQ ID NO: 320), positions 1 (N) to 115 (S) of the naturally occurring *Xanthomonas* spp.-derived protein N-terminus (SEQ ID NO: 321), or positions 1 (G) to 115 (K) of the naturally occurring *Legionella quateirensis*-derived protein N-terminus (SEQ ID NO: 322). In some embodiments, the linker can comprise amino acid residues at positions 1 to 120 of the naturally occurring *Ralstonia solanacearum*-derived protein (SEQ ID NO: 303), *Xanthomonas* spp.-derived protein (SEQ ID NO: 301), or *Legionella quateirensis*-derived protein (SEQ ID N): 304). In some embodiments, the linker can comprise the naturally occurring N-terminus of *Ralstonia solanacearum* truncated to any length. For example, the naturally occurring N-terminus of *Ralstonia solanacearum* can be truncated to amino acid residues at positions 1 to 120, 1 to 115, 1 to 50, 1 to 70, 1 to 100, 1 to 120, 1 to 130, 10 to 40, 60 to 100, or 100 to 120 and used at the N-terminus of the engineered DNA binding domain as a linker to a nuclease or a repressor.

In other embodiments, the linker can be the C-terminus of a naturally occurring *Ralstonia solanacearum*-derived protein, *Xanthomonas* spp.-derived protein, or animal pathogen-derived protein, wherein any functional domain disclosed herein is fused to the C-terminus of the engineered DNA binding domain. In some embodiments, the linker comprising the C-terminus can comprise the full length naturally occurring C-terminus of a naturally occurring *Ralstonia solanacearum*-derived protein, *Xanthomonas* spp.-derived protein, or animal pathogen-derived protein, or a truncation of the naturally occurring C-terminus, such as positions 1 to 63 of the naturally occurring *Ralstonia solanacearum*-derived protein (SEQ ID NO: 266), *Xanthomonas* spp.-derived protein (SEQ ID NO: 298), or *Legionella quateirensis*-derived protein (SEQ ID NO: 306). In some embodiments, the naturally occurring C-terminus of *Ralstonia solanacearum*-derived protein, *Xanthomonas* spp.-derived protein, or *Legionella quateirensis*-derived protein can be truncated to any length and used at the C-terminus of the engineered DNA binding domain and used as a linker to a nuclease or repressor. For example, the naturally occurring C-terminus of *Ralstonia solanacearum*-derived protein, *Xanthomonas* spp.-derived protein, or *Legionella quateirensis*-derived protein can be truncated to amino acid residues at positions 1 to 63, 1 to 50, 1 to 70, 1 to 100, 1 to 120, 1 to 130, 10 to 40, 60 to 100, or 100 to 120 and used at the C-terminus of the engineered DNA binding domain.

Functional Domains

An RNBD (e.g., *Ralstonia solanacearum*-derived), or another binding domain (e.g., MAP-NBD or TALE), can be linked to a functional domain. The functional domain can provide different types activity, such as genome editing, gene regulation (e.g., activation or repression), or visualization of a genomic locus via imaging.

A. Genome Editing Domains

For example, an RNBD (e.g., *Ralstonia solanacearum*-derived), or another binding domain (e.g., MAP-NBD or TALE), can be linked to a nuclease, wherein the RNBD provides specificity and targeting and the nuclease provides genome editing functionality. In some embodiments, the nuclease can be a cleavage domain, which dimerizes with another copy of the same cleavage domain to form an active full domain capable of cleaving DNA. In other embodiments, the nuclease can be a cleavage domain, which is capable of cleaving DNA without needing to dimerize. For example, a nuclease comprising a cleavage domain can be an endonuclease, such as FokI or Bfil. In some embodiments, two cleavage domains (e.g., FokI or Bfil) can be fused together to form a fully functional single cleavage domain. When cleavage domains are used as the nuclease, two RNBDs can be engineered, the first RNBD binding to a top strand of a target nucleic acid sequence and comprising a first FokI cleavage domain and a second RNBD binding to a bottom strand of a target nucleic acid sequence and comprising a second FokI cleavage domain.

In some embodiments, a fully functional cleavage domain, capable of cleaving DNA without needing to dimerize include meganucleases, also referred to as homing endonucleases. For example, a meganuclease can include I-AniI or I-OnuI. In some embodiments, the nuclease can be a type IIS restriction enzyme, such as FokI or Bfil.

A nuclease domain fused to an RNBD (e.g., *Ralstonia solanacearum*-derived), or another binding domain (e.g., MAP-NBD or TALE), can be an endonuclease or an exonuclease. An endonuclease can include restriction endonucleases and homing endonucleases. An endonuclease can also include S 1 Nuclease, mung bean nuclease, pancreatic DNase I, micrococcal nuclease, or yeast HO endonuclease. An exonuclease can include a 3'-5' exonuclease or a 5'-3' exonuclease. An exonuclease can also include a DNA exonuclease or an RNA exonuclease. Examples of exonuclease includes exonucleases I, II, III, IV, V, and VIII; DNA polymerase I, RNA exonuclease 2, and the like.

A nuclease domain fused to an RNBD (e.g., *Ralstonia solanacearum*-derived), or another binding domain (e.g., MAP-NBD or TALE), can be a restriction endonuclease (or restriction enzyme). In some instances, a restriction enzyme cleaves DNA at a site removed from the recognition site and has a separate binding and cleavage domains. In some instances, such restriction enzyme is a Type IIS restriction enzyme.

A nuclease domain fused to an RNBD (e.g., *Ralstonia solanacearum*-derived), or another binding domain (e.g., MAP-NBD or TALE), can be a Type IIS nuclease. A Type IIS nuclease can be FokI or Bfil. In some cases, a nuclease domain fused to an RNBD (e.g., *Ralstonia solanacearum*-derived) is FokI. In other cases, a nuclease domain fused to an RNBD (e.g., *Ralstonia solanacearum*-derived) is Bfil.

FokI can be a wild-type FokI or can comprise one or more mutations. In some cases, FokI can comprise 1, 2, 3, 4, 5, 6, 7, 8, 9, 10, or more mutations. A mutation can enhance cleavage efficiency. A mutation can abolish cleavage activity. In some cases, a mutation can modulate homodimerization. For example, FokI can have a mutation at one or more amino acid residue positions 446, 447, 479, 483, 484, 486, 487, 490, 491, 496, 498, 499, 500, 531, 534, 537, and 538 to modulate homodimerization.

In some instances, a FokI cleavage domain is, for example, as described in Kim et al. "Hybrid restriction enzymes: Zinc finger fusions to Fok I cleavage domain," PNAS 93: 1156-1160 (1996), which is incorporated herein by reference in its entirety. In some cases, a FokI cleavage domain described herein has a sequence as follows: QLVKSELEEKKSELRHKLKYVPHEYIELIEIARN-STQDRILEMKVMEFFMKVYGYRGKHLG GSRKPD-GAIYTVGSPIDYGVIVDTKAYSGGY-NLPIGQADEMQRYVEENQTRNKHINPNEWW KVYPSSVTEFKFLFVSGHFKGNYKAQLTRLN-
HITNCNGAVLSVEELLIGGEMIKAGTLTLEE
VRRKFNNGEINF (SEQ ID NO: 163). In other instances, a FokI cleavage domain described herein is a FokI, for example, as described in U.S. Pat. No. 8,586,526, which is incorporated herein by reference in its entirety.

An RNBD (e.g., *Ralstonia solanacearum*-derived) can be linked to a functional group that modifies DNA nucleotides, for example an adenosine deaminase.

In some embodiments, an RNBD (e.g., *Ralstonia solanacearum*-derived) can be linked to any nuclease as set forth in TABLE 7 showing exemplary amino acid sequences (SEQ ID NO: 1-SEQ ID NO: 81) of endonucleases for genome editing and the corresponding back-translated nucleic acid sequences (SEQ ID NO: 82-SEQ ID NO: 162) of the endonucleases.

For purposes of gene editing, a first DNA binding domain (e.g., of a TALE, RNBD, or MAP-NBD) linked to a cleavage domain and a second DNA binding domain (e.g., of a TALE, RNBD, or MAP-NBD) linked to a cleavage domain can be provided. The first DNA binding domain (e.g., of a TALE, RNBD, or MAP-NBD) linked to a cleavage domain can recognize a top strand of double stranded DNA and bind to said region of double stranded DNA. The second DNA binding domain (e.g., of a TALE, RNBD, or MAP-NBD) linked to a cleavage domain can recognize a separate, non-overlapping bottom strand of double stranded DNA and bind to said region of double stranded DNA. The target nucleic acid sequence on the bottom strand can have its complementary nucleic acid sequence in the top strand positioned 10 to 20 nucleotides towards the 3' end from the first region. In some embodiments this stretch of 10 to 20 nucleotides can be referred to as the spacer region. In some embodiments, this first DNA binding domain (e.g., of a TALE, RNBD, or MAP-NBD) linked to a cleavage domain and the second DNA binding domain (e.g., of a TALE, RNBD, or MAP-NBD) linked to a cleavage domain both bind at a target site, allowing for dimerization of the two cleavage domains in the spacer region and allowing for catalytic activity and cleaving of the target DNA.

a. Potency and Specificity of Genome Editing

In some embodiments, the efficiency of genome editing with a genome editing complex of the present disclosure (e.g., any one of an RNBD, MAP-NBD, or TALE fused to any nuclease disclosed herein) can be determined. Specifically, the potency and specificity of the genome editing complex can indicate whether a particular modular nucleic acid binding domain fused to a nuclease provides efficient editing. Potency can be defined as the percent indels (insertions/deletions) that are generated via the non-homologous end joining (NHEJ) pathway at a target site after administering a modular nucleic acid binding domain fused to a nuclease to a subject. A modular nucleic acid binding domain can have a potency of greater than 50%, greater than 55%, greater than 60%, greater than 65%, greater than 70%, greater than 75%, greater than 80%, greater than 85%, greater than 90%, greater than 95%, greater than 92%, greater than 95%, greater than 97%, or greater than 99%. A modular nucleic acid binding domain can have a potency of from 50% to 100%, 50% to 60%, 60% to 70%, 70% to 80%, 80% to 90%, or 90% to 100%.

Specificity can be defined as a specificity ratio, wherein the ratio is the percent indels at a target site of interest over the percent indels at the top-ranked off-target site for a particular genome editing complex (e.g., any DNA binding domain linked to a nuclease described herein) of interest. A high specificity ratio would indicate that a modular nucleic acid binding domain fused to a nuclease edits primarily at the desired target site and exhibits fewer instances of undesirable, off-target editing. A low specificity ratio would indicate that a modular nucleic acid binding domain fused to a nuclease does not edit efficiently at the desired target site and/or can indicate that the modular nucleic acid binding domain fused to a nuclease exhibits high off-target activity. A modular nucleic acid binding domain can have a specificity ratio for the target site of at least 50:1, 55:1, 60:1, 65:1, 70:1, 75:1, 80:1, 85:1, 90:1, 92:1, 95:1, 97:1, 99:1, 50:2, 55:2, 60:2, 65:2, 70:2, 75:2, 80:2, 85:2, 90:2, 92:2, 95:2, 97:2, 99:2, 50:3, 55:3, 60:3, 65:3, 70:3, 75:3, 80:3, 85:3, 90:3, 92:3, 95:3, 97:3, 99:3, 50:4, 55:4, 60:4, 65:4, 70:4, 75:4, 80:4, 85:4, 90:4, 92:4, 95:4, 97:4, 99:4, 50:5, 55:5, 60:5, 65:5, 70:5, 75:5, 80:5, 85:5, 90:5, 92:5, 95:5, 97:5, or 99:5. Percent indels generated via non-homologous end joining (NHEJ) can be measured via deep sequencing techniques.

In some embodiments, the composition further comprises a cleavage domain linked to the modular nucleic acid binding domain to form a non-naturally occurring fusion protein. In some aspects, the modular nucleic acid binding domain comprises a potency for a target site greater than 65% and a specificity ratio for the target site of 50:1; and a functional domain; wherein the modular nucleic acid binding domain comprises a plurality of repeat units, wherein at least one repeat unit of the plurality comprises a binding region configured to bind to a target nucleic acid base in the target site, wherein the potency comprises indel percentage at the target site, and wherein the specificity ratio comprises indel percentage at the target site over indel percentage at a top-ranked off-target site of the non-naturally occurring fusion protein.

In some embodiments, the repeat unit comprises a sequence of $A_{1-11}X_1X_2B_{14-35}$ (SEQ ID NO: 448), wherein each amino acid residue of $A_{1-11}$ comprises any amino acid residue; wherein $X_1X_2$ comprises the binding region; wherein each amino acid residue of $B_{14-35}$ comprises any amino acid; and wherein a first repeat unit of the plurality of repeat units comprises at least one residue in $A_{1-11}$, $B_{14-35}$, or a combination thereof that differs from a corresponding residue in a second repeat unit of the plurality of repeat units.

In some embodiments, the binding region comprises an amino acid residue at position 13 or an amino acid residue at position 12 and the amino acid residue at position 13. In further aspects, the amino acid residue at position 13 binds to the target nucleic acid base. In still further aspects, the amino acid residue at position 12 stabilizes the configuration of the binding region. In some aspects, the indel percentage is measured by deep sequencing. In some aspects, the modular nucleic acid binding domain further comprises one or more properties selected from the following: (a) binds the target site, wherein the target site comprises a 5' guanine; (b) comprises from 7 repeat units to 25 repeat units; and (c) upon binding to the target site, the modular nucleic acid binding domain is separated from a second modular nucleic acid binding domain bound to a second target site by from 2 to 50 base pairs.

The top-ranked off-target site for a composition (e.g., a modular nucleic acid binding domain linked to a cleavage domain) can be determined using the predicted report of genome-wide nuclease off-target sites (PROGNOS) ranking algorithms as described in Fine et al. (Nucleic Acids Res. 2014 April; 42(6):e42. doi: 10.1093/nar/gkt1326. Epub 2013 Dec. 30.). As described in Fine et al, the PROGNOS algorithm TALEN v2.0 can use the DNA target sequence as input; prior construction and experimental characterization of the specific nucleases are not necessary. Based on the differences between the sequence of a potential off-target site in the genome and the intended target sequence, the algorithm can generate a score that is used to rank potential off-target sites. If two (or more) potential off-target sites have equal scores, they can be further ranked by the type of genomic region annotated for each site with the following order: Exon>Promoter>Intron>Intergenic. A final ranking by chromosomal location can be employed as a tie-breaker to ensure consistency in the ranking order. Thus, a score can be generated for each potential off-target site.

B. Regulatory Domains

As another example, an RNBD (e.g., *Ralstonia solanacearum*-derived), or another binding domain (e.g., MAP-NBD or TALE), can be linked to a gene regulating domain. A gene regulation domain can be an activator or a repressor. For example, an RNBD (e.g., *Ralstonia solanacearum*-derived), or another binding domain (e.g., MAP-NBD or TALE), can be linked to an activation domain, such as VP16, VP64, p65, p300 catalytic domain, TET1 catalytic domain, TDG, Ldb1 self-associated domain, SAM activator (VP64, p65, HSF1), or VPR (VP64, p65, Rta). Alternatively, an RNBD (e.g., *Ralstonia solanacearum*-derived), or another binding domain (e.g., MAP-NBD or TALE), can be linked to a repressor, such as KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2.

In some embodiments, an RNBD (e.g., *Ralstonia solanacearum*-derived), or another binding domain (e.g., MAP-NBD or TALE), can be linked to a DNA modifying protein, such as DNMT3a. An RNBD (e.g., *Ralstonia solanacearum*-derived), or another binding domain (e.g., MAP-NBD or TALE), can be linked to a chromatin-modifying protein, such as lysine-specific histone demethylase 1 (LSD1). An RNBD (e.g., *Ralstonia solanacearum*-derived), or another binding domain (e.g., MAP-NBD or TALE), can be linked to a protein that is capable of recruiting other proteins, such as KRAB. The DNA modifying protein (e.g., DNMT3a) and proteins capable of recruiting other proteins (e.g., KRAB) can serve as repressors of transcription. Thus, RNBDs (e.g., *Ralstonia solanacearum*-derived), or another binding domain (e.g., MAP-NBD or TALE), linked to a DNA modifying protein (e.g., DNMT3a) or a domain capable of recruiting other proteins (e.g., KRAB, a domain found in transcriptional repressors, such as Kox1) can provide gene repression functionality, can serve as transcription factors, wherein the RNBD (e.g., *Ralstonia solanacearum*-derived), or another binding domain (e.g., MAP-NBD or TALE), provides specificity and targeting and the DNA modifying protein and the protein capable of recruiting other proteins provides gene repression functionality, which can be referred to as a TALE-transcription factor (TALE-TF), RNBD-transcription factor (RNBD-TF), or MAP-NBD-transcription factor (MAP-NBD-TF).

In some embodiments, expression of the target gene can be reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 92%, at least 95%, at least 97%, or at least 99% by using a DNA binding domain fused to a repression domain (e.g., an RNBD-TF, a MAP-NBD-TF, or TALE-TF) of the present disclosure as compared to non-treated cells. In some embodiments, expression of the target gene can be reduced by 5% to 10%, 10% to 15%, 15% to 20%, 20%, to 25%, 25% to 30%, 30% to 35%, 35% to 40%, 40% to 45%, 45% to 50%, 50% to 55%, 55% to 60%, 60% to 65%, 65% to 70%, 70% to 75%, 75% to 80%, 80% to 85%, 85% to 90%, 90% to 95%, or 95% to 99% by using an RNBD-TF, a MAP-NBD-TF, or TALE-TF of the present disclosure as compared to non-treated cells. In some embodiments, expression of the checkpoint gene can be reduced by over 90% by using an RNBD-TF, a MAP-NBD-TF, or TALE-TF of the present disclosure as compared to non-treated cells.

In some embodiments, repression of the target gene with a DNA binding domain fused to a repression domain (e.g., an RNBD-TF, a MAP-NBD-TF, or TALE-TF) of the present disclosure and subsequent reduced expression of the target gene can last for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, or at least 28 days. In some embodiments, repression of the target gene with an RNBD-TF, a MAP-NBD-TF, or TALE-TF of the present disclosure and subsequent reduced expression of the target gene can last for 1 days to 3 days, 3 days to 5 days, 5 days to 7 days, 7 days to 9 days, 9 days to 11 days, 11 days to 13 days, 13 days to 15 days, 15 days to 17 days, 17 days to 19 days, 19 days to 21 days, 21 days to 23 days, 23 days to 25 days, or 25 days to 28 days.

In various aspects, the present disclosure provides a method of identifying a target binding site in a target gene of a cell, the method comprising: (a) contacting a cell with an engineered genomic regulatory complex comprising a DNA binding domain, a repressor domain, and a linker; (b) measuring expression of the target gene; and (c) determining expression of the target gene is repressed by at least 50%, at least 60%, at least 70%, at least 80%, at least 85%, at least 90%, at least 92%, at least 95%, at least 97%, or at least 99% for at least 3 days, wherein the target gene is selected from: a checkpoint gene and a T cell surface receptor.

In some aspects, expression of the target gene is repressed in at least 75%, at least 80%, at least 85%, at least 90%, at least 95%, or at least 99% of a plurality of the cells. In some aspects, the engineered genomic regulatory complex is undetectable after at least 3 days. In some aspects, determining the engineered genomic regulatory complex is undetectable is measured by qPCR, imaging of a FLAG-tag, or a combination thereof. In some aspects, the measuring expression of the target gene comprises flow cytometry quantification of expression of the target gene.

In some embodiments, repression of the target gene with a DNA binding domain fused to a repression domain (e.g., an RNBD-TF, a MAP-NBD-TF, or TALE-TF) of the present disclosure can last even after the DNA binding domain-gene regulator becomes undetectable. The DNA binding domain fused to a repression domain (e.g., an RNBD-TF, a MAP-NBD-TF, or TALE-TF) can become undetectable after at least 3 days. In some embodiments, the DNA binding domain fused to a repression domain (e.g., an RNBD-TF, a MAP-NBD-TF, or TALE-TF) can become undetectable after at least 1 day, at least 2 days, at least 3 days, at least 4 days, at least 5 days, at least 6 days, at least 1 week, at least 2 weeks, at least 3 weeks, or at least 4 weeks. In some embodiments, qPCR or imaging via the FLAG-tag can be used to confirm that the DNA binding domain fused to a repression domain (e.g., an RNBD-TF, a MAP-NBD-TF, or TALE-TF) is no longer detectable.

C. Imaging Moieties

An RNBD (e.g., *Ralstonia solanacearum*-derived), or another binding domain (e.g., MAP-NBD or TALE), can be linked to a fluorophore, such as Hydroxycoumarin, methoxycoumarin, Alexa fluor, aminocoumarin, Cy2, FAM, Alexa fluor 488, Fluorescein FITC, Alexa fluor 430, Alexa fluor 532, HEX, Cy3, TRITC, Alexa fluor 546, Alexa fluor 555, R-phycoerythrin (PE), Rhodamine Red-X, Tamara, Cy3.5, Rox, Alexa fluor 568, Red 613, Texas Red, Alexa fluor 594, Alexa fluor 633, Allophycocyanin, Alexa fluor 633, Cy5, Alexa fluor 660, Cy5.5, TruRed, Alexa fluor 680, Cy7, GFP, or mCHERRY. An RNBD (e.g., *Ralstonia solanacearum*-derived) can be linked to a biotinylation reagent.

Genes and Indications of Interest

In some embodiments, genome editing can be performed by fusing a nuclease of the present disclosure with a DNA binding domain for a particular genomic locus of interest. Genetic modification can involve introducing a functional gene for therapeutic purposes, knocking out a gene for therapeutic gene, or engineering a cell ex vivo (e.g., HSCs or CAR T cells) to be administered back into a subject in need thereof. For example, the genome editing complex can have a target site within PDCD1, CTLA4, LAGS, TET2, BTLA, HAVCR2, CCR5, CXCR4, TRA, TRB, B2M, albumin, HBB, HBA1, TTR, NR3C1, CD52, erythroid specific enhancer of the BCL11A gene, CBLB, TGFBR1, SERPINA1, HBV genomic DNA in infected cells, CEP290, DMD, CFTR, IL2RG, CS-1, or any combination thereof. In some embodiments, a genome editing complex can cleave double stranded DNA at a target site in order to insert a chimeric antigen receptor (CAR), alpha-L iduronidase (IDUA), iduronate-2-sulfatase (IDS), or Factor 9 (F9). Cells, such as hematopoietic stem cells (HSCs) and T cells, can be engineered ex vivo with the genome editing complex. Alternatively, genome editing complexes can be directly administered to a subject in need thereof.

The subject receiving treatment can be suffering from a disease such as transthyretin amyloidosis (ATTR), HIV, glioblastoma multiforme, cancer, acute lymphoblastic leukemia, acute myeloid leukemia, beta-thalassemia, sickle cell disease, MPSI, MPSII, Hemophilia B, multiple myeloma, melanoma, sarcoma, Leber congenital amaurosis (LCA10), CD19 malignancies, BCMA-related malignancies, duchenne muscular dystrophy (DMD), cystic fibrosis, alpha-1 antitrypsin deficiency, X-linked severe combined immunodeficiency (X-SCID), or Hepatitis B.

Samples for Analysis

In some aspects, described herein include methods of modifying the genetic material of a target cell utilizing an RNBD described herein. A sample described herein may be a fresh sample. The sample may be a live sample.

The sample may be a cell sample. The cell sample may be obtained from the cells or tissue of an animal. The animal cell may comprise a cell from an invertebrate, fish, amphibian, reptile, or mammal. The mammalian cell may be obtained from a primate, ape, equine, bovine, porcine, canine, feline, or rodent. The mammal may be a primate, ape, dog, cat, rabbit, ferret, or the like. The rodent may be a mouse, rat, hamster, gerbil, hamster, chinchilla, or guinea pig. The bird cell may be from a canary, parakeet, or parrot. The reptile cell may be from a turtle, lizard, or snake. The fish cell may be from a tropical fish. For example, the fish cell may be from a zebrafish (such as *Danio rerio*). The amphibian cell may be from a frog. An invertebrate cell may be from an insect, arthropod, marine invertebrate, or worm. The worm cell may be from a nematode (such as *Caenorhabditis elegans*). The arthropod cell may be from a tarantula or hermit crab.

The cell sample may be obtained from a mammalian cell. For example, the mammalian cell may be an epithelial cell, connective tissue cell, hormone secreting cell, a nerve cell, a skeletal muscle cell, a blood cell, an immune system cell, or a stem cell. A cell may be a fresh cell, live cell, fixed cell, intact cell, or cell lysate. Cell samples can be any primary cell, such as a hematopoetic stem cell (HSCs) or naïve or stimulated T cells (e.g., CD4+ T cells).

Cell samples may be cells derived from a cell line, such as an immortalized cell line. Exemplary cell lines include, but are not limited to, 293A cell line, 293FT cell line, 293F cell line, 293 H cell line, HEK 293 cell line, CHO DG44 cell line, CHO-S cell line, CHO-K1 cell line, Expi293F™ cell line, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cell line, FreeStyle™ CHO-S cell line, GripTite™ 293 MSR cell line, GS-CHO cell line, HepaRG™ cell line, T-REx™ Jurkat cell line, Per.C6 cell line, T-REx™-293 cell line, T-REx™-CHO cell line, T-REx™-HeLa cell line, NC-HIMT cell line, PC12 cell line, A549 cells, and K562 cells.

In some embodiments, an RNBD of the present disclosure can be used to modify a target cell. The target cell can itself be unmodified or modified. For example, an unmodified cell can be edited with an RNBD of the present disclosure to introduce an insertion, deletion, or mutation in its genome. In some embodiments, a modified cell already having a mutation can be repaired with an RNBD of the present disclosure.

In some instances, a target cell is a cell comprising one or more single nucleotide polymorphism (SNP). In some instances, an RNBD-nuclease described herein is designed to target and edit a target cell comprising a SNP.

In some cases, a target cell is a cell that does not contain a modification. For example, a target cell can comprise a genome without genetic defect (e.g., without genetic mutation) and an RNBD-nuclease described herein can be used to introduce a modification (e.g., a mutation) within the genome.

The cell sample may be obtained from cells of a primate. The primate may be a human, or a non-human primate. The cell sample may be obtained from a human. For example, the cell sample may comprise cells obtained from blood, urine, stool, saliva, lymph fluid, cerebrospinal fluid, synovial fluid, cystic fluid, ascites, pleural effusion, amniotic fluid, chorionic villus sample, vaginal fluid, interstitial fluid, buccal swab sample, sputum, bronchial lavage, Pap smear sample, or ocular fluid. The cell sample may comprise cells obtained from a blood sample, an aspirate sample, or a smear sample.

The cell sample may be a circulating tumor cell sample. A circulating tumor cell sample may comprise lymphoma cells, fetal cells, apoptotic cells, epithelia cells, endothelial cells, stem cells, progenitor cells, mesenchymal cells, osteoblast cells, osteocytes, hematopoietic stem cells (HSC) (e.g., a CD34+ HSC), foam cells, adipose cells, transcervical cells, circulating cardiocytes, circulating fibrocytes, circulating cancer stem cells, circulating myocytes, circulating cells from a kidney, circulating cells from a gastrointestinal tract, circulating cells from a lung, circulating cells from reproductive organs, circulating cells from a central nervous system, circulating hepatic cells, circulating cells from a spleen, circulating cells from a thymus, circulating cells from a thyroid, circulating cells from an endocrine gland, circulating cells from a parathyroid, circulating cells from a pituitary, circulating cells from an adrenal gland, circulating cells from islets of Langerhans, circulating cells from a pancreas, circulating cells from a hypothalamus, circulating cells from prostate tissues, circulating cells from breast tissues, circulating cells from circulating retinal cells, circulating ophthalmic cells, circulating auditory cells, circulating epidermal cells, circulating cells from the urinary tract, or combinations thereof.

The cell can be a T cell. For example, in some embodiments, the T cell can be an engineered T cell transduced to express a chimeric antigen receptor (CAR). The CAR T cell can be engineered to bind to BCMA, CD19, CD22, WT1, L1CAM, MUC16, ROR1, or LeY.

A cell sample may be a peripheral blood mononuclear cell sample.

A cell sample may comprise cancerous cells. The cancerous cells may form a cancer which may be a solid tumor or a hematologic malignancy. The cancerous cell sample may comprise cells obtained from a solid tumor. The solid tumor may include a sarcoma or a carcinoma. Exemplary sarcoma cell sample may include, but are not limited to, cell sample obtained from alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, or telangiectatic osteosarcoma.

Exemplary carcinoma cell samples may include, but are not limited to, cell samples obtained from an anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

The cancerous cell sample may comprise cells obtained from a hematologic malignancy. Hematologic malignancy may comprise a leukemia, a lymphoma, a myeloma, a non-Hodgkin's lymphoma, or a Hodgkin's lymphoma. The hematologic malignancy may be a T-cell based hematologic malignancy. The hematologic malignancy may be a B-cell based hematologic malignancy. Exemplary B-cell based hematologic malignancy may include, but are not limited to, chronic lymphocytic leukemia (CLL), small lymphocytic lymphoma (SLL), high risk CLL, a non-CLL/SLL lymphoma, prolymphocytic leukemia (PLL), follicular lymphoma (FL), diffuse large B-cell lymphoma (DLBCL), mantle cell lymphoma (MCL), Waldenström's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. Exemplary T-cell based hematologic malignancy may include, but are not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

A cell sample described herein may comprise a tumor cell line sample. Exemplary tumor cell line sample may include, but are not limited to, cell samples from tumor cell lines such as 600MPE, AU565, BT-20, BT-474, BT-483, BT-549, Evsa-T, Hs578T, MCF-7, MDA-MB-231, SkBr3, T-47D, HeLa, DU145, PC3, LNCaP, A549, H1299, NCI-H460, A2780, SKOV-3/Luc, Neuro2a, RKO, RKO-AS45-1, HT-29, SW1417, SW948, DLD-1, SW480, Capan-1, MC/9, B72.3, B25.2, B6.2, B38.1, DMS 153, SU.86.86, SNU-182, SNU-423, SNU-449, SNU-475, SNU-387, Hs 817.T, LMH, LMH/2A, SNU-398, PLHC-1, HepG2/SF, OCI-Ly1, OCI-Ly2, OCI-Ly3, OCI-Ly4, OCI-Ly6, OCI-Ly7, OCI-Ly10, OCI-Ly18, OCI-Ly19, U2932, DB, HBL-1, RIVA, SUDHL2, TMD8, MEC1, MEC2, 8E5, CCRF-CEM, MOLT-3, TALL-104, AML-193, THP-1, BDCM, HL-60, Jurkat, RPMI 8226, MOLT-4, RS4, K-562, KASUMI-1, Daudi, GA-10, Raji, JeKo-1, NK-92, and Mino.

A cell sample may comprise cells obtained from a biopsy sample, necropsy sample, or autopsy sample.

The cell samples (such as a biopsy sample) may be obtained from an individual by any suitable means of obtaining the sample using well-known and routine clinical methods. Procedures for obtaining tissue samples from an individual are well known. For example, procedures for drawing and processing tissue sample such as from a needle aspiration biopsy are well-known and may be employed to obtain a sample for use in the methods provided. Typically, for collection of such a tissue sample, a thin hollow needle is inserted into a mass such as a tumor mass for sampling of cells that, after being stained, will be examined under a microscope.

A cell may be a live cell. A cell may be a eukaryotic cell. A cell may be a yeast cell. A cell may be a plant cell. A cell may be obtained from an agricultural plant.

EXAMPLES

These examples are provided for illustrative purposes only and not to limit the scope of the claims provided herein.

Example 1

Genome Editing Complexes and Gene Regulators with Expanded Repeat Units

This example describes genome editing complexes and gene regulators with expanded repeat units. DNA binding domains (e.g., RNBD, MAP-NBD, TALE) are engineered from a plurality of repeat units and fused to a nuclease disclosed herein (e.g., FokI or SEQ ID NO: 1-SEQ ID NO: 81), an activation domain (VP16, VP64, p65, p300 catalytic domain, TET1 catalytic domain, TDG, Ldb1 self-associated domain, SAM activator (VP64, p65, HSF1), or VPR (VP64, p65, Rta), or a repression domain (e.g., KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2). At least one repeat unit of the DNA binding domain has greater than 39 amino acid residues and binds to a target nucleotide. The expanded repeat unit has altered affinity for its target nucleotide. The DNA binding domain with expanded repeat units exhibits altered binding to a target gene.

Example 2

Genome Editing Complexes and Gene Regulators with Contracted Repeat Units

This example describes genome editing complexes and gene regulators with contracted repeat units. DNA binding domains (e.g., RNBD, MAP-NBD, TALE) are engineered from a plurality of repeat units and fused to a nuclease disclosed herein (e.g., FokI or SEQ ID NO: 1-SEQ ID NO: 81), an activation domain (VP16, VP64, p65, p300 catalytic domain, TET1 catalytic domain, TDG, Ldb1 self-associated domain, SAM activator (VP64, p65, HSF1), or VPR (VP64, p65, Rta), or a repression domain (e.g., KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2). At least one repeat unit of the DNA binding domain has less than 32 amino acid residues and binds to a target nucleotide. The contracted repeat unit has altered affinity for its target nucleotide. The DNA binding domain with contracted repeat units exhibits altered binding to a target gene. (e.g., RNBD, MAP-NBD, TALE) are engineered from a plurality of repeat units

Example 3

Genome Editing Complexes and Gene Regulators with Gapped Repeat Units Having Recognition Sites This example describes genome editing complexes and gene regulators with gapped repeat units having recognition sites. DNA binding domains (e.g., RNBD, MAP-NBD, TALE) are engineered from a plurality of repeat units and fused via a linker to a nuclease disclosed herein (e.g., FokI or SEQ ID NO: 1-SEQ ID NO: 81), an activation domain (VP16, VP64, p65, p300 catalytic domain, TET1 catalytic domain, TDG, Ldb1 self-associated domain, SAM activator (VP64, p65, HSF1), or VPR (VP64, p65, Rta), or a repression domain (e.g., KRAB, Sin3a, LSD1, SUV39H1, G9A (EHMT2), DNMT1, DNMT3A-DNMT3L, DNMT3B, KOX, TGF-beta-inducible early gene (TIEG), v-erbA, SID, MBD2, MBD3, Rb, or MeCP2). Said linker has a recognition site for a small molecule, a protease, or a kinase or serves as a localization signal. Said linker having a recognition site separating each repeat unit from a neighboring repeat unit within the DNA binding domain and are, thus, gapped. Engineered DNA binding domains with gapped repeat units exhibit genome editing or gene regulation activity along with secondary activity.

Example 4

Genome Editing with DNA Binding Domain Comprising Expanded Repeat Units and Fused to a Nuclease This example illustrates genome editing with a DNA binding domain comprising expanded repeat units and fused to a nuclease. A DNA binding domain (e.g., RNBD, MAP-NBD, TALE) in which at least one repeat unit has greater than 39 amino acid residues is fused to a cleavage domain, such as an endonuclease to form a genome editing complex. The DNA binding domain is fused to the nuclease optionally, via a naturally occurring linker, a variant or truncation of a naturally occurring linker, or a synthetic linker.

Direct Administration to Introduce a Gene

The genome editing complex is administered directly to a subject in need thereof and is taken up by a cell. The subject has a disease. The DNA binding domain of the genome editing complex binds a region of DNA in a target cell and the cleavage domain induces a double strand break in the DNA of the target cell to introduce a gene. The introduced gene is a mutated gene or a functional gene.

Factor IX. The genome editing complex with a cleavage domain introduces a double strand break into the albumin gene locus (e.g., into intron 1) concomitant with delivery to the cell of an ectopic nucleic acid bearing a cDNA of the factor IX gene. The double strand break leads to the integration of the ectopic nucleic acid into intron 1 of the albumin gene; the factor IX protein is secreted by the cell into the circulation. The target cell is a hepatocyte and the subject in need thereof has Hemophilia B.

Ex Vivo Engineering of a Cell to Introduce a Gene

The genome editing complex is transfected into cells ex vivo along with an ectopic nucleic acid bearing a gene. Upon transfection of cells ex vivo, the DNA binding domain of the genome editing complex binds a region of DNA in a target cell and the cleavage domain induces a double strand break in the DNA of the target cell to introduce an ectopically provided gene (also provided to the cell) in the region cleaved by the genome editing complex. The resulting engineered cells with modified DNA are administered to a subject in need thereof. The subject has a disease.

CAR. The genome editing complex with a cleavage domain introduces a chimeric antigen receptor (CAR) by editing the DNA of a target cell. The target cell is a T cell and the subject has cancer, such as a blood cancer. Upon administration of the engineered cells to a subject, the engineered CAR T cells effectively eliminate cancer in the subject.

Direct Administration to Partially or Completely Knock Out a Gene

The genome editing complex is administered directly to a subject in need thereof and is taken up by a cell. The subject has a disease. The DNA binding domain of the genome editing complex binds a region of DNA in a target cell and the cleavage domain induces a double strand break in the DNA of the target cell to partially or completely knock out a gene.

TTR. The genome editing complex with a cleavage domain partially or completely knocks out the transthyretin (TTR) gene by editing the DNA of a target cell. The target cell is a liver cell and the subject in need thereof has transthyretin amyloidosis (ATTR).

SERPINA1. The genome editing complex with a cleavage domain partially or completely knocks out the SERPINA1 gene by editing the DNA of a target cell. The target cell is a liver cell and the subject in need thereof has alpha-1 antitrypsin deficiency (dA1AT def).

Ex Vivo Engineering of a Cell to Partially or Completely Knock Out a Gene or a Gene Regulatory Region The genome editing complex is transfected in cells ex vivo. Upon transfection of cells ex vivo, the DNA binding domain of the genome editing complex binds a region of DNA in a target cell and the cleavage domain induces a double strand break in the DNA of the target cell to partially or completely knock out a gene or a gene regulatory region. The subject has a disease.

BCL11A Enhancer. The genome editing complex with a cleavage domain partially or completely knocks out the BCL11A erythroid enhancer by editing the DNA of a target cell. The target cell is an HPSC and the subject in need thereof has b-thalassemia or sickle cell disease.

CCR5. The genome editing complex with a cleavage domain partially or completely knocks the CCR5 gene by editing the DNA of a target cell, thereby allowing for introduction of a mutated version of CCR5. Target cells, in which mutated versions of CCR5 are introduced via the action of the genome editing complex, are not infected by HIV via the modified CCR5 receptor. The target cell is a T cell or a hematopoietic stem cell (HPSC) and the subject has HIV.

Upon administration of the genome editing complex directly to a subject or upon administration of an engineered cell with DNA that has been modified with the genome editing complex, the disease symptoms are eliminated or reduced.

Example 5

Genome Editing with a DNA Binding Domain Comprising Contracted Repeat Units and Fused to a Nuclease This example illustrates genome editing with a DNA binding domain comprising contracted repeat units and fused to a nuclease. A DNA binding domain (e.g., RNBD, MAP-NBD, TALE) in which at least one repeat unit has less than 32 amino acid residues is fused to a cleavage domain, such as an endonuclease to form a genome editing complex. The DNA binding domain is fused to the nuclease optionally, via a naturally occurring linker, a variant or truncation of a naturally occurring linker, or a synthetic linker.

Direct Administration to Introduce a Gene

The genome editing complex is administered directly to a subject in need thereof and is taken up by a cell. The subject has a disease. The DNA binding domain of the genome editing complex binds a region of DNA in a target cell and the cleavage domain induces a double strand break in the DNA of the target cell to introduce a gene. The introduced gene is a mutated gene or a functional gene.

Factor IX. The genome editing complex with a cleavage domain introduces a double strand break into the albumin gene locus (e.g., into intron 1) concomitant with delivery to the cell of an ectopic nucleic acid bearing a cDNA of the factor IX gene. The double strand break leads to the integration of the ectopic nucleic acid into intron 1 of the albumin gene; the factor IX protein is secreted by the cell into the circulation. The target cell is a hepatocyte and the subject in need thereof has Hemophilia B.

Ex Vivo Engineering of a Cell to Introduce a Gene

The genome editing complex is transfected into cells ex vivo along with an ectopic nucleic acid bearing a gene. Upon transfection of cells ex vivo, the DNA binding domain of the genome editing complex binds a region of DNA in a target cell and the cleavage domain induces a double strand break in the DNA of the target cell to introduce an ectopically provided gene (also provided to the cell) in the region cleaved by the genome editing complex. The resulting engineered cells with modified DNA are administered to a subject in need thereof. The subject has a disease.

CAR. The genome editing complex with a cleavage domain introduces a chimeric antigen receptor (CAR) by editing the DNA of a target cell. The target cell is a T cell and the subject has cancer, such as a blood cancer. Upon administration of the engineered cells to a subject, the engineered CAR T cells effectively eliminate cancer in the subject.

Direct Administration to Partially or Completely Knock Out a Gene

The genome editing complex is administered directly to a subject in need thereof and is taken up by a cell. The subject has a disease. The DNA binding domain of the genome editing complex binds a region of DNA in a target cell and the cleavage domain induces a double strand break in the DNA of the target cell to partially or completely knock out a gene.

TTR. The genome editing complex with a cleavage domain partially or completely knocks out the transthyretin (TTR) gene by editing the DNA of a target cell. The target cell is a liver cell and the subject in need thereof has transthyretin amyloidosis (ATTR).

SERPINA1. The genome editing complex with a cleavage domain partially or completely knocks out the SERPINA1 gene by editing the DNA of a target cell. The target cell is a liver cell and the subject in need thereof has alpha-1 antitrypsin deficiency (dA1AT def).

Ex Vivo Engineering of a Cell to Partially or Completely Knock Out a Gene or a Gene Regulatory Region The genome editing complex is transfected in cells ex vivo. Upon transfection of cells ex vivo, the DNA binding domain of the genome editing complex binds a region of DNA in a target cell and the cleavage domain induces a double strand break in the DNA of the target cell to partially or completely knock out a gene or a gene regulatory region. The subject has a disease.

BCL11A Enhancer. The genome editing complex with a cleavage domain partially or completely knocks out the BCL11A erythroid enhancer by editing the DNA of a target cell. The target cell is an HPSC and the subject in need thereof has b-thalassemia or sickle cell disease.

CCR5. The genome editing complex with a cleavage domain partially or completely knocks the CCR5 gene by editing the DNA of a target cell, thereby allowing for introduction of a mutated version of CCR5. Target cells, in which mutated versions of CCR5 are introduced via the action of the genome editing complex, are not infected by HIV via the modified CCR5 receptor. The target cell is a T cell or a hematopoietic stem cell (HPSC) and the subject has HIV.

Upon administration of the genome editing complex directly to a subject or upon administration of an engineered cell with DNA that has been modified with the genome editing complex, the disease symptoms are eliminated or reduced.

Example 6

Genome Editing with DNA Binding Domain Having Gapped Repeat Units and Fused to a Nuclease This example illustrates genome editing DNA binding domains fused to a nuclease, wherein the DNA binding domains have gapped repeat units. A DNA binding domain (e.g., RNBD, MAP-NBD, TALE) in which all repeat units are separated from neighboring repeat units with a linker comprising a recognition site is fused to a cleavage domain, such as an endonuclease to form a genome editing complex. Said linker has a recognition site for a small molecule, a protease, or a kinase or serves as a localization signal. The DNA binding domain is fused to the nuclease optionally, via a naturally occurring linker, a variant or truncation of a naturally occurring linker, or a synthetic linker.

Direct Administration to Introduce a Gene

The genome editing complex is administered directly to a subject in need thereof and is taken up by a cell. The subject has a disease. The DNA binding domain of the genome editing complex binds a region of DNA in a target cell and the cleavage domain induces a double strand break in the DNA of the target cell to introduce a gene. The introduced gene is a mutated gene or a functional gene.

Factor IX. The genome editing complex with a cleavage domain introduces a double strand break into the albumin gene locus (e.g., into intron 1) concomitant with delivery to the cell of an ectopic nucleic acid bearing a cDNA of the factor IX gene. The double strand break leads to the integration of the ectopic nucleic acid into intron 1 of the albumin gene; the factor IX protein is secreted by the cell into the circulation. The target cell is a hepatocyte and the subject in need thereof has Hemophilia B.

Ex Vivo Engineering of a Cell to Introduce a Gene

The genome editing complex is transfected into cells ex vivo along with an ectopic nucleic acid bearing a gene. Upon transfection of cells ex vivo, the DNA binding domain of the genome editing complex binds a region of DNA in a target cell and the cleavage domain induces a double strand break in the DNA of the target cell to introduce an ectopically provided gene (also provided to the cell) in the region cleaved by the genome editing complex. The resulting engineered cells with modified DNA are administered to a subject in need thereof. The subject has a disease.

CAR. The genome editing complex with a cleavage domain introduces a chimeric antigen receptor (CAR) by editing the DNA of a target cell. The target cell is a T cell and the subject has cancer, such as a blood cancer. Upon administration of the engineered cells to a subject, the engineered CAR T cells effectively eliminate cancer in the subject.

Direct Administration to Partially or Completely Knock Out a Gene

The genome editing complex is administered directly to a subject in need thereof and is taken up by a cell. The subject has a disease. The DNA binding domain of the genome editing complex binds a region of DNA in a target cell and the cleavage domain induces a double strand break in the DNA of the target cell to partially or completely knock out a gene.

TTR. The genome editing complex with a cleavage domain partially or completely knocks out the transthyretin (TTR) gene by editing the DNA of a target cell. The target cell is a liver cell and the subject in need thereof has transthyretin amyloidosis (ATTR).

SERPINA1. The genome editing complex with a cleavage domain partially or completely knocks out the SERPINA1 gene by editing the DNA of a target cell. The target cell is a liver cell and the subject in need thereof has alpha-1 antitrypsin deficiency (dA1AT def).

Ex Vivo Engineering of a Cell to Partially or Completely Knock Out a Gene or a Gene Regulatory Region The genome editing complex is transfected in cells ex vivo. Upon transfection of cells ex vivo, the DNA binding domain of the genome editing complex binds a region of DNA in a target cell and the cleavage domain induces a double strand break in the DNA of the target cell to partially or completely knock out a gene or a gene regulatory region. The subject has a disease.

BCL11A Enhancer. The genome editing complex with a cleavage domain partially or completely knocks out the BCL11A erythroid enhancer by editing the DNA of a target cell. The target cell is an HPSC and the subject in need thereof has b-thalassemia or sickle cell disease.

CCR5. The genome editing complex with a cleavage domain partially or completely knocks the CCR5 gene by editing the DNA of a target cell, thereby allowing for introduction of a mutated version of CCR5. Target cells, in which mutated versions of CCR5 are introduced via the action of the genome editing complex, are not infected by HIV via the modified CCR5 receptor. The target cell is a T cell or a hematopoietic stem cell (HPSC) and the subject has HIV.

Upon administration of the genome editing complex directly to a subject or upon administration of an engineered cell with DNA that has been modified with the genome editing complex, the disease symptoms are eliminated or reduced.

Example 7

TALE Protein with N-Terminus Fragment

A DNA binding protein engineered to have a shortened N-terminus derived from a TALE protein was generated. U.S. Pat. No. 8,586,526 shows that while the N-terminus region (referred to as N-cap) from a TALE protein can be shortened by deleting amino acids at the N-terminus, deleting amino acids beyond amino acid position N+134 decreased DNA binding affinity, with the decrease in DNA binding apparent even with deletion of amino acids beyond amino acid position N+137. U.S. Pat. No. 8,586,526 concluded that amino acid sequence from N+1 through N+137 are required for binding to DNA while the first 152 amino acids of the N-cap sequence are dispensable.

However, it has been discovered that further deleting amino acids till position N+116 surprising leads to recovery of DNA binding. Even shorter N-terminus regions such as a fragment having deletion till position N+111 also retains DNA binding activity. Deleting amino acids till position N+106 significantly decreases DNA binding. Further deletion of the N-terminus region, such as, deleting amino acids till position N+101 does not lead to recovery of DNA binding. See FIG. 2.

TALEN monomers recognizing 5'-TTTCTGTCAC-CAATCCT-3' (SEQ ID NO: 449) and 5'-TCCCCTC-CACCCCACAGT-3' (SEQ ID NO: 450) in the human AAVS1 locus were engineered to harbor N-terminus regions that included deletions encompassing residues N137-116, N137-111, N137-106 and N137-101. While these residues are numbered with reference to the N+137 construct in U.S. Pat. No. 8,586,526, N137-116 refers to deletion of amino acids starting at the N-terminus of the N-cap sequence (N+228) and extending through amino acid residue 116 such that the resulting fragment retains amino acids residues from position N+115 to position N+1, and so on. The amino acid sequence of the N-terminal truncation del_N137-116 is set forth in SEQ ID NO:321. The amino acid sequence of the N-terminal truncation del_N137-111 is set forth in SEQ ID NO:447.

NK562 cells were transfected with 2 vg plasmid DNA for each TALEN monomer using an AMAXA™ Nucleofector™ 96-well Shuttle™ system as per the manufacturer's recommendations. Full length TALEN monomers were included ("AAVS1 control"), together with N137-116/full length and full length/N137-116 heterodimers. Cells were cold shocked at 30° C. and genomic DNA was harvested at 72 h using QuickExtract™ (Lucigen). Indel rates were determined by amplicon sequencing. The TALE repeats present in the TALE monomers have the sequence LTPDQVVAIAS(RVD)GGKQALETVQRLLPVLCQDHG (SEQ ID NO: 451), with a RVD selected based on the target sequence.

Figure 2:
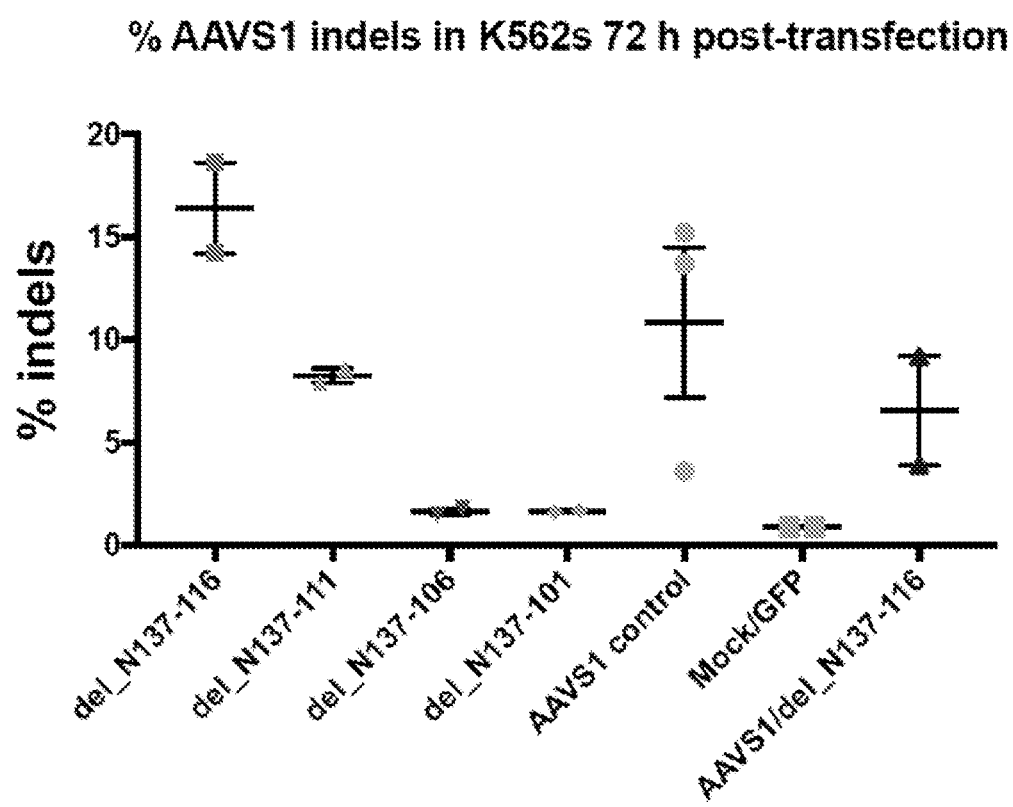
FIG. 2 shows nuclease activity mediated by DNA binding protein dimers that each include from N-terminus to C-terminus: a N-terminus region of a TALE protein, TALE repeat units, C-terminus region of a TALE protein, and a FokI endonuclease.

FIG. 2 represents DNA binding activity assayed by measuring nuclease activity of FokI fused to C-terminus of the polypeptides. AAVS1 control data set correspond to TALENS using the standard full-length N-terminus (N+288 to N+1). N-terminal truncation del_N137-116 (N-terminus extending from N+115 to N+1) showed higher activity than standard full-length N-terminus (N+288 to N+1). N-terminal truncation del_N137-111 (N-terminus extending from N+110 to N+1) was also active. Further truncation del_N137-106 (N-terminus extending from N+105 to N+1) significantly decreased DNA binding. Further deletion of the N-terminus region del_N137-101 (N-terminus extending from N+100 to N+1) did not lead to recovery of DNA binding. Thus, a fragment of the N-terminus of a TALE protein extending from N+115 to N+1 shows full activity. Mock/GFP is a negative control. The AAVS1/del_N137-116 data shows that an N1-115 TALEN monomer can be combined with a monomer comprising full-length N-terminus region of a TALE protein.

While preferred embodiments of the present invention have been shown and, it will be apparent to those skilled in the art that such embodiments are provided by way of example only. Numerous variations, changes, and substitutions will now occur to those skilled in the art without departing from the invention. It should be understood that various alternatives to the embodiments of the invention may be employed in practicing the invention. It is intended that the following claims define the scope of the invention and that methods and structures within the scope of these claims and their equivalents be covered thereby.

What is claimed is:

1. A polypeptide for modulating expression of an endogenous gene, the polypeptide comprising a modular nucleic acid binding domain comprising a plurality of repeat units, wherein a repeat unit of the plurality of repeat units comprises a sequence $A_{1-11}X_1X_2B_{14-35}$ (SEQ ID NO: 448), wherein $X_1X_2$ comprises a binding region configured to bind to a target nucleic acid base in a target site; and $B_{14-35}$ has at least 92% sequence identity to GGKQALEAVRAQLLDLRAAPYG (SEQ ID NO: 280), $A_{1-11}$ is the amino acid sequence from position 1 through position 11 of any one of SEQ ID NO: 168-SEQ ID NO: 263; and a first repeat unit of the plurality of repeat units comprises at least one residue in $A_{1-11}$, $B_{14-35}$, or a combination thereof that differs from a corresponding residue in a second repeat unit of the plurality of repeat units.

2. The polypeptide of claim 1, wherein the at least one repeat unit comprises at least 90% sequence identity with any one of SEQ ID NO: 168-SEQ ID NO: 263.

3. The polypeptide of claim 1, wherein each repeat unit of the plurality of repeat units is separated from a neighboring repeat unit by a linker comprising a recognition site.

4. The polypeptide of claim 3, wherein the recognition site is for a small molecule, a protease, or a kinase.

5. The polypeptide of claim 3, wherein the recognition site serves as a localization signal.

6. The polypeptide of claim 1, wherein the polypeptide further comprises a cleavage domain linked to the modular nucleic acid binding domain to form a non-naturally occurring fusion protein.

7. The polypeptide of claim 1, wherein the modular nucleic acid binding domain further comprises one or more properties selected from the following:
(a) binds the target site, wherein the target site comprises a 5' guanine;
(b) comprises from 7 repeat units to 25 repeat units; and
(c) upon binding to the target site, the modular nucleic acid binding domain is separated from a second modular nucleic acid binding domain bound to a second target site by from 2 to 50 base pairs.

8. The polypeptide of claim 1, wherein the binding region comprises HD for binding to cytosine, NG for binding to thymidine, NK for binding to guanine, SI for binding to adenosine, RS for binding to adenosine, HN for binding to guanine, or NT for binding to adenosine.

9. The polypeptide of claim 1, wherein the modular nucleic acid binding domain comprises an N-terminus amino acid sequence and a C-terminus amino acid sequence from *Xanthomonas* spp. or *Ralstonia solanacearum*.

10. The polypeptide of claim 9, wherein the N-terminus amino acid sequence comprises at least 80% sequence identity to SEQ ID NO: 264.

11. The polypeptide of claim 10, wherein the C-terminus amino acid sequence comprises at least 80% sequence identity to SEQ ID NO: 266.

12. The polypeptide of claim 1, wherein the modular nucleic acid binding domain comprises a half repeat comprises at least 80% sequence identity to SEQ ID NO: 265.

13. A method of modulating expression of an endogenous gene in a cell, the method comprising:
introducing into the cell the polypeptide of claim 1,
wherein the DNA binding polypeptide binds to a target nucleic acid sequence present in the endogenous gene and the heterologous functional domain modulates expression of the endogenous gene.

14. The polypeptide of claim 11, wherein the binding region comprises HD for binding to cytosine, NG for binding to thymidine, NK for binding to guanine, SI for binding to adenosine, RS for binding to adenosine, HN for binding to guanine, or NT for binding to adenosine.

15. The polypeptide of claim 1, wherein the modular nucleic acid binding domain comprises an amino acid sequence having at least 90% identity to one of SEQ ID NO: 311, SEQ ID NO: 313, or SEQ ID NO: 315.

16. The polypeptide of claim 1, wherein the plurality of repeat units comprises 9-36 repeat units.

* * * * *

SEQUENCE LISTING

```
<160> NUMBER OF SEQ ID NOS: 452

<210> SEQ ID NO 1
<211> LENGTH: 196
<212> TYPE: PRT
<213> ORGANISM: Artificial Sequence
<220> FEATURE:
<223> OTHER INFORMATION: Synthetic Sequence

<400> SEQUENCE: 1

Phe Leu Val Lys Gly Ala Met Glu Ile Lys Lys Ser Glu Leu Arg His
1               5                   10                  15

Lys Leu Arg His Val Pro His Glu Tyr Ile Glu Leu Ile Glu Ile Ala
            20                  25                  30

Gln Asp Ser Lys Gln Asn Arg Leu Leu Glu Phe Lys Val Val Glu Phe
        35                  40                  45

Phe Lys Lys Ile Tyr Gly Tyr Arg Gly Lys His Leu Gly Gly Ser Arg
    50                  55                  60

Lys Pro Asp Gly Ala Leu Phe Thr Asp Gly Leu Val Leu Asn His Gly
65                  70                  75                  80

Ile Ile Leu Asp Thr Lys Ala Tyr Lys Asp Gly Tyr Arg Leu Pro Ile
                85                  90                  95

Ser Gln Ala Asp Glu Met Gln Arg Tyr Val Asp Glu Asn Asn Lys Arg
            100                 105                 110

Ser Gln Val Ile Asn Pro Asn Glu Trp Trp Glu Ile Tyr Pro Thr Ser
        115                 120                 125

Ile Thr Asp Phe Lys Phe Leu Phe Val Ser Gly Phe Phe Gln Gly Asp
    130                 135                 140

Tyr Arg Lys Gln Leu Glu Arg Val Ser His Leu Thr Lys Cys Gln Gly
145                 150                 155                 160

Ala Val Met Ser Val Glu Gln Leu Leu Leu Gly Gly Glu Lys Ile Lys
                165                 170                 175

Glu Gly Ser Leu Thr Leu Glu Glu Val Gly Lys Lys Phe Lys Asn Asp
```

```
              180                 185                 190

Glu Ile Val Phe
        195

<210> SEQ ID NO 2
<211> LENGTH: 192
<212> TYPE: PRT
<213> ORGANISM: Artificial Sequence
<220> FEATURE:
<223> OTHER INFORMATION: Synthetic Sequence

<400> SEQUENCE: 2

Gln Ile Val Lys Ser Ser Ile Glu Met Ser Lys Ala Asn Met Arg Asp
1               5                   10                  15

Asn Leu Gln Met Leu Pro His Asp Tyr Ile Glu Leu Ile Glu Ile Ser
            20                  25                  30

Gln Asp Pro Tyr Gln Asn Arg Ile Phe Glu Met Lys Val Met Asp Leu
        35                  40                  45

Phe Ile Asn Glu Tyr Gly Phe Ser Gly Ser His Leu Gly Gly Ser Arg
    50                  55                  60

Lys Pro Asp Gly Ala Met Tyr Ala His Gly Phe Gly Val Ile Val Asp
65                  70                  75                  80

Thr Lys Ala Tyr Lys Asp Gly Tyr Asn Leu Pro Ile Ser Gln Ala Asp
                85                  90                  95

Glu Met Glu Arg Tyr Val Arg Glu Asn Ile Asp Arg Asn Glu His Val
            100                 105                 110

Asn Ser Asn Arg Trp Trp Asn Ile Phe Pro Glu Asp Thr Asn Glu Tyr
        115                 120                 125

Lys Phe Leu Phe Val Ser Gly Phe Phe Lys Gly Asn Phe Glu Lys Gln
    130                 135                 140

Leu Glu Arg Ile Ser Ile Asp Thr Gly Val Gln Gly Gly Ala Leu Ser
145                 150                 155                 160

Val Glu His Leu Leu Leu Gly Ala Glu Tyr Ile Lys Arg Gly Ile Leu
                165                 170                 175

Thr Leu Tyr Asp Phe Lys Asn Ser Phe Leu Asn Lys Glu Ile Gln Phe
            180                 185                 190

<210> SEQ ID NO 3
<211> LENGTH: 196
<212> TYPE: PRT
<213> ORGANISM: Artificial Sequence
<220> FEATURE:
<223> OTHER INFORMATION: Synthetic Sequence

<400> SEQUENCE: 3

Gln Thr Ile Lys Ser Ser Ile Glu Glu Leu Lys Ser Glu Leu Arg Thr
1               5                   10                  15

Gln Leu Asn Val Ile Ser His Asp Tyr Leu Gln Leu Val Asp Ile Ser
            20                  25                  30

Gln Asp Ser Gln Gln Asn Arg Leu Phe Glu Met Lys Val Met Asp Leu
        35                  40                  45

Phe Ile Asn Glu Phe Gly Tyr Asn Gly Ser His Leu Gly Gly Ser Arg
    50                  55                  60

Lys Pro Asp Gly Ile Leu Tyr Thr Glu Gly Leu Ser Lys Asp Tyr Gly
65                  70                  75                  80

Ile Ile Val Asp Thr Lys Ala Tyr Lys Asp Gly Tyr Asn Leu Pro Ile
                85                  90                  95
```

Ala Gln Ala Asp Glu Met Glu Arg Tyr Ile Arg Glu Asn Ile Asp Arg
            100                 105                 110

Asn Glu Val Val Asn Pro Asn Arg Trp Trp Glu Val Phe Pro Ser Lys
        115                 120                 125

Ile Asn Asp Tyr Lys Phe Leu Phe Val Ser Ala Tyr Phe Lys Gly Asn
    130                 135                 140

Phe Lys Glu Gln Leu Glu Arg Ile Ser Ile Asn Thr Gly Ile Leu Gly
145                 150                 155                 160

Gly Ala Ile Ser Val Glu His Leu Leu Gly Ala Glu Tyr Phe Lys
                165                 170                 175

Arg Gly Ile Leu Ser Leu Glu Asp Val Arg Asp Lys Phe Cys Asn Thr
            180                 185                 190

Glu Ile Glu Phe
        195

<210> SEQ ID NO 4
<211> LENGTH: 195
<212> TYPE: PRT
<213> ORGANISM: Artificial Sequence
<220> FEATURE:
<223> OTHER INFORMATION: Synthetic Sequence

<400> SEQUENCE: 4

Gly Lys Ser Glu Val Glu Thr Ile Lys Glu Gln Met Arg Gly Glu Leu
1               5                   10                  15

Thr His Leu Ser His Glu Tyr Leu Gly Leu Leu Asp Leu Ala Tyr Asp
            20                  25                  30

Ser Lys Gln Asn Arg Leu Phe Glu Leu Lys Thr Met Gln Leu Leu Thr
        35                  40                  45

Glu Glu Cys Gly Phe Gly Leu His Leu Gly Gly Ser Arg Lys Pro
    50                  55                  60

Asp Gly Ile Val Tyr Thr Lys Asp Glu Asn Glu Gln Val Gly Lys Glu
65                  70                  75                  80

Asn Tyr Gly Ile Ile Ile Asp Thr Lys Ala Tyr Ser Gly Gly Tyr Ser
                85                  90                  95

Leu Pro Ile Ser Gln Ala Asp Glu Met Glu Arg Tyr Ile Gly Glu Asn
            100                 105                 110

Gln Thr Arg Asp Ile Arg Ile Asn Pro Asn Glu Trp Trp Lys Asn Phe
        115                 120                 125

Gly Asp Gly Val Thr Glu Tyr Tyr Leu Phe Val Ala Gly His Phe
    130                 135                 140

Lys Gly Lys Tyr Gln Glu Gln Ile Asp Arg Ile Asn Cys Asn Lys Asn
145                 150                 155                 160

Ile Lys Gly Ala Ala Val Ser Ile Gln Gln Leu Leu Arg Ile Val Asn
                165                 170                 175

Asp Tyr Lys Ala Gly Lys Leu Thr His Glu Asp Met Lys Leu Lys Ile
            180                 185                 190

Phe His Tyr
        195

<210> SEQ ID NO 5
<211> LENGTH: 151
<212> TYPE: PRT
<213> ORGANISM: Artificial Sequence
<220> FEATURE:
<223> OTHER INFORMATION: Synthetic Sequence

<400> SEQUENCE: 5

```
Met Lys Ile Leu Glu Leu Ile Asn Glu Cys Gly Tyr Lys Gly Leu
1               5                   10                  15

His Leu Gly Gly Ala Arg Lys Pro Asp Gly Ile Ile Tyr Thr Glu Lys
            20                  25                  30

Glu Lys Tyr Asn Tyr Gly Val Ile Ile Asp Thr Lys Ala Tyr Ser Lys
            35                  40                  45

Gly Tyr Asn Leu Pro Ile Gly Gln Ile Asp Glu Met Ile Arg Tyr Ile
        50                  55                  60

Ile Glu Asn Asn Glu Arg Asn Ile Lys Arg Asn Thr Asn Cys Trp Trp
65                  70                  75                  80

Asn Asn Phe Glu Lys Asn Val Asn Glu Phe Tyr Phe Ser Phe Ile Ser
                85                  90                  95

Gly Glu Phe Thr Gly Asn Ile Glu Glu Lys Leu Asn Arg Ile Phe Ile
                100                 105                 110

Ser Thr Asn Ile Lys Gly Asn Ala Met Ser Val Lys Thr Leu Leu Tyr
            115                 120                 125

Leu Ala Asn Glu Ile Lys Ala Asn Arg Ile Ser Tyr Ile Glu Leu Leu
        130                 135                 140

Asn Tyr Phe Asp Asn Lys Val
145                 150
```

<210> SEQ ID NO 6
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 6

```
Ala Lys Ser Ser Gln Ser Glu Thr Lys Glu Lys Leu Arg Glu Lys Leu
1               5                   10                  15

Arg Asn Leu Pro His Glu Tyr Leu Ser Leu Val Asp Leu Ala Tyr Asp
            20                  25                  30

Ser Lys Gln Asn Arg Leu Phe Glu Met Lys Val Ile Glu Leu Leu Thr
            35                  40                  45

Glu Glu Cys Gly Phe Gln Gly Leu His Leu Gly Gly Ser Arg Arg Pro
        50                  55                  60

Asp Gly Val Leu Tyr Thr Ala Gly Leu Thr Asp Asn Tyr Gly Ile Ile
65                  70                  75                  80

Leu Asp Thr Lys Ala Tyr Ser Ser Gly Tyr Ser Leu Pro Ile Ala Gln
                85                  90                  95

Ala Asp Glu Met Glu Arg Tyr Val Arg Glu Asn Gln Thr Arg Asp Glu
                100                 105                 110

Leu Val Asn Pro Asn Gln Trp Trp Glu Asn Phe Glu Asn Gly Leu Gly
            115                 120                 125

Thr Phe Tyr Phe Leu Phe Val Ala Gly His Phe Asn Gly Asn Val Gln
        130                 135                 140

Ala Gln Leu Glu Arg Ile Ser Arg Asn Thr Gly Val Leu Gly Ala Ala
145                 150                 155                 160

Ala Ser Ile Ser Gln Leu Leu Leu Ala Asp Ala Ile Arg Gly Gly
                165                 170                 175

Arg Met Asp Arg Glu Arg Leu Arg His Leu Met Phe Gln Asn Glu Glu
                180                 185                 190

Phe Leu
```

<210> SEQ ID NO 7
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 7

```
Asn Ser Glu Lys Ser Glu Phe Thr Gln Glu Lys Asp Asn Leu Arg Glu
1               5                   10                  15

Lys Leu Asp Thr Leu Ser His Glu Tyr Leu Ser Leu Val Asp Leu Ala
            20                  25                  30

Phe Asp Ser Gln Gln Asn Arg Leu Phe Glu Met Lys Thr Val Glu Leu
        35                  40                  45

Leu Thr Lys Glu Cys Asn Tyr Lys Gly Val His Leu Gly Gly Ser Arg
    50                  55                  60

Lys Pro Asp Gly Ile Ile Tyr Thr Glu Asn Ser Thr Asp Asn Tyr Gly
65                  70                  75                  80

Val Ile Ile Asp Thr Lys Ala Tyr Ser Asn Gly Tyr Asn Leu Pro Ile
                85                  90                  95

Ser Gln Val Asp Glu Met Val Arg Tyr Val Glu Glu Asn Asn Lys Arg
            100                 105                 110

Glu Lys Glu Arg Asn Ser Asn Glu Trp Trp Lys Glu Phe Gly Asp Asn
        115                 120                 125

Ile Asn Lys Phe Tyr Phe Ser Phe Ile Ser Gly Lys Phe Ile Gly Asn
    130                 135                 140

Ile Glu Glu Lys Leu Gln Arg Ile Thr Ile Phe Thr Asn Val Tyr Gly
145                 150                 155                 160

Asn Ala Met Thr Ile Ile Thr Leu Leu Tyr Leu Ala Asn Glu Ile Lys
                165                 170                 175

Ala Asn Arg Leu Lys Thr Met Glu Val Val Lys Tyr Phe Asp Asn Lys
            180                 185                 190

Val
```

<210> SEQ ID NO 8
<211> LENGTH: 200
<212> TYPE: PRT
<213> ORGANISM: Artificial Sequence
<220> FEATURE:
<223> OTHER INFORMATION: Synthetic Sequence

<400> SEQUENCE: 8

```
Asn Leu Thr Cys Ser Asp Leu Thr Glu Ile Lys Glu Glu Val Arg Asn
1               5                   10                  15

Ala Leu Thr His Leu Ser His Glu Tyr Leu Ala Leu Ile Asp Leu Ala
            20                  25                  30

Tyr Asp Ser Thr Gln Asn Arg Leu Phe Glu Met Lys Thr Leu Gln Leu
        35                  40                  45

Leu Val Glu Glu Cys Gly Tyr Gln Gly Thr His Leu Gly Gly Ser Arg
    50                  55                  60

Lys Pro Asp Gly Ile Cys Tyr Ser Glu Ala Lys Ser Glu Gly Leu
65                  70                  75                  80

Glu Ala Asn Tyr Gly Ile Ile Ile Asp Thr Lys Ser Tyr Ser Gly Gly
                85                  90                  95

Tyr Gly Leu Pro Ile Ser Gln Ala Asp Glu Met Glu Arg Tyr Ile Arg
            100                 105                 110
```

```
Glu Asn Gln Thr Arg Asp Ala Glu Val Asn Arg Asn Lys Trp Trp Glu
            115                 120                 125

Ala Phe Pro Glu Thr Ile Asp Ile Phe Tyr Phe Met Phe Val Ala Gly
130                 135                 140

His Phe Lys Gly Asn Tyr Phe Asn Gln Leu Glu Arg Leu Gln Arg Ser
145                 150                 155                 160

Thr Gly Ile Lys Gly Ala Ala Val Asp Ile Lys Thr Leu Leu Leu Thr
                165                 170                 175

Ala Asn Arg Cys Lys Thr Gly Glu Leu Asp His Ala Gly Ile Glu Ser
            180                 185                 190

Cys Phe Phe Asn Asn Cys Arg Leu
        195                 200

<210> SEQ ID NO 9
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 9

Asp Asn Val Lys Ser Asn Phe Asn Gln Glu Lys Asp Glu Leu Arg Glu
1               5                   10                  15

Lys Leu Asp Thr Leu Ser His Glu Tyr Leu Tyr Leu Leu Asp Leu Ala
            20                  25                  30

Tyr Asp Ser Lys Gln Asn Lys Leu Phe Glu Met Lys Ile Leu Glu Leu
        35                  40                  45

Leu Ile Asn Glu Cys Gly Tyr Arg Gly Leu His Leu Gly Gly Val Arg
    50                  55                  60

Lys Pro Asp Gly Ile Ile Tyr Thr Glu Lys Glu Lys Tyr Asn Tyr Gly
65                  70                  75                  80

Val Ile Ile Asp Thr Lys Ala Tyr Ser Lys Gly Tyr Asn Leu Pro Ile
                85                  90                  95

Gly Gln Ile Asp Glu Met Ile Arg Tyr Ile Ile Glu Asn Asn Glu Arg
            100                 105                 110

Asn Ile Lys Arg Asn Thr Asn Cys Trp Trp Asn Asn Phe Glu Lys Asn
        115                 120                 125

Val Asn Glu Phe Tyr Phe Ser Phe Ile Ser Gly Glu Phe Thr Gly Asn
    130                 135                 140

Ile Glu Glu Lys Leu Asn Arg Ile Phe Ile Ser Thr Asn Ile Lys Gly
145                 150                 155                 160

Asn Ala Met Ser Val Lys Thr Leu Leu Tyr Leu Ala Asn Glu Ile Lys
                165                 170                 175

Ala Asn Arg Ile Ser Phe Leu Glu Met Glu Lys Tyr Phe Asp Asn Lys
            180                 185                 190

Val

<210> SEQ ID NO 10
<211> LENGTH: 196
<212> TYPE: PRT
<213> ORGANISM: Artificial Sequence
<220> FEATURE:
<223> OTHER INFORMATION: Synthetic Sequence

<400> SEQUENCE: 10

Glu Gly Ile Lys Ser Asn Ile Ser Leu Leu Lys Asp Glu Leu Arg Gly
1               5                   10                  15
```

```
Gln Ile Ser His Ile Ser His Glu Tyr Leu Ser Leu Ile Asp Leu Ala
             20                  25                  30

Phe Asp Ser Lys Gln Asn Arg Leu Phe Glu Met Lys Val Leu Glu Leu
         35                  40                  45

Leu Val Asn Glu Tyr Gly Phe Lys Gly Arg His Leu Gly Gly Ser Arg
     50                  55                  60

Lys Pro Asp Gly Ile Val Tyr Ser Thr Thr Leu Glu Asp Asn Phe Gly
65                  70                  75                  80

Ile Ile Val Asp Thr Lys Ala Tyr Ser Glu Gly Tyr Ser Leu Pro Ile
                 85                  90                  95

Ser Gln Ala Asp Glu Met Glu Arg Tyr Val Arg Glu Asn Ser Asn Arg
            100                 105                 110

Asp Glu Glu Val Asn Pro Asn Lys Trp Trp Glu Asn Phe Ser Glu Glu
        115                 120                 125

Val Lys Lys Tyr Tyr Phe Val Phe Ile Ser Gly Ser Phe Lys Gly Lys
    130                 135                 140

Phe Glu Glu Gln Leu Arg Arg Leu Ser Met Thr Thr Gly Val Asn Gly
145                 150                 155                 160

Ser Ala Val Asn Val Val Asn Leu Leu Leu Gly Ala Glu Lys Ile Arg
                165                 170                 175

Ser Gly Glu Met Thr Ile Glu Glu Leu Glu Arg Ala Met Phe Asn Asn
            180                 185                 190

Ser Glu Phe Ile
            195

<210> SEQ ID NO 11
<211> LENGTH: 191
<212> TYPE: PRT
<213> ORGANISM: Artificial Sequence
<220> FEATURE:
<223> OTHER INFORMATION: Synthetic Sequence

<400> SEQUENCE: 11

Ile Ser Lys Thr Asn Val Leu Glu Leu Lys Asp Lys Val Arg Asp Lys
1               5                  10                  15

Leu Lys Tyr Val Asp Asn Arg Tyr Leu Ala Leu Ile Asp Leu Ala Tyr
             20                  25                  30

Asp Gly Thr Ala Asn Arg Asp Phe Glu Ile Gln Thr Ile Asp Leu Leu
         35                  40                  45

Ile Asn Glu Leu Lys Phe Lys Gly Val Arg Leu Gly Glu Ser Arg Lys
     50                  55                  60

Pro Asp Gly Ile Ile Ser Tyr Asp Ile Asn Gly Val Ile Asp Asn
65                  70                  75                  80

Lys Ala Tyr Ser Ser Gly Tyr Asn Leu Pro Ile Asn Gln Ala Asp Glu
                 85                  90                  95

Met Ile Arg Tyr Ile Glu Glu Asn Gln Thr Arg Asp Lys Lys Ile Asn
            100                 105                 110

Pro Asn Lys Trp Trp Glu Ser Phe Asp Asp Lys Val Lys Asp Phe Asn
        115                 120                 125

Tyr Leu Phe Val Ser Ser Phe Phe Lys Gly Asn Phe Lys Asn Asn Leu
    130                 135                 140

Lys His Ile Ala Asn Arg Thr Gly Val Asn Gly Gly Val Ile Asn Val
145                 150                 155                 160

Glu Asn Leu Leu Tyr Phe Ala Glu Glu Leu Lys Ser Gly Arg Leu Ser
                165                 170                 175
```

Tyr Val Asp Leu Phe Lys Met Tyr Asp Asn Asp Glu Ile Asn Ile
            180                 185                 190

<210> SEQ ID NO 12
<211> LENGTH: 191
<212> TYPE: PRT
<213> ORGANISM: Artificial Sequence
<220> FEATURE:
<223> OTHER INFORMATION: Synthetic Sequence

<400> SEQUENCE: 12

Ile Ser Lys Thr Asn Val Leu Glu Leu Lys Asp Lys Val Arg Asp Lys
1               5                   10                  15

Leu Lys Tyr Val Asp His Arg Tyr Leu Ala Leu Ile Asp Leu Ala Tyr
            20                  25                  30

Asp Gly Thr Ala Asn Arg Asp Phe Glu Ile Gln Thr Ile Asp Leu Leu
        35                  40                  45

Ile Asn Glu Leu Lys Phe Lys Gly Val Arg Leu Gly Glu Ser Arg Lys
    50                  55                  60

Pro Asp Gly Ile Ile Ser Tyr Asp Ile Asn Gly Val Ile Ile Asp Asn
65                  70                  75                  80

Lys Ala Tyr Ser Thr Gly Tyr Asn Leu Pro Ile Asn Gln Ala Asp Glu
                85                  90                  95

Met Ile Arg Tyr Ile Glu Glu Asn Gln Thr Arg Asp Lys Lys Ile Asn
            100                 105                 110

Ser Asn Lys Trp Trp Glu Ser Phe Asp Asp Lys Val Lys Asn Phe Asn
        115                 120                 125

Tyr Leu Phe Val Ser Ser Phe Phe Lys Gly Asn Phe Lys Asn Asn Leu
    130                 135                 140

Lys His Ile Ala Asn Arg Thr Gly Val Asn Gly Gly Ala Ile Asn Val
145                 150                 155                 160

Glu Asn Leu Leu Tyr Phe Ala Glu Glu Leu Lys Ala Gly Arg Leu Ser
                165                 170                 175

Tyr Val Asp Ser Phe Thr Met Tyr Asp Asn Asp Glu Ile Tyr Val
            180                 185                 190

<210> SEQ ID NO 13
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 13

Lys Ala Glu Lys Ser Glu Phe Leu Ile Glu Lys Asp Lys Leu Arg Glu
1               5                   10                  15

Lys Leu Asp Thr Leu Pro His Asp Tyr Leu Ser Met Val Asp Leu Ala
            20                  25                  30

Tyr Asp Ser Lys Gln Asn Arg Leu Phe Glu Met Lys Thr Ile Glu Leu
        35                  40                  45

Leu Ile Asn Glu Cys Asn Tyr Lys Gly Leu His Leu Gly Gly Thr Arg
    50                  55                  60

Lys Pro Asp Gly Ile Val Tyr Thr Asn Asn Glu Val Glu Asn Tyr Gly
65                  70                  75                  80

Ile Ile Ile Asp Thr Lys Ala Tyr Ser Lys Gly Tyr Asn Leu Pro Ile
                85                  90                  95

Ser Gln Val Asp Glu Met Thr Arg Tyr Val Glu Glu Asn Asn Lys Arg
            100                 105                 110

-continued

Glu Lys Lys Arg Asn Pro Asn Glu Trp Trp Asn Asn Phe Asp Ser Asn
    115                 120                 125

Val Lys Lys Phe Tyr Phe Ser Phe Ile Ser Gly Lys Phe Val Gly Asn
    130                 135                 140

Ile Glu Glu Lys Leu Gln Arg Ile Thr Leu Phe Thr Glu Ile Tyr Gly
145                 150                 155                 160

Asn Ala Ile Thr Val Thr Thr Leu Leu Tyr Ile Ala Asn Glu Ile Lys
                165                 170                 175

Ala Asn Arg Met Lys Lys Ser Asp Ile Met Glu Tyr Phe Asn Asp Lys
                180                 185                 190

Val

<210> SEQ ID NO 14
<211> LENGTH: 191
<212> TYPE: PRT
<213> ORGANISM: Artificial Sequence
<220> FEATURE:
<223> OTHER INFORMATION: Synthetic Sequence

<400> SEQUENCE: 14

Ile Ser Lys Thr Asn Val Leu Glu Leu Lys Asp Lys Val Arg Asp Lys
1               5                   10                  15

Leu Lys Tyr Val Asp His Arg Tyr Leu Ala Leu Ile Asp Leu Ala Tyr
                20                  25                  30

Asp Gly Thr Ala Asn Arg Asp Phe Glu Ile Gln Thr Ile Asp Leu Leu
                35                  40                  45

Ile Asn Glu Leu Lys Phe Lys Gly Val Arg Leu Gly Glu Ser Arg Lys
50                  55                  60

Pro Asp Gly Ile Ile Ser Tyr Asn Ile Asn Gly Val Ile Ile Asp Asn
65                  70                  75                  80

Lys Ala Tyr Ser Thr Gly Tyr Asn Leu Pro Ile Asn Gln Ala Asp Glu
                85                  90                  95

Met Ile Arg Tyr Ile Glu Glu Asn Gln Thr Arg Asp Glu Lys Ile Asn
                100                 105                 110

Ser Asn Lys Trp Trp Glu Ser Phe Asp Asp Glu Val Lys Asp Phe Asn
                115                 120                 125

Tyr Leu Phe Val Ser Ser Phe Phe Lys Gly Asn Phe Lys Asn Asn Leu
130                 135                 140

Lys His Ile Ala Asn Arg Thr Gly Val Asn Gly Gly Ala Ile Asn Val
145                 150                 155                 160

Glu Asn Leu Leu Tyr Phe Ala Glu Glu Leu Lys Ala Gly Arg Leu Ser
                165                 170                 175

Tyr Val Asp Ser Phe Thr Met Tyr Asp Asn Asp Glu Ile Tyr Val
                180                 185                 190

<210> SEQ ID NO 15
<211> LENGTH: 191
<212> TYPE: PRT
<213> ORGANISM: Artificial Sequence
<220> FEATURE:
<223> OTHER INFORMATION: Synthetic Sequence

<400> SEQUENCE: 15

Ile Ser Lys Thr Asn Ile Leu Glu Leu Lys Asp Lys Val Arg Asp Lys
1               5                   10                  15

Leu Lys Tyr Val Asp His Arg Tyr Leu Ala Leu Ile Asp Leu Ala Tyr
                20                  25                  30

```
Asp Gly Thr Ala Asn Arg Asp Phe Glu Ile Gln Thr Ile Asp Leu Leu
        35                  40                  45

Ile Asn Glu Leu Lys Phe Lys Gly Val Arg Leu Gly Glu Ser Arg Lys
 50                  55                  60

Pro Asp Gly Ile Ile Ser Tyr Asn Ile Asn Gly Val Ile Ile Asp Asn
 65                  70                  75                  80

Lys Ala Tyr Ser Thr Gly Tyr Asn Leu Pro Ile Asn Gln Ala Asp Glu
                 85                  90                  95

Met Ile Arg Tyr Ile Glu Glu Asn Gln Thr Arg Asp Glu Lys Ile Asn
                100                 105                 110

Ser Asn Lys Trp Trp Glu Ser Phe Asp Glu Lys Val Lys Asp Phe Asn
                115                 120                 125

Tyr Leu Phe Val Ser Ser Phe Phe Lys Gly Asn Phe Lys Asn Asn Leu
        130                 135                 140

Lys His Ile Ala Asn Arg Thr Gly Val Asn Gly Gly Ala Ile Asn Val
145                 150                 155                 160

Glu Asn Leu Leu Tyr Phe Ala Glu Glu Leu Lys Ala Gly Arg Ile Ser
                165                 170                 175

Tyr Leu Asp Ser Phe Lys Met Tyr Asn Asn Asp Glu Ile Tyr Leu
        180                 185                 190

<210> SEQ ID NO 16
<211> LENGTH: 191
<212> TYPE: PRT
<213> ORGANISM: Artificial Sequence
<220> FEATURE:
<223> OTHER INFORMATION: Synthetic Sequence

<400> SEQUENCE: 16

Ile Ser Lys Thr Asn Val Leu Glu Leu Lys Asp Lys Val Arg Asp Lys
 1               5                  10                  15

Leu Lys Tyr Val Asp His Arg Tyr Leu Ala Leu Ile Asp Leu Ala Tyr
                 20                  25                  30

Asp Gly Thr Ala Asn Arg Asp Phe Glu Ile Gln Thr Ile Asp Leu Leu
        35                  40                  45

Ile Asn Glu Leu Lys Phe Lys Gly Val Arg Leu Gly Glu Ser Arg Lys
 50                  55                  60

Pro Asp Gly Ile Ile Ser Tyr Asn Ile Asn Gly Val Ile Ile Asp Asn
 65                  70                  75                  80

Lys Ala Tyr Ser Thr Gly Tyr Asn Leu Pro Ile Asn Gln Ala Asp Glu
                 85                  90                  95

Met Ile Arg Tyr Ile Glu Glu Asn Gln Thr Arg Asp Glu Lys Ile Asn
                100                 105                 110

Ser Asn Lys Trp Trp Glu Ser Phe Asp Asp Lys Val Lys Asp Phe Asn
                115                 120                 125

Tyr Leu Phe Val Ser Ser Phe Phe Lys Gly Asn Phe Lys Asn Asn Leu
        130                 135                 140

Lys His Ile Ala Asn Arg Thr Gly Val Ser Gly Gly Ala Ile Asn Val
145                 150                 155                 160

Glu Asn Leu Leu Tyr Phe Ala Glu Glu Leu Lys Ala Gly Arg Leu Ser
                165                 170                 175

Tyr Val Asp Ser Phe Lys Met Tyr Asp Asn Asp Glu Ile Tyr Val
        180                 185                 190

<210> SEQ ID NO 17
```

```
<211> LENGTH: 191
<212> TYPE: PRT
<213> ORGANISM: Artificial Sequence
<220> FEATURE:
<223> OTHER INFORMATION: Synthetic Sequence

<400> SEQUENCE: 17

Ile Ser Lys Thr Asn Val Leu Glu Leu Lys Asp Lys Val Arg Asn Lys
1               5                   10                  15

Leu Lys Tyr Val Asp His Arg Tyr Leu Ala Leu Ile Asp Leu Ala Tyr
            20                  25                  30

Asp Gly Thr Ala Asn Arg Asp Phe Glu Ile Gln Thr Ile Asp Leu Leu
            35                  40                  45

Ile Asn Glu Leu Lys Phe Lys Gly Val Arg Leu Gly Glu Ser Arg Lys
        50                  55                  60

Pro Asp Gly Ile Ile Ser Tyr Asp Ile Asn Gly Val Ile Ile Asp Asn
65                  70                  75                  80

Lys Ser Tyr Ser Thr Gly Tyr Asn Leu Pro Ile Asn Gln Ala Asp Glu
                85                  90                  95

Met Ile Arg Tyr Ile Glu Glu Asn Gln Thr Arg Asp Glu Lys Ile Asn
            100                 105                 110

Ser Asn Lys Trp Trp Glu Ser Phe Asp Glu Lys Val Lys Asp Phe Asn
        115                 120                 125

Tyr Leu Phe Val Ser Ser Phe Phe Lys Gly Asn Phe Lys Asn Asn Leu
    130                 135                 140

Lys His Ile Ala Asn Arg Thr Gly Val Asn Gly Ala Ile Asn Val
145                 150                 155                 160

Glu Asn Leu Leu Tyr Phe Ala Glu Gly Leu Lys Ser Gly Arg Leu Ser
                165                 170                 175

Tyr Val Asp Ser Phe Thr Met Tyr Asp Asn Asp Glu Ile Tyr Val
            180                 185                 190

<210> SEQ ID NO 18
<211> LENGTH: 191
<212> TYPE: PRT
<213> ORGANISM: Artificial Sequence
<220> FEATURE:
<223> OTHER INFORMATION: Synthetic Sequence

<400> SEQUENCE: 18

Ile Ser Lys Thr Asn Val Leu Glu Leu Lys Asp Lys Val Arg Asp Lys
1               5                   10                  15

Leu Lys Tyr Val Asp His Arg Tyr Leu Ser Leu Ile Asp Leu Ala Tyr
            20                  25                  30

Asp Gly Asn Ala Asn Arg Asp Phe Glu Ile Gln Thr Ile Asp Leu Leu
            35                  40                  45

Ile Asn Glu Leu Asn Phe Lys Gly Val Arg Leu Gly Glu Ser Arg Lys
        50                  55                  60

Pro Asp Gly Ile Ile Ser Tyr Asn Ile Asn Gly Val Ile Ile Asp Asn
65                  70                  75                  80

Lys Ala Tyr Ser Thr Gly Tyr Asn Leu Pro Ile Asn Gln Ala Asp Glu
                85                  90                  95

Met Ile Arg Tyr Ile Glu Glu Asn Gln Thr Arg Asp Glu Lys Ile Asn
            100                 105                 110

Ser Asn Lys Trp Trp Glu Ser Phe Asp Asp Lys Val Lys Asp Phe Asn
        115                 120                 125

Tyr Leu Phe Val Ser Ser Phe Phe Lys Gly Asn Phe Lys Asn Asn Leu
```

```
            130                 135                 140

Lys His Ile Ala Asn Arg Thr Gly Val Ser Gly Gly Ala Ile Asn Val
145                 150                 155                 160

Glu Asn Leu Leu Tyr Phe Ala Glu Glu Leu Lys Ala Gly Arg Leu Ser
                165                 170                 175

Tyr Ala Asp Ser Phe Thr Met Tyr Asp Asn Asp Glu Ile Tyr Val
            180                 185                 190

<210> SEQ ID NO 19
<211> LENGTH: 191
<212> TYPE: PRT
<213> ORGANISM: Artificial Sequence
<220> FEATURE:
<223> OTHER INFORMATION: Synthetic Sequence

<400> SEQUENCE: 19

Ile Ala Lys Thr Asn Val Leu Gly Leu Lys Asp Lys Val Arg Asp Arg
1               5                   10                  15

Leu Lys Tyr Val Asp His Arg Tyr Leu Ala Leu Ile Asp Leu Ala Tyr
                20                  25                  30

Asp Gly Thr Ala Asn Arg Asp Phe Glu Ile Gln Thr Ile Asp Leu Leu
            35                  40                  45

Ile Asn Glu Leu Lys Phe Lys Gly Val Arg Leu Gly Glu Ser Arg Lys
        50                  55                  60

Pro Asp Gly Ile Ile Ser Tyr Asn Val Asn Gly Val Ile Ile Asp Asn
65                  70                  75                  80

Lys Ala Tyr Ser Lys Gly Tyr Asn Leu Pro Ile Asn Gln Ala Asp Glu
                85                  90                  95

Met Ile Arg Tyr Ile Glu Glu Asn Gln Thr Arg Asp Glu Lys Ile Asn
            100                 105                 110

Ala Asn Lys Trp Trp Glu Ser Phe Asp Asp Lys Val Glu Glu Phe Ser
        115                 120                 125

Tyr Leu Phe Val Ser Ser Phe Phe Lys Gly Asn Phe Lys Asn Asn Leu
    130                 135                 140

Lys His Ile Ala Asn Arg Thr Gly Val Asn Gly Gly Ala Ile Asn Val
145                 150                 155                 160

Glu Asn Leu Leu Tyr Phe Ala Glu Glu Leu Lys Ser Gly Arg Leu Ser
                165                 170                 175

Tyr Met Asp Ser Phe Ser Leu Tyr Asp Asn Asp Glu Ile Cys Val
            180                 185                 190

<210> SEQ ID NO 20
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 20

Glu Leu Lys Asp Glu Gln Ser Glu Lys Arg Lys Ala Lys Phe Leu Lys
1               5                   10                  15

Glu Thr Lys Leu Pro Met Lys Tyr Ile Glu Leu Leu Asp Ile Ala Tyr
                20                  25                  30

Asp Gly Lys Arg Asn Arg Asp Phe Glu Ile Val Thr Met Glu Leu Phe
            35                  40                  45

Arg Glu Val Tyr Arg Leu Asn Ser Lys Leu Leu Gly Gly Gly Arg Lys
        50                  55                  60
```

Pro Asp Gly Leu Ile Tyr Thr Asp Asp Phe Gly Val Ile Val Asp Thr
65                  70                  75                  80

Lys Ala Tyr Gly Glu Gly Tyr Ser Lys Ser Ile Asn Gln Ala Asp Glu
                85                  90                  95

Met Ile Arg Tyr Ile Glu Asp Asn Lys Arg Arg Asp Glu Lys Arg Asn
            100                 105                 110

Pro Ile Lys Trp Trp Glu Ser Phe Pro Ser Ser Ile Ser Gln Asn Asn
        115                 120                 125

Phe Tyr Phe Leu Trp Val Ser Ser Lys Phe Val Gly Lys Phe Gln Glu
    130                 135                 140

Gln Leu Ala Tyr Thr Ala Asn Glu Thr Gln Thr Lys Gly Gly Ala Ile
145                 150                 155                 160

Asn Val Glu Gln Ile Leu Ile Gly Ala Asp Leu Ile Met Gln Lys Met
                165                 170                 175

Leu Asp Ile Asn Thr Ile Pro Ser Phe Glu Asn Gln Glu Ile Ile
            180                 185                 190

Phe

<210> SEQ ID NO 21
<211> LENGTH: 191
<212> TYPE: PRT
<213> ORGANISM: Artificial Sequence
<220> FEATURE:
<223> OTHER INFORMATION: Synthetic Sequence

<400> SEQUENCE: 21

Ile Phe Lys Thr Asn Val Leu Glu Leu Lys Asp Ser Ile Arg Glu Lys
1               5                   10                  15

Leu Asp Tyr Ile Asp His Arg Tyr Leu Ser Leu Val Asp Leu Ala Tyr
            20                  25                  30

Asp Ser Lys Ala Asn Arg Asp Phe Glu Ile Gln Thr Ile Asp Leu Leu
        35                  40                  45

Ile Asn Glu Leu Asp Phe Lys Gly Leu Arg Leu Gly Glu Ser Arg Lys
    50                  55                  60

Pro Asp Gly Ile Ile Ser Tyr Asp Ile Asn Gly Val Ile Ile Asp Asn
65                  70                  75                  80

Lys Ala Tyr Ser Lys Gly Tyr Asn Leu Pro Ile Asn Gln Ala Asp Glu
                85                  90                  95

Met Ile Arg Tyr Ile Gln Glu Asn Gln Ser Arg Asn Glu Lys Ile Asn
            100                 105                 110

Pro Asn Lys Trp Trp Glu Asn Phe Glu Asp Lys Val Ile Lys Phe Asn
        115                 120                 125

Tyr Leu Phe Ile Ser Ser Leu Phe Val Gly Gly Phe Lys Lys Asn Leu
    130                 135                 140

Gln His Ile Ala Asn Arg Thr Gly Val Asn Gly Gly Ala Ile Asp Val
145                 150                 155                 160

Glu Asn Leu Leu Tyr Phe Ala Glu Glu Ile Lys Ser Gly Arg Leu Thr
                165                 170                 175

Tyr Lys Asp Ser Phe Ser Arg Tyr Ile Asn Asp Glu Ile Lys Met
            180                 185                 190

<210> SEQ ID NO 22
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 22

```
Leu Pro Val Lys Ser Glu Val Ser Val Phe Lys Asp Tyr Leu Arg Thr
1               5                   10                  15

His Leu Thr His Val Asp His Arg Tyr Leu Ile Leu Val Asp Leu Gly
            20                  25                  30

Phe Asp Gly Ser Ser Asp Arg Asp Tyr Glu Met Lys Thr Ala Glu Leu
        35                  40                  45

Phe Thr Ala Glu Leu Gly Phe Met Gly Ala Arg Leu Gly Asp Thr Arg
50                  55                  60

Lys Pro Asp Val Cys Val Tyr His Gly Ala Asn Gly Leu Ile Ile Asp
65                  70                  75                  80

Asn Lys Ala Tyr Gly Lys Gly Tyr Ser Leu Pro Ile Lys Gln Ala Asp
                85                  90                  95

Glu Ile Tyr Arg Tyr Ile Glu Glu Asn Lys Glu Arg Asp Ala Arg Leu
            100                 105                 110

Asn Pro Asn Gln Trp Trp Lys Val Phe Asp Glu Ser Val Thr His Phe
        115                 120                 125

Arg Phe Ala Phe Ile Ser Gly Ser Phe Thr Gly Gly Phe Lys Asp Arg
    130                 135                 140

Ile Glu Leu Ile Ser Met Arg Ser Gly Ile Cys Gly Ala Ala Val Asn
145                 150                 155                 160

Ser Val Asn Leu Leu Met Ala Glu Glu Leu Lys Ser Gly Arg Leu
                165                 170                 175

Asp Tyr Glu Glu Trp Phe Gln Tyr Phe Asp Cys Asn Asp Glu Ile Ser
            180                 185                 190

Phe
```

<210> SEQ ID NO 23
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 23

```
Ile Ser Val Lys Ser Asp Met Ala Val Val Lys Asp Ser Val Arg Glu
1               5                   10                  15

Arg Leu Ala His Val Ser His Glu Tyr Leu Ile Leu Ile Asp Leu Gly
            20                  25                  30

Phe Asp Gly Thr Ser Asp Arg Asp Tyr Glu Ile Gln Thr Ala Glu Leu
        35                  40                  45

Phe Thr Arg Glu Leu Asp Phe Leu Gly Gly Arg Leu Gly Asp Thr Arg
50                  55                  60

Lys Pro Asp Val Cys Ile Tyr Tyr Gly Lys Asp Gly Met Ile Ile Asp
65                  70                  75                  80

Asn Lys Ala Tyr Gly Lys Gly Tyr Ser Leu Pro Ile Lys Gln Ala Asp
                85                  90                  95

Glu Met Tyr Arg Tyr Leu Glu Glu Asn Lys Glu Arg Asn Glu Lys Ile
            100                 105                 110

Asn Pro Asn Arg Trp Trp Lys Val Phe Asp Glu Gly Val Thr Asp Tyr
        115                 120                 125

Arg Phe Ala Phe Val Ser Gly Ser Phe Thr Gly Gly Phe Lys Asp Arg
    130                 135                 140

Leu Glu Asn Ile His Met Arg Ser Gly Leu Cys Gly Gly Ala Ile Asp
```

```
145                 150                 155                 160
Ser Val Thr Leu Leu Leu Ala Glu Glu Leu Lys Ala Gly Arg Met
                165                 170                 175
Glu Tyr Ser Glu Phe Phe Arg Leu Phe Asp Cys Asn Asp Val Thr
                180                 185                 190

Phe

<210> SEQ ID NO 24
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 24

Glu Leu Lys Asp Lys Ala Ala Asp Ala Val Lys Ala Lys Phe Leu Lys
1               5                   10                  15

Leu Thr Gly Leu Ser Met Lys Tyr Ile Glu Leu Leu Asp Ile Ala Tyr
            20                  25                  30

Asp Ser Ser Arg Asn Arg Asp Phe Glu Ile Leu Thr Ala Asp Leu Phe
                35                  40                  45

Lys Asn Val Tyr Gly Leu Asp Ala Met His Leu Gly Gly Gly Arg Lys
50                  55                  60

Pro Asp Ala Ile Ala Gln Thr Ser His Phe Gly Ile Ile Ile Asp Thr
65                  70                  75                  80

Lys Ala Tyr Gly Asn Gly Tyr Ser Lys Ser Ile Ser Gln Glu Asp Glu
                85                  90                  95

Met Val Arg Tyr Ile Glu Asp Asn Gln Gln Arg Ser Ile Thr Arg Asn
                100                 105                 110

Ser Val Glu Trp Trp Lys Asn Phe Asn Ser Ser Ile Pro Ser Thr Ala
            115                 120                 125

Phe Tyr Phe Leu Trp Val Ser Ser Lys Phe Val Gly Lys Phe Asp Asp
        130                 135                 140

Gln Leu Leu Ala Thr Tyr Asn Arg Thr Asn Thr Cys Gly Gly Ala Leu
145                 150                 155                 160

Asn Val Glu Gln Leu Leu Ile Gly Ala Tyr Lys Val Lys Ala Gly Leu
                165                 170                 175

Leu Gly Ile Gly Gln Ile Pro Ser Tyr Phe Lys Asn Lys Glu Ile Ala
            180                 185                 190

Trp

<210> SEQ ID NO 25
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 25

Ile Ser Val Lys Ser Asp Met Ala Val Val Lys Asp Ser Val Arg Glu
1               5                   10                  15

Arg Leu Ala His Val Ser His Glu Tyr Leu Leu Leu Ile Asp Leu Gly
            20                  25                  30

Phe Asp Gly Thr Ser Asp Arg Asp Tyr Glu Ile Gln Thr Ala Glu Leu
        35                  40                  45

Leu Thr Arg Glu Leu Asp Phe Leu Gly Gly Arg Leu Gly Asp Thr Arg
50                  55                  60
```

```
Lys Pro Asp Val Cys Ile Tyr Gly Lys Asp Gly Met Ile Ile Asp
 65                  70                  75                  80

Asn Lys Ala Tyr Gly Lys Gly Tyr Ser Leu Pro Ile Lys Gln Ala Asp
                 85                  90                  95

Glu Met Tyr Arg Tyr Leu Glu Glu Asn Lys Glu Arg Asn Glu Lys Ile
            100                 105                 110

Asn Pro Asn Arg Trp Trp Lys Val Phe Asp Glu Gly Val Thr Asp Tyr
            115                 120                 125

Arg Phe Ala Phe Val Ser Gly Ser Phe Thr Gly Gly Phe Lys Asp Arg
            130                 135                 140

Leu Glu Asn Ile His Met Arg Ser Gly Leu Cys Gly Gly Ala Ile Asp
145                 150                 155                 160

Ser Val Thr Leu Leu Leu Ala Glu Glu Leu Lys Ala Gly Arg Met
                165                 170                 175

Glu Tyr Ser Glu Phe Phe Arg Leu Phe Asp Cys Asn Asp Glu Val Thr
            180                 185                 190

Phe
```

<210> SEQ ID NO 26
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 26

```
Glu Leu Lys Asp Glu Gln Ala Glu Lys Arg Lys Ala Lys Phe Leu Lys
  1               5                  10                  15

Glu Thr Asn Leu Pro Met Lys Tyr Ile Glu Leu Leu Asp Ile Ala Tyr
             20                  25                  30

Asp Gly Lys Arg Asn Arg Asp Phe Glu Ile Val Thr Met Glu Leu Phe
            35                  40                  45

Arg Asn Val Tyr Arg Leu His Ser Lys Leu Leu Gly Gly Gly Arg Lys
 50                  55                  60

Pro Asp Gly Leu Leu Tyr Gln Asp Arg Phe Gly Val Ile Val Asp Thr
 65                  70                  75                  80

Lys Ala Tyr Gly Lys Gly Tyr Ser Lys Ser Ile Asn Gln Ala Asp Glu
                 85                  90                  95

Met Ile Arg Tyr Ile Glu Asp Asn Lys Arg Arg Asp Glu Asn Arg Asn
            100                 105                 110

Pro Ile Lys Trp Trp Glu Ala Phe Pro Asp Thr Ile Pro Gln Glu Glu
            115                 120                 125

Phe Tyr Phe Met Trp Val Ser Ser Lys Phe Ile Gly Lys Phe Gln Glu
            130                 135                 140

Gln Leu Asp Tyr Thr Ser Asn Glu Thr Gln Ile Lys Gly Ala Ala Leu
145                 150                 155                 160

Asn Val Glu Gln Leu Leu Gly Ala Asp Leu Val Leu Lys Gly Gln
                165                 170                 175

Leu His Ile Ser Asp Leu Pro Ser Tyr Phe Gln Asn Lys Glu Ile Glu
            180                 185                 190

Phe
```

<210> SEQ ID NO 27
<211> LENGTH: 195
<212> TYPE: PRT

<213> ORGANISM: Artificial Sequence
<220> FEATURE:
<223> OTHER INFORMATION: Synthetic Sequence

<400> SEQUENCE: 27

```
Arg Asn Leu Asp Asn Val Glu Arg Asp Asn Arg Lys Ala Glu Phe Leu
1               5                   10                  15

Ala Lys Thr Ser Leu Pro Pro Arg Phe Ile Glu Leu Leu Ser Ile Ala
            20                  25                  30

Tyr Glu Ser Lys Ser Asn Arg Asp Phe Glu Met Ile Thr Ala Glu Leu
        35                  40                  45

Phe Lys Asp Val Tyr Gly Leu Gly Ala Val His Leu Gly Asn Ala Lys
50                  55                  60

Lys Pro Asp Ala Leu Ala Phe Asn Asp Asp Phe Gly Ile Ile Ile Asp
65                  70                  75                  80

Thr Lys Ala Tyr Ser Asn Gly Tyr Ser Lys Asn Ile Asn Gln Glu Asp
                85                  90                  95

Glu Met Val Arg Tyr Ile Glu Asp Asn Gln Ile Arg Ser Pro Asp Arg
            100                 105                 110

Asn Asn Asn Glu Trp Trp Leu Ser Phe Pro Pro Ser Ile Pro Glu Asn
        115                 120                 125

Asp Phe His Phe Leu Trp Val Ser Ser Tyr Phe Thr Gly Arg Phe Glu
    130                 135                 140

Glu Gln Leu Gln Glu Thr Ser Ala Arg Thr Gly Gly Thr Thr Gly Gly
145                 150                 155                 160

Ala Leu Asp Val Glu Gln Leu Leu Ile Gly Gly Ser Leu Ile Gln Glu
                165                 170                 175

Gly Ser Leu Ala Pro His Glu Val Pro Ala Tyr Met Gln Asn Arg Val
            180                 185                 190

Ile His Phe
        195
```

<210> SEQ ID NO 28
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 28

```
Ser Pro Val Lys Ser Glu Val Ser Val Phe Lys Asp Tyr Leu Arg Thr
1               5                   10                  15

His Leu Thr His Val Asp His Arg Tyr Leu Ile Leu Val Asp Leu Gly
            20                  25                  30

Phe Asp Gly Ser Ser Asp Arg Asp Tyr Glu Met Lys Thr Ala Glu Leu
        35                  40                  45

Phe Thr Ala Glu Leu Gly Phe Met Gly Ala Arg Leu Gly Asp Thr Arg
    50                  55                  60

Lys Pro Asp Val Cys Val Tyr His Gly Ala His Gly Leu Ile Ile Asp
65                  70                  75                  80

Asn Lys Ala Tyr Gly Lys Gly Tyr Ser Leu Pro Ile Lys Gln Ala Asp
                85                  90                  95

Glu Ile Tyr Arg Tyr Ile Glu Glu Asn Lys Glu Arg Ala Val Arg Leu
            100                 105                 110

Asn Pro Asn Gln Trp Trp Lys Val Phe Asp Glu Ser Val Ala His Phe
        115                 120                 125
```

```
Arg Phe Ala Phe Ile Ser Gly Ser Phe Thr Gly Gly Phe Lys Asp Arg
            130                 135                 140

Ile Glu Leu Ile Ser Met Arg Ser Gly Ile Cys Gly Ala Ala Val Asn
145                 150                 155                 160

Ser Val Asn Leu Leu Met Ala Glu Leu Lys Ser Gly Arg Leu
                165                 170                 175

Asn Tyr Glu Glu Trp Phe Gln Tyr Phe Asp Cys Asn Asp Glu Ile Ser
                180                 185                 190

Leu
```

<210> SEQ ID NO 29
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 29

```
Thr Leu Val Asp Ile Glu Lys Glu Arg Lys Ala Tyr Phe Leu Lys
1               5                   10                  15

Glu Thr Ser Leu Ser Pro Arg Tyr Ile Glu Leu Leu Glu Ile Ala Phe
                20                  25                  30

Asp Pro Lys Arg Asn Arg Asp Phe Glu Val Ile Thr Ala Glu Leu Leu
                35                  40                  45

Lys Ala Gly Tyr Gly Leu Lys Ala Lys Val Leu Gly Gly Arg Arg
    50                  55                  60

Pro Asp Gly Ile Ala Tyr Thr Lys Asp Tyr Gly Leu Ile Val Asp Thr
65                  70                  75                  80

Lys Ala Tyr Ser Asn Gly Tyr Gly Lys Asn Ile Gly Gln Ala Asp Glu
                85                  90                  95

Met Ile Arg Tyr Ile Glu Asp Asn Gln Lys Arg Asp Asn Lys Arg Asn
                100                 105                 110

Pro Ile Glu Trp Trp Arg Glu Phe Glu Val Gln Ile Pro Ala Asn Ser
                115                 120                 125

Tyr Tyr Tyr Leu Trp Val Ser Gly Arg Phe Thr Gly Arg Phe Asp Glu
                130                 135                 140

Gln Leu Val Tyr Thr Ser Ser Gln Thr Asn Thr Arg Gly Gly Ala Leu
145                 150                 155                 160

Glu Val Glu Gln Leu Leu Trp Gly Ala Asp Ala Val Met Lys Gly Lys
                165                 170                 175

Leu Asn Val Ser Asp Leu Pro Lys Tyr Met Asn Asn Ser Ile Ile Lys
                180                 185                 190

Leu
```

<210> SEQ ID NO 30
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 30

```
Glu Leu Arg Asp Lys Val Ile Glu Glu Gln Lys Ala Ile Phe Leu Gln
1               5                   10                  15

Lys Thr Lys Leu Pro Leu Ser Tyr Ile Glu Leu Leu Glu Ile Ala Arg
                20                  25                  30

Asp Gly Lys Arg Ser Arg Asp Phe Glu Leu Ile Thr Ile Glu Leu Phe
```

```
                35                  40                  45
Lys Asn Ile Tyr Lys Ile Asn Ala Arg Ile Leu Gly Gly Ala Arg Lys
 50                  55                  60

Pro Asp Gly Val Leu Tyr Met Pro Glu Phe Gly Val Ile Val Asp Thr
 65                  70                  75                  80

Lys Ala Tyr Ala Asp Gly Tyr Ser Lys Ser Ile Ala Gln Ala Asp Glu
                 85                  90                  95

Met Ile Arg Tyr Ile Glu Asp Asn Lys Arg Arg Asp Pro Ser Arg Asn
                100                 105                 110

Ser Thr Lys Trp Trp Glu His Phe Pro Thr Ser Ile Pro Ala Asn Asn
            115                 120                 125

Phe Tyr Phe Leu Trp Val Ser Ser Val Phe Val Asn Lys Phe His Glu
        130                 135                 140

Gln Leu Ser Tyr Thr Ala Gln Glu Thr Gln Thr Val Gly Ala Ala Leu
145                 150                 155                 160

Ser Val Glu Gln Leu Leu Leu Gly Ala Asp Ser Val Leu Lys Gly Asn
                165                 170                 175

Leu Thr Thr Glu Lys Phe Ile Asp Ser Phe Lys Asn Gln Glu Ile Val
                180                 185                 190

Phe

<210> SEQ ID NO 31
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 31

Gly Ala Thr Lys Ser Asp Leu Ser Leu Leu Lys Asp Asp Ile Arg Lys
  1               5                  10                  15

Lys Leu Asn His Ile Asn His Lys Tyr Leu Val Leu Ile Asp Leu Gly
                 20                  25                  30

Phe Asp Gly Thr Ala Asp Arg Asp Tyr Glu Leu Gln Thr Ala Asp Leu
             35                  40                  45

Leu Thr Ser Glu Leu Ala Phe Lys Gly Ala Arg Leu Gly Asp Ser Arg
 50                  55                  60

Lys Pro Asp Val Cys Val Tyr His Asp Lys Asn Gly Leu Ile Ile Asp
 65                  70                  75                  80

Asn Lys Ala Tyr Gly Ser Gly Tyr Ser Leu Pro Ile Lys Gln Ala Asp
                 85                  90                  95

Glu Met Leu Arg Tyr Ile Glu Glu Asn Gln Lys Arg Asp Lys Ala Leu
                100                 105                 110

Asn Pro Asn Glu Trp Trp Thr Ile Phe Asp Asp Ala Val Ser Lys Phe
            115                 120                 125

Asn Phe Ala Phe Val Ser Gly Glu Phe Thr Gly Gly Phe Lys Asp Arg
        130                 135                 140

Leu Glu Asn Ile Ser Arg Arg Ser Tyr Thr Asn Gly Ala Ala Ile Asn
145                 150                 155                 160

Ser Val Asn Leu Leu Leu Ala Glu Glu Ile Lys Ser Gly Arg Ile
                165                 170                 175

Ser Tyr Gly Asp Ala Phe Thr Lys Phe Glu Cys Asn Asp Glu Ile Ile
                180                 185                 190

Ile
```

<210> SEQ ID NO 32
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 32

```
Glu Leu Arg Asn Ala Ala Leu Asp Lys Gln Lys Val Asn Phe Ile Asn
1               5                   10                  15

Lys Thr Gly Leu Pro Met Lys Tyr Ile Glu Leu Leu Glu Ile Ala Phe
            20                  25                  30

Asp Gly Ser Arg Asn Arg Asp Phe Glu Met Val Thr Ala Asp Leu Phe
        35                  40                  45

Lys Asn Val Tyr Gly Phe Asn Ser Ile Leu Leu Gly Gly Arg Lys
    50                  55                  60

Pro Asp Gly Leu Ile Phe Thr Asp Arg Phe Gly Val Ile Ile Asp Thr
65                  70                  75                  80

Lys Ala Tyr Gly Asn Gly Tyr Ser Lys Ser Ile Gly Gln Glu Asp Glu
                85                  90                  95

Met Val Arg Tyr Ile Glu Asp Asn Gln Leu Arg Asp Ser Asn Arg Asn
            100                 105                 110

Ser Val Glu Trp Trp Lys Asn Phe Asp Glu Lys Ile Glu Ser Glu Asn
        115                 120                 125

Phe Tyr Phe Met Trp Ile Ser Ser Lys Phe Ile Gly Gln Phe Ser Asp
    130                 135                 140

Gln Leu Gln Ser Thr Ser Asp Arg Thr Asn Thr Lys Gly Ala Ala Leu
145                 150                 155                 160

Asn Val Glu Gln Leu Leu Leu Gly Ala Ala Ala Arg Asp Gly Lys
                165                 170                 175

Leu Asp Ile Asn Ser Leu Pro Ile Tyr Met Asn Asn Lys Glu Ile Leu
            180                 185                 190

Trp
```

<210> SEQ ID NO 33
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 33

```
Glu Leu Lys Asp Glu Gln Ser Glu Lys Arg Lys Ala Tyr Phe Leu Lys
1               5                   10                  15

Glu Thr Asn Leu Pro Leu Lys Tyr Ile Glu Leu Leu Asp Ile Ala Tyr
            20                  25                  30

Asp Gly Lys Arg Asn Arg Asp Phe Glu Ile Val Thr Met Glu Leu Phe
        35                  40                  45

Arg Asn Val Tyr Arg Leu Gln Ser Lys Leu Leu Gly Gly Val Arg Lys
    50                  55                  60

Pro Asp Gly Leu Leu Tyr Lys His Arg Phe Gly Ile Ile Val Asp Thr
65                  70                  75                  80

Lys Ala Tyr Gly Glu Gly Tyr Ser Lys Ser Ile Ser Gln Ala Asp Glu
                85                  90                  95

Met Ile Arg Tyr Ile Glu Asp Asn Lys Arg Arg Asp Gly Asn Arg Asn
            100                 105                 110
```

```
Ser Thr Lys Trp Trp Glu His Phe Pro Asp Cys Ile Pro Lys Gln Ser
            115                 120                 125

Phe Tyr Phe Met Trp Val Ser Ser Lys Phe Val Gly Lys Phe Gln Glu
    130                 135                 140

Gln Leu Asp Tyr Thr Ala Asn Glu Thr Lys Thr Asn Gly Ala Ala Leu
145                 150                 155                 160

Asn Val Glu Gln Leu Leu Trp Gly Ala Asp Leu Val Ala Lys Gly Lys
                165                 170                 175

Leu Asp Ile Ser Gln Leu Pro Ser Tyr Phe Gln Asn Lys Glu Ile Glu
                180                 185                 190

Phe

<210> SEQ ID NO 34
<211> LENGTH: 188
<212> TYPE: PRT
<213> ORGANISM: Artificial Sequence
<220> FEATURE:
<223> OTHER INFORMATION: Synthetic Sequence

<400> SEQUENCE: 34

His Asn Asn Lys Phe Lys Asn Tyr Leu Arg Glu Asn Ser Glu Leu Ser
1               5                   10                  15

Phe Lys Phe Ile Glu Leu Ile Asp Ile Ala Tyr Asp Gly Asn Arg Asn
                20                  25                  30

Arg Asp Met Glu Ile Ile Thr Ala Glu Leu Leu Lys Glu Ile Tyr Gly
            35                  40                  45

Leu Asn Val Lys Leu Leu Gly Gly Arg Lys Pro Asp Ile Leu Ala
50                  55                  60

Tyr Thr Asp Asp Ile Gly Ile Ile Asp Thr Lys Ala Tyr Lys Asp
65                  70                  75                  80

Gly Tyr Gly Lys Gln Ile Asn Gln Ala Asp Glu Met Ile Arg Tyr Ile
                85                  90                  95

Glu Asp Asn Gln Arg Arg Asp Leu Ile Arg Asn Pro Asn Glu Trp Trp
            100                 105                 110

Arg Tyr Phe Pro Lys Ser Ile Ser Lys Glu Lys Ile Tyr Phe Met Trp
        115                 120                 125

Ile Ser Ser Tyr Phe Lys Asn Asn Phe Tyr Glu Gln Val Gln Tyr Thr
    130                 135                 140

Ala Gln Glu Thr Lys Ser Ile Gly Ala Ala Leu Asn Val Arg Gln Leu
145                 150                 155                 160

Leu Leu Cys Ala Asp Ala Ile Gln Lys Glu Val Leu Ser Leu Asp Thr
                165                 170                 175

Phe Leu Gly Ser Phe Arg Asn Glu Glu Ile Asn Leu
                180                 185

<210> SEQ ID NO 35
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 35

Leu Pro Val Lys Ser Glu Val Ser Ile Leu Lys Asp Tyr Leu Arg Ser
1               5                   10                  15

His Leu Thr His Ile Asp His Lys Tyr Leu Ile Leu Val Asp Leu Gly
                20                  25                  30
```

```
Tyr Asp Gly Thr Ser Asp Arg Asp Tyr Glu Ile Gln Thr Ala Gln Leu
             35                  40                  45

Leu Thr Ala Glu Leu Ser Phe Leu Gly Gly Arg Leu Gly Asp Thr Arg
 50                  55                  60

Lys Pro Asp Val Cys Ile Tyr Tyr Glu Asp Asn Gly Leu Ile Ile Asp
 65                  70                  75                  80

Asn Lys Ala Tyr Gly Lys Gly Tyr Ser Leu Pro Met Lys Gln Ala Asp
                 85                  90                  95

Glu Met Tyr Arg Tyr Ile Glu Glu Asn Lys Glu Arg Ser Glu Leu Leu
            100                 105                 110

Asn Pro Asn Cys Trp Trp Asn Ile Phe Asp Lys Asp Val Lys Thr Phe
            115                 120                 125

His Phe Ala Phe Leu Ser Gly Glu Phe Thr Gly Gly Phe Arg Asp Arg
            130                 135                 140

Leu Asn His Ile Ser Met Arg Ser Gly Met Arg Gly Ala Ala Val Asn
145                 150                 155                 160

Ser Ala Asn Leu Leu Ile Met Ala Glu Lys Leu Lys Ala Gly Thr Met
                165                 170                 175

Glu Tyr Glu Glu Phe Phe Arg Leu Phe Asp Thr Asn Asp Glu Ile Leu
            180                 185                 190

Phe

<210> SEQ ID NO 36
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 36

Leu Pro Val Lys Ser Gln Val Ser Ile Leu Lys Asp Tyr Leu Arg Ser
 1               5                  10                  15

Tyr Leu Ser His Val Asp His Lys Tyr Leu Ile Leu Leu Asp Leu Gly
                 20                  25                  30

Phe Asp Gly Thr Ser Asp Arg Asp Tyr Glu Ile Trp Thr Ala Gln Leu
             35                  40                  45

Leu Thr Ala Glu Leu Ser Phe Leu Gly Gly Arg Leu Gly Asp Thr Arg
 50                  55                  60

Lys Pro Asp Val Cys Ile Tyr Tyr Glu Asp Asn Gly Leu Ile Ile Asp
 65                  70                  75                  80

Asn Lys Ala Tyr Gly Lys Gly Tyr Ser Leu Pro Ile Lys Gln Ala Asp
                 85                  90                  95

Glu Met Tyr Arg Tyr Ile Glu Glu Asn Lys Glu Arg Ser Asp Leu Leu
            100                 105                 110

Asn Pro Asn Cys Trp Trp Asn Ile Phe Gly Glu Gly Val Lys Thr Phe
            115                 120                 125

Arg Phe Ala Phe Leu Ser Gly Phe Thr Gly Gly Phe Lys Asp Arg
            130                 135                 140

Leu Asn His Ile Ser Met Arg Ser Gly Ile Lys Gly Ala Ala Val Asn
145                 150                 155                 160

Ser Ala Asn Leu Leu Ile Met Ala Glu Gln Leu Lys Ser Gly Thr Met
                165                 170                 175

Ser Tyr Glu Glu Phe Phe Gln Leu Phe Asp Tyr Asn Asp Glu Ile Ile
            180                 185                 190

Phe
```

<210> SEQ ID NO 37
<211> LENGTH: 191
<212> TYPE: PRT
<213> ORGANISM: Artificial Sequence
<220> FEATURE:
<223> OTHER INFORMATION: Synthetic Sequence

<400> SEQUENCE: 37

```
Val Ser Lys Thr Asn Ile Leu Glu Leu Lys Asp Asn Thr Arg Glu Lys
1               5                   10                  15

Leu Val Tyr Leu Asp His Arg Tyr Leu Ser Leu Phe Asp Leu Ala Tyr
            20                  25                  30

Asp Asp Lys Ala Ser Arg Asp Phe Glu Ile Gln Thr Ile Asp Leu Leu
        35                  40                  45

Ile Asn Glu Leu Gln Phe Lys Gly Leu Arg Leu Gly Glu Arg Arg Lys
    50                  55                  60

Pro Asp Gly Ile Ile Ser Tyr Gly Val Asn Gly Val Ile Ile Asp Asn
65                  70                  75                  80

Lys Ala Tyr Ser Lys Gly Tyr Asn Leu Pro Ile Arg Gln Ala Asp Glu
                85                  90                  95

Met Ile Arg Tyr Ile Gln Glu Asn Gln Ser Arg Asp Glu Lys Leu Asn
            100                 105                 110

Pro Asn Lys Trp Trp Glu Asn Phe Glu Glu Glu Thr Ser Lys Phe Asn
        115                 120                 125

Tyr Leu Phe Ile Ser Ser Lys Phe Ile Ser Gly Phe Lys Lys Asn Leu
    130                 135                 140

Gln Tyr Ile Ala Asp Arg Thr Gly Val Asn Gly Gly Ala Ile Asn Val
145                 150                 155                 160

Glu Asn Leu Leu Cys Phe Ala Glu Met Leu Lys Ser Gly Lys Leu Glu
                165                 170                 175

Tyr Asn Asp Phe Phe Asn Gln Tyr Asn Asn Asp Glu Ile Ile Met
            180                 185                 190
```

<210> SEQ ID NO 38
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 38

```
Leu Pro Val Lys Ser Gln Val Ser Ile Leu Lys Asp Tyr Leu Arg Ser
1               5                   10                  15

Cys Leu Ser His Val Asp His Lys Tyr Leu Ile Leu Asp Leu Gly
            20                  25                  30

Phe Asp Gly Thr Ser Asp Arg Asp Tyr Glu Ile Gln Thr Ala Gln Leu
        35                  40                  45

Leu Thr Ala Glu Leu Ser Phe Leu Gly Arg Leu Gly Asp Thr Arg
    50                  55                  60

Lys Pro Asp Val Cys Ile Tyr Tyr Glu Asp Asn Gly Leu Ile Ile Asp
65                  70                  75                  80

Asn Lys Ala Tyr Gly Lys Gly Tyr Ser Leu Pro Ile Lys Gln Ala Asp
                85                  90                  95

Glu Met Tyr Arg Tyr Ile Glu Glu Asn Lys Glu Arg Ser Glu Leu Leu
            100                 105                 110

Asn Pro Asn Cys Trp Trp Asn Ile Phe Asp Glu Gly Val Lys Thr Phe
```

```
              115                 120                 125
Arg Phe Ala Phe Leu Ser Gly Glu Phe Thr Gly Gly Phe Lys Asp Arg
    130                 135                 140

Leu Asn His Ile Ser Met Arg Ser Gly Ile Lys Gly Ala Ala Val Asn
145                 150                 155                 160

Ser Ala Asn Leu Leu Ile Ile Ala Glu Gln Leu Lys Ser Gly Thr Met
                    165                 170                 175

Ser Tyr Glu Glu Phe Phe Gln Leu Phe Asp Gln Asn Asp Glu Ile Thr
                180                 185                 190

Val
```

<210> SEQ ID NO 39
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 39

```
Met Ser Ser Lys Ser Glu Ile Ser Val Ile Lys Asp Asn Ile Arg Lys
1               5                   10                  15

Arg Leu Asn His Ile Asn His Lys Tyr Leu Val Leu Ile Asp Leu Gly
                20                  25                  30

Phe Asp Gly Thr Ala Asp Arg Asp Tyr Glu Leu Gln Thr Ala Asp Leu
            35                  40                  45

Leu Thr Ser Glu Leu Ser Phe Lys Gly Ala Arg Leu Gly Asp Thr Arg
    50                  55                  60

Lys Pro Asp Val Cys Val Tyr His Gly Thr Asn Gly Leu Ile Ile Asp
65                  70                  75                  80

Asn Lys Ala Tyr Gly Lys Gly Tyr Ser Leu Pro Ile Lys Gln Ala Asp
                85                  90                  95

Glu Met Leu Arg Tyr Ile Glu Glu Asn Gln Lys Arg Asp Lys Ser Leu
            100                 105                 110

Asn Pro Asn Glu Trp Trp Thr Ile Phe Asp Asp Ala Val Ser Lys Phe
        115                 120                 125

Asn Phe Ala Phe Val Ser Gly Glu Phe Thr Gly Gly Phe Lys Asp Arg
    130                 135                 140

Leu Glu Asn Ile Ser Arg Arg Ser Ser Val Asn Gly Ala Ala Ile Asn
145                 150                 155                 160

Ser Val Asn Leu Leu Leu Leu Ala Glu Glu Ile Lys Ser Gly Arg Met
                165                 170                 175

Ser Tyr Ser Asp Ala Phe Lys Asn Phe Asp Cys Asn Lys Glu Ile Thr
                180                 185                 190

Ile
```

<210> SEQ ID NO 40
<211> LENGTH: 195
<212> TYPE: PRT
<213> ORGANISM: Artificial Sequence
<220> FEATURE:
<223> OTHER INFORMATION: Synthetic Sequence

<400> SEQUENCE: 40

```
Arg Asn Leu Asp Lys Val Glu Arg Asp Ser Arg Lys Ala Glu Phe Leu
1               5                   10                  15

Ala Lys Thr Ser Leu Pro Pro Arg Phe Ile Glu Leu Leu Ser Ile Ala
                20                  25                  30
```

```
Tyr Glu Ser Lys Ser Asn Arg Asp Phe Glu Met Ile Thr Ala Glu Phe
            35                  40                  45

Phe Lys Asp Val Tyr Gly Leu Gly Ala Val His Leu Gly Asn Ala Arg
 50                  55                  60

Lys Pro Asp Ala Leu Ala Phe Thr Asp Asn Phe Gly Ile Val Ile Asp
 65                  70                  75                  80

Thr Lys Ala Tyr Ser Asn Gly Tyr Ser Lys Asn Ile Asn Gln Glu Asp
                 85                  90                  95

Glu Met Val Arg Tyr Ile Glu Asp Asn Gln Ile Arg Ser Pro Glu Arg
            100                 105                 110

Asn Lys Asn Glu Trp Trp Leu Ser Phe Pro Ser Ile Pro Glu Asn
            115                 120                 125

Asn Phe His Phe Leu Trp Val Ser Ser Tyr Phe Thr Gly Tyr Phe Glu
            130                 135                 140

Glu Gln Leu Gln Glu Thr Ser Asp Arg Ala Gly Gly Met Thr Gly Gly
145                 150                 155                 160

Ala Leu Asp Ile Glu Gln Leu Leu Ile Gly Gly Ser Leu Val Gln Glu
                165                 170                 175

Gly Lys Leu Ala Pro His Asp Ile Pro Glu Tyr Met Gln Asn Arg Val
            180                 185                 190

Ile His Phe
        195

<210> SEQ ID NO 41
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 41

Ala Pro Val Lys Ser Glu Val Ser Leu Cys Lys Asp Ile Leu Arg Ser
 1               5                  10                  15

His Leu Thr His Val Asp His Lys Tyr Leu Ile Leu Asp Leu Gly
             20                  25                  30

Phe Asp Gly Thr Ser Asp Arg Asp Tyr Glu Ile Gln Thr Ala Gln Leu
            35                  40                  45

Leu Thr Ala Glu Leu Asp Phe Lys Gly Ala Arg Leu Gly Asp Thr Arg
 50                  55                  60

Lys Pro Asp Val Cys Val Tyr Tyr Gly Glu Asp Gly Leu Ile Leu Asp
 65                  70                  75                  80

Asn Lys Ala Tyr Gly Lys Gly Tyr Ser Leu Pro Ile Lys Gln Ala Asp
                 85                  90                  95

Glu Met Tyr Arg Tyr Ile Glu Glu Asn Lys Glu Arg Asn Glu Arg Leu
            100                 105                 110

Asn Pro Asn Lys Trp Trp Glu Ile Phe Asp Lys Asp Val Val Arg Tyr
            115                 120                 125

His Phe Ala Phe Val Ser Gly Thr Phe Thr Gly Gly Phe Lys Glu Arg
            130                 135                 140

Leu Asp Asn Ile Arg Met Arg Ser Gly Ile Cys Gly Ala Ala Val Asn
145                 150                 155                 160

Ser Met Asn Leu Leu Leu Met Ala Glu Glu Leu Lys Ser Gly Arg Leu
                165                 170                 175

Gly Tyr Lys Glu Cys Phe Ala Leu Phe Asp Cys Asn Asp Glu Ile Ala
            180                 185                 190
```

Phe

<210> SEQ ID NO 42
<211> LENGTH: 201
<212> TYPE: PRT
<213> ORGANISM: Artificial Sequence
<220> FEATURE:
<223> OTHER INFORMATION: Synthetic Sequence

<400> SEQUENCE: 42

```
Ser Cys Val Lys Asp Glu Val Asn Asp Ile Val Asp Arg Val Arg Val
1               5                   10                  15

Lys Leu Lys Asn Ile Asp His Lys Tyr Leu Ile Leu Ile Ser Leu Ala
            20                  25                  30

Tyr Ser Asp Glu Thr Glu Arg Thr Lys Lys Asn Ser Asp Ala Arg Asp
        35                  40                  45

Phe Glu Ile Gln Thr Ala Glu Leu Phe Thr Lys Glu Leu Gly Phe Asn
    50                  55                  60

Gly Ile Arg Leu Gly Glu Ser Asn Lys Pro Asp Val Leu Ile Ser Phe
65                  70                  75                  80

Gly Ala Asn Gly Thr Ile Ile Asp Asn Lys Ser Tyr Lys Asp Gly Phe
                85                  90                  95

Asn Ile Pro Arg Val Thr Ser Asp Gln Met Ile Arg Tyr Ile Asn Glu
            100                 105                 110

Asn Asn Gln Arg Thr Thr Gln Leu Asn Pro Asn Glu Trp Trp Lys Asn
        115                 120                 125

Phe Asp Ser Ser Val Ser Asn Tyr Thr Phe Leu Phe Val Thr Ser Phe
    130                 135                 140

Leu Lys Gly Ser Phe Lys Asn Gln Ile Glu Tyr Ile Ser Asn Ala Thr
145                 150                 155                 160

Asn Gly Thr Arg Gly Ala Ala Ile Asn Val Glu Ser Leu Leu Tyr Ile
                165                 170                 175

Ser Glu Asp Ile Lys Ser Gly Lys Ile Lys Gln Ser Asp Phe Tyr Ser
            180                 185                 190

Glu Phe Lys Asn Asp Glu Ile Val Tyr
        195                 200
```

<210> SEQ ID NO 43
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 43

```
Ser Gln Gly Asp Lys Ala Arg Glu Gln Leu Lys Ala Lys Phe Leu Ala
1               5                   10                  15

Lys Thr Asn Leu Leu Pro Arg Tyr Val Glu Leu Leu Asp Ile Ala Tyr
            20                  25                  30

Asp Ser Lys Arg Asn Arg Asp Phe Glu Met Val Thr Ala Glu Leu Phe
        35                  40                  45

Asn Phe Ala Tyr Leu Leu Pro Ala Val His Leu Gly Gly Val Arg Lys
    50                  55                  60

Pro Asp Ala Leu Val Ala Thr Lys Lys Phe Gly Ile Ile Val Asp Thr
65                  70                  75                  80

Lys Ala Tyr Ala Asn Gly Tyr Ser Arg Asn Ala Asn Gln Ala Asp Glu
                85                  90                  95
```

```
Met Ala Arg Tyr Ile Thr Glu Asn Gln Lys Arg Asp Pro Lys Thr Asn
                100                 105                 110

Pro Asn Arg Trp Trp Asp Asn Phe Asp Ala Arg Ile Pro Pro Asn Ala
            115                 120                 125

Tyr Tyr Phe Leu Trp Val Ser Ser Phe Phe Thr Gly Gln Phe Asp Asp
        130                 135                 140

Gln Leu Ser Tyr Thr Ala His Arg Thr Asn Thr His Gly Gly Ala Leu
145                 150                 155                 160

Asn Val Glu Gln Leu Leu Ile Gly Ala Asn Met Ile Gln Thr Gly Gln
                165                 170                 175

Leu Asp Arg Asn Lys Leu Pro Glu Tyr Met Gln Asp Lys Glu Ile Thr
            180                 185                 190

Phe

<210> SEQ ID NO 44
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 44

Lys Val Gln Lys Ser Asn Ile Leu Asp Val Ile Glu Lys Cys Arg Glu
1               5                   10                  15

Lys Ile Asn Asn Ile Pro His Glu Tyr Leu Ala Leu Ile Pro Met Ser
                20                  25                  30

Phe Asp Glu Asn Glu Ser Thr Met Phe Glu Ile Lys Thr Ile Glu Leu
            35                  40                  45

Leu Thr Glu His Cys Lys Phe Asp Gly Leu His Cys Gly Gly Ala Ser
        50                  55                  60

Lys Pro Asp Gly Leu Ile Tyr Ser Glu Asp Tyr Gly Val Ile Ile Asp
65                  70                  75                  80

Thr Lys Ser Tyr Lys Asp Gly Phe Asn Ile Gln Thr Pro Glu Arg Asp
                85                  90                  95

Lys Met Lys Arg Tyr Ile Glu Glu Asn Gln Asn Arg Asn Pro Gln His
                100                 105                 110

Asn Lys Thr Arg Trp Trp Asp Glu Phe Pro His Asn Ile Ser Asn Phe
            115                 120                 125

Leu Phe Leu Phe Val Ser Gly Lys Phe Gly Gly Asn Phe Lys Glu Gln
        130                 135                 140

Leu Arg Ile Leu Ser Glu Gln Thr Asn Asn Thr Leu Gly Gly Ala Leu
145                 150                 155                 160

Ser Ser Tyr Val Leu Leu Asn Ile Ala Glu Gln Ile Ala Ile Asn Lys
                165                 170                 175

Ile Asp His Cys Asp Phe Lys Thr Arg Ile Ser Cys Leu Asp Glu Val
            180                 185                 190

Ala

<210> SEQ ID NO 45
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 45
```

Val Pro Val Lys Ser Glu Val Ser Leu Cys Lys Asp Tyr Leu Arg Ser
1               5                   10                  15

Tyr Leu Thr His Val Asp His Lys Tyr Leu Ile Leu Leu Asp Leu Gly
            20                  25                  30

Phe Asp Gly Thr Ser Asp Arg Asp Tyr Glu Ile Gln Thr Ala Gln Leu
            35                  40                  45

Leu Thr Ala Glu Leu Asp Phe Lys Gly Ala Arg Leu Gly Asp Thr Arg
50                  55                  60

Lys Pro Asp Val Cys Val Tyr Tyr Gly Glu Asp Gly Leu Ile Ile Asp
65                  70                  75                  80

Asn Lys Ala Tyr Gly Lys Gly Tyr Ser Leu Pro Ile Lys Gln Ala Asp
            85                  90                  95

Glu Ile Tyr Arg Tyr Ile Glu Glu Asn Lys Lys Arg Asp Glu Lys Leu
            100                 105                 110

Asn Pro Asn Lys Trp Trp Glu Ile Phe Asp Lys Gly Val Val Arg Tyr
            115                 120                 125

His Phe Ala Phe Val Ser Gly Ala Phe Thr Gly Gly Phe Lys Glu Arg
            130                 135                 140

Leu Asp Asn Ile Arg Met Arg Ser Gly Ile Cys Gly Ala Ala Ile Asn
145                 150                 155                 160

Ser Met Asn Leu Leu Leu Met Ala Glu Glu Leu Lys Ser Gly Arg Leu
            165                 170                 175

Gly Tyr Glu Glu Cys Phe Ala Leu Phe Asp Cys Asn Asp Glu Ile Thr
            180                 185                 190

Phe

<210> SEQ ID NO 46
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 46

Val Pro Val Lys Ser Glu Val Ser Leu Cys Lys Asp Tyr Leu Arg Ser
1               5                   10                  15

His Leu Asn His Val Asp His Arg Tyr Leu Ile Leu Leu Asp Leu Gly
            20                  25                  30

Phe Asp Gly Thr Ser Asp Arg Asp Tyr Glu Ile Gln Thr Ala Gln Leu
            35                  40                  45

Leu Thr Gly Glu Leu Asn Phe Lys Gly Ala Arg Leu Gly Asp Thr Arg
50                  55                  60

Lys Pro Asp Val Cys Val Tyr Tyr Gly Glu Asp Gly Leu Ile Ile Asp
65                  70                  75                  80

Asn Lys Ala Tyr Gly Lys Gly Tyr Ser Leu Pro Ile Lys Gln Ala Asp
            85                  90                  95

Glu Met Tyr Arg Tyr Ile Glu Glu Asn Lys Glu Arg Asn Glu Lys Leu
            100                 105                 110

Asn Pro Asn Lys Trp Trp Glu Ile Phe Asp Lys Asp Val Ile His Tyr
            115                 120                 125

His Phe Ala Phe Val Ser Gly Ala Phe Thr Gly Gly Phe Lys Glu Arg
            130                 135                 140

Leu Glu Asn Ile Arg Met Arg Ser Gly Ile Tyr Gly Ala Ala Val Asn
145                 150                 155                 160

Ser Met Asn Leu Leu Leu Met Ala Glu Glu Leu Lys Ser Gly Arg Leu

```
Asp Tyr Lys Glu Cys Phe Lys Leu Phe Asp Cys Asn Asp Glu Ile Val
            180                 185                 190

Leu

<210> SEQ ID NO 47
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 47

Val Pro Val Lys Ser Glu Val Ser Leu Leu Lys Asp Tyr Leu Arg Ser
1               5                   10                  15

His Leu Val His Val Asp His Lys Tyr Leu Val Leu Leu Asp Leu Gly
            20                  25                  30

Phe Asp Gly Thr Ser Asp Arg Asp Tyr Glu Ile Gln Thr Ala Gln Leu
        35                  40                  45

Leu Thr Gly Glu Leu Asn Phe Lys Gly Ala Arg Leu Gly Asp Thr Arg
    50                  55                  60

Lys Pro Asp Val Cys Val Tyr Tyr Gly Glu Asp Gly Leu Ile Ile Asp
65                  70                  75                  80

Asn Lys Ala Tyr Gly Lys Gly Tyr Ser Leu Pro Ile Lys Gln Ala Asp
                85                  90                  95

Glu Met Tyr Arg Tyr Ile Glu Glu Asn Lys Glu Arg Asn Glu Lys Leu
            100                 105                 110

Asn Pro Asn Lys Trp Trp Glu Ile Phe Gly Asn Asp Val Ile His Tyr
        115                 120                 125

His Phe Ala Phe Val Ser Gly Ala Phe Thr Gly Gly Phe Lys Glu Arg
    130                 135                 140

Leu Asp Asn Ile Arg Met Arg Ser Gly Ile Tyr Gly Ala Ala Val Asn
145                 150                 155                 160

Ser Met Asn Leu Leu Leu Ala Glu Glu Leu Lys Ser Gly Arg Leu
                165                 170                 175

Gly Tyr Lys Glu Cys Phe Lys Leu Phe Asp Cys Asn Asp Glu Ile Val
            180                 185                 190

Leu

<210> SEQ ID NO 48
<211> LENGTH: 201
<212> TYPE: PRT
<213> ORGANISM: Artificial Sequence
<220> FEATURE:
<223> OTHER INFORMATION: Synthetic Sequence

<400> SEQUENCE: 48

Glu Cys Val Lys Asp Asn Val Val Asp Ile Lys Asp Arg Val Arg Asn
1               5                   10                  15

Lys Leu Ile His Leu Asp His Lys Tyr Leu Ala Leu Ile Asp Leu Ala
            20                  25                  30

Tyr Ser Asp Ala Ala Ser Arg Ala Lys Lys Asn Ala Asp Ala Arg Glu
        35                  40                  45

Phe Glu Ile Gln Thr Ala Asp Leu Phe Thr Lys Glu Leu Ser Phe Asn
    50                  55                  60

Gly Gln Arg Leu Gly Asp Ser Arg Lys Pro Asp Val Ile Ile Ser Tyr
65                  70                  75                  80
```

```
Gly Leu Asp Gly Thr Ile Val Asp Asn Lys Ser Tyr Lys Asp Gly Phe
            85                  90                  95

Asn Ile Ser Arg Thr Cys Ala Asp Glu Met Ser Arg Tyr Ile Asn Glu
            100                 105                 110

Asn Asn Leu Arg Gln Lys Ser Leu Asn Pro Asn Glu Trp Trp Lys Asn
            115                 120                 125

Phe Asp Ser Thr Ile Thr Ala Tyr Thr Phe Leu Phe Ile Thr Ser Tyr
            130                 135                 140

Leu Lys Gly Gln Phe Glu Asp Gln Leu Glu Tyr Val Ser Asn Ala Asn
145                 150                 155                 160

Gly Gly Ile Lys Gly Ala Ala Ile Gly Val Glu Ser Leu Leu Tyr Leu
            165                 170                 175

Ser Glu Gly Ile Lys Ala Gly Arg Ile Ser His Ala Asp Phe Tyr Ser
            180                 185                 190

Asn Phe Asn Asn Lys Glu Met Ile Tyr
            195                 200

<210> SEQ ID NO 49
<211> LENGTH: 192
<212> TYPE: PRT
<213> ORGANISM: Artificial Sequence
<220> FEATURE:
<223> OTHER INFORMATION: Synthetic Sequence

<400> SEQUENCE: 49

Ile Ala Lys Ser Asp Phe Ser Ile Ile Lys Asp Asn Ile Arg Arg Lys
1               5                   10                  15

Leu Gln Tyr Val Asn His Lys Tyr Leu Leu Ile Asp Leu Gly Phe
            20                  25                  30

Asp Ser Asp Ser Asn Arg Asp Tyr Glu Ile Gln Thr Ala Glu Leu Leu
            35                  40                  45

Thr Thr Glu Leu Ala Phe Lys Gly Ala Arg Leu Gly Asp Thr Arg Lys
            50                  55                  60

Pro Asp Val Cys Val Tyr Tyr Gly Glu Asn Gly Leu Ile Ile Asp Asn
65                  70                  75                  80

Lys Ala Tyr Ser Lys Gly Tyr Ser Leu Pro Met Ser Gln Ala Asp Glu
            85                  90                  95

Met Val Arg Tyr Ile Glu Glu Asn Lys Ala Arg Gln Ser Ser Ile Asn
            100                 105                 110

Pro Asn Gln Trp Trp Lys Ile Phe Glu Asp Thr Val Cys Asn Phe Asn
            115                 120                 125

Tyr Ala Phe Val Ser Gly Glu Phe Thr Gly Gly Phe Lys Asp Arg Leu
            130                 135                 140

Asn Asn Ile Cys Glu Arg Thr Arg Val Ser Gly Gly Ala Ile Asn Thr
145                 150                 155                 160

Ile Asn Leu Leu Leu Leu Ala Glu Glu Leu Lys Ser Gly Arg Met Ser
            165                 170                 175

Tyr Pro Lys Cys Phe Ser Tyr Phe Asp Thr Asn Asp Glu Val His Ile
            180                 185                 190

<210> SEQ ID NO 50
<211> LENGTH: 166
<212> TYPE: PRT
<213> ORGANISM: Artificial Sequence
<220> FEATURE:
<223> OTHER INFORMATION: Synthetic Sequence
```

<400> SEQUENCE: 50

```
Leu Lys Tyr Leu Gly Ile Lys Lys Gln Asn Arg Ala Phe Glu Ile Ile
1               5                   10                  15

Thr Ala Glu Leu Phe Asn Thr Ser Tyr Lys Leu Ser Ala Thr His Leu
            20                  25                  30

Gly Gly Gly Arg Arg Pro Asp Val Leu Val Tyr Asn Asp Asn Phe Gly
        35                  40                  45

Ile Ile Val Asp Thr Lys Ala Tyr Lys Asp Gly Tyr Gly Arg Asn Val
50                  55                  60

Asn Gln Glu Asp Glu Met Val Arg Tyr Ile Thr Glu Asn Asn Ile Arg
65                  70                  75                  80

Lys Gln Asp Ile Asn Lys Asn Asp Trp Trp Lys Tyr Phe Ser Lys Ser
                85                  90                  95

Ile Pro Ser Thr Ser Tyr Tyr His Leu Trp Ile Ser Ser Gln Phe Val
            100                 105                 110

Gly Met Phe Ser Asp Gln Leu Arg Glu Thr Ser Ser Arg Thr Gly Glu
        115                 120                 125

Asn Gly Gly Ala Met Asn Val Glu Gln Leu Leu Ile Gly Ala Asn Gln
130                 135                 140

Val Leu Asn Asn Val Leu Asp Pro Asn Cys Leu Pro Lys Tyr Met Glu
145                 150                 155                 160

Asn Lys Glu Ile Ile Phe
                165
```

<210> SEQ ID NO 51
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 51

```
Val Pro Val Lys Ser Glu Val Ser Leu Cys Lys Asp Tyr Leu Arg Ser
1               5                   10                  15

His Leu Asn His Val Asp His Lys Tyr Leu Ile Leu Leu Asp Leu Gly
            20                  25                  30

Phe Asp Gly Thr Ser Asp Arg Asp Tyr Glu Ile Gln Thr Ala Gln Leu
        35                  40                  45

Leu Thr Gly Glu Leu Asn Phe Lys Gly Ala Arg Leu Gly Asp Thr Arg
50                  55                  60

Lys Pro Asp Val Cys Val Tyr Tyr Gly Glu Asp Gly Leu Ile Ile Asp
65                  70                  75                  80

Asn Lys Ala Tyr Gly Lys Gly Tyr Ser Leu Pro Ile Lys Gln Ala Asp
                85                  90                  95

Glu Met Tyr Arg Tyr Ile Glu Glu Asn Lys Glu Arg Asn Glu Lys Leu
            100                 105                 110

Asn Pro Asn Lys Trp Trp Glu Ile Phe Asp Lys Asp Val Ile His Tyr
        115                 120                 125

His Phe Ala Phe Val Ser Gly Ala Phe Thr Gly Gly Phe Arg Glu Arg
130                 135                 140

Leu Glu Asn Ile Arg Met Arg Ser Gly Ile Tyr Gly Ala Ala Val Asn
145                 150                 155                 160

Ser Met Asn Leu Leu Leu Met Ala Glu Glu Leu Lys Ser Gly Arg Leu
                165                 170                 175

Gly Tyr Lys Glu Cys Phe Lys Leu Phe Asp Cys Asn Asp Glu Ile Val
```

```
                    180                 185                 190

Leu

<210> SEQ ID NO 52
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 52

Val Pro Val Lys Ser Glu Val Ser Leu Leu Lys Asp Tyr Leu Arg Thr
1               5                   10                  15

His Leu Leu His Val Asp His Arg Tyr Leu Ile Leu Leu Asp Leu Gly
            20                  25                  30

Phe Asp Gly Thr Ser Asp Arg Asp Tyr Glu Ile Gln Thr Ala Gln Leu
        35                  40                  45

Leu Thr Gly Glu Leu Asn Phe Lys Gly Ala Arg Leu Gly Asp Thr Arg
    50                  55                  60

Lys Pro Asp Val Cys Val Tyr Tyr Gly Glu Asp Gly Leu Ile Ile Asp
65                  70                  75                  80

Asn Lys Ala Tyr Gly Lys Gly Tyr Ser Leu Pro Ile Lys Gln Ala Asp
                85                  90                  95

Glu Met Tyr Arg Tyr Ile Glu Glu Asn Lys Glu Arg Asn Glu Lys Leu
            100                 105                 110

Asn Pro Asn Lys Trp Trp Glu Ile Phe Asp Asn Asp Val Ile His Tyr
        115                 120                 125

His Phe Ala Phe Ile Ser Gly Ala Phe Thr Gly Gly Phe Lys Glu Arg
    130                 135                 140

Leu Asp Asn Ile Arg Met Arg Ser Gly Ile Tyr Gly Ala Ala Val Asn
145                 150                 155                 160

Ser Met Asn Leu Leu Met Ala Glu Glu Leu Lys Ser Gly Arg Leu
                165                 170                 175

Gly Tyr Lys Glu Cys Phe Lys Leu Phe Asp Cys Asn Asp Glu Ile Val
            180                 185                 190

Leu

<210> SEQ ID NO 53
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 53

Val Pro Val Lys Ser Glu Val Ser Leu Cys Lys Asp Tyr Leu Arg Ser
1               5                   10                  15

His Leu Asn His Val Asp His Lys Tyr Leu Ile Leu Leu Asp Leu Gly
            20                  25                  30

Phe Asp Gly Thr Ser Asp Arg Asp Tyr Glu Ile Gln Thr Ala Gln Leu
        35                  40                  45

Leu Thr Gly Glu Leu Asn Phe Lys Gly Ala Arg Leu Gly Asp Thr Arg
    50                  55                  60

Lys Pro Asp Val Cys Val Tyr Tyr Gly Glu Asp Gly Leu Ile Ile Asp
65                  70                  75                  80

Asn Lys Ala Tyr Gly Lys Gly Tyr Ser Leu Pro Ile Lys Gln Ala Asp
                85                  90                  95
```

Glu Met Tyr Arg Tyr Ile Glu Glu Asn Lys Glu Arg Asn Glu Lys Leu
                    100                 105                 110

Asn Pro Asn Lys Trp Trp Glu Ile Phe Asp Asn Asp Val Ile His Tyr
            115                 120                 125

His Phe Ala Phe Val Ser Gly Ala Phe Thr Gly Gly Phe Arg Glu Arg
        130                 135                 140

Leu Glu Asn Ile Arg Met Arg Ser Gly Ile Tyr Gly Ala Ala Val Asn
145                 150                 155                 160

Ser Met Asn Leu Leu Leu Met Ala Glu Glu Leu Lys Ser Gly Arg Leu
                165                 170                 175

Gly Tyr Lys Glu Cys Phe Lys Leu Phe Asp Cys Asn Asp Glu Ile Val
                180                 185                 190

Leu

<210> SEQ ID NO 54
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 54

Val Pro Val Lys Ser Glu Met Ser Leu Leu Lys Asp Tyr Leu Arg Thr
1               5                   10                  15

His Leu Leu His Val Asp His Arg Tyr Leu Ile Leu Leu Asp Leu Gly
            20                  25                  30

Phe Asp Gly Ala Ser Asp Arg Asp Tyr Glu Ile Gln Thr Ala Gln Leu
        35                  40                  45

Leu Thr Gly Glu Leu Asn Phe Lys Gly Ala Arg Leu Gly Asp Thr Arg
    50                  55                  60

Lys Pro Asp Val Cys Val Tyr Tyr Gly Glu Asp Gly Leu Ile Ile Asp
65                  70                  75                  80

Asn Lys Ala Tyr Gly Lys Gly Tyr Ser Leu Pro Ile Lys Gln Ala Asp
                85                  90                  95

Glu Met Tyr Arg Tyr Ile Glu Glu Asn Lys Arg Asn Glu Lys Leu
                    100                 105                 110

Asn Pro Asn Lys Trp Trp Glu Ile Phe Asp Asn Asp Val Ile His Tyr
            115                 120                 125

His Phe Ala Phe Val Ser Gly Ala Phe Thr Gly Gly Phe Lys Glu Arg
        130                 135                 140

Leu Asp Asn Ile Arg Met Arg Ser Gly Ile Tyr Gly Ala Ala Val Asn
145                 150                 155                 160

Ser Met Asn Leu Leu Leu Met Ala Glu Glu Leu Lys Ser Gly Arg Leu
                165                 170                 175

Gly Tyr Lys Glu Cys Phe Lys Leu Phe Asp Cys Asn Asp Glu Ile Val
                180                 185                 190

Leu

<210> SEQ ID NO 55
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 55

```
Ile Leu Val Asp Lys Glu Arg Glu Met Arg Lys Ala Lys Phe Leu Lys
1               5                   10                  15

Glu Thr Val Leu Asp Ser Lys Phe Ile Ser Leu Leu Asp Leu Ala Ala
            20                  25                  30

Asp Ala Thr Lys Ser Arg Asp Phe Glu Ile Val Thr Ala Glu Leu Phe
            35                  40                  45

Lys Glu Ala Tyr Asn Leu Asn Ser Val Leu Leu Gly Gly Ser Asn Lys
50                  55                  60

Pro Asp Gly Leu Val Phe Thr Asp Asp Phe Gly Ile Leu Leu Asp Thr
65                  70                  75                  80

Lys Ala Tyr Lys Asn Gly Phe Ser Ile Tyr Ala Lys Asp Arg Asp Gln
            85                  90                  95

Met Ile Arg Tyr Val Asp Asp Asn Asn Lys Arg Asp Lys Ile Arg Asn
            100                 105                 110

Pro Asn Glu Trp Trp Lys Ser Phe Ser Pro Leu Ile Pro Asn Asp Lys
            115                 120                 125

Phe Tyr Tyr Leu Trp Val Ser Asn Phe Phe Lys Gly Gln Phe Lys Asn
    130                 135                 140

Gln Ile Glu Tyr Val Asn Arg Glu Thr Asn Thr Tyr Gly Ala Val Leu
145                 150                 155                 160

Asn Val Glu Gln Leu Leu Tyr Gly Ala Asp Ala Val Ile Lys Gly Ile
                165                 170                 175

Ile Asn Pro Asn Lys Leu His Glu Tyr Phe Ser Asn Glu Ile Lys
            180                 185                 190

Phe

<210> SEQ ID NO 56
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 56

Thr Val Asp Glu Lys Glu Arg Leu Glu Leu Lys Glu Tyr Phe Ile Ser
1               5                   10                  15

Asn Thr Arg Ile Pro Ser Lys Tyr Ile Thr Leu Leu Asp Leu Ala Tyr
            20                  25                  30

Asp Gly Asn Ala Asn Arg Asp Phe Glu Ile Val Thr Ala Glu Leu Phe
            35                  40                  45

Lys Asp Ile Phe Lys Leu Gln Ser Lys His Met Gly Gly Thr Arg Lys
50                  55                  60

Pro Asp Ile Leu Ile Trp Thr Asp Lys Phe Gly Val Ile Ala Asp Thr
65                  70                  75                  80

Lys Ala Tyr Ser Lys Gly Tyr Lys Lys Asn Ile Ser Glu Ala Asp Lys
            85                  90                  95

Met Val Arg Tyr Val Asn Glu Asn Thr Asn Arg Asn Lys Val Asp Asn
            100                 105                 110

Thr Asn Glu Trp Trp Asn Ser Phe Asp Ser Arg Ile Pro Lys Asp Ala
            115                 120                 125

Tyr Tyr Phe Leu Trp Ile Ser Ser Glu Phe Val Gly Lys Phe Asp Glu
    130                 135                 140

Gln Leu Thr Glu Thr Ser Ser Arg Thr Gly Arg Asn Gly Ala Ser Ile
145                 150                 155                 160

Asn Val Tyr Gln Leu Leu Arg Gly Ala Asp Leu Val Gln Lys Ser Lys
```

Phe Asn Ile His Asp Leu Pro Asn Leu Met Gln Asn Asn Glu Ile Lys
                180                 185                 190

Phe

<210> SEQ ID NO 57
<211> LENGTH: 195
<212> TYPE: PRT
<213> ORGANISM: Artificial Sequence
<220> FEATURE:
<223> OTHER INFORMATION: Synthetic Sequence

<400> SEQUENCE: 57

Thr Leu Gln Lys Ser Asp Ile Glu Lys Phe Lys Asn Gln Leu Arg Thr
1               5                   10                  15

Glu Leu Thr Asn Ile Asp His Ser Tyr Leu Lys Gly Ile Asp Ile Ala
                20                  25                  30

Ser Lys Lys Thr Thr Thr Asn Val Glu Asn Thr Glu Phe Glu Ala Ile
            35                  40                  45

Ser Thr Lys Val Phe Thr Asp Glu Leu Gly Phe Phe Gly Glu His Leu
50                  55                  60

Gly Gly Ser Asn Lys Pro Asp Gly Leu Ile Trp Asp Asn Asp Cys Ala
65                  70                  75                  80

Ile Ile Leu Asp Ser Lys Ala Tyr Ser Glu Gly Phe Pro Leu Thr Ala
                85                  90                  95

Ser His Thr Asp Ala Met Gly Arg Tyr Leu Arg Gln Phe Lys Glu Arg
            100                 105                 110

Lys Glu Glu Ile Lys Pro Thr Trp Trp Asp Ile Ala Pro Asp Asn Leu
        115                 120                 125

Ala Asn Thr Tyr Phe Ala Tyr Val Ser Gly Ser Phe Ser Gly Asn Tyr
130                 135                 140

Lys Ala Gln Leu Gln Lys Phe Arg Gln Asp Thr Asn His Met Gly Gly
145                 150                 155                 160

Ala Leu Glu Phe Val Lys Leu Leu Leu Ala Asn Asn Tyr Lys Ala
                165                 170                 175

His Lys Met Ser Ile Asn Glu Val Lys Glu Ser Ile Leu Asp Tyr Asn
            180                 185                 190

Ile Ser Tyr
        195

<210> SEQ ID NO 58
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 58

Val Lys Glu Lys Thr Asp Ala Ala Leu Val Lys Glu Arg Val Arg Leu
1               5                   10                  15

Gln Leu His Asn Ile Asn His Lys Tyr Leu Ala Leu Ile Asp Tyr Ala
                20                  25                  30

Phe Ser Gly Lys Asn Asn Ser Arg Asp Phe Glu Val Tyr Thr Ile Asp
            35                  40                  45

Leu Leu Val Asn Glu Leu Thr Phe Gly Gly Leu His Leu Gly Gly Thr
50                  55                  60

Arg Lys Pro Asp Gly Ile Phe Tyr His Gly Ser Asn Gly Ile Ile Ile

```
                65                  70                  75                  80

Asp Asn Lys Ala Tyr Ala Lys Gly Phe Val Ile Thr Arg Asn Met Ala
                85                  90                  95

Asp Glu Met Ile Arg Tyr Val Gln Glu Asn Asn Asp Arg Asn Pro Glu
                100                 105                 110

Arg Asn Pro Asn Cys Trp Trp Lys Gly Phe Pro His Asp Val Thr Arg
                115                 120                 125

Tyr Asn Tyr Val Phe Ile Ser Ser Met Phe Lys Gly Glu Val Glu His
                130                 135                 140

Met Leu Asp Asn Ile Arg Gln Ser Thr Gly Ile Asp Gly Cys Val Leu
145                 150                 155                 160

Thr Ile Glu Asn Leu Leu Tyr Tyr Ala Asp Ala Ile Lys Gly Gly Thr
                165                 170                 175

Leu Ser Lys Ala Thr Phe Ile Asn Gly Phe Asn Ala Asn Lys Glu Met
                180                 185                 190

Val Phe

<210> SEQ ID NO 59
<211> LENGTH: 195
<212> TYPE: PRT
<213> ORGANISM: Artificial Sequence
<220> FEATURE:
<223> OTHER INFORMATION: Synthetic Sequence

<400> SEQUENCE: 59

Val Lys Glu Thr Thr Asp Ser Val Ile Ile Lys Asp Arg Val Arg Leu
1               5                   10                  15

Lys Leu His His Val Asn His Lys Tyr Leu Thr Leu Ile Asp Tyr Ala
                20                  25                  30

Phe Ser Gly Lys Asn Asn Cys Met Asp Phe Glu Val Tyr Thr Ile Asp
                35                  40                  45

Leu Leu Val Asn Glu Leu Ala Phe Asn Gly Val His Leu Gly Gly Thr
            50                  55                  60

Arg Lys Pro Asp Gly Ile Phe Tyr His Asn Arg Asn Gly Ile Ile Ile
65                  70                  75                  80

Asp Asn Lys Ala Tyr Ser His Gly Phe Thr Leu Ser Arg Ala Met Ala
                85                  90                  95

Asp Glu Met Ile Arg Tyr Ile Gln Glu Asn Asn Asp Arg Asn Pro Glu
                100                 105                 110

Arg Asn Pro Asn Lys Trp Trp Glu Asn Phe Asp Lys Gly Val Asn Gln
                115                 120                 125

Phe Asn Phe Val Phe Ile Ser Ser Leu Phe Lys Gly Glu Ile Glu His
                130                 135                 140

Met Leu Thr Asn Ile Lys Gln Ser Thr Asp Gly Val Glu Gly Cys Val
145                 150                 155                 160

Leu Ser Ala Glu Asn Leu Leu Tyr Phe Ala Glu Ala Met Lys Ser Gly
                165                 170                 175

Val Met Pro Lys Thr Glu Phe Ile Ser Tyr Phe Gly Ala Gly Lys Glu
                180                 185                 190

Ile Gln Phe
        195

<210> SEQ ID NO 60
<211> LENGTH: 201
<212> TYPE: PRT
<213> ORGANISM: Artificial Sequence
```

<220> FEATURE:
<223> OTHER INFORMATION: Synthetic Sequence

<400> SEQUENCE: 60

Ser Ala Cys Lys Ala Asp Ile Thr Glu Leu Lys Asp Lys Ile Arg Lys
1               5                   10                  15

Ser Leu Lys Val Leu Asp His Lys Tyr Leu Val Leu Asp Leu Ala
            20                  25                  30

Tyr Ser Asp Ala Ser Thr Lys Ser Lys Asn Ser Asp Ala Arg Glu
        35                  40                  45

Phe Glu Ile Gln Thr Ala Asp Leu Phe Thr Lys Glu Leu Lys Phe Asp
    50                  55                  60

Gly Met Arg Leu Gly Asp Ser Asn Arg Pro Asp Val Ile Ile Ser His
65                  70                  75                  80

Asp Asn Phe Gly Thr Ile Ile Asp Asn Lys Ser Tyr Lys Asp Gly Phe
                85                  90                  95

Asn Ile Asp Lys Lys Cys Ala Asp Glu Met Ser Arg Tyr Ile Asn Glu
            100                 105                 110

Asn Gln Arg Arg Ile Pro Glu Leu Pro Lys Asn Glu Trp Trp Lys Asn
        115                 120                 125

Phe Asp Val Asn Val Asp Ile Phe Thr Phe Leu Phe Ile Thr Ser Tyr
    130                 135                 140

Leu Lys Gly Asn Phe Lys Asp Gln Leu Glu Tyr Ile Ser Lys Ser Gln
145                 150                 155                 160

Ser Asp Ile Lys Gly Ala Ala Ile Ser Val Glu His Leu Leu Tyr Ile
                165                 170                 175

Ser Glu Lys Val Lys Asn Gly Ser Met Asp Lys Ala Asp Phe Phe Lys
            180                 185                 190

Leu Phe Asn Asn Asp Glu Ile Arg Val
        195                 200

<210> SEQ ID NO 61
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 61

Val Leu Lys Asp Lys His Leu Glu Lys Ile Lys Glu Lys Phe Leu Glu
1               5                   10                  15

Asn Thr Ser Leu Asp Pro Arg Phe Ile Ser Leu Ile Glu Ile Ser Arg
            20                  25                  30

Asp Lys Lys Gln Asn Arg Ala Phe Glu Ile Ile Thr Ala Glu Leu Phe
        35                  40                  45

Asn Thr Ser Tyr Asn Leu Ser Ala Ile His Leu Gly Gly Arg Arg
    50                  55                  60

Pro Asp Val Leu Ala Tyr Asn Asp Asn Phe Gly Ile Ile Val Asp Thr
65                  70                  75                  80

Lys Ala Tyr Lys Asn Gly Tyr Gly Arg Asn Val Asn Gln Glu Asp Glu
                85                  90                  95

Met Val Arg Tyr Ile Thr Glu Asn Lys Ile Arg Lys Gln Asp Ile Ser
            100                 105                 110

Lys Asn Asn Trp Trp Lys Tyr Phe Ser Lys Ser Ile Pro Ser Thr Ser
        115                 120                 125

Tyr Tyr His Leu Trp Ile Ser Ser Glu Phe Val Gly Met Phe Ser Asp

```
                    130                 135                 140

Gln Leu Arg Glu Thr Ser Ser Arg Thr Gly Glu Asn Gly Gly Ala Met
145                 150                 155                 160

Asn Val Glu Gln Leu Leu Ile Gly Ala Asn Gln Val Leu Asn Asn Val
                    165                 170                 175

Leu Asp Pro Asn Arg Leu Pro Glu Tyr Met Glu Asn Lys Glu Ile Ile
                180                 185                 190

Phe

<210> SEQ ID NO 62
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 62

Ala Leu Lys Asp Lys His Leu Glu Lys Ile Lys Glu Lys Phe Leu Glu
1               5                   10                  15

Asn Thr Ser Leu Asp Pro Arg Phe Ile Ser Leu Ile Glu Ile Ser Arg
                20                  25                  30

Asp Lys Lys Gln Asn Arg Ala Phe Glu Ile Ile Thr Ala Glu Leu Phe
            35                  40                  45

Asn Thr Ser Tyr Lys Leu Ser Ala Thr His Leu Gly Gly Gly Arg Arg
        50                  55                  60

Pro Asp Val Leu Val Tyr Asn Asp Asn Phe Gly Ile Ile Val Asp Thr
65                  70                  75                  80

Lys Ala Tyr Lys Asp Gly Tyr Gly Arg Asn Val Asn Gln Glu Asp Glu
                85                  90                  95

Met Val Arg Tyr Ile Thr Glu Asn Asn Ile Arg Lys Gln Asp Ile Asn
                100                 105                 110

Lys Asn Asp Trp Trp Lys Tyr Phe Ser Lys Ser Ile Pro Ser Thr Ser
            115                 120                 125

Tyr Tyr His Leu Trp Ile Ser Ser Gln Phe Val Gly Met Phe Ser Asp
        130                 135                 140

Gln Leu Arg Glu Thr Ser Ser Arg Thr Gly Glu Asn Gly Gly Ala Met
145                 150                 155                 160

Asn Val Glu Gln Leu Leu Ile Gly Ala Asn Gln Val Leu Asn Asn Val
                165                 170                 175

Leu Asp Pro Asn Cys Leu Pro Lys Tyr Met Glu Asn Lys Glu Ile Ile
                180                 185                 190

Phe

<210> SEQ ID NO 63
<211> LENGTH: 195
<212> TYPE: PRT
<213> ORGANISM: Artificial Sequence
<220> FEATURE:
<223> OTHER INFORMATION: Synthetic Sequence

<400> SEQUENCE: 63

Val Leu Glu Lys Ser Asp Ile Glu Lys Phe Lys Asn Gln Leu Arg Thr
1               5                   10                  15

Glu Leu Thr Asn Ile Asp His Ser Tyr Leu Lys Gly Ile Asp Ile Ala
                20                  25                  30

Ser Lys Lys Lys Thr Ser Asn Val Glu Asn Thr Glu Phe Glu Ala Ile
            35                  40                  45
```

Ser Thr Lys Ile Phe Thr Asp Glu Leu Gly Phe Ser Gly Lys His Leu
    50                  55                  60

Gly Gly Ser Asn Lys Pro Asp Gly Leu Leu Trp Asp Asp Cys Ala
65              70                  75                  80

Ile Ile Leu Asp Ser Lys Ala Tyr Ser Glu Gly Phe Pro Leu Thr Ala
                85                  90                  95

Ser His Thr Asp Ala Met Gly Arg Tyr Leu Arg Gln Phe Thr Glu Arg
                100                 105                 110

Lys Glu Glu Ile Lys Pro Thr Trp Trp Asp Ile Ala Pro Glu His Leu
            115                 120                 125

Asp Asn Thr Tyr Phe Ala Tyr Val Ser Gly Ser Phe Ser Gly Asn Tyr
        130                 135                 140

Lys Glu Gln Leu Gln Lys Phe Arg Gln Asp Thr Asn His Leu Gly Gly
145                 150                 155                 160

Ala Leu Glu Phe Val Lys Leu Leu Leu Ala Asn Asn Tyr Lys Thr
                165                 170                 175

Gln Lys Met Ser Lys Lys Glu Val Lys Ser Ile Leu Asp Tyr Asn
                180                 185                 190

Ile Ser Tyr
        195

<210> SEQ ID NO 64
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 64

Ala Glu Ala Asp Val Thr Ser Glu Lys Ile Lys Asn His Phe Arg Arg
1               5                   10                  15

Val Thr Glu Leu Pro Glu Arg Tyr Leu Glu Leu Leu Asp Ile Ala Phe
            20                  25                  30

Asp His Lys Arg Asn Arg Asp Phe Glu Met Val Thr Ala Gly Leu Phe
        35                  40                  45

Lys Asp Val Tyr Gly Leu Glu Ser Val His Leu Gly Gly Ala Asn Lys
50                  55                  60

Pro Asp Gly Val Val Tyr Asn Asp Asn Phe Gly Ile Ile Leu Asp Thr
65                  70                  75                  80

Lys Ala Tyr Glu Asn Gly Tyr Gly Lys His Ile Ser Gln Ile Asp Glu
                85                  90                  95

Met Val Arg Tyr Ile Asp Asp Asn Arg Leu Arg Asp Thr Thr Arg Asn
                100                 105                 110

Pro Asn Lys Trp Trp Glu Asn Phe Asp Ala Asp Ile Pro Ser Asp Gln
            115                 120                 125

Phe Tyr Tyr Leu Trp Val Ser Gly Lys Phe Leu Pro Asn Phe Ala Glu
        130                 135                 140

Gln Leu Lys Gln Thr Asn Tyr Arg Ser His Ala Asn Gly Gly Gly Leu
145                 150                 155                 160

Glu Val Gln Gln Leu Leu Leu Gly Ala Asp Ala Val Lys Arg Arg Lys
                165                 170                 175

Leu Asp Val Asn Thr Ile Pro Asn Tyr Met Lys Asn Glu Val Ile Thr
                180                 185                 190

Leu

<210> SEQ ID NO 65
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 65

```
Ala Glu Ala Asp Leu Asn Ser Glu Lys Ile Lys Asn His Tyr Arg Lys
1               5                   10                  15

Ile Thr Asn Leu Pro Glu Lys Tyr Ile Glu Leu Leu Asp Ile Ala Phe
            20                  25                  30

Asp His Arg Arg His Gln Asp Phe Glu Ile Val Thr Ala Gly Leu Phe
        35                  40                  45

Lys Asp Cys Tyr Gly Leu Ser Ser Ile His Leu Gly Gly Gln Asn Lys
    50                  55                  60

Pro Asp Gly Val Val Phe Asn Asn Lys Phe Gly Ile Ile Leu Asp Thr
65                  70                  75                  80

Lys Ala Tyr Glu Lys Gly Tyr Gly Met His Ile Gly Gln Ile Asp Glu
                85                  90                  95

Met Cys Arg Tyr Ile Asp Asp Asn Lys Lys Arg Asp Ile Val Arg Gln
            100                 105                 110

Pro Asn Glu Trp Trp Lys Asn Phe Gly Asp Asn Ile Pro Lys Asp Gln
        115                 120                 125

Phe Tyr Tyr Leu Trp Ile Ser Gly Lys Phe Leu Pro Arg Phe Asn Glu
    130                 135                 140

Gln Leu Lys Gln Thr His Tyr Arg Thr Ser Ile Asn Gly Gly Gly Leu
145                 150                 155                 160

Glu Val Ser Gln Leu Leu Leu Gly Ala Asn Ala Ala Met Lys Gly Lys
                165                 170                 175

Leu Asp Val Asn Thr Leu Pro Lys His Met Asn Asn Gln Val Ile Lys
            180                 185                 190

Leu
```

<210> SEQ ID NO 66
<211> LENGTH: 203
<212> TYPE: PRT
<213> ORGANISM: Artificial Sequence
<220> FEATURE:
<223> OTHER INFORMATION: Synthetic Sequence

<400> SEQUENCE: 66

```
Val Leu Lys Asp Ala Ala Leu Gln Lys Thr Lys Asn Thr Leu Leu Asn
1               5                   10                  15

Glu Leu Thr Glu Ile Asp Pro Ala Asp Ile Glu Val Ile Glu Met Ser
            20                  25                  30

Trp Lys Lys Ala Thr Thr Arg Ser Gln Asn Thr Leu Glu Ala Thr Leu
        35                  40                  45

Phe Glu Val Lys Val Val Glu Ile Phe Lys Lys Tyr Phe Glu Leu Asn
    50                  55                  60

Gly Glu His Leu Gly Gly Gln Asn Arg Pro Asp Gly Ala Val Tyr Tyr
65                  70                  75                  80

Asn Ser Thr Tyr Gly Ile Ile Leu Asp Thr Lys Ala Tyr Ser Asn Gly
                85                  90                  95

Tyr Asn Ile Pro Val Asp Gln Gln Arg Glu Met Val Asp Tyr Ile Thr
            100                 105                 110
```

Asp Val Ile Asp Lys Asn Gln Asn Val Thr Pro Asn Arg Trp Trp Glu
            115                 120                 125

Ala Phe Pro Ala Thr Leu Leu Lys Asn Ile Tyr Tyr Leu Trp Val
        130                 135                 140

Ala Gly Gly Phe Thr Gly Lys Tyr Leu Asp Gln Leu Thr Arg Thr His
145                 150                 155                 160

Asn Gln Thr Asn Met Asp Gly Gly Ala Met Thr Thr Glu Val Leu Leu
                165                 170                 175

Arg Leu Ala Asn Lys Val Ser Ser Gly Asn Leu Lys Thr Thr Asp Ile
            180                 185                 190

Pro Lys Leu Met Thr Asn Lys Leu Ile Leu Ser
        195                 200

<210> SEQ ID NO 67
<211> LENGTH: 192
<212> TYPE: PRT
<213> ORGANISM: Artificial Sequence
<220> FEATURE:
<223> OTHER INFORMATION: Synthetic Sequence

<400> SEQUENCE: 67

Ala Glu Ala Asp Leu Asp Ser Glu Arg Ile Lys Asn His Tyr Arg Lys
1               5                   10                  15

Ile Thr Asn Leu Pro Glu Lys Tyr Ile Glu Leu Leu Asp Ile Ala Phe
            20                  25                  30

Asp His His Arg His Gln Asp Phe Glu Ile Ile Thr Ala Gly Leu Phe
        35                  40                  45

Lys Asp Cys Tyr Gly Leu Ser Ser Ile His Leu Gly Gly Gln Asn Lys
50                  55                  60

Pro Asp Gly Val Val Phe Asn Gly Lys Phe Gly Ile Ile Leu Asp Thr
65                  70                  75                  80

Lys Ala Tyr Glu Lys Gly Tyr Gly Met His Ile Asn Gln Ile Asp Glu
                85                  90                  95

Met Cys Arg Tyr Ile Glu Asp Asn Lys Gln Arg Asp Lys Ile Arg Gln
            100                 105                 110

Pro Asn Glu Trp Trp Asn Asn Phe Gly Asp Asn Ile Pro Glu Asn Lys
        115                 120                 125

Phe Tyr Tyr Leu Trp Val Ser Gly Lys Phe Leu Pro Lys Phe Asn Glu
    130                 135                 140

Gln Leu Lys Gln Thr His Tyr Arg Thr Gly Ile Asn Gly Gly Gly Leu
145                 150                 155                 160

Glu Val Ser Gln Leu Leu Gly Ala Asp Ala Val Met Lys Gly Ala
                165                 170                 175

Leu Asn Val Asn Ile Leu Pro Thr Tyr Met His Asn Asn Val Ile Gln
            180                 185                 190

<210> SEQ ID NO 68
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 68

Glu Ile Ser Asp Ile Ala Leu Gln Lys Glu Lys Ala Tyr Phe Tyr Lys
1               5                   10                  15

Asn Thr Ala Leu Ser Lys Arg His Ile Ser Ile Leu Glu Ile Ala Phe
            20                  25                  30

```
Asp Gly Ser Lys Asn Arg Asp Leu Glu Ile Leu Ser Ala Glu Val Phe
            35                  40                  45

Lys Asp Tyr Tyr Gln Leu Glu Ser Ile His Leu Gly Gly Gly Leu Lys
 50                  55                  60

Pro Asp Gly Ile Ala Phe Asn Gln Asn Phe Gly Ile Ile Val Asp Thr
 65                  70                  75                  80

Lys Ala Tyr Lys Gly Val Tyr Ser Arg Ser Arg Ala Glu Ala Asp Lys
                 85                  90                  95

Met Phe Arg Tyr Ile Glu Asp Asn Lys Lys Arg Asp Pro Lys Arg Asn
            100                 105                 110

Gln Ser Leu Trp Trp Arg Ser Phe Asn Glu His Ile Pro Ala Asn Asn
            115                 120                 125

Phe Tyr Phe Leu Trp Ile Ser Gly Lys Phe Gln Arg Asn Phe Asp Thr
            130                 135                 140

Gln Ile Asn Gln Leu Asn Tyr Glu Thr Gly Tyr Arg Gly Gly Ala Leu
145                 150                 155                 160

Ser Ala Arg Gln Phe Leu Ile Gly Ala Asp Ala Ile Gln Lys Gly Lys
                165                 170                 175

Ile Asp Ile Asn Asp Leu Pro Ser Tyr Phe Asn Asn Ser Val Ile Ser
            180                 185                 190

Phe

<210> SEQ ID NO 69
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 69

Thr Ser Arg Glu Lys Ser Arg Leu Asn Leu Lys Glu Tyr Phe Val Ser
 1               5                  10                  15

Asn Thr Asn Leu Pro Asn Lys Phe Ile Thr Leu Leu Asp Leu Ala Tyr
                 20                  25                  30

Asp Gly Lys Ala Asn Arg Asp Phe Glu Leu Ile Thr Ser Glu Leu Phe
            35                  40                  45

Arg Glu Ile Tyr Lys Leu Asn Thr Arg His Leu Gly Gly Thr Arg Lys
 50                  55                  60

Pro Asp Ile Leu Ile Trp Asn Glu Asn Phe Gly Ile Ile Ala Asp Thr
 65                  70                  75                  80

Lys Ala Tyr Ser Lys Gly Tyr Lys Lys Asn Ile Ser Glu Glu Asp Lys
                 85                  90                  95

Met Val Arg Tyr Ile Asp Glu Asn Ile Lys Arg Ser Lys Asp Tyr Asn
            100                 105                 110

Pro Asn Glu Trp Trp Lys Val Phe Asp Asn Glu Ile Ser Ser Asn Asn
            115                 120                 125

Tyr Phe Tyr Leu Trp Ile Ser Ser Glu Phe Ile Gly Lys Phe Glu Glu
            130                 135                 140

Gln Leu Gln Glu Thr Ala Gln Arg Thr Asn Val Lys Gly Ala Ser Ile
145                 150                 155                 160

Asn Val Tyr Gln Leu Leu Met Gly Ala His Lys Val Gln Thr Lys Glu
                165                 170                 175

Leu Asn Val Asn Ser Ile Pro Lys Tyr Met Asn Asn Thr Glu Ile Lys
            180                 185                 190
```

Phe

<210> SEQ ID NO 70
<211> LENGTH: 201
<212> TYPE: PRT
<213> ORGANISM: Artificial Sequence
<220> FEATURE:
<223> OTHER INFORMATION: Synthetic Sequence

<400> SEQUENCE: 70

```
Asn Cys Ile Lys Asp Ser Ile Ile Asp Ile Lys Asp Arg Val Arg Thr
1               5                   10                  15
Lys Leu Val His Leu Asp His Lys Tyr Leu Ala Leu Ile Asp Leu Ala
            20                  25                  30
Phe Ser Asp Ala Asp Thr Arg Thr Lys Lys Asn Ser Asp Ala Arg Glu
        35                  40                  45
Phe Glu Ile Gln Thr Ala Asp Leu Phe Thr Lys Glu Leu Ser Phe Asn
    50                  55                  60
Gly Gln Arg Leu Gly Asp Ser Arg Lys Pro Asp Ile Ile Ser Phe
65                  70                  75                  80
Asp Lys Ile Gly Thr Ile Ile Asp Asn Lys Ser Tyr Lys Asp Gly Phe
                85                  90                  95
Asn Ile Ser Arg Pro Cys Ala Asp Glu Met Ile Arg Tyr Ile Asn Glu
            100                 105                 110
Asn Asn Leu Arg Lys Lys Ser Leu Asn Ala Asn Glu Trp Trp Asn Lys
        115                 120                 125
Phe Asp Pro Thr Ile Thr Ala Tyr Ser Phe Leu Phe Ile Thr Ser Tyr
    130                 135                 140
Leu Lys Gly Gln Phe Gln Glu Gln Leu Glu Tyr Ile Ser Asn Ala Asn
145                 150                 155                 160
Gly Gly Ile Lys Gly Ala Ala Ile Gly Ile Glu Asn Leu Leu Tyr Leu
                165                 170                 175
Ser Glu Ala Leu Lys Ser Gly Lys Ile Ser His Lys Asp Phe Tyr Gln
            180                 185                 190
Asn Phe Asn Asn Lys Glu Ile Thr Tyr
        195                 200
```

<210> SEQ ID NO 71
<211> LENGTH: 197
<212> TYPE: PRT
<213> ORGANISM: Artificial Sequence
<220> FEATURE:
<223> OTHER INFORMATION: Synthetic Sequence

<400> SEQUENCE: 71

```
Leu Pro Gln Lys Asp Gln Val Gln Gln Gln Asp Glu Leu Arg Pro
1               5                   10                  15
Met Leu Lys Asn Val Asp His Arg Tyr Leu Gln Leu Val Glu Leu Ala
            20                  25                  30
Leu Asp Ser Asp Gln Asn Ser Glu Tyr Ser Gln Phe Glu Gln Leu Thr
        35                  40                  45
Met Glu Leu Val Leu Lys His Leu Asp Phe Asp Gly Lys Pro Leu Gly
    50                  55                  60
Gly Ser Asn Lys Pro Asp Gly Ile Ala Trp Asp Asn Asp Gly Asn Phe
65                  70                  75                  80
Ile Ile Phe Asp Thr Lys Ala Tyr Asn Lys Gly Tyr Ser Leu Ala Gly
                85                  90                  95
```

Asn Thr Asp Lys Val Lys Arg Tyr Ile Asp Asp Val Arg Asp Arg Asp
                100                 105                 110

Thr Ser Arg Thr Ser Thr Trp Trp Gln Leu Val Pro Lys Ser Ile Asp
            115                 120                 125

Val His Asn Leu Leu Arg Phe Val Tyr Val Ser Gly Asn Phe Thr Gly
        130                 135                 140

Asn Tyr Met Lys Leu Leu Asp Ser Leu Arg Ser Trp Ser Asn Ala Gln
145                 150                 155                 160

Gly Gly Leu Ala Ser Val Glu Lys Leu Leu Leu Thr Ser Glu Leu Tyr
                165                 170                 175

Leu Arg Asn Met Tyr Ser His Gln Glu Leu Ile Asp Ser Trp Thr Asp
            180                 185                 190

Asn Asn Val Lys His
            195

<210> SEQ ID NO 72
<211> LENGTH: 189
<212> TYPE: PRT
<213> ORGANISM: Artificial Sequence
<220> FEATURE:
<223> OTHER INFORMATION: Synthetic Sequence

<400> SEQUENCE: 72

Thr Thr Asp Ala Val Val Lys Asp Arg Ala Arg Val Arg Leu His
1               5                   10                  15

Asn Ile Asn His Lys Tyr Leu Thr Leu Ile Asp Tyr Ala Phe Ser Gly
            20                  25                  30

Lys Asn Asn Cys Thr Glu Phe Glu Ile Tyr Thr Ile Asp Leu Leu Val
        35                  40                  45

Asn Glu Leu Ala Phe Asn Gly Ile His Leu Gly Gly Thr Arg Lys Pro
    50                  55                  60

Asp Gly Ile Phe Asp Tyr Asn Gln Gln Gly Ile Ile Ile Asp Asn Lys
65                  70                  75                  80

Ala Tyr Ser Lys Gly Phe Thr Ile Thr Arg Ser Met Ala Asp Glu Met
                85                  90                  95

Val Arg Tyr Val Gln Glu Asn Asn Asp Arg Asn Pro Glu Arg Asn Lys
            100                 105                 110

Thr Gln Trp Trp Leu Asn Phe Gly Asp Asn Val Asn His Phe Asn Phe
        115                 120                 125

Val Phe Ile Ser Ser Met Phe Lys Gly Glu Val Arg His Met Leu Asn
    130                 135                 140

Asn Ile Lys Gln Ser Thr Gly Val Asp Gly Cys Val Leu Thr Ala Glu
145                 150                 155                 160

Asn Leu Leu Tyr Phe Ala Asp Ala Ile Lys Gly Gly Thr Val Lys Arg
                165                 170                 175

Thr Asp Phe Ile Asn Leu Phe Gly Lys Asn Asp Glu Leu
            180                 185

<210> SEQ ID NO 73
<211> LENGTH: 198
<212> TYPE: PRT
<213> ORGANISM: Artificial Sequence
<220> FEATURE:
<223> OTHER INFORMATION: Synthetic Sequence

<400> SEQUENCE: 73

Leu Pro Lys Lys Asp Asn Val Gln Arg Gln Gln Asp Glu Leu Arg Pro
1               5                   10                  15

```
Leu Leu Lys His Val Asp His Arg Tyr Leu Gln Leu Val Glu Leu Ala
             20                  25                  30

Leu Asp Ser Ser Gln Asn Ser Glu Tyr Ser Met Leu Glu Ser Met Thr
         35                  40                  45

Met Glu Leu Leu Leu Thr His Leu Asp Phe Asp Gly Ala Ser Leu Gly
 50                  55                  60

Gly Ala Ser Lys Pro Asp Gly Ile Ala Trp Asp Lys Asp Gly Asn Phe
 65                  70                  75                  80

Leu Ile Val Asp Thr Lys Ala Tyr Asp Asn Gly Tyr Ser Leu Ala Gly
                 85                  90                  95

Asn Thr Asp Lys Val Ala Arg Tyr Ile Asp Asp Val Ala Lys Asp
             100                 105                 110

Pro Asn Arg Ala Ser Thr Trp Trp Thr Gln Val Pro Glu Ser Leu Asn
         115                 120                 125

Val Asp Asp Asn Leu Ser Phe Met Tyr Val Ser Gly Ser Phe Thr Gly
130                 135                 140

Asn Tyr Gln Arg Leu Leu Lys Asp Leu Arg Ala Arg Thr Asn Ala Arg
145                 150                 155                 160

Gly Gly Leu Thr Thr Val Glu Lys Leu Leu Thr Ser Glu Ala Tyr
                 165                 170                 175

Leu Ala Lys Ser Gly Tyr Gly His Thr Gln Leu Leu Asn Asp Trp Thr
             180                 185                 190

Asp Asp Asn Ile Asp His
             195

<210> SEQ ID NO 74
<211> LENGTH: 193
<212> TYPE: PRT
<213> ORGANISM: Artificial Sequence
<220> FEATURE:
<223> OTHER INFORMATION: Synthetic Sequence

<400> SEQUENCE: 74

Gln Ile Lys Asp Lys Tyr Leu Glu Asp Leu Lys Leu Glu Leu Tyr Lys
1               5                  10                  15

Lys Thr Asn Leu Pro Asn Lys Tyr Tyr Glu Met Val Asp Ile Ala Tyr
             20                  25                  30

Asp Gly Lys Arg Asn Arg Glu Phe Glu Ile Tyr Thr Ser Asp Leu Met
         35                  40                  45

Gln Glu Ile Tyr Gly Phe Lys Thr Thr Leu Leu Gly Gly Thr Arg Lys
 50                  55                  60

Pro Asp Val Val Ser Tyr Ser Asp Ala His Gly Tyr Ile Ile Asp Thr
 65                  70                  75                  80

Lys Ala Tyr Ala Asn Gly Tyr Arg Lys Glu Ile Lys Gln Glu Asp Glu
                 85                  90                  95

Met Val Arg Tyr Ile Glu Asp Asn Gln Leu Lys Asp Val Leu Arg Asn
             100                 105                 110

Pro Asn Lys Trp Trp Glu Cys Phe Asp Asp Ala Glu His Lys Lys Glu
         115                 120                 125

Tyr Tyr Phe Leu Trp Ile Ser Ser Lys Phe Val Gly Glu Phe Ser Ser
130                 135                 140

Gln Leu Gln Asp Thr Ser Arg Arg Thr Gly Ile Lys Gly Gly Ala Val
145                 150                 155                 160

Asn Ile Val Gln Leu Leu Leu Gly Ala His Leu Val Tyr Ser Gly Glu
                 165                 170                 175
```

```
Ile Ser Lys Asp Gln Phe Ala Ala Tyr Met Asn Asn Thr Glu Ile Asn
                180                 185                 190
Phe

<210> SEQ ID NO 75
<211> LENGTH: 146
<212> TYPE: PRT
<213> ORGANISM: Artificial Sequence
<220> FEATURE:
<223> OTHER INFORMATION: Synthetic Sequence

<400> SEQUENCE: 75

Met Asn Pro Arg Asn Glu Ile Val Ile Ala Lys His Leu Ser Gly Gly
1               5                   10                  15

Asn Arg Pro Glu Ile Val Cys Tyr His Pro Glu Asp Lys Pro Asp His
            20                  25                  30

Gly Leu Ile Leu Asp Ser Lys Ala Tyr Lys Ser Gly Phe Thr Ile Pro
        35                  40                  45

Ser Gly Glu Arg Asp Lys Met Val Arg Tyr Ile Glu Tyr Ile Thr
    50                  55                  60

Lys Asn Gln Leu Gln Asn Pro Asn Glu Trp Trp Lys Asn Leu Lys Gly
65                  70                  75                  80

Ala Glu Tyr Pro Gly Ile Val Gly Phe Gly Phe Ile Ser Asn Ser Phe
                85                  90                  95

Leu Gly His Tyr Arg Lys Gln Leu Asp Tyr Ile Met Arg Arg Thr Lys
            100                 105                 110

Ile Lys Gly Ser Ser Ile Thr Thr Glu His Leu Leu Lys Thr Val Glu
        115                 120                 125

Asp Val Leu Ser Glu Lys Gly Asn Val Ile Asp Phe Phe Lys Tyr Phe
    130                 135                 140

Leu Glu
145

<210> SEQ ID NO 76
<211> LENGTH: 195
<212> TYPE: PRT
<213> ORGANISM: Artificial Sequence
<220> FEATURE:
<223> OTHER INFORMATION: Synthetic Sequence

<400> SEQUENCE: 76

Glu Ile Lys Asn Gln Glu Ile Glu Gly Leu Lys Gln Ile Ala Leu Asn
1               5                   10                  15

Lys Tyr Thr Ala Leu Pro Ser Glu Trp Val Glu Leu Ile Glu Ile Ser
            20                  25                  30

Arg Asp Lys Asp Gln Ser Thr Ile Phe Glu Met Lys Val Ala Glu Leu
        35                  40                  45

Phe Lys Thr Cys Tyr Arg Ile Lys Ser Leu His Leu Gly Gly Ala Ser
    50                  55                  60

Lys Pro Asp Cys Leu Leu Trp Asp Asp Ser Phe Ser Val Ile Val Asp
65                  70                  75                  80

Ala Lys Ala Tyr Lys Asp Gly Phe Pro Phe Gln Ala Ser Glu Lys Asp
                85                  90                  95

Lys Met Val Arg Tyr Leu Arg Glu Cys Glu Arg Lys Asp Lys Ala Glu
            100                 105                 110

Asn Ala Thr Glu Trp Trp Asn Asn Phe Pro Pro Glu Leu Asn Ser Asn
        115                 120                 125
```

Gln Leu Phe Phe Met Phe Ala Ser Ser Phe Ser Ser Thr Ala Glu
    130                 135                 140

Lys His Leu Glu Ser Val Ser Ile Ala Ser Lys Phe Ser Gly Cys Ala
145                 150                 155                 160

Trp Asp Val Asp Asn Leu Leu Ser Gly Ala Asn Phe Phe Leu Gln Asn
                165                 170                 175

Pro Gln Ala Thr Leu Gln Tyr His Leu Ile Arg Val Phe Ser Asn Lys
            180                 185                 190

Val Val Asp
        195

<210> SEQ ID NO 77
<211> LENGTH: 198
<212> TYPE: PRT
<213> ORGANISM: Artificial Sequence
<220> FEATURE:
<223> OTHER INFORMATION: Synthetic Sequence

<400> SEQUENCE: 77

Leu Pro His Lys Asp Asn Val Ile Lys Gln Gln Asp Glu Leu Arg Pro
1               5                   10                  15

Met Leu Lys His Val Asn His Lys Tyr Leu Gln Leu Val Glu Leu Ala
                20                  25                  30

Phe Glu Ser Ser Arg Asn Ser Glu Tyr Ser Gln Phe Gly Thr Leu Thr
            35                  40                  45

Met Glu Leu Val Leu Lys Tyr Leu Asp Phe Ser Gly Lys Ser Leu Gly
        50                  55                  60

Gly Ala Asn Lys Pro Asp Gly Ile Ala Trp Asp Pro Leu Gly Asn Phe
65                  70                  75                  80

Leu Ile Phe Asp Thr Lys Ala Tyr Lys His Gly Tyr Thr Leu Ser Asn
                85                  90                  95

Asn Thr Asp Arg Val Ala Arg Tyr Ile Asn Asp Val Arg Asp Lys Asp
            100                 105                 110

Ile Gln Arg Ile Ser Arg Trp Trp Gln Ser Ile Pro Thr Tyr Ile Asp
        115                 120                 125

Val Lys Asn Lys Leu Gln Phe Val Tyr Ile Ser Gly Ser Phe Thr Gly
    130                 135                 140

His Tyr Leu Arg Leu Leu Asn Asp Leu Arg Ser Arg Thr Arg Ala Lys
145                 150                 155                 160

Gly Gly Leu Val Thr Val Glu Lys Leu Leu Thr Thr Glu Arg Tyr
                165                 170                 175

Leu Ala Glu Ala Asp Tyr Thr His Lys Glu Leu Phe Asp Asp Trp Met
            180                 185                 190

Asp Asp Asn Ile Glu His
        195

<210> SEQ ID NO 78
<211> LENGTH: 200
<212> TYPE: PRT
<213> ORGANISM: Artificial Sequence
<220> FEATURE:
<223> OTHER INFORMATION: Synthetic Sequence

<400> SEQUENCE: 78

Arg Ile Ser Pro Ser Asn Leu Glu Gln Thr Lys Gln Gln Leu Arg Glu
1               5                   10                  15

Glu Leu Ile Asn Leu Asp His Gln Tyr Leu Asp Ile Leu Asp Phe Ser

```
            20                  25                  30

Ile Ala Gly Asn Val Gly Ala Arg Gln Phe Glu Val Arg Ile Val Glu
        35                  40                  45

Leu Leu Asn Glu Ile Ile Ile Ala Lys His Leu Ser Gly Gly Asn Arg
    50                  55                  60

Pro Glu Ile Ile Gly Phe Asn Pro Lys Glu Asn Pro Glu Asp Cys Ile
65                  70                  75                  80

Ile Met Asp Ser Lys Ala Tyr Lys Glu Gly Phe Asn Ile Pro Ala Asn
                85                  90                  95

Glu Arg Asp Lys Met Ile Arg Tyr Val Glu Glu Tyr Asn Ala Lys Asp
            100                 105                 110

Asn Thr Leu Asn Asn Asn Lys Trp Trp Lys Asn Phe Glu Ser Pro Asn
        115                 120                 125

Tyr Pro Thr Asn Gln Val Lys Phe Ser Phe Val Ser Ser Ser Phe Ile
    130                 135                 140

Gly Gln Phe Thr Asn Gln Leu Thr Tyr Ile Asn Asn Arg Thr Asn Val
145                 150                 155                 160

Asn Gly Ser Ala Ile Thr Ala Glu Thr Leu Leu Arg Lys Val Glu Asn
                165                 170                 175

Val Met Asn Val Asn Thr Glu Tyr Asn Leu Asn Asn Phe Phe Glu Glu
            180                 185                 190

Leu Gly Ser Asn Thr Leu Val Ala
        195                 200

<210> SEQ ID NO 79
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 79

Thr Phe Asp Ser Thr Val Ala Asp Asn Leu Lys Asn Leu Ile Leu Pro
1               5                   10                  15

Lys Leu Lys Glu Leu Asp His Lys Tyr Leu Gln Ala Ile Asp Ile Ala
            20                  25                  30

Tyr Lys Arg Ser Asn Thr Thr Asn His Glu Asn Thr Leu Leu Glu Val
        35                  40                  45

Leu Ser Ala Asp Leu Phe Thr Lys Glu Met Asp Tyr His Gly Lys His
    50                  55                  60

Leu Gly Gly Ala Asn Lys Pro Asp Gly Phe Val Tyr Asp Glu Glu Thr
65                  70                  75                  80

Gly Trp Ile Leu Asp Ser Lys Ala Tyr Arg Asp Gly Phe Ala Val Thr
                85                  90                  95

Ala His Thr Thr Asp Ala Met Gly Arg Tyr Ile Asp Gln Tyr Arg Asp
            100                 105                 110

Arg Asp Asp Lys Ser Thr Trp Trp Glu Asp Phe Pro Lys Asp Leu Pro
        115                 120                 125

Gln Thr Tyr Phe Ala Tyr Val Ser Gly Phe Tyr Ile Gly Lys Tyr Gln
    130                 135                 140

Glu Gln Leu Gln Asp Phe Glu Asn Arg Lys His Met Lys Gly Gly Leu
145                 150                 155                 160

Ile Glu Val Ala Lys Leu Ile Leu Ala Glu Lys Tyr Lys Glu Asn
                165                 170                 175

Lys Ile Thr His Asp Gln Ile Thr Leu Gln Ile Leu Asn Asp His Ile
```

```
                    180                 185                 190

Ser Gln

<210> SEQ ID NO 80
<211> LENGTH: 186
<212> TYPE: PRT
<213> ORGANISM: Artificial Sequence
<220> FEATURE:
<223> OTHER INFORMATION: Synthetic Sequence

<400> SEQUENCE: 80

Pro Leu Asp Val Val Glu Gln Met Lys Ala Glu Leu Arg Pro Leu Leu
1               5                   10                  15

Asn His Val Asn His Arg Leu Leu Ala Ile Ile Asp Phe Ser Tyr Asn
                20                  25                  30

Met Ser Arg Gly Asp Asp Lys Arg Leu Glu Asp Tyr Thr Ala Gln Ile
            35                  40                  45

Tyr Lys Leu Ile Ser His Asp Thr His Leu Leu Ala Gly Pro Ser Arg
    50                  55                  60

Pro Asp Val Val Ser Val Ile Asn Asp Leu Gly Ile Ile Ile Asp Ser
65                  70                  75                  80

Lys Ala Tyr Lys Gln Gly Phe Asn Ile Pro Gln Ala Glu Glu Asp Lys
                85                  90                  95

Met Val Arg Tyr Leu Asp Glu Ser Ile Arg Arg Asp Pro Ala Ile Asn
            100                 105                 110

Pro Thr Lys Trp Trp Glu Tyr Leu Gly Ala Ser Thr Glu Tyr Val Phe
        115                 120                 125

Gln Phe Val Ser Ser Ser Phe Ser Ser Gly Ala Ser Ala Lys Leu Arg
    130                 135                 140

Gln Ile His Arg Arg Ser Ser Ile Glu Gly Ser Ile Ile Thr Ala Lys
145                 150                 155                 160

Asn Leu Leu Leu Leu Ala Glu Asn Phe Leu Cys Thr Asn Thr Ile Asn
                165                 170                 175

Ile Asp Leu Phe Arg Gln Asn Asn Glu Ile
            180                 185

<210> SEQ ID NO 81
<211> LENGTH: 201
<212> TYPE: PRT
<213> ORGANISM: Artificial Sequence
<220> FEATURE:
<223> OTHER INFORMATION: Synthetic Sequence

<400> SEQUENCE: 81

Gln Leu Val Pro Ser Tyr Ile Thr Gln Thr Lys Leu Arg Leu Ser Gly
1               5                   10                  15

Leu Ile Asn Tyr Ile Asp His Ser Tyr Phe Asp Leu Ile Asp Leu Gly
                20                  25                  30

Phe Asp Gly Arg Gln Asn Arg Leu Tyr Glu Leu Arg Ile Val Glu Leu
            35                  40                  45

Leu Asn Leu Ile Asn Ser Leu Lys Ala Leu His Leu Ser Gly Gly Asn
    50                  55                  60

Arg Pro Glu Ile Ile Ala Tyr Ser Pro Asp Val Asn Pro Ile Asn Gly
65                  70                  75                  80

Val Ile Met Asp Ser Lys Ser Tyr Arg Gly Gly Phe Asn Ile Pro Asn
                85                  90                  95

Ser Glu Arg Asp Lys Met Ile Arg Tyr Ile Asn Glu Tyr Asn Gln Lys
```

```
                100                 105                 110
Asn Pro Thr Leu Asn Ser Asn Arg Trp Trp Glu Asn Phe Arg Ala Pro
            115                 120                 125

Asp Tyr Pro Gln Ser Pro Leu Lys Tyr Ser Phe Val Ser Gly Asn Phe
130                 135                 140

Ile Gly Gln Phe Leu Asn Gln Ile Gln Tyr Ile Leu Thr Gln Thr Gly
145                 150                 155                 160

Ile Asn Gly Gly Ala Ile Thr Ser Glu Lys Leu Ile Glu Lys Val Asn
                165                 170                 175

Ala Val Leu Asn Pro Asn Ile Ser Tyr Thr Ile Asn Asn Phe Phe Asn
            180                 185                 190

Asp Leu Gly Cys Asn Arg Leu Val Gln
            195                 200

<210> SEQ ID NO 82
<211> LENGTH: 588
<212> TYPE: DNA
<213> ORGANISM: Artificial Sequence
<220> FEATURE:
<223> OTHER INFORMATION: Synthetic Sequence

<400> SEQUENCE: 82
ttcctggtga agggcgccat ggagatcaag aagagcgagc tgaggcacaa gctgaggcac      60
gtgccccacg agtacatcga gctgatcgag atcgcccagg acagcaagca gaacaggctg     120
ctggagttca aggtggtgga gttcttcaag aagatctacg ctacaggggc aagcaccctg     180
ggcggcagca ggaagcccga cggcgccctg ttcaccgacg gcctggtgct gaaccacggc     240
atcatcctgg acaccaaggc ctacaaggac ggctacaggc tgcccatcag ccaggccgac     300
gagatgcaga ggtacgtgga cgagaacaac aagaggagcc aggtgatcaa ccccaacgag     360
tggtgggaga tctaccccac cagcatcacc gacttcaagt tcctgttcgt gagcggcttc     420
ttccagggcg actacaggaa gcagctggag agggtgagcc acctgaccaa gtgccagggc     480
gccgtgatga gcgtggagca gctgctgctg ggcggcgaga gatcaagga gggcagcctg     540 accctggagg aggtgggcaa gaagttcaag aacgacgaga tcgtgttc                  588

<210> SEQ ID NO 83
<211> LENGTH: 576
<212> TYPE: DNA
<213> ORGANISM: Artificial Sequence
<220> FEATURE:
<223> OTHER INFORMATION: Synthetic Sequence

<400> SEQUENCE: 83
cagatcgtga agagcagcat cgagatgagc aaggccaaca tgagggacaa cctgcagatg      60
ctgccccacg actacatcga gctgatcgag atcagccagg acccctacca gaacaggatc     120 tcgagatga aggtgatgga cctgttcatc aacgagtacg gcttcagcgg cagccacctg     180
ggcggcagca ggaagcccga cggcgccatg tacgcccacg gcttcggcgt gatcgtggac     240
accaaggcct acaaggacgg ctacaacctg cccatcagcc aggccgacga gatggagagg     300
tacgtgaggg agaacatcga caggaacgag cacgtgaaca gcaacaggtg gtggaacatc     360
ttccccgagg acaccaacga gtacaagttc ctgttcgtga gcggcttctt caagggcaac     420
ttcgagaagc agctggagag gatcagcatc gacaccggcg tgcagggcgg cgccctgagc     480
gtggagcacc tgctgctggg cgccgagtac atcaagaggg gcatcctgac cctgtacgac     540
ttcaagaaca gcttcctgaa caaggagatc cagttc                                576
```

<210> SEQ ID NO 84
<211> LENGTH: 588
<212> TYPE: DNA
<213> ORGANISM: Artificial Sequence
<220> FEATURE:
<223> OTHER INFORMATION: Synthetic Sequence

<400> SEQUENCE: 84

```
cagaccatca agagcagcat cgaggagctg aagagcgagc tgaggaccca gctgaacgtg      60
atcagccacg actacctgca gctggtggac atcagccagg acagccagca gaacaggctg     120
ttcgagatga aggtgatgga cctgttcatc aacgagttcg gctacaacgg cagccacctg     180
ggcggcagca ggaagcccga cggcatcctg tacaccgagg gcctgagcaa ggactacggc     240
atcatcgtgg acaccaaggc ctacaaggac ggctacaacc tgcccatcgc ccaggccgac     300
gagatggaga ggtacatcag ggagaacatc gacaggaacg aggtggtgaa ccccaacagg     360
tggtgggagt gttccccag caagatcaac gactacaagt tcctgttcgt gagcgcctac     420
ttcaagggca acttcaagga gcagctggag aggatcagca tcaacaccgg catcctgggc     480
ggcgccatca gcgtggagca cctgctgctg ggcgccgagt acttcaagag gggcatcctg     540
agcctggagg acgtgaggga caagttctgc aacaccgaga tcgagttc                   588
```

<210> SEQ ID NO 85
<211> LENGTH: 585
<212> TYPE: DNA
<213> ORGANISM: Artificial Sequence
<220> FEATURE:
<223> OTHER INFORMATION: Synthetic Sequence

<400> SEQUENCE: 85

```
ggcaagagcg aggtggagac catcaaggag cagatgaggg gcgagctgac ccacctgagc      60
cacgagtacc tgggcctgct ggacctggcc tacgacagca agcagaacag gctgttcgag     120
ctgaagacca tgcagctgct gaccgaggag tgcggcttcg agggcctgca cctgggcggc     180
agcaggaagc ccgacggcat cgtgtacacc aaggacgaga acgagcaggt gggcaaggag     240
aactacggca tcatcatcga caccaaggcc tacagcggcg gctacagcct gcccatcagc     300
caggccgacg agatggagag gtacatcggc gagaaccaga ccagggacat caggatcaac     360
cccaacgagt ggtggaagaa cttcggcgac ggcgtgaccg agtactacta cctgttcgtg     420
gccggccact tcaagggcaa gtaccaggag cagatcgaca ggatcaactg caacaagaac     480
atcaagggcg ccgccgtgag catccagcag ctgctgagga tcgtgaacga ctacaaggcc     540
ggcaagctga cccacgagga catgaagctg aagatcttcc actac                      585
```

<210> SEQ ID NO 86
<211> LENGTH: 453
<212> TYPE: DNA
<213> ORGANISM: Artificial Sequence
<220> FEATURE:
<223> OTHER INFORMATION: Synthetic Sequence

<400> SEQUENCE: 86

```
atgaagatcc tggagctgct gatcaacgag tgcggctaca agggcctgca cctgggcggc      60
gccaggaagc ccgacggcat catctacacc gagaaggaga agtacaacta cggcgtgatc     120
atcgacacca aggcctacag caagggctac aacctgccca tcggccagat cgacgagatg     180
atcaggtaca tcatcgagaa caacgagagg aacatcaaga gaacaccaa ctgctggtgg     240
```

| | |
|---|---|
| aacaacttcg agaagaacgt gaacgagttc tacttcagct tcatcagcgg cgagttcacc | 300 |
| ggcaacatcg aggagaagct gaacaggatc ttcatcagca ccaacatcaa gggcaacgcc | 360 |
| atgagcgtga agaccctgct gtacctggcc aacgagatca aggccaacag gatcagctac | 420 |
| atcgagctgc tgaactactt cgacaacaag gtg | 453 |

<210> SEQ ID NO 87
<211> LENGTH: 582
<212> TYPE: DNA
<213> ORGANISM: Artificial Sequence
<220> FEATURE:
<223> OTHER INFORMATION: Synthetic Sequence

<400> SEQUENCE: 87

| | |
|---|---|
| gccaagagca gccagagcga gaccaaggag aagctgaggg agaagctgag gaacctgccc | 60 |
| cacgagtacc tgagcctggt ggacctggcc tacgacagca agcagaacag gctgttcgag | 120 |
| atgaaggtga tcgagctgct gaccgaggag tgcggcttcc agggcctgca cctgggcggc | 180 |
| agcaggaggc ccgacggcgt gctgtacacc gccggcctga ccgacaacta cggcatcatc | 240 |
| ctggacacca aggcctacag cagcggctac agcctgccca tcgcccaggc cgacgagatg | 300 |
| gagaggtacg tgagggagaa ccagaccagg gacgagctgg tgaaccccaa ccagtggtgg | 360 |
| gagaacttcg agaacggcct gggcaccttc tacttcctgt tcgtggccgg ccacttcaac | 420 |
| ggcaacgtgc aggcccagct ggagaggatc agcaggaaca ccggcgtgct gggcgccgcc | 480 |
| gccagcatca gccagctgct gctgctggcc gacgccatca ggggcggcag gatggacagg | 540 |
| gagaggctga ggcacctgat gttccagaac gaggagttcc tg | 582 |

<210> SEQ ID NO 88
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 88

| | |
|---|---|
| aacagcgaga gagcgagtt cacccaggag aaggacaacc tgagggagaa gctggacacc | 60 |
| ctgagccacg agtacctgag cctggtggac ctggccttcg acagccagca gaacaggctg | 120 |
| ttcgagatga agaccgtgga gctgctgacc aaggagtgca actacaaggg cgtgcacctg | 180 |
| ggcggcagca ggaagcccga cggcatcatc tacaccgaga cagcaccga caactacggc | 240 |
| gtgatcatcg acaccaaggc ctacagcaac ggctacaacc tgcccatcag ccaggtggac | 300 |
| gagatggtga ggtacgtgga ggagaacaac aagagggaga aggagaggaa cagcaacgag | 360 |
| tggtggaagg agttcggcga caacatcaac aagttctact tcagcttcat cagcggcaag | 420 |
| ttcatcggca acatcgagga gaagctgcag aggatcacca tcttccaccaa cgtgtacggc | 480 |
| aacgccatga ccatcatcac cctgctgtac ctggccaacg agatcaaggc caacaggctg | 540 |
| aagaccatgg aggtggtgaa gtacttcgac aacaaggtg | 579 |

<210> SEQ ID NO 89
<211> LENGTH: 600
<212> TYPE: DNA
<213> ORGANISM: Artificial Sequence
<220> FEATURE:
<223> OTHER INFORMATION: Synthetic Sequence

<400> SEQUENCE: 89

| | |
|---|---|
| aacctgacct gcagcgacct gaccgagatc aaggaggagg tgaggaacgc cctgacccac | 60 |

```
ctgagccacg agtacctggc cctgatcgac ctggcctacg acagcaccca gaacaggctg      120
ttcgagatga agaccctgca gctgctggtg gaggagtgcg gctaccaggg cacccacctg      180
ggcggcagca ggaagcccga cggcatctgc tacagcgagg aggccaagag cgagggcctg      240
gaggccaact acggcatcat catcgacacc aagagctaca gcggcggcta cggcctgccc      300
atcagccagg ccgacgagat ggagaggtac atcagggaga accagaccag ggacgccgag      360
gtgaacagga acaagtggtg ggaggccttc cccgagacca tcgacatctt ctacttcatg      420
ttcgtggccg ccacttcaa gggcaactac ttcaaccagc tggagaggct gcagaggagc      480
accggcatca gggcgccgc cgtggacatc aagaccctgc tgctgaccgc caacaggtgc      540
aagaccggcg agctggacca cgccggcatc gagagctgct tcttcaacaa ctgcaggctg      600
```

<210> SEQ ID NO 90
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 90

```
gacaacgtga agagcaactt caaccaggag aaggacgagc tgagggagaa gctggacacc       60
ctgagccacg agtacctgta cctgctggac ctggcctacg acagcaagca gaacaagctg      120
ttcgagatga agatcctgga gctgctgatc aacgagtgcg gctacagggg cctgcacctg      180
ggcggcgtga ggaagcccga cggcatcatc tacaccgaga aggagaagta caactacggc      240
gtgatcatcg acaccaaggc ctacagcaag ggctacaacc tgcccatcgg ccagatcgac      300
gagatgatca ggtacatcat cgagaacaac gagaggaaca tcaagaggaa caccaactgc      360
tggtggaaca acttcgagaa gaacgtgaac gagttctact tcagcttcat cagcggcgag      420
ttcaccggca acatcgagga agctgaac aggatcttca tcagcaccaa catcaagggc      480
aacgccatga gcgtgaagac cctgctgtac ctggccaacg agatcaaggc caacaggatc      540
agcttcctgg agatggagaa gtacttcgac aacaaggtg                            579
```

<210> SEQ ID NO 91
<211> LENGTH: 588
<212> TYPE: DNA
<213> ORGANISM: Artificial Sequence
<220> FEATURE:
<223> OTHER INFORMATION: Synthetic Sequence

<400> SEQUENCE: 91

```
gagggcatca agagcaacat cagcctgctg aaggacgagc tgaggggcca gatcagccac       60
atcagccacg agtacctgag cctgatcgac ctggccttcg acagcaagca gaacaggctg      120
ttcgagatga aggtgctgga gctgctggtg aacgagtacg cttcaaggg caggcacctg      180 ggcggcagca ggaagcccga cggcatcgtg tacagcacca ccctggagga caacttcggc      240
atcatcgtgg acaccaaggc ctacagcgag ggctacagcc tgcccatcag ccaggccgac      300
gagatggaga ggtacgtgag ggagaacagc aacagggacg aggaggtgaa ccccaacaag      360
tggtgggaga acttcagcga ggaggtgaag aagtactact tcgtgttcat cagcggcagc      420
ttcaagggca gttcgagga gcagctgagg aggctgagca tgaccaccgg cgtgaacggc      480
agcgccgtga acgtggtgaa cctgctgctg ggcgccgaga agatcaggag cggcgagatg      540
accatcgagg agctggagag ggccatgttc aacaacagcg agttcatc                 588
```

<210> SEQ ID NO 92
<211> LENGTH: 573
<212> TYPE: DNA
<213> ORGANISM: Artificial Sequence
<220> FEATURE:
<223> OTHER INFORMATION: Synthetic Sequence

<400> SEQUENCE: 92

| atcagcaaga ccaacgtgct ggagctgaag acaaggtga gggacaagct gaagtacgtg | 60 |
| gacaacaggt acctggccct gatcgacctg cctacgacg gcaccgccaa cagggacttc | 120 |
| gagatccaga ccatcgacct gctgatcaac gagctgaagt tcaagggcgt gaggctgggc | 180 |
| gagagcagga agcccgacgg catcatcagc tacgacatca acggcgtgat catcgacaac | 240 |
| aaggcctaca gcagcggcta caacctgccc atcaaccagg ccgacgagat gatcaggtac | 300 |
| atcgaggaga accagaccag ggacaagaag atcaacccca caagtggtg ggagagcttc | 360 |
| gacgacaagg tgaaggactt caactacctg ttcgtgagca gcttcttcaa gggcaacttc | 420 |
| aagaacaacc tgaagcacat cgccaacagg accggcgtga acgcggcgt gatcaacgtg | 480 |
| gagaacctgc tgtacttcgc cgaggagctg aagagcggca ggctgagcta cgtggacctg | 540 |
| ttcaagatgt acgacaacga cgagatcaac atc | 573 |

<210> SEQ ID NO 93
<211> LENGTH: 573
<212> TYPE: DNA
<213> ORGANISM: Artificial Sequence
<220> FEATURE:
<223> OTHER INFORMATION: Synthetic Sequence

<400> SEQUENCE: 93

| atcagcaaga ccaacgtgct ggagctgaag acaaggtga gggacaagct gaagtacgtg | 60 |
| gaccacaggt acctggccct gatcgacctg cctacgacg gcaccgccaa cagggacttc | 120 |
| gagatccaga ccatcgacct gctgatcaac gagctgaagt tcaagggcgt gaggctgggc | 180 |
| gagagcagga agcccgacgg catcatcagc tacgacatca acggcgtgat catcgacaac | 240 |
| aaggcctaca gcaccggcta caacctgccc atcaaccagg ccgacgagat gatcaggtac | 300 |
| atcgaggaga accagaccag ggacaagaag atcaacagca caagtggtg ggagagcttc | 360 |
| gacgacaagg tgaagaactt caactacctg ttcgtgagca gcttcttcaa gggcaacttc | 420 |
| aagaacaacc tgaagcacat cgccaacagg accggcgtga acgcggcgc catcaacgtg | 480 |
| gagaacctgc tgtacttcgc cgaggagctg aaggccggca ggctgagcta cgtggacagc | 540 |
| ttcaccatgt acgacaacga cgagatctac gtg | 573 |

<210> SEQ ID NO 94
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 94

| aaggccgaga gagcgagtt cctgatcgag aaggacaagc tgagggagaa gctggacacc | 60 |
| ctgcccacg actacctgag catggtggac ctggcctacg acagcaagca gaacaggctg | 120 |
| ttcgagatga agaccatcga gctgctgatc aacgagtgca actacaaggg cctgcacctg | 180 |
| ggcggcacca ggaagcccga cggcatcgtg tacaccaaca acgaggtgga gaactacggc | 240 |
| atcatcatcg acaccaaggc ctacagcaag ggctacaacc tgcccatcag ccaggtggac | 300 |

```
gagatgacca ggtacgtgga ggagaacaac aagagggaga agaagaggaa ccccaacgag      360
tggtggaaca acttcgacag caacgtgaag aagttctact tcagcttcat cagcggcaag      420
ttcgtgggca acatcgagga gaagctgcag aggatcaccc tgttcaccga gatctacggc      480
aacgccatca ccgtgaccac cctgctgtac atcgccaacg agatcaaggc caacaggatg      540
aagaagagcg acatcatgga gtacttcaac gacaaggtg                            579

<210> SEQ ID NO 95
<211> LENGTH: 573
<212> TYPE: DNA
<213> ORGANISM: Artificial Sequence
<220> FEATURE:
<223> OTHER INFORMATION: Synthetic Sequence

<400> SEQUENCE: 95
atcagcaaga ccaacgtgct ggagctgaag acaaggtga gggacaagct gaagtacgtg       60
gaccacaggt acctggccct gatcgacctg gcctacgacg gcaccgccaa cagggacttc     120
gagatccaga ccatcgacct gctgatcaac gagctgaagt tcaagggcgt gaggctgggc     180
gagagcagga agcccgacgg catcatcagc tacaacatca cggcgtgat catcgacaac     240 aaggcctaca gcaccggcta caacctgccc atcaaccagg ccgacgagat gatcaggtac     300
atcgaggaga accagaccag ggacgagaag atcaacagca caagtggtg ggagagcttc     360 gacgacgagg tgaaggactt caactacctg ttcgtgagca gcttcttcaa gggcaacttc     420
aagaacaacc tgaagcacat cgccaacagg accggcgtga acggcggcgc catcaacgtg     480
gagaacctgc tgtacttcgc cgaggagctg aaggccggca ggctgagcta cgtggacagc     540
ttcaccatgt acgacaacga cgagatctac gtg                                 573

<210> SEQ ID NO 96
<211> LENGTH: 573
<212> TYPE: DNA
<213> ORGANISM: Artificial Sequence
<220> FEATURE:
<223> OTHER INFORMATION: Synthetic Sequence

<400> SEQUENCE: 96
atcagcaaga ccaacatcct ggagctgaag acaaggtga gggacaagct gaagtacgtg       60
gaccacaggt acctggccct gatcgacctg gcctacgacg gcaccgccaa cagggacttc     120
gagatccaga ccatcgacct gctgatcaac gagctgaagt tcaagggcgt gaggctgggc     180
gagagcagga agcccgacgg catcatcagc tacaacatca cggcgtgat catcgacaac     240 aaggcctaca gcaccggcta caacctgccc atcaaccagg ccgacgagat gatcaggtac     300
atcgaggaga accagaccag ggacgagaag atcaacagca caagtggtg ggagagcttc     360 gacgagaagg tgaaggactt caactacctg ttcgtgagca gcttcttcaa gggcaacttc     420
aagaacaacc tgaagcacat cgccaacagg accggcgtga acggcggcgc catcaacgtg     480
gagaacctgc tgtacttcgc cgaggagctg aaggccggca ggatcagcta cctggacagc     540
ttcaagatgt acaacaacga cgagatctac ctg                                 573

<210> SEQ ID NO 97
<211> LENGTH: 573
<212> TYPE: DNA
<213> ORGANISM: Artificial Sequence
<220> FEATURE:
<223> OTHER INFORMATION: Synthetic Sequence
```

<400> SEQUENCE: 97

```
atcagcaaga ccaacgtgct ggagctgaag acaaggtga gggacaagct gaagtacgtg    60
gaccacaggt acctggccct gatcgacctg cctacgacg gcaccgccaa cagggacttc    120
gagatccaga ccatcgacct gctgatcaac gagctgaagt caagggcgt gaggctgggc    180
gagagcagga agcccgacgg catcatcagc tacaacatca acggcgtgat catcgacaac    240
aaggcctaca gcaccggcta caacctgccc atcaaccagg ccgacgagat gatcaggtac    300
atcgaggaga ccagaccag ggacgagaag atcaacagca caagtggtg ggagagcttc    360
gacgacaagg tgaaggactt caactacctg ttcgtgagca gcttcttcaa gggcaacttc    420
aagaacaacc tgaagcacat cgccaacagg accggcgtga gcggcggcgc catcaacgtg    480
gagaacctgc tgtacttcgc cgaggagctg aaggccggca ggctgagcta cgtggacagc    540
ttcaagatgt acgacaacga cgagatctac gtg                                573
```

<210> SEQ ID NO 98
<211> LENGTH: 573
<212> TYPE: DNA
<213> ORGANISM: Artificial Sequence
<220> FEATURE:
<223> OTHER INFORMATION: Synthetic Sequence

<400> SEQUENCE: 98

```
atcagcaaga ccaacgtgct ggagctgaag acaaggtga ggaacaagct gaagtacgtg    60
gaccacaggt acctggccct gatcgacctg cctacgacg gcaccgccaa cagggacttc    120
gagatccaga ccatcgacct gctgatcaac gagctgaagt caagggcgt gaggctgggc    180
gagagcagga agcccgacgg catcatcagc tacgacatca acggcgtgat catcgacaac    240
aagagctaca gcaccggcta caacctgccc atcaaccagg ccgacgagat gatcaggtac    300
atcgaggaga ccagaccag ggacgagaag atcaacagca caagtggtg ggagagcttc    360
gacgagaagg tgaaggactt caactacctg ttcgtgagca gcttcttcaa gggcaacttc    420
aagaacaacc tgaagcacat cgccaacagg accggcgtga acggcggcgc catcaacgtg    480
gagaacctgc tgtacttcgc cgaggagctg aagagcggca ggctgagcta cgtggacagc    540
ttcaccatgt acgacaacga cgagatctac gtg                                573
```

<210> SEQ ID NO 99
<211> LENGTH: 573
<212> TYPE: DNA
<213> ORGANISM: Artificial Sequence
<220> FEATURE:
<223> OTHER INFORMATION: Synthetic Sequence

<400> SEQUENCE: 99

```
atcagcaaga ccaacgtgct ggagctgaag acaaggtga gggacaagct gaagtacgtg    60
gaccacaggt acctgagcct gatcgacctg cctacgacg gcaacgccaa cagggacttc    120
gagatccaga ccatcgacct gctgatcaac gagctgaact caagggcgt gaggctgggc    180
gagagcagga agcccgacgg catcatcagc tacaacatca acggcgtgat catcgacaac    240
aaggcctaca gcaccggcta caacctgccc atcaaccagg ccgacgagat gatcaggtac    300
atcgaggaga ccagaccag ggacgagaag atcaacagca caagtggtg ggagagcttc    360
gacgacaagg tgaaggactt caactacctg ttcgtgagca gcttcttcaa gggcaacttc    420
aagaacaacc tgaagcacat cgccaacagg accggcgtga gcggcggcgc catcaacgtg    480
gagaacctgc tgtacttcgc cgaggagctg aaggccggca ggctgagcta cgccgacagc    540
```

```
ttcaccatgt acgacaacga cgagatctac gtg                              573
```

```
<210> SEQ ID NO 100
<211> LENGTH: 573
<212> TYPE: DNA
<213> ORGANISM: Artificial Sequence
<220> FEATURE:
<223> OTHER INFORMATION: Synthetic Sequence

<400> SEQUENCE: 100
atcgccaaga ccaacgtgct gggcctgaag acaaggtga gggacaggct gaagtacgtg      60
gaccacaggt acctggccct gatcgacctg gcctacgacg gcaccgccaa cagggacttc    120
gagatccaga ccatcgacct gctgatcaac gagctgaagt tcaagggcgt gaggctgggc    180
gagagcagga agcccgacgg catcatcagc tacaacgtga acggcgtgat catcgacaac    240
aaggcctaca gcaagggcta caacctgccc atcaaccagg ccgacgagat gatcaggtac    300
atcgaggaga accagaccag ggacgagaag atcaacgcca acaagtggtg ggagagcttc    360
gacgacaagg tggaggagtt cagctacctg ttcgtgagca gcttcttcaa gggcaacttc    420
aagaacaacc tgaagcacat cgccaacagg accggcgtga acggcggcgc catcaacgtg    480
gagaacctgc tgtacttcgc cgaggagctg aagagcggca ggctgagcta catggacagc    540
ttcagcctgt acgacaacga cgagatctgc gtg                                573
```

```
<210> SEQ ID NO 101
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 101
gagctgaagg acgagcagag cgagaagagg aaggccaagt tcctgaagga gaccaagctg     60
cccatgaagt acatcgagct gctggacatc gcctacgacg gcaagaggaa cagggacttc    120
gagatcgtga ccatggagct gttcaggag gtgtacaggc tgaacagcaa gctgctgggc    180
ggcggcagga agcccgacgg cctgatctac accgacgact cggcgtgat cgtggacacc    240
aaggcctacg cgagggcta cagcaagagc atcaaccagg ccgacgagat gatcaggtac    300
atcgaggaca caagaggag ggacgagaag aggaacccca tcaagtggtg ggagagcttc    360
cccagcagca tcagccagaa caacttctac ttcctgtggg tgagcagcaa gttcgtgggc    420
aagttccagg agcagctggc ctacaccgcc aacgagaccc agaccaaggg cggcgccatc    480
aacgtggagc agatcctgat cggcgccgac ctgatcatgc agaagatgct ggacatcaac    540
accatcccca gcttcttcga gaaccaggag atcatcttc                           579
```

```
<210> SEQ ID NO 102
<211> LENGTH: 573
<212> TYPE: DNA
<213> ORGANISM: Artificial Sequence
<220> FEATURE:
<223> OTHER INFORMATION: Synthetic Sequence

<400> SEQUENCE: 102
atcttcaaga ccaacgtgct ggagctgaag acagcatca gggagaagct ggactacatc      60
gaccacaggt acctgagcct ggtggacctg gcctacgaca gcaaggccaa cagggacttc    120
gagatccaga ccatcgacct gctgatcaac gagctggact tcaagggcct gaggctgggc    180
```

```
gagagcagga agcccgacgg catcatcagc tacgacatca acggcgtgat catcgacaac    240
aaggcctaca gcaagggcta caacctgccc atcaaccagg ccgacgagat gatcaggtac    300
atccaggaga accagagcag gaacgagaag atcaaccccea acaagtggtg ggagaacttc    360
gaggacaagg tgatcaagtt caactacctg ttcatcagca gcctgttcgt gggcggcttc    420
aagaagaacc tgcagcacat cgccaacagg accggcgtga acgcggcgc catcgacgtg    480 gagaacctgc tgtacttcgc cgaggagatc aagagcggca ggctgaccta caaggacagc    540
ttcagcaggt acatcaacga cgagatcaag atg                                 573

<210> SEQ ID NO 103
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 103
ctgcccgtga agagcgaggt gagcgtgttc aaggactacc tgaggaccca cctgacccac     60
gtggaccaca ggtacctgat cctggtggac ctgggcttcg acggcagcag cgacagggac    120
tacgagatga agaccgccga gctgttcacc gccgagctgg gcttcatggg cgccaggctg    180
ggcgacacca ggaagcccga cgtgtgcgtg taccacggcg ccaacggcct gatcatcgac    240
aacaaggcct acggcaaggg ctacagcctg cccatcaagc aggccgacga gatctacagg    300
tacatcgagg agaacaagga gagggacgcc aggctgaacc ccaaccagtg gtggaaggtg    360
ttcgacgaga gcgtgaccca cttcaggttc gccttcatca gcggcagctt caccggcggc    420
ttcaaggaca ggatcgagct gatcagcatg aggagcggca tctgcggcgc cgccgtgaac    480
agcgtgaacc tgctgctgat ggccgaggag ctgaagagcg gcaggctgga ctacgaggag    540
tggttccagt acttcgactg caacgacgag atcagcttc                           579

<210> SEQ ID NO 104
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 104
atcagcgtga agagcgacat ggccgtggtg aaggacagcg tgagggagag gctggcccac     60
gtgagccacg agtacctgat cctgatcgac ctgggcttcg acggcaccag cgacagggac    120
tacgagatcc agaccgccga gctgttcacc agggagctgg acttcctggg cggcaggctg    180
ggcgacacca ggaagcccga cgtgtgcatc tactacggca aggacggcat gatcatcgac    240
aacaaggcct acggcaaggg ctacagcctg cccatcaagc aggccgacga gatgtacagg    300
tacctggagg agaacaagga gaggaacgag aagatcaacc ccaacaggtg gtggaaggtg    360
ttcgacgagg gcgtgaccga ctacaggttc gccttcgtga gcggcagctt caccggcggc    420
ttcaaggaca ggctggagaa catccacatg aggagcggcc tgtgcggcgg cgccatcgac    480
agcgtgaccc tgctgctgct ggccgaggag ctgaaggccg gcaggatgga gtacagcgag    540
ttcttcaggc tgttcgactg caacgacgag gtgaccttc                           579

<210> SEQ ID NO 105
<211> LENGTH: 579
<212> TYPE: DNA
<213> ORGANISM: Artificial Sequence
```

<220> FEATURE:
<223> OTHER INFORMATION: Synthetic Sequence

<400> SEQUENCE: 105

| gagctgaagg acaaggccgc cgacgccgtg aaggccaagt tcctgaagct gaccggcctg | 60 |
| agcatgaagt acatcgagct gctggacatc gcctacgaca gcagcaggaa cagggacttc | 120 |
| gagatcctga ccgccgacct gttcaagaac gtgtacggcc tggacgccat gcacctgggc | 180 |
| ggcggcagga agcccgacgc catcgcccag accagccact cggcatcat catcgacacc | 240 |
| aaggcctacg gcaacggcta cagcaagagc atcagccagg aggacgagat ggtgaggtac | 300 |
| atcgaggaca accagcagag gagcatcacc aggaacagcg tggagtggtg gaagaacttc | 360 |
| aacagcagca tccccagcac cgccttctac ttcctgtggg tgagcagcaa gttcgtgggc | 420 |
| aagttcgacg accagctgct ggccacctac aacaggacca cacctgcgg cggcgccctg | 480 |
| aacgtggagc agctgctgat cggcgcctac aaggtgaagg ccggcctgct gggcatcggc | 540 |
| cagatcccca gctacttcaa gaacaaggag atcgcctgg | 579 |

<210> SEQ ID NO 106
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 106

| atcagcgtga agagcgacat ggccgtggtg aaggacagcg tgagggagag gctggcccac | 60 |
| gtgagccacg agtacctgct gctgatcgac ctgggcttcg acggcaccag cgacagggac | 120 |
| tacgagatcc agaccgccga gctgctgacc agggagctgg acttcctggg cggcaggctg | 180 |
| ggcgacacca ggaagcccga cgtgtgcatc tactacggca aggacggcat gatcatcgac | 240 |
| aacaaggcct acggcaaggg ctacagcctg cccatcaagc aggccgacga gatgtacagg | 300 |
| tacctggagg agaacaagga gaggaacgag aagatcaacc ccaacaggtg gtggaaggtg | 360 |
| ttcgacgagg gcgtgaccga ctacaggttc gccttcgtga gcggcagctt caccggcggc | 420 |
| ttcaaggaca ggctggagaa catccacatg aggagcggc tgtgcggcgg cgccatcgac | 480 |
| agcgtgaccc tgctgctgct ggccgaggag ctgaaggccg gcaggatgga gtacagcgag | 540 |
| ttcttcaggc tgttcgactg caacgacgag gtgaccttc | 579 |

<210> SEQ ID NO 107
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 107

| gagctgaagg acgagcaggc cgagaagagg aaggccaagt tcctgaagga gaccaacctg | 60 |
| cccatgaagt acatcgagct gctggacatc gcctacgacg gcaagaggaa cagggacttc | 120 |
| gagatcgtga ccatggagct gttcaggaac gtgtacaggc tgcacagcaa gctgctgggc | 180 |
| ggcggcagga agcccgacgg cctgctgtac caggacaggt tcggcgtgat cgtggacacc | 240 |
| aaggcctacg gcaagggcta cagcaagagc atcaaccagg ccgacgagat gatcaggtac | 300 |
| atcgaggaca acaagaggag ggacgagaac aggaacccca tcaagtggtg ggaggccttc | 360 |
| cccgacacca tcccccagga ggagttctac ttcatgtggg tgagcagcaa gttcatcggc | 420 |

```
aagttccagg agcagctgga ctacaccagc aacgagaccc agatcaaggg cgccgccctg    480
aacgtggagc agctgctgct gggcgccgac ctggtgctga agggccagct gcacatcagc    540
gacctgccca gctacttcca gaacaaggag atcgagttc                           579
```

```
<210> SEQ ID NO 108
<211> LENGTH: 585
<212> TYPE: DNA
<213> ORGANISM: Artificial Sequence
<220> FEATURE:
<223> OTHER INFORMATION: Synthetic Sequence

<400> SEQUENCE: 108
aggaacctgg acaacgtgga gagggacaac aggaaggccg agttcctggc caagaccagc     60 ctgccccca ggttcatcga gctgctgagc atcgcctacg agagcaagag caacagggac    120
ttcgagatga tcaccgccga gctgttcaag gacgtgtacg gcctgggcgc cgtgcacctg    180
ggcaacgcca agaagcccga cgccctggcc ttcaacgacg acttcggcat catcatcgac    240
accaaggcct acagcaacgg ctacagcaag aacatcaacc aggaggacga gatggtgagg    300
tacatcgagg acaaccagat caggagcccc gacaggaaca caacgagtg gtggctgagc     360 ttccccccca gcatccccga gaacgacttc cacttcctgt gggtgagcag ctacttcacc    420
ggcaggttcg aggagcagct gcaggagacc agcgccagga ccggcggcac caccggcggc    480
gccctggacg tggagcagct gctgatcggc ggcagcctga tccaggaggg cagcctggcc    540
ccccacgagg tgcccgccta catgcagaac agggtgatcc acttc                    585
```

```
<210> SEQ ID NO 109
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 109
agccccgtga agagcgaggt gagcgtgttc aaggactacc tgaggaccca cctgacccac     60
gtggaccaca ggtacctgat cctggtggac ctgggcttcg acggcagcag cgacagggac    120
tacgagatga agaccgccga gctgttcacc gccgagctgg gcttcatggg cgccaggctg    180
ggcgacacca ggaagcccga cgtgtgcgtg taccacggcg cccacggcct gatcatcgac    240
aacaaggcct acggcaaggg ctacagcctg cccatcaagc aggccgacga gatctacagg    300
tacatcgagg agaacaagga gagggccgtg aggctgaacc ccaaccagtg gtggaaggtg    360
ttcgacgaga gcgtggccca cttcaggttc gccttcatca gcggcagctt caccggcggc    420
ttcaaggaca ggatcgagct gatcagcatg aggagcggca tctgcggcgc cgccgtgaac    480
agcgtgaacc tgctgctgat ggccgaggag ctgaagagcg gcaggctgaa ctacgaggag    540
tggttccagt acttcgactg caacgacgag atcagcctg                           579
```

```
<210> SEQ ID NO 110
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 110
accctggtgg acatcgagaa ggagaggaag aaggcctact tcctgaagga gaccagcctg     60
agccccaggt acatcgagct gctggagatc gccttcgacc ccaagaggaa cagggacttc    120
```

```
gaggtgatca ccgccgagct gctgaaggcc ggctacggcc tgaaggccaa ggtgctgggc      180
ggcggcagga ggcccgacgg catcgcctac accaaggact acggcctgat cgtggacacc      240
aaggcctaca gcaacggcta cggcaagaac atcggccagg ccgacgagat gatcaggtac      300
atcgaggaca accagaagag ggacaacaag aggaacccca tcgagtggtg gagggagttc      360
gaggtgcaga tccccgccaa cagctactac tacctgtggg tgagcggcag gttcaccggc      420
aggttcgacg agcagctggt gtacaccagc agccagacca caccagggg cggcgccctg       480 gaggtggagc agctgctgtg gggcgccgac gccgtgatga agggcaagct gaacgtgagc      540
gacctgccca gtacatgaa caacagcatc atcaagctg                              579
```

```
<210> SEQ ID NO 111
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 111
gagctgaggg acaaggtgat cgaggagcag aaggccatct tcctgcagaa gaccaagctg       60
cccctgagct acatcgagct gctggagatc gccagggacg gcaagaggag cagggacttc      120
gagctgatca ccatcgagct gttcaagaac atctacaaga tcaacgccag gatcctgggc      180
ggcgccagga agcccgacgg cgtgctgtac atgcccgagt tcggcgtgat cgtggacacc      240
aaggcctacg ccgacggcta cagcaagagc atcgcccagg ccgacgagat gatcaggtac      300
atcgaggaca acaagaggag ggaccccagc aggaacagca ccaagtggtg ggagcacttc      360
cccaccagca tccccgccaa caacttctac ttcctgtggg tgagcagcgt gttcgtgaac      420
aagttccacg agcagctgag ctacaccgcc caggagaccc agaccgtggg cgccgccctg      480
agcgtggagc agctgctgct gggcgccgac agcgtgctga agggcaacct gaccaccgag      540
aagttcatcg acagcttcaa gaaccaggag atcgtgttc                             579
```

```
<210> SEQ ID NO 112
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 112
ggcgccacca gagcgacct gagcctgctg aaggacgaca tcaggaagaa gctgaaccac        60
atcaaccaca gtacctggt gctgatcgac ctgggcttcg acggcaccgc cgacagggac       120
tacgagctgc agaccgccga cctgctgacc agcgagctgg ccttcaaggg cgccaggctg      180
ggcgacagca ggaagcccga cgtgtgcgtg taccacgaca agaacggcct gatcatcgac      240
aacaaggcct acggcagcgg ctacagcctg cccatcaagc aggccgacga gatgctgagg      300
tacatcgagg agaaccagaa gagggacaag gccctgaacc ccaacgagtg gtggaccatc      360
ttcgacgacg ccgtgagcaa gttcaacttc gccttcgtga gcggcgagtt caccggcggc      420
ttcaaggaca ggctggagaa catcagcagg aggagctaca ccaacggcgc cgccatcaac      480
agcgtgaacc tgctgctgct ggccgaggag atcaagagcg gcaggatcag ctacggcgac      540
gccttcacca gttcgagtg caacgacgag atcatcatc                              579
```

```
<210> SEQ ID NO 113
```

```
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 113
gagctgagga acgccgccct ggacaagcag aaggtgaact tcatcaacaa gaccggcctg      60
cccatgaagt acatcgagct gctggagatc gccttcgacg gcagcaggaa cagggacttc     120
gagatggtga ccgccgacct gttcaagaac gtgtacggct caacagcat cctgctgggc      180
ggcggcagga agcccgacgg cctgatcttc accgacaggt tcggcgtgat catcgacacc     240
aaggcctacg gcaacggcta cagcaagagc atcggccagg aggacgagat ggtgaggtac     300
atcgaggaca accagctgag ggacagcaac aggaacagcg tggagtggtg aagaacttc      360
gacgagaaga tcgagagcga gaacttctac ttcatgtgga tcagcagcaa gttcatcggc     420
cagttcagcg accagctgca gagcaccagc gacaggacca acaccaaggg cgccgccctg     480
aacgtggagc agctgctgct gggcgccgcc gccgccaggg acggcaagct ggacatcaac     540
agcctgccca tctacatgaa caacaaggag atcctgtgg                            579

<210> SEQ ID NO 114
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 114
gagctgaagg acgagcagag cgagaagagg aaggcctact tcctgaagga gaccaacctg      60
cccctgaagt acatcgagct gctggacatc gcctacgacg gcaagaggaa cagggacttc     120
gagatcgtga ccatggagct gttcaggaac gtgtacaggc tgcagagcaa gctgctgggc     180
ggcgtgagga agcccgacgg cctgctgtac aagcacaggt tcggcatcat cgtggacacc     240
aaggcctacg gcgagggcta cagcaagagc atcagccagg ccgacgagat gatcaggtac     300
atcgaggaca caagaggag ggacgagaac aggaacagca ccaagtggtg ggagcacttc      360
cccgactgca tccccaagca gagcttctac ttcatgtggg tgagcagcaa gttcgtgggc     420
aagttccagg agcagctgga ctacaccgcc aacgagacca agaccaacgg cgccgccctg     480
aacgtggagc agctgctgtg gggcgccgac ctggtggcca agggcaagct ggacatcagc     540
cagctgccca gctacttcca gaacaaggag atcgagttc                            579

<210> SEQ ID NO 115
<211> LENGTH: 564
<212> TYPE: DNA
<213> ORGANISM: Artificial Sequence
<220> FEATURE:
<223> OTHER INFORMATION: Synthetic Sequence

<400> SEQUENCE: 115
cacaacaaca agttcaagaa ctacctgagg gagaacagcg agctgagctt caagttcatc      60
gagctgatcg acatcgccta cgacggcaac aggaacaggg acatggagat catcaccgcc     120
gagctgctga aggagatcta cggcctgaac gtgaagctgc tgggcggcgg caggaagccc     180
gacatcctgg cctacaccga cgacatcggc atcatcatcg acaccaaggc ctacaaggac     240
ggctacggca gcagatcaa ccaggccgac gagatgatca ggtacatcga ggacaaccag      300
aggagggacc tgatcaggaa ccccaacgag tggtggaggt acttccccaa gagcatcagc     360
```

```
aaggagaaga tctacttcat gtggatcagc agctacttca agaacaactt ctacgagcag    420
gtgcagtaca ccgcccagga gaccaagagc atcggcgccg ccctgaacgt gaggcagctg    480
ctgctgtgcg ccgacgccat ccagaaggag gtgctgagcc tggacacctt cctgggcagc    540
ttcaggaacg aggagatcaa cctg                                           564
```

<210> SEQ ID NO 116
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 116

```
ctgcccgtga agagcgaggt gagcatcctg aaggactacc tgaggagcca cctgacccac     60
atcgaccaca agtacctgat cctggtggac ctgggctacg acggcaccag cgacagggac    120
tacgagatcc agaccgccca gctgctgacc gccgagctga gcttcctggg cggcaggctg    180
ggcgacacca ggaagcccga cgtgtgcatc tactacgagg acaacggcct gatcatcgac    240
aacaaggcct acggcaaggg ctacagcctg cccatgaagc aggccgacga gatgtacagg    300
tacatcgagg agaacaagga gaggagcgag ctgctgaacc ccaactgctg gtggaacatc    360
ttcgacaagg acgtgaagac cttccacttc gccttcctga gcggcgagtt caccggcggc    420
ttcagggaca ggctgaacca catcagcatg aggagcggca tgaggggcgc cgccgtgaac    480
agcgccaacc tgctgatcat ggccgagaag ctgaaggccg gcaccatgga gtacgaggag    540
ttcttcaggc tgttcgacac caacgacgag atcctgttc                           579
```

<210> SEQ ID NO 117
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 117

```
ctgcccgtga agagccaggt gagcatcctg aaggactacc tgaggagcta cctgagccac     60
gtggaccaca agtacctgat cctgctggac ctgggcttcg acggcaccag cgacagggac    120
tacgagatct ggaccgccca gctgctgacc gccgagctga gcttcctggg cggcaggctg    180
ggcgacacca ggaagcccga cgtgtgcatc tactacgagg acaacggcct gatcatcgac    240
aacaaggcct acggcaaggg ctacagcctg cccatcaagc aggccgacga gatgtacagg    300
tacatcgagg agaacaagga gaggagcgac ctgctgaacc ccaactgctg gtggaacatc    360
ttcggcgagg gcgtgaagac cttcaggttc gccttcctga gcggcgagtt caccggcggc    420
ttcaaggaca ggctgaacca catcagcatg aggagcggca tcaagggcgc cgccgtgaac    480
agcgccaacc tgctgatcat ggccgagcag ctgaagagcg gcaccatgag ctacgaggag    540
ttcttccagc tgttcgacta caacgacgag atcatcttc                           579
```

<210> SEQ ID NO 118
<211> LENGTH: 573
<212> TYPE: DNA
<213> ORGANISM: Artificial Sequence
<220> FEATURE:
<223> OTHER INFORMATION: Synthetic Sequence

<400> SEQUENCE: 118

```
gtgagcaaga ccaacatcct ggagctgaag acaacacca gggagaagct ggtgtacctg    60
gaccacaggt acctgagcct gttcgacctg gcctacgacg acaaggccag cagggacttc   120
gagatccaga ccatcgacct gctgatcaac gagctgcagt tcaagggcct gaggctgggc   180
gagaggagga agcccgacgg catcatcagc tacggcgtga acggcgtgat catcgacaac   240
aaggcctaca gcaagggcta caacctgccc atcaggcagg ccgacgagat gatcaggtac   300
atccaggaga accagagcag ggacgagaag ctgaacccca caagtggtg ggagaacttc   360 gaggaggaga ccagcaagtt caactacctg ttcatcagca gcaagttcat cagcggcttc   420
aagaagaacc tgcagtacat cgccgacagg accggcgtga acggcggcgc catcaacgtg   480
gagaacctgc tgtgcttcgc cgagatgctg aagagcggca gctggagta caacgacttc   540 ttcaaccagt acaacaacga cgagatcatc atg                                573

<210> SEQ ID NO 119
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 119
ctgcccgtga agagccaggt gagcatcctg aaggactacc tgaggagctg cctgagccac    60
gtggaccaca agtacctgat cctgctggac ctgggcttcg acggcaccag cgacagggac   120
tacgagatcc agaccgccca gctgctgacc gccgagctga gcttcctggg cggcaggctg   180
ggcgacacca ggaagcccga cgtgtgcatc tactacgagg acaacggcct gatcatcgac   240
aacaaggcct acggcaaggg ctacagcctg cccatcaagc aggccgacga gatgtacagg   300
tacatcgagg agaacaagga gaggagcgag ctgctgaacc ccaactgctg gtggaacatc   360
ttcgacgagg gcgtgaagac cttcaggttc gccttcctga gcggcgagtt caccggcggc   420
ttcaaggaca ggctgaacca catcagcatg aggagcggca tcagggcgc cgccgtgaac   480 agcgccaacc tgctgatcat cgccgagcag ctgaagagcg gcaccatgag ctacgaggag   540
ttcttccagc tgttcgacca gaacgacgag atcaccgtg                          579

<210> SEQ ID NO 120
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 120
atgagcagca agagcgagat cagcgtgatc aaggacaaca tcaggaagag gctgaaccac    60
atcaaccaca agtacctggt gctgatcgac ctgggcttcg acggcaccgc cgacagggac   120
tacgagctgc agaccgccga cctgctgacc agcgagctga gcttcaaggg cgccaggctg   180
ggcgacacca ggaagcccga cgtgtgcgtg taccacggca ccaacggcct gatcatcgac   240
aacaaggcct acggcaaggg ctacagcctg cccatcaagc aggccgacga gatgctgagg   300
tacatcgagg agaaccagaa gagggacaag agcctgaacc ccaacgagtg gtggaccatc   360
ttcgacgacg ccgtgagcaa gttcaacttc gccttcgtga gcggcgagtt caccggcggc   420
ttcaaggaca ggctggagaa catcagcagg aggagcagcg tgaacggcgc cgccatcaac   480
agcgtgaacc tgctgctgct ggccgaggag atcaagagcg gcaggatgag ctacagcgac   540
gccttcaaga acttcgactg caacaaggag atcaccatc                          579
```

<210> SEQ ID NO 121
<211> LENGTH: 585
<212> TYPE: DNA
<213> ORGANISM: Artificial Sequence
<220> FEATURE:
<223> OTHER INFORMATION: Synthetic Sequence

<400> SEQUENCE: 121

```
aggaacctgg acaaggtgga gagggacagc aggaaggccg agttcctggc caagaccagc    60
ctgccccca ggttcatcga gctgctgagc atcgcctacg agagcaagag caacagggac    120
ttcgagatga tcaccgccga gttcttcaag gacgtgtacg gcctgggcgc cgtgcacctg    180
ggcaacgcca ggaagcccga cgccctggcc ttcaccgaca acttcggcat cgtgatcgac    240
accaaggcct acagcaacgg ctacagcaag aacatcaacc aggaggacga gatggtgagg    300
tacatcgagg acaaccagat caggagcccc gagaggaaca gaacgagtg gtggctgagc    360
ttccccccca gcatccccga gaacaacttc cacttcctgt gggtgagcag ctacttcacc    420
ggctacttcg aggagcagct gcaggagacc agcgacaggg ccggcggcat gaccggcggc    480
gccctggaca tcgagcagct gctgatcggc ggcagcctgg tgcaggaggg caagctggcc    540
ccccacgaca tccccgagta catgcagaac aggtgatcc acttc              585
```

<210> SEQ ID NO 122
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 122

```
gccccgtga agagcgaggt gagcctgtgc aaggacatcc tgaggagcca cctgacccac    60
gtggaccaca agtacctgat cctgctggac ctgggcttcg acggcaccag cgacagggac    120
tacgagatcc agaccgccca gctgctgacc gccgagctgg acttcaaggg cgccaggctg    180
ggcgacacca ggaagcccga cgtgtgcgtg tactacggcg aggacggcct gatcctggac    240
aacaaggcct acggcaaggg ctacagcctg cccatcaagc aggccgacga gatgtacagg    300
tacatcgagg agaacaagga gaggaacgag aggctgaacc ccaacaagtg gtgggagatc    360
ttcgacaagg acgtggtgag gtaccacttc gccttcgtga gcggcacctt caccggcggc    420
ttcaaggaga ggctggacaa catcaggatg aggagcggca tctgcggcgc cgccgtgaac    480
agcatgaacc tgctgctgat ggccgaggag ctgaagagcg gcaggctggg ctacaaggag    540
tgcttcgccc tgttcgactg caacgacgag atcgccttc                    579
```

<210> SEQ ID NO 123
<211> LENGTH: 603
<212> TYPE: DNA
<213> ORGANISM: Artificial Sequence
<220> FEATURE:
<223> OTHER INFORMATION: Synthetic Sequence

<400> SEQUENCE: 123

```
agctgcgtga aggacgaggt gaacgacatc gtggacaggg tgagggtgaa gctgaagaac    60
atcgaccaca agtacctgat cctgatcagc ctggcctaca gcgacgagac cgagaggacc    120
aagaagaaca gcgacgccag ggacttcgag atccagaccg ccgagctgtt caccaaggag    180
ctgggcttca acggcatcag gctgggcgag agcaacaagc ccgacgtgct gatcagcttc    240
```

```
ggcgccaacg gcaccatcat cgacaacaag agctacaagg acggcttcaa catccccagg    300
gtgaccagcg accagatgat caggtacatc aacgagaaca accagaggac cacccagctg    360
aaccccaacg agtggtggaa gaacttcgac agcagcgtga gcaactacac cttcctgttc    420
gtgaccagct tcctgaaggg cagcttcaag aaccagatcg agtacatcag caacgccacc    480
aacggcacca ggggcgccgc catcaacgtg gagagcctgc tgtacatcag cgaggacatc    540
aagagcggca agatcaagca gagcgacttc tacagcgagt tcaagaacga cgagatcgtg    600
tac                                                                  603
```

<210> SEQ ID NO 124
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 124

```
agccagggcg acaaggccag ggagcagctg aaggccaagt tcctggccaa gaccaacctg     60
ctgcccaggt acgtggagct gctggacatc gcctacgaca gcaaggagaa cagggacttc    120
gagatggtga ccgccgagct gttcaacttc gcctacctgc tgcccgccgt gcacctgggc    180
ggcgtgagga agcccgacgc cctggtggcc accaagaagt tcggcatcat cgtggacacc    240
aaggcctacg ccaacggcta cagcaggaac gccaaccagg ccgacgagat ggccaggtac    300
atcaccgaga accagaagag ggaccccaag accaacccca caggtggtg gacaacttc      360 gacgccagga tccccccccaa cgcctactac ttcctgtggg tgagcagctt cttcaccggc    420
cagttcgacg accagctgag ctacaccgcc cacaggacca cacccacgg cggcgccctg    480 aacgtggagc agctgctgat cggcgccaac atgatccaga ccggccagct ggacaggaac    540
aagctgcccg agtacatgca ggacaaggag atcaccttc                            579
```

<210> SEQ ID NO 125
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 125

```
aaggtgcaga agagcaacat cctggacgtg atcgagaagt gcagggagaa gatcaacaac     60 atccccacg agtacctggc cctgatcccc atgagcttcg acgagaacga gagcaccatg    120
ttcgagatca agaccatcga gctgctgacc gagcactgca gttcgacgg cctgcactgc    180 ggcggcgcca gcaagcccga cggcctgatc tacagcgagg actacggcgt gatcatcgac    240
accaagagct acaaggacgg cttcaacatc cagacccccg agagggacaa gatgaagagg    300
tacatcgagg agaaccagaa caggaacccc agcacaaca agaccaggtg gtgggacgag    360 ttccccccaca acatcagcaa cttcctgttc ctgttcgtga gcggcaagtt cggcggcaac    420
ttcaaggagc agctgaggat cctgagcgag cagaccaaca cacccctggg cggcgccctg    480
agcagctacg tgctgctgaa catcgccgag cagatcgcca tcaacaagat cgaccactgc    540
gacttcaaga ccaggatcag ctgcctggac gaggtggcc                            579
```

<210> SEQ ID NO 126
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 126

| | | | | | |
|---|---|---|---|---|---|
| gtgcccgtga | agagcgaggt | gagcctgtgc | aaggactacc | tgaggagcta | cctgacccac | 60 |
| gtggaccaca | agtacctgat | cctgctggac | ctgggcttcg | acggcaccag | cgacagggac | 120 |
| tacgagatcc | agaccgccca | gctgctgacc | gccgagctgg | acttcaaggg | cgccaggctg | 180 |
| ggcgacacca | ggaagcccga | cgtgtgcgtg | tactacggcg | aggacggcct | gatcatcgac | 240 |
| aacaaggcct | acggcaaggg | ctacagcctg | cccatcaagc | aggccgacga | gatctacagg | 300 |
| tacatcgagg | agaacaagaa | gagggacgag | aagctgaacc | ccaacaagtg | gtgggagatc | 360 |
| ttcgacaagg | gcgtggtgag | gtaccacttc | gccttcgtga | gcggcgcctt | caccggcggc | 420 |
| ttcaaggaga | ggctggacaa | catcaggatg | aggagcggca | tctgcggcgc | cgccatcaac | 480 |
| agcatgaacc | tgctgctgat | ggccgaggag | ctgaagagcg | gcaggctggg | ctacgaggag | 540 |
| tgcttcgccc | tgttcgactg | caacgacgag | atcaccttc | | | 579 |

<210> SEQ ID NO 127
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 127

| | | | | | |
|---|---|---|---|---|---|
| gtgcccgtga | agagcgaggt | gagcctgtgc | aaggactacc | tgaggagcca | cctgaaccac | 60 |
| gtggaccaca | ggtacctgat | cctgctggac | ctgggcttcg | acggcaccag | cgacagggac | 120 |
| tacgagatcc | agaccgccca | gctgctgacc | ggcgagctga | acttcaaggg | cgccaggctg | 180 |
| ggcgacacca | ggaagcccga | cgtgtgcgtg | tactacggcg | aggacggcct | gatcatcgac | 240 |
| aacaaggcct | acggcaaggg | ctacagcctg | cccatcaagc | aggccgacga | gatgtacagg | 300 |
| tacatcgagg | agaacaagga | gaggaacgag | aagctgaacc | ccaacaagtg | gtgggagatc | 360 |
| ttcgacaagg | acgtgatcca | ctaccacttc | gccttcgtga | gcggcgcctt | caccggcggc | 420 |
| ttcaaggaga | ggctggagaa | catcaggatg | aggagcggca | tctacggcgc | cgccgtgaac | 480 |
| agcatgaacc | tgctgctgat | ggccgaggag | ctgaagagcg | gcaggctgga | ctacaaggag | 540 |
| tgcttcaagc | tgttcgactg | caacgacgag | atcgtgctg | | | 579 |

<210> SEQ ID NO 128
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 128

| | | | | | |
|---|---|---|---|---|---|
| gtgcccgtga | agagcgaggt | gagcctgctg | aaggactacc | tgaggagcca | cctggtgcac | 60 |
| gtggaccaca | agtacctggt | gctgctggac | ctgggcttcg | acggcaccag | cgacagggac | 120 |
| tacgagatcc | agaccgccca | gctgctgacc | ggcgagctga | acttcaaggg | cgccaggctg | 180 |
| ggcgacacca | ggaagcccga | cgtgtgcgtg | tactacggcg | aggacggcct | gatcatcgac | 240 |
| aacaaggcct | acggcaaggg | ctacagcctg | cccatcaagc | aggccgacga | gatgtacagg | 300 |
| tacatcgagg | agaacaagga | gaggaacgag | aagctgaacc | ccaacaagtg | gtgggagatc | 360 |
| ttcggcaacg | acgtgatcca | ctaccacttc | gccttcgtga | gcggcgcctt | caccggcggc | 420 |

| | |
|---|---|
| ttcaaggaga ggctggacaa catcaggatg aggagcggca tctacggcgc cgccgtgaac | 480 |
| agcatgaacc tgctgctgct ggccgaggag ctgaagagcg gcaggctggg ctacaaggag | 540 |
| tgcttcaagc tgttcgactg caacgacgag atcgtgctg | 579 |

<210> SEQ ID NO 129
<211> LENGTH: 603
<212> TYPE: DNA
<213> ORGANISM: Artificial Sequence
<220> FEATURE:
<223> OTHER INFORMATION: Synthetic Sequence

<400> SEQUENCE: 129

| | |
|---|---|
| gagtgcgtga aggacaacgt ggtggacatc aaggacaggg tgaggaacaa gctgatccac | 60 |
| ctggaccaca agtacctggc cctgatcgac ctggcctaca gcgacgccgc cagcagggcc | 120 |
| aagaagaacg ccgacgccag ggagttcgag atccagaccg ccgacctgtt caccaaggag | 180 |
| ctgagcttca cggccagag gctgggcgac agcaggaagc ccgacgtgat catcagctac | 240 |
| ggcctggacg gcaccatcgt ggacaacaag agctacaagg acggcttcaa catcagcagg | 300 |
| acctgcgccg acgagatgag caggtacatc aacgagaaca acctgaggca gaagagcctg | 360 |
| aaccccaacg agtggtggaa gaacttcgac agcaccatca ccgcctacac cttcctgttc | 420 |
| atcaccagct acctgaaggg ccagttcgag gaccagctgg agtacgtgag caacgccaac | 480 |
| ggcggcatca agggcgccgc catcggcgtg gagagcctgc tgtacctgag cgagggcatc | 540 |
| aaggccggca ggatcagcca cgccgacttc tacagcaact tcaacaacaa ggagatgatc | 600 |
| tac | 603 |

<210> SEQ ID NO 130
<211> LENGTH: 576
<212> TYPE: DNA
<213> ORGANISM: Artificial Sequence
<220> FEATURE:
<223> OTHER INFORMATION: Synthetic Sequence

<400> SEQUENCE: 130

| | |
|---|---|
| atcgccaaga gcgacttcag catcatcaag gacaacatca ggaggaagct gcagtacgtg | 60 |
| aaccacaagt acctgctgct gatcgacctg ggcttcgaca gcgacagcaa cagggactac | 120 |
| gagatccaga ccgccgagct gctgaccacc gagctggcct tcaagggcgc caggctgggc | 180 |
| gacaccagga agcccgacgt gtgcgtgtac tacggcgaga acgcctgat catcgacaac | 240 |
| aaggcctaca gcaagggcta cagcctgccc atgagccagg ccgacgagat ggtgaggtac | 300 |
| atcgaggaga acaaggccag gcagagcagc atcaaccca accagtggtg gaagatcttc | 360 |
| gaggacaccg tgtgcaactt caactacgcc ttcgtgagcg cgagttcac cggcggcttc | 420 |
| aaggacaggc tgaacaacat ctgcgagagg accagggtga gcggcggcgc catcaacacc | 480 |
| atcaacctgc tgctgctggc cgaggagctg aagagcggca ggatgagcta ccccaagtgc | 540 |
| ttcagctact tcgacaccaa cgacgaggtg cacatc | 576 |

<210> SEQ ID NO 131
<211> LENGTH: 498
<212> TYPE: DNA
<213> ORGANISM: Artificial Sequence
<220> FEATURE:
<223> OTHER INFORMATION: Synthetic Sequence

<400> SEQUENCE: 131

| | |
|---|---|
| ctgaagtacc tgggcatcaa gaagcagaac agggccttcg agatcatcac cgccgagctg | 60 |

```
ttcaacacca gctacaagct gagcgccacc cacctgggcg gcggcaggag gcccgacgtg    120
ctggtgtaca acgacaactt cggcatcatc gtggacacca aggcctacaa ggacggctac    180
ggcaggaacg tgaaccagga ggacgagatg gtgaggtaca tcaccgagaa caacatcagg    240
aagcaggaca tcaacaagaa cgactggtgg aagtacttca gcaagagcat ccccagcacc    300
agctactacc acctgtggat cagcagccag ttcgtgggca tgttcagcga ccagctgagg    360
gagaccagca gcaggaccgg cgagaacggc ggcgccatga acgtggagca gctgctgatc    420
ggcgccaacc aggtgctgaa caacgtgctg acccccaact gcctgcccaa gtacatggag    480
aacaaggaga tcatcttc                                                  498

<210> SEQ ID NO 132
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 132
gtgcccgtga agagcgaggt gagcctgtgc aaggactacc tgaggagcca cctgaaccac     60
gtggaccaca agtacctgat cctgctggac ctgggcttcg acggcaccag cgacagggac    120
tacgagatcc agaccgccca gctgctgacc ggcgagctga acttcaaggg cgccaggctg    180
ggcgacacca ggaagcccga cgtgtgcgtg tactacggcg aggacggcct gatcatcgac    240
aacaaggcct acggcaaggg ctacagcctg cccatcaagc aggccgacga gatgtacagg    300
tacatcgagg agaacaagga gaggaacgag aagctgaacc ccaacaagtg gtgggagatc    360
ttcgacaagg acgtgatcca ctaccacttc gccttcgtga gcggcgcctt caccggcggc    420
ttcagggaga ggctggagaa catcaggatg aggagcggca tctacggcgc cgccgtgaac    480
agcatgaacc tgctgctgat ggccgaggag ctgaagagcg gcaggctggg ctacaaggag    540
tgcttcaagc tgttcgactg caacgacgag atcgtgctg                           579

<210> SEQ ID NO 133
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 133
gtgcccgtga agagcgaggt gagcctgctg aaggactacc tgaggaccca cctgctgcac     60
gtggaccaca ggtacctgat cctgctggac ctgggcttcg acggcaccag cgacagggac    120
tacgagatcc agaccgccca gctgctgacc ggcgagctga acttcaaggg cgccaggctg    180
ggcgacacca ggaagcccga cgtgtgcgtg tactacggcg aggacggcct gatcatcgac    240
aacaaggcct acggcaaggg ctacagcctg cccatcaagc aggccgacga gatgtacagg    300
tacatcgagg agaacaagga gaggaacgag aagctgaacc ccaacaagtg gtgggagatc    360
ttcgacaacg acgtgatcca ctaccacttc gccttcatca gcggcgcctt caccggcggc    420
ttcaaggaga ggctggacaa catcaggatg aggagcggca tctacggcgc cgccgtgaac    480
agcatgaacc tgctgctgat ggccgaggag ctgaagagcg gcaggctggg ctacaaggag    540
tgcttcaagc tgttcgactg caacgacgag atcgtgctg                           579

<210> SEQ ID NO 134
```

```
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 134
gtgcccgtga agagcgaggt gagcctgtgc aaggactacc tgaggagcca cctgaaccac      60
gtggaccaca agtacctgat cctgctggac ctgggcttcg acggcaccag cgacagggac     120
tacgagatcc agaccgccca gctgctgacc ggcgagctga acttcaaggg cgccaggctg     180
ggcgacacca ggaagcccga cgtgtgcgtg tactacggcg aggacggcct gatcatcgac     240
aacaaggcct acggcaaggg ctacagcctg cccatcaagc aggccgacga gatgtacagg     300
tacatcgagg agaacaagga gaggaacgag aagctgaacc ccaacaagtg gtgggagatc     360
ttcgacaacg acgtgatcca ctaccacttc gccttcgtga gcggcgcctt caccggcggc     420
ttcagggaga ggctggagaa catcaggatg aggagcggca tctacggcgc cgccgtgaac     480
agcatgaacc tgctgctgat ggccgaggag ctgaagagcg gcaggctggg ctacaaggag     540
tgcttcaagc tgttcgactg caacgacgag atcgtgctg                           579

<210> SEQ ID NO 135
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 135
gtgcccgtga agagcgagat gagcctgctg aaggactacc tgaggaccca cctgctgcac      60
gtggaccaca ggtacctgat cctgctggac ctgggcttcg acggcgccag cgacagggac     120
tacgagatcc agaccgccca gctgctgacc ggcgagctga acttcaaggg cgccaggctg     180
ggcgacacca ggaagcccga cgtgtgcgtg tactacggcg aggacggcct gatcatcgac     240
aacaaggcct acggcaaggg ctacagcctg cccatcaagc aggccgacga gatgtacagg     300
tacatcgagg agaacaagga gaggaacgag aagctgaacc ccaacaagtg gtgggagatc     360
ttcgacaacg acgtgatcca ctaccacttc gccttcgtga gcggcgcctt caccggcggc     420
ttcaaggaga ggctggacaa catcaggatg aggagcggca tctacggcgc cgccgtgaac     480
agcatgaacc tgctgctgat ggccgaggag ctgaagagcg gcaggctggg ctacaaggag     540
tgcttcaagc tgttcgactg caacgacgag atcgtgctg                           579

<210> SEQ ID NO 136
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 136
atcctggtgg acaaggagag ggagatgagg aaggccaagt cctgaaggga gaccgtgctg      60
gacagcaagt tcatcagcct gctggacctg gccgccgacg ccaccaagag cagggacttc     120
gagatcgtga ccgccgagct gttcaaggag gcctacaacc tgaacagcgt gctgctgggc     180
ggcagcaaca agcccgacgg cctggtgttc accgacgact cggcatcct gctggacacc     240
aaggcctaca gaacggcett cagcatctac gccaaggaca gggaccagat gatcaggtac     300
gtggacgaca acaacaagag ggacaagatc aggaacccca cgagtggtg aagagcttc     360
```

```
agccccctga tccccaacga caagttctac tacctgtggg tgagcaactt cttcaagggc    420
cagttcaaga accagatcga gtacgtgaac agggagacca acacctacgg cgccgtgctg    480
aacgtggagc agctgctgta cggcgccgac gccgtgatca agggcatcat caaccccaac    540
aagctgcacg agtacttcag caacgacgag atcaagttc                           579
```

<210> SEQ ID NO 137
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 137

```
accgtggacg agaaggagag gctggagctg aaggagtact tcatcagcaa caccaggatc     60
cccagcaagt acatcaccct gctggacctg gcctacgacg gcaacgccaa cagggacttc    120
gagatcgtga ccgccgagct gttcaaggac atcttcaagc tgcagagcaa gcacatgggc    180
ggcaccagga agcccgacat cctgatctgg accgacaagt tcggcgtgat cgccgacacc    240
aaggcctaca gcaagggcta caagaagaac atcagcgagg ccgacaagat ggtgaggtac    300
gtgaacgaga acaccaacag gaacaaggtg gacaacacca cgagtggtg gaacagcttc    360 gacagcagga tccccaagga cgcctactac ttcctgtgga tcagcagcga gttcgtgggc    420
aagttcgacg agcagctgac cgagaccagc agcaggaccg gcaggaacgg cgccagcatc    480
aacgtgtacc agctgctgag gggcgccgac ctggtgcaga agagcaagtt caacatccac    540
gacctgccca acctgatgca gaacaacgag atcaagttc                           579
```

<210> SEQ ID NO 138
<211> LENGTH: 585
<212> TYPE: DNA
<213> ORGANISM: Artificial Sequence
<220> FEATURE:
<223> OTHER INFORMATION: Synthetic Sequence

<400> SEQUENCE: 138

```
accctgcaga agagcgacat cgagaagttc aagaaccagc tgaggaccga gctgaccaac     60
atcgaccaca gctacctgaa gggcatcgac atcgccagca agaagaccac caccaacgtg    120
gagaacaccg agttcgaggc catcagcacc aaggtgttca ccgacgagct gggcttcttc    180
ggcgagcacc tgggcggcag caacaagccc gacggcctga tctgggacaa cgactgcgcc    240
atcatcctgg acagcaaggc ctacagcgag ggcttccccc tgaccgccag ccacaccgac    300
gccatgggca ggtacctgag gcagttcaag gagaggaagg aggagatcaa gcccacctgg    360
tgggacatcg cccccgacaa cctggccaac acctacttcg cctacgtgag cggcagcttc    420
agcggcaact acaaggccca gctgcagaag ttcaggcagg acaccaacca catgggcggc    480
gccctggagt tcgtgaagct gctgctgctg gccaacaact acaaggccca caagatgagc    540
atcaacgagg tgaaggagag catcctggac tacaacatca gctac                    585
```

<210> SEQ ID NO 139
<211> LENGTH: 582
<212> TYPE: DNA
<213> ORGANISM: Artificial Sequence
<220> FEATURE:
<223> OTHER INFORMATION: Synthetic Sequence

<400> SEQUENCE: 139

```
gtgaaggaga agaccgacgc cgccctggtg aaggagaggg tgaggctgca gctgcacaac    60
atcaaccaca agtacctggc cctgatcgac tacgccttca gcggcaagaa caacagcagg   120
gacttcgagg tgtacaccat cgacctgctg gtgaacgagc tgaccttcgg cggcctgcac   180
ctgggcggca ccaggaagcc cgacggcatc ttctaccacg gcagcaacgg catcatcatc   240
gacaacaagg cctacgccaa gggcttcgtg atcaccagga acatggccga cgagatgatc   300
aggtacgtgc aggagaacaa cgacaggaac cccgagagga accccaactg ctggtggaag   360
ggcttccccc acgacgtgac caggtacaac tacgtgttca tcagcagcat gttcaagggc   420
gaggtggagc acatgctgga caacatcagg cagagcaccg gcatcgacgg ctgcgtgctg   480
accatcgaga acctgctgta ctacgccgac gccatcaagg gcggcaccct gagcaaggcc   540
accttcatca acggcttcaa cgccaacaag gagatggtgt tc                     582

<210> SEQ ID NO 140
<211> LENGTH: 585
<212> TYPE: DNA
<213> ORGANISM: Artificial Sequence
<220> FEATURE:
<223> OTHER INFORMATION: Synthetic Sequence

<400> SEQUENCE: 140
gtgaaggaga ccaccgacag cgtgatcatc aaggacaggg tgaggctgaa gctgcaccac    60
gtgaaccaca agtacctgac cctgatcgac tacgccttca gcggcaagaa caactgcatg   120
gacttcgagg tgtacaccat cgacctgctg gtgaacgagc tggccttcaa cggcgtgcac   180
ctgggcggca ccaggaagcc cgacggcatc ttctaccaca acaggaacgg catcatcatc   240
gacaacaagg cctacagcca cggcttcacc ctgagcaggg ccatggccga cgagatgatc   300
aggtacatcc aggagaacaa cgacaggaac cccgagagga accccaacaa gtggtgggag   360
aacttcgaca agggcgtgaa ccagttcaac ttcgtgttca tcagcagcct gttcaagggc   420
gagatcgagc acatgctgac caacatcaag cagagcaccg acggcgtgga gggctgcgtg   480
ctgagcgccg agaacctgct gtacttcgcc gaggccatga gagcggcgt gatgcccaag   540 accgagttca tcagctactt cggcgccggc aaggagatcc agttc                  585

<210> SEQ ID NO 141
<211> LENGTH: 603
<212> TYPE: DNA
<213> ORGANISM: Artificial Sequence
<220> FEATURE:
<223> OTHER INFORMATION: Synthetic Sequence

<400> SEQUENCE: 141
agcgcctgca aggccgacat caccgagctg aaggacaaga tcaggaagag cctgaaggtg    60
ctggaccaca gtacctggt gctggtggac ctggcctaca gcgacgccag caccaagagc   120
aagaagaaca gcgacgccag ggagttcgag atccagaccg ccgacctgtt caccaaggag   180
ctgaagttcg acggcatgag gctgggcgac agcaacaggc ccgacgtgat catcagccac   240
gacaacttcg gcaccatcat cgacaacaag agctacaagg acggcttcaa catcgacaag   300
aagtgcgccg acgagatgag caggtacatc aacgagaacc agaggaggat ccccgagctg   360
cccaagaacg agtggtggaa gaacttcgac gtgaacgtgg acatcttcac cttcctgttc   420
atcaccagct acctgaaggg caacttcaag gaccagctgg agtacatcag caagagccag   480
agcgacatca gggcgccgc catcagcgtg gagcacctgc tgtacatcag cgagaaggtg   540
aagaacggca gcatggacaa ggccgacttc ttcaagctgt tcaacaacga cgagatcagg   600
```

```
gtg                                                             603

<210> SEQ ID NO 142
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 142
gtgctgaagg acaagcacct ggagaagatc aaggagaagt tcctggagaa caccagcctg    60
gaccccaggt tcatcagcct gatcgagatc agcagggaca gaagcagaa cagggccttc   120 gagatcatca ccgccgagct gttcaacacc agctacaacc tgagcgccat ccacctgggc   180
ggcggcagga ggcccgacgt gctggcctac aacgacaact tcggcatcat cgtggacacc   240
aaggcctaca gaacggcta cggcaggaac gtgaaccagg aggacgagat ggtgaggtac   300
atcaccgaga caagatcag gaagcaggac atcagcaaga caactggtg gaagtacttc   360 agcaagagca tccccagcac cagctactac cacctgtgga tcagcagcga gttcgtgggc   420
atgttcagcg accagctgag ggagaccagc agcaggaccg cgagaacgg cggcgccatg   480 aacgtggagc agctgctgat cggcgccaac caggtgctga caacgtgct ggaccccaac   540 aggctgcccg agtacatgga gaacaaggag atcatcttc                         579

<210> SEQ ID NO 143
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 143
gccctgaagg acaagcacct ggagaagatc aaggagaagt tcctggagaa caccagcctg    60
gaccccaggt tcatcagcct gatcgagatc agcagggaca gaagcagaa cagggccttc   120 gagatcatca ccgccgagct gttcaacacc agctacaagc tgagcgccac ccacctgggc   180
ggcggcagga ggcccgacgt gctggtgtac aacgacaact tcggcatcat cgtggacacc   240
aaggcctaca ggacggcta cggcaggaac gtgaaccagg aggacgagat ggtgaggtac   300
atcaccgaga caacatcag gaagcaggac atcaacaaga cgactggtg gaagtacttc   360 agcaagagca tccccagcac cagctactac cacctgtgga tcagcagcca gttcgtgggc   420
atgttcagcg accagctgag ggagaccagc agcaggaccg cgagaacgg cggcgccatg   480 aacgtggagc agctgctgat cggcgccaac caggtgctga caacgtgct ggaccccaac   540 tgcctgccca gtacatgga gaacaaggag atcatcttc                           579

<210> SEQ ID NO 144
<211> LENGTH: 585
<212> TYPE: DNA
<213> ORGANISM: Artificial Sequence
<220> FEATURE:
<223> OTHER INFORMATION: Synthetic Sequence

<400> SEQUENCE: 144
gtgctggaga agagcgacat cgagaagttc aagaaccagc tgaggaccga gctgaccaac    60
atcgaccaca gctacctgaa gggcatcgac atcgccagca agaagaagac cagcaacgtg   120
gagaacaccg agttcgaggc catcagcacc aagatcttca ccgacgagct gggcttcagc   180
```

| | |
|---|---|
| ggcaagcacc tgggcggcag caacaagccc gacggcctgc tgtgggacga cgactgcgcc | 240 |
| atcatcctgg acagcaaggc ctacagcgag ggcttccccc tgaccgccag ccacaccgac | 300 |
| gccatgggca ggtacctgag gcagttcacc gagaggaagg aggagatcaa gcccacctgg | 360 |
| tgggacatcg cccccgagca cctgacaac acctacttcg cctacgtgag cggcagcttc | 420 |
| agcggcaact acaaggagca gctgcagaag ttcaggcagg acaccaacca cctgggcggc | 480 |
| gccctggagt tcgtgaagct gctgctgctg ccaacaact acaagaccca gaagatgagc | 540 |
| aagaaggagg tgaagaagag catcctggac tacaacatca gctac | 585 |

<210> SEQ ID NO 145
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 145

| | |
|---|---|
| gccgaggccg acgtgaccag cgagaagatc aagaaccact tcaggagggt gaccgagctg | 60 |
| cccgagaggt acctggagct gctggacatc gccttcgacc acaagaggaa cagggacttc | 120 |
| gagatggtga ccgccggcct gttcaaggac gtgtacggcc tggagagcgt gcacctgggc | 180 |
| ggcgccaaca gcccgacgg cgtggtgtac aacgacaact cggcatcat cctggacacc | 240 |
| aaggcctacg agaacggcta cggcaagcac atcagccaga tcgacgagat ggtgaggtac | 300 |
| atcgacgaca caggctgag ggacaccacc aggaacccca caagtggtg ggagaacttc | 360 |
| gacgccgaca tccccagcga ccagttctac tacctgtggg tgagcggcaa gttcctgccc | 420 |
| aacttcgccg agcagctgaa gcagaccaac tacaggagcc acgccaacgg cggcggcctg | 480 |
| gaggtgcagc agctgctgct gggcgccgac gccgtgaaga ggaggaagct ggacgtgaac | 540 |
| accatcccca actacatgaa gaacgaggtg atcaccctg | 579 |

<210> SEQ ID NO 146
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 146

| | |
|---|---|
| gccgaggccg acctgaacag cgagaagatc aagaaccact acaggaagat caccaacctg | 60 |
| cccgagaagt acatcgagct gctggacatc gccttcgacc acaggaggca ccaggacttc | 120 |
| gagatcgtga ccgccggcct gttcaaggac tgctacggcc tgagcagcat ccacctgggc | 180 |
| ggccagaaca gcccgacgg cgtggtgttc aacaacaagt cggcatcat cctggacacc | 240 |
| aaggcctacg agaagggcta cggcatgcac atcggccaga tcgacgagat gtgcaggtac | 300 |
| atcgacgaca acaagaagag ggacatcgtg aggcagccca cgagtggtg gaagaacttc | 360 |
| ggcgacaaca tccccaagga ccagttctac tacctgtgga tcagcggcaa gttcctgccc | 420 |
| aggttcaacg agcagctgaa gcagacccac tacaggacca gcatcaacgg cggcggcctg | 480 |
| gaggtgagcc agctgctgct gggcgccaac gccgccatga agggcaagct ggacgtgaac | 540 |
| acccctgccca agcacatgaa caaccaggtg atcaagctg | 579 |

<210> SEQ ID NO 147
<211> LENGTH: 609
<212> TYPE: DNA
<213> ORGANISM: Artificial Sequence

```
<220> FEATURE:
<223> OTHER INFORMATION: Synthetic Sequence

<400> SEQUENCE: 147
gtgctgaagg acgccgccct gcagaagacc aagaacaccc tgctgaacga gctgaccgag      60
atcgaccccg ccgacatcga ggtgatcgag atgagctgga agaaggccac caccaggagc     120
cagaacaccc tggaggccac cctgttcgag gtgaaggtgg tggagatctt caagaagtac     180
ttcgagctga acgcgagca cctgggcggc agaacaggc ccgacggcgc cgtgtactac       240
aacagcacct acggcatcat cctggacacc aaggcctaca gcaacggcta caacatcccc     300
gtggaccagc agagggagat ggtggactac atcaccgacg tgatcgacaa gaaccagaac     360
gtgaccccca acaggtggtg ggaggccttc cccgccaccc tgctgaagaa caacatctac     420
tacctgtggg tggccggcgg cttcaccggc aagtacctgg accagctgac caggacccac     480
aaccagacca acatggacgg cggcgccatg accaccgagg tgctgctgag gctggccaac     540
aaggtgagca gcggcaacct gaagaccacc gacatcccca gctgatgac caacaagctg      600 atcctgagc                                                             609

<210> SEQ ID NO 148
<211> LENGTH: 576
<212> TYPE: DNA
<213> ORGANISM: Artificial Sequence
<220> FEATURE:
<223> OTHER INFORMATION: Synthetic Sequence

<400> SEQUENCE: 148
gccgaggccg acctggacag cgagaggatc aagaaccact acaggaagat caccaacctg      60
cccgagaagt acatcgagct gctggacatc gccttcgacc accacaggca ccaggacttc     120
gagatcatca ccgccggcct gttcaaggac tgctacggcc tgagcagcat ccacctgggc     180
ggccagaaca gcccgacgg cgtggtgttc aacggcaagt tcggcatcat cctggacacc      240
aaggcctacg agaagggcta cggcatgcac atcaaccaga tcgacgagat gtgcaggtac     300
atcgaggaca caagcagag ggacaagatc aggcagccca cgagtggtg gaacaacttc       360 ggcgacaaca tccccgagaa caagttctac tacctgtggg tgagcggcaa gttcctgccc     420
aagttcaacg agcagctgaa gcagacccac tacaggaccg gcatcaacgg cggcggcctg     480
gaggtgagcc agctgctgct gggcgccgac gccgtgatga agggcgccct gaacgtgaac     540
atcctgccca cctacatgca acaacgtg atccag                                 576

<210> SEQ ID NO 149
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 149
gagatcagcg acatcgccct gcagaaggag aaggcctact tctacaagaa caccgccctg      60
agcaagaggc acatcagcat cctggagatc gccttcgacg gcagcaagaa cagggacctg     120
gagatcctga gcgccgaggt gttcaaggac tactaccagc tggagagcat ccacctgggc     180
ggcggcctga gcccgacgg catcgccttc aaccagaact tcggcatcat cgtggacacc      240
aaggcctaca gggcgtgta cagcaggagc agggccgagg ccgacaagat gttcaggtac     300
atcgaggaca caagaagag ggaccccaag aggaaccaga gcctgtggtg gaggagcttc      360
```

```
aacgagcaca tccccgccaa caacttctac ttcctgtgga tcagcggcaa gttccagagg    420
aacttcgaca cccagatcaa ccagctgaac tacgagaccg gctacagggg cggcgccctg    480
agcgccaggc agttcctgat cggcgccgac gccatccaga agggcaagat cgacatcaac    540
gacctgccca gctacttcaa caacagcgtg atcagcttc                          579
```

<210> SEQ ID NO 150
<211> LENGTH: 579
<212> TYPE: DNA
<213> ORGANISM: Artificial Sequence
<220> FEATURE:
<223> OTHER INFORMATION: Synthetic Sequence

<400> SEQUENCE: 150

```
accagcaggg agaagagcag gctgaacctg aaggagtact tcgtgagcaa caccaacctg     60
cccaacaagt tcatcaccct gctggacctg gcctacgacg gcaaggccaa cagggacttc    120
gagctgatca ccagcgagct gttcaggag atctacaagc tgaacaccag gcacctgggc    180
ggcaccagga agcccgacat cctgatctgg aacgagaact tcggcatcat cgccgacacc    240
aaggcctaca gcaagggcta caagaagaac atcagcgagg aggacaagat ggtgaggtac    300
atcgacgaga acatcaagag gagcaaggac tacaaccccca cgagtggtg gaaggtgttc    360 gacaacgaga tcagcagcaa caactacttc tacctgtgga tcagcagcga gttcatcggc    420
aagttcgagg agcagctgca ggagaccgcc cagaggacca cgtgaaggg cgccagcatc    480 aacgtgtacc agctgctgat gggcgcccac aaggtgcaga ccaaggagct gaacgtgaac    540
agcatcccca gtacatgaa caacaccgag atcaagttc                          579
```

<210> SEQ ID NO 151
<211> LENGTH: 603
<212> TYPE: DNA
<213> ORGANISM: Artificial Sequence
<220> FEATURE:
<223> OTHER INFORMATION: Synthetic Sequence

<400> SEQUENCE: 151

```
aactgcatca aggacagcat catcgacatc aaggacaggg tgaggaccaa gctggtgcac     60
ctggaccaca agtacctggc cctgatcgac ctggccttca gcgacgccga caccaggacc    120
aagaagaaca gcgacgccag ggagttcgag atccagaccg ccgacctgtt caccaaggag    180
ctgagcttca acggccagag gctgggcgac agcaggaagc ccgacatcat catcagcttc    240
gacaagatcg gcaccatcat cgacaacaag agctacaagg acggcttcaa catcagcagg    300
ccctgcgccg acgagatgat caggtacatc aacgagaaca acctgaggaa gaagagcctg    360
aacgccaacg agtggtggaa caagttcgac cccaccatca ccgcctacag cttcctgttc    420
atcaccagct acctgaaggg ccagttccag gagcagctgg agtacatcag caacgccaac    480
ggcggcatca agggcgccgc catcggcatc gagaacctgc tgtacctgag cgaggccctg    540
aagagcggca agatcagcca caaggacttc taccagaact tcaacaacaa ggagatcacc    600
tac                                                                 603
```

<210> SEQ ID NO 152
<211> LENGTH: 591
<212> TYPE: DNA
<213> ORGANISM: Artificial Sequence
<220> FEATURE:
<223> OTHER INFORMATION: Synthetic Sequence

<400> SEQUENCE: 152

```
ctgccccaga aggaccaggt gcagcagcag caggacgagc tgaggcccat gctgaagaac      60
gtggaccaca ggtacctgca gctggtggag ctggccctgg acagcgacca gaacagcgag     120
tacagccagt tcgagcagct gaccatggag ctggtgctga agcacctgga cttcgacggc     180
aagcccctgg gcggcagcaa caagcccgac ggcatcgcct gggacaacga cggcaacttc     240
atcatcttcg acaccaaggc ctacaacaag gctacagcc tggccggcaa caccgacaag      300
gtgaagaggt acatcgacga cgtgagggac agggacacca gcaggaccag cacctggtgg     360
cagctggtgc ccaagagcat cgacgtgcac aacctgctga ggttcgtgta cgtgagcggc     420
aacttcaccg gcaactacat gaagctgctg acagcctga ggagctggag caacgcccag      480
ggcggcctgg ccagcgtgga gaagctgctg ctgaccagcg agctgtacct gaggaacatg     540
tacagccacc aggagctgat cgacagctgg accgacaaca cgtgaagca c              591

<210> SEQ ID NO 153
<211> LENGTH: 567
<212> TYPE: DNA
<213> ORGANISM: Artificial Sequence
<220> FEATURE:
<223> OTHER INFORMATION: Synthetic Sequence

<400> SEQUENCE: 153
accaccgacg ccgtggtggt gaaggacagg gccagggtga ggctgcacaa catcaaccac      60
aagtacctga ccctgatcga ctacgccttc agcggcaaga caactgcac cgagttcgag     120 atctacacca tcgacctgct ggtgaacgag ctggccttca cggcatcca cctgggcggc     180 accaggaagc ccgacggcat cttcgactac aaccagcagg catcatcat cgacaacaag     240 gcctacagca agggcttcac catcaccagg agcatggccg acgagatggt gaggtacgtg     300
caggagaaca cgacaggaa ccccgagagg aacaagaccc agtggtggct gaacttcggc      360
gacaacgtga accacttcaa cttcgtgttc atcagcagca tgttcaaggg cgaggtgagg     420
cacatgctga caacatcaa gcagagcacc ggcgtggacg gctgcgtgct gaccgccgag      480
aacctgctgt acttcgccga cgccatcaag ggcggcaccg tgaagaggac cgacttcatc     540
aacctgttcg gcaagaacga cgagctg                                         567

<210> SEQ ID NO 154
<211> LENGTH: 594
<212> TYPE: DNA
<213> ORGANISM: Artificial Sequence
<220> FEATURE:
<223> OTHER INFORMATION: Synthetic Sequence

<400> SEQUENCE: 154
ctgcccaaga aggacaacgt gcagaggcag caggacgagc tgaggcccct gctgaagcac      60
gtggaccaca ggtacctgca gctggtggag ctggccctgg acagcagcca gaacagcgag     120
tacagcatgc tggagagcat gaccatggag ctgctgctga cccacctgga cttcgacggc     180
gccagcctgg gcggcgccag caagcccgac ggcatcgcct gggacaagga cggcaacttc     240
ctgatcgtgg acaccaaggc ctacgacaac ggctacagcc tggccggcaa caccgacaag     300
gtggccaggt acatcgacga cgtgagggcc aaggacccca cagggccag cacctggtgg      360 acccaggtgc ccgagagcct gaacgtggac gacaacctga gcttcatgta cgtgagcggc     420
agcttcaccg gcaactacca gaggctgctg aaggacctga gggccaggac caacgccagg     480
ggcggcctga ccaccgtgga gaagctgctg ctgaccagcg aggcctacct ggccaagagc     540
```

```
ggctacggcc acacccagct gctgaacgac tggaccgacg acaacatcga ccac        594
```

<210> SEQ ID NO 155
<211> LENGTH: 579
<212> TYPE: DNA
<213> ORGANISM: Artificial Sequence
<220> FEATURE:
<223> OTHER INFORMATION: Synthetic Sequence
<400> SEQUENCE: 155

```
cagatcaagg acaagtacct ggaggacctg aagctggagc tgtacaagaa gaccaacctg    60
cccaacaagt actacgagat ggtggacatc gcctacgacg gcaagaggaa cagggagttc   120
gagatctaca ccagcgacct gatgcaggag atctacggct tcaagaccac cctgctgggc   180
ggcaccagga agcccgacgt ggtgagctac agcgacgccc acggctacat catcgacacc   240
aaggcctacg ccaacggcta caggaaggag atcaagcagg aggacgagat ggtgaggtac   300
atcgaggaca accagctgaa ggacgtgctg aggaacccca acaagtggtg ggagtgcttc   360
gacgacgccg agcacaagaa ggagtactac ttcctgtgga tcagcagcaa gttcgtgggc   420
gagttcagca gccagctgca ggacaccagc aggaggaccg gcatcaaggg cggcgccgtg   480
aacatcgtgc agctgctgct gggcgcccac ctggtgtaca cggcgagat cagcaaggac    540
cagttcgccg cctacatgaa caacaccgag atcaacttc                           579
```

<210> SEQ ID NO 156
<211> LENGTH: 438
<212> TYPE: DNA
<213> ORGANISM: Artificial Sequence
<220> FEATURE:
<223> OTHER INFORMATION: Synthetic Sequence
<400> SEQUENCE: 156

```
atgaacccca ggaacgagat cgtgatcgcc aagcacctga gcggcggcaa caggcccgag    60
atcgtgtgct accaccccga ggacaagccc gaccacggcc tgatcctgga cagcaaggcc   120
tacaagagcg gcttcaccat ccccagcggc gagagggaca gatggtgag gtacatcgag    180
gagtacatca ccaagaacca gctgcagaac cccaacgagt ggtggaagaa cctgaagggc   240
gccgagtacc ccggcatcgt gggcttcggc ttcatcagca acagcttcct gggccactac   300
aggaagcagc tggactacat catgaggagg accaagatca agggcagcag catcaccacc   360
gagcacctgc tgaagaccgt ggaggacgtg ctgagcgaga agggcaacgt gatcgacttc   420
ttcaagtact cctggag                                                  438
```

<210> SEQ ID NO 157
<211> LENGTH: 585
<212> TYPE: DNA
<213> ORGANISM: Artificial Sequence
<220> FEATURE:
<223> OTHER INFORMATION: Synthetic Sequence
<400> SEQUENCE: 157

```
gagatcaaga accaggagat cgaggagctg aagcagatcg ccctgaacaa gtacaccgcc    60
ctgcccagcg agtgggtgga gctgatcgag atcagcaggg acaaggacca gagcaccatc   120
ttcgagatga aggtggccga gctgttcaag acctgctaca ggatcaagag cctgcacctg   180
ggcggcgcca gcaagcccga ctgcctgctg tgggacgaca gcttcagcgt gatcgtggac   240
gccaaggcct acaaggacgg cttccccttc caggccagcg agaaggacaa gatggtgagg   300
tacctgaggg agtgcgagag gaaggacaag gccgagaacg ccaccgagtg gtggaacaac   360
```

```
ttcccccccg agctgaacag caaccagctg ttcttcatgt tcgccagcag cttcttcagc    420
agcaccgccg agaagcacct ggagagcgtg agcatcgcca gcaagttcag cggctgcgcc    480
tgggacgtgg acaacctgct gagcggcgcc aacttcttcc tgcagaaccc ccaggccacc    540
ctgcagtacc acctgatcag ggtgttcagc aacaaggtgg tggac                    585

<210> SEQ ID NO 158
<211> LENGTH: 594
<212> TYPE: DNA
<213> ORGANISM: Artificial Sequence
<220> FEATURE:
<223> OTHER INFORMATION: Synthetic Sequence

<400> SEQUENCE: 158
ctgccccaca aggacaacgt gatcaagcag caggacgagc tgaggcccat gctgaagcac     60
gtgaaccaca agtacctgca gctggtggag ctggccttcg agagcagcag gaacagcgag    120
tacagccagt tcgagaccct gaccatggag ctggtgctga agtacctgga cttcagcggc    180
aagagcctgg gcggcgccaa caagcccgac ggcatcgcct gggacccct gggcaacttc     240 ctgatcttcg acaccaaggc ctacaagcac ggctacaccc tgagcaacaa caccgacagg    300
gtggccaggt acatcaacga cgtgagggac aaggacatcc agaggatcag caggtggtgg    360
cagagcatcc ccacctacat cgacgtgaag aacaagctgc agttcgtgta catcagcggc    420
agcttcaccg ccactacct gaggctgctg aacgacctga ggagcaggac cagggccaag    480
ggcggcctgg tgaccgtgga gaagctgctg ctgaccaccg agaggtacct ggccgaggcc    540
gactacaccc acaaggagct gttcgacgac tggatggacg acaacatcga gcac          594

<210> SEQ ID NO 159
<211> LENGTH: 600
<212> TYPE: DNA
<213> ORGANISM: Artificial Sequence
<220> FEATURE:
<223> OTHER INFORMATION: Synthetic Sequence

<400> SEQUENCE: 159
aggatcagcc ccagcaacct ggagcagacc aagcagcagc tgagggagga gctgatcaac     60
ctggaccacc agtacctgga catcctggac ttcagcatcg ccggcaacgt gggcgccagg    120
cagttcgagg tgaggatcgt ggagctgctg aacgagatca tcatcgccaa gcacctgagc    180
ggcggcaaca ggcccgagat catcggcttc aaccccaagg agaaccccga ggactgcatc    240
atcatggaca gcaaggccta caggagggc ttcaacatcc ccgccaacga gagggacaag    300
atgatcaggt acgtggagga gtacaacgcc aaggacaaca ccctgaacaa caacaagtgg    360
tggaagaact tcgagagccc caactacccc accaaccagg tgaagttcag cttcgtgagc    420
agcagcttca tcggccagtt caccaaccag ctgacctaca tcaacaacag gaccaacgtg    480
aacggcagcg ccatcaccgc cgagaccctg ctgaggaagg tggagaacgt gatgaacgtg    540
aacaccgagt acaacctgaa caacttcttc gaggagctgg gcagcaacac cctggtggcc    600

<210> SEQ ID NO 160
<211> LENGTH: 582
<212> TYPE: DNA
<213> ORGANISM: Artificial Sequence
<220> FEATURE:
<223> OTHER INFORMATION: Synthetic Sequence

<400> SEQUENCE: 160
```

| | | |
|---|---|---|
| accttcgaca gcaccgtggc cgacaacctg aagaacctga tcctgcccaa gctgaaggag | | 60 |
| ctggaccaca agtacctgca ggccatcgac atcgcctaca agaggagcaa caccaccaac | | 120 |
| cacgagaaca ccctgctgga ggtgctgagc gccgacctgt tcaccaagga gatggactac | | 180 |
| cacggcaagc acctgggcgg cgccaacaag cccgacggct tcgtgtacga cgaggagacc | | 240 |
| ggctggatcc tggacagcaa ggcctacagg gacggcttcg ccgtgaccgc ccacaccacc | | 300 |
| gacgccatgg gcaggtacat cgaccagtac agggacaggg acgacaagag cacctggtgg | | 360 |
| gaggacttcc ccaaggacct gccccagacc tacttcgcct acgtgagcgg cttctacatc | | 420 |
| ggcaagtacc aggagcagct gcaggacttc gagaacagga agcacatgaa gggcggcctg | | 480 |
| atcgaggtgg ccaagctgat cctgctggcc gagaagtaca aggagaacaa gatcacccac | | 540 |
| gaccagatca ccctgcagat cctgaacgac cacatcagcc ag | | 582 |

<210> SEQ ID NO 161
<211> LENGTH: 558
<212> TYPE: DNA
<213> ORGANISM: Artificial Sequence
<220> FEATURE:
<223> OTHER INFORMATION: Synthetic Sequence

<400> SEQUENCE: 161

| | | |
|---|---|---|
| cccctggacg tggtggagca gatgaaggcc gagctgaggc ccctgctgaa ccacgtgaac | | 60 |
| cacaggctgc tggccatcat cgacttcagc tacaacatga gcagggggcga cgacaagagg | | 120 |
| ctggaggact acaccgccca gatctacaag ctgatcagcc acgacaccca cctgctggcc | | 180 |
| ggccccagca ggcccgacgt ggtgagcgtg atcaacgacc tgggcatcat catcgacagc | | 240 |
| aaggcctaca gcagggctt caacatcccc caggccgagg aggacaagat ggtgaggtac | | 300 |
| ctggacgaga gcatcaggag ggaccccgcc atcaacccca ccaagtggtg ggagtacctg | | 360 |
| ggcgccagca ccgagtacgt gttccagttc gtgagcagca gcttcagcag cggcgccagc | | 420 |
| gccaagctga ggcagatcca caggaggagc agcatcgagg gcagcatcat caccgccaag | | 480 |
| aacctgctgc tgctggccga gaacttcctg tgcaccaaca ccatcaacat cgacctgttc | | 540 |
| aggcagaaca acgagatc | | 558 |

<210> SEQ ID NO 162
<211> LENGTH: 603
<212> TYPE: DNA
<213> ORGANISM: Artificial Sequence
<220> FEATURE:
<223> OTHER INFORMATION: Synthetic Sequence

<400> SEQUENCE: 162

| | | |
|---|---|---|
| cagctggtgc ccagctacat cacccagacc aagctgaggc tgagcggcct gatcaactac | | 60 |
| atcgaccaca gctacttcga cctgatcgac ctgggcttcg acggcaggca gaacaggctg | | 120 |
| tacgagctga ggatcgtgga gctgctgaac ctgatcaaca gcctgaaggc cctgcacctg | | 180 |
| agcggcggca acaggcccga gatcatcgcc tacagccccg acgtgaaccc catcaacggc | | 240 |
| gtgatcatgg acagcaagag ctacagggc ggcttcaaca tccccaacag cgagagggac | | 300 |
| aagatgatca ggtacatcaa cgagtacaac cagaagaacc ccaccctgaa cagcaacagg | | 360 |
| tggtgggaga acttcagggc ccccgactac ccccagagcc ccctgaagta cagcttcgtg | | 420 |
| agcggcaact tcatcggcca gttcctgaac cagatccagt acatcctgac ccagaccggc | | 480 |
| atcaacggcg cgccatcac cagcgagaag ctgatcgaga ggtgaacgc cgtgctgaac | | 540 |
| cccaacatca gctacaccat caacaacttc ttcaacgacc tgggctgcaa caggctggtg | | 600 |

-continued cag                                                                                                          603

<210> SEQ ID NO 163
<211> LENGTH: 196
<212> TYPE: PRT
<213> ORGANISM: Artificial Sequence
<220> FEATURE:
<223> OTHER INFORMATION: Synthetic Sequence

<400> SEQUENCE: 163

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195

<210> SEQ ID NO 164

<400> SEQUENCE: 164

000

<210> SEQ ID NO 165
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 165
ggcggtggcg gagggatgga tgctaagtca ctaactgcct ggtcc                            45

<210> SEQ ID NO 166
<211> LENGTH: 15
<212> TYPE: PRT
<213> ORGANISM: Artificial Sequence
<220> FEATURE:
<223> OTHER INFORMATION: Synthetic Sequence

```
<400> SEQUENCE: 166

Gly Gly Gly Gly Gly Met Asp Ala Lys Ser Leu Thr Ala Trp Ser
1               5                   10                  15

<210> SEQ ID NO 167

<400> SEQUENCE: 167

000

<210> SEQ ID NO 168
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 168

Leu Asp Thr Glu Gln Val Val Ala Ile Ala Ser His Asn Gly Gly Lys
1               5                   10                  15

Gln Ala Leu Glu Ala Val Lys Ala Asp Leu Leu Asp Leu Leu Gly Ala
            20                  25                  30

Pro Tyr Val
        35

<210> SEQ ID NO 169
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 169

Leu Asp Thr Glu Gln Val Val Ala Ile Ala Ser His Asn Gly Gly Lys
1               5                   10                  15

Gln Ala Leu Glu Ala Val Lys Ala Asp Leu Leu Asp Leu Arg Gly Ala
            20                  25                  30

Pro Tyr Ala
        35

<210> SEQ ID NO 170
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 170

Leu Asp Thr Glu Gln Val Val Ala Ile Ala Ser His Asn Gly Gly Lys
1               5                   10                  15

Gln Ala Leu Glu Ala Val Lys Ala Asp Leu Leu Glu Leu Arg Gly Ala
            20                  25                  30

Pro Tyr Ala
        35

<210> SEQ ID NO 171
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 171
```

-continued

```
Leu Asp Thr Glu Gln Val Val Ala Ile Ala Ser His Asn Gly Gly Lys
1               5                   10                  15

Gln Ala Leu Glu Ala Val Lys Ala His Leu Leu Asp Leu Arg Gly Ala
            20                  25                  30

Pro Tyr Ala
        35

<210> SEQ ID NO 172
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 172

Leu Asn Thr Glu Gln Val Val Ala Ile Ala Ser His Asn Gly Gly Lys
1               5                   10                  15

Gln Ala Leu Glu Ala Val Lys Ala Asp Leu Leu Asp Leu Arg Gly Ala
            20                  25                  30

Pro Tyr Ala
        35

<210> SEQ ID NO 173
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 173

Leu Asn Thr Glu Gln Val Val Ala Ile Ala Ser Asn Asn Gly Gly Lys
1               5                   10                  15

Gln Ala Leu Glu Ala Val Lys Thr His Leu Leu Asp Leu Arg Gly Ala
            20                  25                  30

Arg Tyr Ala
        35

<210> SEQ ID NO 174
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 174

Leu Asn Thr Glu Gln Val Val Ala Ile Ala Ser Asn Pro Gly Gly Lys
1               5                   10                  15

Gln Ala Leu Glu Ala Val Arg Ala Leu Phe Pro Asp Leu Arg Ala Ala
            20                  25                  30

Pro Tyr Ala
        35

<210> SEQ ID NO 175
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 175

Leu Asn Thr Glu Gln Val Val Ala Ile Ala Ser Ser His Gly Gly Lys
1               5                   10                  15
```

Gln Ala Leu Glu Ala Val Arg Ala Leu Phe Pro Asp Leu Arg Ala Ala
            20                  25                  30

Pro Tyr Ala
        35

<210> SEQ ID NO 176
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 176

Leu Asn Thr Glu Gln Val Val Ala Val Ala Ser Asn Lys Gly Gly Lys
1               5                   10                  15

Gln Ala Leu Glu Ala Val Gly Ala Gln Leu Leu Ala Leu Arg Ala Val
            20                  25                  30

Pro Tyr Ala
        35

<210> SEQ ID NO 177
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 177

Leu Asn Thr Glu Gln Val Val Ala Val Ala Ser Asn Lys Gly Gly Lys
1               5                   10                  15

Gln Ala Leu Glu Ala Val Gly Ala Gln Leu Leu Ala Leu Arg Ala Val
            20                  25                  30

Pro Tyr Glu
        35

<210> SEQ ID NO 178
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 178

Leu Ser Ala Ala Gln Val Val Ala Ile Ala Ser His Asp Gly Gly Lys
1               5                   10                  15

Gln Ala Leu Glu Ala Val Gly Thr Gln Leu Val Ala Leu Arg Ala Ala
            20                  25                  30

Pro Tyr Ala
        35

<210> SEQ ID NO 179
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 179

Leu Ser Ile Ala Gln Val Val Ala Val Ala Ser Arg Ser Gly Gly Lys
1               5                   10                  15

Gln Ala Leu Glu Ala Val Arg Ala Gln Leu Leu Ala Leu Arg Ala Ala
            20                  25                  30

```
Pro Tyr Gly
        35

<210> SEQ ID NO 180
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 180

Leu Ser Pro Glu Gln Val Val Ala Ile Ala Ser Asn His Gly Gly Lys
1               5                   10                  15

Gln Ala Leu Glu Ala Val Arg Ala Leu Phe Arg Gly Leu Arg Ala Ala
            20                  25                  30

Pro Tyr Gly
        35

<210> SEQ ID NO 181
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 181

Leu Ser Pro Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu
        35

<210> SEQ ID NO 182
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 182

Leu Ser Thr Ala Gln Leu Val Ala Ile Ala Ser Asn Pro Gly Gly Lys
1               5                   10                  15

Gln Ala Leu Glu Ala Ile Arg Ala Leu Phe Arg Glu Leu Arg Ala Ala
            20                  25                  30

Pro Tyr Ala
        35

<210> SEQ ID NO 183
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 183

Leu Ser Thr Ala Gln Leu Val Ala Ile Ala Ser Asn Pro Gly Gly Lys
1               5                   10                  15

Gln Ala Leu Glu Ala Val Arg Ala Leu Phe Arg Glu Leu Arg Ala Ala
            20                  25                  30

Pro Tyr Ala
        35
```

<210> SEQ ID NO 184
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 184

Leu Ser Thr Ala Gln Leu Val Ala Ile Ala Ser Asn Pro Gly Gly Lys
1               5                   10                  15

Gln Ala Leu Glu Ala Val Arg Ala Pro Phe Arg Glu Val Arg Ala Ala
            20                  25                  30

Pro Tyr Ala
        35

<210> SEQ ID NO 185
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 185

Leu Ser Thr Ala Gln Leu Val Ser Ile Ala Ser Asn Pro Gly Gly Lys
1               5                   10                  15

Gln Ala Leu Glu Ala Val Arg Ala Leu Phe Arg Glu Leu Arg Ala Ala
            20                  25                  30

Pro Tyr Ala
        35

<210> SEQ ID NO 186
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 186

Leu Ser Thr Ala Gln Val Ala Ala Ile Ala Ser His Asp Gly Gly Lys
1               5                   10                  15

Gln Ala Leu Glu Ala Val Gly Thr Gln Leu Val Val Leu Arg Ala Ala
            20                  25                  30

Pro Tyr Ala
        35

<210> SEQ ID NO 187
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 187

Leu Ser Thr Ala Gln Val Ala Thr Ile Ala Ser Ser Ile Gly Gly Arg
1               5                   10                  15

Gln Ala Leu Glu Ala Leu Lys Val Gln Leu Pro Val Leu Arg Ala Ala
            20                  25                  30

Pro Tyr Gly
        35

<210> SEQ ID NO 188
<211> LENGTH: 35

```
<212> TYPE: PRT
<213> ORGANISM: Artificial Sequence
<220> FEATURE:
<223> OTHER INFORMATION: Synthetic Sequence

<400> SEQUENCE: 188

Leu Ser Thr Ala Gln Val Ala Thr Ile Ala Ser Ser Ile Gly Gly Arg
1               5                   10                  15

Gln Ala Leu Glu Ala Val Lys Val Gln Leu Pro Val Leu Arg Ala Ala
            20                  25                  30

Pro Tyr Gly
        35

<210> SEQ ID NO 189
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 189

Leu Ser Thr Ala Gln Val Val Ala Ile Ala Ala Asn Asn Gly Gly Lys
1               5                   10                  15

Gln Ala Leu Glu Ala Val Arg Ala Leu Leu Pro Val Leu Arg Val Ala
            20                  25                  30

Pro Tyr Glu
        35

<210> SEQ ID NO 190
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 190

Leu Ser Thr Ala Gln Val Val Ala Ile Ala Gly Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 191
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 191

Leu Ser Thr Ala Gln Val Val Ala Ile Ala Ser His Asp Gly Gly Lys
1               5                   10                  15

Gln Ala Leu Glu Ala Ala Gly Thr Gln Leu Val Ala Leu Arg Ala Ala
            20                  25                  30

Pro Tyr Ala
        35

<210> SEQ ID NO 192
<211> LENGTH: 35
<212> TYPE: PRT
<213> ORGANISM: Artificial Sequence
<220> FEATURE:
```

<223> OTHER INFORMATION: Synthetic Sequence

<400> SEQUENCE: 192

Leu Ser Thr Ala Gln Val Val Ala Ile Ala Ser His Asp Gly Gly Lys
1               5                   10                  15

Gln Ala Leu Glu Ala Val Gly Ala Gln Leu Val Glu Leu Arg Ala Ala
            20                  25                  30

Pro Tyr Ala
        35

<210> SEQ ID NO 193
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 193

Leu Ser Thr Ala Gln Val Val Ala Ile Ala Ser His Asp Gly Gly Lys
1               5                   10                  15

Gln Ala Leu Glu Ala Val Gly Thr Gln Leu Val Ala Leu Arg Ala Ala
            20                  25                  30

Pro Tyr Ala
        35

<210> SEQ ID NO 194
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 194

Leu Ser Thr Ala Gln Val Val Ala Ile Ala Ser His Asp Gly Gly Asn
1               5                   10                  15

Gln Ala Leu Glu Ala Val Gly Thr Gln Leu Val Ala Leu Arg Ala Ala
            20                  25                  30

Pro Tyr Ala
        35

<210> SEQ ID NO 195
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 195

Leu Ser Thr Ala Gln Val Val Ala Ile Ala Ser His Asn Gly Gly Lys
1               5                   10                  15

Gln Ala Leu Glu Ala Val Lys Ala Gln Leu Leu Asp Leu Arg Gly Ala
            20                  25                  30

Pro Tyr Ala
        35

<210> SEQ ID NO 196
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 196

```
Leu Ser Thr Ala Gln Val Val Ala Ile Ala Ser Asn Asp Gly Gly Lys
1               5                   10                  15

Gln Ala Leu Glu Val Glu Ala Gln Leu Leu Ala Leu Arg Ala Ala
            20                  25                  30

Pro Tyr Glu
        35

<210> SEQ ID NO 197
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 197

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 198
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 198

Leu Ser Thr Ala Gln Val Val Ala Ile Ala Ser Asn Gly Gly Gly Lys
1               5                   10                  15

Gln Ala Leu Glu Gly Ile Gly Glu Gln Leu Arg Lys Leu Arg Thr Ala
            20                  25                  30

Pro Tyr Gly
        35

<210> SEQ ID NO 199
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 199

Leu Ser Thr Ala Gln Val Val Ala Ile Ala Ser Asn Pro Gly Gly Lys
1               5                   10                  15

Gln Ala Leu Glu Ala Val Arg Ala Leu Phe Arg Glu Leu Arg Ala Ala
            20                  25                  30

Pro Tyr Ala
        35

<210> SEQ ID NO 200
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 200

Leu Ser Thr Ala Gln Val Val Ala Ile Ala Ser Gln Asn Gly Gly Lys
1               5                   10                  15
```

-continued

Gln Ala Leu Glu Ala Val Lys Ala Gln Leu Leu Asp Leu Arg Gly Ala
            20                  25                  30

Pro Tyr Ala
        35

<210> SEQ ID NO 201
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 201

Leu Ser Thr Ala Gln Val Val Ala Ile Ala Ser Ser His Gly Gly Lys
1               5                   10                  15

Gln Ala Leu Glu Ala Val Arg Ala Leu Phe Arg Glu Leu Arg Ala Ala
            20                  25                  30

Pro Tyr Gly
        35

<210> SEQ ID NO 202
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 202

Leu Ser Thr Ala Gln Val Val Ala Ile Ala Ser Ser Asn Gly Gly Lys
1               5                   10                  15

Gln Ala Leu Glu Ala Val Trp Ala Leu Leu Pro Val Leu Arg Ala Thr
            20                  25                  30

Pro Tyr Asp
        35

<210> SEQ ID NO 203
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 203

Leu Ser Thr Ala Gln Val Val Ala Ile Ala Thr Arg Ser Gly Gly Lys
1               5                   10                  15

Gln Ala Leu Glu Ala Val Arg Ala Gln Leu Leu Asp Leu Arg Ala Ala
            20                  25                  30

Pro Tyr Gly
        35

<210> SEQ ID NO 204
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 204

Leu Ser Thr Ala Gln Val Val Ala Val Ala Gly Arg Asn Gly Gly Lys
1               5                   10                  15

Gln Ala Leu Glu Ala Val Arg Ala Gln Leu Pro Ala Leu Arg Ala Ala
            20                  25                  30

Pro Tyr Gly
        35

<210> SEQ ID NO 205
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 205

Leu Ser Thr Ala Gln Val Val Ala Val Ala Ser Ser Asn Gly Gly Lys
1               5                   10                  15

Gln Ala Leu Glu Ala Val Trp Ala Leu Leu Pro Val Leu Arg Ala Thr
            20                  25                  30

Pro Tyr Asp
        35

<210> SEQ ID NO 206
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 206

Leu Ser Thr Ala Gln Val Val Thr Ile Ala Ser Ser Asn Gly Gly Lys
1               5                   10                  15

Gln Ala Leu Glu Ala Val Trp Ala Leu Leu Pro Val Leu Arg Ala Thr
            20                  25                  30

Pro Tyr Asp
        35

<210> SEQ ID NO 207
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 207

Leu Ser Thr Glu Gln Val Val Ala Ile Ala Gly His Asp Gly Gly Lys
1               5                   10                  15

Gln Ala Leu Glu Ala Val Gly Ala Gln Leu Val Ala Leu Arg Ala Ala
            20                  25                  30

Pro Tyr Ala
        35

<210> SEQ ID NO 208
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 208

Leu Ser Thr Glu Gln Val Val Ala Ile Ala Ser His Asp Gly Gly Lys
1               5                   10                  15

Gln Ala Leu Glu Ala Val Gly Ala Gln Leu Val Ala Leu Leu Ala Ala
            20                  25                  30

Pro Tyr Ala
        35

<210> SEQ ID NO 209
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 209

Leu Ser Thr Glu Gln Val Val Ala Ile Ala Ser His Asp Gly Gly Lys
1               5                   10                  15

Gln Ala Leu Glu Ala Val Gly Ala Gln Leu Val Ala Leu Arg Ala Ala
            20                  25                  30

Pro Tyr Ala
        35

<210> SEQ ID NO 210
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 210

Leu Ser Thr Glu Gln Val Val Ala Ile Ala Ser His Asp Gly Gly Lys
1               5                   10                  15

Gln Ala Leu Glu Ala Val Gly Gly Gln Leu Val Ala Leu Arg Ala Ala
            20                  25                  30

Pro Tyr Ala
        35

<210> SEQ ID NO 211
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 211

Leu Ser Thr Glu Gln Val Val Ala Ile Ala Ser His Asp Gly Gly Lys
1               5                   10                  15

Gln Ala Leu Glu Ala Val Gly Thr Gln Leu Val Ala Leu Arg Ala Ala
            20                  25                  30

Pro Tyr Ala
        35

<210> SEQ ID NO 212
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 212

Leu Ser Thr Glu Gln Val Val Ala Ile Ala Ser His Asp Gly Gly Lys
1               5                   10                  15

Gln Ala Leu Glu Ala Val Gly Val Gln Leu Val Ala Leu Arg Ala Ala
            20                  25                  30

Pro Tyr Ala
        35

<210> SEQ ID NO 213

```
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 213

Leu Ser Thr Glu Gln Val Val Ala Ile Ala Ser His Asp Gly Gly Lys
 1               5                  10                  15

Gln Ala Leu Glu Ala Val Val Ala Gln Leu Val Ala Leu Arg Ala Ala
            20                  25                  30

Pro Tyr Ala
        35

<210> SEQ ID NO 214
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 214

Leu Ser Thr Glu Gln Val Val Ala Ile Ala Ser His Asp Gly Gly Lys
 1               5                  10                  15

Gln Pro Leu Glu Ala Val Gly Ala Gln Leu Val Ala Leu Arg Ala Ala
            20                  25                  30

Pro Tyr Ala
        35

<210> SEQ ID NO 215
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 215

Leu Ser Thr Glu Gln Val Val Ala Ile Ala Ser His Gly Gly Gly Lys
 1               5                  10                  15

Gln Val Leu Glu Gly Ile Gly Glu Gln Leu Leu Lys Leu Arg Ala Ala
            20                  25                  30

Pro Tyr Gly
        35

<210> SEQ ID NO 216
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 216

Leu Ser Thr Glu Gln Val Val Ala Ile Ala Ser His Lys Gly Gly Lys
 1               5                  10                  15

Gln Ala Leu Glu Gly Ile Gly Glu Gln Leu Leu Lys Leu Arg Ala Ala
            20                  25                  30

Pro Tyr Gly
        35

<210> SEQ ID NO 217
<211> LENGTH: 35
<212> TYPE: PRT
<213> ORGANISM: Artificial Sequence
```

<220> FEATURE:
<223> OTHER INFORMATION: Synthetic Sequence

<400> SEQUENCE: 217

Leu Ser Thr Glu Gln Val Val Ala Ile Ala Ser His Asn Gly Gly Lys
1               5                   10                  15

Gln Ala Leu Glu Ala Val Lys Ala Asp Leu Leu Asp Leu Arg Gly Ala
            20                  25                  30

Pro Tyr Ala
        35

<210> SEQ ID NO 218
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 218

Leu Ser Thr Glu Gln Val Val Ala Ile Ala Ser His Asn Gly Gly Lys
1               5                   10                  15

Gln Ala Leu Glu Ala Val Lys Ala Asp Leu Leu Glu Leu Arg Gly Ala
            20                  25                  30

Pro Tyr Ala
        35

<210> SEQ ID NO 219
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 219

Leu Ser Thr Glu Gln Val Val Ala Ile Ala Ser His Asn Gly Gly Lys
1               5                   10                  15

Gln Ala Leu Glu Ala Val Lys Ala His Leu Leu Asp Leu Arg Gly Ala
            20                  25                  30

Pro Tyr Ala
        35

<210> SEQ ID NO 220
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 220

Leu Ser Thr Glu Gln Val Val Ala Ile Ala Ser His Asn Gly Gly Lys
1               5                   10                  15

Gln Ala Leu Glu Ala Val Lys Ala His Leu Leu Asp Leu Arg Gly Val
            20                  25                  30

Pro Tyr Ala
        35

<210> SEQ ID NO 221
<211> LENGTH: 35
<212> TYPE: PRT
<213> ORGANISM: Artificial Sequence
<220> FEATURE:
<223> OTHER INFORMATION: Synthetic Sequence

```
<400> SEQUENCE: 221

Leu Ser Thr Glu Gln Val Val Ala Ile Ala Ser His Asn Gly Gly Lys
1               5                   10                  15

Gln Ala Leu Glu Ala Val Lys Ala His Leu Leu Glu Leu Arg Gly Ala
            20                  25                  30

Pro Tyr Ala
        35

<210> SEQ ID NO 222
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 222

Leu Ser Thr Glu Gln Val Val Ala Ile Ala Ser His Asn Gly Gly Lys
1               5                   10                  15

Gln Ala Leu Glu Ala Val Lys Ala Gln Leu Leu Asp Leu Arg Gly Ala
            20                  25                  30

Pro Tyr Ala
        35

<210> SEQ ID NO 223
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 223

Leu Ser Thr Glu Gln Val Val Ala Ile Ala Ser His Asn Gly Gly Lys
1               5                   10                  15

Gln Ala Leu Glu Ala Val Lys Ala Gln Leu Leu Glu Leu Arg Gly Ala
            20                  25                  30

Pro Tyr Ala
        35

<210> SEQ ID NO 224
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 224

Leu Ser Thr Glu Gln Val Val Ala Ile Ala Ser His Asn Gly Gly Lys
1               5                   10                  15

Gln Ala Leu Glu Ala Val Lys Ala Gln Leu Pro Val Leu Arg Arg Ala
            20                  25                  30

Pro Tyr Gly
        35

<210> SEQ ID NO 225
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 225

Leu Ser Thr Glu Gln Val Val Ala Ile Ala Ser His Asn Gly Gly Lys
```

```
1               5                   10                  15
Gln Ala Leu Glu Ala Val Lys Thr Gln Leu Leu Glu Leu Arg Gly Ala
            20                  25                  30

Pro Tyr Ala
        35

<210> SEQ ID NO 226
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 226

Leu Ser Thr Glu Gln Val Val Ala Ile Ala Ser His Asn Gly Gly Lys
1               5                   10                  15

Gln Ala Leu Glu Ala Val Arg Ala Gln Leu Pro Ala Leu Arg Ala Ala
            20                  25                  30

Pro Tyr Gly
        35

<210> SEQ ID NO 227
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 227

Leu Ser Thr Glu Gln Val Val Ala Ile Ala Ser His Asn Gly Ser Lys
1               5                   10                  15

Gln Ala Leu Glu Ala Val Lys Ala Gln Leu Leu Asp Leu Arg Gly Ala
            20                  25                  30

Pro Tyr Ala
        35

<210> SEQ ID NO 228
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 228

Leu Ser Thr Glu Gln Val Val Ala Ile Ala Ser Asn Gly Gly Gly Lys
1               5                   10                  15

Gln Ala Leu Glu Gly Ile Gly Lys Gln Leu Gln Glu Leu Arg Ala Ala
            20                  25                  30

Pro His Gly
        35

<210> SEQ ID NO 229
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 229

Leu Ser Thr Glu Gln Val Val Ala Ile Ala Ser Asn Gly Gly Gly Lys
1               5                   10                  15

Gln Ala Leu Glu Gly Ile Gly Lys Gln Leu Gln Glu Leu Arg Ala Ala
```

```
            20                  25                  30

Pro Tyr Gly
        35

<210> SEQ ID NO 230
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 230

Leu Ser Thr Glu Gln Val Val Ala Ile Ala Ser Asn His Gly Gly Lys
1               5                  10                  15

Gln Ala Leu Glu Ala Val Arg Ala Leu Phe Arg Glu Leu Arg Ala Ala
            20                  25                  30

Pro Tyr Ala
        35

<210> SEQ ID NO 231
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 231

Leu Ser Thr Glu Gln Val Val Ala Ile Ala Ser Asn His Gly Gly Lys
1               5                  10                  15

Gln Ala Leu Glu Ala Val Arg Ala Leu Phe Arg Gly Leu Arg Ala Ala
            20                  25                  30

Pro Tyr Gly
        35

<210> SEQ ID NO 232
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 232

Leu Ser Thr Glu Gln Val Val Ala Ile Ala Ser Asn Lys Gly Gly Lys
1               5                  10                  15

Gln Ala Leu Glu Ala Val Lys Ala Asp Leu Leu Asp Leu Arg Gly Ala
            20                  25                  30

Pro Tyr Val
        35

<210> SEQ ID NO 233
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 233

Leu Ser Thr Glu Gln Val Val Ala Ile Ala Ser Asn Lys Gly Gly Lys
1               5                  10                  15

Gln Ala Leu Glu Ala Val Lys Ala His Leu Leu Asp Leu Leu Gly Ala
            20                  25                  30

Pro Tyr Val
```

35

<210> SEQ ID NO 234
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 234

Leu Ser Thr Glu Gln Val Val Ala Ile Ala Ser Asn Lys Gly Gly Lys
1               5                   10                  15

Gln Ala Leu Glu Ala Val Lys Ala Gln Leu Leu Ala Leu Arg Ala Ala
            20                  25                  30

Pro Tyr Ala
        35

<210> SEQ ID NO 235
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 235

Leu Ser Thr Glu Gln Val Val Ala Ile Ala Ser Asn Lys Gly Gly Lys
1               5                   10                  15

Gln Ala Leu Glu Ala Val Lys Ala Gln Leu Leu Glu Leu Arg Gly Ala
            20                  25                  30

Pro Tyr Ala
        35

<210> SEQ ID NO 236
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 236

Leu Ser Thr Glu Gln Val Val Ala Ile Ala Ser Asn Asn Gly Gly Lys
1               5                   10                  15

Gln Ala Leu Glu Ala Val Lys Ala Leu Leu Leu Glu Leu Arg Ala Ala
            20                  25                  30

Pro Tyr Glu
        35

<210> SEQ ID NO 237
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 237

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Ala Leu Arg Ala Ala
            20                  25                  30

Pro Tyr Glu
        35

```
<210> SEQ ID NO 238
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 238

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Asp Leu Arg Gly Ala
            20                  25                  30

Pro Tyr Ala
        35

<210> SEQ ID NO 239
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 239

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Val Leu Arg Ala Ala
            20                  25                  30

Pro Tyr Gly
        35

<210> SEQ ID NO 240
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 240

Leu Ser Thr Glu Gln Val Val Ala Ile Ala Ser Asn Asn Gly Gly Lys
1               5                   10                  15

Gln Ala Leu Glu Ala Val Lys Ala Gln Leu Pro Ala Leu Arg Ala Ala
            20                  25                  30

Pro Tyr Glu
        35

<210> SEQ ID NO 241
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 241

Leu Ser Thr Glu Gln Val Val Ala Ile Ala Ser Asn Asn Gly Gly Lys
1               5                   10                  15

Gln Ala Leu Glu Ala Val Lys Ala Gln Leu Pro Val Leu Arg Arg Ala
            20                  25                  30

Pro Cys Gly
        35

<210> SEQ ID NO 242
<211> LENGTH: 35
<212> TYPE: PRT
```

```
<213> ORGANISM: Artificial Sequence
<220> FEATURE:
<223> OTHER INFORMATION: Synthetic Sequence

<400> SEQUENCE: 242

Leu Ser Thr Glu Gln Val Val Ala Ile Ala Ser Asn Asn Gly Gly Lys
1               5                   10                  15

Gln Ala Leu Glu Ala Val Lys Ala Gln Leu Pro Val Leu Arg Arg Ala
            20                  25                  30

Pro Tyr Gly
        35

<210> SEQ ID NO 243
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 243

Leu Ser Thr Glu Gln Val Val Ala Ile Ala Ser Asn Asn Gly Gly Lys
1               5                   10                  15

Gln Ala Leu Glu Ala Val Lys Ala Arg Leu Leu Asp Leu Arg Gly Ala
            20                  25                  30

Pro Tyr Ala
        35

<210> SEQ ID NO 244
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 244

Leu Ser Thr Glu Gln Val Val Ala Ile Ala Ser Asn Asn Gly Gly Lys
1               5                   10                  15

Gln Ala Leu Glu Ala Val Lys Thr Gln Leu Leu Ala Leu Arg Thr Ala
            20                  25                  30

Pro Tyr Glu
        35

<210> SEQ ID NO 245
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 245

Leu Ser Thr Glu Gln Val Val Ala Ile Ala Ser Asn Pro Gly Gly Lys
1               5                   10                  15

Gln Ala Leu Glu Ala Val Arg Ala Leu Phe Pro Asp Leu Arg Ala Ala
            20                  25                  30

Pro Tyr Ala
        35

<210> SEQ ID NO 246
<211> LENGTH: 35
<212> TYPE: PRT
<213> ORGANISM: Artificial Sequence
<220> FEATURE:
<223> OTHER INFORMATION: Synthetic Sequence
```

```
<400> SEQUENCE: 246

Leu Ser Thr Glu Gln Val Val Ala Ile Ala Ser Ser His Gly Gly Lys
1               5                   10                  15

Gln Ala Leu Glu Ala Val Arg Ala Leu Phe Pro Asp Leu Arg Ala Ala
            20                  25                  30

Pro Tyr Ala
        35

<210> SEQ ID NO 247
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 247

Leu Ser Thr Glu Gln Val Val Ala Ile Ala Ser Ser His Gly Gly Lys
1               5                   10                  15

Gln Ala Leu Glu Ala Val Arg Ala Leu Leu Pro Val Leu Arg Ala Thr
            20                  25                  30

Pro Tyr Asp
        35

<210> SEQ ID NO 248
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 248

Leu Ser Thr Glu Gln Val Val Ala Val Ala Ser His Asn Gly Gly Lys
1               5                   10                  15

Gln Ala Leu Glu Ala Val Arg Ala Gln Leu Leu Asp Leu Arg Ala Ala
            20                  25                  30

Pro Tyr Glu
        35

<210> SEQ ID NO 249
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 249

Leu Ser Thr Glu Gln Val Val Ala Val Ala Ser Asn Lys Gly Gly Lys
1               5                   10                  15

Gln Ala Leu Ala Ala Val Glu Ala Gln Leu Leu Arg Leu Arg Ala Ala
            20                  25                  30

Pro Tyr Glu
        35

<210> SEQ ID NO 250
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 250
```

Leu Ser Thr Glu Gln Val Val Ala Val Ala Ser Asn Lys Gly Gly Lys
1               5                   10                  15

Gln Ala Leu Glu Glu Val Glu Ala Gln Leu Leu Arg Leu Arg Ala Ala
            20                  25                  30

Pro Tyr Glu
        35

<210> SEQ ID NO 251
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 251

Leu Ser Thr Glu Gln Val Val Ala Val Ala Ser Asn Lys Gly Gly Lys
1               5                   10                  15

Gln Val Leu Glu Ala Val Gly Ala Gln Leu Leu Ala Leu Arg Ala Val
            20                  25                  30

Pro Tyr Glu
        35

<210> SEQ ID NO 252
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 252

Leu Ser Thr Glu Gln Val Val Ala Val Ala Ser Asn Gly Gly Lys
1               5                   10                  15

Gln Ala Leu Lys Ala Val Lys Ala Gln Leu Leu Ala Leu Arg Ala Ala
            20                  25                  30

Pro Tyr Glu
        35

<210> SEQ ID NO 253
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 253

Leu Ser Thr Glu Gln Val Val Val Ile Ala Asn Ser Ile Gly Gly Lys
1               5                   10                  15

Gln Ala Leu Glu Ala Val Lys Val Gln Leu Pro Val Leu Arg Ala Ala
            20                  25                  30

Pro Tyr Glu
        35

<210> SEQ ID NO 254
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 254

Leu Ser Thr Gly Gln Val Val Ala Ile Ala Ser Asn Gly Gly Gly Arg
1               5                   10                  15

Gln Ala Leu Glu Ala Val Arg Glu Gln Leu Ala Leu Arg Ala Val
            20                  25                  30

Pro Tyr Glu
        35

<210> SEQ ID NO 255
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 255

Leu Ser Val Ala Gln Val Val Thr Ile Ala Ser His Asn Gly Gly Lys
1               5                   10                  15

Gln Ala Leu Glu Ala Val Arg Ala Gln Leu Leu Ala Leu Arg Ala Ala
            20                  25                  30

Pro Tyr Gly
        35

<210> SEQ ID NO 256
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 256

Leu Thr Ile Ala Gln Val Val Ala Val Ala Ser His Asn Gly Gly Lys
1               5                   10                  15

Gln Ala Leu Glu Ala Ile Gly Ala Gln Leu Leu Ala Leu Arg Ala Ala
            20                  25                  30

Pro Tyr Ala
        35

<210> SEQ ID NO 257
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 257

Leu Thr Ile Ala Gln Val Val Ala Val Ala Ser His Asn Gly Gly Lys
1               5                   10                  15

Gln Ala Leu Glu Val Ile Gly Ala Gln Leu Leu Ala Leu Arg Ala Ala
            20                  25                  30

Pro Tyr Ala
        35

<210> SEQ ID NO 258
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 258

Leu Thr Pro Gln Gln Val Val Ala Ile Ala Ala Asn Thr Gly Gly Lys
1               5                   10                  15

Gln Ala Leu Gly Ala Ile Thr Thr Gln Leu Pro Ile Leu Arg Ala Ala
            20                  25                  30

```
Pro Tyr Glu
        35

<210> SEQ ID NO 259
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 259

Leu Thr Pro Gln Gln Val Val Ala Ile Ala Ser Asn Thr Gly Gly Lys
1               5                   10                  15

Gln Ala Leu Glu Ala Val Thr Val Gln Leu Arg Val Leu Arg Gly Ala
            20                  25                  30

Arg Tyr Gly
        35

<210> SEQ ID NO 260
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 260

Leu Thr Pro Gln Gln Val Val Ala Ile Ala Ser Asn Thr Gly Gly Lys
1               5                   10                  15

Arg Ala Leu Glu Ala Val Cys Val Gln Leu Pro Val Leu Arg Ala Ala
            20                  25                  30

Pro Tyr Arg
        35

<210> SEQ ID NO 261
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 261

Leu Thr Pro Gln Gln Val Val Ala Ile Ala Ser Asn Thr Gly Gly Lys
1               5                   10                  15

Arg Ala Leu Glu Ala Val Arg Val Gln Leu Pro Val Leu Arg Ala Ala
            20                  25                  30

Pro Tyr Glu
        35

<210> SEQ ID NO 262
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 262

Leu Thr Thr Ala Gln Val Val Ala Ile Ala Ser Asn Asp Gly Gly Lys
1               5                   10                  15

Gln Ala Leu Glu Ala Val Gly Ala Gln Leu Leu Val Leu Arg Ala Val
            20                  25                  30

Pro Tyr Glu
        35
```

<210> SEQ ID NO 263
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 263

Leu Thr Thr Ala Gln Val Val Ala Ile Ala Ser Asn Asp Gly Gly Lys
1               5                   10                  15

Gln Thr Leu Glu Val Ala Gly Ala Gln Leu Leu Ala Leu Arg Ala Val
            20                  25                  30

Pro Tyr Glu
        35

<210> SEQ ID NO 264
<211> LENGTH: 137
<212> TYPE: PRT
<213> ORGANISM: Artificial Sequence
<220> FEATURE:
<223> OTHER INFORMATION: Synthetic Sequence

<400> SEQUENCE: 264

Phe Gly Lys Leu Val Ala Leu Gly Tyr Ser Arg Glu Gln Ile Arg Lys
1               5                   10                  15

Leu Lys Gln Glu Ser Leu Ser Glu Ile Ala Lys Tyr His Thr Thr Leu
            20                  25                  30

Thr Gly Gln Gly Phe Thr His Ala Asp Ile Cys Arg Ile Ser Arg Arg
        35                  40                  45

Arg Gln Ser Leu Arg Val Val Ala Arg Asn Tyr Pro Glu Leu Ala Ala
    50                  55                  60

Ala Leu Pro Glu Leu Thr Arg Ala His Ile Val Asp Ile Ala Arg Gln
65                  70                  75                  80

Arg Ser Gly Asp Leu Ala Leu Gln Ala Leu Leu Pro Val Ala Thr Ala
                85                  90                  95

Leu Thr Ala Ala Pro Leu Arg Leu Ser Ala Ser Gln Ile Ala Thr Val
            100                 105                 110

Ala Gln Tyr Gly Glu Arg Pro Ala Ile Gln Ala Leu Tyr Arg Leu Arg
        115                 120                 125

Arg Lys Leu Thr Arg Ala Pro Leu His
    130                 135

<210> SEQ ID NO 265
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 265

Leu Ser Thr Ala Gln Val Val Ala Ile Ala Cys Ile Ser Gly Gln Gln
1               5                   10                  15

Ala Leu Glu

<210> SEQ ID NO 266
<211> LENGTH: 62
<212> TYPE: PRT
<213> ORGANISM: Artificial Sequence
<220> FEATURE:
<223> OTHER INFORMATION: Synthetic Sequence

<400> SEQUENCE: 266

Ala Ile Glu Ala His Met Pro Thr Leu Arg Gln Ala Ser His Ser Leu
1               5                   10                  15

Ser Pro Glu Arg Val Ala Ala Ile Ala Cys Ile Gly Gly Arg Ser Ala
            20                  25                  30

Val Glu Ala Val Arg Gln Gly Leu Pro Val Lys Ala Ile Arg Arg Ile
        35                  40                  45

Arg Arg Glu Lys Ala Pro Val Ala Gly Pro Pro Ala Ser
    50                  55                  60

<210> SEQ ID NO 267
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (2)..(4)
<223> OTHER INFORMATION: Xaa can be any naturally occurring amino acid
<220> FEATURE:
<221> NAME/KEY: SITE
<222> LOCATION: (8)..(9)
<223> OTHER INFORMATION: Xaa can be any naturally occurring amino acid
<220> FEATURE:
<221> NAME/KEY: SITE
<222> LOCATION: (15)..(15)
<223> OTHER INFORMATION: Xaa can be any naturally occurring amino acid
<220> FEATURE:
<221> NAME/KEY: SITE
<222> LOCATION: (21)..(25)
<223> OTHER INFORMATION: Xaa can be any naturally occurring amino acid
<220> FEATURE:
<221> NAME/KEY: SITE
<222> LOCATION: (27)..(28)
<223> OTHER INFORMATION: Xaa can be any naturally occurring amino acid
<220> FEATURE:
<221> NAME/KEY: SITE
<222> LOCATION: (30)..(32)
<223> OTHER INFORMATION: Xaa can be any naturally occurring amino acid
<220> FEATURE:
<221> NAME/KEY: SITE
<222> LOCATION: (35)..(35)
<223> OTHER INFORMATION: Xaa can be any naturally occurring amino acid

<400> SEQUENCE: 267

Leu Xaa Xaa Xaa Gln Val Val Xaa Xaa Ala Ser His Asn Gly Xaa Lys
1               5                   10                  15

Gln Ala Leu Glu Xaa Xaa Xaa Xaa Xaa Leu Xaa Xaa Leu Xaa Xaa Xaa
            20                  25                  30

Pro Tyr Xaa
        35

<210> SEQ ID NO 268
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (2)..(4)
<223> OTHER INFORMATION: Xaa can be any naturally occurring amino acid
<220> FEATURE:
<221> NAME/KEY: SITE
<222> LOCATION: (9)..(9)
<223> OTHER INFORMATION: Xaa can be any naturally occurring amino acid
<220> FEATURE:
<221> NAME/KEY: SITE
<222> LOCATION: (11)..(11)

-continued

<223> OTHER INFORMATION: Xaa can be any naturally occurring amino acid
<220> FEATURE:
<221> NAME/KEY: SITE
<222> LOCATION: (20)..(20)
<223> OTHER INFORMATION: Xaa can be any naturally occurring amino acid
<220> FEATURE:
<221> NAME/KEY: SITE
<222> LOCATION: (23)..(25)
<223> OTHER INFORMATION: Xaa can be any naturally occurring amino acid
<220> FEATURE:
<221> NAME/KEY: SITE
<222> LOCATION: (27)..(28)
<223> OTHER INFORMATION: Xaa can be any naturally occurring amino acid
<220> FEATURE:
<221> NAME/KEY: SITE
<222> LOCATION: (31)..(31)
<223> OTHER INFORMATION: Xaa can be any naturally occurring amino acid
<220> FEATURE:
<221> NAME/KEY: SITE
<222> LOCATION: (33)..(35)
<223> OTHER INFORMATION: Xaa can be any naturally occurring amino acid

<400> SEQUENCE: 268

Leu Xaa Xaa Xaa Gln Val Val Ala Xaa Ala Xaa Asn Asn Gly Gly Lys
1               5                   10                  15

Gln Ala Leu Xaa Ala Val Xaa Xaa Xaa Leu Xaa Xaa Leu Arg Xaa Ala
            20                  25                  30

Xaa Xaa Xaa
        35

<210> SEQ ID NO 269
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (2)..(2)
<223> OTHER INFORMATION: Xaa can be any naturally occurring amino acid
<220> FEATURE:
<221> NAME/KEY: SITE
<222> LOCATION: (4)..(4)
<223> OTHER INFORMATION: Xaa can be any naturally occurring amino acid
<220> FEATURE:
<221> NAME/KEY: SITE
<222> LOCATION: (6)..(6)
<223> OTHER INFORMATION: Xaa can be any naturally occurring amino acid
<220> FEATURE:
<221> NAME/KEY: SITE
<222> LOCATION: (8)..(8)
<223> OTHER INFORMATION: Xaa can be any naturally occurring amino acid
<220> FEATURE:
<221> NAME/KEY: SITE
<222> LOCATION: (22)..(22)
<223> OTHER INFORMATION: Xaa can be any naturally occurring amino acid
<220> FEATURE:
<221> NAME/KEY: SITE
<222> LOCATION: (25)..(25)
<223> OTHER INFORMATION: Xaa can be any naturally occurring amino acid
<220> FEATURE:
<221> NAME/KEY: SITE
<222> LOCATION: (27)..(29)
<223> OTHER INFORMATION: Xaa can be any naturally occurring amino acid

<400> SEQUENCE: 269

Leu Xaa Thr Xaa Gln Xaa Val Xaa Ile Ala Ser Asn Pro Gly Gly Lys
1               5                   10                  15

Gln Ala Leu Glu Ala Xaa Arg Ala Xaa Phe Xaa Xaa Xaa Arg Ala Ala
            20                  25                  30

Pro Tyr Ala
        35

```
<210> SEQ ID NO 270
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (2)..(2)
<223> OTHER INFORMATION: Xaa can be any naturally occurring amino acid
<220> FEATURE:
<221> NAME/KEY: SITE
<222> LOCATION: (4)..(4)
<223> OTHER INFORMATION: Xaa can be any naturally occurring amino acid
<220> FEATURE:
<221> NAME/KEY: SITE
<222> LOCATION: (26)..(28)
<223> OTHER INFORMATION: Xaa can be any naturally occurring amino acid
<220> FEATURE:
<221> NAME/KEY: SITE
<222> LOCATION: (32)..(32)
<223> OTHER INFORMATION: Xaa can be any naturally occurring amino acid
<220> FEATURE:
<221> NAME/KEY: SITE
<222> LOCATION: (35)..(35)
<223> OTHER INFORMATION: Xaa can be any naturally occurring amino acid

<400> SEQUENCE: 270

Leu Xaa Thr Xaa Gln Val Val Ala Ile Ala Ser Ser His Gly Gly Lys
1               5                   10                  15

Gln Ala Leu Glu Ala Val Arg Ala Leu Xaa Xaa Xaa Leu Arg Ala Xaa
            20                  25                  30

Pro Tyr Xaa
        35

<210> SEQ ID NO 271
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (2)..(2)
<223> OTHER INFORMATION: Xaa can be any naturally occurring amino acid
<220> FEATURE:
<221> NAME/KEY: SITE
<222> LOCATION: (9)..(9)
<223> OTHER INFORMATION: Xaa can be any naturally occurring amino acid
<220> FEATURE:
<221> NAME/KEY: SITE
<222> LOCATION: (18)..(18)
<223> OTHER INFORMATION: Xaa can be any naturally occurring amino acid
<220> FEATURE:
<221> NAME/KEY: SITE
<222> LOCATION: (20)..(21)
<223> OTHER INFORMATION: Xaa can be any naturally occurring amino acid
<220> FEATURE:
<221> NAME/KEY: SITE
<222> LOCATION: (23)..(23)
<223> OTHER INFORMATION: Xaa can be any naturally occurring amino acid
<220> FEATURE:
<221> NAME/KEY: SITE
<222> LOCATION: (25)..(25)
<223> OTHER INFORMATION: Xaa can be any naturally occurring amino acid
<220> FEATURE:
<221> NAME/KEY: SITE
<222> LOCATION: (28)..(28)
<223> OTHER INFORMATION: Xaa can be any naturally occurring amino acid
<220> FEATURE:
<221> NAME/KEY: SITE
<222> LOCATION: (30)..(32)
<223> OTHER INFORMATION: Xaa can be any naturally occurring amino acid
```

```
<220> FEATURE:
<221> NAME/KEY: SITE
<222> LOCATION: (35)..(35)
<223> OTHER INFORMATION: Xaa can be any naturally occurring amino acid

<400> SEQUENCE: 271

Leu Xaa Thr Glu Gln Val Val Ala Xaa Ala Ser Asn Lys Gly Gly Lys
1               5                   10                  15

Gln Xaa Leu Xaa Xaa Val Xaa Ala Xaa Leu Leu Xaa Leu Xaa Xaa Xaa
            20                  25                  30

Pro Tyr Xaa
        35

<210> SEQ ID NO 272
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (3)..(4)
<223> OTHER INFORMATION: Xaa can be any naturally occurring amino acid
<220> FEATURE:
<221> NAME/KEY: SITE
<222> LOCATION: (7)..(7)
<223> OTHER INFORMATION: Xaa can be any naturally occurring amino acid
<220> FEATURE:
<221> NAME/KEY: SITE
<222> LOCATION: (11)..(11)
<223> OTHER INFORMATION: Xaa can be any naturally occurring amino acid
<220> FEATURE:
<221> NAME/KEY: SITE
<222> LOCATION: (16)..(16)
<223> OTHER INFORMATION: Xaa can be any naturally occurring amino acid
<220> FEATURE:
<221> NAME/KEY: SITE
<222> LOCATION: (18)..(18)
<223> OTHER INFORMATION: Xaa can be any naturally occurring amino acid
<220> FEATURE:
<221> NAME/KEY: SITE
<222> LOCATION: (22)..(24)
<223> OTHER INFORMATION: Xaa can be any naturally occurring amino acid
<220> FEATURE:
<221> NAME/KEY: SITE
<222> LOCATION: (28)..(28)
<223> OTHER INFORMATION: Xaa can be any naturally occurring amino acid
<220> FEATURE:
<221> NAME/KEY: SITE
<222> LOCATION: (30)..(30)
<223> OTHER INFORMATION: Xaa can be any naturally occurring amino acid

<400> SEQUENCE: 272

Leu Ser Xaa Xaa Gln Val Xaa Ala Ile Ala Xaa His Asp Gly Gly Xaa
1               5                   10                  15

Gln Xaa Leu Glu Ala Xaa Xaa Xaa Gln Leu Val Xaa Leu Xaa Ala Ala
            20                  25                  30

Pro Tyr Ala
        35

<210> SEQ ID NO 273
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (3)..(3)
<223> OTHER INFORMATION: Xaa can be any naturally occurring amino acid
<220> FEATURE:
```

```
<221> NAME/KEY: SITE
<222> LOCATION: (9)..(9)
<223> OTHER INFORMATION: Xaa can be any naturally occurring amino acid
<220> FEATURE:
<221> NAME/KEY: SITE
<222> LOCATION: (11)..(11)
<223> OTHER INFORMATION: Xaa can be any naturally occurring amino acid
<220> FEATURE:
<221> NAME/KEY: SITE
<222> LOCATION: (28)..(28)
<223> OTHER INFORMATION: Xaa can be any naturally occurring amino acid

<400> SEQUENCE: 273

Leu Ser Xaa Ala Gln Val Val Ala Xaa Ala Xaa Arg Ser Gly Gly Lys
1               5                   10                  15

Gln Ala Leu Glu Ala Val Arg Ala Gln Leu Leu Xaa Leu Arg Ala Ala
            20                  25                  30

Pro Tyr Gly
        35

<210> SEQ ID NO 274
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (3)..(3)
<223> OTHER INFORMATION: Xaa can be any naturally occurring amino acid
<220> FEATURE:
<221> NAME/KEY: SITE
<222> LOCATION: (28)..(28)
<223> OTHER INFORMATION: Xaa can be any naturally occurring amino acid
<220> FEATURE:
<221> NAME/KEY: SITE
<222> LOCATION: (35)..(35)
<223> OTHER INFORMATION: Xaa can be any naturally occurring amino acid

<400> SEQUENCE: 274

Leu Ser Xaa Glu Gln Val Val Ala Ile Ala Ser Asn His Gly Gly Lys
1               5                   10                  15

Gln Ala Leu Glu Ala Val Arg Ala Leu Phe Arg Xaa Leu Arg Ala Ala
            20                  25                  30

Pro Tyr Xaa
        35

<210> SEQ ID NO 275
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (4)..(4)
<223> OTHER INFORMATION: Xaa can be any naturally occurring amino acid
<220> FEATURE:
<221> NAME/KEY: SITE
<222> LOCATION: (7)..(8)
<223> OTHER INFORMATION: Xaa can be any naturally occurring amino acid
<220> FEATURE:
<221> NAME/KEY: SITE
<222> LOCATION: (11)..(11)
<223> OTHER INFORMATION: Xaa can be any naturally occurring amino acid
<220> FEATURE:
<221> NAME/KEY: SITE
<222> LOCATION: (16)..(16)
<223> OTHER INFORMATION: Xaa can be any naturally occurring amino acid
<220> FEATURE:
<221> NAME/KEY: SITE
```

```
<222> LOCATION: (22)..(22)
<223> OTHER INFORMATION: Xaa can be any naturally occurring amino acid
<220> FEATURE:
<221> NAME/KEY: SITE
<222> LOCATION: (35)..(35)
<223> OTHER INFORMATION: Xaa can be any naturally occurring amino acid

<400> SEQUENCE: 275

Leu Ser Thr Xaa Gln Val Xaa Xaa Ile Ala Xaa Ser Ile Gly Gly Xaa
1               5                   10                  15

Gln Ala Leu Glu Ala Xaa Lys Val Gln Leu Pro Val Leu Arg Ala Ala
            20                  25                  30

Pro Tyr Xaa
        35

<210> SEQ ID NO 276
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (2)..(2)
<223> OTHER INFORMATION: Xaa can be any naturally occurring amino acid
<220> FEATURE:
<221> NAME/KEY: SITE
<222> LOCATION: (18)..(18)
<223> OTHER INFORMATION: Xaa can be any naturally occurring amino acid
<220> FEATURE:
<221> NAME/KEY: SITE
<222> LOCATION: (21)..(23)
<223> OTHER INFORMATION: Xaa can be any naturally occurring amino acid
<220> FEATURE:
<221> NAME/KEY: SITE
<222> LOCATION: (28)..(28)
<223> OTHER INFORMATION: Xaa can be any naturally occurring amino acid
<220> FEATURE:
<221> NAME/KEY: SITE
<222> LOCATION: (32)..(32)
<223> OTHER INFORMATION: Xaa can be any naturally occurring amino acid

<400> SEQUENCE: 276

Leu Xaa Thr Ala Gln Val Val Ala Ile Ala Ser Asn Asp Gly Gly Lys
1               5                   10                  15

Gln Xaa Leu Glu Xaa Xaa Xaa Ala Gln Leu Leu Xaa Leu Arg Ala Xaa
            20                  25                  30

Pro Tyr Glu
        35

<210> SEQ ID NO 277
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (8)..(9)
<223> OTHER INFORMATION: Xaa can be any naturally occurring amino acid

<400> SEQUENCE: 277

Leu Ser Thr Ala Gln Val Val Xaa Xaa Ala Ser Ser Asn Gly Gly Lys
1               5                   10                  15

Gln Ala Leu Glu Ala Val Trp Ala Leu Leu Pro Val Leu Arg Ala Thr
            20                  25                  30

Pro Tyr Asp
        35
```

```
<210> SEQ ID NO 278
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (4)..(4)
<223> OTHER INFORMATION: Xaa can be any naturally occurring amino acid
<220> FEATURE:
<221> NAME/KEY: SITE
<222> LOCATION: (11)..(11)
<223> OTHER INFORMATION: Xaa can be any naturally occurring amino acid
<220> FEATURE:
<221> NAME/KEY: SITE
<222> LOCATION: (16)..(16)
<223> OTHER INFORMATION: Xaa can be any naturally occurring amino acid
<220> FEATURE:
<221> NAME/KEY: SITE
<222> LOCATION: (21)..(24)
<223> OTHER INFORMATION: Xaa can be any naturally occurring amino acid
<220> FEATURE:
<221> NAME/KEY: SITE
<222> LOCATION: (27)..(28)
<223> OTHER INFORMATION: Xaa can be any naturally occurring amino acid
<220> FEATURE:
<221> NAME/KEY: SITE
<222> LOCATION: (31)..(32)
<223> OTHER INFORMATION: Xaa can be any naturally occurring amino acid
<220> FEATURE:
<221> NAME/KEY: SITE
<222> LOCATION: (34)..(35)
<223> OTHER INFORMATION: Xaa can be any naturally occurring amino acid

<400> SEQUENCE: 278

Leu Ser Thr Xaa Gln Val Val Ala Ile Ala Xaa Asn Gly Gly Gly Xaa
1               5                   10                  15

Gln Ala Leu Glu Xaa Xaa Xaa Xaa Gln Leu Xaa Xaa Leu Arg Xaa Xaa
            20                  25                  30

Pro Xaa Xaa
        35

<210> SEQ ID NO 279
<211> LENGTH: 35
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (11)..(11)
<223> OTHER INFORMATION: Xaa can be any naturally occurring amino acid
<220> FEATURE:
<221> NAME/KEY: SITE
<222> LOCATION: (17)..(17)
<223> OTHER INFORMATION: Xaa can be any naturally occurring amino acid
<220> FEATURE:
<221> NAME/KEY: SITE
<222> LOCATION: (20)..(20)
<223> OTHER INFORMATION: Xaa can be any naturally occurring amino acid
<220> FEATURE:
<221> NAME/KEY: SITE
<222> LOCATION: (22)..(24)
<223> OTHER INFORMATION: Xaa can be any naturally occurring amino acid
<220> FEATURE:
<221> NAME/KEY: SITE
<222> LOCATION: (27)..(28)
<223> OTHER INFORMATION: Xaa can be any naturally occurring amino acid
<220> FEATURE:
<221> NAME/KEY: SITE
<222> LOCATION: (31)..(31)
<223> OTHER INFORMATION: Xaa can be any naturally occurring amino acid
```

```
<220> FEATURE:
<221> NAME/KEY: SITE
<222> LOCATION: (33)..(33)
<223> OTHER INFORMATION: Xaa can be any naturally occurring amino acid
<220> FEATURE:
<221> NAME/KEY: SITE
<222> LOCATION: (35)..(35)
<223> OTHER INFORMATION: Xaa can be any naturally occurring amino acid

<400> SEQUENCE: 279

Leu Thr Pro Gln Gln Val Val Ala Ile Ala Xaa Asn Thr Gly Gly Lys
1               5                   10                  15

Xaa Ala Leu Xaa Ala Xaa Xaa Xaa Gln Leu Xaa Xaa Leu Arg Xaa Ala
            20                  25                  30

Xaa Tyr Xaa
        35

<210> SEQ ID NO 280
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 280

Gly Gly Lys Gln Ala Leu Glu Ala Val Arg Ala Gln Leu Leu Asp Leu
1               5                   10                  15

Arg Ala Ala Pro Tyr Gly
            20

<210> SEQ ID NO 281
<211> LENGTH: 635
<212> TYPE: PRT
<213> ORGANISM: Artificial Sequence
<220> FEATURE:
<223> OTHER INFORMATION: Synthetic Sequence

<400> SEQUENCE: 281

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
            20                  25                  30

Ser Ser Ser Tyr Ser Ser Lys Ser Ser Pro Ala Ser Ala Asn Ala Arg
        35                  40                  45

Lys Arg Thr Ser Arg Lys Glu Met Ser Gly Pro Pro Ser Lys Glu Pro
    50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
        115                 120                 125

Leu Cys Lys His Glu Glu Leu Leu Asn Leu Ile Ser Pro Asp Gly Leu
    130                 135                 140

Gly His Lys Glu Leu Ile Lys Ile Ala Ala Arg Asn Gly Gly Gly Asn
145                 150                 155                 160

Asn Leu Ile Ala Val Leu Ser Cys Tyr Ala Lys Leu Lys Glu Met Gly
                165                 170                 175
```

```
Phe Ser Ser Gln Gln Ile Ile Arg Met Val Ser His Ala Gly Ala
                180                 185                 190

Asn Asn Leu Lys Ala Val Thr Ala Asn His Asp Asp Leu Gln Asn Met
            195                 200                 205

Gly Phe Asn Val Glu Gln Ile Val Arg Met Val Ser His Asn Gly Gly
        210                 215                 220

Ser Lys Asn Leu Lys Ala Val Thr Asp Asn His Asp Asp Leu Lys Asn
225                 230                 235                 240

Met Gly Phe Asn Ala Glu Gln Ile Val Arg Met Val Ser His Gly Gly
                245                 250                 255

Gly Ser Lys Asn Leu Lys Ala Val Thr Asp Asn His Asp Asp Leu Lys
            260                 265                 270

Asn Met Gly Phe Asn Ala Glu Gln Ile Val Ser Met Val Ser Asn Asn
        275                 280                 285

Gly Gly Ser Lys Asn Leu Lys Ala Val Thr Asp Asn His Asp Asp Leu
    290                 295                 300

Lys Asn Met Gly Phe Asn Ala Glu Gln Ile Val Ser Met Val Ser Asn
305                 310                 315                 320

Gly Gly Gly Ser Leu Asn Leu Lys Ala Val Lys Lys Tyr His Asp Ala
                325                 330                 335

Leu Lys Asp Arg Gly Phe Asn Thr Glu Gln Ile Val Arg Met Val Ser
            340                 345                 350

His Asp Gly Gly Ser Leu Asn Leu Lys Ala Val Lys Lys Tyr His Asp
        355                 360                 365

Ala Leu Arg Glu Arg Lys Phe Asn Val Glu Gln Ile Val Ser Ile Val
    370                 375                 380

Ser His Gly Gly Gly Ser Leu Asn Leu Lys Ala Val Lys Lys Tyr His
385                 390                 395                 400

Asp Val Leu Lys Asp Arg Glu Phe Asn Ala Glu Gln Ile Val Arg Met
                405                 410                 415

Val Ser His Asp Gly Gly Ser Leu Asn Leu Lys Ala Val Thr Asp Asn
            420                 425                 430

His Asp Asp Leu Lys Asn Met Gly Phe Asn Ala Glu Gln Ile Val Arg
        435                 440                 445

Met Val Ser His Lys Gly Gly Ser Lys Asn Leu Ala Leu Val Lys Glu
    450                 455                 460

Tyr Phe Pro Val Phe Ser Ser Phe His Phe Thr Ala Asp Gln Ile Val
465                 470                 475                 480

Ala Leu Ile Cys Gln Ser Lys Gln Cys Phe Arg Asn Leu Lys Lys Asn
                485                 490                 495

His Gln Gln Trp Lys Asn Lys Gly Leu Ser Ala Glu Gln Ile Val Asp
            500                 505                 510

Leu Ile Leu Gln Glu Thr Pro Pro Lys Pro Asn Phe Asn Asn Thr Ser
        515                 520                 525

Ser Ser Thr Pro Ser Pro Ser Ala Pro Ser Phe Phe Gln Gly Pro Ser
    530                 535                 540

Thr Pro Ile Pro Thr Pro Val Leu Asp Asn Ser Pro Ala Pro Ile Phe
545                 550                 555                 560

Ser Asn Pro Val Cys Phe Phe Ser Ser Arg Ser Glu Asn Asn Thr Glu
                565                 570                 575

Gln Tyr Leu Gln Asp Ser Thr Leu Asp Leu Asp Ser Gln Leu Gly Asp
            580                 585                 590

Pro Thr Lys Asn Phe Asn Val Asn Asn Phe Trp Ser Leu Phe Pro Phe
```

```
                595                 600                 605
Asp Asp Val Gly Tyr His Pro His Ser Asn Asp Val Gly Tyr His Leu
    610                 615                 620
His Ser Asp Glu Glu Ser Pro Phe Phe Asp Phe
625                 630                 635

<210> SEQ ID NO 282
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 282

Phe Ser Ser Gln Gln Ile Ile Arg Met Val Ser His Ala Gly Gly Ala
1               5                   10                  15
Asn Asn Leu Lys Ala Val Thr Ala Asn His Asp Asp Leu Gln Asn Met
            20                  25                  30
Gly

<210> SEQ ID NO 283
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 283

Phe Asn Val Glu Gln Ile Val Arg Met Val Ser His Asn Gly Gly Ser
1               5                   10                  15
Lys Asn Leu Lys Ala Val Thr Asp Asn His Asp Asp Leu Lys Asn Met
            20                  25                  30
Gly

<210> SEQ ID NO 284
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 284

Phe Asn Ala Glu Gln Ile Val Arg Met Val Ser His Gly Gly Gly Ser
1               5                   10                  15
Lys Asn Leu Lys Ala Val Thr Asp Asn His Asp Asp Leu Lys Asn Met
            20                  25                  30
Gly

<210> SEQ ID NO 285
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 285

Phe Asn Ala Glu Gln Ile Val Ser Met Val Ser Asn Asn Gly Gly Ser
1               5                   10                  15
Lys Asn Leu Lys Ala Val Thr Asp Asn His Asp Asp Leu Lys Asn Met
            20                  25                  30
Gly
```

<210> SEQ ID NO 286
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 286

Phe Asn Ala Glu Gln Ile Val Ser Met Val Ser Asn Gly Gly Ser
1               5                   10                  15

Leu Asn Leu Lys Ala Val Lys Lys Tyr His Asp Ala Leu Lys Asp Arg
            20                  25                  30

Gly

<210> SEQ ID NO 287
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 287

Phe Asn Thr Glu Gln Ile Val Arg Met Val Ser His Asp Gly Gly Ser
1               5                   10                  15

Leu Asn Leu Lys Ala Val Lys Lys Tyr His Asp Ala Leu Arg Glu Arg
            20                  25                  30

Lys

<210> SEQ ID NO 288
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 288

Phe Asn Val Glu Gln Ile Val Ser Ile Val Ser His Gly Gly Gly Ser
1               5                   10                  15

Leu Asn Leu Lys Ala Val Lys Lys Tyr His Asp Val Leu Lys Asp Arg
            20                  25                  30

Glu

<210> SEQ ID NO 289
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 289

Phe Asn Ala Glu Gln Ile Val Arg Met Val Ser His Asp Gly Gly Ser
1               5                   10                  15

Leu Asn Leu Lys Ala Val Thr Asp Asn His Asp Asp Leu Lys Asn Met
            20                  25                  30

Gly

<210> SEQ ID NO 290
<211> LENGTH: 19
<212> TYPE: PRT
<213> ORGANISM: Artificial Sequence
<220> FEATURE:

<223> OTHER INFORMATION: Synthetic Sequence

<400> SEQUENCE: 290

Phe Asn Ala Glu Gln Ile Val Arg Met Val Ser His Lys Gly Gly Ser
1               5                   10                  15

Lys Asn Leu

<210> SEQ ID NO 291
<211> LENGTH: 143
<212> TYPE: PRT
<213> ORGANISM: Artificial Sequence
<220> FEATURE:
<223> OTHER INFORMATION: Synthetic Sequence

<400> SEQUENCE: 291

Met Pro Asp Leu Glu Leu Asn Phe Ala Ile Pro Leu His Leu Phe Asp
1               5                   10                  15

Asp Glu Thr Val Phe Thr His Asp Ala Thr Asn Asp Asn Ser Gln Ala
            20                  25                  30

Ser Ser Ser Tyr Ser Ser Lys Ser Pro Ala Ser Ala Asn Ala Arg
        35                  40                  45

Lys Arg Thr Ser Arg Lys Glu Met Ser Gly Pro Pro Ser Lys Glu Pro
50                  55                  60

Ala Asn Thr Lys Ser Arg Arg Ala Asn Ser Gln Asn Asn Lys Leu Ser
65                  70                  75                  80

Leu Ala Asp Arg Leu Thr Lys Tyr Asn Ile Asp Glu Glu Phe Tyr Gln
                85                  90                  95

Thr Arg Ser Asp Ser Leu Leu Ser Leu Asn Tyr Thr Lys Lys Gln Ile
            100                 105                 110

Glu Arg Leu Ile Leu Tyr Lys Gly Arg Thr Ser Ala Val Gln Gln Leu
        115                 120                 125

Leu Cys Lys His Glu Glu Leu Leu Asn Leu Ile Ser Pro Asp Gly
    130                 135                 140

<210> SEQ ID NO 292
<211> LENGTH: 60
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (1)..(1)
<223> OTHER INFORMATION: Xaa is chosen from Ala, Phe, Ile, Leu, Met,
      Thr, or Val
<220> FEATURE:
<221> NAME/KEY: SITE
<222> LOCATION: (2)..(4)
<223> OTHER INFORMATION: Xaa can be any naturally occurring amino acid
<220> FEATURE:
<221> NAME/KEY: SITE
<222> LOCATION: (5)..(5)
<223> OTHER INFORMATION: Xaa is chosen from Asp, Glu, Lys, Asn, Met,
      Ser, Arg, or Gln
<220> FEATURE:
<221> NAME/KEY: SITE
<222> LOCATION: (6)..(7)
<223> OTHER INFORMATION: Xaa is chosen from Ala, Phe, Ile, Leu, Met,
      Thr, or Val
<220> FEATURE:
<221> NAME/KEY: SITE
<222> LOCATION: (8)..(8)
<223> OTHER INFORMATION: Xaa can be any naturally occurring amino acid
<220> FEATURE:
<221> NAME/KEY: SITE
<222> LOCATION: (9)..(9)

```
<223> OTHER INFORMATION: Xaa is chosen from Ala, Phe, Ile, Leu, Met,
      Thr, or Val
<220> FEATURE:
<221> NAME/KEY: SITE
<222> LOCATION: (10)..(12)
<223> OTHER INFORMATION: Xaa can be any naturally occurring amino acid
<220> FEATURE:
<221> NAME/KEY: SITE
<222> LOCATION: (13)..(13)
<223> OTHER INFORMATION: Xaa is chosen from Ala, Gly, Asn, or Ser
<220> FEATURE:
<221> NAME/KEY: SITE
<222> LOCATION: (14)..(15)
<223> OTHER INFORMATION: Xaa can be any naturally occurring amino acid
<220> FEATURE:
<221> NAME/KEY: SITE
<222> LOCATION: (16)..(16)
<223> OTHER INFORMATION: Xaa is chosen from Asp, Glu, Lys, Asn, Met,
      Ser, Arg, or Gln
<220> FEATURE:
<221> NAME/KEY: SITE
<222> LOCATION: (17)..(17)
<223> OTHER INFORMATION: Xaa can be any naturally occurring amino acid
<220> FEATURE:
<221> NAME/KEY: SITE
<222> LOCATION: (18)..(18)
<223> OTHER INFORMATION: Xaa is chosen from Ala, Phe, Ile, Leu, Met,
      Thr, or Val
<220> FEATURE:
<221> NAME/KEY: SITE
<222> LOCATION: (19)..(27)
<223> OTHER INFORMATION: Xaa can be any naturally occurring amino acid
<220> FEATURE:
<221> NAME/KEY: SITE
<222> LOCATION: (28)..(28)
<223> OTHER INFORMATION: Xaa is chosen from Ala, Phe, Ile, Leu, Met,
      Thr, or Val
<220> FEATURE:
<221> NAME/KEY: SITE
<222> LOCATION: (29)..(32)
<223> OTHER INFORMATION: Xaa can be any naturally occurring amino acid
<220> FEATURE:
<221> NAME/KEY: SITE
<222> LOCATION: (33)..(33)
<223> OTHER INFORMATION: Xaa is chosen from Ala, Phe, Ile, Leu, Met,
      Thr, or Val
<220> FEATURE:
<221> NAME/KEY: SITE
<222> LOCATION: (34)..(36)
<223> OTHER INFORMATION: Xaa can be any naturally occurring amino acid
<220> FEATURE:
<221> NAME/KEY: SITE
<222> LOCATION: (37)..(37)
<223> OTHER INFORMATION: Xaa is chosen from Asp, Glu, Lys, Asn, Met,
      Ser, Arg, or Gln
<220> FEATURE:
<221> NAME/KEY: SITE
<222> LOCATION: (38)..(39)
<223> OTHER INFORMATION: Xaa is chosen from Ala, Phe, Ile, Leu, Met,
      Thr, or Val
<220> FEATURE:
<221> NAME/KEY: SITE
<222> LOCATION: (40)..(40)
<223> OTHER INFORMATION: Xaa can be any naturally occurring amino acid
<220> FEATURE:
<221> NAME/KEY: SITE
<222> LOCATION: (41)..(41)
<223> OTHER INFORMATION: Xaa is chosen from Ala, Phe, Ile, Leu, Met,
      Thr, or Val
<220> FEATURE:
<221> NAME/KEY: SITE
<222> LOCATION: (42)..(47)
<223> OTHER INFORMATION: Xaa can be any naturally occurring amino acid
<220> FEATURE:
<221> NAME/KEY: SITE
<222> LOCATION: (48)..(48)
<223> OTHER INFORMATION: Xaa is chosen from Asp, Glu, Lys, Asn, Met,
      Ser, Arg, or Gln
<220> FEATURE:
```

```
<221> NAME/KEY: SITE
<222> LOCATION: (49)..(49)
<223> OTHER INFORMATION: Xaa can be any naturally occurring amino acid
<220> FEATURE:
<221> NAME/KEY: SITE
<222> LOCATION: (50)..(50)
<223> OTHER INFORMATION: Xaa is chosen from Ala, Phe, Ile, Leu, Met,
      Thr, or Val
<220> FEATURE:
<221> NAME/KEY: SITE
<222> LOCATION: (51)..(59)
<223> OTHER INFORMATION: Xaa can be any naturally occurring amino acid
<220> FEATURE:
<221> NAME/KEY: SITE
<222> LOCATION: (60)..(60)
<223> OTHER INFORMATION: Xaa is chosen from Ala, Phe, Ile, Leu, Met,
      Thr, or Val

<400> SEQUENCE: 292

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
    50                  55                  60

<210> SEQ ID NO 293
<211> LENGTH: 61
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (1)..(1)
<223> OTHER INFORMATION: Xaa is Ala, Phe, Ile, Leu, Met, Thr or Val
<220> FEATURE:
<221> NAME/KEY: SITE
<222> LOCATION: (2)..(4)
<223> OTHER INFORMATION: Xaa can be any naturally occurring amino acid
<220> FEATURE:
<221> NAME/KEY: SITE
<222> LOCATION: (5)..(5)
<223> OTHER INFORMATION: Xaa is Asp, Glu, Lys, Asn, Met, Ser, Arg or Gln
<220> FEATURE:
<221> NAME/KEY: SITE
<222> LOCATION: (6)..(7)
<223> OTHER INFORMATION: Xaa is Ala, Phe, Ile, Leu, Met, Thr or Val
<220> FEATURE:
<221> NAME/KEY: SITE
<222> LOCATION: (8)..(8)
<223> OTHER INFORMATION: Xaa can be any naturally occurring amino acid
<220> FEATURE:
<221> NAME/KEY: SITE
<222> LOCATION: (9)..(9)
<223> OTHER INFORMATION: Xaa is Ala, Phe, Ile, Leu, Met, Thr or Val
<220> FEATURE:
<221> NAME/KEY: SITE
<222> LOCATION: (10)..(12)
<223> OTHER INFORMATION: Xaa can be any naturally occurring amino acid
<220> FEATURE:
<221> NAME/KEY: SITE
<222> LOCATION: (13)..(14)
<223> OTHER INFORMATION: Xaa is Ala, Gly, Asn or Ser
<220> FEATURE:
<221> NAME/KEY: SITE
<222> LOCATION: (15)..(15)
<223> OTHER INFORMATION: Xaa can be any naturally occurring amino acid
<220> FEATURE:
<221> NAME/KEY: SITE
<222> LOCATION: (16)..(16)
<223> OTHER INFORMATION: Xaa is Asp, Glu, Lys, Asn, Met, Ser, Arg or Gln
```

```
<220> FEATURE:
<221> NAME/KEY: SITE
<222> LOCATION: (17)..(17)
<223> OTHER INFORMATION: Xaa can be any naturally occurring amino acid
<220> FEATURE:
<221> NAME/KEY: SITE
<222> LOCATION: (18)..(18)
<223> OTHER INFORMATION: Xaa is Ala, Phe, Ile, Leu, Met, Thr or Val
<220> FEATURE:
<221> NAME/KEY: SITE
<222> LOCATION: (19)..(27)
<223> OTHER INFORMATION: Xaa can be any naturally occurring amino acid
<220> FEATURE:
<221> NAME/KEY: SITE
<222> LOCATION: (28)..(28)
<223> OTHER INFORMATION: Xaa is Ala, Phe, Ile, Leu, Met, Thr or Val
<220> FEATURE:
<221> NAME/KEY: SITE
<222> LOCATION: (29)..(33)
<223> OTHER INFORMATION: Xaa can be any naturally occurring amino acid
<220> FEATURE:
<221> NAME/KEY: SITE
<222> LOCATION: (34)..(34)
<223> OTHER INFORMATION: Xaa is Ala, Phe, Ile, Leu, Met, Thr or Val
<220> FEATURE:
<221> NAME/KEY: SITE
<222> LOCATION: (35)..(37)
<223> OTHER INFORMATION: Xaa can be any naturally occurring amino acid
<220> FEATURE:
<221> NAME/KEY: SITE
<222> LOCATION: (38)..(38)
<223> OTHER INFORMATION: Xaa is Asp, Glu, Lys, Asn, Met, Ser, Arg or Gln
<220> FEATURE:
<221> NAME/KEY: SITE
<222> LOCATION: (39)..(40)
<223> OTHER INFORMATION: Xaa is Ala, Phe, Ile, Leu, Met, Thr or Val
<220> FEATURE:
<221> NAME/KEY: SITE
<222> LOCATION: (41)..(41)
<223> OTHER INFORMATION: Xaa can be any naturally occurring amino acid
<220> FEATURE:
<221> NAME/KEY: SITE
<222> LOCATION: (42)..(42)
<223> OTHER INFORMATION: Xaa is Ala, Phe, Ile, Leu, Met, Thr or Val
<220> FEATURE:
<221> NAME/KEY: SITE
<222> LOCATION: (43)..(45)
<223> OTHER INFORMATION: Xaa can be any naturally occurring amino acid
<220> FEATURE:
<221> NAME/KEY: SITE
<222> LOCATION: (46)..(47)
<223> OTHER INFORMATION: Xaa is Ala, Gly, Asn or Ser
<220> FEATURE:
<221> NAME/KEY: SITE
<222> LOCATION: (48)..(48)
<223> OTHER INFORMATION: Xaa can be any naturally occurring amino acid
<220> FEATURE:
<221> NAME/KEY: SITE
<222> LOCATION: (49)..(49)
<223> OTHER INFORMATION: Xaa is Asp, Glu, Lys, Asn, Met, Ser, Arg or Gln
<220> FEATURE:
<221> NAME/KEY: SITE
<222> LOCATION: (50)..(50)
<223> OTHER INFORMATION: Xaa can be any naturally occurring amino acid
<220> FEATURE:
<221> NAME/KEY: SITE
<222> LOCATION: (51)..(51)
<223> OTHER INFORMATION: Xaa is Ala, Phe, Ile, Leu, Met, Thr or Val
<220> FEATURE:
<221> NAME/KEY: SITE
<222> LOCATION: (52)..(60)
<223> OTHER INFORMATION: Xaa can be any naturally occurring amino acid
<220> FEATURE:
<221> NAME/KEY: SITE
<222> LOCATION: (61)..(61)
<223> OTHER INFORMATION: Xaa is Ala, Phe, Ile, Leu, Met, Thr or Val

<400> SEQUENCE: 293
```

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
    50                  55                  60

<210> SEQ ID NO 294
<211> LENGTH: 62
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (1)..(1)
<223> OTHER INFORMATION: Xaa is Ala, Phe, Ile, Leu, Met, Thr or Val
<220> FEATURE:
<221> NAME/KEY: SITE
<222> LOCATION: (2)..(4)
<223> OTHER INFORMATION: Xaa can be any naturally occurring amino acid
<220> FEATURE:
<221> NAME/KEY: SITE
<222> LOCATION: (5)..(5)
<223> OTHER INFORMATION: Xaa is Asp, Glu, Lys, Asn, Met, Ser, Arg or Gln
<220> FEATURE:
<221> NAME/KEY: SITE
<222> LOCATION: (6)..(7)
<223> OTHER INFORMATION: Xaa is Ala, Phe, Ile, Leu, Met, Thr or Val
<220> FEATURE:
<221> NAME/KEY: SITE
<222> LOCATION: (8)..(8)
<223> OTHER INFORMATION: Xaa can be any naturally occurring amino acid
<220> FEATURE:
<221> NAME/KEY: SITE
<222> LOCATION: (9)..(9)
<223> OTHER INFORMATION: Xaa is Ala, Phe, Ile, Leu, Met, Thr or Val
<220> FEATURE:
<221> NAME/KEY: SITE
<222> LOCATION: (10)..(12)
<223> OTHER INFORMATION: Xaa can be any naturally occurring amino acid
<220> FEATURE:
<221> NAME/KEY: SITE
<222> LOCATION: (13)..(14)
<223> OTHER INFORMATION: Xaa is Ala, Gly, Asn or Ser
<220> FEATURE:
<221> NAME/KEY: SITE
<222> LOCATION: (15)..(15)
<223> OTHER INFORMATION: Xaa can be any naturally occurring amino acid
<220> FEATURE:
<221> NAME/KEY: SITE
<222> LOCATION: (16)..(16)
<223> OTHER INFORMATION: Xaa is Asp, Glu, Lys, Asn, Met, Ser, Arg or Gln
<220> FEATURE:
<221> NAME/KEY: SITE
<222> LOCATION: (17)..(17)
<223> OTHER INFORMATION: Xaa can be any naturally occurring amino acid
<220> FEATURE:
<221> NAME/KEY: SITE
<222> LOCATION: (18)..(18)
<223> OTHER INFORMATION: Xaa is Ala, Phe, Ile, Leu, Met, Thr or Val
<220> FEATURE:
<221> NAME/KEY: SITE
<222> LOCATION: (19)..(27)
<223> OTHER INFORMATION: Xaa can be any naturally occurring amino acid
<220> FEATURE:
<221> NAME/KEY: SITE
<222> LOCATION: (28)..(28)
<223> OTHER INFORMATION: Xaa is Ala, Phe, Ile, Leu, Met, Thr or Val
<220> FEATURE:
<221> NAME/KEY: SITE
<222> LOCATION: (29)..(34)
<223> OTHER INFORMATION: Xaa can be any naturally occurring amino acid
```

```
<220> FEATURE:
<221> NAME/KEY: SITE
<222> LOCATION: (35)..(35)
<223> OTHER INFORMATION: Xaa is Ala, Phe, Ile, Leu, Met, Thr or Val
<220> FEATURE:
<221> NAME/KEY: SITE
<222> LOCATION: (36)..(38)
<223> OTHER INFORMATION: Xaa can be any naturally occurring amino acid
<220> FEATURE:
<221> NAME/KEY: SITE
<222> LOCATION: (39)..(39)
<223> OTHER INFORMATION: Xaa is Asp, Glu, Lys, Asn, Met, Ser, Arg or Gln
<220> FEATURE:
<221> NAME/KEY: SITE
<222> LOCATION: (40)..(41)
<223> OTHER INFORMATION: Xaa is Ala, Phe, Ile, Leu, Met, Thr or Val
<220> FEATURE:
<221> NAME/KEY: SITE
<222> LOCATION: (42)..(42)
<223> OTHER INFORMATION: Xaa can be any naturally occurring amino acid
<220> FEATURE:
<221> NAME/KEY: SITE
<222> LOCATION: (43)..(43)
<223> OTHER INFORMATION: Xaa is Ala, Phe, Ile, Leu, Met, Thr or Val
<220> FEATURE:
<221> NAME/KEY: SITE
<222> LOCATION: (44)..(46)
<223> OTHER INFORMATION: Xaa can be any naturally occurring amino acid
<220> FEATURE:
<221> NAME/KEY: SITE
<222> LOCATION: (47)..(48)
<223> OTHER INFORMATION: Xaa is Ala, Gly, Asn or Ser
<220> FEATURE:
<221> NAME/KEY: SITE
<222> LOCATION: (49)..(49)
<223> OTHER INFORMATION: Xaa can be any naturally occurring amino acid
<220> FEATURE:
<221> NAME/KEY: SITE
<222> LOCATION: (50)..(50)
<223> OTHER INFORMATION: Xaa is Asp, Glu, Lys, Asn, Met, Ser, Arg or Gln
<220> FEATURE:
<221> NAME/KEY: SITE
<222> LOCATION: (51)..(51)
<223> OTHER INFORMATION: Xaa can be any naturally occurring amino acid
<220> FEATURE:
<221> NAME/KEY: SITE
<222> LOCATION: (52)..(52)
<223> OTHER INFORMATION: Xaa is Ala, Phe, Ile, Leu, Met, Thr or Val
<220> FEATURE:
<221> NAME/KEY: SITE
<222> LOCATION: (53)..(61)
<223> OTHER INFORMATION: Xaa can be any naturally occurring amino acid
<220> FEATURE:
<221> NAME/KEY: SITE
<222> LOCATION: (62)..(62)
<223> OTHER INFORMATION: Xaa is Ala, Phe, Ile, Leu, Met, Thr or Val

<400> SEQUENCE: 294

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

<210> SEQ ID NO 295
<211> LENGTH: 63
<212> TYPE: PRT
<213> ORGANISM: Artificial Sequence
<220> FEATURE:
<223> OTHER INFORMATION: Synthetic Sequence
<220> FEATURE:
```

```
<221> NAME/KEY: SITE
<222> LOCATION: (1)..(1)
<223> OTHER INFORMATION: Xaa is Ala, Phe, Ile, Leu, Met, Thr or Val
<220> FEATURE:
<221> NAME/KEY: SITE
<222> LOCATION: (2)..(4)
<223> OTHER INFORMATION: Xaa can be any naturally occurring amino acid
<220> FEATURE:
<221> NAME/KEY: SITE
<222> LOCATION: (5)..(5)
<223> OTHER INFORMATION: Xaa is Asp, Glu, Lys, Asn, Met, Ser, Arg or Gln
<220> FEATURE:
<221> NAME/KEY: SITE
<222> LOCATION: (6)..(7)
<223> OTHER INFORMATION: Xaa is Ala, Phe, Ile, Leu, Met, Thr or Val
<220> FEATURE:
<221> NAME/KEY: SITE
<222> LOCATION: (8)..(8)
<223> OTHER INFORMATION: Xaa can be any naturally occurring amino acid
<220> FEATURE:
<221> NAME/KEY: SITE
<222> LOCATION: (9)..(9)
<223> OTHER INFORMATION: Xaa is Ala, Phe, Ile, Leu, Met, Thr or Val
<220> FEATURE:
<221> NAME/KEY: SITE
<222> LOCATION: (10)..(12)
<223> OTHER INFORMATION: Xaa can be any naturally occurring amino acid
<220> FEATURE:
<221> NAME/KEY: SITE
<222> LOCATION: (13)..(14)
<223> OTHER INFORMATION: Xaa is Ala, Gly, Asn or Ser
<220> FEATURE:
<221> NAME/KEY: SITE
<222> LOCATION: (15)..(15)
<223> OTHER INFORMATION: Xaa can be any naturally occurring amino acid
<220> FEATURE:
<221> NAME/KEY: SITE
<222> LOCATION: (16)..(16)
<223> OTHER INFORMATION: Xaa is Asp, Glu, Lys, Asn, Met, Ser, Arg or Gln
<220> FEATURE:
<221> NAME/KEY: SITE
<222> LOCATION: (17)..(17)
<223> OTHER INFORMATION: Xaa can be any naturally occurring amino acid
<220> FEATURE:
<221> NAME/KEY: SITE
<222> LOCATION: (18)..(18)
<223> OTHER INFORMATION: Xaa is Ala, Phe, Ile, Leu, Met, Thr or Val
<220> FEATURE:
<221> NAME/KEY: SITE
<222> LOCATION: (19)..(27)
<223> OTHER INFORMATION: Xaa can be any naturally occurring amino acid
<220> FEATURE:
<221> NAME/KEY: SITE
<222> LOCATION: (28)..(28)
<223> OTHER INFORMATION: Xaa is Ala, Phe, Ile, Leu, Met, Thr or Val
<220> FEATURE:
<221> NAME/KEY: SITE
<222> LOCATION: (29)..(35)
<223> OTHER INFORMATION: Xaa can be any naturally occurring amino acid
<220> FEATURE:
<221> NAME/KEY: SITE
<222> LOCATION: (36)..(36)
<223> OTHER INFORMATION: Xaa is Ala, Phe, Ile, Leu, Met, Thr or Val
<220> FEATURE:
<221> NAME/KEY: SITE
<222> LOCATION: (37)..(39)
<223> OTHER INFORMATION: Xaa can be any naturally occurring amino acid
<220> FEATURE:
<221> NAME/KEY: SITE
<222> LOCATION: (40)..(40)
<223> OTHER INFORMATION: Xaa is Asp, Glu, Lys, Asn, Met, Ser, Arg or Gln
<220> FEATURE:
<221> NAME/KEY: SITE
<222> LOCATION: (41)..(42)
<223> OTHER INFORMATION: Xaa is Ala, Phe, Ile, Leu, Met, Thr or Val
<220> FEATURE:
<221> NAME/KEY: SITE
<222> LOCATION: (43)..(43)
<223> OTHER INFORMATION: Xaa can be any naturally occurring amino acid
```

```
<220> FEATURE:
<221> NAME/KEY: SITE
<222> LOCATION: (44)..(44)
<223> OTHER INFORMATION: Xaa is Ala, Phe, Ile, Leu, Met, Thr or Val
<220> FEATURE:
<221> NAME/KEY: SITE
<222> LOCATION: (45)..(47)
<223> OTHER INFORMATION: Xaa can be any naturally occurring amino acid
<220> FEATURE:
<221> NAME/KEY: SITE
<222> LOCATION: (48)..(49)
<223> OTHER INFORMATION: Xaa is Ala, Gly, Asn or Ser
<220> FEATURE:
<221> NAME/KEY: SITE
<222> LOCATION: (50)..(50)
<223> OTHER INFORMATION: Xaa can be any naturally occurring amino acid
<220> FEATURE:
<221> NAME/KEY: SITE
<222> LOCATION: (51)..(51)
<223> OTHER INFORMATION: Xaa is Asp, Glu, Lys, Asn, Met, Ser, Arg or Gln
<220> FEATURE:
<221> NAME/KEY: SITE
<222> LOCATION: (52)..(52)
<223> OTHER INFORMATION: Xaa can be any naturally occurring amino acid
<220> FEATURE:
<221> NAME/KEY: SITE
<222> LOCATION: (53)..(53)
<223> OTHER INFORMATION: Xaa is Ala, Phe, Ile, Leu, Met, Thr or Val
<220> FEATURE:
<221> NAME/KEY: SITE
<222> LOCATION: (54)..(62)
<223> OTHER INFORMATION: Xaa can be any naturally occurring amino acid
<220> FEATURE:
<221> NAME/KEY: SITE
<222> LOCATION: (63)..(63)
<223> OTHER INFORMATION: Xaa is Ala, Phe, Ile, Leu, Met, Thr or Val

<400> SEQUENCE: 295

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

<210> SEQ ID NO 296
<211> LENGTH: 64
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (1)..(1)
<223> OTHER INFORMATION: Xaa is Ala, Phe, Ile, Leu, Met, Thr or Val
<220> FEATURE:
<221> NAME/KEY: SITE
<222> LOCATION: (2)..(4)
<223> OTHER INFORMATION: Xaa can be any naturally occurring amino acid
<220> FEATURE:
<221> NAME/KEY: SITE
<222> LOCATION: (5)..(5)
<223> OTHER INFORMATION: Xaa is Asp, Glu, Lys, Asn, Met, Set, Arg or Gln
<220> FEATURE:
<221> NAME/KEY: SITE
<222> LOCATION: (6)..(6)
<223> OTHER INFORMATION: Xaa is Ala, Phe, Ile, Leu, Met, Thr or Val
<220> FEATURE:
<221> NAME/KEY: SITE
<222> LOCATION: (7)..(8)
<223> OTHER INFORMATION: Xaa can be any naturally occurring amino acid
<220> FEATURE:
```

```
<221> NAME/KEY: SITE
<222> LOCATION: (9)..(9)
<223> OTHER INFORMATION: Xaa is Ala, Phe, Ile, Leu, Met, Thr or Val
<220> FEATURE:
<221> NAME/KEY: SITE
<222> LOCATION: (10)..(12)
<223> OTHER INFORMATION: Xaa can be any naturally occurring amino acid
<220> FEATURE:
<221> NAME/KEY: SITE
<222> LOCATION: (13)..(14)
<223> OTHER INFORMATION: Xaa is Ala, Gly, Asn or Ser
<220> FEATURE:
<221> NAME/KEY: SITE
<222> LOCATION: (15)..(15)
<223> OTHER INFORMATION: Xaa can be any naturally occurring amino acid
<220> FEATURE:
<221> NAME/KEY: SITE
<222> LOCATION: (16)..(16)
<223> OTHER INFORMATION: Xaa is Asp, Glu, Lys, Asn, Met, Set, Arg or Gln
<220> FEATURE:
<221> NAME/KEY: SITE
<222> LOCATION: (17)..(17)
<223> OTHER INFORMATION: Xaa can be any naturally occurring amino acid
<220> FEATURE:
<221> NAME/KEY: SITE
<222> LOCATION: (18)..(18)
<223> OTHER INFORMATION: Xaa is Ala, Phe, Ile, Leu, Met, Thr or Val
<220> FEATURE:
<221> NAME/KEY: SITE
<222> LOCATION: (19)..(27)
<223> OTHER INFORMATION: Xaa can be any naturally occurring amino acid
<220> FEATURE:
<221> NAME/KEY: SITE
<222> LOCATION: (28)..(28)
<223> OTHER INFORMATION: Xaa is Ala, Phe, Ile, Leu, Met, Thr or Val
<220> FEATURE:
<221> NAME/KEY: SITE
<222> LOCATION: (29)..(36)
<223> OTHER INFORMATION: Xaa can be any naturally occurring amino acid
<220> FEATURE:
<221> NAME/KEY: SITE
<222> LOCATION: (37)..(37)
<223> OTHER INFORMATION: Xaa is Ala, Phe, Ile, Leu, Met, Thr or Val
<220> FEATURE:
<221> NAME/KEY: SITE
<222> LOCATION: (38)..(40)
<223> OTHER INFORMATION: Xaa can be any naturally occurring amino acid
<220> FEATURE:
<221> NAME/KEY: SITE
<222> LOCATION: (41)..(41)
<223> OTHER INFORMATION: Xaa is Asp, Glu, Lys, Asn, Met, Set, Arg or Gln
<220> FEATURE:
<221> NAME/KEY: SITE
<222> LOCATION: (42)..(43)
<223> OTHER INFORMATION: Xaa is Ala, Phe, Ile, Leu, Met, Thr or Val
<220> FEATURE:
<221> NAME/KEY: SITE
<222> LOCATION: (44)..(44)
<223> OTHER INFORMATION: Xaa can be any naturally occurring amino acid
<220> FEATURE:
<221> NAME/KEY: SITE
<222> LOCATION: (45)..(45)
<223> OTHER INFORMATION: Xaa is Ala, Phe, Ile, Leu, Met, Thr or Val
<220> FEATURE:
<221> NAME/KEY: SITE
<222> LOCATION: (46)..(48)
<223> OTHER INFORMATION: Xaa can be any naturally occurring amino acid
<220> FEATURE:
<221> NAME/KEY: SITE
<222> LOCATION: (49)..(50)
<223> OTHER INFORMATION: Xaa is Ala, Gly, Asn or Ser
<220> FEATURE:
<221> NAME/KEY: SITE
<222> LOCATION: (51)..(51)
<223> OTHER INFORMATION: Xaa can be any naturally occurring amino acid
<220> FEATURE:
<221> NAME/KEY: SITE
<222> LOCATION: (52)..(52)
<223> OTHER INFORMATION: Xaa is Asp, Glu, Lys, Asn, Met, Set, Arg or Gln
```

```
<220> FEATURE:
<221> NAME/KEY: SITE
<222> LOCATION: (53)..(53)
<223> OTHER INFORMATION: Xaa can be any naturally occurring amino acid
<220> FEATURE:
<221> NAME/KEY: SITE
<222> LOCATION: (54)..(54)
<223> OTHER INFORMATION: Xaa is Ala, Phe, Ile, Leu, Met, Thr or Val
<220> FEATURE:
<221> NAME/KEY: SITE
<222> LOCATION: (55)..(63)
<223> OTHER INFORMATION: Xaa can be any naturally occurring amino acid
<220> FEATURE:
<221> NAME/KEY: SITE
<222> LOCATION: (64)..(64)
<223> OTHER INFORMATION: Xaa is Ala, Phe, Ile, Leu, Met, Thr or Val

<400> SEQUENCE: 296

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa
    50                  55                  60

<210> SEQ ID NO 297
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 297

Leu Thr Pro Gln Gln Val Val Ala Ile Ala Ser Asn Gly Gly Gly Arg
1               5                   10                  15

Pro Ala Leu Glu
            20

<210> SEQ ID NO 298
<211> LENGTH: 63
<212> TYPE: PRT
<213> ORGANISM: Artificial Sequence
<220> FEATURE:
<223> OTHER INFORMATION: Synthetic Sequence

<400> SEQUENCE: 298

Ser Ile Val Ala Gln Leu Ser Arg Pro Asp Pro Ala Leu Ala Ala Leu
1               5                   10                  15

Thr Asn Asp His Leu Val Ala Leu Ala Cys Leu Gly Gly Arg Pro Ala
                20                  25                  30

Leu Asp Ala Val Lys Lys Gly Leu Pro His Ala Pro Ala Leu Ile Lys
            35                  40                  45

Arg Thr Asn Arg Arg Ile Pro Glu Arg Thr Ser His Arg Val Ala
    50                  55                  60

<210> SEQ ID NO 299
<211> LENGTH: 1164
<212> TYPE: PRT
<213> ORGANISM: Artificial Sequence
<220> FEATURE:
<223> OTHER INFORMATION: Synthetic Sequence

<400> SEQUENCE: 299
```

```
Met Asp Pro Ile Arg Ser Arg Thr Pro Ser Pro Ala Arg Glu Leu Leu
1               5                   10                  15

Pro Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Gly Ser Phe Ser Asp Leu Leu Arg Gln Phe Asp Pro Ser Leu
65              70                  75                  80

Phe Asn Thr Ser Leu Phe Asp Ser Leu Pro Pro Phe Gly Ala His His
            85                  90                  95

Thr Glu Ala Ala Thr Gly Glu Trp Asp Glu Val Gln Ser Gly Leu Arg
            100                 105                 110

Ala Ala Asp Ala Pro Pro Thr Met Arg Val Ala Val Thr Ala Ala
            115                 120                 125

Arg Pro Pro Arg Ala Lys Pro Ala Pro Arg Arg Ala Ala Gln Pro
130             135                 140

Ser Asp Ala Ser Pro Ala Ala Gln Val Asp Leu Arg Thr Leu Gly Tyr
145             150                 155                 160

Ser Gln Gln Gln Glu Lys Ile Lys Pro Lys Val Arg Ser Thr Val
            165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
            195                 200                 205

Lys Tyr Gln Asp Met Ile Ala Ala Leu Pro Glu Ala Thr His Glu Ala
            210                 215                 220

Ile Val Gly Val Gly Lys Gln Trp Ser Gly Ala Arg Ala Leu Glu Ala
225             230                 235                 240

Leu Leu Thr Val Ala Gly Glu Leu Arg Gly Pro Pro Leu Gln Leu Asp
            245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
            275                 280                 285

Leu Thr Pro Glu Gln Val Val Ala Ile Ala Ser His Asp Gly Gly Lys
            290                 295                 300

Gln Ala Leu Glu Thr Val Gln Arg Leu Leu Pro Val Leu Cys Gln Ala
305             310                 315                 320

His Gly Leu Thr Pro Gln Gln Val Val Ala Ile Ala Ser Asn Gly Gly
            325                 330                 335

Gly Lys Gln Ala Leu Glu Thr Val Gln Arg Leu Leu Pro Val Leu Cys
            340                 345                 350

Gln Ala His Gly Leu Thr Pro Gln Gln Val Val Ala Ile Ala Ser Asn
            355                 360                 365

Ser Gly Gly Lys Gln Ala Leu Glu Thr Val Gln Arg Leu Leu Pro Val
    370                 375                 380

Leu Cys Gln Ala His Gly Leu Thr Pro Glu Gln Val Val Ala Ile Ala
385                 390                 395                 400

Ser Asn Gly Gly Gly Lys Gln Ala Leu Glu Thr Val Gln Arg Leu Leu
            405                 410                 415

Pro Val Leu Cys Gln Ala His Gly Leu Thr Pro Glu Gln Val Val Ala
```

```
              420             425             430
Ile Ala Ser Asn Ile Gly Gly Lys Gln Ala Leu Glu Thr Val Gln Ala
            435             440             445

Leu Leu Pro Val Leu Cys Gln Ala His Gly Leu Thr Pro Glu Gln Val
            450             455             460

Val Ala Ile Ala Ser Asn Ile Gly Gly Lys Gln Ala Leu Glu Thr Val
465             470             475             480

Gln Ala Leu Leu Pro Val Leu Cys Gln Ala His Gly Leu Thr Pro Glu
                485             490             495

Gln Val Val Ala Ile Ala Ser Asn Ile Gly Gly Lys Gln Ala Leu Glu
                500             505             510

Thr Val Gln Ala Leu Leu Pro Val Leu Cys Gln Ala His Gly Leu Thr
            515             520             525

Pro Glu Gln Val Val Ala Ile Ala Ser His Asp Gly Gly Lys Gln Ala
            530             535             540

Leu Glu Thr Val Gln Arg Leu Leu Pro Val Leu Cys Gln Ala His Gly
545             550             555             560

Leu Thr Pro Glu Gln Val Val Ala Ile Ala Ser His Asp Gly Gly Lys
                565             570             575

Gln Ala Leu Glu Thr Val Gln Arg Leu Leu Pro Val Leu Cys Gln Ala
            580             585             590

His Gly Leu Thr Pro Gln Gln Val Val Ala Ile Ala Ser Asn Gly Gly
            595             600             605

Gly Lys Gln Ala Leu Glu Thr Val Gln Arg Leu Leu Pro Val Leu Cys
            610             615             620

Gln Ala His Gly Leu Thr Pro Glu Gln Val Val Ala Ile Ala Ser Asn
625             630             635             640

Ser Gly Gly Lys Gln Ala Leu Glu Thr Val Gln Ala Leu Leu Pro Val
                645             650             655

Leu Cys Gln Ala His Gly Leu Thr Pro Glu Gln Val Val Ala Ile Ala
                660             665             670

Ser Asn Ser Gly Gly Lys Gln Ala Leu Glu Thr Val Gln Arg Leu Leu
            675             680             685

Pro Val Leu Cys Gln Ala His Gly Leu Thr Pro Glu Gln Val Val Ala
            690             695             700

Ile Ala Ser His Asp Gly Gly Lys Gln Ala Leu Glu Thr Val Gln Arg
705             710             715             720

Leu Leu Pro Val Leu Cys Gln Ala His Gly Leu Thr Pro Glu Gln Val
                725             730             735

Val Ala Ile Ala Ser His Asp Gly Gly Lys Gln Ala Leu Glu Thr Val
                740             745             750

Gln Arg Leu Leu Pro Val Leu Cys Gln Ala His Gly Leu Thr Pro Glu
            755             760             765

Gln Val Val Ala Ile Ala Ser His Asp Gly Gly Lys Gln Ala Leu Glu
            770             775             780

Thr Val Gln Arg Leu Leu Pro Val Leu Cys Gln Ala His Gly Leu Thr
785             790             795             800

Pro Gln Gln Val Val Ala Ile Ala Ser Asn Gly Gly Gly Arg Pro Ala
                805             810             815

Leu Glu Thr Val Gln Arg Leu Leu Pro Val Leu Cys Gln Ala His Gly
            820             825             830

Leu Thr Pro Glu Gln Val Val Ala Ile Ala Ser His Asp Gly Gly Lys
            835             840             845
```

```
Gln Ala Leu Glu Thr Val Gln Arg Leu Leu Pro Val Leu Cys Gln Ala
    850                 855                 860

His Gly Leu Thr Pro Gln Val Val Ala Ile Ala Ser Asn Gly Gly
865                 870                 875                 880

Gly Arg Pro Ala Leu Glu Ser Ile Val Ala Gln Leu Ser Arg Pro Asp
                885                 890                 895

Pro Ala Leu Ala Ala Leu Thr Asn Asp His Leu Val Ala Leu Ala Cys
                900                 905                 910

Leu Gly Gly Arg Pro Ala Leu Asp Ala Val Lys Lys Gly Leu Pro His
                915                 920                 925

Ala Pro Ala Leu Ile Lys Arg Thr Asn Arg Arg Ile Pro Glu Arg Thr
                930                 935                 940

Ser His Arg Val Ala Asp His Ala Gln Val Val Arg Val Leu Gly Phe
945                 950                 955                 960

Phe Gln Cys His Ser His Pro Ala Gln Ala Phe Asp Asp Ala Met Thr
                965                 970                 975

Gln Phe Gly Met Ser Arg His Gly Leu Leu Gln Leu Phe Arg Arg Val
                980                 985                 990

Gly Val Thr Glu Leu Glu Ala Arg Ser Gly Thr Leu Pro Pro Ala Ser
                995                 1000                1005

Gln Arg Trp Asp Arg Ile Leu Gln Ala Ser Gly Met Lys Arg Ala
    1010                1015                1020

Lys Pro Ser Pro Thr Ser Thr Gln Thr Pro Gln Ala Ser Leu
    1025                1030                1035

His Ala Phe Ala Asp Ser Leu Glu Arg Asp Leu Asp Ala Pro Ser
    1040                1045                1050

Pro Met His Glu Gly Asp Gln Thr Arg Ala Ser Ser Arg Lys Arg
    1055                1060                1065

Ser Arg Ser Asp Arg Ala Val Thr Gly Pro Ser Ala Gln Gln Ser
    1070                1075                1080

Phe Glu Val Arg Val Pro Glu Gln Arg Asp Ala Leu His Leu Pro
    1085                1090                1095

Leu Ser Trp Arg Val Lys Arg Pro Arg Thr Ser Ile Gly Gly Gly
    1100                1105                1110

Leu Pro Asp Pro Gly Thr Pro Thr Ala Ala Asp Leu Ala Ala Ser
    1115                1120                1125

Ser Thr Val Met Arg Glu Gln Asp Glu Asp Pro Phe Ala Gly Ala
    1130                1135                1140

Ala Asp Asp Phe Pro Ala Phe Asn Glu Glu Glu Leu Ala Trp Leu
    1145                1150                1155

Met Glu Leu Leu Pro Gln
    1160

<210> SEQ ID NO 300
<211> LENGTH: 137
<212> TYPE: PRT
<213> ORGANISM: Artificial Sequence
<220> FEATURE:
<223> OTHER INFORMATION: Synthetic Sequence

<400> SEQUENCE: 300

Met Val Asp Leu Arg Thr Leu Gly Tyr Ser Gln Gln Gln Gln Glu Lys
1               5                   10                  15

Ile Lys Pro Lys Val Arg Ser Thr Val Ala Gln His His Glu Ala Leu
            20                  25                  30
```

```
Val Gly His Gly Phe Thr His Ala His Ile Val Ala Leu Ser Gln His
        35                  40                  45

Pro Ala Ala Leu Gly Thr Val Ala Val Lys Tyr Gln Asp Met Ile Ala
    50                  55                  60

Ala Leu Pro Glu Ala Thr His Glu Ala Ile Val Gly Val Gly Lys Gln
65                  70                  75                  80

Trp Ser Gly Ala Arg Ala Leu Glu Ala Leu Leu Thr Val Ala Gly Glu
                85                  90                  95

Leu Arg Gly Pro Pro Leu Gln Leu Asp Thr Gly Gln Leu Leu Lys Ile
            100                 105                 110

Ala Lys Arg Gly Gly Val Thr Ala Val Glu Ala Val His Ala Trp Arg
        115                 120                 125

Asn Ala Leu Thr Gly Ala Pro Leu Asn
    130                 135

<210> SEQ ID NO 301
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 301

Lys Pro Lys Val Arg Ser Thr Val Ala Gln His His Glu Ala Leu Val
1               5                   10                  15

Gly His Gly Phe Thr His Ala His Ile Val Ala Leu Ser Gln His Pro
            20                  25                  30

Ala Ala Leu Gly Thr Val Ala Val Lys Tyr Gln Asp Met Ile Ala Ala
        35                  40                  45

Leu Pro Glu Ala Thr His Glu Ala Ile Val Gly Val Gly Lys Gln Trp
    50                  55                  60

Ser Gly Ala Arg Ala Leu Glu Ala Leu Leu Thr Val Ala Gly Glu Leu
65                  70                  75                  80

Arg Gly Pro Pro Leu Gln Leu Asp Thr Gly Gln Leu Leu Lys Ile Ala
                85                  90                  95

Lys Arg Gly Gly Val Thr Ala Val Glu Ala Val His Ala Trp Arg Asn
            100                 105                 110

Ala Leu Thr Gly Ala Pro Leu Asn
        115                 120

<210> SEQ ID NO 302
<211> LENGTH: 278
<212> TYPE: PRT
<213> ORGANISM: Artificial Sequence
<220> FEATURE:
<223> OTHER INFORMATION: Synthetic Sequence

<400> SEQUENCE: 302

Ser Ile Val Ala Gln Leu Ser Arg Pro Asp Pro Ala Leu Ala Ala Leu
1               5                   10                  15

Thr Asn Asp His Leu Val Ala Leu Ala Cys Leu Gly Gly Arg Pro Ala
            20                  25                  30

Leu Asp Ala Val Lys Lys Gly Leu Pro His Ala Pro Ala Leu Ile Lys
        35                  40                  45

Arg Thr Asn Arg Arg Ile Pro Glu Arg Thr Ser His Arg Val Ala Asp
    50                  55                  60

His Ala Gln Val Val Arg Val Leu Gly Phe Phe Gln Cys His Ser His
```

```
            65                  70                  75                  80

Pro Ala Gln Ala Phe Asp Asp Ala Met Thr Gln Phe Gly Met Ser Arg
                85                  90                  95

His Gly Leu Leu Gln Leu Phe Arg Arg Val Gly Val Thr Glu Leu Glu
            100                 105                 110

Ala Arg Ser Gly Thr Leu Pro Pro Ala Ser Gln Arg Trp Asp Arg Ile
            115                 120                 125

Leu Gln Ala Ser Gly Met Lys Arg Ala Lys Pro Ser Pro Thr Ser Thr
        130                 135                 140

Gln Thr Pro Asp Gln Ala Ser Leu His Ala Phe Ala Asp Ser Leu Glu
145                 150                 155                 160

Arg Asp Leu Asp Ala Pro Ser Pro Thr His Glu Gly Asp Gln Arg Arg
                165                 170                 175

Ala Ser Ser Arg Lys Arg Ser Arg Ser Asp Arg Ala Val Thr Gly Pro
            180                 185                 190

Ser Ala Gln Gln Ser Phe Glu Val Arg Ala Pro Glu Gln Arg Asp Ala
            195                 200                 205

Leu His Leu Pro Leu Ser Trp Arg Val Lys Arg Pro Arg Thr Ser Ile
        210                 215                 220

Gly Gly Gly Leu Pro Asp Pro Gly Thr Pro Thr Ala Ala Asp Leu Ala
225                 230                 235                 240

Ala Ser Ser Thr Val Met Arg Glu Gln Asp Glu Asp Pro Phe Ala Gly
                245                 250                 255

Ala Ala Asp Asp Phe Pro Ala Phe Asn Glu Glu Glu Leu Ala Trp Leu
                260                 265                 270

Met Glu Leu Leu Pro Gln
        275

<210> SEQ ID NO 303
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 303

Lys Gln Glu Ser Leu Ser Glu Ile Ala Lys Tyr His Thr Thr Leu Thr
1               5                   10                  15

Gly Gln Gly Phe Thr His Ala Asp Ile Cys Arg Ile Ser Arg Arg Arg
            20                  25                  30

Gln Ser Leu Arg Val Val Ala Arg Asn Tyr Pro Glu Leu Ala Ala Ala
        35                  40                  45

Leu Pro Glu Leu Thr Arg Ala His Ile Val Asp Ile Ala Arg Gln Arg
    50                  55                  60

Ser Gly Asp Leu Ala Leu Gln Ala Leu Leu Pro Val Ala Thr Ala Leu
65                  70                  75                  80

Thr Ala Ala Pro Leu Arg Leu Ser Ala Ser Gln Ile Ala Thr Val Ala
                85                  90                  95

Gln Tyr Gly Glu Arg Pro Ala Ile Gln Ala Leu Tyr Arg Leu Arg Arg
            100                 105                 110

Lys Leu Thr Arg Ala Pro Leu His
        115                 120

<210> SEQ ID NO 304
<211> LENGTH: 120
<212> TYPE: PRT
```

<213> ORGANISM: Artificial Sequence
<220> FEATURE:
<223> OTHER INFORMATION: Synthetic Sequence

<400> SEQUENCE: 304

Asp Ala Thr Asn Asp Asn Ser Gln Ala Ser Ser Ser Tyr Ser Ser Lys
1               5                   10                  15

Ser Ser Pro Ala Ser Ala Asn Ala Arg Lys Arg Thr Ser Arg Lys Glu
            20                  25                  30

Met Ser Gly Pro Pro Ser Lys Glu Pro Ala Asn Thr Lys Ser Arg Arg
        35                  40                  45

Ala Asn Ser Gln Asn Asn Lys Leu Ser Leu Ala Asp Arg Leu Thr Lys
    50                  55                  60

Tyr Asn Ile Asp Glu Glu Phe Tyr Gln Thr Arg Ser Asp Ser Leu Leu
65                  70                  75                  80

Ser Leu Asn Tyr Thr Lys Lys Gln Ile Glu Arg Leu Ile Leu Tyr Lys
                85                  90                  95

Gly Arg Thr Ser Ala Val Gln Gln Leu Leu Cys Lys His Glu Glu Leu
            100                 105                 110

Leu Asn Leu Ile Ser Pro Asp Gly
        115                 120

<210> SEQ ID NO 305
<211> LENGTH: 176
<212> TYPE: PRT
<213> ORGANISM: Artificial Sequence
<220> FEATURE:
<223> OTHER INFORMATION: Synthetic Sequence

<400> SEQUENCE: 305

Ala Leu Val Lys Glu Tyr Phe Pro Val Phe Ser Ser Phe His Phe Thr
1               5                   10                  15

Ala Asp Gln Ile Val Ala Leu Ile Cys Gln Ser Lys Gln Cys Phe Arg
            20                  25                  30

Asn Leu Lys Lys Asn His Gln Gln Trp Lys Asn Lys Gly Leu Ser Ala
        35                  40                  45

Glu Gln Ile Val Asp Leu Ile Leu Gln Glu Thr Pro Pro Lys Pro Asn
    50                  55                  60

Phe Asn Asn Thr Ser Ser Ser Thr Pro Ser Pro Ser Ala Pro Ser Phe
65                  70                  75                  80

Phe Gln Gly Pro Ser Thr Pro Ile Pro Thr Pro Val Leu Asp Asn Ser
                85                  90                  95

Pro Ala Pro Ile Phe Ser Asn Pro Val Cys Phe Ser Ser Arg Ser
            100                 105                 110

Glu Asn Asn Thr Glu Gln Tyr Leu Gln Asp Ser Thr Leu Asp Leu Asp
        115                 120                 125

Ser Gln Leu Gly Asp Pro Thr Lys Asn Phe Asn Val Asn Asn Phe Trp
    130                 135                 140

Ser Leu Phe Pro Phe Asp Asp Val Gly Tyr His Pro His Ser Asn Asp
145                 150                 155                 160

Val Gly Tyr His Leu His Ser Asp Glu Glu Ser Pro Phe Phe Asp Phe
                165                 170                 175

<210> SEQ ID NO 306
<211> LENGTH: 63
<212> TYPE: PRT
<213> ORGANISM: Artificial Sequence
<220> FEATURE:

<223> OTHER INFORMATION: Synthetic Sequence

<400> SEQUENCE: 306

Ala Leu Val Lys Glu Tyr Phe Pro Val Phe Ser Ser Phe His Phe Thr
1               5                   10                  15

Ala Asp Gln Ile Val Ala Leu Ile Cys Gln Ser Lys Gln Cys Phe Arg
                20                  25                  30

Asn Leu Lys Lys Asn His Gln Gln Trp Lys Asn Lys Gly Leu Ser Ala
            35                  40                  45

Glu Gln Ile Val Asp Leu Ile Leu Gln Glu Thr Pro Pro Lys Pro
        50                  55                  60

<210> SEQ ID NO 307
<211> LENGTH: 1199
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (35)..(74)
<223> OTHER INFORMATION: Xaa is Gly, Ala, Thr or His
<220> FEATURE:
<221> NAME/KEY: SITE
<222> LOCATION: (36)..(74)
<223> OTHER INFORMATION: Each amino acid at positions 36 to 74 is either
      present or absent
<220> FEATURE:
<221> NAME/KEY: SITE
<222> LOCATION: (109)..(148)
<223> OTHER INFORMATION: Xaa is Gly, Ala, Thr or His
<220> FEATURE:
<221> NAME/KEY: SITE
<222> LOCATION: (110)..(148)
<223> OTHER INFORMATION: Each amino acid at positions 110 to 148 is
      either present or absent
<220> FEATURE:
<221> NAME/KEY: SITE
<222> LOCATION: (183)..(222)
<223> OTHER INFORMATION: Xaa is Gly, Ala, Thr or His
<220> FEATURE:
<221> NAME/KEY: SITE
<222> LOCATION: (184)..(222)
<223> OTHER INFORMATION: Each amino acid at positions 184 to 222 is
      either present or absent
<220> FEATURE:
<221> NAME/KEY: SITE
<222> LOCATION: (257)..(296)
<223> OTHER INFORMATION: Xaa is Gly, Ala, Thr or His
<220> FEATURE:
<221> NAME/KEY: SITE
<222> LOCATION: (258)..(296)
<223> OTHER INFORMATION: Each amino acid at positions 259 to 296 is
      either present or absent
<220> FEATURE:
<221> NAME/KEY: SITE
<222> LOCATION: (331)..(370)
<223> OTHER INFORMATION: Xaa is Gly, Ala, Thr or His
<220> FEATURE:
<221> NAME/KEY: SITE
<222> LOCATION: (332)..(370)
<223> OTHER INFORMATION: Each amino acid at positions 332 to 370 is
      either present or absent
<220> FEATURE:
<221> NAME/KEY: SITE
<222> LOCATION: (405)..(444)
<223> OTHER INFORMATION: Xaa is Gly, Ala, Thr or His
<220> FEATURE:
<221> NAME/KEY: SITE
<222> LOCATION: (406)..(444)
<223> OTHER INFORMATION: Each amino acid at positions 406 to 444 is
      either present or absent
<220> FEATURE:
<221> NAME/KEY: SITE

```
<222> LOCATION: (479)..(518)
<223> OTHER INFORMATION: Xaa is Gly, Ala, Thr or His
<220> FEATURE:
<221> NAME/KEY: SITE
<222> LOCATION: (480)..(518)
<223> OTHER INFORMATION: Each amino acid at positions 480 to 518 is
      either present or absent
<220> FEATURE:
<221> NAME/KEY: SITE
<222> LOCATION: (553)..(592)
<223> OTHER INFORMATION: Xaa is Gly, Ala, Thr or His
<220> FEATURE:
<221> NAME/KEY: SITE
<222> LOCATION: (554)..(592)
<223> OTHER INFORMATION: Each amino acid at positions 554 to 592 is
      either present or absent
<220> FEATURE:
<221> NAME/KEY: SITE
<222> LOCATION: (627)..(666)
<223> OTHER INFORMATION: Xaa is Gly, Ala, Thr or His
<220> FEATURE:
<221> NAME/KEY: SITE
<222> LOCATION: (628)..(666)
<223> OTHER INFORMATION: Each amino acid at positions 628 to 666 is
      either present or absent
<220> FEATURE:
<221> NAME/KEY: SITE
<222> LOCATION: (701)..(740)
<223> OTHER INFORMATION: Xaa is Gly, Ala, Thr or His
<220> FEATURE:
<221> NAME/KEY: SITE
<222> LOCATION: (702)..(740)
<223> OTHER INFORMATION: Each amino acid at positions 702 to 740 is
      either present or absent
<220> FEATURE:
<221> NAME/KEY: SITE
<222> LOCATION: (775)..(814)
<223> OTHER INFORMATION: Xaa is Gly, Ala, Thr or His
<220> FEATURE:
<221> NAME/KEY: SITE
<222> LOCATION: (776)..(814)
<223> OTHER INFORMATION: Each amino acid at positions 776 to 814 is
      either present or absent
<220> FEATURE:
<221> NAME/KEY: SITE
<222> LOCATION: (849)..(888)
<223> OTHER INFORMATION: Xaa is Gly, Ala, Thr or His
<220> FEATURE:
<221> NAME/KEY: SITE
<222> LOCATION: (850)..(888)
<223> OTHER INFORMATION: Each amino acid at positions 850 to 888 is
      either present or absent
<220> FEATURE:
<221> NAME/KEY: SITE
<222> LOCATION: (923)..(962)
<223> OTHER INFORMATION: Xaa is Gly, Ala, Thr or His
<220> FEATURE:
<221> NAME/KEY: SITE
<222> LOCATION: (924)..(962)
<223> OTHER INFORMATION: Each amino acid at positions 924 to 962 is
      either present or absent
<220> FEATURE:
<221> NAME/KEY: SITE
<222> LOCATION: (997)..(1036)
<223> OTHER INFORMATION: Xaa is Gly, Ala, Thr or His
<220> FEATURE:
<221> NAME/KEY: SITE
<222> LOCATION: (998)..(1036)
<223> OTHER INFORMATION: Each amino acid at positions 998 to 1036 is
      either present or absent
<220> FEATURE:
<221> NAME/KEY: SITE
<222> LOCATION: (1071)..(1110)
<223> OTHER INFORMATION: Xaa is Gly, Ala, Thr or His
<220> FEATURE:
<221> NAME/KEY: SITE
<222> LOCATION: (1072)..(1110)
<223> OTHER INFORMATION: Each amino acid at positions 1072 to 1110 is
      either present or absent
```

-continued

```
<220> FEATURE:
<221> NAME/KEY: SITE
<222> LOCATION: (1145)..(1184)
<223> OTHER INFORMATION: Xaa is Gly, Ala, Thr or His
<220> FEATURE:
<221> NAME/KEY: SITE
<222> LOCATION: (1146)..(1184)
<223> OTHER INFORMATION: Each amino acid at positions 1146 to 1184 is
      either present or absent

<400> SEQUENCE: 307

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Leu Thr Pro Asp Gln Val Val
65                  70                  75                  80

Val Ala Ile Ala Ser His Asp Gly Gly Lys Gln Ala Leu Glu Thr Val
                85                  90                  95

Gln Arg Leu Leu Pro Val Leu Cys Gln Asp His Gly Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Leu Thr Pro Asp Gln Val Val Ala Ile Ala Ser His
145                 150                 155                 160

Asp Gly Gly Lys Gln Ala Leu Glu Thr Val Gln Arg Leu Leu Pro Val
                165                 170                 175

Leu Cys Gln Asp His Gly Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Leu Thr
    210                 215                 220

Pro Asp Gln Val Val Ala Ile Ala Ser His Asp Gly Gly Lys Gln Ala
225                 230                 235                 240

Leu Glu Thr Val Gln Arg Leu Leu Pro Val Leu Cys Gln Asp His Gly
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Leu Thr Pro Asp Gln Val Val Ala
    290                 295                 300

Ile Ala Ser Asn Gly Gly Gly Lys Gln Ala Leu Glu Thr Val Gln Arg
305                 310                 315                 320

Leu Leu Pro Val Leu Cys Gln Asp His Gly Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
```

-continued

```
            355                 360                 365
Xaa Xaa Leu Thr Pro Asp Gln Val Val Ala Ile Ala Ser His Asp Gly
    370                 375                 380

Gly Lys Gln Ala Leu Glu Thr Val Gln Arg Leu Leu Pro Val Leu Cys
385                 390                 395                 400

Gln Asp His Gly Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Leu Thr Pro Asp
            435                 440                 445

Gln Val Val Ala Ile Ala Ser His Asp Gly Gly Lys Gln Ala Leu Glu
    450                 455                 460

Thr Val Gln Arg Leu Leu Pro Val Leu Cys Gln Asp His Gly Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Leu Thr Pro Asp Gln Val Val Ala Ile Ala
            515                 520                 525

Ser Asn Ile Gly Gly Lys Gln Ala Leu Glu Thr Val Gln Arg Leu Leu
    530                 535                 540

Pro Val Leu Cys Gln Asp His Gly Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa Xaa
                565                 570                 575

Xaa Xaa Xaa Xaa Xaa Xaa Xaa Xaa Xaa Xaa Xaa Xaa Xaa Xaa Xaa Xaa
            580                 585                 590

Leu Thr Pro Asp Gln Val Val Ala Ile Ala Ser His Asp Gly Gly Lys
    595                 600                 605

Gln Ala Leu Glu Thr Val Gln Arg Leu Leu Pro Val Leu Cys Gln Asp
610                 615                 620

His Gly Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Leu Thr Pro Asp Gln Val
            660                 665                 670

Val Ala Ile Ala Ser His Asp Gly Gly Lys Gln Ala Leu Glu Thr Val
        675                 680                 685

Gln Arg Leu Leu Pro Val Leu Cys Gln Asp His Gly Xaa Xaa Xaa Xaa
    690                 695                 700

Xaa Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa Xaa
                725                 730                 735

Xaa Xaa Xaa Xaa Leu Thr Pro Asp Gln Val Val Ala Ile Ala Ser His
            740                 745                 750

Asp Gly Gly Lys Gln Ala Leu Glu Thr Val Gln Arg Leu Leu Pro Val
    755                 760                 765

Leu Cys Gln Asp His Gly Xaa Xaa Xaa Xaa Xaa Xaa Xaa Xaa Xaa Xaa
770                 775                 780
```

```
Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Leu Thr
            805                 810                 815

Pro Asp Gln Val Val Ala Ile Ala Ser His Asp Gly Lys Gln Ala
        820                 825                 830

Leu Glu Thr Val Gln Arg Leu Leu Pro Val Leu Cys Gln Asp His Gly
            835                 840                 845

Xaa Xaa Xaa Xaa Xaa Xaa Xaa Xaa Xaa Xaa Xaa Xaa Xaa Xaa
850                 855                 860

Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Leu Thr Pro Asp Gln Val Val Ala
            885                 890                 895

Ile Ala Ser Asn Ile Gly Gly Lys Gln Ala Leu Glu Thr Val Gln Arg
        900                 905                 910

Leu Leu Pro Val Leu Cys Gln Asp His Gly Xaa Xaa Xaa Xaa Xaa
            915                 920                 925

Xaa Xaa Xaa Xaa Xaa Xaa Xaa Xaa Xaa Xaa Xaa Xaa Xaa Xaa
930                 935                 940

Xaa Xaa Xaa Xaa Xaa Xaa Xaa Xaa Xaa Xaa Xaa Xaa Xaa Xaa
945                 950                 955                 960

Xaa Xaa Leu Thr Pro Asp Gln Val Val Ala Ile Ala Ser His Asp Gly
            965                 970                 975

Gly Lys Gln Ala Leu Glu Thr Val Gln Arg Leu Leu Pro Val Leu Cys
        980                 985                 990

Gln Asp His Gly Xaa Xaa Xaa Xaa Xaa Xaa Xaa Xaa Xaa Xaa Xaa
            995                 1000                1005

Xaa Xaa Xaa Xaa Xaa Xaa Xaa Xaa Xaa Xaa Xaa Xaa Xaa Xaa
    1010                1015                1020

Xaa Xaa Xaa Xaa Xaa Xaa Xaa Xaa Xaa Xaa Xaa Xaa Leu Thr
    1025                1030                1035

Pro Asp Gln Val Val Ala Ile Ala Ser Asn Ile Gly Gly Lys Gln
    1040                1045                1050

Ala Leu Glu Thr Val Gln Arg Leu Leu Pro Val Leu Cys Gln Asp
    1055                1060                1065

His Gly Xaa Xaa Xaa Xaa Xaa Xaa Xaa Xaa Xaa Xaa Xaa Xaa
    1070                1075                1080

Xaa Xaa Xaa Xaa Xaa Xaa Xaa Xaa Xaa Xaa Xaa Xaa Xaa Xaa
    1085                1090                1095

Xaa Xaa Xaa Xaa Xaa Xaa Xaa Xaa Xaa Xaa Xaa Leu Thr Pro
    1100                1105                1110

Asp Gln Val Val Ala Ile Ala Ser Asn His Gly Gly Lys Gln Ala
    1115                1120                1125

Leu Glu Thr Val Gln Arg Leu Leu Pro Val Leu Cys Gln Asp His
    1130                1135                1140

Gly Xaa Xaa Xaa Xaa Xaa Xaa Xaa Xaa Xaa Xaa Xaa Xaa Xaa
    1145                1150                1155

Xaa Xaa Xaa Xaa Xaa Xaa Xaa Xaa Xaa Xaa Xaa Xaa Xaa Xaa
    1160                1165                1170

Xaa Xaa Xaa Xaa Xaa Xaa Xaa Xaa Xaa Xaa Xaa Leu Thr Pro Asp
    1175                1180                1185
```

```
Gln Val Val Ala Ile Ala Ser Asn Gly Gly Gly
    1190                1195

<210> SEQ ID NO 308
<211> LENGTH: 1218
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (35)..(74)
<223> OTHER INFORMATION: Xaa is Gly, Ala, Thr or His
<220> FEATURE:
<221> NAME/KEY: SITE
<222> LOCATION: (36)..(74)
<223> OTHER INFORMATION: Each amino acid at positions 36 to 74 is either
      present or absent
<220> FEATURE:
<221> NAME/KEY: SITE
<222> LOCATION: (109)..(148)
<223> OTHER INFORMATION: Xaa is Gly, Ala, Thr or His
<220> FEATURE:
<221> NAME/KEY: SITE
<222> LOCATION: (110)..(148)
<223> OTHER INFORMATION: Each amino acid at positions 110 to 148 is
      either present or absent
<220> FEATURE:
<221> NAME/KEY: SITE
<222> LOCATION: (183)..(222)
<223> OTHER INFORMATION: Xaa is Gly, Ala, Thr or His
<220> FEATURE:
<221> NAME/KEY: SITE
<222> LOCATION: (184)..(222)
<223> OTHER INFORMATION: Each amino acid at positions 184 to 222 is
      either present or absent
<220> FEATURE:
<221> NAME/KEY: SITE
<222> LOCATION: (257)..(296)
<223> OTHER INFORMATION: Xaa is Gly, Ala, Thr or His
<220> FEATURE:
<221> NAME/KEY: SITE
<222> LOCATION: (258)..(296)
<223> OTHER INFORMATION: Each amino acid at positions 258 to 296 is
      either present or absent
<220> FEATURE:
<221> NAME/KEY: SITE
<222> LOCATION: (331)..(370)
<223> OTHER INFORMATION: Xaa is Gly, Ala, Thr or His
<220> FEATURE:
<221> NAME/KEY: SITE
<222> LOCATION: (332)..(370)
<223> OTHER INFORMATION: Each amino acid at positions 332 to 370 is
      either present or absent
<220> FEATURE:
<221> NAME/KEY: SITE
<222> LOCATION: (405)..(444)
<223> OTHER INFORMATION: Xaa is Gly, Ala, Thr or His
<220> FEATURE:
<221> NAME/KEY: SITE
<222> LOCATION: (406)..(444)
<223> OTHER INFORMATION: Each amino acid at positions 406 to 444 is
      either present or absent
<220> FEATURE:
<221> NAME/KEY: SITE
<222> LOCATION: (479)..(518)
<223> OTHER INFORMATION: Xaa is Gly, Ala, Thr or His
<220> FEATURE:
<221> NAME/KEY: SITE
<222> LOCATION: (480)..(518)
<223> OTHER INFORMATION: Each amino acid at positions 480 to 518 is
      either present or absent
<220> FEATURE:
<221> NAME/KEY: SITE
<222> LOCATION: (553)..(592)
<223> OTHER INFORMATION: Xaa is Gly, Ala, Thr or His
<220> FEATURE:
<221> NAME/KEY: SITE
```

```
<222> LOCATION: (554)..(592)
<223> OTHER INFORMATION: Each amino acid at positions 554 to 592 is
      either present or absent
<220> FEATURE:
<221> NAME/KEY: SITE
<222> LOCATION: (627)..(666)
<223> OTHER INFORMATION: Xaa is Gly, Ala, Thr or His
<220> FEATURE:
<221> NAME/KEY: SITE
<222> LOCATION: (628)..(666)
<223> OTHER INFORMATION: Each amino acid at positions 628 to 666 is
      either present or absent
<220> FEATURE:
<221> NAME/KEY: SITE
<222> LOCATION: (701)..(740)
<223> OTHER INFORMATION: Xaa is Gly, Ala, Thr or His
<220> FEATURE:
<221> NAME/KEY: SITE
<222> LOCATION: (702)..(740)
<223> OTHER INFORMATION: Each amino acid at positions 702 to 740 is
      either present or absent
<220> FEATURE:
<221> NAME/KEY: SITE
<222> LOCATION: (775)..(814)
<223> OTHER INFORMATION: Xaa is Gly, Ala, Thr or His
<220> FEATURE:
<221> NAME/KEY: SITE
<222> LOCATION: (776)..(814)
<223> OTHER INFORMATION: Each amino acid at positions 776 to 814 is
      either present or absent
<220> FEATURE:
<221> NAME/KEY: SITE
<222> LOCATION: (849)..(888)
<223> OTHER INFORMATION: Xaa is Gly, Ala, Thr or His
<220> FEATURE:
<221> NAME/KEY: SITE
<222> LOCATION: (850)..(888)
<223> OTHER INFORMATION: Each amino acid at positions 850 to 888 is
      either present or absent
<220> FEATURE:
<221> NAME/KEY: SITE
<222> LOCATION: (923)..(962)
<223> OTHER INFORMATION: Xaa is Gly, Ala, Thr or His
<220> FEATURE:
<221> NAME/KEY: SITE
<222> LOCATION: (924)..(962)
<223> OTHER INFORMATION: Each amino acid at positions 924 to 962 is
      either present or absent
<220> FEATURE:
<221> NAME/KEY: SITE
<222> LOCATION: (997)..(1036)
<223> OTHER INFORMATION: Xaa is Gly, Ala, Thr or His
<220> FEATURE:
<221> NAME/KEY: SITE
<222> LOCATION: (998)..(1036)
<223> OTHER INFORMATION: Each amino acid at positions 998 to 1036 is
      either present or absent
<220> FEATURE:
<221> NAME/KEY: SITE
<222> LOCATION: (1071)..(1110)
<223> OTHER INFORMATION: Xaa is Gly, Ala, Thr or His
<220> FEATURE:
<221> NAME/KEY: SITE
<222> LOCATION: (1072)..(1110)
<223> OTHER INFORMATION: Each amino acid at positions 1072 to 1110 is
      either present or absent
<220> FEATURE:
<221> NAME/KEY: SITE
<222> LOCATION: (1145)..(1184)
<223> OTHER INFORMATION: Xaa is Gly, Ala, Thr or His
<220> FEATURE:
<221> NAME/KEY: SITE
<222> LOCATION: (1146)..(1184)
<223> OTHER INFORMATION: Each amino acid at positions 1146 to 1184 is
      either present or absent

<400> SEQUENCE: 308

Leu Thr Pro Asp Gln Val Val Ala Ile Ala Ser Asn Gly Gly Gly Lys
```

```
            1               5                  10                 15
Gln Ala Leu Glu Thr Val Gln Arg Leu Leu Pro Val Leu Cys Gln Asp
                20                  25                  30

His Gly Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Leu Thr Pro Asp Gln Val
 65                  70                  75                  80

Val Ala Ile Ala Ser Asn Gly Gly Lys Gln Ala Leu Glu Thr Val
                85                  90                  95

Gln Arg Leu Leu Pro Val Leu Cys Gln Asp His Gly Xaa Xaa Xaa Xaa
                100                 105                 110

Xaa Xaa Xaa Xaa Xaa Xaa Xaa Xaa Xaa Xaa Xaa Xaa Xaa Xaa Xaa Xaa
                115                 120                 125

Xaa Xaa Xaa Xaa Xaa Xaa Xaa Xaa Xaa Xaa Xaa Xaa Xaa Xaa Xaa Xaa
 130                 135                 140

Xaa Xaa Xaa Xaa Leu Thr Pro Asp Gln Val Val Ala Ile Ala Ser Asn
145                 150                 155                 160

Gly Gly Lys Gln Ala Leu Glu Thr Val Gln Arg Leu Leu Pro Val
                165                 170                 175

Leu Cys Gln Asp His Gly Xaa Xaa Xaa Xaa Xaa Xaa Xaa Xaa Xaa
                180                 185                 190

Xaa Xaa Xaa Xaa Xaa Xaa Xaa Xaa Xaa Xaa Xaa Xaa Xaa Xaa Xaa
                195                 200                 205

Xaa Xaa Xaa Xaa Xaa Xaa Xaa Xaa Xaa Xaa Xaa Xaa Xaa Leu Thr
 210                 215                 220

Pro Asp Gln Val Val Ala Ile Ala Ser His Asp Gly Gly Lys Gln Ala
225                 230                 235                 240

Leu Glu Thr Val Gln Arg Leu Leu Pro Val Leu Cys Gln Asp His Gly
                245                 250                 255

Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa
                275                 280                 285

Xaa Xaa Xaa Xaa Xaa Xaa Xaa Xaa Leu Thr Pro Asp Gln Val Val Ala
                290                 295                 300

Ile Ala Ser Asn Gly Gly Lys Gln Ala Leu Glu Thr Val Gln Arg
305                 310                 315                 320

Leu Leu Pro Val Leu Cys Gln Asp His Gly Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa Xaa Xaa
                355                 360                 365

Xaa Xaa Leu Thr Pro Asp Gln Val Val Ala Ile Ala Ser Asn His Gly
                370                 375                 380

Gly Lys Gln Ala Leu Glu Thr Val Gln Arg Leu Leu Pro Val Leu Cys
385                 390                 395                 400

Gln Asp His Gly Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa
                420                 425                 430
```

```
Xaa Xaa Xaa Xaa Xaa Xaa Xaa Xaa Xaa Xaa Xaa Leu Thr Pro Asp
        435                 440                 445

Gln Val Val Ala Ile Ala Ser Asn Gly Gly Lys Gln Ala Leu Glu
450                 455                 460

Thr Val Gln Arg Leu Leu Pro Val Leu Cys Gln Asp His Gly Xaa Xaa
465                 470                 475                 480

Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa
        500                 505                 510

Xaa Xaa Xaa Xaa Xaa Leu Thr Pro Asp Gln Val Val Ala Ile Ala
        515                 520                 525

Ser His Asp Gly Gly Lys Gln Ala Leu Glu Thr Val Gln Arg Leu Leu
530                 535                 540

Pro Val Leu Cys Gln Asp His Gly Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa
                565                 570                 575

Xaa Xaa Xaa Xaa Xaa Xaa Xaa Xaa Xaa Xaa Xaa Xaa Xaa Xaa Xaa
            580                 585                 590

Leu Thr Pro Asp Gln Val Val Ala Ile Ala Ser Asn Ile Gly Gly Lys
        595                 600                 605

Gln Ala Leu Glu Thr Val Gln Arg Leu Leu Pro Val Leu Cys Gln Asp
        610                 615                 620

His Gly Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Leu Thr Pro Asp Gln Val
            660                 665                 670

Val Ala Ile Ala Ser His Asp Gly Gly Lys Gln Ala Leu Glu Thr Val
        675                 680                 685

Gln Arg Leu Leu Pro Val Leu Cys Gln Asp His Gly Xaa Xaa Xaa Xaa
        690                 695                 700

Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa
                725                 730                 735

Xaa Xaa Xaa Xaa Leu Thr Pro Asp Gln Val Val Ala Ile Ala Ser His
        740                 745                 750

Asp Gly Gly Lys Gln Ala Leu Glu Thr Val Gln Arg Leu Leu Pro Val
        755                 760                 765

Leu Cys Gln Asp His Gly Xaa Xaa Xaa Xaa Xaa Xaa Xaa Xaa Xaa
770                 775                 780

Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Leu Thr
                805                 810                 815

Pro Asp Gln Val Val Ala Ile Ala Ser Asn Ile Gly Gly Lys Gln Ala
        820                 825                 830

Leu Glu Thr Val Gln Arg Leu Leu Pro Val Leu Cys Gln Asp His Gly
        835                 840                 845
```

```
Xaa Xaa Xaa Xaa Xaa Xaa Xaa Xaa Xaa Xaa Xaa Xaa Xaa Xaa Xaa
            850                 855                 860

Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Leu Thr Pro Asp Gln Val Ala
            885                 890                 895

Ile Ala Ser Asn Ile Gly Gly Lys Gln Ala Leu Glu Thr Val Gln Arg
        900                 905                 910

Leu Leu Pro Val Leu Cys Gln Asp His Gly Xaa Xaa Xaa Xaa Xaa
            915                 920                 925

Xaa Xaa Xaa Xaa Xaa Xaa Xaa Xaa Xaa Xaa Xaa Xaa Xaa Xaa Xaa
930                 935                 940

Xaa Xaa Xaa Xaa Xaa Xaa Xaa Xaa Xaa Xaa Xaa Xaa Xaa Xaa Xaa
945                 950                 955                 960

Xaa Xaa Leu Thr Pro Asp Gln Val Val Ala Ile Ala Ser Asn Gly Gly
            965                 970                 975

Gly Lys Gln Ala Leu Glu Thr Val Gln Arg Leu Leu Pro Val Leu Cys
        980                 985                 990

Gln Asp His Gly Xaa Xaa Xaa Xaa Xaa Xaa Xaa Xaa Xaa Xaa Xaa
            995                 1000                1005

Xaa Xaa Xaa Xaa Xaa Xaa Xaa Xaa Xaa Xaa Xaa Xaa Xaa Xaa Xaa
1010                1015                1020

Xaa Xaa Xaa Xaa Xaa Xaa Xaa Xaa Xaa Xaa Xaa Xaa Xaa Leu Thr
1025                1030                1035

Pro Asp Gln Val Val Ala Ile Ala Ser His Asp Gly Gly Lys Gln
        1040                1045                1050

Ala Leu Glu Thr Val Gln Arg Leu Leu Pro Val Leu Cys Gln Asp
        1055                1060                1065

His Gly Xaa Xaa Xaa Xaa Xaa Xaa Xaa Xaa Xaa Xaa Xaa Xaa
        1070                1075                1080

Xaa Xaa Xaa Xaa Xaa Xaa Xaa Xaa Xaa Xaa Xaa Xaa Xaa Xaa Xaa
1085                1090                1095

Xaa Xaa Xaa Xaa Xaa Xaa Xaa Xaa Xaa Xaa Xaa Leu Thr Pro
1100                1105                1110

Asp Gln Val Val Ala Ile Ala Ser His Asp Gly Gly Lys Gln Ala
1115                1120                1125

Leu Glu Thr Val Gln Arg Leu Leu Pro Val Leu Cys Gln Asp His
        1130                1135                1140

Gly Xaa Xaa Xaa Xaa Xaa Xaa Xaa Xaa Xaa Xaa Xaa Xaa Xaa
        1145                1150                1155

Xaa Xaa Xaa Xaa Xaa Xaa Xaa Xaa Xaa Xaa Xaa Xaa Xaa Xaa Xaa
1160                1165                1170

Xaa Xaa Xaa Xaa Xaa Xaa Xaa Xaa Xaa Xaa Xaa Leu Thr Pro Asp
1175                1180                1185

Gln Val Val Ala Ile Ala Ser Asn Gly Gly Gly Lys Gln Ala Leu
        1190                1195                1200

Glu Ser Ile Val Ala Gln Leu Ser Arg Pro Asp Pro Ala Leu Ala
        1205                1210                1215

<210> SEQ ID NO 309
<211> LENGTH: 1348
<212> TYPE: PRT
<213> ORGANISM: Artificial Sequence
<220> FEATURE:
<223> OTHER INFORMATION: Synthetic Sequence
```

```
<220> FEATURE:
<221> NAME/KEY: SITE
<222> LOCATION: (35)..(74)
<223> OTHER INFORMATION: Xaa is Gly, Ala, Thr or His
<220> FEATURE:
<221> NAME/KEY: SITE
<222> LOCATION: (36)..(74)
<223> OTHER INFORMATION: Each amino acid at positions 36 to 74 is either
      present or absent
<220> FEATURE:
<221> NAME/KEY: SITE
<222> LOCATION: (109)..(148)
<223> OTHER INFORMATION: Xaa is Gly, Ala, Thr or His
<220> FEATURE:
<221> NAME/KEY: SITE
<222> LOCATION: (110)..(148)
<223> OTHER INFORMATION: Each amino acid at positions 110 to 148 is
      either present or absent
<220> FEATURE:
<221> NAME/KEY: SITE
<222> LOCATION: (183)..(222)
<223> OTHER INFORMATION: Xaa is Gly, Ala, Thr or His
<220> FEATURE:
<221> NAME/KEY: SITE
<222> LOCATION: (184)..(222)
<223> OTHER INFORMATION: Each amino acid at positions 184 to 222 is
      either present or absent
<220> FEATURE:
<221> NAME/KEY: SITE
<222> LOCATION: (257)..(296)
<223> OTHER INFORMATION: Xaa is Gly, Ala, Thr or His
<220> FEATURE:
<221> NAME/KEY: SITE
<222> LOCATION: (258)..(296)
<223> OTHER INFORMATION: Each amino acid at positions 258 to 296 is
      either present or absent
<220> FEATURE:
<221> NAME/KEY: SITE
<222> LOCATION: (331)..(370)
<223> OTHER INFORMATION: Xaa is Gly, Ala, Thr or His
<220> FEATURE:
<221> NAME/KEY: SITE
<222> LOCATION: (332)..(370)
<223> OTHER INFORMATION: Each amino acid at positions 332 to 370 is
      either present or absent
<220> FEATURE:
<221> NAME/KEY: SITE
<222> LOCATION: (405)..(444)
<223> OTHER INFORMATION: Xaa is Gly, Ala, Thr or His
<220> FEATURE:
<221> NAME/KEY: SITE
<222> LOCATION: (406)..(444)
<223> OTHER INFORMATION: Each amino acid at positions 406 to 444 is
      either present or absent
<220> FEATURE:
<221> NAME/KEY: SITE
<222> LOCATION: (479)..(518)
<223> OTHER INFORMATION: Xaa is Gly, Ala, Thr or His
<220> FEATURE:
<221> NAME/KEY: SITE
<222> LOCATION: (480)..(518)
<223> OTHER INFORMATION: Each amino acid at positions 480 to 518 is
      either present or absent
<220> FEATURE:
<221> NAME/KEY: SITE
<222> LOCATION: (553)..(592)
<223> OTHER INFORMATION: Xaa is Gly, Ala, Thr or His
<220> FEATURE:
<221> NAME/KEY: SITE
<222> LOCATION: (554)..(592)
<223> OTHER INFORMATION: Each amino acid at positions 554 to 592 is
      either present or absent
<220> FEATURE:
<221> NAME/KEY: SITE
<222> LOCATION: (627)..(666)
<223> OTHER INFORMATION: Xaa is Gly, Ala, Thr or His
<220> FEATURE:
<221> NAME/KEY: SITE
<222> LOCATION: (628)..(666)
```

```
<223> OTHER INFORMATION: Each amino acid at positions 628 to 666 is
      either present or absent
<220> FEATURE:
<221> NAME/KEY: SITE
<222> LOCATION: (701)..(740)
<223> OTHER INFORMATION: Xaa is Gly, Ala, Thr or His
<220> FEATURE:
<221> NAME/KEY: SITE
<222> LOCATION: (702)..(740)
<223> OTHER INFORMATION: Each amino acid at positions 702 to 740 is
      either present or absent
<220> FEATURE:
<221> NAME/KEY: SITE
<222> LOCATION: (775)..(814)
<223> OTHER INFORMATION: Xaa is Gly, Ala, Thr or His
<220> FEATURE:
<221> NAME/KEY: SITE
<222> LOCATION: (776)..(814)
<223> OTHER INFORMATION: Each amino acid at positions 776 to 814 is
      either present or absent
<220> FEATURE:
<221> NAME/KEY: SITE
<222> LOCATION: (849)..(888)
<223> OTHER INFORMATION: Xaa is Gly, Ala, Thr or His
<220> FEATURE:
<221> NAME/KEY: SITE
<222> LOCATION: (850)..(888)
<223> OTHER INFORMATION: Each amino acid at positions 850 to 888 is
      either present or absent
<220> FEATURE:
<221> NAME/KEY: SITE
<222> LOCATION: (923)..(962)
<223> OTHER INFORMATION: Xaa is Gly, Ala, Thr or His
<220> FEATURE:
<221> NAME/KEY: SITE
<222> LOCATION: (924)..(962)
<223> OTHER INFORMATION: Each amino acid at positions 924 to 962 is
      either present or absent
<220> FEATURE:
<221> NAME/KEY: SITE
<222> LOCATION: (997)..(1036)
<223> OTHER INFORMATION: Xaa is Gly, Ala, Thr or His
<220> FEATURE:
<221> NAME/KEY: SITE
<222> LOCATION: (998)..(1036)
<223> OTHER INFORMATION: Each amino acid at positions 998 to 1036 is
      either present or absent
<220> FEATURE:
<221> NAME/KEY: SITE
<222> LOCATION: (1071)..(1110)
<223> OTHER INFORMATION: Xaa is Gly, Ala, Thr or His
<220> FEATURE:
<221> NAME/KEY: SITE
<222> LOCATION: (1072)..(1110)
<223> OTHER INFORMATION: Each amino acid at positions 1072 to 1110 is
      either present or absent
<220> FEATURE:
<221> NAME/KEY: SITE
<222> LOCATION: (1145)..(1184)
<223> OTHER INFORMATION: Xaa is Gly, Ala, Thr or His
<220> FEATURE:
<221> NAME/KEY: SITE
<222> LOCATION: (1146)..(1184)
<223> OTHER INFORMATION: Each amino acid at positions 1146 to 1184 is
      either present or absent
<220> FEATURE:
<221> NAME/KEY: SITE
<222> LOCATION: (1219)..(1258)
<223> OTHER INFORMATION: Xaa is Gly, Ala, Thr or His
<220> FEATURE:
<221> NAME/KEY: SITE
<222> LOCATION: (1220)..(1258)
<223> OTHER INFORMATION: Each amino acid at positions 1220 to 1258 is
      either present or absent
<220> FEATURE:
<221> NAME/KEY: SITE
<222> LOCATION: (1293)..(1332)
<223> OTHER INFORMATION: Xaa is Gly, Ala, Thr or His
<220> FEATURE:
```

```
<221> NAME/KEY: SITE
<222> LOCATION: (1294)..(1332)
<223> OTHER INFORMATION: Each amino acid at positions 1294 to 1332 is
      either present or absent

<400> SEQUENCE: 309

Leu Thr Pro Asp Gln Val Val Ala Ile Ala Ser Asn His Gly Gly Lys
1               5                   10                  15

Gln Ala Leu Glu Thr Val Gln Arg Leu Leu Pro Val Leu Cys Gln Asp
            20                  25                  30

His Gly Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Leu Thr Pro Asp Gln Val
65                  70                  75                  80

Val Ala Ile Ala Ser His Asp Gly Gly Lys Gln Ala Leu Glu Thr Val
                85                  90                  95

Gln Arg Leu Leu Pro Val Leu Cys Gln Asp His Gly Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Leu Thr Pro Asp Gln Val Val Ala Ile Ala Ser Asn
145                 150                 155                 160

Gly Gly Gly Lys Gln Ala Leu Glu Thr Val Gln Arg Leu Leu Pro Val
                165                 170                 175

Leu Cys Gln Asp His Gly Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Leu Thr
    210                 215                 220

Pro Asp Gln Val Val Ala Ile Ala Ser His Asp Gly Gly Lys Gln Ala
225                 230                 235                 240

Leu Glu Thr Val Gln Arg Leu Leu Pro Val Leu Cys Gln Asp His Gly
            245                 250                 255

Xaa Xaa Xaa Xaa Xaa Xaa Xaa Xaa Xaa Xaa Xaa Xaa Xaa Xaa Xaa Xaa
        260                 265                 270

Xaa Xaa Xaa Xaa Xaa Xaa Xaa Xaa Xaa Xaa Xaa Xaa Xaa Xaa Xaa Xaa
    275                 280                 285

Xaa Xaa Xaa Xaa Xaa Xaa Xaa Leu Thr Pro Asp Gln Val Val Ala
290                 295                 300

Ile Ala Ser Asn Ile Gly Gly Lys Gln Ala Leu Glu Thr Val Gln Arg
305                 310                 315                 320

Leu Leu Pro Val Leu Cys Gln Asp His Gly Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa Xaa
        340                 345                 350

Xaa Xaa Xaa Xaa Xaa Xaa Xaa Xaa Xaa Xaa Xaa Xaa Xaa Xaa Xaa Xaa
    355                 360                 365

Xaa Xaa Leu Thr Pro Asp Gln Val Val Ala Ile Ala Ser Asn His Gly
370                 375                 380
```

```
Gly Lys Gln Ala Leu Glu Thr Val Gln Arg Leu Leu Pro Val Leu Cys
385                 390                 395                 400

Gln Asp His Gly Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Leu Thr Pro Asp
        435                 440                 445

Gln Val Val Ala Ile Ala Ser His Asp Gly Lys Gln Ala Leu Glu
    450                 455                 460

Thr Val Gln Arg Leu Leu Pro Val Leu Cys Gln Asp His Gly Xaa Xaa
465                 470                 475                 480

Xaa Xaa Xaa Xaa Xaa Xaa Xaa Xaa Xaa Xaa Xaa Xaa Xaa Xaa
        485                 490                 495

Xaa Xaa Xaa Xaa Xaa Xaa Xaa Xaa Xaa Xaa Xaa Xaa Xaa Xaa
        500                 505                 510

Xaa Xaa Xaa Xaa Xaa Xaa Leu Thr Pro Asp Gln Val Val Ala Ile Ala
        515                 520                 525

Ser His Asp Gly Gly Lys Gln Ala Leu Glu Thr Val Gln Arg Leu Leu
530                 535                 540

Pro Val Leu Cys Gln Asp His Gly Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa
            565                 570                 575

Xaa Xaa Xaa Xaa Xaa Xaa Xaa Xaa Xaa Xaa Xaa Xaa Xaa Xaa Xaa
            580                 585                 590

Leu Thr Pro Asp Gln Val Val Ala Ile Ala Ser His Asp Gly Gly Lys
            595                 600                 605

Gln Ala Leu Glu Thr Val Gln Arg Leu Leu Pro Val Leu Cys Gln Asp
    610                 615                 620

His Gly Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Leu Thr Pro Asp Gln Val
            660                 665                 670

Val Ala Ile Ala Ser Asn Ile Gly Gly Lys Gln Ala Leu Glu Thr Val
        675                 680                 685

Gln Arg Leu Leu Pro Val Leu Cys Gln Asp His Gly Xaa Xaa Xaa Xaa
    690                 695                 700

Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa
            725                 730                 735

Xaa Xaa Xaa Xaa Leu Thr Pro Asp Gln Val Val Ala Ile Ala Ser Asn
        740                 745                 750

His Gly Gly Lys Gln Ala Leu Glu Thr Val Gln Arg Leu Leu Pro Val
    755                 760                 765

Leu Cys Gln Asp His Gly Xaa Xaa Xaa Xaa Xaa Xaa Xaa Xaa Xaa
        770                 775                 780

Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Leu Thr
```

-continued

```
                805                 810                 815
Pro Asp Gln Val Val Ala Ile Ala Ser His Asp Gly Gly Lys Gln Ala
            820                 825                 830

Leu Glu Thr Val Gln Arg Leu Leu Pro Val Leu Cys Gln Asp His Gly
            835                 840                 845

Xaa Xaa Xaa Xaa Xaa Xaa Xaa Xaa Xaa Xaa Xaa Xaa Xaa Xaa Xaa Xaa
        850                 855                 860

Xaa Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Leu Thr Pro Asp Gln Val Val Ala
                885                 890                 895

Ile Ala Ser Asn Gly Gly Lys Gln Ala Leu Glu Thr Val Gln Arg
            900                 905                 910

Leu Leu Pro Val Leu Cys Gln Asp His Gly Xaa Xaa Xaa Xaa Xaa
            915                 920                 925

Xaa Xaa Xaa Xaa Xaa Xaa Xaa Xaa Xaa Xaa Xaa Xaa Xaa Xaa Xaa
        930                 935                 940

Xaa Xaa Xaa Xaa Xaa Xaa Xaa Xaa Xaa Xaa Xaa Xaa Xaa Xaa Xaa
945                 950                 955                 960

Xaa Xaa Leu Thr Pro Asp Gln Val Val Ala Ile Ala Ser His Asp Gly
                965                 970                 975

Gly Lys Gln Ala Leu Glu Thr Val Gln Arg Leu Leu Pro Val Leu Cys
            980                 985                 990

Gln Asp His Gly Xaa Xaa Xaa Xaa Xaa Xaa Xaa Xaa Xaa Xaa Xaa
            995                1000                1005

Xaa Xaa Xaa Xaa Xaa Xaa Xaa Xaa Xaa Xaa Xaa Xaa Xaa Xaa Xaa
       1010                1015                1020

Xaa Xaa Xaa Xaa Xaa Xaa Xaa Xaa Xaa Xaa Xaa Xaa Xaa Leu Thr
       1025                1030                1035

Pro Asp Gln Val Val Ala Ile Ala Ser Asn Ile Gly Gly Lys Gln
       1040                1045                1050

Ala Leu Glu Thr Val Gln Arg Leu Leu Pro Val Leu Cys Gln Asp
       1055                1060                1065

His Gly Xaa Xaa Xaa Xaa Xaa Xaa Xaa Xaa Xaa Xaa Xaa Xaa Xaa
       1070                1075                1080

Xaa Xaa Xaa Xaa Xaa Xaa Xaa Xaa Xaa Xaa Xaa Xaa Xaa Xaa Xaa
       1085                1090                1095

Xaa Xaa Xaa Xaa Xaa Xaa Xaa Xaa Xaa Xaa Xaa Xaa Leu Thr Pro
       1100                1105                1110

Asp Gln Val Val Ala Ile Ala Ser Asn His Gly Gly Lys Gln Ala
       1115                1120                1125

Leu Glu Thr Val Gln Arg Leu Leu Pro Val Leu Cys Gln Asp His
       1130                1135                1140

Gly Xaa Xaa Xaa Xaa Xaa Xaa Xaa Xaa Xaa Xaa Xaa Xaa Xaa Xaa
       1145                1150                1155

Xaa Xaa Xaa Xaa Xaa Xaa Xaa Xaa Xaa Xaa Xaa Xaa Xaa Xaa Xaa
       1160                1165                1170

Xaa Xaa Xaa Xaa Xaa Xaa Xaa Xaa Xaa Xaa Xaa Leu Thr Pro Asp
       1175                1180                1185

Gln Val Val Ala Ile Ala Ser His Asp Gly Gly Lys Gln Ala Leu
       1190                1195                1200

Glu Thr Val Gln Arg Leu Leu Pro Val Leu Cys Gln Asp His Gly
       1205                1210                1215
```

```
Xaa Xaa Xaa Xaa Xaa Xaa Xaa  Xaa Xaa Xaa Xaa Xaa  Xaa Xaa Xaa
    1220                1225                1230

Xaa Xaa Xaa Xaa Xaa Xaa Xaa  Xaa Xaa Xaa Xaa Xaa  Xaa Xaa Xaa
    1235                1240                1245

Xaa Xaa Xaa Xaa Xaa Xaa Xaa  Xaa Xaa Xaa Leu Thr  Pro Asp Gln
    1250                1255                1260

Val Val Ala Ile Ala Ser His  Asp Gly Gly Lys Gln  Ala Leu Glu
    1265                1270                1275

Thr Val Gln Arg Leu Leu Pro  Val Leu Cys Gln Asp  His Gly Xaa
    1280                1285                1290

Xaa Xaa Xaa Xaa Xaa Xaa Xaa  Xaa Xaa Xaa Xaa Xaa  Xaa Xaa Xaa
    1295                1300                1305

Xaa Xaa Xaa Xaa Xaa Xaa Xaa  Xaa Xaa Xaa Xaa Xaa  Xaa Xaa Xaa
    1310                1315                1320

Xaa Xaa Xaa Xaa Xaa Xaa Xaa  Xaa Xaa Leu Thr Pro  Asp Gln Val
    1325                1330                1335

Val Ala Ile Ala Ser Asn Gly  Gly Gly Lys
    1340                1345

<210> SEQ ID NO 310
<211> LENGTH: 1514
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (35)..(74)
<223> OTHER INFORMATION: Xaa is Gly, Ala, Thr or His
<220> FEATURE:
<221> NAME/KEY: SITE
<222> LOCATION: (36)..(74)
<223> OTHER INFORMATION: Each amino acid at positions 36 to 74 is either
      present or absent
<220> FEATURE:
<221> NAME/KEY: SITE
<222> LOCATION: (109)..(148)
<223> OTHER INFORMATION: Xaa is Gly, Ala, Thr or His
<220> FEATURE:
<221> NAME/KEY: SITE
<222> LOCATION: (110)..(148)
<223> OTHER INFORMATION: Each amino acid at positions 110 to 148 is
      either present or absent
<220> FEATURE:
<221> NAME/KEY: SITE
<222> LOCATION: (183)..(222)
<223> OTHER INFORMATION: Xaa is Gly, Ala, Thr or His
<220> FEATURE:
<221> NAME/KEY: SITE
<222> LOCATION: (184)..(222)
<223> OTHER INFORMATION: Each amino acid at positions 184 to 221 is
      either present or absent
<220> FEATURE:
<221> NAME/KEY: SITE
<222> LOCATION: (257)..(296)
<223> OTHER INFORMATION: Xaa is Gly, Ala, Thr or His
<220> FEATURE:
<221> NAME/KEY: SITE
<222> LOCATION: (258)..(296)
<223> OTHER INFORMATION: Each amino acid at positions 258 to 296 is
      either present or absent
<220> FEATURE:
<221> NAME/KEY: SITE
<222> LOCATION: (331)..(370)
<223> OTHER INFORMATION: Xaa is Gly, Ala, Thr or His
<220> FEATURE:
<221> NAME/KEY: SITE
<222> LOCATION: (332)..(370)
<223> OTHER INFORMATION: Each amino acid at positions 332 to 370 is
```

```
      either present or absent
<220> FEATURE:
<221> NAME/KEY: SITE
<222> LOCATION: (405)..(444)
<223> OTHER INFORMATION: Xaa is Gly, Ala, Thr or His
<220> FEATURE:
<221> NAME/KEY: SITE
<222> LOCATION: (406)..(444)
<223> OTHER INFORMATION: Each amino acid at positions 406 to 444 is
      either present or absent
<220> FEATURE:
<221> NAME/KEY: SITE
<222> LOCATION: (479)..(518)
<223> OTHER INFORMATION: Xaa is Gly, Ala, Thr or His
<220> FEATURE:
<221> NAME/KEY: SITE
<222> LOCATION: (480)..(518)
<223> OTHER INFORMATION: Each amino acid at positions 480 to 518 is
      either present or absent
<220> FEATURE:
<221> NAME/KEY: SITE
<222> LOCATION: (553)..(592)
<223> OTHER INFORMATION: Xaa is Gly, Ala, Thr or His
<220> FEATURE:
<221> NAME/KEY: SITE
<222> LOCATION: (554)..(592)
<223> OTHER INFORMATION: Each amino acid at positions 554 to 592 is
      either present or absent
<220> FEATURE:
<221> NAME/KEY: SITE
<222> LOCATION: (627)..(666)
<223> OTHER INFORMATION: Xaa is Gly, Ala, Thr or His
<220> FEATURE:
<221> NAME/KEY: SITE
<222> LOCATION: (628)..(666)
<223> OTHER INFORMATION: Each amino acid at positions 628 to 666 is
      either present or absent
<220> FEATURE:
<221> NAME/KEY: SITE
<222> LOCATION: (701)..(740)
<223> OTHER INFORMATION: Xaa is Gly, Ala, Thr or His
<220> FEATURE:
<221> NAME/KEY: SITE
<222> LOCATION: (702)..(740)
<223> OTHER INFORMATION: Each amino acid at positions 702 to 740 is
      either present or absent
<220> FEATURE:
<221> NAME/KEY: SITE
<222> LOCATION: (775)..(814)
<223> OTHER INFORMATION: Xaa is Gly, Ala, Thr or His
<220> FEATURE:
<221> NAME/KEY: SITE
<222> LOCATION: (776)..(814)
<223> OTHER INFORMATION: Each amino acid at positions 776 to 814 is
      either present or absent
<220> FEATURE:
<221> NAME/KEY: SITE
<222> LOCATION: (849)..(888)
<223> OTHER INFORMATION: Xaa is Gly, Ala, Thr or His
<220> FEATURE:
<221> NAME/KEY: SITE
<222> LOCATION: (850)..(888)
<223> OTHER INFORMATION: Each amino acid at positions 850 to 888 is
      either present or absent
<220> FEATURE:
<221> NAME/KEY: SITE
<222> LOCATION: (923)..(962)
<223> OTHER INFORMATION: Xaa is Gly, Ala, Thr or His
<220> FEATURE:
<221> NAME/KEY: SITE
<222> LOCATION: (924)..(962)
<223> OTHER INFORMATION: Each amino acid at positions 924 to 962 is
      either present or absent
<220> FEATURE:
<221> NAME/KEY: SITE
<222> LOCATION: (997)..(1036)
<223> OTHER INFORMATION: Xaa is Gly, Ala, Thr or His
<220> FEATURE:
<221> NAME/KEY: SITE
```

```
<222> LOCATION: (998)..(1036)
<223> OTHER INFORMATION: Each amino acid at positions 998 to 1036 is
      either present or absent
<220> FEATURE:
<221> NAME/KEY: SITE
<222> LOCATION: (1071)..(1110)
<223> OTHER INFORMATION: Xaa is Gly, Ala, Thr or His
<220> FEATURE:
<221> NAME/KEY: SITE
<222> LOCATION: (1072)..(1110)
<223> OTHER INFORMATION: Each amino acid at positions 1072 to 1110 is
      either present or absent
<220> FEATURE:
<221> NAME/KEY: SITE
<222> LOCATION: (1145)..(1184)
<223> OTHER INFORMATION: Xaa is Gly, Ala, Thr or His
<220> FEATURE:
<221> NAME/KEY: SITE
<222> LOCATION: (1146)..(1184)
<223> OTHER INFORMATION: Each amino acid at positions 1146 to 1184 is
      either present or absent
<220> FEATURE:
<221> NAME/KEY: SITE
<222> LOCATION: (1219)..(1258)
<223> OTHER INFORMATION: Xaa is Gly, Ala, Thr or His
<220> FEATURE:
<221> NAME/KEY: SITE
<222> LOCATION: (1220)..(1258)
<223> OTHER INFORMATION: Each amino acid at positions 1220 to 1258 is
      either present or absent
<220> FEATURE:
<221> NAME/KEY: SITE
<222> LOCATION: (1293)..(1332)
<223> OTHER INFORMATION: Xaa is Gly, Ala, Thr or His
<220> FEATURE:
<221> NAME/KEY: SITE
<222> LOCATION: (1294)..(1332)
<223> OTHER INFORMATION: Each amino acid at positions 1294 to 1332 is
      either present or absent
<220> FEATURE:
<221> NAME/KEY: SITE
<222> LOCATION: (1367)..(1406)
<223> OTHER INFORMATION: Xaa is Gly, Ala, Thr or His
<220> FEATURE:
<221> NAME/KEY: SITE
<222> LOCATION: (1368)..(1406)
<223> OTHER INFORMATION: Each amino acid at positions 1368 to 1406 is
      either present or absent
<220> FEATURE:
<221> NAME/KEY: SITE
<222> LOCATION: (1441)..(1480)
<223> OTHER INFORMATION: Xaa is Gly, Ala, Thr or His
<220> FEATURE:
<221> NAME/KEY: SITE
<222> LOCATION: (1442)..(1480)
<223> OTHER INFORMATION: Each amino acid at positions 1442 to 1480 is
      either present or absent

<400> SEQUENCE: 310

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Leu Thr Pro Asp Gln Val
65                  70                  75                  80

Val Ala Ile Ala Ser His Asp Gly Gly Lys Gln Ala Leu Glu Thr Val
                85                  90                  95

Gln Arg Leu Leu Pro Val Leu Cys Gln Asp His Gly Xaa Xaa Xaa Xaa
```

-continued

```
                100                 105                 110
Xaa Xaa Xaa Xaa Xaa Xaa Xaa Xaa Xaa Xaa Xaa Xaa Xaa Xaa
                115                 120                 125
Xaa Xaa Xaa Xaa Xaa Xaa Xaa Xaa Xaa Xaa Xaa Xaa Xaa Xaa
                130                 135                 140
Xaa Xaa Xaa Xaa Leu Thr Pro Asp Gln Val Val Ala Ile Ala Ser His
145                 150                 155                 160
Asp Gly Gly Lys Gln Ala Leu Glu Thr Val Gln Arg Leu Leu Pro Val
                165                 170                 175
Leu Cys Gln Asp His Gly Xaa Xaa Xaa Xaa Xaa Xaa Xaa Xaa
                180                 185                 190
Xaa Xaa Xaa Xaa Xaa Xaa Xaa Xaa Xaa Xaa Xaa Xaa Xaa Xaa
                195                 200                 205
Xaa Xaa Xaa Xaa Xaa Xaa Xaa Xaa Xaa Xaa Xaa Xaa Leu Thr
                210                 215                 220
Pro Asp Gln Val Val Ala Ile Ala Ser His Asp Gly Gly Lys Gln Ala
225                 230                 235                 240
Leu Glu Thr Val Gln Arg Leu Leu Pro Val Leu Cys Gln Asp His Gly
                245                 250                 255
Xaa Xaa Xaa Xaa Xaa Xaa Xaa Xaa Xaa Xaa Xaa Xaa Xaa Xaa
                260                 265                 270
Xaa Xaa Xaa Xaa Xaa Xaa Xaa Xaa Xaa Xaa Xaa Xaa Xaa Xaa
                275                 280                 285
Xaa Xaa Xaa Xaa Xaa Xaa Xaa Xaa Leu Thr Pro Asp Gln Val Val Ala
                290                 295                 300
Ile Ala Ser His Asp Gly Gly Lys Gln Ala Leu Glu Thr Val Gln Arg
305                 310                 315                 320
Leu Leu Pro Val Leu Cys Gln Asp His Gly Xaa Xaa Xaa Xaa Xaa
                325                 330                 335
Xaa Xaa Xaa Xaa Xaa Xaa Xaa Xaa Xaa Xaa Xaa Xaa Xaa Xaa
                340                 345                 350
Xaa Xaa Xaa Xaa Xaa Xaa Xaa Xaa Xaa Xaa Xaa Xaa Xaa Xaa
                355                 360                 365
Xaa Xaa Leu Thr Pro Asp Gln Val Val Ala Ile Ala Ser Asn Gly Gly
        370                 375                 380
Gly Lys Gln Ala Leu Glu Thr Val Gln Arg Leu Leu Pro Val Leu Cys
385                 390                 395                 400
Gln Asp His Gly Xaa Xaa Xaa Xaa Xaa Xaa Xaa Xaa Xaa Xaa
                405                 410                 415
Xaa Xaa Xaa Xaa Xaa Xaa Xaa Xaa Xaa Xaa Xaa Xaa Xaa Xaa
                420                 425                 430
Xaa Xaa Xaa Xaa Xaa Xaa Xaa Xaa Xaa Xaa Leu Thr Pro Asp
                435                 440                 445
Gln Val Val Ala Ile Ala Ser His Asp Gly Gly Lys Gln Ala Leu Glu
        450                 455                 460
Thr Val Gln Arg Leu Leu Pro Val Leu Cys Gln Asp His Gly Xaa Xaa
465                 470                 475                 480
Xaa Xaa Xaa Xaa Xaa Xaa Xaa Xaa Xaa Xaa Xaa Xaa Xaa Xaa
                485                 490                 495
Xaa Xaa Xaa Xaa Xaa Xaa Xaa Xaa Xaa Xaa Xaa Xaa Xaa Xaa
                500                 505                 510
Xaa Xaa Xaa Xaa Xaa Xaa Leu Thr Pro Asp Gln Val Val Ala Ile Ala
                515                 520                 525
```

```
Ser Asn Gly Gly Gly Lys Gln Ala Leu Glu Thr Val Gln Arg Leu Leu
530                 535                 540

Pro Val Leu Cys Gln Asp His Gly Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa Xaa
                565                 570                 575

Xaa Xaa Xaa Xaa Xaa Xaa Xaa Xaa Xaa Xaa Xaa Xaa Xaa Xaa Xaa Xaa
            580                 585                 590

Leu Thr Pro Asp Gln Val Val Ala Ile Ala Ser His Asp Gly Gly Lys
        595                 600                 605

Gln Ala Leu Glu Thr Val Gln Arg Leu Leu Pro Val Leu Cys Gln Asp
610                 615                 620

His Gly Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Leu Thr Pro Asp Gln Val
                660                 665                 670

Val Ala Ile Ala Ser Asn Ile Gly Gly Lys Gln Ala Leu Glu Thr Val
        675                 680                 685

Gln Arg Leu Leu Pro Val Leu Cys Gln Asp His Gly Xaa Xaa Xaa Xaa
690                 695                 700

Xaa Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa Xaa
                725                 730                 735

Xaa Xaa Xaa Xaa Leu Thr Pro Asp Gln Val Val Ala Ile Ala Ser Asn
        740                 745                 750

Gly Gly Gly Lys Gln Ala Leu Glu Thr Val Gln Arg Leu Leu Pro Val
        755                 760                 765

Leu Cys Gln Asp His Gly Xaa Xaa Xaa Xaa Xaa Xaa Xaa Xaa Xaa Xaa
770                 775                 780

Xaa Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Leu Thr
                805                 810                 815

Pro Asp Gln Val Val Ala Ile Ala Ser Asn Gly Gly Gly Lys Gln Ala
        820                 825                 830

Leu Glu Thr Val Gln Arg Leu Leu Pro Val Leu Cys Gln Asp His Gly
        835                 840                 845

Xaa Xaa Xaa Xaa Xaa Xaa Xaa Xaa Xaa Xaa Xaa Xaa Xaa Xaa Xaa Xaa
                850                 855                 860

Xaa Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Leu Thr Pro Asp Gln Val Val Ala
            885                 890                 895

Ile Ala Ser His Asp Gly Gly Lys Gln Ala Leu Glu Thr Val Gln Arg
        900                 905                 910

Leu Leu Pro Val Leu Cys Gln Asp His Gly Xaa Xaa Xaa Xaa Xaa
        915                 920                 925

Xaa Xaa Xaa Xaa Xaa Xaa Xaa Xaa Xaa Xaa Xaa Xaa Xaa Xaa Xaa Xaa
930                 935                 940
```

```
Xaa Xaa Xaa Xaa Xaa Xaa Xaa Xaa Xaa Xaa Xaa Xaa Xaa Xaa
945                 950                 955                 960

Xaa Xaa Leu Thr Pro Asp Gln Val Val Ala Ile Ala Ser Asn Gly Gly
        965                 970                 975

Gly Lys Gln Ala Leu Glu Thr Val Gln Arg Leu Leu Pro Val Leu Cys
            980                 985                 990

Gln Asp His Gly Xaa Xaa Xaa Xaa  Xaa Xaa Xaa Xaa  Xaa Xaa Xaa
        995                 1000                1005

Xaa Xaa Xaa Xaa Xaa Xaa Xaa  Xaa Xaa Xaa Xaa  Xaa Xaa Xaa
    1010                1015                1020

Xaa Xaa Xaa Xaa Xaa Xaa Xaa  Xaa Xaa Xaa Xaa  Xaa Leu Thr
    1025                1030                1035

Pro Asp Gln Val Val Ala Ile  Ala Ser His Asp  Gly Gly Lys Gln
    1040                1045                1050

Ala Leu Glu Thr Val Gln Arg  Leu Leu Pro Val Leu  Cys Gln Asp
    1055                1060                1065

His Gly Xaa Xaa Xaa Xaa Xaa  Xaa Xaa Xaa Xaa  Xaa Xaa Xaa
    1070                1075                1080

Xaa Xaa Xaa Xaa Xaa Xaa Xaa  Xaa Xaa Xaa Xaa  Xaa Xaa Xaa
    1085                1090                1095

Xaa Xaa Xaa Xaa Xaa Xaa Xaa  Xaa Xaa Xaa Xaa  Leu Thr Pro
    1100                1105                1110

Asp Gln Val Val Ala Ile Ala  Ser Asn Gly Gly  Gly Lys Gln Ala
    1115                1120                1125

Leu Glu Thr Val Gln Arg Leu  Leu Pro Val Leu Cys  Gln Asp His
    1130                1135                1140

Gly Xaa Xaa Xaa Xaa Xaa Xaa  Xaa Xaa Xaa Xaa  Xaa Xaa Xaa
    1145                1150                1155

Xaa Xaa Xaa Xaa Xaa Xaa Xaa  Xaa Xaa Xaa Xaa  Xaa Xaa Xaa
    1160                1165                1170

Xaa Xaa Xaa Xaa Xaa Xaa Xaa  Xaa Xaa Xaa Xaa  Leu Thr Pro Asp
    1175                1180                1185

Gln Val Val Ala Ile Ala Ser  Asn Ile Gly Gly  Lys Gln Ala Leu
    1190                1195                1200

Glu Thr Val Gln Arg Leu Leu  Pro Val Leu Cys  Gln Asp His Gly
    1205                1210                1215

Xaa Xaa Xaa Xaa Xaa Xaa Xaa  Xaa Xaa Xaa Xaa  Xaa Xaa Xaa
    1220                1225                1230

Xaa Xaa Xaa Xaa Xaa Xaa Xaa  Xaa Xaa Xaa Xaa  Xaa Xaa Xaa
    1235                1240                1245

Xaa Xaa Xaa Xaa Xaa Xaa Xaa  Xaa Xaa Xaa Leu  Thr Pro Asp Gln
    1250                1255                1260

Val Val Ala Ile Ala Ser His  Asp Gly Gly Lys Gln  Ala Leu Glu
    1265                1270                1275

Thr Val Gln Arg Leu Leu Pro  Val Leu Cys Gln Asp  His Gly Xaa
    1280                1285                1290

Xaa Xaa Xaa Xaa Xaa Xaa Xaa  Xaa Xaa Xaa Xaa  Xaa Xaa Xaa
    1295                1300                1305

Xaa Xaa Xaa Xaa Xaa Xaa Xaa  Xaa Xaa Xaa Xaa  Xaa Xaa Xaa
    1310                1315                1320

Xaa Xaa Xaa Xaa Xaa Xaa Xaa  Xaa Xaa Leu Thr  Pro Asp Gln Val
    1325                1330                1335

Val Ala Ile Ala Ser His Asp  Gly Gly Lys Gln Ala  Leu Glu Thr
```

```
                    1340                1345                1350

Val  Gln  Arg  Leu  Leu  Pro  Val  Leu  Cys  Gln  Asp  His  Gly  Xaa  Xaa
         1355                1360                1365

Xaa  Xaa  Xaa  Xaa  Xaa  Xaa  Xaa  Xaa  Xaa  Xaa  Xaa  Xaa  Xaa  Xaa  Xaa
    1370                1375                1380

Xaa  Xaa  Xaa  Xaa  Xaa  Xaa  Xaa  Xaa  Xaa  Xaa  Xaa  Xaa  Xaa  Xaa  Xaa
    1385                1390                1395

Xaa  Xaa  Xaa  Xaa  Xaa  Xaa  Xaa  Leu  Thr  Pro  Asp  Gln  Val  Val
    1400                1405                1410

Ala  Ile  Ala  Ser  Asn  Ile  Gly  Gly  Lys  Gln  Ala  Leu  Glu  Thr  Val
    1415                1420                1425

Gln  Arg  Leu  Leu  Pro  Val  Leu  Cys  Gln  Asp  His  Gly  Xaa  Xaa  Xaa
    1430                1435                1440

Xaa  Xaa  Xaa  Xaa  Xaa  Xaa  Xaa  Xaa  Xaa  Xaa  Xaa  Xaa  Xaa  Xaa  Xaa
    1445                1450                1455

Xaa  Xaa  Xaa  Xaa  Xaa  Xaa  Xaa  Xaa  Xaa  Xaa  Xaa  Xaa  Xaa  Xaa  Xaa
    1460                1465                1470

Xaa  Xaa  Xaa  Xaa  Xaa  Xaa  Xaa  Leu  Thr  Pro  Asp  Gln  Val  Val  Ala
    1475                1480                1485

Ser  Ala  Ser  Asn  Gly  Gly  Gly  Lys  Gln  Ala  Leu  Glu  Ser  Ile  Val
    1490                1495                1500

Ala  Gln  Leu  Ser  Arg  Pro  Asp  Pro  Ala  Leu  Ala
    1505                1510

<210> SEQ ID NO 311
<211> LENGTH: 883
<212> TYPE: PRT
<213> ORGANISM: Artificial Sequence
<220> FEATURE:
<223> OTHER INFORMATION: Synthetic Sequence

<400> SEQUENCE: 311

Phe  Gly  Lys  Leu  Val  Ala  Leu  Gly  Tyr  Ser  Arg  Glu  Gln  Ile  Arg  Lys
 1                    5                   10                  15

Leu  Lys  Gln  Glu  Ser  Leu  Ser  Glu  Ile  Ala  Lys  Tyr  His  Thr  Thr  Leu
            20                  25                  30

Thr  Gly  Gln  Gly  Phe  Thr  His  Ala  Asp  Ile  Cys  Arg  Ile  Ser  Arg  Arg
        35                  40                  45

Arg  Gln  Ser  Leu  Arg  Val  Val  Ala  Arg  Asn  Tyr  Pro  Glu  Leu  Ala  Ala
    50                  55                  60

Ala  Leu  Pro  Glu  Leu  Thr  Arg  Ala  His  Ile  Val  Asp  Ile  Ala  Arg  Gln
65                   70                  75                  80

Arg  Ser  Gly  Asp  Leu  Ala  Leu  Gln  Ala  Leu  Leu  Pro  Val  Ala  Thr  Ala
                85                  90                  95

Leu  Thr  Ala  Ala  Pro  Leu  Arg  Leu  Ser  Ala  Ser  Gln  Ile  Ala  Thr  Val
            100                 105                 110

Ala  Gln  Tyr  Gly  Glu  Arg  Pro  Ala  Ile  Gln  Ala  Leu  Tyr  Arg  Leu  Arg
        115                 120                 125

Arg  Lys  Leu  Thr  Arg  Ala  Pro  Leu  His  Leu  Thr  Pro  Gln  Gln  Val  Val
    130                 135                 140

Ala  Ile  Ala  Ser  Asn  Thr  Gly  Gly  Lys  Arg  Ala  Leu  Glu  Ala  Val  Cys
145                 150                 155                 160

Val  Gln  Leu  Pro  Val  Leu  Arg  Ala  Ala  Pro  Tyr  Arg  Leu  Ser  Thr  Glu
                165                 170                 175

Gln  Val  Val  Ala  Ile  Ala  Ser  His  Asp  Gly  Gly  Lys  Gln  Ala  Leu  Glu
```

```
            180                 185                 190
Ala Val Gly Ala Gln Leu Val Ala Leu Arg Ala Ala Pro Tyr Ala Leu
            195                 200                 205
Ser Thr Glu Gln Val Val Ala Ile Ala Ser His Asp Gly Gly Lys Gln
            210                 215                 220
Ala Leu Glu Ala Val Gly Ala Gln Leu Val Ala Leu Arg Ala Ala Pro
225                 230                 235                 240
Tyr Ala Leu Ser Thr Ala Gln Val Val Ala Ile Ala Ser Asn Gly Gly
                    245                 250                 255
Gly Lys Gln Ala Leu Glu Gly Ile Gly Glu Gln Leu Leu Lys Leu Arg
                    260                 265                 270
Thr Ala Pro Tyr Gly Leu Ser Thr Glu Gln Val Val Ala Ile Ala Ser
            275                 280                 285
Asn Lys Gly Gly Lys Gln Ala Leu Glu Ala Val Lys Ala His Leu Leu
            290                 295                 300
Asp Leu Leu Gly Ala Pro Tyr Val Leu Ser Thr Glu Gln Val Val Ala
305                 310                 315                 320
Ile Ala Ser Asn Lys Gly Gly Lys Gln Ala Leu Glu Ala Val Lys Ala
                    325                 330                 335
His Leu Leu Asp Leu Leu Gly Ala Pro Tyr Val Leu Ser Thr Glu Gln
                    340                 345                 350
Val Val Ala Ile Ala Ser Asn Lys Gly Gly Lys Gln Ala Leu Glu Ala
            355                 360                 365
Val Lys Ala His Leu Leu Asp Leu Leu Gly Ala Pro Tyr Val Leu Ser
            370                 375                 380
Thr Glu Gln Val Val Val Ile Ala Asn Ser Ile Gly Gly Lys Gln Ala
385                 390                 395                 400
Leu Glu Ala Val Lys Val Gln Leu Pro Val Leu Arg Ala Ala Pro Tyr
                    405                 410                 415
Glu Leu Ser Thr Glu Gln Val Val Ala Ile Ala Ser His Asp Gly Gly
                    420                 425                 430
Lys Gln Ala Leu Glu Ala Val Gly Ala Gln Leu Val Ala Leu Arg Ala
            435                 440                 445
Ala Pro Tyr Ala Leu Ser Thr Glu Gln Val Val Ile Ala Asn Ser
            450                 455                 460
Ile Gly Gly Lys Gln Ala Leu Glu Ala Val Lys Val Gln Leu Pro Val
465                 470                 475                 480
Leu Arg Ala Ala Pro Tyr Glu Leu Ser Thr Glu Gln Val Val Ala Ile
                    485                 490                 495
Ala Ser Asn Lys Gly Gly Lys Gln Ala Leu Glu Ala Val Lys Ala His
                    500                 505                 510
Leu Leu Asp Leu Leu Gly Ala Pro Tyr Val Leu Ser Thr Ala Gln Val
            515                 520                 525
Val Ala Ile Ala Ser Asn Gly Gly Lys Gln Ala Leu Glu Gly Ile
            530                 535                 540
Gly Glu Gln Leu Leu Lys Leu Arg Thr Ala Pro Tyr Gly Leu Ser Thr
545                 550                 555                 560
Ala Gln Val Val Ala Ile Ala Ser Asn Gly Gly Lys Gln Ala Leu
                    565                 570                 575
Glu Gly Ile Gly Glu Gln Leu Leu Lys Leu Arg Thr Ala Pro Tyr Gly
                    580                 585                 590
Leu Ser Thr Ala Gln Val Val Ala Ile Ala Ser Asn Gly Gly Gly Lys
            595                 600                 605
```

```
Gln Ala Leu Glu Gly Ile Gly Glu Gln Leu Leu Lys Leu Arg Thr Ala
            610                 615                 620
Pro Tyr Gly Leu Ser Thr Glu Gln Val Val Ala Ile Ala Ser His Asp
625                 630                 635                 640
Gly Gly Lys Gln Ala Leu Glu Ala Val Gly Ala Gln Leu Val Ala Leu
                645                 650                 655
Arg Ala Ala Pro Tyr Ala Leu Ser Thr Glu Gln Val Val Ala Ile Ala
                660                 665                 670
Ser His Asp Gly Gly Lys Gln Ala Leu Glu Ala Val Gly Ala Gln Leu
            675                 680                 685
Val Ala Leu Arg Ala Ala Pro Tyr Ala Leu Ser Thr Glu Gln Val Val
            690                 695                 700
Ala Ile Ala Ser His Asp Gly Gly Lys Gln Ala Leu Glu Ala Val Gly
705                 710                 715                 720
Ala Gln Leu Val Ala Leu Arg Ala Ala Pro Tyr Ala Leu Ser Thr Ala
                725                 730                 735
Gln Val Val Ala Ile Ala Ser Asn Gly Gly Lys Gln Ala Leu Glu
                740                 745                 750
Gly Ile Gly Glu Gln Leu Leu Lys Leu Arg Thr Ala Pro Tyr Gly Leu
            755                 760                 765
Ser Thr Ala Gln Val Val Ala Ile Ala Ser Asn Gly Gly Lys Gln
770                 775                 780
Ala Leu Glu Gly Ile Gly Glu Gln Leu Leu Lys Leu Arg Thr Ala Pro
785                 790                 795                 800
Tyr Gly Leu Ser Thr Ala Gln Val Val Ala Ile Ala Cys Ile Ser Gly
                805                 810                 815
Gln Gln Ala Leu Glu Ala Ile Glu Ala His Met Pro Thr Leu Arg Gln
            820                 825                 830
Ala Ser His Ser Leu Ser Pro Glu Arg Val Ala Ala Ile Ala Cys Ile
            835                 840                 845
Gly Gly Arg Ser Ala Val Glu Ala Val Arg Gln Gly Leu Pro Val Lys
850                 855                 860
Ala Ile Arg Arg Ile Arg Arg Glu Lys Ala Pro Val Ala Gly Pro Pro
865                 870                 875                 880
Pro Ala Ser

<210> SEQ ID NO 312
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 312
gacctgggac agtttccctt                                              20

<210> SEQ ID NO 313
<211> LENGTH: 813
<212> TYPE: PRT
<213> ORGANISM: Artificial Sequence
<220> FEATURE:
<223> OTHER INFORMATION: Synthetic Sequence

<400> SEQUENCE: 313

Phe Gly Lys Leu Val Ala Leu Gly Tyr Ser Arg Glu Gln Ile Arg Lys
1               5                   10                  15
```

-continued

```
Leu Lys Gln Glu Ser Leu Ser Glu Ile Ala Lys Tyr His Thr Thr Leu
             20                  25                  30
Thr Gly Gln Gly Phe Thr His Ala Asp Ile Cys Arg Ile Ser Arg Arg
         35                  40                  45
Arg Gln Ser Leu Arg Val Val Ala Arg Asn Tyr Pro Glu Leu Ala Ala
     50                  55                  60
Ala Leu Pro Glu Leu Thr Arg Ala His Ile Val Asp Ile Ala Arg Gln
 65                  70                  75                  80
Arg Ser Gly Asp Leu Ala Leu Gln Ala Leu Pro Val Ala Thr Ala
                 85                  90                  95
Leu Thr Ala Ala Pro Leu Arg Leu Ser Ala Ser Gln Ile Ala Thr Val
                100                 105                 110
Ala Gln Tyr Gly Glu Arg Pro Ala Ile Gln Ala Leu Tyr Arg Leu Arg
            115                 120                 125
Arg Lys Leu Thr Arg Ala Pro Leu His Leu Thr Pro Gln Gln Val Val
        130                 135                 140
Ala Ile Ala Ser Asn Thr Gly Gly Lys Arg Ala Leu Glu Ala Val Cys
145                 150                 155                 160
Val Gln Leu Pro Val Leu Arg Ala Ala Pro Tyr Arg Leu Ser Thr Ala
                165                 170                 175
Gln Val Val Ala Ile Ala Ser Asn Gly Gly Gly Lys Gln Ala Leu Glu
            180                 185                 190
Gly Ile Gly Glu Gln Leu Leu Lys Leu Arg Thr Ala Pro Tyr Gly Leu
        195                 200                 205
Ser Thr Glu Gln Val Val Ala Ile Ala Ser His Asp Gly Gly Lys Gln
210                 215                 220
Ala Leu Glu Ala Val Gly Ala Gln Leu Val Ala Leu Arg Ala Ala Pro
225                 230                 235                 240
Tyr Ala Leu Ser Thr Ala Gln Val Val Ala Ile Ala Ser Asn Gly Gly
                245                 250                 255
Gly Lys Gln Ala Leu Glu Gly Ile Gly Glu Gln Leu Leu Lys Leu Arg
            260                 265                 270
Thr Ala Pro Tyr Gly Leu Ser Thr Glu Gln Val Val Ala Ile Ala Ser
        275                 280                 285
His Asn Gly Gly Lys Gln Ala Leu Glu Ala Val Lys Ala Asp Leu Leu
        290                 295                 300
Glu Leu Arg Gly Ala Pro Tyr Ala Leu Ser Thr Glu Gln Val Val Ala
305                 310                 315                 320
Ile Ala Ser His Asp Gly Gly Lys Gln Ala Leu Glu Ala Val Gly Ala
                325                 330                 335
Gln Leu Val Ala Leu Arg Ala Ala Pro Tyr Ala Leu Ser Thr Glu Gln
            340                 345                 350
Val Val Val Ile Ala Asn Ser Ile Gly Gly Lys Gln Ala Leu Glu Ala
        355                 360                 365
Val Lys Val Gln Leu Pro Val Leu Arg Ala Ala Pro Tyr Glu Leu Ser
    370                 375                 380
Thr Ala Gln Val Val Ala Ile Ala Ser Asn Gly Gly Gly Lys Gln Ala
385                 390                 395                 400
Leu Glu Gly Ile Gly Glu Gln Leu Leu Lys Leu Arg Thr Ala Pro Tyr
                405                 410                 415
Gly Leu Ser Thr Glu Gln Val Val Ala Ile Ala Ser His Asn Gly Gly
            420                 425                 430
Lys Gln Ala Leu Glu Ala Val Lys Ala Asp Leu Leu Glu Leu Arg Gly
```

```
                435                 440                 445
Ala Pro Tyr Ala Leu Ser Thr Glu Gln Val Val Ala Ile Ala Ser His
450                 455                 460

Asp Gly Gly Lys Gln Ala Leu Glu Ala Val Gly Ala Gln Leu Val Ala
465                 470                 475                 480

Leu Arg Ala Ala Pro Tyr Ala Leu Ser Thr Glu Gln Val Val Ala Ile
                485                 490                 495

Ala Ser His Asp Gly Gly Lys Gln Ala Leu Glu Ala Val Gly Ala Gln
            500                 505                 510

Leu Val Ala Leu Arg Ala Ala Pro Tyr Ala Leu Ser Thr Ala Gln Val
        515                 520                 525

Val Ala Ile Ala Ser Asn Gly Gly Lys Gln Ala Leu Glu Gly Ile
    530                 535                 540

Gly Glu Gln Leu Leu Lys Leu Arg Thr Ala Pro Tyr Gly Leu Ser Thr
545                 550                 555                 560

Glu Gln Val Val Ala Ile Ala Ser His Asn Gly Gly Lys Gln Ala Leu
                565                 570                 575

Glu Ala Val Lys Ala Asp Leu Leu Glu Leu Arg Gly Ala Pro Tyr Ala
            580                 585                 590

Leu Ser Thr Glu Gln Val Val Ala Ile Ala Ser His Asn Gly Gly Lys
        595                 600                 605

Gln Ala Leu Glu Ala Val Lys Ala Asp Leu Leu Glu Leu Arg Gly Ala
    610                 615                 620

Pro Tyr Ala Leu Ser Thr Glu Gln Val Val Ile Ala Asn Ser Ile
625                 630                 635                 640

Gly Gly Lys Gln Ala Leu Glu Ala Val Lys Val Gln Leu Pro Val Leu
                645                 650                 655

Arg Ala Ala Pro Tyr Glu Leu Ser Thr Glu Gln Val Val Ala Ile Ala
            660                 665                 670

Ser His Asn Gly Gly Lys Gln Ala Leu Glu Ala Val Lys Ala Asp Leu
        675                 680                 685

Leu Glu Leu Arg Gly Ala Pro Tyr Ala Leu Ser Thr Glu Gln Val Val
    690                 695                 700

Ala Ile Ala Ser His Asp Gly Gly Lys Gln Ala Leu Glu Ala Val Gly
705                 710                 715                 720

Ala Gln Leu Val Ala Leu Arg Ala Ala Pro Tyr Ala Leu Ser Thr Ala
                725                 730                 735

Gln Val Val Ala Ile Ala Cys Ile Ser Gly Gln Gln Ala Leu Glu Ala
            740                 745                 750

Ile Glu Ala His Met Pro Thr Leu Arg Gln Ala Ser His Ser Leu Ser
        755                 760                 765

Pro Glu Arg Val Ala Ala Ile Ala Cys Ile Gly Gly Arg Ser Ala Val
    770                 775                 780

Glu Ala Val Arg Gln Gly Leu Pro Val Lys Ala Ile Arg Arg Ile Arg
785                 790                 795                 800

Arg Glu Lys Ala Pro Val Ala Gly Pro Pro Ala Ser
                805                 810

<210> SEQ ID NO 314
<211> LENGTH: 18
<212> TYPE: DNA
<213> ORGANISM: Artificial Sequence
<220> FEATURE:
<223> OTHER INFORMATION: Synthetic Sequence
```

<400> SEQUENCE: 314
gatctgcatg cctggagc                                                         18

<210> SEQ ID NO 315
<211> LENGTH: 813
<212> TYPE: PRT
<213> ORGANISM: Artificial Sequence
<220> FEATURE:
<223> OTHER INFORMATION: Synthetic Sequence

<400> SEQUENCE: 315

```
Phe Gly Lys Leu Val Ala Leu Gly Tyr Ser Arg Glu Gln Ile Arg Lys
  1               5                  10                  15

Leu Lys Gln Glu Ser Leu Ser Glu Ile Ala Lys Tyr His Thr Thr Leu
             20                  25                  30

Thr Gly Gln Gly Phe Thr His Ala Asp Ile Cys Arg Ile Ser Arg Arg
         35                  40                  45

Arg Gln Ser Leu Arg Val Val Ala Arg Asn Tyr Pro Glu Leu Ala Ala
     50                  55                  60

Ala Leu Pro Glu Leu Thr Arg Ala His Ile Val Asp Ile Ala Arg Gln
 65                  70                  75                  80

Arg Ser Gly Asp Leu Ala Leu Gln Ala Leu Leu Pro Val Ala Thr Ala
                 85                  90                  95

Leu Thr Ala Ala Pro Leu Arg Leu Ser Ala Ser Gln Ile Ala Thr Val
            100                 105                 110

Ala Gln Tyr Gly Glu Arg Pro Ala Ile Gln Ala Leu Tyr Arg Leu Arg
        115                 120                 125

Arg Lys Leu Thr Arg Ala Pro Leu His Leu Thr Pro Gln Gln Val Val
    130                 135                 140

Ala Ile Ala Ser Asn Thr Gly Gly Lys Arg Ala Leu Glu Ala Val Cys
145                 150                 155                 160

Val Gln Leu Pro Val Leu Arg Ala Ala Pro Tyr Arg Leu Ser Thr Ala
                165                 170                 175

Gln Val Val Ala Ile Ala Ser Asn Gly Gly Lys Gln Ala Leu Glu
            180                 185                 190

Gly Ile Gly Glu Gln Leu Leu Lys Leu Arg Thr Ala Pro Tyr Gly Leu
        195                 200                 205

Ser Thr Glu Gln Val Val Ala Ile Ala Ser His Asp Gly Gly Lys Gln
    210                 215                 220

Ala Leu Glu Ala Val Gly Ala Gln Leu Val Ala Leu Arg Ala Ala Pro
225                 230                 235                 240

Tyr Ala Leu Ser Thr Ala Gln Val Val Ala Ile Ala Ser Asn Gly Gly
                245                 250                 255

Gly Lys Gln Ala Leu Glu Gly Ile Gly Glu Gln Leu Leu Lys Leu Arg
            260                 265                 270

Thr Ala Pro Tyr Gly Leu Ser Thr Glu Gln Val Val Ala Ile Ala Ser
        275                 280                 285

His Asn Gly Gly Lys Gln Ala Leu Glu Ala Val Lys Ala Asp Leu Leu
    290                 295                 300

Glu Leu Arg Gly Ala Pro Tyr Ala Leu Ser Thr Glu Gln Val Val Ala
305                 310                 315                 320

Ile Ala Ser His Asp Gly Gly Lys Gln Ala Leu Glu Ala Val Gly Ala
                325                 330                 335

Gln Leu Val Ala Leu Arg Ala Ala Pro Tyr Ala Leu Ser Thr Ala Gln
            340                 345                 350
```

Val Val Ala Ile Ala Thr Arg Ser Gly Gly Lys Gln Ala Leu Glu Ala
            355                 360                 365

Val Arg Ala Gln Leu Leu Asp Leu Arg Ala Ala Pro Tyr Gly Leu Ser
370                 375                 380

Thr Ala Gln Val Val Ala Ile Ala Ser Asn Gly Gly Lys Gln Ala
385                 390                 395                 400

Leu Glu Gly Ile Gly Glu Gln Leu Leu Lys Leu Arg Thr Ala Pro Tyr
                405                 410                 415

Gly Leu Ser Thr Glu Gln Val Val Ala Ile Ala Ser His Asn Gly Gly
            420                 425                 430

Lys Gln Ala Leu Glu Ala Val Lys Ala Asp Leu Leu Glu Leu Arg Gly
            435                 440                 445

Ala Pro Tyr Ala Leu Ser Thr Glu Gln Val Val Ala Ile Ala Ser His
            450                 455                 460

Asp Gly Gly Lys Gln Ala Leu Glu Ala Val Gly Ala Gln Leu Val Ala
465                 470                 475                 480

Leu Arg Ala Ala Pro Tyr Ala Leu Ser Thr Glu Gln Val Val Ala Ile
                485                 490                 495

Ala Ser His Asp Gly Gly Lys Gln Ala Leu Glu Ala Val Gly Ala Gln
            500                 505                 510

Leu Val Ala Leu Arg Ala Ala Pro Tyr Ala Leu Ser Thr Ala Gln Val
            515                 520                 525

Val Ala Ile Ala Ser Asn Gly Gly Lys Gln Ala Leu Glu Gly Ile
            530                 535                 540

Gly Glu Gln Leu Leu Lys Leu Arg Thr Ala Pro Tyr Gly Leu Ser Thr
545                 550                 555                 560

Glu Gln Val Val Ala Ile Ala Ser His Asn Gly Gly Lys Gln Ala Leu
                565                 570                 575

Glu Ala Val Lys Ala Asp Leu Leu Glu Leu Arg Gly Ala Pro Tyr Ala
            580                 585                 590

Leu Ser Thr Glu Gln Val Val Ala Ile Ala Ser His Asn Gly Gly Lys
            595                 600                 605

Gln Ala Leu Glu Ala Val Lys Ala Asp Leu Leu Glu Leu Arg Gly Ala
            610                 615                 620

Pro Tyr Ala Leu Ser Thr Ala Gln Val Val Ala Ile Ala Thr Arg Ser
625                 630                 635                 640

Gly Gly Lys Gln Ala Leu Glu Ala Val Arg Ala Gln Leu Leu Asp Leu
                645                 650                 655

Arg Ala Ala Pro Tyr Gly Leu Ser Thr Glu Gln Val Val Ala Ile Ala
            660                 665                 670

Ser His Asn Gly Gly Lys Gln Ala Leu Glu Ala Val Lys Ala Asp Leu
            675                 680                 685

Leu Glu Leu Arg Gly Ala Pro Tyr Ala Leu Ser Thr Glu Gln Val Val
            690                 695                 700

Ala Ile Ala Ser His Asp Gly Gly Lys Gln Ala Leu Glu Ala Val Gly
705                 710                 715                 720

Ala Gln Leu Val Ala Leu Arg Ala Ala Pro Tyr Ala Leu Ser Thr Ala
                725                 730                 735

Gln Val Val Ala Ile Ala Cys Ile Ser Gly Gln Gln Ala Leu Glu Ala
            740                 745                 750

Ile Glu Ala His Met Pro Thr Leu Arg Gln Ala Ser His Ser Leu Ser
            755                 760                 765

```
Pro Glu Arg Val Ala Ala Ile Ala Cys Ile Gly Gly Arg Ser Ala Val
        770                 775                 780

Glu Ala Val Arg Gln Gly Leu Pro Val Lys Ala Ile Arg Arg Ile Arg
785                 790                 795                 800

Arg Glu Lys Ala Pro Val Ala Gly Pro Pro Pro Ala Ser
                805                 810

<210> SEQ ID NO 316
<211> LENGTH: 202
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (1)..(1)
<223> OTHER INFORMATION: Xaa is Phe, Gln, Asn, Asp or absent
<220> FEATURE:
<221> NAME/KEY: SITE
<222> LOCATION: (2)..(2)
<223> OTHER INFORMATION: Xaa is Leu, Ile, Thr, Ser, Asn or absent
<220> FEATURE:
<221> NAME/KEY: SITE
<222> LOCATION: (3)..(3)
<223> OTHER INFORMATION: Xaa is Val, Ile, Gly, Ala, Glu, Thr or absent
<220> FEATURE:
<221> NAME/KEY: SITE
<222> LOCATION: (4)..(4)
<223> OTHER INFORMATION: Xaa is Lys, Cys or absent
<220> FEATURE:
<221> NAME/KEY: SITE
<222> LOCATION: (5)..(5)
<223> OTHER INFORMATION: Xaa is Gly, Ser or absent
<220> FEATURE:
<221> NAME/KEY: SITE
<222> LOCATION: (6)..(6)
<223> OTHER INFORMATION: Xaa is Ala, Ser, Glu, Asp, Asn or absent
<220> FEATURE:
<221> NAME/KEY: SITE
<222> LOCATION: (7)..(7)
<223> OTHER INFORMATION: Xaa is Met, Ile, Val, Gln, Phe, Leu or absent
<220> FEATURE:
<221> NAME/KEY: SITE
<222> LOCATION: (8)..(8)
<223> OTHER INFORMATION: Xaa is Glu, Ser, Thr, Asn or absent
<220> FEATURE:
<221> NAME/KEY: SITE
<222> LOCATION: (9)..(9)
<223> OTHER INFORMATION: Xaa is Ile, Met, Glu, Thr, Gln or absent
<220> FEATURE:
<221> NAME/KEY: SITE
<222> LOCATION: (10)..(10)
<223> OTHER INFORMATION: Xaa is Lys, Ser, Leu, Ile, Thr, Glu or absent
<220> FEATURE:
<221> NAME/KEY: SITE
<222> LOCATION: (11)..(11)
<223> OTHER INFORMATION: Xaa is Lys or absent
<220> FEATURE:
<221> NAME/KEY: SITE
<222> LOCATION: (12)..(12)
<223> OTHER INFORMATION: Xaa is Ser, Ala, Glu, Asp or absent
<220> FEATURE:
<221> NAME/KEY: SITE
<222> LOCATION: (13)..(13)
<223> OTHER INFORMATION: Xaa is Glu, Asn, Gln, Lys or absent
<220> FEATURE:
<221> NAME/KEY: SITE
<222> LOCATION: (14)..(14)
<223> OTHER INFORMATION: Xaa is Leu, Met, Val or absent
<220> FEATURE:
<221> NAME/KEY: SITE
<222> LOCATION: (15)..(15)
<223> OTHER INFORMATION: Xaa is Arg or absent
<220> FEATURE:
<221> NAME/KEY: SITE
<222> LOCATION: (16)..(16)
```

```
<223> OTHER INFORMATION: Xaa is His, Asp, Thr, Gly, Glu, Asn or absent
<220> FEATURE:
<221> NAME/KEY: SITE
<222> LOCATION: (17)..(17)
<223> OTHER INFORMATION: Xaa is Lys, Asn, Gln, Glu, Ala or absent
<220> FEATURE:
<221> NAME/KEY: SITE
<222> LOCATION: (18)..(18)
<223> OTHER INFORMATION: Xaa is Leu or absent
<220> FEATURE:
<221> NAME/KEY: SITE
<222> LOCATION: (19)..(19)
<223> OTHER INFORMATION: Xaa is Arg, Gln, Asn, Thr, Asp or absent
<220> FEATURE:
<221> NAME/KEY: SITE
<222> LOCATION: (20)..(20)
<223> OTHER INFORMATION: Xaa is His, Met, Val, Asn, Thr or absent
<220> FEATURE:
<221> NAME/KEY: SITE
<222> LOCATION: (21)..(21)
<223> OTHER INFORMATION: Xaa is Val, Lei, Ile or absent
<220> FEATURE:
<221> NAME/KEY: SITE
<222> LOCATION: (22)..(22)
<223> OTHER INFORMATION: Xaa is Pro, Ser or absent
<220> FEATURE:
<221> NAME/KEY: SITE
<222> LOCATION: (23)..(23)
<223> OTHER INFORMATION: Xaa is His or absent
<220> FEATURE:
<221> NAME/KEY: SITE
<222> LOCATION: (24)..(24)
<223> OTHER INFORMATION: Xaa is Glu, Asp or absent
<220> FEATURE:
<221> NAME/KEY: SITE
<222> LOCATION: (25)..(25)
<223> OTHER INFORMATION: Xaa is Tyr or absent
<220> FEATURE:
<221> NAME/KEY: SITE
<222> LOCATION: (26)..(26)
<223> OTHER INFORMATION: Xaa is Ile, Leu or absent
<220> FEATURE:
<221> NAME/KEY: SITE
<222> LOCATION: (27)..(27)
<223> OTHER INFORMATION: Xaa is Glu, Gln, Gly, Ser, Ala, Tyr or absent
<220> FEATURE:
<221> NAME/KEY: SITE
<222> LOCATION: (28)..(28)
<223> OTHER INFORMATION: Xaa is Leu or absent
<220> FEATURE:
<221> NAME/KEY: SITE
<222> LOCATION: (29)..(29)
<223> OTHER INFORMATION: Xaa is Ile, Val, Leu or absent
<220> FEATURE:
<221> NAME/KEY: SITE
<222> LOCATION: (30)..(30)
<223> OTHER INFORMATION: Xaa is Glu, Asp or absent
<220> FEATURE:
<221> NAME/KEY: SITE
<222> LOCATION: (31)..(31)
<223> OTHER INFORMATION: Xaa is Ile, Leu or absent
<220> FEATURE:
<221> NAME/KEY: SITE
<222> LOCATION: (32)..(32)
<223> OTHER INFORMATION: Xaa is Ala, Ser or absent
<220> FEATURE:
<221> NAME/KEY: SITE
<222> LOCATION: (33)..(33)
<223> OTHER INFORMATION: Xaa is Gln, Tyr, Phe or absent
<220> FEATURE:
<221> NAME/KEY: SITE
<222> LOCATION: (34)..(34)
<223> OTHER INFORMATION: Xaa is Asp or absent
<220> FEATURE:
<221> NAME/KEY: SITE
<222> LOCATION: (35)..(35)
<223> OTHER INFORMATION: Xaa is Ser, Pro or absent
<220> FEATURE:
<221> NAME/KEY: SITE
```

```
<222> LOCATION: (36)..(36)
<223> OTHER INFORMATION: Xaa is Lys, Tyr, Gln, Thr or absent
<220> FEATURE:
<221> NAME/KEY: SITE
<222> LOCATION: (37)..(37)
<223> OTHER INFORMATION: Xaa is Gln or absent
<220> FEATURE:
<221> NAME/KEY: SITE
<222> LOCATION: (38)..(38)
<223> OTHER INFORMATION: Xaa is Asn or absent
<220> FEATURE:
<221> NAME/KEY: SITE
<222> LOCATION: (39)..(39)
<223> OTHER INFORMATION: Xaa is Arg, Lys or absent
<220> FEATURE:
<221> NAME/KEY: SITE
<222> LOCATION: (40)..(40)
<223> OTHER INFORMATION: Xaa is Leu, Ile or absent
<220> FEATURE:
<221> NAME/KEY: SITE
<222> LOCATION: (41)..(41)
<223> OTHER INFORMATION: Xaa is Leu, Phe or absent
<220> FEATURE:
<221> NAME/KEY: SITE
<222> LOCATION: (42)..(42)
<223> OTHER INFORMATION: Xaa is Glu or absent
<220> FEATURE:
<221> NAME/KEY: SITE
<222> LOCATION: (43)..(43)
<223> OTHER INFORMATION: Xaa is Phe, Met, Leu or absent
<220> FEATURE:
<221> NAME/KEY: SITE
<222> LOCATION: (45)..(45)
<223> OTHER INFORMATION: Xaa is Val, Thr, or Ile
<220> FEATURE:
<221> NAME/KEY: SITE
<222> LOCATION: (46)..(46)
<223> OTHER INFORMATION: Xaa is Val, Met, Leu or Ile
<220> FEATURE:
<221> NAME/KEY: SITE
<222> LOCATION: (47)..(47)
<223> OTHER INFORMATION: Xaa is Glu, Asp or Gln
<220> FEATURE:
<221> NAME/KEY: SITE
<222> LOCATION: (48)..(48)
<223> OTHER INFORMATION: Xaa is Phe or Leu
<220> FEATURE:
<221> NAME/KEY: SITE
<222> LOCATION: (49)..(49)
<223> OTHER INFORMATION: Xaa is Phe or Leu
<220> FEATURE:
<221> NAME/KEY: SITE
<222> LOCATION: (50)..(50)
<223> OTHER INFORMATION: Xaa is Lys, Ile, Thr or Val
<220> FEATURE:
<221> NAME/KEY: SITE
<222> LOCATION: (51)..(51)
<223> OTHER INFORMATION: Xaa is Lys, Asn, or Glu
<220> FEATURE:
<221> NAME/KEY: SITE
<222> LOCATION: (52)..(52)
<223> OTHER INFORMATION: Xaa is Ile or Glu
<220> FEATURE:
<221> NAME/KEY: SITE
<222> LOCATION: (53)..(53)
<223> OTHER INFORMATION: Xaa is Tyr, Phe or Cys
<220> FEATURE:
<221> NAME/KEY: SITE
<222> LOCATION: (54)..(54)
<223> OTHER INFORMATION: Xaa is Gly or Asn
<220> FEATURE:
<221> NAME/KEY: SITE
<222> LOCATION: (55)..(55)
<223> OTHER INFORMATION: Xaa is Tyr or Phe
<220> FEATURE:
<221> NAME/KEY: SITE
<222> LOCATION: (56)..(56)
<223> OTHER INFORMATION: Xaa is Arg, Ser, Asn, Glu, Lys or Gln
<220> FEATURE:
```

```
<221> NAME/KEY: SITE
<222> LOCATION: (58)..(58)
<223> OTHER INFORMATION: Xaa is Lys, Ser, Leu, Val or Thr
<220> FEATURE:
<221> NAME/KEY: SITE
<222> LOCATION: (63)..(63)
<223> OTHER INFORMATION: Xaa is Ser, Ala or Val
<220> FEATURE:
<221> NAME/KEY: SITE
<222> LOCATION: (65)..(65)
<223> OTHER INFORMATION: Xaa is Lys or Arg
<220> FEATURE:
<221> NAME/KEY: SITE
<222> LOCATION: (69)..(69)
<223> OTHER INFORMATION: Xaa is Ala, Ile or Val
<220> FEATURE:
<221> NAME/KEY: SITE
<222> LOCATION: (70)..(70)
<223> OTHER INFORMATION: Xaa is Leu, Met, Val, Ile or Cys
<220> FEATURE:
<221> NAME/KEY: SITE
<222> LOCATION: (71)..(71)
<223> OTHER INFORMATION: Xaa is Phe or Tyr
<220> FEATURE:
<221> NAME/KEY: SITE
<222> LOCATION: (72)..(72)
<223> OTHER INFORMATION: Xaa is Thr, Ala or Ser
<220> FEATURE:
<221> NAME/KEY: SITE
<222> LOCATION: (73)..(73)
<223> OTHER INFORMATION: Xaa is Lys, Glu or absent
<220> FEATURE:
<221> NAME/KEY: SITE
<222> LOCATION: (74)..(74)
<223> OTHER INFORMATION: Xaa is Glu, Ala or absent
<220> FEATURE:
<221> NAME/KEY: SITE
<222> LOCATION: (75)..(75)
<223> OTHER INFORMATION: Xaa is Glu, Ala or absent
<220> FEATURE:
<221> NAME/KEY: SITE
<222> LOCATION: (76)..(76)
<223> OTHER INFORMATION: Xaa is Asn, Lys or absent
<220> FEATURE:
<221> NAME/KEY: SITE
<222> LOCATION: (77)..(77)
<223> OTHER INFORMATION: Xaa is Glu, Ser or absent
<220> FEATURE:
<221> NAME/KEY: SITE
<222> LOCATION: (78)..(78)
<223> OTHER INFORMATION: Xaa is Asp, Glu, Gln, Ala or absent
<220> FEATURE:
<221> NAME/KEY: SITE
<222> LOCATION: (79)..(79)
<223> OTHER INFORMATION: Xaa is Gly, Val, Lys, Asn or absent
<220> FEATURE:
<221> NAME/KEY: SITE
<222> LOCATION: (80)..(80)
<223> OTHER INFORMATION: Xaa is Leu, Gly, Glu, Ser or absent
<220> FEATURE:
<221> NAME/KEY: SITE
<222> LOCATION: (81)..(81)
<223> OTHER INFORMATION: Xaa is Val, Ser, Lys, Thr, Glu or absent
<220> FEATURE:
<221> NAME/KEY: SITE
<222> LOCATION: (82)..(82)
<223> OTHER INFORMATION: Xaa is Leu, His, Lys, Gly Tyr, Asp or Ala
<220> FEATURE:
<221> NAME/KEY: SITE
<222> LOCATION: (83)..(83)
<223> OTHER INFORMATION: Xaa is Asn, Gly or Asp
<220> FEATURE:
<221> NAME/KEY: SITE
<222> LOCATION: (84)..(84)
<223> OTHER INFORMATION: Xaa is His, Phe or Tyr
<220> FEATURE:
<221> NAME/KEY: SITE
<222> LOCATION: (86)..(86)
<223> OTHER INFORMATION: Xaa is Ile or Val
```

-continued

```
<220> FEATURE:
<221> NAME/KEY: SITE
<222> LOCATION: (88)..(88)
<223> OTHER INFORMATION: Xaa is Leu, Val or Ile
<220> FEATURE:
<221> NAME/KEY: SITE
<222> LOCATION: (92)..(92)
<223> OTHER INFORMATION: Xaa is Ala or Ser
<220> FEATURE:
<221> NAME/KEY: SITE
<222> LOCATION: (94)..(94)
<223> OTHER INFORMATION: Xaa is Lys or Ser
<220> FEATURE:
<221> NAME/KEY: SITE
<222> LOCATION: (95)..(95)
<223> OTHER INFORMATION: Xaa is Asp, Gly, Lys, Ser or Asn
<220> FEATURE:
<221> NAME/KEY: SITE
<222> LOCATION: (98)..(98)
<223> OTHER INFORMATION: Xaa is Arg, Asn, Ser or Gly
<220> FEATURE:
<221> NAME/KEY: SITE
<222> LOCATION: (102)..(102)
<223> OTHER INFORMATION: Xaa is Ser, Ala or Gly
<220> FEATURE:
<221> NAME/KEY: SITE
<222> LOCATION: (104)..(104)
<223> OTHER INFORMATION: Xaa is Ala, Ile or Val
<220> FEATURE:
<221> NAME/KEY: SITE
<222> LOCATION: (108)..(108)
<223> OTHER INFORMATION: Xaa is Gln, Glu, Ile or Val
<220> FEATURE:
<221> NAME/KEY: SITE
<222> LOCATION: (111)..(111)
<223> OTHER INFORMATION: Xaa is Val or Ile
<220> FEATURE:
<221> NAME/KEY: SITE
<222> LOCATION: (112)..(112)
<223> OTHER INFORMATION: Xaa is Asp, Arg, Gly, Ile or Glu
<220> FEATURE:
<221> NAME/KEY: SITE
<222> LOCATION: (115)..(115)
<223> OTHER INFORMATION: Xaa is Asn, Ile or Gln
<220> FEATURE:
<221> NAME/KEY: SITE
<222> LOCATION: (116)..(116)
<223> OTHER INFORMATION: Xaa is Lys, Asp, Thr, Glu or Lys
<220> FEATURE:
<221> NAME/KEY: SITE
<222> LOCATION: (118)..(118)
<223> OTHER INFORMATION: Xaa is Ser, Asn, Asp or Glu
<220> FEATURE:
<221> NAME/KEY: SITE
<222> LOCATION: (119)..(119)
<223> OTHER INFORMATION: Xaa is Gln, Glu, Ile, Lys or Ala
<220> FEATURE:
<221> NAME/KEY: SITE
<222> LOCATION: (120)..(120)
<223> OTHER INFORMATION: Xaa is Val, His, Arg, Lys, Leu or Glu
<220> FEATURE:
<221> NAME/KEY: SITE
<222> LOCATION: (121)..(121)
<223> OTHER INFORMATION: Xaa is Ile, Val or Arg
<220> FEATURE:
<221> NAME/KEY: SITE
<222> LOCATION: (123)..(123)
<223> OTHER INFORMATION: Xaa is Pro, Ser, Thr or Arg
<220> FEATURE:
<221> NAME/KEY: SITE
<222> LOCATION: (125)..(125)
<223> OTHER INFORMATION: Xaa is Glu, Arg, Cys, Gln or Lys
<220> FEATURE:
<221> NAME/KEY: SITE
<222> LOCATION: (128)..(128)
<223> OTHER INFORMATION: Xaa is Glu, Asn or Lys
<220> FEATURE:
<221> NAME/KEY: SITE
<222> LOCATION: (129)..(129)
```

```
<223> OTHER INFORMATION: Xaa is Ile, Val, Asn, Glu or Ala
<220> FEATURE:
<221> NAME/KEY: SITE
<222> LOCATION: (130)..(130)
<223> OTHER INFORMATION: Xaa is Tyr or Phe
<220> FEATURE:
<221> NAME/KEY: SITE
<222> LOCATION: (131)..(131)
<223> OTHER INFORMATION: Xaa is Pro, Gly or Glu
<220> FEATURE:
<221> NAME/KEY: SITE
<222> LOCATION: (132)..(132)
<223> OTHER INFORMATION: Xaa is Thr, Glu, Ser, Asp, Lys or Asn
<220> FEATURE:
<221> NAME/KEY: SITE
<222> LOCATION: (133)..(133)
<223> OTHER INFORMATION: Xaa is Ser, Asp, Lys, Gly, Asn or Thr
<220> FEATURE:
<221> NAME/KEY: SITE
<222> LOCATION: (134)..(134)
<223> OTHER INFORMATION: Xaa is Ile, Thr, Val or Leu
<220> FEATURE:
<221> NAME/KEY: SITE
<222> LOCATION: (135)..(135)
<223> OTHER INFORMATION: Xaa is Thr, Asn, Gly or Asp
<220> FEATURE:
<221> NAME/KEY: SITE
<222> LOCATION: (136)..(136)
<223> OTHER INFORMATION: Xaa is Asp, Glu, Thr, Lys or Ile
<220> FEATURE:
<221> NAME/KEY: SITE
<222> LOCATION: (137)..(137)
<223> OTHER INFORMATION: Xaa is Phe or Tyr
<220> FEATURE:
<221> NAME/KEY: SITE
<222> LOCATION: (138)..(138)
<223> OTHER INFORMATION: Xaa is Lys or Tyr
<220> FEATURE:
<221> NAME/KEY: SITE
<222> LOCATION: (139)..(139)
<223> OTHER INFORMATION: Xaa is Phe or Tyr
<220> FEATURE:
<221> NAME/KEY: SITE
<222> LOCATION: (140)..(140)
<223> OTHER INFORMATION: Xaa is Leu, Ser or Met
<220> FEATURE:
<221> NAME/KEY: SITE
<222> LOCATION: (142)..(142)
<223> OTHER INFORMATION: Xaa is Val or Ile
<220> FEATURE:
<221> NAME/KEY: SITE
<222> LOCATION: (143)..(143)
<223> OTHER INFORMATION: Xaa is Ser or Ala
<220> FEATURE:
<221> NAME/KEY: SITE
<222> LOCATION: (144)..(144)
<223> OTHER INFORMATION: Xaa is Gly or Ala
<220> FEATURE:
<221> NAME/KEY: SITE
<222> LOCATION: (145)..(145)
<223> OTHER INFORMATION: Xaa is Gly or Ala
<220> FEATURE:
<221> NAME/KEY: SITE
<222> LOCATION: (147)..(147)
<223> OTHER INFORMATION: Xaa is Gln, Lys, Thr, Asn or Ile
<220> FEATURE:
<221> NAME/KEY: SITE
<222> LOCATION: (149)..(149)
<223> OTHER INFORMATION: Xaa is Asp, Asn or Lys
<220> FEATURE:
<221> NAME/KEY: SITE
<222> LOCATION: (150)..(150)
<223> OTHER INFORMATION: Xaa is Tyr, Phe, Ile or Val
<220> FEATURE:
<221> NAME/KEY: SITE
<222> LOCATION: (151)..(151)
<223> OTHER INFORMATION: Xaa is Arg, Glu, Lys, Gln or Phe
<220> FEATURE:
<221> NAME/KEY: SITE
```

```
<222> LOCATION: (152)..(152)
<223> OTHER INFORMATION: Xaa is Lys, Glu, Ala or Asn
<220> FEATURE:
<221> NAME/KEY: SITE
<222> LOCATION: (153)..(153)
<223> OTHER INFORMATION: Xaa is Gln or Lys
<220> FEATURE:
<221> NAME/KEY: SITE
<222> LOCATION: (154)..(154)
<223> OTHER INFORMATION: Xaa is Leu or Ile
<220> FEATURE:
<221> NAME/KEY: SITE
<222> LOCATION: (155)..(155)
<223> OTHER INFORMATION: Xaa is Glu, Asp, Asn or Gln
<220> FEATURE:
<221> NAME/KEY: SITE
<222> LOCATION: (157)..(157)
<223> OTHER INFORMATION: Xaa is Val, Ile or Leu
<220> FEATURE:
<221> NAME/KEY: SITE
<222> LOCATION: (158)..(158)
<223> OTHER INFORMATION: Xaa is Ser, Asn, Phe, Thr or Gln
<220> FEATURE:
<221> NAME/KEY: SITE
<222> LOCATION: (159)..(159)
<223> OTHER INFORMATION: Xaa is His, Ile, Cys or Arg
<220> FEATURE:
<221> NAME/KEY: SITE
<222> LOCATION: (160)..(160)
<223> OTHER INFORMATION: Xaa is Leu, Asp, Asn, Ser, or Phe
<220> FEATURE:
<221> NAME/KEY: SITE
<222> LOCATION: (161)..(161)
<223> OTHER INFORMATION: Xaa is Thr or Lys
<220> FEATURE:
<221> NAME/KEY: SITE
<222> LOCATION: (162)..(162)
<223> OTHER INFORMATION: Xaa is Lys, Gly or Asn
<220> FEATURE:
<221> NAME/KEY: SITE
<222> LOCATION: (163)..(163)
<223> OTHER INFORMATION: Xaa is Cys, Val or Ile
<220> FEATURE:
<221> NAME/KEY: SITE
<222> LOCATION: (164)..(164)
<223> OTHER INFORMATION: Xaa is Gln, Leu, Lys or Tyr
<220> FEATURE:
<221> NAME/KEY: SITE
<222> LOCATION: (166)..(166)
<223> OTHER INFORMATION: Xaa is Ala, Gly or Asn
<220> FEATURE:
<221> NAME/KEY: SITE
<222> LOCATION: (167)..(167)
<223> OTHER INFORMATION: Xaa is Val or Ala
<220> FEATURE:
<221> NAME/KEY: SITE
<222> LOCATION: (168)..(168)
<223> OTHER INFORMATION: Xaa is Met, Leu, Ile, Val or Ala
<220> FEATURE:
<221> NAME/KEY: SITE
<222> LOCATION: (169)..(169)
<223> OTHER INFORMATION: Xaa is Ser, Thr or Asp
<220> FEATURE:
<221> NAME/KEY: SITE
<222> LOCATION: (170)..(170)
<223> OTHER INFORMATION: Xaa is Val or Ile
<220> FEATURE:
<221> NAME/KEY: SITE
<222> LOCATION: (171)..(171)
<223> OTHER INFORMATION: Xaa is Glu, Gln, Lys, Ser or Ile
<220> FEATURE:
<221> NAME/KEY: SITE
<222> LOCATION: (172)..(172)
<223> OTHER INFORMATION: Xaa is Gln, His or Thr
<220> FEATURE:
<221> NAME/KEY: SITE
<222> LOCATION: (175)..(175)
<223> OTHER INFORMATION: Xaa is Leu, Arg or Tyr
<220> FEATURE:
```

```
<221> NAME/KEY: SITE
<222> LOCATION: (176)..(176)
<223> OTHER INFORMATION: Xaa is Gly, Ile, Leu or Thr
<220> FEATURE:
<221> NAME/KEY: SITE
<222> LOCATION: (177)..(177)
<223> OTHER INFORMATION: Xaa is Gly, Ala or Val
<220> FEATURE:
<221> NAME/KEY: SITE
<222> LOCATION: (178)..(178)
<223> OTHER INFORMATION: Xaa is Glu, Asn or Asp
<220> FEATURE:
<221> NAME/KEY: SITE
<222> LOCATION: (179)..(179)
<223> OTHER INFORMATION: Xaa is Lys, Tyr, Asp, Glu, Ala or Arg
<220> FEATURE:
<221> NAME/KEY: SITE
<222> LOCATION: (180)..(180)
<223> OTHER INFORMATION: Xaa is Ile, Phe, Tyr or Cys
<220> FEATURE:
<221> NAME/KEY: SITE
<222> LOCATION: (181)..(181)
<223> OTHER INFORMATION: Xaa is Lys or Arg
<220> FEATURE:
<221> NAME/KEY: SITE
<222> LOCATION: (182)..(182)
<223> OTHER INFORMATION: Xaa is Glu, Arg, Ala, Gly or Thr
<220> FEATURE:
<221> NAME/KEY: SITE
<222> LOCATION: (183)..(183)
<223> OTHER INFORMATION: Xaa is Gly or Asn
<220> FEATURE:
<221> NAME/KEY: SITE
<222> LOCATION: (184)..(184)
<223> OTHER INFORMATION: Xaa is Ser, Ile, Lys, Arg or Glu
<220> FEATURE:
<221> NAME/KEY: SITE
<222> LOCATION: (185)..(185)
<223> OTHER INFORMATION: Xaa is Leu, Ile or Met
<220> FEATURE:
<221> NAME/KEY: SITE
<222> LOCATION: (186)..(186)
<223> OTHER INFORMATION: Xaa is Thr, Ser, Asp or Lys
<220> FEATURE:
<221> NAME/KEY: SITE
<222> LOCATION: (187)..(187)
<223> OTHER INFORMATION: Xaa is Leu, His, Tyr, Arg, Thr or Phe
<220> FEATURE:
<221> NAME/KEY: SITE
<222> LOCATION: (188)..(188)
<223> OTHER INFORMATION: Xaa is Glu, Tyr, Ile, Met, Ala or Leu
<220> FEATURE:
<221> NAME/KEY: SITE
<222> LOCATION: (189)..(189)
<223> OTHER INFORMATION: Xaa is Glu, Asp, Arg or Gly
<220> FEATURE:
<221> NAME/KEY: SITE
<222> LOCATION: (190)..(190)
<223> OTHER INFORMATION: Xaa is Val, Phe, Met, Leu or Ile
<220> FEATURE:
<221> NAME/KEY: SITE
<222> LOCATION: (191)..(191)
<223> OTHER INFORMATION: Xaa is Gly, Lys, Arg, Leu, Val or Glu
<220> FEATURE:
<221> NAME/KEY: SITE
<222> LOCATION: (192)..(192)
<223> OTHER INFORMATION: Xaa is Lys, Asn, Asp, Leu, His or Ser
<220> FEATURE:
<221> NAME/KEY: SITE
<222> LOCATION: (193)..(193)
<223> OTHER INFORMATION: Xaa is Lys, Leu, Cys or absent
<220> FEATURE:
<221> NAME/KEY: SITE
<222> LOCATION: (194)..(194)
<223> OTHER INFORMATION: Xaa is Lys, Ser, Ile, Tyr, Met or Phe
<220> FEATURE:
<221> NAME/KEY: SITE
<222> LOCATION: (196)..(196)
<223> OTHER INFORMATION: Xaa is Lys, Leu, Cys, His, Asp, Gln, or Asn
```

```
<220> FEATURE:
<221> NAME/KEY: SITE
<222> LOCATION: (197)..(197)
<223> OTHER INFORMATION: Xaa is Asn or Tyr
<220> FEATURE:
<221> NAME/KEY: SITE
<222> LOCATION: (198)..(198)
<223> OTHER INFORMATION: Xaa is Asp, Lys, Thr, Glu, Cys or absent
<220> FEATURE:
<221> NAME/KEY: SITE
<222> LOCATION: (199)..(199)
<223> OTHER INFORMATION: Xaa is Glu, Val, Arg or absent
<220> FEATURE:
<221> NAME/KEY: SITE
<222> LOCATION: (200)..(200)
<223> OTHER INFORMATION: Xaa is Ile, Phe, Leu or absent
<220> FEATURE:
<221> NAME/KEY: SITE
<222> LOCATION: (201)..(201)
<223> OTHER INFORMATION: Xaa is Val, Gln, Glu, Leu or absent
<220> FEATURE:
<221> NAME/KEY: SITE
<222> LOCATION: (202)..(202)
<223> OTHER INFORMATION: Xaa is Phe or absent

<400> SEQUENCE: 316

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Gly Xaa His Leu Gly Gly Xaa Arg
        35                  40              45

Xaa Pro Asp Gly Xaa Xaa Xaa Xaa Xaa Xaa Xaa Xaa Xaa Xaa
65              70                  75                  80

Xaa Xaa Xaa Xaa Gly Xaa Ile Xaa Asp Thr Lys Xaa Tyr Xaa Xaa Gly
                85              90                  95

Tyr Xaa Leu Pro Ile Xaa Gln Xaa Asp Glu Met Xaa Arg Tyr Xaa Xaa
            100                 105                 110

Glu Asn Xaa Xaa Arg Xaa Xaa Xaa Xaa Asn Xaa Asn Xaa Trp Trp Xaa
        115                 120                 125

Xaa Xaa Xaa Xaa Xaa Xaa Xaa Xaa Xaa Xaa Xaa Phe Xaa Xaa Xaa
        130                 135                 140

Xaa Phe Xaa Gly Xaa Xaa Xaa Xaa Xaa Xaa Arg Xaa Xaa Xaa Xaa
145             150                 155                 160

Xaa Xaa Xaa Xaa Gly Xaa Xaa Xaa Xaa Xaa Xaa Leu Leu Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Phe Xaa Xaa Xaa Xaa Xaa Xaa Xaa
            195                 200

<210> SEQ ID NO 317
<211> LENGTH: 202
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (1)..(1)
<223> OTHER INFORMATION: Xaa is Phe, Gln, Asn or absent
<220> FEATURE:
<221> NAME/KEY: SITE
```

```
<222> LOCATION: (2)..(2)
<223> OTHER INFORMATION: Xaa is Leu, Ile, Thr, Ser or absent
<220> FEATURE:
<221> NAME/KEY: SITE
<222> LOCATION: (3)..(3)
<223> OTHER INFORMATION: Xaa is Val, Ile, Gly, Ala, Glu, Thr or absent
<220> FEATURE:
<221> NAME/KEY: SITE
<222> LOCATION: (4)..(4)
<223> OTHER INFORMATION: Xaa is Lys, Cys or absent
<220> FEATURE:
<221> NAME/KEY: SITE
<222> LOCATION: (5)..(5)
<223> OTHER INFORMATION: Xaa is Gly, Ser or absent
<220> FEATURE:
<221> NAME/KEY: SITE
<222> LOCATION: (6)..(6)
<223> OTHER INFORMATION: Xaa is Ala, Ser, Glu, Asp or absent
<220> FEATURE:
<221> NAME/KEY: SITE
<222> LOCATION: (7)..(7)
<223> OTHER INFORMATION: Xaa is Met, Ile, Val, Gln, Phe, Leu or absent
<220> FEATURE:
<221> NAME/KEY: SITE
<222> LOCATION: (8)..(8)
<223> OTHER INFORMATION: Xaa is Glu, Ser, Thr or absent
<220> FEATURE:
<221> NAME/KEY: SITE
<222> LOCATION: (9)..(9)
<223> OTHER INFORMATION: Xaa is Ile, Met, Glu, Thr, Gln or absent
<220> FEATURE:
<221> NAME/KEY: SITE
<222> LOCATION: (10)..(10)
<223> OTHER INFORMATION: Xaa is Lys, Ser, Leu, Ile, Thr, Glu or absent
<220> FEATURE:
<221> NAME/KEY: SITE
<222> LOCATION: (11)..(11)
<223> OTHER INFORMATION: Xaa is Lys or absent
<220> FEATURE:
<221> NAME/KEY: SITE
<222> LOCATION: (12)..(12)
<223> OTHER INFORMATION: Xaa is Ser, Ala, Glu, Asp or absent
<220> FEATURE:
<221> NAME/KEY: SITE
<222> LOCATION: (13)..(13)
<223> OTHER INFORMATION: Xaa is Glu, Asn, Gln, Lys or absent
<220> FEATURE:
<221> NAME/KEY: SITE
<222> LOCATION: (14)..(14)
<223> OTHER INFORMATION: Xaa is Leu, Met, Val or absent
<220> FEATURE:
<221> NAME/KEY: SITE
<222> LOCATION: (15)..(15)
<223> OTHER INFORMATION: Xaa is Arg or absent
<220> FEATURE:
<221> NAME/KEY: SITE
<222> LOCATION: (16)..(16)
<223> OTHER INFORMATION: Xaa is His, Asp, Thr, Gly, Glu, Asn or absent
<220> FEATURE:
<221> NAME/KEY: SITE
<222> LOCATION: (17)..(17)
<223> OTHER INFORMATION: Xaa is Lys, Asn, Gln, Glu, Ala or absent
<220> FEATURE:
<221> NAME/KEY: SITE
<222> LOCATION: (18)..(18)
<223> OTHER INFORMATION: Xaa is Leu or absent
<220> FEATURE:
<221> NAME/KEY: SITE
<222> LOCATION: (19)..(19)
<223> OTHER INFORMATION: Xaa is Arg, Gln, Asn, Thr, Asp or absent
<220> FEATURE:
<221> NAME/KEY: SITE
<222> LOCATION: (20)..(20)
<223> OTHER INFORMATION: Xaa is His, Met, Val, Asn, Thr or absent
<220> FEATURE:
<221> NAME/KEY: SITE
<222> LOCATION: (21)..(21)
<223> OTHER INFORMATION: Xaa is Val, Lei, Ile or absent
<220> FEATURE:
```

```
<221> NAME/KEY: SITE
<222> LOCATION: (22)..(22)
<223> OTHER INFORMATION: Xaa is Pro, Ser or absent
<220> FEATURE:
<221> NAME/KEY: SITE
<222> LOCATION: (23)..(23)
<223> OTHER INFORMATION: Xaa is His or absent
<220> FEATURE:
<221> NAME/KEY: SITE
<222> LOCATION: (24)..(24)
<223> OTHER INFORMATION: Xaa is Glu, Asp or absent
<220> FEATURE:
<221> NAME/KEY: SITE
<222> LOCATION: (25)..(25)
<223> OTHER INFORMATION: Xaa is Tyr or absent
<220> FEATURE:
<221> NAME/KEY: SITE
<222> LOCATION: (26)..(26)
<223> OTHER INFORMATION: Xaa is Ile, Leu or absent
<220> FEATURE:
<221> NAME/KEY: SITE
<222> LOCATION: (27)..(27)
<223> OTHER INFORMATION: Xaa is Glu, Gln, Gly, Ser, Ala or absent
<220> FEATURE:
<221> NAME/KEY: SITE
<222> LOCATION: (28)..(28)
<223> OTHER INFORMATION: Xaa is Leu or absent
<220> FEATURE:
<221> NAME/KEY: SITE
<222> LOCATION: (29)..(29)
<223> OTHER INFORMATION: Xaa is Ile, Val, Leu or absent
<220> FEATURE:
<221> NAME/KEY: SITE
<222> LOCATION: (30)..(30)
<223> OTHER INFORMATION: Xaa is Glu, Asp or absent
<220> FEATURE:
<221> NAME/KEY: SITE
<222> LOCATION: (31)..(31)
<223> OTHER INFORMATION: Xaa is Ile, Leu or absent
<220> FEATURE:
<221> NAME/KEY: SITE
<222> LOCATION: (32)..(32)
<223> OTHER INFORMATION: Xaa is Ala, Ser or absent
<220> FEATURE:
<221> NAME/KEY: SITE
<222> LOCATION: (33)..(33)
<223> OTHER INFORMATION: Xaa is Gln, Tyr, Phe or absent
<220> FEATURE:
<221> NAME/KEY: SITE
<222> LOCATION: (34)..(34)
<223> OTHER INFORMATION: Xaa is Asp or absent
<220> FEATURE:
<221> NAME/KEY: SITE
<222> LOCATION: (35)..(35)
<223> OTHER INFORMATION: Xaa is Ser, Pro or absent
<220> FEATURE:
<221> NAME/KEY: SITE
<222> LOCATION: (36)..(36)
<223> OTHER INFORMATION: Xaa is Lys, Tyr, Gln, Thr or absent
<220> FEATURE:
<221> NAME/KEY: SITE
<222> LOCATION: (37)..(37)
<223> OTHER INFORMATION: Xaa is Gln or absent
<220> FEATURE:
<221> NAME/KEY: SITE
<222> LOCATION: (38)..(38)
<223> OTHER INFORMATION: Xaa is Asn or absent
<220> FEATURE:
<221> NAME/KEY: SITE
<222> LOCATION: (39)..(39)
<223> OTHER INFORMATION: Xaa is Arg or absent
<220> FEATURE:
<221> NAME/KEY: SITE
<222> LOCATION: (40)..(40)
<223> OTHER INFORMATION: Xaa is Leu, Ile or absent
<220> FEATURE:
<221> NAME/KEY: SITE
<222> LOCATION: (41)..(41)
<223> OTHER INFORMATION: Xaa is Leu, Phe or absent
```

```
<220> FEATURE:
<221> NAME/KEY: SITE
<222> LOCATION: (42)..(42)
<223> OTHER INFORMATION: Xaa is Glu or absent
<220> FEATURE:
<221> NAME/KEY: SITE
<222> LOCATION: (43)..(43)
<223> OTHER INFORMATION: Xaa is Phe, Met, Leu or absent
<220> FEATURE:
<221> NAME/KEY: SITE
<222> LOCATION: (45)..(45)
<223> OTHER INFORMATION: Xaa is Val, Thr, or Ile
<220> FEATURE:
<221> NAME/KEY: SITE
<222> LOCATION: (46)..(46)
<223> OTHER INFORMATION: Xaa is Val, Met, Leu or Ile
<220> FEATURE:
<221> NAME/KEY: SITE
<222> LOCATION: (47)..(47)
<223> OTHER INFORMATION: Xaa is Glu, Asp or Gln
<220> FEATURE:
<221> NAME/KEY: SITE
<222> LOCATION: (48)..(48)
<223> OTHER INFORMATION: Xaa is Phe or Leu
<220> FEATURE:
<221> NAME/KEY: SITE
<222> LOCATION: (49)..(49)
<223> OTHER INFORMATION: Xaa is Phe or Leu
<220> FEATURE:
<221> NAME/KEY: SITE
<222> LOCATION: (50)..(50)
<223> OTHER INFORMATION: Xaa is Lys, Ile, Thr or Val
<220> FEATURE:
<221> NAME/KEY: SITE
<222> LOCATION: (51)..(51)
<223> OTHER INFORMATION: Xaa is Lys, Asn, or Glu
<220> FEATURE:
<221> NAME/KEY: SITE
<222> LOCATION: (52)..(52)
<223> OTHER INFORMATION: Xaa is Ile or Glu
<220> FEATURE:
<221> NAME/KEY: SITE
<222> LOCATION: (53)..(53)
<223> OTHER INFORMATION: Xaa is Tyr, Phe or Cys
<220> FEATURE:
<221> NAME/KEY: SITE
<222> LOCATION: (54)..(54)
<223> OTHER INFORMATION: Xaa is Gly or Asn
<220> FEATURE:
<221> NAME/KEY: SITE
<222> LOCATION: (55)..(55)
<223> OTHER INFORMATION: Xaa is Tyr or Phe
<220> FEATURE:
<221> NAME/KEY: SITE
<222> LOCATION: (56)..(56)
<223> OTHER INFORMATION: Xaa is Arg, Ser, Asn, Glu, Lys or Gln
<220> FEATURE:
<221> NAME/KEY: SITE
<222> LOCATION: (58)..(58)
<223> OTHER INFORMATION: Xaa is Lys, Ser, Leu, Val or Thr
<220> FEATURE:
<221> NAME/KEY: SITE
<222> LOCATION: (63)..(63)
<223> OTHER INFORMATION: Xaa is Ser or Ala
<220> FEATURE:
<221> NAME/KEY: SITE
<222> LOCATION: (65)..(65)
<223> OTHER INFORMATION: Xaa is Lys or Arg
<220> FEATURE:
<221> NAME/KEY: SITE
<222> LOCATION: (69)..(69)
<223> OTHER INFORMATION: Xaa is Ala, Ile or Val
<220> FEATURE:
<221> NAME/KEY: SITE
<222> LOCATION: (70)..(70)
<223> OTHER INFORMATION: Xaa is Leu, Met, Val, Ile or Cys
<220> FEATURE:
<221> NAME/KEY: SITE
<222> LOCATION: (71)..(71)
```

```
<223> OTHER INFORMATION: Xaa is Phe or Tyr
<220> FEATURE:
<221> NAME/KEY: SITE
<222> LOCATION: (72)..(72)
<223> OTHER INFORMATION: Xaa is Thr, Ala or Ser
<220> FEATURE:
<221> NAME/KEY: SITE
<222> LOCATION: (73)..(73)
<223> OTHER INFORMATION: Xaa is Lys, Glu or absent
<220> FEATURE:
<221> NAME/KEY: SITE
<222> LOCATION: (74)..(74)
<223> OTHER INFORMATION: Xaa is Glu, Ala or absent
<220> FEATURE:
<221> NAME/KEY: SITE
<222> LOCATION: (75)..(75)
<223> OTHER INFORMATION: Xaa is Glu, Ala or absent
<220> FEATURE:
<221> NAME/KEY: SITE
<222> LOCATION: (76)..(76)
<223> OTHER INFORMATION: Xaa is Asn, Lys or absent
<220> FEATURE:
<221> NAME/KEY: SITE
<222> LOCATION: (77)..(77)
<223> OTHER INFORMATION: Xaa is Glu, Ser or absent
<220> FEATURE:
<221> NAME/KEY: SITE
<222> LOCATION: (78)..(78)
<223> OTHER INFORMATION: Xaa is Asp, Glu, Gln, Ala or absent
<220> FEATURE:
<221> NAME/KEY: SITE
<222> LOCATION: (79)..(79)
<223> OTHER INFORMATION: Xaa is Gly, Val, Lys, Asn or absent
<220> FEATURE:
<221> NAME/KEY: SITE
<222> LOCATION: (80)..(80)
<223> OTHER INFORMATION: Xaa is Leu, Gly, Glu, Ser or absent
<220> FEATURE:
<221> NAME/KEY: SITE
<222> LOCATION: (81)..(81)
<223> OTHER INFORMATION: Xaa is Val, Ser, Lys, Thr, Glu or absent
<220> FEATURE:
<221> NAME/KEY: SITE
<222> LOCATION: (82)..(82)
<223> OTHER INFORMATION: Xaa is Leu, His, Lys, Gly Tyr, Asp or Ala
<220> FEATURE:
<221> NAME/KEY: SITE
<222> LOCATION: (83)..(83)
<223> OTHER INFORMATION: Xaa is Asn, Gly or Asp
<220> FEATURE:
<221> NAME/KEY: SITE
<222> LOCATION: (84)..(84)
<223> OTHER INFORMATION: Xaa is His, Phe or Tyr
<220> FEATURE:
<221> NAME/KEY: SITE
<222> LOCATION: (86)..(86)
<223> OTHER INFORMATION: Xaa is Ile or Val
<220> FEATURE:
<221> NAME/KEY: SITE
<222> LOCATION: (88)..(88)
<223> OTHER INFORMATION: Xaa is Leu, Val or Ile
<220> FEATURE:
<221> NAME/KEY: SITE
<222> LOCATION: (92)..(92)
<223> OTHER INFORMATION: Xaa is Ala or Ser
<220> FEATURE:
<221> NAME/KEY: SITE
<222> LOCATION: (94)..(94)
<223> OTHER INFORMATION: Xaa is Lys or Ser
<220> FEATURE:
<221> NAME/KEY: SITE
<222> LOCATION: (95)..(95)
<223> OTHER INFORMATION: Xaa is Asp, Gly, Lys, Ser or Asn
<220> FEATURE:
<221> NAME/KEY: SITE
<222> LOCATION: (98)..(98)
<223> OTHER INFORMATION: Xaa is Arg, Asn, Ser or Gly
<220> FEATURE:
<221> NAME/KEY: SITE
```

```
<222> LOCATION: (102)..(102)
<223> OTHER INFORMATION: Xaa is Ser, Ala or Gly
<220> FEATURE:
<221> NAME/KEY: SITE
<222> LOCATION: (104)..(104)
<223> OTHER INFORMATION: Xaa is Ala, Ile or Val
<220> FEATURE:
<221> NAME/KEY: SITE
<222> LOCATION: (108)..(108)
<223> OTHER INFORMATION: Xaa is Gln, Glu, Ile or Val
<220> FEATURE:
<221> NAME/KEY: SITE
<222> LOCATION: (111)..(111)
<223> OTHER INFORMATION: Xaa is Val or Ile
<220> FEATURE:
<221> NAME/KEY: SITE
<222> LOCATION: (112)..(112)
<223> OTHER INFORMATION: Xaa is Asp, Arg, Gly, Ile or Glu
<220> FEATURE:
<221> NAME/KEY: SITE
<222> LOCATION: (115)..(115)
<223> OTHER INFORMATION: Xaa is Asn, Ile or Gln
<220> FEATURE:
<221> NAME/KEY: SITE
<222> LOCATION: (116)..(116)
<223> OTHER INFORMATION: Xaa is Lys, Asp, Thr, Glu or Lys
<220> FEATURE:
<221> NAME/KEY: SITE
<222> LOCATION: (118)..(118)
<223> OTHER INFORMATION: Xaa is Ser, Asn, Asp or Glu
<220> FEATURE:
<221> NAME/KEY: SITE
<222> LOCATION: (119)..(119)
<223> OTHER INFORMATION: Xaa is Gln, Glu, Ile, Lys or Ala
<220> FEATURE:
<221> NAME/KEY: SITE
<222> LOCATION: (120)..(120)
<223> OTHER INFORMATION: Xaa is Val, His, Arg, Lys, Leu or Glu
<220> FEATURE:
<221> NAME/KEY: SITE
<222> LOCATION: (121)..(121)
<223> OTHER INFORMATION: Xaa is Ile, Val or Arg
<220> FEATURE:
<221> NAME/KEY: SITE
<222> LOCATION: (123)..(123)
<223> OTHER INFORMATION: Xaa is Pro, Ser, Thr or Arg
<220> FEATURE:
<221> NAME/KEY: SITE
<222> LOCATION: (125)..(125)
<223> OTHER INFORMATION: Xaa is Glu, Arg, Cys, Gln or Lys
<220> FEATURE:
<221> NAME/KEY: SITE
<222> LOCATION: (128)..(128)
<223> OTHER INFORMATION: Xaa is Glu, Asn or Lys
<220> FEATURE:
<221> NAME/KEY: SITE
<222> LOCATION: (129)..(129)
<223> OTHER INFORMATION: Xaa is Ile, Val, Asn, Glu or Ala
<220> FEATURE:
<221> NAME/KEY: SITE
<222> LOCATION: (130)..(130)
<223> OTHER INFORMATION: Xaa is Tyr or Phe
<220> FEATURE:
<221> NAME/KEY: SITE
<222> LOCATION: (131)..(131)
<223> OTHER INFORMATION: Xaa is Pro, Gly or Glu
<220> FEATURE:
<221> NAME/KEY: SITE
<222> LOCATION: (132)..(132)
<223> OTHER INFORMATION: Xaa is Thr, Glu, Ser, Asp, Lys or Asn
<220> FEATURE:
<221> NAME/KEY: SITE
<222> LOCATION: (133)..(133)
<223> OTHER INFORMATION: Xaa is Ser, Asp, Lys, Gly, Asn or Thr
<220> FEATURE:
<221> NAME/KEY: SITE
<222> LOCATION: (134)..(134)
<223> OTHER INFORMATION: Xaa is Ile, Thr, Val or Leu
<220> FEATURE:
```

```
<221> NAME/KEY: SITE
<222> LOCATION: (135)..(135)
<223> OTHER INFORMATION: Xaa is Thr, Asn, Gly or Asp
<220> FEATURE:
<221> NAME/KEY: SITE
<222> LOCATION: (136)..(136)
<223> OTHER INFORMATION: Xaa is Asp, Glu, Thr, Lys or Ile
<220> FEATURE:
<221> NAME/KEY: SITE
<222> LOCATION: (137)..(137)
<223> OTHER INFORMATION: Xaa is Phe or Tyr
<220> FEATURE:
<221> NAME/KEY: SITE
<222> LOCATION: (138)..(138)
<223> OTHER INFORMATION: Xaa is Lys or Tyr
<220> FEATURE:
<221> NAME/KEY: SITE
<222> LOCATION: (139)..(139)
<223> OTHER INFORMATION: Xaa is Phe or Tyr
<220> FEATURE:
<221> NAME/KEY: SITE
<222> LOCATION: (140)..(140)
<223> OTHER INFORMATION: Xaa is Leu, Ser or Met
<220> FEATURE:
<221> NAME/KEY: SITE
<222> LOCATION: (142)..(142)
<223> OTHER INFORMATION: Xaa is Val or Ile
<220> FEATURE:
<221> NAME/KEY: SITE
<222> LOCATION: (143)..(143)
<223> OTHER INFORMATION: Xaa is Ser or Ala
<220> FEATURE:
<221> NAME/KEY: SITE
<222> LOCATION: (144)..(144)
<223> OTHER INFORMATION: Xaa is Gly or Ala
<220> FEATURE:
<221> NAME/KEY: SITE
<222> LOCATION: (145)..(145)
<223> OTHER INFORMATION: Xaa is Gly or Ala
<220> FEATURE:
<221> NAME/KEY: SITE
<222> LOCATION: (147)..(147)
<223> OTHER INFORMATION: Xaa is Gln, Lys, Thr, Asn or Ile
<220> FEATURE:
<221> NAME/KEY: SITE
<222> LOCATION: (149)..(149)
<223> OTHER INFORMATION: Xaa is Asp, Asn or Lys
<220> FEATURE:
<221> NAME/KEY: SITE
<222> LOCATION: (150)..(150)
<223> OTHER INFORMATION: Xaa is Tyr, Phe, Ile or Val
<220> FEATURE:
<221> NAME/KEY: SITE
<222> LOCATION: (151)..(151)
<223> OTHER INFORMATION: Xaa is Arg, Glu, Lys, Gln or Phe
<220> FEATURE:
<221> NAME/KEY: SITE
<222> LOCATION: (152)..(152)
<223> OTHER INFORMATION: Xaa is Lys, Glu, Ala or Asn
<220> FEATURE:
<221> NAME/KEY: SITE
<222> LOCATION: (153)..(153)
<223> OTHER INFORMATION: Xaa is Gln or Lys
<220> FEATURE:
<221> NAME/KEY: SITE
<222> LOCATION: (154)..(154)
<223> OTHER INFORMATION: Xaa is Leu or Ile
<220> FEATURE:
<221> NAME/KEY: SITE
<222> LOCATION: (155)..(155)
<223> OTHER INFORMATION: Xaa is Glu, Asp, Asn or Gln
<220> FEATURE:
<221> NAME/KEY: SITE
<222> LOCATION: (157)..(157)
<223> OTHER INFORMATION: Xaa is Val, Ile or Leu
<220> FEATURE:
<221> NAME/KEY: SITE
<222> LOCATION: (158)..(158)
<223> OTHER INFORMATION: Xaa is Ser, Asn, Phe, Thr or Gln
```

```
<220> FEATURE:
<221> NAME/KEY: SITE
<222> LOCATION: (159)..(159)
<223> OTHER INFORMATION: Xaa is His, Ile, Cys or Arg
<220> FEATURE:
<221> NAME/KEY: SITE
<222> LOCATION: (160)..(160)
<223> OTHER INFORMATION: Xaa is Leu, Asp, Asn, Ser, or Phe
<220> FEATURE:
<221> NAME/KEY: SITE
<222> LOCATION: (161)..(161)
<223> OTHER INFORMATION: Xaa is Thr or Lys
<220> FEATURE:
<221> NAME/KEY: SITE
<222> LOCATION: (162)..(162)
<223> OTHER INFORMATION: Xaa is Lys, Gly or Asn
<220> FEATURE:
<221> NAME/KEY: SITE
<222> LOCATION: (163)..(163)
<223> OTHER INFORMATION: Xaa is Cys, Val or Ile
<220> FEATURE:
<221> NAME/KEY: SITE
<222> LOCATION: (164)..(164)
<223> OTHER INFORMATION: Xaa is Gln, Leu, Lys or Tyr
<220> FEATURE:
<221> NAME/KEY: SITE
<222> LOCATION: (166)..(166)
<223> OTHER INFORMATION: Xaa is Ala, Gly or Asn
<220> FEATURE:
<221> NAME/KEY: SITE
<222> LOCATION: (167)..(167)
<223> OTHER INFORMATION: Xaa is Val or Ala
<220> FEATURE:
<221> NAME/KEY: SITE
<222> LOCATION: (168)..(168)
<223> OTHER INFORMATION: Xaa is Met, Leu, Ile, Val or Ala
<220> FEATURE:
<221> NAME/KEY: SITE
<222> LOCATION: (169)..(169)
<223> OTHER INFORMATION: Xaa is Ser, Thr or Asp
<220> FEATURE:
<221> NAME/KEY: SITE
<222> LOCATION: (170)..(170)
<223> OTHER INFORMATION: Xaa is Val or Ile
<220> FEATURE:
<221> NAME/KEY: SITE
<222> LOCATION: (171)..(171)
<223> OTHER INFORMATION: Xaa is Glu, Gln, Lys, Ser or Ile
<220> FEATURE:
<221> NAME/KEY: SITE
<222> LOCATION: (172)..(172)
<223> OTHER INFORMATION: Xaa is Gln, His or Thr
<220> FEATURE:
<221> NAME/KEY: SITE
<222> LOCATION: (175)..(175)
<223> OTHER INFORMATION: Xaa is Leu, Arg or Tyr
<220> FEATURE:
<221> NAME/KEY: SITE
<222> LOCATION: (176)..(176)
<223> OTHER INFORMATION: Xaa is Gly, Ile, Leu or Thr
<220> FEATURE:
<221> NAME/KEY: SITE
<222> LOCATION: (177)..(177)
<223> OTHER INFORMATION: Xaa is Gly, Ala or Val
<220> FEATURE:
<221> NAME/KEY: SITE
<222> LOCATION: (178)..(178)
<223> OTHER INFORMATION: Xaa is Glu, Asn or Asp
<220> FEATURE:
<221> NAME/KEY: SITE
<222> LOCATION: (179)..(179)
<223> OTHER INFORMATION: Xaa is Lys, Tyr, Asp, Glu, Ala or Arg
<220> FEATURE:
<221> NAME/KEY: SITE
<222> LOCATION: (180)..(180)
<223> OTHER INFORMATION: Xaa is Ile, Phe, Tyr or Cys
<220> FEATURE:
<221> NAME/KEY: SITE
<222> LOCATION: (181)..(181)
```

```
<223> OTHER INFORMATION: Xaa is Lys or Arg
<220> FEATURE:
<221> NAME/KEY: SITE
<222> LOCATION: (182)..(182)
<223> OTHER INFORMATION: Xaa is Glu, Arg, Ala, Gly or Thr
<220> FEATURE:
<221> NAME/KEY: SITE
<222> LOCATION: (183)..(183)
<223> OTHER INFORMATION: Xaa is Gly or Asn
<220> FEATURE:
<221> NAME/KEY: SITE
<222> LOCATION: (184)..(184)
<223> OTHER INFORMATION: Xaa is Ser, Ile, Lys, Arg or Glu
<220> FEATURE:
<221> NAME/KEY: SITE
<222> LOCATION: (185)..(185)
<223> OTHER INFORMATION: Xaa is Leu, Ile or Met
<220> FEATURE:
<221> NAME/KEY: SITE
<222> LOCATION: (186)..(186)
<223> OTHER INFORMATION: Xaa is Thr, Ser, Asp or Lys
<220> FEATURE:
<221> NAME/KEY: SITE
<222> LOCATION: (187)..(187)
<223> OTHER INFORMATION: Xaa is Leu, His, Tyr, Arg or Thr
<220> FEATURE:
<221> NAME/KEY: SITE
<222> LOCATION: (188)..(188)
<223> OTHER INFORMATION: Xaa is Glu, Tyr, Ile, Met or Ala
<220> FEATURE:
<221> NAME/KEY: SITE
<222> LOCATION: (189)..(189)
<223> OTHER INFORMATION: Xaa is Glu, Asp, Arg or Gly
<220> FEATURE:
<221> NAME/KEY: SITE
<222> LOCATION: (190)..(190)
<223> OTHER INFORMATION: Xaa is Val, Phe, Met, Leu or Ile
<220> FEATURE:
<221> NAME/KEY: SITE
<222> LOCATION: (191)..(191)
<223> OTHER INFORMATION: Xaa is Gly, Lys, Arg, Leu, Val or Glu
<220> FEATURE:
<221> NAME/KEY: SITE
<222> LOCATION: (192)..(192)
<223> OTHER INFORMATION: Xaa is Lys, Asn, Asp, Leu, His or Ser
<220> FEATURE:
<221> NAME/KEY: SITE
<222> LOCATION: (193)..(193)
<223> OTHER INFORMATION: Xaa is Lys, Leu, Cys or absent
<220> FEATURE:
<221> NAME/KEY: SITE
<222> LOCATION: (194)..(194)
<223> OTHER INFORMATION: Xaa is Lys, Ser, Ile, Tyr, Met or Phe
<220> FEATURE:
<221> NAME/KEY: SITE
<222> LOCATION: (196)..(196)
<223> OTHER INFORMATION: Xaa is Lys, Leu, Cys, His, Asp, Gln, or Asn
<220> FEATURE:
<221> NAME/KEY: SITE
<222> LOCATION: (197)..(197)
<223> OTHER INFORMATION: Xaa is Asn or Tyr
<220> FEATURE:
<221> NAME/KEY: SITE
<222> LOCATION: (198)..(198)
<223> OTHER INFORMATION: Xaa is Asp, Lys, Thr, Glu, Cys or absent
<220> FEATURE:
<221> NAME/KEY: SITE
<222> LOCATION: (199)..(199)
<223> OTHER INFORMATION: Xaa is Glu, Val, Arg or absent
<220> FEATURE:
<221> NAME/KEY: SITE
<222> LOCATION: (200)..(200)
<223> OTHER INFORMATION: Xaa is Ile, Phe, Leu or absent
<220> FEATURE:
<221> NAME/KEY: SITE
<222> LOCATION: (201)..(201)
<223> OTHER INFORMATION: Xaa is Val, Gln, Glu, Leu or absent
<220> FEATURE:
<221> NAME/KEY: SITE
```

<222> LOCATION: (202)..(202)
<223> OTHER INFORMATION: Xaa is Phe or absent

<400> SEQUENCE: 317

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Lys Xaa Xaa Xaa Xaa
            35                  40                  45

Xaa Xaa Xaa Xaa Xaa Xaa Xaa Xaa Gly Xaa His Leu Gly Gly Xaa Arg
50                      55                  60

Xaa Pro Asp Gly Xaa Xaa Xaa Xaa Xaa Xaa Xaa Xaa Xaa Xaa Xaa Xaa
65                  70                  75                  80

Xaa Xaa Xaa Xaa Gly Xaa Ile Xaa Asp Thr Lys Xaa Tyr Xaa Xaa Gly
                85                  90                  95

Tyr Xaa Leu Pro Ile Xaa Gln Xaa Asp Glu Met Xaa Arg Tyr Xaa Xaa
        100                 105                 110

Glu Asn Xaa Xaa Arg Xaa Xaa Xaa Xaa Asn Xaa Asn Xaa Trp Trp Xaa
        115                 120                 125

Xaa Xaa Xaa Xaa Xaa Xaa Xaa Xaa Xaa Xaa Xaa Phe Xaa Xaa Xaa
    130                 135                 140

Xaa Phe Xaa Gly Xaa Xaa Xaa Xaa Xaa Xaa Xaa Arg Xaa Xaa Xaa Xaa
145                 150                 155                 160

Xaa Xaa Xaa Xaa Gly Xaa Xaa Xaa Xaa Xaa Xaa Leu Leu Xaa Xaa
                165                 170                 175

Xaa Xaa Xaa Xaa Xaa Xaa Xaa Xaa Xaa Xaa Xaa Xaa Xaa Xaa Xaa
        180                 185                 190

Xaa Xaa Phe Xaa Xaa Xaa Xaa Xaa Xaa Xaa
        195                 200

<210> SEQ ID NO 318
<211> LENGTH: 196
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (1)..(1)
<223> OTHER INFORMATION: Xaa is Phe, Gln, Asn, Asp or absent
<220> FEATURE:
<221> NAME/KEY: SITE
<222> LOCATION: (7)..(7)
<223> OTHER INFORMATION: Xaa is Met, Ile, Val, Gln, Phe, Leu or absent
<220> FEATURE:
<221> NAME/KEY: SITE
<222> LOCATION: (10)..(10)
<223> OTHER INFORMATION: Xaa is Lys, Ser, Leu, Ile, Thr, Glu or absent
<220> FEATURE:
<221> NAME/KEY: SITE
<222> LOCATION: (19)..(19)
<223> OTHER INFORMATION: Xaa is Arg, Gln, Asn, Thr, Asp or absent
<220> FEATURE:
<221> NAME/KEY: SITE
<222> LOCATION: (27)..(27)
<223> OTHER INFORMATION: Xaa is Glu, Gln, Gly, Ser, Ala, Tyr or absent
<220> FEATURE:
<221> NAME/KEY: SITE
<222> LOCATION: (29)..(29)
<223> OTHER INFORMATION: Xaa is Ile, Val, Leu or absent
<220> FEATURE:
<221> NAME/KEY: SITE
<222> LOCATION: (46)..(46)
<223> OTHER INFORMATION: Xaa is Val, Met, Leu or Ile

```
<220> FEATURE:
<221> NAME/KEY: SITE
<222> LOCATION: (56)..(56)
<223> OTHER INFORMATION: Xaa is Arg, Ser, Asn, Glu, Lys or Gln
<220> FEATURE:
<221> NAME/KEY: SITE
<222> LOCATION: (70)..(70)
<223> OTHER INFORMATION: Xaa is Leu, Met, Val, Ile or Cys
<220> FEATURE:
<221> NAME/KEY: SITE
<222> LOCATION: (77)..(77)
<223> OTHER INFORMATION: Xaa is Leu, His, Lys, Glu, Tyr, Asp or Ala
<220> FEATURE:
<221> NAME/KEY: SITE
<222> LOCATION: (114)..(114)
<223> OTHER INFORMATION: Xaa is Gln, Glu, Ile, Lys or Ala
<220> FEATURE:
<221> NAME/KEY: SITE
<222> LOCATION: (115)..(115)
<223> OTHER INFORMATION: Xaa is Val, His, Arg, Lys, Leu or Glu
<220> FEATURE:
<221> NAME/KEY: SITE
<222> LOCATION: (127)..(127)
<223> OTHER INFORMATION: Xaa is Thr, Glu, Ser, Asp, Lys or Asn
<220> FEATURE:
<221> NAME/KEY: SITE
<222> LOCATION: (145)..(145)
<223> OTHER INFORMATION: Xaa is Tyr, Phe, Ile or Val
<220> FEATURE:
<221> NAME/KEY: SITE
<222> LOCATION: (155)..(155)
<223> OTHER INFORMATION: Xaa is Leu, Asp, Asn, Ser or Phe
<220> FEATURE:
<221> NAME/KEY: SITE
<222> LOCATION: (157)..(157)
<223> OTHER INFORMATION: Xaa is Lys, Gly or Asn
<220> FEATURE:
<221> NAME/KEY: SITE
<222> LOCATION: (166)..(166)
<223> OTHER INFORMATION: Xaa is Glu, Gln, Lys, Ser or Ile
<220> FEATURE:
<221> NAME/KEY: SITE
<222> LOCATION: (181)..(181)
<223> OTHER INFORMATION: Xaa is Thr, Ser, Asp or Lys
<220> FEATURE:
<221> NAME/KEY: SITE
<222> LOCATION: (186)..(186)
<223> OTHER INFORMATION: Xaa is Gly, Lys, Arg, Leu, Val or Glu
<220> FEATURE:
<221> NAME/KEY: SITE
<222> LOCATION: (195)..(195)
<223> OTHER INFORMATION: Xaa is Val, Gln, Glu, Leu or absent

<400> SEQUENCE: 318

Xaa Leu Val Lys Ser Ser Xaa Glu Glu Xaa Lys Glu Glu Leu Arg Glu
1               5                   10                  15

Lys Leu Xaa His Leu Ser His Glu Tyr Leu Xaa Leu Xaa Asp Leu Ala
            20                  25                  30

Tyr Asp Ser Lys Gln Asn Arg Leu Phe Glu Met Lys Val Xaa Glu Leu
        35                  40                  45

Leu Ile Asn Glu Cys Gly Tyr Xaa Gly Leu His Leu Gly Gly Ser Arg
50                  55                  60

Lys Pro Asp Gly Ile Xaa Tyr Thr Glu Gly Leu Lys Xaa Asn Tyr Gly
65                  70                  75                  80

Ile Ile Ile Asp Thr Lys Ala Tyr Ser Asp Gly Tyr Asn Leu Pro Ile
                85                  90                  95

Ser Gln Ala Asp Glu Met Glu Arg Tyr Ile Arg Glu Asn Asn Thr Arg
            100                 105                 110

Asn Xaa Xaa Val Asn Pro Asn Glu Trp Trp Glu Asn Phe Pro Xaa Asn
        115                 120                 125
```

```
Ile Asn Glu Phe Tyr Phe Leu Phe Val Ser Gly His Phe Lys Gly Asn
    130                 135                 140

Xaa Glu Glu Gln Leu Glu Arg Ile Ser Ile Xaa Thr Xaa Ile Lys Gly
145                 150                 155                 160

Ala Ala Met Ser Val Xaa Thr Leu Leu Leu Ala Asn Glu Ile Lys
                165                 170                 175

Ala Gly Arg Leu Xaa Leu Glu Glu Val Xaa Lys Tyr Phe Asp Asn Lys
            180                 185                 190

Glu Ile Xaa Phe
        195
```

<210> SEQ ID NO 319
<211> LENGTH: 196
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (1)..(1)
<223> OTHER INFORMATION: Xaa is Phe, Gln, Asn or absent
<220> FEATURE:
<221> NAME/KEY: SITE
<222> LOCATION: (7)..(7)
<223> OTHER INFORMATION: Xaa is Met, Ile, Val, Gln, Phe, Leu or absent
<220> FEATURE:
<221> NAME/KEY: SITE
<222> LOCATION: (10)..(10)
<223> OTHER INFORMATION: Xaa is Lys, Ser, Leu, Ile, Thr, Glu or absent
<220> FEATURE:
<221> NAME/KEY: SITE
<222> LOCATION: (19)..(19)
<223> OTHER INFORMATION: Xaa is Arg, Gln, Asn, Thr, Asp or absent
<220> FEATURE:
<221> NAME/KEY: SITE
<222> LOCATION: (27)..(27)
<223> OTHER INFORMATION: Xaa is Glu, Gln, Gly, Ser, Ala or absent
<220> FEATURE:
<221> NAME/KEY: SITE
<222> LOCATION: (29)..(29)
<223> OTHER INFORMATION: Xaa is Ile, Val, Leu or absent
<220> FEATURE:
<221> NAME/KEY: SITE
<222> LOCATION: (46)..(46)
<223> OTHER INFORMATION: Xaa is Val, Met, Leu or Ile
<220> FEATURE:
<221> NAME/KEY: SITE
<222> LOCATION: (56)..(56)
<223> OTHER INFORMATION: Xaa is Arg, Ser, Asn, Glu, Lys or Gln
<220> FEATURE:
<221> NAME/KEY: SITE
<222> LOCATION: (70)..(70)
<223> OTHER INFORMATION: Xaa is Leu, Met, Val, Ile or Cys
<220> FEATURE:
<221> NAME/KEY: SITE
<222> LOCATION: (77)..(77)
<223> OTHER INFORMATION: Xaa is Leu, His, Lys, Glu, Tyr, Asp or Ala
<220> FEATURE:
<221> NAME/KEY: SITE
<222> LOCATION: (114)..(114)
<223> OTHER INFORMATION: Xaa is Gln, Glu, Ile, Lys or Ala
<220> FEATURE:
<221> NAME/KEY: SITE
<222> LOCATION: (115)..(115)
<223> OTHER INFORMATION: Xaa is Val, His, Arg, Lys, Leu or Glu
<220> FEATURE:
<221> NAME/KEY: SITE
<222> LOCATION: (127)..(127)
<223> OTHER INFORMATION: Xaa is Thr, Glu, Ser, Asp, Lys or Asn
<220> FEATURE:
<221> NAME/KEY: SITE
<222> LOCATION: (145)..(145)
<223> OTHER INFORMATION: Xaa is Tyr, Phe, Ile or Val
<220> FEATURE:

```
<221> NAME/KEY: SITE
<222> LOCATION: (155)..(155)
<223> OTHER INFORMATION: Xaa is Leu, Asp, Asn, Ser or Phe
<220> FEATURE:
<221> NAME/KEY: SITE
<222> LOCATION: (157)..(157)
<223> OTHER INFORMATION: Xaa is Lys, Gly or Asn
<220> FEATURE:
<221> NAME/KEY: SITE
<222> LOCATION: (166)..(166)
<223> OTHER INFORMATION: Xaa is Glu, Gln, Lys, Ser or Ile
<220> FEATURE:
<221> NAME/KEY: SITE
<222> LOCATION: (181)..(181)
<223> OTHER INFORMATION: Xaa is Thr, Ser, Asp or Lys
<220> FEATURE:
<221> NAME/KEY: SITE
<222> LOCATION: (186)..(186)
<223> OTHER INFORMATION: Xaa is Gly, Lys, Arg, Leu, Val or Glu
<220> FEATURE:
<221> NAME/KEY: SITE
<222> LOCATION: (195)..(195)
<223> OTHER INFORMATION: Xaa is Val, Gln, Glu, Leu or absent

<400> SEQUENCE: 319
```

Xaa Leu Val Lys Ser Ser Xaa Glu Glu Xaa Lys Glu Leu Arg Glu
1               5                   10                  15

Lys Leu Xaa His Leu Ser His Glu Tyr Leu Xaa Leu Xaa Asp Leu Ala
            20                  25                  30

Tyr Asp Ser Lys Gln Asn Arg Leu Phe Glu Met Lys Val Xaa Glu Leu
        35                  40                  45

Leu Ile Asn Glu Cys Gly Tyr Xaa Gly Leu His Leu Gly Gly Ser Arg
    50                  55                  60

Lys Pro Asp Gly Ile Xaa Tyr Thr Glu Gly Leu Lys Xaa Asn Tyr Gly
65                  70                  75                  80

Ile Ile Ile Asp Thr Lys Ala Tyr Ser Asp Gly Tyr Asn Leu Pro Ile
            85                  90                  95

Ser Gln Ala Asp Glu Met Glu Arg Tyr Ile Arg Glu Asn Asn Thr Arg
        100                 105                 110

Asn Xaa Xaa Val Asn Pro Asn Glu Trp Trp Glu Asn Phe Pro Xaa Asn
    115                 120                 125

Ile Asn Glu Phe Tyr Phe Leu Phe Val Ser Gly His Phe Lys Gly Asn
130                 135                 140

Xaa Glu Glu Gln Leu Glu Arg Ile Ser Ile Xaa Thr Xaa Ile Lys Gly
145                 150                 155                 160

Ala Ala Met Ser Val Xaa Thr Leu Leu Leu Ala Asn Glu Ile Lys
            165                 170                 175

Ala Gly Arg Leu Xaa Leu Glu Glu Val Xaa Lys Tyr Phe Asp Asn Lys
        180                 185                 190

Glu Ile Xaa Phe
        195

```
<210> SEQ ID NO 320
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 320
```

Ser Glu Ile Ala Lys Tyr His Thr Thr Leu Thr Gly Gln Gly Phe Thr
1               5                   10                  15

His Ala Asp Ile Cys Arg Ile Ser Arg Arg Arg Gln Ser Leu Arg Val

```
                    20                  25                  30
Val Ala Arg Asn Tyr Pro Glu Leu Ala Ala Leu Pro Glu Leu Thr
            35                  40                  45

Arg Ala His Ile Val Asp Ile Ala Arg Gln Arg Ser Gly Asp Leu Ala
            50                  55                  60

Leu Gln Ala Leu Leu Pro Val Ala Thr Ala Leu Thr Ala Pro Leu
65                  70                  75                  80

Arg Leu Ser Ala Ser Gln Ile Ala Thr Val Ala Gln Tyr Gly Glu Arg
                85                  90                  95

Pro Ala Ile Gln Ala Leu Tyr Arg Leu Arg Arg Lys Leu Thr Arg Ala
                100                 105                 110

Pro Leu His
        115

<210> SEQ ID NO 321
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 321

Ser Thr Val Ala Gln His His Glu Ala Leu Val Gly His Gly Phe Thr
1               5                   10                  15

His Ala His Ile Val Ala Leu Ser Gln His Pro Ala Ala Leu Gly Thr
                20                  25                  30

Val Ala Val Lys Tyr Gln Asp Met Ile Ala Ala Leu Pro Glu Ala Thr
            35                  40                  45

His Glu Ala Ile Val Gly Val Gly Lys Gln Trp Ser Gly Ala Arg Ala
        50                  55                  60

Leu Glu Ala Leu Leu Thr Val Ala Gly Glu Leu Arg Gly Pro Pro Leu
65                  70                  75                  80

Gln Leu Asp Thr Gly Gln Leu Leu Lys Ile Ala Lys Arg Gly Gly Val
                85                  90                  95

Thr Ala Val Glu Ala Val His Ala Trp Arg Asn Ala Leu Thr Gly Ala
                100                 105                 110

Pro Leu Asn
        115

<210> SEQ ID NO 322
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 322

Asn Ser Gln Ala Ser Ser Tyr Ser Ser Lys Ser Ser Pro Ala Ser
1               5                   10                  15

Ala Asn Ala Arg Lys Arg Thr Ser Arg Lys Glu Met Ser Gly Pro Pro
                20                  25                  30

Ser Lys Glu Pro Ala Asn Thr Lys Ser Arg Arg Ala Asn Ser Gln Asn
            35                  40                  45

Asn Lys Leu Ser Leu Ala Asp Arg Leu Thr Lys Tyr Asn Ile Asp Glu
        50                  55                  60

Glu Phe Tyr Gln Thr Arg Ser Asp Ser Leu Leu Ser Leu Asn Tyr Thr
65                  70                  75                  80
```

```
Lys Lys Gln Ile Glu Arg Leu Ile Leu Tyr Lys Gly Arg Thr Ser Ala
                85                  90                  95

Val Gln Gln Leu Leu Cys Lys His Glu Glu Leu Leu Asn Leu Ile Ser
            100                 105                 110

Pro Asp Gly
        115

<210> SEQ ID NO 323
<211> LENGTH: 34
<212> TYPE: PRT
<213> ORGANISM: Artificial Sequence
<220> FEATURE:
<223> OTHER INFORMATION: Synthetic Sequence

<400> SEQUENCE: 323

Leu Thr Pro Asp Gln Val Val Ala Ile Ala Ser Asn His Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 324
<211> LENGTH: 34
<212> TYPE: PRT
<213> ORGANISM: Artificial Sequence
<220> FEATURE:
<223> OTHER INFORMATION: Synthetic Sequence

<400> SEQUENCE: 324

Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 325
<211> LENGTH: 34
<212> TYPE: PRT
<213> ORGANISM: Artificial Sequence
<220> FEATURE:
<223> OTHER INFORMATION: Synthetic Sequence

<400> SEQUENCE: 325

Leu Thr Pro Asp Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 326
<211> LENGTH: 34
<212> TYPE: PRT
<213> ORGANISM: Artificial Sequence
<220> FEATURE:
<223> OTHER INFORMATION: Synthetic Sequence

<400> SEQUENCE: 326

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30
```

His Gly

<210> SEQ ID NO 327
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 327

Leu Thr Pro Glu Gln Val Val Ala Ile Ala Ser Asn Gly Gly Gly Arg
1               5                   10                  15

Pro Ala Leu Glu
            20

<210> SEQ ID NO 328
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 328

Leu Thr Pro Asp Gln Val Val Ala Ile Ala Ser Asn Gly Gly Gly Arg
1               5                   10                  15

Pro Ala Leu Glu
            20

<210> SEQ ID NO 329
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 329

Leu Thr Pro Glu Gln Val Val Ala Ile Ala Ser Asn Ile Gly Gly Arg
1               5                   10                  15

Pro Ala Leu Glu
            20

<210> SEQ ID NO 330
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 330

Leu Thr Pro Asp Gln Val Val Ala Ile Ala Ser Asn Ile Gly Gly Arg
1               5                   10                  15

Pro Ala Leu Glu
            20

<210> SEQ ID NO 331
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 331

Leu Thr Pro Glu Gln Val Val Ala Ile Ala Ser His Asp Gly Gly Arg
1               5                   10                  15

-continued

Pro Ala Leu Glu
        20

<210> SEQ ID NO 332
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 332

Leu Thr Pro Asp Gln Val Val Ala Ile Ala Ser His Asp Gly Gly Arg
1               5                   10                  15

Pro Ala Leu Glu
        20

<210> SEQ ID NO 333
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 333

Leu Thr Pro Glu Gln Val Val Ala Ile Ala Ser Asn His Gly Gly Arg
1               5                   10                  15

Pro Ala Leu Glu
        20

<210> SEQ ID NO 334
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 334

Leu Thr Pro Asp Gln Val Val Ala Ile Ala Ser Asn His Gly Gly Arg
1               5                   10                  15

Pro Ala Leu Glu
        20

<210> SEQ ID NO 335
<211> LENGTH: 137
<212> TYPE: PRT
<213> ORGANISM: Artificial Sequence
<220> FEATURE:
<223> OTHER INFORMATION: Synthetic Sequence

<400> SEQUENCE: 335

Asn Phe Ala Ile Pro Leu His Leu Phe Asp Asp Glu Thr Val Phe Thr
1               5                   10                  15

His Asp Ala Thr Asn Asp Asn Ser Gln Ala Ser Ser Ser Tyr Ser Ser
                20                  25                  30

Lys Ser Ser Pro Ala Ser Ala Asn Ala Arg Lys Arg Thr Ser Arg Lys
            35                  40                  45

Glu Met Ser Gly Pro Pro Ser Lys Glu Pro Ala Asn Thr Lys Ser Arg
        50                  55                  60

Arg Ala Asn Ser Gln Asn Asn Lys Leu Ser Leu Ala Asp Arg Leu Thr
65                  70                  75                  80

Lys Tyr Asn Ile Asp Glu Glu Phe Tyr Gln Thr Arg Ser Asp Ser Leu
                85                  90                  95

Leu Ser Leu Asn Tyr Thr Lys Lys Gln Ile Glu Arg Leu Ile Leu Tyr
                100                 105                 110

Lys Gly Arg Thr Ser Ala Val Gln Gln Leu Leu Cys Lys His Glu Glu
            115                 120                 125

Leu Leu Asn Leu Ile Ser Pro Asp Gly
        130                 135

<210> SEQ ID NO 336
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 336

Leu Ser Thr Ala Gln Val Val Ala Val Ala Ser Gly Ser Gly Gly Lys
1               5                   10                  15

Pro Ala Leu Glu Ala Val Arg Ala Gln Leu Leu Ala Leu Arg Ala Ala
            20                  25                  30

Pro Tyr Gly
        35

<210> SEQ ID NO 337
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 337

Leu Ser Thr Ala Gln Val Val Ala Val Ala Ser Gly Ser Gly Gly Lys
1               5                   10                  15

Pro Ala Leu Glu Ala Val Arg Ala Gln Leu Leu Ala Leu Arg Ala Ala
            20                  25                  30

Pro Tyr Gly
        35

<210> SEQ ID NO 338
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 338

Leu Asn Thr Ala Gln Ile Val Ala Ile Ala Ser His Asp Gly Gly Lys
1               5                   10                  15

Pro Ala Leu Glu Ala Val Trp Ala Lys Leu Pro Val Leu Arg Gly Ala
            20                  25                  30

Pro Tyr Ala
        35

<210> SEQ ID NO 339
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 339

Leu Asn Thr Ala Gln Val Val Ala Ile Ala Ser His Asp Gly Gly Lys
1               5                   10                  15

Pro Ala Leu Glu Ala Val Arg Ala Lys Leu Pro Val Leu Arg Gly Val
            20                  25                  30

Pro Tyr Ala
        35

<210> SEQ ID NO 340
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 340

Leu Asn Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Ala
        35

<210> SEQ ID NO 341
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 341

Leu Asn Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Glu
        35

<210> SEQ ID NO 342
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 342

Leu Ser Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Ala
            20                  25                  30

Pro Tyr Ala
        35

<210> SEQ ID NO 343
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 343

Leu Ser Thr Ala Gln Val Val Ala Val Ala Ser His Asp Gly Gly Lys
1               5                   10                  15

Pro Ala Leu Glu Ala Val Arg Lys Gln Leu Pro Val Leu Arg Gly Val
            20                  25                  30

Pro His Gln
        35

<210> SEQ ID NO 344
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 344

Leu Ser Thr Ala Gln Val Val Ala Val Ala Ser His Asp Gly Gly Lys
1               5                   10                  15

Pro Ala Leu Glu Ala Val Arg Lys Gln Leu Pro Val Leu Arg Gly Val
            20                  25                  30

Pro His Gln
        35

<210> SEQ ID NO 345
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 345

Leu Asn Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Ala
        35

<210> SEQ ID NO 346
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 346

Leu Ser Thr Glu Gln Val Val Ala Ile Ala Ser His Asn Gly Gly Lys
1               5                   10                  15

Leu Ala Leu Glu Ala Val Lys Ala His Leu Leu Asp Leu Arg Gly Ala
            20                  25                  30

Pro Tyr Ala
        35

<210> SEQ ID NO 347
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 347

Leu Ser Thr Glu Gln Val Val Ala Ile Ala Ser His Asn Gly Gly Lys
1               5                   10                  15

Pro Ala Leu Glu Ala Val Lys Ala His Leu Leu Ala Leu Arg Ala Ala
            20                  25                  30

Pro Tyr Ala
        35

```
<210> SEQ ID NO 348
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 348

Leu Asn Thr Ala Gln Val Val Ala Ile Ala Ser His Tyr Gly Gly Lys
1               5                   10                  15

Pro Ala Leu Glu Ala Val Trp Ala Lys Leu Pro Val Leu Arg Gly Val
            20                  25                  30

Pro Tyr Ala
        35

<210> SEQ ID NO 349
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 349

Leu Asn Thr Glu Gln Val Val Ala Ile Ala Ser Asn Asn Gly Gly Lys
1               5                   10                  15

Pro Ala Leu Glu Ala Val Lys Ala Gln Leu Leu Glu Leu Arg Ala Ala
            20                  25                  30

Pro Tyr Glu
        35

<210> SEQ ID NO 350
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 350

Leu Ser Pro Glu Gln Val Val Ala Ile Ala Ser Asn Asn Gly Gly Lys
1               5                   10                  15

Pro Ala Leu Glu Ala Val Lys Ala Leu Leu Leu Ala Leu Arg Ala Ala
            20                  25                  30

Pro Tyr Glu
        35

<210> SEQ ID NO 351
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 351

Leu Ser Pro Glu Gln Val Val Ala Ile Ala Ser Asn Asn Gly Gly Lys
1               5                   10                  15

Pro Ala Leu Glu Ala Val Lys Ala Gln Leu Leu Glu Leu Arg Ala Ala
            20                  25                  30

Pro Tyr Glu
        35

<210> SEQ ID NO 352
<211> LENGTH: 35
```

```
<212> TYPE: PRT
<213> ORGANISM: Artificial Sequence
<220> FEATURE:
<223> OTHER INFORMATION: Synthetic Sequence

<400> SEQUENCE: 352

Leu Ser Thr Glu Gln Val Val Ala Ile Ala Ser Asn Asn Gly Gly Lys
1               5                   10                  15

Pro Ala Leu Glu Ala Val Lys Ala Leu Leu Leu Ala Leu Arg Ala Ala
            20                  25                  30

Pro Tyr Glu
        35

<210> SEQ ID NO 353
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 353

Leu Ser Thr Glu Gln Val Val Ala Ile Ala Ser Asn Asn Gly Gly Lys
1               5                   10                  15

Pro Ala Leu Glu Ala Val Lys Ala Leu Leu Glu Leu Arg Ala Ala
            20                  25                  30

Pro Tyr Glu
        35

<210> SEQ ID NO 354
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 354

Leu Ser Pro Glu Gln Val Val Ala Ile Ala Ser Asn Asn Gly Gly Lys
1               5                   10                  15

Pro Ala Leu Glu Ala Val Lys Ala Leu Leu Leu Ala Leu Arg Ala Ala
            20                  25                  30

Pro Tyr Glu
        35

<210> SEQ ID NO 355
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 355

Leu Ser Pro Glu Gln Val Val Ala Ile Ala Ser Asn Asn Gly Gly Lys
1               5                   10                  15

Pro Ala Leu Glu Ala Val Lys Ala Gln Leu Glu Leu Arg Ala Ala
            20                  25                  30

Pro Tyr Glu
        35

<210> SEQ ID NO 356
<211> LENGTH: 35
<212> TYPE: PRT
<213> ORGANISM: Artificial Sequence
<220> FEATURE:
```

<223> OTHER INFORMATION: Synthetic Sequence

<400> SEQUENCE: 356

Leu Ser Thr Glu Gln Val Val Ala Ile Ala Ser Asn Asn Gly Gly Lys
1               5                   10                  15

Pro Ala Leu Glu Ala Val Lys Ala Leu Leu Glu Leu Arg Ala Ala
            20                  25                  30

Pro Tyr Glu
        35

<210> SEQ ID NO 357
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 357

Leu Gly His Lys Glu Leu Ile Lys Ile Ala Ala Arg Asn Gly Gly Gly
1               5                   10                  15

Asn Asn Leu Ile Ala Val Leu Ser Cys Tyr Ala Lys Leu Lys Glu Met
            20                  25                  30

Gly

<210> SEQ ID NO 358
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 358

Phe Ser Ala Glu Gln Ile Val Arg Ile Ala Ala His Asp Gly Gly Ser
1               5                   10                  15

Arg Asn Ile Glu Ala Val Gln Gln Ala Gln His Val Leu Lys Glu Leu
            20                  25                  30

Gly

<210> SEQ ID NO 359
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 359

Phe Ser Ala Glu Gln Ile Val Ser Ile Val Ala His Asp Gly Gly Ser
1               5                   10                  15

Arg Asn Ile Glu Ala Val Gln Gln Ala Gln His Ile Leu Lys Glu Leu
            20                  25                  30

Gly

<210> SEQ ID NO 360
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 360

Phe Ser Arg Gln Gln Ile Leu Arg Ile Ala Ser His Asp Gly Gly Ser
1               5                   10                  15

```
Lys Asn Ile Ala Ala Val Gln Lys Phe Leu Pro Lys Leu Met Asn Phe
            20                  25                  30

Gly Phe Asn
        35
```

<210> SEQ ID NO 361
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 361

```
Phe Ser Ala Glu Gln Ile Val Arg Ile Ala Ala His Asp Gly Gly Ser
1               5                   10                  15

Leu Asn Ile Asp Ala Val Gln Gln Ala Gln Gln Ala Leu Lys Glu Leu
            20                  25                  30

Gly
```

<210> SEQ ID NO 362
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 362

```
Phe Ser Thr Glu Gln Ile Val Cys Ile Ala Gly His Gly Gly Ser
1               5                   10                  15

Leu Asn Ile Lys Ala Val Leu Leu Ala Gln Gln Ala Leu Lys Asp Leu
            20                  25                  30

Gly
```

<210> SEQ ID NO 363
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 363

```
Phe Ser Ser Glu Gln Ile Val Arg Val Ala Ala His Gly Gly Gly Ser
1               5                   10                  15

Leu Asn Ile Lys Ala Val Leu Gln Ala His Gln Ala Leu Lys Glu Leu
            20                  25                  30

Asp
```

<210> SEQ ID NO 364
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 364

```
Phe Ser Ala Glu Gln Ile Val His Ile Ala Ala His Gly Gly Gly Ser
1               5                   10                  15

Leu Asn Ile Lys Ala Ile Leu Gln Ala His Gln Thr Leu Lys Glu Leu
            20                  25                  30

Asn
```

```
<210> SEQ ID NO 365
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 365

Phe Ser Ala Glu Gln Ile Val Arg Ile Ala Ala His Ile Gly Gly Ser
1               5                   10                  15

Arg Asn Ile Glu Ala Ile Gln Gln Ala His His Ala Leu Lys Glu Leu
            20                  25                  30

Gly

<210> SEQ ID NO 366
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 366

Phe Ser Ala Glu Gln Ile Val Arg Ile Ala Ala His Ile Gly Gly Ser
1               5                   10                  15

His Asn Leu Lys Ala Val Leu Gln Ala Gln Gln Ala Leu Lys Glu Leu
            20                  25                  30

Asp

<210> SEQ ID NO 367
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 367

Phe Ser Ala Lys His Ile Val Arg Ile Ala Ala His Ile Gly Gly Ser
1               5                   10                  15

Leu Asn Ile Lys Ala Val Gln Gln Ala Gln Gln Ala Leu Lys Glu Leu
            20                  25                  30

Gly

<210> SEQ ID NO 368
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 368

Phe Asn Ala Glu Gln Ile Val Arg Met Val Ser His Lys Gly Gly Ser
1               5                   10                  15

Lys Asn Leu Ala Leu Val Lys Glu Tyr Phe Pro Val Phe Ser Ser Phe
            20                  25                  30

His

<210> SEQ ID NO 369
<211> LENGTH: 35
<212> TYPE: PRT
<213> ORGANISM: Artificial Sequence
<220> FEATURE:
<223> OTHER INFORMATION: Synthetic Sequence
```

<400> SEQUENCE: 369

Phe Asn Ala Glu Gln Ile Val Arg Met Val Ser His Lys Gly Gly Ser
1               5                   10                  15

Lys Asn Leu Ala Leu Val Lys Glu Tyr Phe Pro Val Phe Ser Ser Phe
            20                  25                  30

His Phe Thr
        35

<210> SEQ ID NO 370
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 370

Phe Ser Ala Asp Gln Ile Val Arg Ile Ala Ala His Lys Gly Gly Ser
1               5                   10                  15

His Asn Ile Val Ala Val Gln Gln Gln Gln Ala Leu Lys Glu Leu
            20                  25                  30

Asp

<210> SEQ ID NO 371
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 371

Phe Asn Val Glu Gln Ile Val Arg Met Val Ser His Asn Gly Gly Ser
1               5                   10                  15

Lys Asn Leu Lys Ala Val Thr Asp Asn His Asp Asp Leu Lys Asn Met
            20                  25                  30

Gly Phe Asn
        35

<210> SEQ ID NO 372
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 372

Phe Ser Ala Asp Gln Val Val Lys Ile Ala Gly His Ser Gly Gly Ser
1               5                   10                  15

Asn Asn Ile Ala Val Met Leu Ala Val Phe Pro Arg Leu Arg Asp Phe
            20                  25                  30

Gly Phe Lys
        35

<210> SEQ ID NO 373
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 373

Phe Ser Ala Glu Gln Ile Val Ser Ile Ala Ala His Val Gly Gly Ser

```
1               5                   10                  15
His Asn Ile Glu Ala Val Gln Lys Ala His Gln Ala Leu Lys Glu Leu
            20                  25                  30
Asp

<210> SEQ ID NO 374
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 374

Phe Asn Ala Glu Gln Ile Val Ser Met Val Ser Asn Asn Gly Gly Ser
1               5                   10                  15

Lys Asn Leu Lys Ala Val Thr Asp Asn His Asp Leu Lys Asn Met
            20                  25                  30

Gly Phe Asn
        35

<210> SEQ ID NO 375
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 375

Phe Ser His Lys Glu Leu Ile Lys Ile Ala Ala Arg Asn Gly Gly Gly
1               5                   10                  15

Asn Asn Leu Ile Ala Val Leu Ser Cys Tyr Ala Lys Leu Lys Glu Met
            20                  25                  30

Gly

<210> SEQ ID NO 376
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 376

Phe Ser His Lys Glu Leu Ile Lys Ile Ala Ala Arg Asn Gly Gly Gly
1               5                   10                  15

Asn Asn Leu Ile Ala Val Leu Ser Cys Tyr Ala Lys Leu Lys Glu Met
            20                  25                  30

Gly Phe Ser
        35

<210> SEQ ID NO 377
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 377

Phe Ser Ser Gly Glu Thr Val Gly Ala Thr Val Gly Ala Gly Gly Thr
1               5                   10                  15

Glu Thr Val Ala Gln Gly Gly Thr Ala Ser Asn Thr Thr Val Ser Ser
            20                  25                  30
```

```
Gly Gly Tyr
        35

<210> SEQ ID NO 378
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 378

Phe Ser Gly Gly Met Ala Thr Ser Thr Thr Val Ser Gly Thr
1               5                   10                  15

Gln Asp Val Leu Ala Gly Gly Ala Ala Val Gly Gly Thr Val Gly Thr
            20                  25                  30

Gly Gly Val
        35

<210> SEQ ID NO 379
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 379

Phe Ser Ala Ala Asp Ile Val Lys Ile Ala Gly Lys Ile Gly Gly Ala
1               5                   10                  15

Gln Ala Leu Gln Ala Phe Ile Thr His Arg Ala Ala Leu Ile Gln Ala
            20                  25                  30

Gly Phe Ser
        35

<210> SEQ ID NO 380
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 380

Phe Asn Pro Thr Asp Ile Val Lys Ile Ala Gly Asn Asp Gly Gly Ala
1               5                   10                  15

Gln Ala Leu Gln Ala Val Leu Glu Leu Glu Pro Ala Leu Arg Glu Arg
            20                  25                  30

Gly Phe Ser
        35

<210> SEQ ID NO 381
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 381

Phe Asn Pro Thr Asp Ile Val Arg Met Ala Gly Asn Asp Gly Gly Ala
1               5                   10                  15

Gln Ala Leu Gln Ala Val Phe Glu Leu Glu Pro Ala Phe Arg Glu Arg
            20                  25                  30

Ser Phe Ser
        35
```

<210> SEQ ID NO 382
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 382

Phe Asn Pro Thr Asp Ile Val Arg Met Ala Gly Asn Asp Gly Ala
1               5                   10                  15

Gln Ala Leu Gln Ala Val Leu Glu Leu Glu Pro Ala Phe Arg Glu Arg
            20                  25                  30

Gly Phe Ser
        35

<210> SEQ ID NO 383
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 383

Phe Ser Gln Val Asp Ile Val Lys Ile Ala Ser Asn Asp Gly Gly Ala
1               5                   10                  15

Gln Ala Leu Tyr Ser Val Leu Asp Val Glu Pro Thr Phe Arg Glu Arg
            20                  25                  30

Gly Phe Ser
        35

<210> SEQ ID NO 384
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 384

Phe Ser Arg Ala Asp Ile Val Lys Ile Ala Gly Asn Asp Gly Gly Ala
1               5                   10                  15

Gln Ala Leu Tyr Ser Val Leu Asp Val Glu Pro Pro Leu Arg Glu Arg
            20                  25                  30

Gly Phe Ser
        35

<210> SEQ ID NO 385
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 385

Phe Ser Arg Gly Asp Ile Val Lys Ile Ala Gly Asn Asp Gly Gly Ala
1               5                   10                  15

Gln Ala Leu Tyr Ser Val Leu Asp Val Glu Pro Pro Leu Arg Glu Arg
            20                  25                  30

Gly Phe Ser
        35

<210> SEQ ID NO 386
<211> LENGTH: 35

```
<212> TYPE: PRT
<213> ORGANISM: Artificial Sequence
<220> FEATURE:
<223> OTHER INFORMATION: Synthetic Sequence

<400> SEQUENCE: 386

Phe Asn Arg Ala Asp Ile Val Arg Ile Ala Gly Asn Gly Gly Ala
1               5                   10                  15

Gln Ala Leu Tyr Ser Val Arg Asp Ala Gly Pro Thr Leu Gly Lys Arg
            20                  25                  30

Gly Phe Ser
        35

<210> SEQ ID NO 387
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 387

Phe Arg Gln Ala Asp Ile Val Lys Ile Ala Ser Asn Gly Gly Ser Ala
1               5                   10                  15

Gln Ala Leu Asn Ala Val Ile Lys Leu Gly Pro Thr Leu Arg Gln Arg
            20                  25                  30

Gly Phe Ser
        35

<210> SEQ ID NO 388
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 388

Phe Arg Gln Ala Asp Ile Val Lys Met Ala Ser Asn Gly Gly Ser Ala
1               5                   10                  15

Gln Ala Leu Asn Ala Val Ile Lys Leu Gly Pro Thr Leu Arg Gln Arg
            20                  25                  30

Gly Phe Ser
        35

<210> SEQ ID NO 389
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 389

Phe Ser Arg Ala Asp Ile Val Lys Ile Ala Gly Asn Gly Gly Gly Ala
1               5                   10                  15

Gln Ala Leu Gln Ala Val Leu Glu Leu Glu Pro Thr Phe Arg Glu Arg
            20                  25                  30

Gly Phe Ser
        35

<210> SEQ ID NO 390
<211> LENGTH: 35
<212> TYPE: PRT
<213> ORGANISM: Artificial Sequence
<220> FEATURE:
```

<223> OTHER INFORMATION: Synthetic Sequence

<400> SEQUENCE: 390

Phe Ser Arg Ala Asp Ile Val Arg Ile Ala Gly Asn Gly Gly Gly Ala
1               5                   10                  15

Gln Ala Leu Tyr Ser Val Leu Asp Val Gly Pro Thr Leu Gly Lys Arg
            20                  25                  30

Gly Phe Ser
        35

<210> SEQ ID NO 391
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 391

Phe Ser Arg Gly Asp Ile Val Arg Ile Ala Gly Asn Gly Gly Gly Ala
1               5                   10                  15

Gln Ala Leu Gln Ala Val Leu Glu Leu Glu Pro Thr Leu Gly Glu Arg
            20                  25                  30

Gly Phe Ser
        35

<210> SEQ ID NO 392
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 392

Phe Ser Arg Ala Asp Ile Val Lys Ile Ala Gly Asn Gly Gly Gly Ala
1               5                   10                  15

Gln Ala Leu Gln Ala Val Ile Thr His Arg Ala Ala Leu Thr Gln Ala
            20                  25                  30

Gly Phe Ser
        35

<210> SEQ ID NO 393
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 393

Phe Ser Arg Gly Asp Thr Val Lys Ile Ala Gly Asn Ile Gly Gly Ala
1               5                   10                  15

Gln Ala Leu Gln Ala Val Leu Glu Leu Glu Pro Thr Leu Arg Glu Arg
            20                  25                  30

Gly Phe Ser
        35

<210> SEQ ID NO 394
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 394

```
Phe Asn Pro Thr Asp Ile Val Lys Ile Ala Gly Asn Ile Gly Gly Ala
1               5                   10                  15

Gln Ala Leu Gln Ala Val Leu Glu Leu Glu Pro Ala Phe Arg Glu Arg
            20                  25                  30

Gly Phe Ser
        35

<210> SEQ ID NO 395
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 395

Phe Ser Ala Ala Asp Ile Val Lys Ile Ala Gly Asn Ile Gly Gly Ala
1               5                   10                  15

Gln Ala Leu Gln Ala Ile Phe Thr His Arg Ala Ala Leu Ile Gln Ala
            20                  25                  30

Gly Phe Ser
        35

<210> SEQ ID NO 396
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 396

Phe Ser Ala Ala Asp Ile Val Lys Ile Ala Gly Asn Ile Gly Gly Ala
1               5                   10                  15

Gln Ala Leu Gln Ala Val Ile Thr His Arg Ala Thr Leu Thr Gln Ala
            20                  25                  30

Gly Phe Ser
        35

<210> SEQ ID NO 397
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 397

Phe Ser Ala Thr Asp Ile Val Lys Ile Ala Ser Asn Ile Gly Gly Ala
1               5                   10                  15

Gln Ala Leu Gln Ala Val Ile Ser Arg Arg Ala Ala Leu Ile Gln Ala
            20                  25                  30

Gly Phe Ser
        35

<210> SEQ ID NO 398
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 398

Phe Ser Gln Pro Asp Ile Val Lys Ile Ala Gly Asn Ile Gly Gly Ala
1               5                   10                  15
```

```
Gln Ala Leu Gln Ala Val Leu Glu Leu Glu Pro Ala Phe Arg Glu Arg
            20                  25                  30

Gly Phe Ser
        35

<210> SEQ ID NO 399
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 399

Phe Ser Arg Ala Asp Ile Val Lys Ile Ala Gly Asn Ile Gly Gly Ala
1               5                   10                  15

Gln Ala Leu Gln Ala Val Leu Glu Leu Glu Ser Thr Phe Arg Glu Arg
            20                  25                  30

Ser Phe Asn
        35

<210> SEQ ID NO 400
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 400

Phe Ser Arg Ala Asp Ile Val Lys Ile Ala Gly Asn Ile Gly Gly Ala
1               5                   10                  15

Gln Ala Leu Gln Ala Val Leu Glu Leu Glu Ser Thr Leu Arg Glu Arg
            20                  25                  30

Ser Phe Asn
        35

<210> SEQ ID NO 401
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 401

Phe Ser Arg Gly Asp Ile Val Lys Met Ala Gly Asn Ile Gly Gly Ala
1               5                   10                  15

Gln Ala Leu Gln Ala Gly Leu Glu Leu Glu Pro Ala Phe Arg Glu Arg
            20                  25                  30

Gly Phe Ser
        35

<210> SEQ ID NO 402
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 402

Phe Ser Arg Gly Asp Ile Val Lys Met Ala Gly Asn Ile Gly Gly Ala
1               5                   10                  15

Gln Ala Leu Gln Ala Val Leu Glu Leu Glu Pro Ala Phe His Glu Arg
            20                  25                  30
```

Ser Phe Cys
        35

<210> SEQ ID NO 403
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 403

Phe Thr Leu Thr Asp Ile Val Lys Met Ala Gly Asn Ile Gly Gly Ala
1               5                   10                  15

Gln Ala Leu Lys Ala Val Leu Glu His Gly Pro Thr Leu Arg Gln Arg
            20                  25                  30

Asp Leu Ser
        35

<210> SEQ ID NO 404
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 404

Phe Thr Leu Thr Asp Ile Val Lys Met Ala Gly Asn Ile Gly Gly Ala
1               5                   10                  15

Gln Ala Leu Lys Val Val Leu Glu His Gly Pro Thr Leu Arg Gln Arg
            20                  25                  30

Asp Leu Ser
        35

<210> SEQ ID NO 405
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 405

Phe Asn Pro Thr Asp Ile Val Lys Ile Ala Gly Asn Asn Gly Gly Ala
1               5                   10                  15

Gln Ala Leu Gln Ala Val Leu Glu Leu Glu Pro Ala Leu Arg Glu Arg
            20                  25                  30

Gly Phe Ser
        35

<210> SEQ ID NO 406
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 406

Phe Asn Pro Thr Asp Ile Val Lys Ile Ala Gly Asn Asn Gly Gly Ala
1               5                   10                  15

Gln Ala Leu Gln Ala Val Leu Glu Leu Glu Pro Ala Leu Arg Glu Arg
            20                  25                  30

Ser Phe Ser
        35

<210> SEQ ID NO 407
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 407

Phe Asn Pro Thr Asp Met Val Lys Ile Ala Gly Asn Asn Gly Ala
1               5                   10                  15

Gln Ala Leu Gln Ala Val Leu Glu Leu Glu Pro Ala Leu Arg Glu Arg
            20                  25                  30

Gly Phe Ser
        35

<210> SEQ ID NO 408
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 408

Phe Ser Ala Ala Asp Ile Val Lys Ile Ala Ser Asn Asn Gly Gly Ala
1               5                   10                  15

Gln Ala Leu Gln Ala Leu Ile Asp His Trp Ser Thr Leu Ser Gly Lys
            20                  25                  30

Thr Lys Ala
        35

<210> SEQ ID NO 409
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 409

Phe Ser Ala Ala Asp Ile Val Lys Ile Ala Ser Asn Asn Gly Gly Ala
1               5                   10                  15

Gln Ala Leu Gln Ala Val Ile Ser Arg Arg Ala Ala Leu Ile Gln Ala
            20                  25                  30

Gly Phe Ser
        35

<210> SEQ ID NO 410
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 410

Phe Ser Ala Ala Asp Ile Val Lys Ile Ala Ser Asn Asn Gly Gly Ala
1               5                   10                  15

Gln Ala Leu Gln Ala Val Ile Thr His Arg Ala Ala Leu Ala Gln Ala
            20                  25                  30

Gly Phe Ser
        35

<210> SEQ ID NO 411

```
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 411

Phe Ser Ala Ala Asp Ile Val Lys Ile Ala Ser Asn Asn Gly Gly Ala
1               5                   10                  15
Arg Ala Leu Gln Ala Leu Ile Asp His Trp Ser Thr Leu Ser Gly Lys
            20                  25                  30
Thr Lys Ala
        35

<210> SEQ ID NO 412
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 412

Phe Thr Leu Thr Asp Ile Val Glu Met Ala Gly Asn Asn Gly Gly Ala
1               5                   10                  15
Gln Ala Leu Lys Ala Val Leu Glu His Gly Ser Thr Leu Asp Glu Arg
            20                  25                  30
Gly Phe Thr
        35

<210> SEQ ID NO 413
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 413

Phe Thr Leu Thr Asp Ile Val Lys Met Ala Gly Asn Asn Gly Gly Ala
1               5                   10                  15
Gln Ala Leu Lys Ala Val Leu Glu His Gly Pro Thr Leu Asp Glu Arg
            20                  25                  30
Gly Phe Thr
        35

<210> SEQ ID NO 414
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 414

Phe Thr Leu Thr Asp Ile Val Lys Met Ala Gly Asn Asn Gly Gly Ala
1               5                   10                  15
Gln Ala Leu Lys Val Val Leu Glu His Gly Pro Thr Leu Arg Gln Arg
            20                  25                  30
Gly Phe Ser
        35

<210> SEQ ID NO 415
<211> LENGTH: 35
<212> TYPE: PRT
<213> ORGANISM: Artificial Sequence
```

<220> FEATURE:
<223> OTHER INFORMATION: Synthetic Sequence

<400> SEQUENCE: 415

Phe Thr Leu Thr Asp Ile Val Lys Met Ala Ser Asn Asn Gly Gly Ala
1               5                   10                  15

Gln Ala Leu Lys Ala Val Leu Glu His Gly Pro Thr Leu Asp Glu Arg
            20                  25                  30

Gly Phe Thr
        35

<210> SEQ ID NO 416
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 416

Phe Ser Ala Ala Asp Ile Val Lys Ile Ala Gly Asn Ser Gly Gly Ala
1               5                   10                  15

Gln Ala Leu Gln Ala Val Ile Ser His Arg Ala Ala Leu Thr Gln Ala
            20                  25                  30

Gly Phe Ser
        35

<210> SEQ ID NO 417
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 417

Phe Ser Gly Gly Asp Ala Val Ser Thr Val Val Arg Ser Gly Gly Ala
1               5                   10                  15

Gln Ser Val Ala Ser Gly Gly Thr Ala Ser Gly Thr Thr Val Ser Ala
            20                  25                  30

Gly Ala Thr
        35

<210> SEQ ID NO 418
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 418

Phe Arg Gln Thr Asp Ile Val Lys Met Ala Gly Ser Gly Gly Ser Ala
1               5                   10                  15

Gln Ala Leu Asn Ala Val Ile Lys His Gly Pro Thr Leu Arg Gln Arg
            20                  25                  30

Gly Phe Ser
        35

<210> SEQ ID NO 419
<211> LENGTH: 34
<212> TYPE: PRT
<213> ORGANISM: Artificial Sequence
<220> FEATURE:
<223> OTHER INFORMATION: Synthetic Sequence

```
<400> SEQUENCE: 419

Phe Ser Leu Ile Asp Ile Val Glu Ile Ala Ser Asn Gly Gly Ala Gln
1               5                   10                  15

Ala Leu Lys Ala Val Leu Lys Tyr Gly Pro Val Leu Thr Gln Ala Gly
            20                  25                  30

Arg Ser

<210> SEQ ID NO 420
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 420

Phe Ser Gly Gly Asp Ala Ala Gly Thr Val Val Ser Gly Gly Ala
1               5                   10                  15

Gln Asn Val Thr Gly Gly Leu Ala Ser Gly Thr Thr Val Ala Ser Gly
            20                  25                  30

Gly Ala Ala
        35

<210> SEQ ID NO 421
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 421

Phe Asn Leu Thr Asp Ile Val Glu Met Ala Ala Asn Ser Gly Gly Ala
1               5                   10                  15

Gln Ala Leu Lys Ala Val Leu Glu His Gly Pro Thr Leu Arg Gln Arg
            20                  25                  30

Gly Leu Ser
        35

<210> SEQ ID NO 422
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 422

Phe Asn Arg Ala Ser Ile Val Lys Ile Ala Gly Asn Ser Gly Gly Ala
1               5                   10                  15

Gln Ala Leu Gln Ala Val Leu Lys His Gly Pro Thr Leu Asp Glu Arg
            20                  25                  30

Gly Phe Asn
        35

<210> SEQ ID NO 423
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 423

Phe Ser Gln Ala Asn Ile Val Lys Met Ala Gly Asn Ser Gly Gly Ala
1               5                   10                  15
```

-continued

```
Gln Ala Leu Gln Ala Val Leu Asp Leu Glu Leu Val Phe Arg Glu Arg
            20                  25                  30

Gly Phe Ser
        35

<210> SEQ ID NO 424
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 424

Phe Ser Gln Pro Asp Ile Val Lys Met Ala Gly Asn Ser Gly Gly Ala
1               5                   10                  15

Gln Ala Leu Gln Ala Val Leu Asp Leu Glu Leu Ala Phe Arg Glu Arg
            20                  25                  30

Gly Phe Ser
        35

<210> SEQ ID NO 425
<211> LENGTH: 34
<212> TYPE: PRT
<213> ORGANISM: Artificial Sequence
<220> FEATURE:
<223> OTHER INFORMATION: Synthetic Sequence

<400> SEQUENCE: 425

Phe Ser Leu Ile Asp Ile Val Glu Ile Ala Ser Asn Gly Gly Ala Gln
1               5                   10                  15

Ala Leu Lys Ala Val Leu Lys Tyr Gly Pro Val Leu Met Gln Ala Gly
            20                  25                  30

Arg Ser

<210> SEQ ID NO 426
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 426

Tyr Lys Ser Glu Asp Ile Ile Arg Leu Ala Ser His Asp Gly Gly Ser
1               5                   10                  15

Val Asn Leu Glu Ala Val Leu Arg Leu His Ser Gln Leu Thr Arg Leu
            20                  25                  30

Gly

<210> SEQ ID NO 427
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 427

Tyr Lys Pro Glu Asp Ile Ile Arg Leu Ala Ser His Gly Gly Gly Ser
1               5                   10                  15

Val Asn Leu Glu Ala Val Leu Arg Leu Asn Pro Gln Leu Ile Gly Leu
            20                  25                  30

Gly
```

```
<210> SEQ ID NO 428
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 428

Tyr Lys Ser Glu Asp Ile Ile Arg Leu Ala Ser His Gly Gly Gly Ser
1               5                   10                  15

Val Asn Leu Glu Ala Val Leu Arg Leu His Ser Gln Leu Thr Arg Leu
            20                  25                  30

Gly

<210> SEQ ID NO 429
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 429

Tyr Lys Ser Glu Asp Ile Ile Arg Leu Ala Ser His Gly Gly Gly Ser
1               5                   10                  15

Val Asn Leu Glu Ala Val Leu Arg Leu Asn Pro Gln Leu Ile Gly Leu
            20                  25                  30

Gly

<210> SEQ ID NO 430
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 430

Phe Asn Leu Thr Asp Ile Val Glu Met Ala Gly Lys Gly Gly Gly Ala
1               5                   10                  15

Gln Ala Leu Lys Ala Val Leu Glu His Gly Pro Thr Leu Arg Gln Arg
            20                  25                  30

Gly Phe Asn
        35

<210> SEQ ID NO 431
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 431

Phe Arg Gln Ala Asp Ile Ile Lys Ile Ala Gly Asn Asp Gly Gly Ala
1               5                   10                  15

Gln Ala Leu Gln Ala Val Ile Glu His Gly Pro Thr Leu Arg Gln His
            20                  25                  30

Gly Phe Asn
        35

<210> SEQ ID NO 432
<211> LENGTH: 35
<212> TYPE: PRT
```

```
<213> ORGANISM: Artificial Sequence
<220> FEATURE:
<223> OTHER INFORMATION: Synthetic Sequence

<400> SEQUENCE: 432

Phe Ser Gln Ala Asp Ile Val Lys Ile Ala Gly Asn Asp Gly Thr
1               5                   10                  15

Gln Ala Leu His Ala Val Leu Asp Leu Glu Arg Met Leu Gly Glu Arg
            20                  25                  30

Gly Phe Ser
        35

<210> SEQ ID NO 433
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 433

Phe Ser Arg Ala Asp Ile Val Lys Ile Ala Gly Asn Gly Gly Ala
1               5                   10                  15

Gln Ala Leu Lys Ala Val Leu Glu His Glu Ala Thr Leu Asp Glu Arg
            20                  25                  30

Gly Phe Ser
        35

<210> SEQ ID NO 434
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 434

Phe Ser Arg Ala Asp Ile Val Arg Ile Ala Gly Asn Gly Gly Ala
1               5                   10                  15

Gln Ala Leu Tyr Ser Val Leu Asp Val Glu Pro Thr Leu Gly Lys Arg
            20                  25                  30

Gly Phe Ser
        35

<210> SEQ ID NO 435
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 435

Phe Ser Gln Pro Asp Ile Val Lys Met Ala Ser Asn Ile Gly Ala
1               5                   10                  15

Gln Ala Leu Gln Ala Val Leu Glu Leu Glu Pro Ala Leu Arg Glu Arg
            20                  25                  30

Gly Phe Ser
        35

<210> SEQ ID NO 436
<211> LENGTH: 35
<212> TYPE: PRT
<213> ORGANISM: Artificial Sequence
<220> FEATURE:
<223> OTHER INFORMATION: Synthetic Sequence
```

```
<400> SEQUENCE: 436

Phe Ser Gln Pro Asp Ile Val Lys Met Ala Gly Asn Ile Gly Gly Ala
1               5                   10                  15

Gln Ala Leu Gln Ala Val Leu Ser Leu Gly Pro Ala Leu Arg Glu Arg
            20                  25                  30

Gly Phe Ser
        35

<210> SEQ ID NO 437
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 437

Phe Ser Gln Pro Glu Ile Val Lys Ile Ala Gly Asn Ile Gly Gly Ala
1               5                   10                  15

Gln Ala Leu His Thr Val Leu Glu Leu Glu Pro Thr Leu His Lys Arg
            20                  25                  30

Gly Phe Asn
        35

<210> SEQ ID NO 438
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 438

Phe Ser Gln Ser Asp Ile Val Lys Ile Ala Gly Asn Ile Gly Gly Ala
1               5                   10                  15

Gln Ala Leu Gln Ala Val Leu Asp Leu Glu Ser Met Leu Gly Lys Arg
            20                  25                  30

Gly Phe Ser
        35

<210> SEQ ID NO 439
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 439

Phe Ser Gln Ser Asp Ile Val Lys Ile Ala Gly Asn Ile Gly Gly Ala
1               5                   10                  15

Gln Ala Leu Gln Ala Val Leu Glu Leu Glu Pro Thr Leu Arg Glu Ser
            20                  25                  30

Asp Phe Arg
        35

<210> SEQ ID NO 440
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 440
```

-continued

```
Phe Asn Pro Thr Asp Ile Val Lys Ile Ala Gly Asn Lys Gly Gly Ala
1               5                   10                  15

Gln Ala Leu Gln Ala Val Leu Glu Leu Glu Pro Ala Leu Arg Glu Arg
            20                  25                  30

Gly Phe Asn
        35

<210> SEQ ID NO 441
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 441

Phe Ser Pro Thr Asp Ile Ile Lys Ile Ala Gly Asn Asn Gly Gly Ala
1               5                   10                  15

Gln Ala Leu Gln Ala Val Leu Asp Leu Glu Leu Met Leu Arg Glu Arg
            20                  25                  30

Gly Phe Ser
        35

<210> SEQ ID NO 442
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 442

Phe Ser Gln Ala Asp Ile Val Lys Ile Ala Gly Asn Asn Gly Gly Ala
1               5                   10                  15

Gln Ala Leu Tyr Ser Val Leu Asp Val Glu Pro Thr Leu Gly Lys Arg
            20                  25                  30

Gly Phe Ser
        35

<210> SEQ ID NO 443
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 443

Phe Ser Arg Gly Asp Ile Val Thr Ile Ala Gly Asn Asn Gly Gly Ala
1               5                   10                  15

Gln Ala Leu Gln Ala Val Leu Glu Leu Glu Pro Thr Leu Arg Glu Arg
            20                  25                  30

Gly Phe Asn
        35

<210> SEQ ID NO 444
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 444

Phe Ser Arg Ile Asp Ile Val Lys Ile Ala Ala Asn Asn Gly Gly Ala
1               5                   10                  15
```

```
Gln Ala Leu His Ala Val Leu Asp Leu Gly Pro Thr Leu Arg Glu Cys
            20                  25                  30

Gly Phe Ser
        35

<210> SEQ ID NO 445
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 445

Phe Ser Gln Ala Asp Ile Val Lys Ile Val Gly Asn Asn Gly Gly Ala
1               5                   10                  15

Gln Ala Leu Gln Ala Val Phe Glu Leu Glu Pro Thr Leu Arg Glu Arg
            20                  25                  30

Gly Phe Asn
        35

<210> SEQ ID NO 446
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 446

Phe Ser Gln Pro Asp Ile Val Arg Ile Thr Gly Asn Arg Gly Gly Ala
1               5                   10                  15

Gln Ala Leu Gln Ala Val Leu Ala Leu Glu Leu Thr Leu Arg Glu Arg
            20                  25                  30

Gly Phe Ser
        35

<210> SEQ ID NO 447
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 447

His His Glu Ala Leu Val Gly His Gly Phe Thr His Ala His Ile Val
1               5                   10                  15

Ala Leu Ser Gln His Pro Ala Ala Leu Gly Thr Val Ala Val Lys Tyr
            20                  25                  30

Gln Asp Met Ile Ala Ala Leu Pro Glu Ala Thr His Glu Ala Ile Val
        35                  40                  45

Gly Val Gly Lys Gln Trp Ser Gly Ala Arg Ala Leu Glu Ala Leu Leu
    50                  55                  60

Thr Val Ala Gly Glu Leu Arg Gly Pro Pro Leu Gln Leu Asp Thr Gly
65                  70                  75                  80

Gln Leu Leu Lys Ile Ala Lys Arg Gly Gly Val Thr Ala Val Glu Ala
                85                  90                  95

Val His Ala Trp Arg Asn Ala Leu Thr Gly Ala Pro Leu Asn
                100                 105                 110

<210> SEQ ID NO 448
<211> LENGTH: 35
<212> TYPE: PRT
```

<213> ORGANISM: Artificial sequence
<220> FEATURE:
<223> OTHER INFORMATION: synthetic sequence
<220> FEATURE:
<221> NAME/KEY: SITE
<222> LOCATION: (1)..(35)
<223> OTHER INFORMATION: Xaa can be any naturally occurring amino acid

<400> SEQUENCE: 448

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa
        35

<210> SEQ ID NO 449
<211> LENGTH: 17
<212> TYPE: DNA
<213> ORGANISM: Artificial sequence
<220> FEATURE:
<223> OTHER INFORMATION: synthetic sequence

<400> SEQUENCE: 449
tttctgtcac caatcct                                                  17

<210> SEQ ID NO 450
<211> LENGTH: 18
<212> TYPE: DNA
<213> ORGANISM: Artificial sequence
<220> FEATURE:
<223> OTHER INFORMATION: synthetic sequence

<400> SEQUENCE: 450
tcccctccac cccacagt                                                 18

<210> SEQ ID NO 451
<211> LENGTH: 32
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (11)..(12)
<223> OTHER INFORMATION: A RVD is present between the amino acids at
      positions 11 and 12.

<400> SEQUENCE: 451

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
                20                  25                  30

<210> SEQ ID NO 452
<211> LENGTH: 28
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (1)..(1)
<223> OTHER INFORMATION: Xaa is Ala, Phe, Ile, Leu, Met, Thr or Val
<220> FEATURE:
<221> NAME/KEY: SITE
<222> LOCATION: (2)..(4)
<223> OTHER INFORMATION: Xaa can be any naturally occurring amino acid

```
<220> FEATURE:
<221> NAME/KEY: SITE
<222> LOCATION: (5)..(5)
<223> OTHER INFORMATION: Xaa is Asp, Glu, Lys, Asn, Met, Ser, Arg or Gln
<220> FEATURE:
<221> NAME/KEY: SITE
<222> LOCATION: (6)..(7)
<223> OTHER INFORMATION: Xaa is Ala, Phe, Ile, Leu, Met, Thr or Val
<220> FEATURE:
<221> NAME/KEY: SITE
<222> LOCATION: (8)..(8)
<223> OTHER INFORMATION: Xaa can be any naturally occurring amino acid
<220> FEATURE:
<221> NAME/KEY: SITE
<222> LOCATION: (9)..(9)
<223> OTHER INFORMATION: Xaa is Ala, Phe, Ile, Leu, Met, Thr or Val
<220> FEATURE:
<221> NAME/KEY: SITE
<222> LOCATION: (10)..(12)
<223> OTHER INFORMATION: Xaa can be any naturally occurring amino acid
<220> FEATURE:
<221> NAME/KEY: SITE
<222> LOCATION: (13)..(14)
<223> OTHER INFORMATION: Xaa is Ala, Gly, Asn or Ser
<220> FEATURE:
<221> NAME/KEY: SITE
<222> LOCATION: (15)..(15)
<223> OTHER INFORMATION: Xaa can be any naturally occurring amino acid
<220> FEATURE:
<221> NAME/KEY: SITE
<222> LOCATION: (16)..(16)
<223> OTHER INFORMATION: Xaa is Asp, Glu, Lys, Asn, Met, Ser, Arg or Gln
<220> FEATURE:
<221> NAME/KEY: SITE
<222> LOCATION: (17)..(17)
<223> OTHER INFORMATION: Xaa can be any naturally occurring amino acid
<220> FEATURE:
<221> NAME/KEY: SITE
<222> LOCATION: (18)..(18)
<223> OTHER INFORMATION: Xaa is Ala, Phe, Ile, Leu, Met, Thr or Val
<220> FEATURE:
<221> NAME/KEY: SITE
<222> LOCATION: (19)..(27)
<223> OTHER INFORMATION: Xaa can be any naturally occurring amino acid
<220> FEATURE:
<221> NAME/KEY: SITE
<222> LOCATION: (28)..(28)
<223> OTHER INFORMATION: Xaa is Ala, Phe, Ile, Leu, Met, Thr or Val

<400> SEQUENCE: 452

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25
```